US010647995B2

(12) United States Patent
Hu et al.

(10) Patent No.: US 10,647,995 B2
(45) Date of Patent: May 12, 2020

(54) COMPOSITIONS AND METHODS TO CONTROL INSECT PESTS

(71) Applicants: PIONEER HI-BRED INTERNATIONAL, INC., Johnston, IA (US); E. I. DU PONT DE NEMOURS AND COMPANY, Wilmington, DE (US)

(72) Inventors: Xu Hu, Johnston, IA (US); Bliss Marie Kernodle, Johnston, IA (US); Molly Mary McMahon, Des Moines, IA (US); Adane Kassa, Johnston, IA (US); Xiping Niu, Johnston, IA (US); James Kevin Presnail, St Louis, MO (US); Albert L. Lu, West Des Moines, IA (US); Nina Richtman, Johnston, IA (US); Jonathan William Robeson, Urbandale, IA (US)

(73) Assignees: PIONEER HI-BRED INTERNATIONAL, INC. IA (US); E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 15/736,369

(22) PCT Filed: Jun. 16, 2016

(86) PCT No.: PCT/US2016/037748

§ 371 (c)(1),
(2) Date: Dec. 14, 2017

(87) PCT Pub. No.: WO2016/205445

PCT Pub. Date: Dec. 22, 2016

(65) Prior Publication Data

US 2018/0155739 A1 Jun. 7, 2018

Related U.S. Application Data

(60) Provisional application No. 62/180,504, filed on Jun. 16, 2015, provisional application No. 62/272,994, filed on Dec. 30, 2015.

(51) Int. Cl.

| | |
|---|---|
| ***C12N 15/82*** | (2006.01) |
| ***C07K 14/435*** | (2006.01) |
| ***A01N 37/46*** | (2006.01) |
| ***A01N 65/00*** | (2009.01) |
| ***A01N 63/10*** | (2020.01) |
| ***A01N 63/30*** | (2020.01) |
| ***C12N 15/113*** | (2010.01) |

(52) U.S. Cl.

CPC ......... *C12N 15/8286* (2013.01); *A01N 37/46* (2013.01); *A01N 63/10* (2020.01); *A01N 63/30* (2020.01); *A01N 65/00* (2013.01); *C07K 14/43536* (2013.01); *C07K 14/43563* (2013.01); *C12N 15/113* (2013.01); *C12N 15/8218* (2013.01); *C12N 2310/14* (2013.01); *C12N 2310/531* (2013.01); *Y02A 40/162* (2018.01)

(58) Field of Classification Search

CPC .................................................. C12N 15/8286
USPC .................................................. 800/302, 285
See application file for complete search history.

(56) References Cited

U.S. PATENT DOCUMENTS

| | | | | |
|---|---|---|---|---|
| 2014/0325702 | A1* | 10/2014 | Boukharov ........ | C07K 14/4354 800/279 |
| 2016/0208251 | A1 | 7/2016 | Siegfried et al. | |
| 2016/0208252 | A1 | 7/2016 | Siegfried et al. | |
| 2016/0208253 | A1 | 7/2016 | Siegfried et al. | |
| 2016/0227787 | A1 | 8/2016 | Whyard | |
| 2017/0029843 | A1 | 2/2017 | Grossi De Sa et al. | |

FOREIGN PATENT DOCUMENTS

| | | |
|---|---|---|
| WO | 2015/040574 A1 | 3/2015 |

OTHER PUBLICATIONS

Wang et al. 2013 PLOS ONE vol. 8, No. 7.*
Thomas et al. 2001, The Plant Journal 25(4):417-425.*
Yang, Y et al., "Molecular Characteristics and Efficacy of 16D10 siRNAs in Inhibiting Root-Knot Nematode Infection in Transgenic Grape Hairy Roots," PLoS ONE, (2013); 8(7): e69463.
Wang, Zhijian et al., RNAi Silencing of hte HaHMG-CoA Reductase Gene Inhibits Oviposition in the Helicoverpa armigera Cotton Bollworm, PLoS ONE (2013); 8(7): e67732.
Lu, Kai et al., "Molecular characterization and RNA interference analysis of vitellogenin receptor from Nilaparvata lugens (Stal)," Journal of Insect Physiology, (2015); 73:20-29.
Tian, Geng et al., "Transgenic Cotton Plants Expressing Double-stranded RNAs Target HMG-CoA Reductase (HMGR) Gene Inhibits the Growth, Development and Survival of Cotton Bollworms," International Journal of Biological Sciences, (2015); 11(11):1296-1305.
Khajuria, Chitvan et al., "Parental RNA interference of genes involved in embryonic development of the western corn rootworm, Diabrotica virgifera virgifera Le Conte," Insect Biochemistry and Molecular Biology, (2015); 63:54-62.
Nolan, Tony et al., "Developing transgenic Anopheles mosquitoes for the sterile insect technique," Genetica, (2011); 139:33-39.
Benedict, Mark Q. et al., "The first releases of transgenic mosquitoes: an argument for the sterile insect technique," TRENDS in Parasitology, (2003); 19(8):349-355.
The International Search Report and Written Opinion for International Application No. PCT/US2016/037748, dated Nov. 15, 2016.

* cited by examiner

*Primary Examiner* — Li Zheng

(57) ABSTRACT

The present invention relates generally to methods of molecular biology and gene silencing to control pests.

33 Claims, 26 Drawing Sheets

Specification includes a Sequence Listing.

| VgR dsRNA Dose (ppm) | Total No. eggs produced (day 1-18) | No. Eggs /female (total) | No. Eggs/female (day10-18) | No. Viable eggs / female (total) | Net reduction in fecundity (%) |
|---|---|---|---|---|---|
| 0 | 4794 | 176.5 | 112.7 | 150.8 | 0.0 |
| 0.01 | 6834 | 227.2 | 152.9 | 185.1 | 0.0 |
| 0.1 | 4734 | 165.2 | 105.7 | 116.1 | 23.0 |
| 1 | 2946 | 108.8 | 70.3 | 60.3 | 60.0 |
| 10 | 2662 | 89.9 | 33.9 | 38.6 | 74.4 |
| 75 | 3236 | 92.9 | 11.0 | 46.2 | 69.4 |

FIG. 3A

| SEQ ID NO: | Event No. | Total No. Eggs/female | Reduction in egg production (%) | Fertile eggs /female | Hatch (%) | Net Reduction in Fecundity (%) | Leaf QuantiGene (pg/mg) |
|---|---|---|---|---|---|---|---|
| 3 | 10 | 115.20 | 24.77 | 85.03 | 73.81 | 32.58 | 2.1422 |
| 3 | 6 | 150.25 | 1.88 | 101.34 | 67.45 | 19.65 | 2.5716 |
| 3 | 6 | 142.92 | 6.66 | 81.76 | 57.21 | 35.17 | 1.4633 |
| 4 | 2 | 108.91 | 28.87 | 81.69 | 75.01 | 35.22 | 1.7309 |
| 4 | 26 | 145.53 | 4.96 | 111.20 | 76.41 | 11.83 | 3.1330 |
| 4 | 1 | 128.29 | 16.22 | 103.10 | 80.37 | 18.25 | 3.4365 |
| 5 | 57 | 155.50 | -1.55 | 119.06 | 76.57 | 5.60 | 4.6415 |
| 5 | 18 | 117.73 | 23.12 | 69.63 | 59.15 | 44.79 | 7.0073 |
| 5 | 18 | 92.62 | 39.52 | 81.51 | 88.01 | 35.37 | 4.2992 |
| 5 | 17 | 121.80 | 20.46 | 87.85 | 72.13 | 30.34 | 3.9443 |
| NTG | | 120.81 | | 104.21 | 86.26 | | 0 |
| NTG | | 185.44 | | 148.02 | 79.82 | | 0 |

FIG. 7

| SEQ ID NO: | Event | Avg. No. Eggs / female ±(SEM) | | Avg. No. fertile eggs / female ± (SEM) | | Avg. egg Hatch (%) ± (SEM) | | Avg. reduction in egg production (%) ± (SEM) | | Avg. net reduction in fecundity (%) ± (SEM) | |
|---|---|---|---|---|---|---|---|---|---|---|---|
| 3 | 10 | 116.2 | 8.0 | 102.9 | 12.1 | 88.3 | 4.3 | 42.6 | 4.0 | 42.36 | 6.8 |
| 3 | 2 | 220.5 | 10.6 | 196.1 | 8.4 | 89.0 | 0.7 | -8.9 | 5.2 | -9.86 | 4.7 |
| 3 | 6 | 194.7 | 12.6 | 171.4 | 11.3 | 88.0 | 0.3 | 3.8 | 6.2 | 3.99 | 6.3 |
| 4 | 1 | 184.9 | 11.1 | 168.2 | 10.3 | 90.9 | 0.2 | 8.7 | 5.5 | 5.81 | 5.7 |
| 4 | 26 | 150.0 | 13.8 | 134.6 | 16.1 | 89.2 | 2.7 | 25.9 | 6.8 | 24.63 | 9.0 |
| 4 | 17 | 199.1 | 6.7 | 176.3 | 7.2 | 88.5 | 0.7 | 1.7 | 3.3 | 1.26 | 4.0 |
| 5 | 18 | 151.7 | 19.9 | 134.9 | 19.9 | 88.6 | 1.6 | 25.1 | 9.8 | 24.46 | 11.2 |
| 5 | 57 | 218.5 | 14.1 | 196.3 | 14.7 | 89.7 | 1.5 | -7.9 | 7.0 | -9.96 | 8.2 |
| NTG | | 202.5 | 14.0 | 178.5 | 16.2 | 87.9 | 2.2 | - | - | - | - |

*SEM = Standard error of the means (n = 2-3 replicate/event; at least 12-16 females /replicate), Avg. = Average, NTG= Non-transgenic plant*

FIG. 8

BOULE dsRNA vs Virgin Adult Diet Bioassay

| Treatment | Total No. Eggs/female | Average egg hatch (%) ± (SEM) | No. fertile eggs / female | Reduction in egg production (%) | Net reduction in fecundity (%) |
|---|---|---|---|---|---|
| BOULE dsRNA | 178.5 | 55.4 (5.3) | 98.9 | -36.68 | 0.69 |
| GUS dsRNA | 129.7 | 80.5 (2.2) | 104.4 | 0.70 | -4.83 |
| H20 | 130.6 | 76.3 (3.2) | 99.6 | 0.00 | |

FIG. 9A

Transgenic Events Expressing BOULE FRAG1

| Target Gene of Interest | Avg. No. Eggs / female (± SEM) | | Avg. No. fertile Eggs / female (± SEM) | | Avg. Egg hatch (%) (± SEM) | | Reduction in egg production (%) (± SEM) | | Net reduction in fecundity (%) (± SEM) | |
|---|---|---|---|---|---|---|---|---|---|---|
| MAEL | 139 | 16 | 42 | 5 | 30.1 | 4.3 | 42.63 | 3.6 | 46.34 | 3.4 |
| NCLB | 193 | 16 | 49 | 4 | 25.6 | 3.2 | 20.70 | 6.0 | 36.88 | 4.8 |
| CUL3 | 226 | 22 | 75 | 7 | 33.2 | 3.0 | 7.14 | 9.8 | 4.24 | 10.1 |
| GUS | 391 | 72 | 147 | 27 | 37.6 | 3.7 | -61.11 | 17.1 | -88.00 | 20.0 |
| H20 | 243 | 10 | 78 | 3 | 32.2 | 2.8 | | | | |

*SEM = Standard error of the means (n = 2-3 replicate/event; at least 12-16 pairs (male and female /replicate), Avg. = Average, NTG= Non-transgenic plant*

FIG. 12

COMPOSITIONS AND METHODS TO CONTROL INSECT PESTS

CROSS-REFERENCE TO RELATED APPLICATIONS

This application claims the benefit of International Application Number PCT/US2016/037748 filed Jun. 16, 2016, which claims the benefit of U.S. Provisional Application No. 62/180,504, filed Jun. 16, 2015, and U.S. Provisional Application No. 62/272,994, filed Dec. 30, 2015, which are hereby incorporated herein in its entirety by reference.

REFERENCE TO SEQUENCE LISTING SUBMITTED ELECTRONICALLY

A sequence listing having the file name "6030WOPCT_SequenceList.txt" created on May 19, 2016 and having a size of 531 kilobytes is filed in computer readable form concurrently with the specification. The sequence listing is part of the specification and is herein incorporated by reference in its entirety.

FIELD OF THE INVENTION

The present invention relates generally to methods of molecular biology and gene silencing to control pests.

BACKGROUND

Plant insect pests are a serious problem in agriculture. They destroy millions of acres of staple crops such as corn, soybeans, peas, and cotton. Yearly, plant insect pests cause over $100 billion dollars in crop damage in the U.S. alone. In an ongoing seasonal battle, farmers must apply billions of gallons of synthetic pesticides to combat these pests. Other methods employed in the past delivered insecticidal activity by microorganisms or genes derived from microorganisms expressed in transgenic plants. For example, certain species of microorganisms of the genus *Bacillus* are known to possess pesticidal activity against a broad range of insect pests including Lepidoptera, Diptera, Coleoptera, Hemiptera, and others. In fact, microbial pesticides, particularly those obtained from *Bacillus* strains, have played an important role in agriculture as alternatives to chemical pest control. Agricultural scientists have developed crop plants with enhanced insect resistance by genetically engineering crop plants to produce insecticidal proteins from *Bacillus*. For example, corn and cotton plants genetically engineered to produce Cry toxins (see, e.g., Aronson (2002) *Cell Mol. Life Sci.* 59(3):417-425; Schnepf et al. (1998) *Microbiol. Mol. Biol. Rev.* 62(3):775-806) are now widely used in agriculture and have provided the farmer with an alternative to traditional insect-control methods. However, in some instances these Bt insecticidal proteins may only protect plants from a relatively narrow range of pests. Evolving insect resistance has also presented an issue (Gassmann et al. (2014) *PNAS* 111(14):5141-6). Thus, novel insect control compositions remain desirable.

BRIEF SUMMARY

Methods and compositions are provided which employ a silencing element that, when ingested by a plant insect pest, such as Coleopteran, Hemiptera, or Lepidopteran plant pest, including a *Diabrotica, Leptinotarsa, Phyllotreta, Acyrthosiphan, Bemisia, Halyomorpha, Nezara*, or *Spodoptera* plant pest, is capable of decreasing the expression of a target sequence in the pest. In certain embodiments, the decrease in expression of the target sequence controls the ability of the pest to reproduce, and thereby the methods and compositions are capable of limiting damage to a plant or the spread of insect pests. Described herein are various target polynucleotides as set forth in SEQ ID NOS.: 1-53 or 107-254, or variants or fragments thereof, or complements thereof, that modulate the expression of one or more of the sequences in the target pest RNAs involved in pest reproduction and fecundity. Accordingly, the various target polynucleotides as set forth in SEQ ID NOS.: 1-53 or 107-254, or variants or fragments thereof, or complements thereof, are useful in methods described herein to control target pests by insect sterilization and release of sterile target pests, i.e., sterile insect technique ("SIT"). Also provided are silencing elements, which when ingested by the pest, decrease the level of expression of one or more of the target polynucleotides. Further provided are constructs encoding silencing elements and host cells comprising constructs encoding silencing elements. Plants, plant parts, plant cells, bacteria and other host cells comprising the silencing elements or an active variant or fragment thereof are also provided. Also provided are formulations of sprayable silencing agents for topical applications to pest insects or substrates where pest insects may be found.

In another embodiment, a method for controlling a plant insect pest, such as a Coleopteran, Hemiptera, or Lepidopteran plant pest, including a *Diabrotica, Leptinotarsa, Phyllotreta, Acyrthosiphan, Bemisia, Halyomorpha, Nezara*, or *Spodoptera* plant pest, is provided. The method comprises feeding to a plant insect pest a composition comprising a silencing element, wherein the silencing element, when ingested by the pest, reduces the level of a target sequence in the pest and thereby controls the pest. Further provided are methods to protect a plant from a plant insect pest. Such methods comprise introducing into the plant or plant part a disclosed silencing element. When the plant expressing the silencing element is ingested by the pest, the level of the target sequence is decreased and the pest is controlled.

BRIEF DESCRIPTION OF THE DRAWINGS

FIG. 1A shows the total number of eggs produced within 13-14 days by treatment and age group. For the younger female group, 50 pairs of male and female beetles were used, and for the older female group 50 mated female beetles were used. FIG. 1B shows the average number of eggs produced per female/day during 13-14 day oviposition period by treatment and age group. The box plot graph is produced by Spotfire program indicating 4 quartiles, average, and 95% confidence interval of the mean. FIG. 1C shows the effect of various treatments, as indicated in the figure, on overall average egg hatch rate. Data represents 13-14 days egg collection period; n=6 replication/treatment/day; 5-45 eggs/replication depending on the day ($p<0.001$). FIG. 1D shows gene suppression analysis in WCRW adult beetles 8 days after treatment of female and male insects for younger age group and 4 days after treatment of female insects for older age group. Relative expression of VgR is shown from 4 individual insects for each treatment using the DV-RPS10 gene as reference and untreated older beetle as normalizer. Box plot shows 4 quartiles, average, median, and 95% confidence interval of the mean by treatment and age group.

FIG. 2A shows the average numbers and viable eggs produced per female. Eggs from 15-42 female adult beetles were counted for each treatment. The number in the box shows average numbers of eggs or viable eggs/female. The box plot shows 4 quartiles, average, median, and 95% confidence interval of the mean for each treatment. For the VgR dsRNA exposed group, viable egg production remain very low throughout the study period. Treatment with VgR dsRNA did not affect adult emergence. Mortality of adult beetles due to VgR dsRNA larval exposure was negligible. FIG. 2B shows VgR gene suppression analysis in 4 10-day old beetles and more than 15 28-day old beetles at Days 40 and 58 after treatment, respectively. Box plot of relative expression by qRTPCR shows 4 quartiles, average, median, and 95% confidence interval of the mean for each treatment in 10 and 28 day old beetles. Untreated $3^{rd}$ instar larvae were used as normalizer.

FIGS. 3A-3C show data pertaining to the dose response of WCRW sterilization and gene suppression in WCRW following exposure to an artificial diet comprising a dsRNA comprising a target nucleotide sequence of SEQ ID NO.: 3. FIG. 3A shows the total number of eggs and eggs/female produced during 18 days study period in response to VgR dsRNA doses. Eggs were collected and counted over 18 day oviposition period. Viable eggs/female and net reduction in fecundity (%) are indicated in the last two columns. Net reduction in fecundity (NRF) of VgR dsRNA treated females relative to control (water exposed females) was estimated using the formula described in the Examples. FIG. 3B shows a box plot of percentage of overall egg hatch rates by dose. Data represents 18 days egg collection period; n=1-4 replication/treatment/day; 5-478 eggs/replication depending on the day and availability of eggs. FIG. 3C shows a box plot of relative expression of VgR Day 6 after dsVgR treatment at different doses. Untreated beetles were used as normalizer.

FIG. 4A shows schematic depiction of the VgR fragments and amplicons of qRTPCR assays (indicated by dashed circles) on VgR coding DNA sequence ("CDS"). FIG. 4B shows a box plot of relative VgR expression 6 days after treatment with dsVgR fragments and controls (ddH2O and dsGUS) using 5'-qRTPCR assay. 4 quartiles, average (horizontal solid line), median (horizontal dash line), and 95% confidence interval of the mean are shown. Similar results were also obtained with Mid- and 3'-qRTPCR assays. Data were normalized to results obtained from untreated 3rd instar larvae.

FIG. 5A shows a schematic depiction of the VgR fragments used in screen for gene suppression analysis. FIGS. 5B-5D shows representative gene analysis for the indicated VgR fragments using results obtained in three experiments. In each experiment, treatments by water, GUS, and VgR fragment 1 (SEQ ID NO.:3) were included as controls. Data were normalized to beetles treated with water. Two qRTPCR assays (5'- and Mid-qRTPCR assays) were used to avoid overlapping of VgR fragment and PCR amplicon.

FIG. 6A shows data in plants at about the V4 growth stage which were infested with at least 14 young female beetles in cages. The plant type is as indicated in the figure, with "NTG" indicating non-transgenic control plants; "Frag1" indicates transgenic plants expressing a silencing element comprising VgR-Frag1 (SEQ ID NO.: 3); "Frag2" indicates transgenic plants expressing a silencing element comprising VgR-Frag2 (SEQ ID NO.: 4), and "Frag3" indicates transgenic plants expressing a silencing element comprising VgR-Frag3 (SEQ ID NO.: 5), Beetles were collected 8 days after feeding for gene suppression analysis. Data were normalized to data from beetles ingesting the NTG control. FIG. 6B shows data obtained from individual R1 maize plants were infested with more than 6 young female beetles in cages. Beetles were collected 12 days after feeding. Each fragment and control is represented by 2 plants used for feeding and more than 12 insects used in gene suppression analysis.

FIG. 7 shows data pertaining to a fecundity assessment of VgR T1 adult beetle exposure bioassay. For each construct 2-4 events were tested. Each cage received an oviposition dish daily and/or at interval of 2-4 days and eggs were subsequently processed.

FIG. 8 shows data pertaining to fecundity assessment of VgR T1 larval exposure bioassay. For each event three replicate cages containing at least 8-14 pairs of male and female beetles were arranged. Each cage received oviposition dish every 5 days, and eggs were processed FIGS. 9A-9B show data pertaining to WCRW adult sterilization bioassay and gene suppression by DV-BOULE-FRAG1 (SEQ ID NO: 164) dsRNA treatment. FIG. 9A shows the total number of eggs and fertile eggs produced per female; average egg hatch rate with standard error of the mean; reduction in total egg production per female and net reduction in fecundity of female beetles relative to water control. FIG. 9B shows gene expression in beetles after BOULE dsRNA treatment. Relative expression by qRTPCR assay was described in previous examples. The box plot shows four quartiles, average (horizontal dash line), median (horizontal solid line), and 95% confidence interval of the mean are shown.

FIG. 11A shows the effect of larval exposure to transgenic plants (expressing DV-BOULE-FRAG1, SEQ ID NO: 164) on the overall average egg production per female and average viable eggs produced per female from emerged beetles. Line in each bar represents the standard error of the mean (±SEM) and the same color bars followed by the same upper or lower case letters are not statistically different. FIG. 11B shows the effect of larval exposure to transgenic plants (expressing DV-BOULE-FRAG1, SEQ ID NO: 164) on hatch rate of eggs obtained from the emerged beetles. The box plot shows four quartiles, average (horizontal white line) and 95% confidence interval of the mean (vertical black line). The average and the corresponding standard error of the means ((±SEM) are indicated at the bottom of the box plot. For each treatment egg hatch test was performed for 5 batches of eggs and a total of at least 1200-1285 eggs per treatment were assessed for viability. FIG. 11C indicates the effect of larval exposure to transgenic plants (expressing DV-BOULE-FRAG1, SEQ ID NO: 164) on net reduction in fecundity of emerged adult beetles relative to NTG control. The box plot shows four quartiles, average (horizontal black line) and 95% confidence interval of the mean (vertical black line). The average and the corresponding standard error of the mean are indicated at the bottom of the box plot.

FIG. 12 shows data pertaining to 3rd instar sterilization bioassay of dsRNA targeting DV-CUL3-FRAG1, DV-NCLB-FRAG1, and DV-MAEL-FRAG1 dsRNA (SEQ ID No.: 44, 45, and 46 respectively) at 1 ppm. The average total number of eggs produced per female, the average number of viable eggs produced per female, the average egg hatch rate; average reduction in egg production and net reduction in fecundity (both relative to water control) are shown. For each parameter the respective standard error of the mean are presented.

DETAILED DESCRIPTION

Figure 1A:
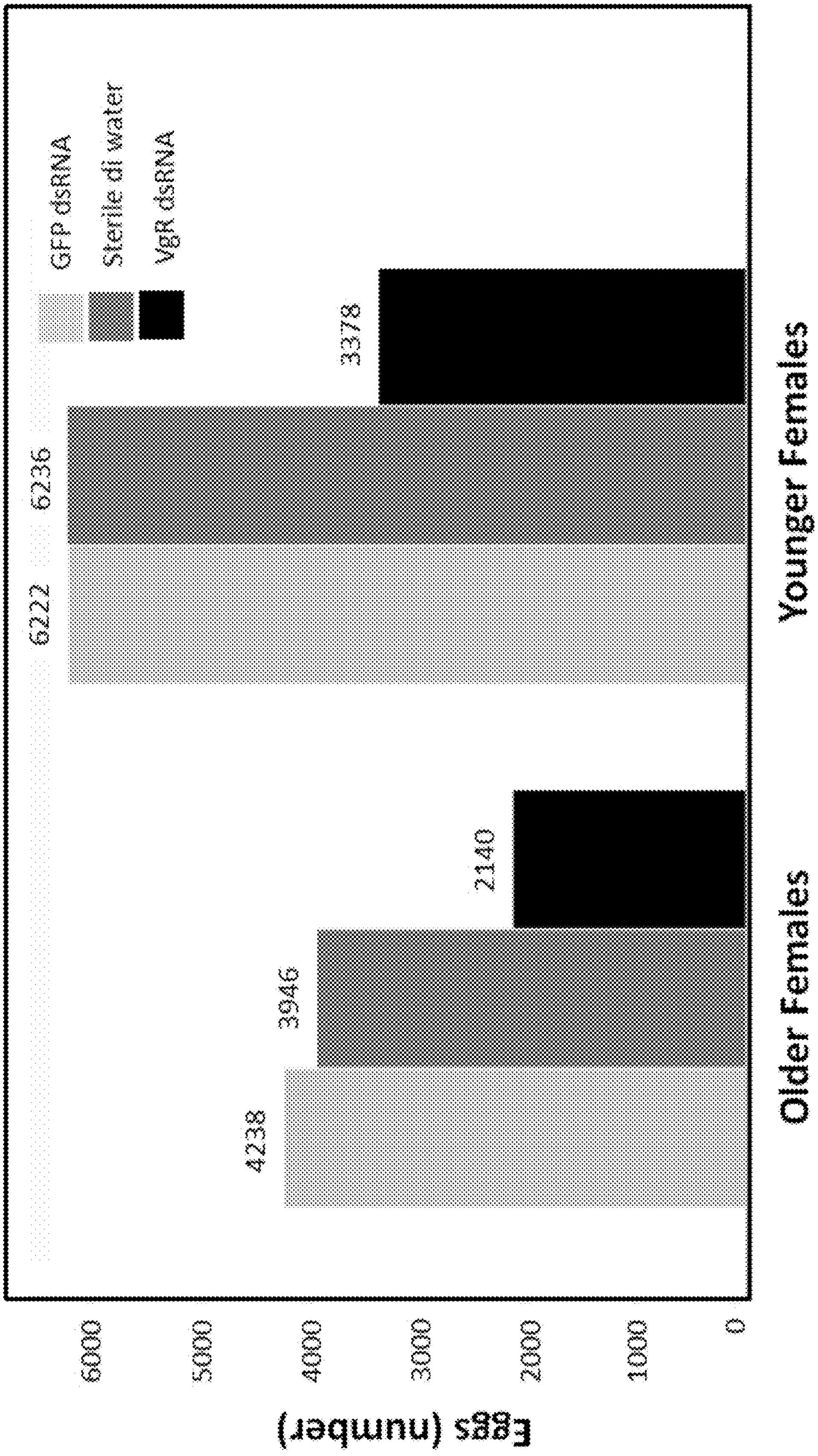
FIGS. 1A-1D show representative data pertaining to sterilization of adult Western Corn Rootworm ("WCRW") following ingestion of an artificial diet comprising a dsRNA construct comprising a target nucleotide sequence of SEQ ID NO.: 4.

The disclosures herein will be described more fully hereinafter with reference to the accompanying drawings, in which some, but not all possible embodiments are shown. Indeed, disclosures may be embodied in many different forms and should not be construed as limited to the embodiments set forth herein; rather, these embodiments are provided so that this disclosure will satisfy applicable legal requirements.

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. Although specific terms are employed herein, they are used in a generic and descriptive sense only and not for purposes of limitation.

It is also to be understood that the terminology used herein is for the purpose of describing particular aspects only and is not intended to be limiting. As used in the specification and in the claims, the term "comprising" can include the aspect of "consisting of." Unless defined otherwise, all technical and scientific terms used herein have the same meaning as commonly understood by one of ordinary skill in the art to which the disclosed compositions and methods belong. In this specification and in the claims which follow, reference will be made to a number of terms which shall be defined herein.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

I. Overview

Methods and compositions are provided which employ one or more silencing elements that, when ingested by a plant insect pest, such as Coleopteran, Hemiptera, or Lepidopteran plant pest, including a *Diabrotica, Leptinotarsa, Phyllotreta, Acyrthosiphan, Bemisia, Halyomorpha, Nezara*, or *Spodoptera* plant pest, are capable of decreasing the expression of a target sequence in the pest. In certain embodiments, the decrease in expression of the target sequence controls the ability of the pest to reproduce, and thereby the methods and compositions are capable of limiting damage to a plant or the spread of insect pests. Disclosed herein are target polynucleotides as set forth in SEQ ID NOS.: 1-53 or 107-254, or variants and fragments thereof, and complements thereof. Silencing elements comprising sequences, complementary sequences, active fragments or variants of these target polynucleotides are provided which, when ingested by or when contacting the pest, decrease the expression of one or more of the target sequences and thereby controls the pest population via, for example, insect sterilization or through the application of sterile insect technique (SIT; i.e., the silencing elements are associated with sterilization activity). In some embodiments, a transgenic plant comprising a polynucleotide encoding silencing elements are provided which, when ingested by or when contacting the pest, decrease the expression of one or more of the target sequences and thereby controls the pest population via, for example, insect sterilization or through the application of SIT.

In one embodiment, a method relates to producing sterile insects; releasing sterile insects into the environment in very large numbers (about 10 to 100 times the number of native insects) in order to mate with the native insects that are present in the environment, wherein the native female that mates with a sterile male produce infertile eggs. In a further embodiment, releasing sterile insects is repeated one or more times, wherein the number of native insects decreases and the ratio of sterile to native insects increases, driving the native population size downwards.

It is understood that target pest RNAs can be involved in one or more of male and/or female sterility, reduction of sperm count, egg production (fecundity), gender ratios, rates of fertilization (fertility), maturation of sexual organs, and sperm or egg viability. SIT has been used to control insect population by mating-based approach through release of sterile insects of one or both genders. In one embodiment, SIT comprises release of large number of sterile male insects that search for and mate with wild females, thereby preventing offspring. SIT using different schemes to generate sterile insects has been reported to control mosquito populations such as *Anopheles* or *Aedes* (e.g., see Whyard, et al. (2015) Parasit. Vectors, 8:96; Benedict, M. Q. and A. S. Robinson (2003) Trends Parasitol. 19(8):349; and Nolan, et al. (2011) Genetica 139:33). SIT has been field evaluated for population control of *Aedes aegypti* in Brazil (Carvalho, D. O. (2015), PLoS. 9(7): e0003864). Dengue, chikungunya, and now Zika virus are all transmitted by *Aedes aegypti*, one of the most widespread disease-carrying vectors on the globe.

In one embodiment, a method relates to producing sterile insects; releasing sterile insects into an environment in about 0.5, 1, 5, 10, 20, 30, 50, 60, 70, 90, to 100 times the number of native insects, wherein the sterile insects mate with the native insects that are present in the environment, and wherein the native female that mates with a sterile male produce infertile eggs. In a further embodiment, releasing sterile insects is repeated one or more times, wherein the number of native insects decreases and the ratio of sterile to native insects increases, driving the native population size downwards.

In one embodiment, compositions and methods are provided which employ a ribonucleic acid construct comprising at least one double-stranded RNA region, at least one strand of which comprises a polynucleotide that is complementary to: (a) a nucleotide sequence comprising a sequence of an RNA transcript expressed in a target pest, wherein the down-regulation of the RNA transcript results in increased sterility in the target; or variants and fragments thereof, and complements of said nucleotide sequence; (b) the nucleotide sequence comprising at least 90% sequence identity to said nucleotide sequence; or variants and fragments thereof, and complements thereof; or (c) the nucleotide sequence comprising at least 19 consecutive nucleotides of said nucleotide sequence; or variants and fragments thereof, and complements thereof; wherein the polynucleotide encodes a silencing element having sterilization activity against an insect plant pest.

In further embodiment, compositions and methods are provided which employ a ribonucleic acid construct comprising at least one double-stranded RNA region, at least one strand of which comprises a polynucleotide that is complementary to: (a) a nucleotide sequence comprising a sequence of an RNA transcript expressed in a Coleopteran pest, wherein the down-regulation of the RNA transcript results in increased sterility in the target; or variants and fragments thereof, and complements of said nucleotide sequence; (b) the nucleotide sequence comprising at least 90% sequence identity to said nucleotide sequence; or variants and fragments thereof, and complements thereof; or (c) the nucleotide sequence comprising at least 19 consecutive nucleotides of said nucleotide sequence; or variants and fragments thereof, and complements thereof; wherein the polynucleotide encodes a silencing element having sterilization activity against an insect plant pest.

In another embodiment, compositions and methods are provided which employ a ribonucleic acid construct comprising at least one double-stranded RNA region, at least one strand of which comprises a polynucleotide that is complementary to: (a) the nucleotide sequence comprising any one of SEQ ID NOS: 1-53 or 107-254; or variants and fragments thereof, and complements thereof; (b) the nucleotide sequence comprising at least 90% sequence identity to any one of nucleotides SEQ ID NOS: 1-53 or 107-254; or variants and fragments thereof, and complements thereof; or (c) the nucleotide sequence comprising at least 19 consecutive nucleotides of any one of SEQ ID NOS: 1-53 or 107-254; or variants and fragments thereof, and complements thereof; wherein the polynucleotide encodes a silencing element having sterilization activity against an insect plant pest.

As used herein, “VgR protein” or “vitellogenin receptor protein” refers to a family of large (180-214 kDa), membrane-bound proteins, and include proteins such as the VgR protein having the sequence of SEQ ID NO.: 106, and variants, homologs, and mutants thereof. It is believed that these proteins bind with high affinity to vitellogenin ($K_d$ values of about 30-180 nM) and are involved in the cellular uptake of vitellogenin. VgR protein is typically expressed in ovarian tissue. As used herein, “BOULE” refers to a family of genes that encode a RNA binding protein with a highly conserved RRM (RNA recognition motif) domain and at least one DAZ (deleted in azoospermia) repeat of 24 amino acids rich in Asn, Tyr, and Gln residues. Deletion or mutations of BOULE in fly usually severely impair spermatogenesis. BOULE is required for meiotic entry and germline differentiation at the transition between G2 and M phases of meiosis. BOULE is typically expressed in germline cells.

As used herein, “VgR mRNA” or “vitellogenin receptor mRNA” refers to a messenger RNA transcript that when translated provides a VgR protein, or a variant, homolog, or mutant protein thereof.

As used herein, by “controlling a plant insect pest” or “controls a plant insect pest” is intended any effect on a plant insect pest that results in limiting the damage that the pest causes. Controlling a plant insect pest includes, but is not limited to, killing the pest, inhibiting development of the pest, altering fertility or growth of the pest in such a manner that the pest provides less damage to the plant, or in a manner for decreasing the number of offspring produced, producing less fit pests, including offspring, producing pests more susceptible to predator attack, producing pests more susceptible to other insecticidal proteins, or deterring the pests from eating the plant.

Reducing the level of expression of the target polynucleotide or the polypeptide encoded thereby, in the pest results in the suppression, control, and/or killing the invading pest. In one embodiment, reducing the level of expression of the target sequence of the pest will reduce the pest damage by at least about 2% to at least about 6%, at least about 5% to about 50%, at least about 10% to about 60%, at least about 30% to about 70%, at least about 40% to about 80%, or at least about 50% to about 90% or greater. Hence, methods disclosed herein can be utilized to control pests, including but not limited to, Coleopteran plant insect pests or a *Diabrotica* plant pest.

Certain assays measuring the control of a plant insect pest are commonly known in the art, as are methods to record nodal injury score. See, for example, Oleson et al. (2005) J. Econ. Entomol. 98:1-8. Other assay methods are provided in the examples below.

Disclosed herein are compositions and methods for protecting plants from a plant insect pest, or inducing resistance in a plant to a plant insect pest, such as Coleopteran plant pests or *Diabrotica* plant pests or other plant insect pests. Plant insect pests include insects selected from the orders Coleoptera, Diptera, Hymenoptera, Lepidoptera, Mallophaga, Homoptera, Hemiptera Orthroptera, Thysanoptera, Dermaptera, Isoptera, Anoplura, Siphonaptera, Trichoptera, etc., particularly Lepidoptera and Coleoptera.

Those skilled in the art will recognize that not all compositions are equally effective against all pests. Disclosed compositions, including the silencing elements disclosed herein, display activity against plant insect pests, which may include economically important agronomic, forest, greenhouse, nursery ornamentals, food and fiber, public and animal health, domestic and commercial structure, household and stored product pests.

As used herein “Coleopteran plant pest” is used to refer to any member of the Coleoptera order. Other plant insect pests that may be targeted by the methods and compositions disclosed herein, but are not limited to Mexican Bean Beetle (*Epilachna varivestis*), and Colorado potato beetle (*Leptinotarsa decemlineata*).

As used herein, the term “*Diabrotica* plant pest” is used to refer to any member of the *Diabrotica* genus. Accordingly, the compositions and methods are also useful in protecting plants against any *Diabrotica* plant pest including, for example, *Diabrotica adelpha; Diabrotica amecameca; Diabrotica balteata; Diabrotica barberi; Diabrotica biannularis; Diabrotica cristata; Diabrotica decempunctata; Diabrotica dissimilis; Diabrotica lemniscata; Dia-*

*brotica limitata* (including, for example, *Diabrotica limitata quindecimpuncata*); *Diabrotica longicornis; Diabrotica nummularis; Diabrotica porracea; Diabrotica scutellata; Diabrotica sexmaculata; Diabrotica speciosa* (including, for example, *Diabrotica speciosa speciosa*); *Diabrotica tibialis; Diabrotica undecimpunctata* (including, for example, Southern corn rootworm (*Diabrotica undecimpunctata*), *Diabrotica undecimpunctata duodecimnotata; Diabrotica undecimpunctata howardi* (spotted cucumber beetle); *Diabrotica undecimpunctata undecimpunctata* (western spotted cucumber beetle)); *Diabrotica virgifera* (including, for example, *Diabrotica virgifera virgifera* (western corn rootworm) and *Diabrotica virgifera zeae* (Mexican corn rootworm)); *Diabrotica viridula; Diabrotica* wartensis; *Diabrotica* sp. JJG335; *Diabrotica* sp. JJG336; *Diabrotica* sp. JJG341; *Diabrotica* sp. JJG356; *Diabrotica* sp. JJG362; and, *Diabrotica* sp. JJG365.

In certain embodiments, the *Diabrotica* plant pest comprises *D. virgifera virgifera, D. barberi, D. virgifera zeae, D. speciosa*, or *D. undecimpunctata howardi.*

Larvae of the order Lepidoptera include, but are not limited to, armyworms, cutworms, loopers and heliothines in the family Noctuidae *Spodoptera frugiperda* JE Smith (fall armyworm); *S. exigua* Hübner (beet armyworm); *S. litura* Fabricius (tobacco cutworm, cluster caterpillar); *Mamestra* configurata Walker (bertha armyworm); *M. brassicae* Linnaeus (cabbage moth); *Agrotis ipsilon* Hufnagel (black cutworm); *A. orthogonia* Morrison (western cutworm); *A. subterranea* Fabricius (granulate cutworm); *Alabama argillacea* Hübner (cotton leaf worm); *Trichoplusia ni* Hübner (cabbage looper); *Pseudoplusia includens* Walker (soybean looper); *Anticarsia gemmatalis* Hübner (velvetbean caterpillar); Hypena *scabra* Fabricius (green cloverworm); *Heliothis virescens* Fabricius (tobacco budworm); *Pseudaletia unipuncta* Haworth (armyworm); *Athetis mindara* Barnes and Mcdunnough (rough skinned cutworm); *Euxoa messoria* Harris (darksided cutworm); *Earias insulana* Boisduval (spiny bollworm); *E. vittella* Fabricius (spotted bollworm); *Helicoverpa armigera* Hübner (American bollworm); *H. zea* Boddie (corn earworm or cotton bollworm); *Melanchra picta* Harris (zebra caterpillar); Egira (Xylomyges) curialis Grote (citrus cutworm); borers, casebearers, webworms, coneworms, and skeletonizers from the family Pyralidae *Ostrinia nubilalis* Hübner (European corn borer); *Amyelois transitella* Walker (naval orangeworm); *Anagasta kuehniella* Zeller (Mediterranean flour moth); *Cadra cautella* Walker (almond moth); *Chilo suppressalis* Walker (rice stem borer); *C. partellus*, (sorghum borer); *Corcyra cephalonica* Stainton (rice moth); *Crambus caliginosellus* Clemens (corn root webworm); *C. teterrellus* Zincken (bluegrass webworm); *Cnaphalocrocis medinalis* Guenée (rice leaf roller); *Desmia funeralis* Hübner (grape leaffolder); *Diaphania hyalinata* Linnaeus (melon worm); *D. nitidalis* Stoll (pickleworm); *Diatraea grandiosella* Dyar (southwestern corn borer), *D. saccharalis* Fabricius (surgarcane borer); *Eoreuma loftini* Dyar (Mexican rice borer); *Ephestia elutella* Hübner (tobacco (cacao) moth); *Galleria mellonella* Linnaeus (greater wax moth); *Herpetogramma licarsisalis* Walker (sod webworm); *Homoeosoma electellum* Hulst (sunflower moth); *Elasmopalpus lignosellus* Zeller (lesser cornstalk borer); *Achroia grisella* Fabricius (lesser wax moth); *Loxostege sticticalis* Linnaeus (beet webworm); *Orthaga thyrisalis* Walker (tea tree web moth); *Maruca testulalis* Geyer (bean pod borer); *Plodia interpunctella* Hübner (Indian meal moth); *Scirpophaga incertulas* Walker (yellow stem borer); *Udea rubigalis* Guenée (celery leaftier); and leafrollers, budworms, seed worms and fruit worms in the family Tortricidae Acleris gloverana Walsingham (Western blackheaded budworm); *A. variana* Fernald (Eastern blackheaded budworm); *Archips argyrospila* Walker (fruit tree leaf roller); *A. rosana* Linnaeus (European leaf roller); and other *Archips* species, *Adoxophyes orana* Fischer von Rosslerstamm (summer fruit *tortrix* moth); *Cochylis hospes* Walsingham (banded sunflower moth); *Cydia latiferreana* Walsingham (filbertworm); *C. pomonella* Linnaeus (coding moth); *Platynota flavedana* Clemens (variegated leafroller); *P. stultana* Walsingham (omnivorous leafroller); *Lobesia botrana* Denis & Schiffermüllier (European grape vine moth); *Spilonota ocellana* Denis & Schiffermüller (eyespotted bud moth); *Endopiza viteana* Clemens (grape berry moth); *Eupoecilia ambiguella* Hübner (vine moth); Bonagota salubricola Meyrick (Brazilian apple leafroller); *Grapholita molesta* Busck (oriental fruit moth); *Suleima helianthana* Riley (sunflower bud moth); *Argyrotaenia* spp.; *Choristoneura* spp.

Selected other agronomic pests in the order Lepidoptera include, but are not limited to, *Alsophila pometaria* Harris (fall cankerworm); *Anarsia lineatella* Zeller (peach twig borer); *Anisota senatoria* J. E. Smith (orange striped oakworm); Antheraea pernyi Guérin-Méneville (Chinese Oak Tussah Moth); *Bombyx mori* Linnaeus (Silkworm); *Bucculatrix thurberiella* Busck (cotton leaf perforator); *Colias eurytheme* Boisduval (alfalfa caterpillar); *Datana integerrima* Grote & Robinson (walnut caterpillar); *Dendrolimus sibiricus* Tschetwerikov (Siberian silk moth), *Ennomos subsignaria* Hübner (elm spanworm); *Erannis tiliaria* Harris (linden looper); *Euproctis chrysorrhoea* Linnaeus (browntail moth); *Harrisina americana* Guérin-Meneville (grapeleaf skeletonizer); *Hemileuca oliviae* Cockrell (range caterpillar); *Hyphantria cunea* Drury (fall webworm); *Keiferia lycopersicella* Walsingham (tomato pinworm); *Lambdina fiscellaria* fiscellaria Hulst (Eastern hemlock looper); *L. fiscellaria* lugubrosa Hulst (Western hemlock looper); *Leucoma salicis* Linnaeus (satin moth); *Lymantria dispar* Linnaeus (gypsy moth); *Manduca quinquemaculata* Haworth (five spotted hawk moth, tomato hornworm); *M. sexta* Haworth (tomato hornworm, tobacco hornworm); *Operophtera brumata* Linnaeus (winter moth); *Paleacrita vernata* Peck (spring cankerworm); *Papilio cresphontes* Cramer (giant swallowtail orange dog); *Phryganidia californica* Packard (California oakworm); *Phyllocnistis citrella* Stainton (citrus leafminer); *Phyllonorycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval and Leconte (Southern cabbageworm); *Sabulodes aegrotata* Guenee (omnivorous looper); *Schizura concinna* J. E. Smith (red humped caterpillar); *Sitotroga cerealella* Olivier (Angoumois grain moth); *Thaumetopoea pityocampa* Schiffermuller (pine processionary caterpillar); *Tineola bisselliella* Hummel (webbing clothesmoth); *Tuta absoluta* Meyrick (tomato leafminer); *Yponomeuta padella* Linnaeus (ermine moth); *Heliothis subflexa* Guenée; *Malacosoma* spp. and *Orgyia* spp.

Of interest are larvae and adults of the order Coleoptera including weevils from the families Anthribidae, Bruchidae and Curculionidae (including, but not limited to: *Anthonomus grandis* Boheman (boll weevil); *Lissorhoptrus oryzophilus* Kuschel (rice water weevil); *Sitophilus granarius* Linnaeus (granary weevil); *S. oryzae* Linnaeus (rice weevil); *Hypera punctata* Fabricius (clover leaf weevil); *Cylindro-*

*copturus adspersus* LeConte (sunflower stem weevil); *Smicronyx fulvus* LeConte (red sunflower seed weevil); *S. sordidus* LeConte (gray sunflower seed weevil); *Sphenophorus maidis* Chittenden (maize billbug)); flea beetles, cucumber beetles, rootworms, leaf beetles, potato beetles and leafminers in the family Chrysomelidae (including, but not limited to: *Leptinotarsa decemlineata* Say (Colorado potato beetle); *Diabrotica virgifera virgifera* LeConte (western corn rootworm); *D. barberi* Smith and Lawrence (northern corn rootworm); *D. undecimpunctata* howardi Barber (southern corn rootworm); *Chaetocnema pulicaria* Melsheimer (corn flea beetle); *Phyllotreta cruciferae* Goeze (Crucifer flea beetle); *Phyllotreta striolata* (stripped flea beetle); *Colaspis brunnea* Fabricius (grape *colaspis*); *Oulema melanopus* Linnaeus (cereal leaf beetle); *Zygogramma exclamationis* Fabricius (sunflower beetle)); beetles from the family Coccinellidae (including, but not limited to: *Epilachna varivestis* Mulsant (Mexican bean beetle)); chafers and other beetles from the family Scarabaeidae (including, but not limited to: *Popillia japonica* Newman (Japanese beetle); *Cyclocephala borealis* Arrow (northern masked chafer, white grub); *C. immaculata* Olivier (southern masked chafer, white grub); *Rhizotrogus majalis* Razoumowsky (European chafer); *Phyllophaga crinita* Burmeister (white grub); *Ligyrus gibbosus* De Geer (carrot beetle)); carpet beetles from the family Dermestidae; wireworms from the family Elateridae, *Eleodes* spp., *Melanotus* spp.; *Conoderus* spp.; *Limonius* spp.; *Agriotes* spp.; *Ctenicera* spp.; *Aeolus* spp.; bark beetles from the family Scolytidae and beetles from the family Tenebrionidae.

Adults and immatures of the order Diptera are of interest, including leafminers *Agromyza parvicornis* Loew (corn blotch leafminer); midges (including, but not limited to: *Contarinia sorghicola* Coquillett (sorghum midge); *Mayetiola destructor* Say (Hessian fly); *Sitodiplosis mosellana* Gain (wheat midge); *Neolasioptera murtfeldtiana* Felt, (sunflower seed midge)); fruit flies (Tephritidae), *Oscinella frit* Linnaeus (fruit flies); maggots (including, but not limited to: *Delia platura* Meigen (seedcorn maggot); *D. coarctate* Fallen (wheat bulb fly) and other *Delia* spp., *Meromyza americana* Fitch (wheat stem maggot); *Musca domestica* Linnaeus (house flies); *Fannia canicularis* Linnaeus, *F. femoralis* Stein (lesser house flies); *Stomoxys calcitrans* Linnaeus (stable flies)); face flies, horn flies, blow flies, *Chrysomya* spp.; *Phormia* spp. and other muscoid fly pests, horse flies *Tabanus* spp.; bot flies *Gastrophilus* spp.; *Oestrus* spp.; cattle grubs *Hypoderma* spp.; deer flies *Chrysops* spp.; *Melophagus ovinus* Linnaeus (keds) and other Brachycera, mosquitoes *Aedes* spp.; *Anopheles* spp.; *Culex* spp.; black flies *Prosimulium* spp.; *Simulium* spp.; biting midges, sand flies, sciarids, and other Nematocera.

Included as insects of interest are adults and nymphs of the orders Hemiptera and Homoptera such as, but not limited to, adelgids from the family Adelgidae, plant bugs from the family Miridae, cicadas from the family Cicadidae, leafhoppers, *Empoasca* spp.; from the family Cicadellidae, planthoppers from the families Cixiidae, Flatidae, Fulgoroidea, Issidae and Delphacidae, treehoppers from the family Membracidae, psyllids from the family Psyllidae, whiteflies from the family Aleyrodidae, aphids from the family Aphididae, *phylloxera* from the family Phylloxeridae, mealybugs from the family Pseudococcidae, scales from the families Asterolecanidae, Coccidae, Dactylopiidae, Diaspididae, Eriococcidae Ortheziidae, Phoenicococcidae and Margarodidae, lace bugs from the family Tingidae, stink bugs from the family Pentatomidae, cinch bugs, *Blissus* spp.; and other seed bugs from the family Lygaeidae, spittlebugs from the family Cercopidae squash bugs from the family Coreidae and red bugs and cotton stainers from the family Pyrrhocoridae.

Agronomically important members from the order Homoptera further include, but are not limited to: *Acyrthisiphon pisum* Harris (pea aphid); *Aphis craccivora* Koch (cowpea aphid); *A. fabae* Scopoli (black bean aphid); *A. gossypii* Glover (cotton aphid, melon aphid); *A. maidiradicis* Forbes (corn root aphid); *A. pomi* De Geer (apple aphid); *A. spiraecola* Patch (spirea aphid); *Aulacorthum solani* Kaltenbach (foxglove aphid); *Chaetosiphon fragaefolii* Cockerell (strawberry aphid); *Diuraphis noxia* Kurdjumov/Mordvilko (Russian wheat aphid); *Dysaphis plantaginea* Paaserini (rosy apple aphid); *Eriosoma lanigerum* Hausmann (woolly apple aphid); *Brevicoryne brassicae* Linnaeus (cabbage aphid); *Hyalopterus pruni* Geoffroy (mealy plum aphid); *Lipaphis erysimi* Kaltenbach (turnip aphid); *Metopolophium dirrhodum* Walker (cereal aphid); *Macrosiphum euphorbiae* Thomas (potato aphid); *Myzus persicae* Sulzer (peach-potato aphid, green peach aphid); *Nasonovia ribisnigri* Mosley (lettuce aphid); Pemphigus spp. (root aphids and gall aphids); *Rhopalosiphum maidis* Fitch (corn leaf aphid); *R. padi* Linnaeus (bird cherry-oat aphid); *Schizaphis graminum* Rondani (greenbug); *Sipha flava* Forbes (yellow sugarcane aphid); *Sitobion avenae* Fabricius (English grain aphid); *Therioaphis maculata* Buckton (spotted alfalfa aphid); *Toxoptera aurantii* Boyer de Fonscolombe (black citrus aphid) and *T. citricida* Kirkaldy (brown citrus aphid); *Adelges* spp. (adelgids); *Phylloxera devastatrix* Pergande (pecan *phylloxera*); *Bemisia tabaci* Gennadius (tobacco whitefly, sweetpotato whitefly); *B. argentifolii* Bellows & Perring (silverleaf whitefly); *Dialeurodes citri* Ashmead (citrus whitefly); *Trialeurodes* abutiloneus (bandedwinged whitefly) and *T. vaporariorum* Westwood (greenhouse whitefly); *Empoasca fabae* Harris (potato leafhopper); *Laodelphax striatellus* Fallen (smaller brown planthopper); *Macrolestes quadrilineatus* Forbes (aster leafhopper); *Nephotettix cinticeps* Uhler (green leafhopper); *N. nigropictus* Stal (rice leafhopper); *Nilaparvata lugens* Stål (brown planthopper); *Peregrinus maidis* Ashmead (corn planthopper); *Sogatella furcifera* Horvath (white-backed planthopper); *Sogatodes orizicola* Muir (rice delphacid); *Typhlocyba pomaria* McAtee (white apple leafhopper); Erythroneoura spp. (grape leafhoppers); Magicicada *septendecim* Linnaeus (periodical cicada); *Icerya purchasi* Maskell (cottony cushion scale); *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear *psylla*); *Trioza diospyri* Ashmead (persimmon *psylla*).

Agronomically important species of interest from the order Hemiptera include, but are not limited to: *Acrosternum hilare* Say (green stink bug); *Anasa tristis* De Geer (squash bug); *Blissus leucopterus leucopterus* Say (chinch bug); *Corythuca gossypii* Fabricius (cotton lace bug); *Cyrtopeltis modesta* Distant (tomato bug); *Dysdercus suturellus* Herrich-Schïffer (cotton stainer); *Euschistus servus* Say (brown stink bug); *E. variolarius* Palisot de Beauvois (one-spotted stink bug); *Graptostethus* spp. (complex of seed bugs); *Leptoglossus corculus* Say (leaf-footed pine seed bug); *Lygus lineolaris* Palisot de Beauvois (tarnished plant bug); *L. Hesperus* Knight (Western tarnished plant bug); *L. pratensis* Linnaeus (common meadow bug); *L. rugulipennis* Poppius (European tarnished plant bug); *Lygocoris pabulinus* Linnaeus (common green capsid); *Nezara viridula* Linnaeus (southern green stink bug); *Oebalus pugnax* Fabricius (rice stink bug); *Oncopeltus fasciatus* Dallas (large milkweed bug); *Pseudatomoscelis seriatus* Reuter (cotton fleahopper).

Furthermore, embodiments may be effective against Hemiptera such, *Calocoris norvegicus* Gmelin (strawberry bug); *Orthops campestris* Linnaeus; *Plesiocoris rugicollis* Fallen (apple capsid); *Cyrtopeltis modestus* Distant (tomato bug); *Cyrtopeltis notatus* Distant (suckfly); *Spanagonicus albofasciatus* Reuter (whitemarked fleahopper); *Diaphnocoris chlorionis* Say (honeylocust plant bug); *Labopidicola allii* Knight (onion plant bug); *Pseudatomoscelis seriatus* Reuter (cotton fleahopper); *Adelphocoris rapidus* Say (rapid plant bug); *Poecilocapsus lineatus* Fabricius (four-lined plant bug); *Nysius ericae* Schilling (false chinch bug); *Nysius raphanus* Howard (false chinch bug); *Nezara viridula* Linnaeus (Southern green stink bug); *Eurygaster* spp.; *Coreidae* spp.; *Pyrrhocoridae* spp.; *Tinidae* spp.; *Blostomatidae* spp.; *Reduviidae* spp. and *Cimicidae* spp.

Also included are adults and larvae of the order Acari (mites) such as *Aceria tosichella* Keifer (wheat curl mite); *Petrobia latens* Müller (brown wheat mite); spider mites and red mites in the family Tetranychidae, *Panonychus ulmi* Koch (European red mite); *Tetranychus urticae* Koch (two spotted spider mite); (*T. mcdanieli* McGregor (McDaniel mite); *T. cinnabarinus* Boisduval (carmine spider mite); *T. turkestani* Ugarov & Nikolski (strawberry spider mite); flat mites in the family Tenuipalpidae, *Brevipalpus lewisi* McGregor (citrus flat mite); rust and bud mites in the family Eriophyidae and other foliar feeding mites and mites important in human and animal health, i.e., dust mites in the family Epidermoptidae, follicle mites in the family Demodicidae, grain mites in the family Glycyphagidae, ticks in the order Ixodidae. *Ixodes scapularis* Say (deer tick); *I. holocyclus* Neumann (Australian paralysis tick); *Dermacentor variabilis* Say (American dog tick); *Amblyomma americanum* Linnaeus (lone star tick) and scab and itch mites in the families Psoroptidae, Pyemotidae and Sarcoptidae.

Insect pests of the order Thysanura are of interest, such as *Lepisma saccharina* Linnaeus (silverfish); *Thermobia domestica* Packard (firebrat).

Insect pests of interest include the superfamily of stink bugs and other related insects including but not limited to species belonging to the family Pentatomidae (*Nezara viridula, Halyomorpha halys, Piezodorus guildini, Euschistus servus, Acrosternum hilare, Euschistus heros, Euschistus tristigmus, Acrosternum hilare, Dichelops furcatus, Dichelops melacanthus*, and *Bagrada hilaris* (Bagrada Bug)), the family Plataspidae (*Megacopta cribraria*—Bean plataspid) and the family Cydnidae (*Scaptocoris castanea*—Root stink bug) and Lepidoptera species including but not limited to: diamond-back moth, e.g., *Helicoverpa zea* Boddie; soybean looper, e.g., *Pseudoplusia includens* Walker and velvet bean caterpillar e.g., *Anticarsia gemmatalis* Hübner.

II. Target Sequences

As used herein, a "target sequence" or "target polynucleotide" comprises any sequence in the pest that one desires to reduce the level of expression thereof. In certain embodiments, decreasing the level of expression of the target sequence in the pest controls the pest. For instance, the target sequence may be essential for growth and development. Non-limiting examples of target sequences include a polynucleotide set forth in SEQ ID NOS.: 1-53 or 107-254, or variants and fragments thereof, and complements thereof. As exemplified elsewhere herein, decreasing the level of expression of one or more of these target sequences in a Coleopteran plant pest or a *Diabrotica* plant pest controls the pest.

III. Silencing Elements

By "silencing element" is intended a polynucleotide which when contacted by or ingested by a plant insect pest, is capable of reducing or eliminating the level or expression of a target polynucleotide or the polypeptide encoded thereby. Accordingly, it is to be understood that "silencing element," as used herein, comprises polynucleotides such as RNA constructs, double stranded RNA (dsRNA), hairpin RNA, and sense and/or antisense RNA. In one embodiment, the silencing element employed can reduce or eliminate the expression level of the target sequence by influencing the level of the target RNA transcript or, alternatively, by influencing translation and thereby affecting the level of the encoded polypeptide. Methods to assay for functional silencing elements that are capable of reducing or eliminating the level of a sequence of interest are disclosed elsewhere herein. A single polynucleotide employed in the disclosed methods can comprise one or more silencing elements to the same or different target polynucleotides. The silencing element can be produced in vivo (i.e., in a host cell such as a plant or microorganism) or in vitro.

In certain embodiments, a silencing element may comprise a chimeric construction molecule comprising two or more disclosed sequences or portions thereof. For example, the chimeric construction may be a hairpin or dsRNA as disclosed herein. A chimera may comprise two or more disclosed sequences or portions thereof. In one embodiment, a chimera contemplates two complementary sequences set forth herein, or portions thereof, having some degree of mismatch between the complementary sequences such that the two sequences are not perfect complements of one another. Providing at least two different sequences in a single silencing element may allow for targeting multiple genes using one silencing element and/or for example, one expression cassette. Targeting multiple genes may allow for slowing or reducing the possibility of resistance by the pest. In addition, providing multiple targeting ability in one expressed molecule may reduce the expression burden of the transformed plant or plant product, or provide topical treatments that are capable of targeting multiple hosts with one application.

In certain embodiments, while the silencing element controls pests, preferably the silencing element has no effect on the normal plant or plant part.

As discussed in further detail below, silencing elements can include, but are not limited to, a sense suppression element, an antisense suppression element, a double stranded RNA, a siRNA, an amiRNA, a miRNA, or a hairpin suppression element. In an embodiment, silencing elements may comprise a chimera where two or more disclosed sequences or active fragments or variants, or complements thereof, are found in the same RNA molecule. In various embodiments, a disclosed sequence or active fragment or variant, or complement thereof, may be present as more than one copy in a DNA construct, silencing element, DNA molecule or RNA molecule. In a hairpin or dsRNA molecule, the location of a sense or antisense sequence in the molecule, for example, in which sequence is transcribed first or is located on a particular terminus of the RNA molecule, is not limiting to the disclosed sequences, and the dsRNA is not to be limited by disclosures herein of a particular location for such a sequence. Non-limiting examples of silencing elements that can be employed to decrease expression of these target sequences comprise fragments or variants of the sense or antisense sequence, or alternatively consists of the sense or antisense sequence, of a sequence set forth in SEQ ID NOS.: 1-53 or 107-254, or variants and fragments thereof, and complements thereof. The silencing element can further comprise additional sequences that advantageously effect transcription and/or the stability of a resulting transcript. For example, the silencing elements can comprise at least one thymine residue at the 3' end. This can aid in stabilization. Thus, the silencing elements can have at least 1, 2, 3, 4, 5, 6, 7, 8, 9, 10 or more thymine residues at the 3' end. As discussed in further detail below, enhancer suppressor elements can also be employed in conjunction with the silencing elements disclosed herein.

By "reduces" or "reducing" the expression level of a polynucleotide or a polypeptide encoded thereby is intended to mean, the polynucleotide or polypeptide level of the target sequence is statistically lower than the polynucleotide level or polypeptide level of the same target sequence in an appropriate control pest which is not exposed to (i.e., has not ingested or come into contact with) the silencing element. In particular embodiments, methods and/or compositions disclosed herein reduce the polynucleotide level and/or the polypeptide level of the target sequence in a plant insect pest to less than 95%, less than 90%, less than 80%, less than 70%, less than 60%, less than 50%, less than 40%, less than 30%, less than 20%, less than 10%, or less than 5% of the polynucleotide level, or the level of the polypeptide encoded thereby, of the same target sequence in an appropriate control pest. In some embodiments, a silencing element has substantial sequence identity to the target polynucleotide, typically greater than about 65% sequence identity, greater than about 85% sequence identity, about 90%, 91%, 92%, 93%, 94%, 95%, 96%, 97%, 98% or 99% sequence identity. Furthermore, a silencing element can be complementary to a portion of the target polynucleotide. Generally, sequences of at least 15, 16, 17, 18, 19, 20, 22, 25, 50, 100, 200, 300, 400, 450 continuous nucleotides or greater of the sequence set forth in any of SEQ ID NOS.: 1-53 or 107-254, or variants and fragments thereof, and complements thereof may be used. Methods to assay for the level of the RNA transcript, the level of the encoded polypeptide, or the activity of the polynucleotide or polypeptide are discussed elsewhere herein.

i. Sense Suppression Elements

As used herein, a "sense suppression element" comprises a polynucleotide designed to express an RNA molecule corresponding to at least a part of a target messenger RNA in the "sense" orientation. Expression of the RNA molecule comprising the sense suppression element reduces or eliminates the level of the target polynucleotide or the polypeptide encoded thereby. The polynucleotide comprising the sense suppression element may correspond to all or part of the sequence of the target polynucleotide, all or part of the 5' and/or 3' untranslated region of the target polynucleotide, all or part of the coding sequence of the target polynucleotide, or all or part of both the coding sequence and the untranslated regions of the target polynucleotide.

Typically, a sense suppression element has substantial sequence identity to the target polynucleotide, typically greater than about 65% sequence identity, greater than about 85% sequence identity, about 90%, 91%, 92%, 93%, 94%, 95%, 96%, 97%, 98% or 99% sequence identity. See, U.S. Pat. Nos. 5,283,184 and 5,034,323; herein incorporated by reference. The sense suppression element can be any length so long as it allows for the suppression of the targeted sequence. The sense suppression element can be, for example, 15, 16, 17, 18, 19, 20, 22, 25, 30, 50, 100, 150, 200, 250, 300, 350, 400, 450, 500, 600, 700, 900, 1000, 1100, 1200, 1300 nucleotides or longer of the target polynucleotides set forth in any of SEQ ID NOS.: 1-53 or 107-254, or variants and fragments thereof, and complements thereof. In other embodiments, the sense suppression element can be, for example, about 15-25, 19-35, 19-50, 25-100, 100-150, 150-200, 200-250, 250-300, 300-350, 350-400, 450-500, 500-550, 550-600, 600-650, 650-700, 700-750, 750-800, 800-850, 850-900, 900-950, 950-1000, 1000-1050, 1050-1100, 1100-1200, 1200-1300, 1300-1400, 1400-1500, 1500-1600, 1600-1700, 1700-1800 nucleotides or longer of the target polynucleotides set forth in any of SEQ ID NOS.: 1-53 or 107-254, or variants and fragments thereof, and complements thereof.

ii. Antisense Suppression Elements

As used herein, an "antisense suppression element" comprises a polynucleotide which is designed to express an RNA molecule complementary to all or part of a target messenger RNA. Expression of the antisense RNA suppression element reduces or eliminates the level of the target polynucleotide. The polynucleotide for use in antisense suppression may correspond to all or part of the complement of the sequence encoding the target polynucleotide, all or part of the complement of the 5' and/or 3' untranslated region of the target polynucleotide, all or part of the complement of the coding sequence of the target polynucleotide, or all or part of the complement of both the coding sequence and the untranslated regions of the target polynucleotide. In addition, the antisense suppression element may be fully complementary (i.e., 100% identical to the complement of the target sequence) or partially complementary (i.e., less than 100% identical to the complement of the target sequence) to the target polynucleotide. In certain embodiments, the antisense suppression element comprises at least 85%, 90%, 91%, 92%, 93%, 94%, 95%, 96%, 97%, 98%, or 99% sequence complementarity to the target polynucleotide. Antisense suppression may be used to inhibit the expression of multiple proteins in the same plant. See, for example, U.S. Pat. No. 5,942,657. Furthermore, the antisense suppression element can be complementary to a portion of the target polynucleotide. Generally, sequences of at least 15, 16, 17, 18, 19, 20, 22, 25, 50, 100, 200, 300, 400, 450 nucleotides or greater of the sequence set forth in any of SEQ ID NOS.: 1-53 or 107-254, or variants and fragments thereof, and complements thereof may be used. Methods for using antisense suppression to inhibit the expression of endogenous genes in plants are described, for example, in Liu et al (2002) *Plant Physiol.* 129:1732-1743 and U.S. Pat. No. 5,942,657, which is herein incorporated by reference.

iii. Double Stranded RNA Suppression Element

A "double stranded RNA silencing element" or "dsRNA," comprises at least one transcript that is capable of forming a dsRNA either before or after ingestion by a plant insect pest. Thus, a "dsRNA silencing element" includes a dsRNA, a transcript or polyribonucleotide capable of forming a dsRNA or more than one transcript or polyribonucleotide capable of forming a dsRNA. "Double stranded RNA" or "dsRNA" refers to a polyribonucleotide structure formed either by a single self-complementary RNA molecule or a polyribonucleotide structure formed by the expression of at least two distinct RNA strands. The dsRNA molecule(s) employed in the disclosed methods and compositions mediate the reduction of expression of a target sequence, for example, by mediating RNA interference "RNAi" or gene silencing in a sequence-specific manner In various embodiments, the dsRNA is capable of reducing or eliminating the level or expression of a target polynucleotide or the polypeptide encoded thereby in a plant insect pest.

The dsRNA can reduce or eliminate the expression level of the target sequence by influencing the level of the target RNA transcript, by influencing translation and thereby affecting the level of the encoded polypeptide, or by influencing expression at the pre-transcriptional level (i.e., via the modulation of chromatin structure, methylation pattern, etc., to alter gene expression). For example, see Verdel et al. (2004) *Science* 303:672-676; Pal-Bhadra et al. (2004) *Science* 303:669-672; Allshire (2002) *Science* 297:1818-1819; Volpe et al. (2002) *Science* 297:1833-1837; Jenuwein (2002) *Science* 297:2215-2218; and Hall et al. (2002) *Science* 297:2232-2237. Methods to assay for functional dsRNA that are capable of reducing or eliminating the level of a sequence of interest are disclosed elsewhere herein. Accordingly, as used herein, the term "dsRNA" is meant to encompass other terms used to describe nucleic acid molecules that are capable of mediating RNA interference or gene silencing, including, for example, short-interfering RNA (siRNA), double-stranded RNA (dsRNA), micro-RNA (miRNA), hairpin RNA, short hairpin RNA (shRNA), post-transcriptional gene silencing RNA (ptgsRNA), and others.

In certain embodiments, at least one strand of the duplex or double-stranded region of the dsRNA shares sufficient sequence identity or sequence complementarity to the target polynucleotide to allow the dsRNA to reduce the level of expression of the target sequence. In some embodiments, a dsRNA has substantial sequence identity to the target polynucleotide, typically greater than about 65% sequence identity, greater than about 85% sequence identity, about 90%, 91%, 92%, 93%, 94%, 95%, 96%, 97%, 98% or 99% sequence identity. Furthermore, a dsRNA element can be complementary to a portion of the target polynucleotide. Generally, sequences of at least 15, 16, 17, 18, 19, 20, 22, 25, 50, 100, 200, 300, 400, 450 nucleotides or greater of the sequence set forth in any of SEQ ID NOS.: 1-53 or 107-254, or variants and fragments thereof, and complements thereof may be used. As used herein, the strand that is complementary to the target polynucleotide is the "antisense strand" and the strand homologous to the target polynucleotide is the "sense strand."

In another embodiment, the dsRNA comprises a hairpin RNA. A hairpin RNA comprises an RNA molecule that is capable of folding back onto itself to form a double stranded structure. Multiple structures can be employed as hairpin elements. In certain embodiments, the dsRNA suppression element comprises a hairpin element which comprises in the following order, a first segment, a second segment, and a third segment, where the first and the third segment share sufficient complementarity to allow the transcribed RNA to form a double-stranded stem-loop structure.

The "second segment" of the hairpin comprises a "loop" or a "loop region." These terms are used synonymously herein and are to be construed broadly to comprise any nucleotide sequence that confers enough flexibility to allow self-pairing to occur between complementary regions of a polynucleotide (i.e., segments 1 and 3 which form the stem of the hairpin). For example, in some embodiments, the loop region may be substantially single stranded and act as a spacer between the self-complementary regions of the hairpin stem-loop. In some embodiments, the loop region can comprise a random or nonsense nucleotide sequence and thus not share sequence identity to a target polynucleotide. In other embodiments, the loop region comprises a sense or an antisense RNA sequence or fragment thereof that shares identity to a target polynucleotide. See, for example, International Patent Publication No. WO 02/00904. In certain embodiments, the loop sequence can include an intron sequence, a sequence derived from an intron sequence, a sequence homologous to an intron sequence, or a modified intron sequence. The intron sequence can be one found in the same or a different species from which segments 1 and 3 are derived. In certain embodiments, the loop region can be optimized to be as short as possible while still providing enough intramolecular flexibility to allow the formation of the base-paired stem region. Accordingly, the loop sequence is generally less than 1000, 900, 800, 700, 600, 500, 400, 300, 200, 100, 50, 25, 20, 19, 18, 17, 16, 15, 10 nucleotides or less.

The "first" and the "third" segment of the hairpin RNA molecule comprise the base-paired stem of the hairpin structure. The first and the third segments are inverted repeats of one another and share sufficient complementarity to allow the formation of the base-paired stem region. In certain embodiments, the first and the third segments are fully complementary to one another. Alternatively, the first and the third segment may be partially complementary to each other so long as they are capable of hybridizing to one another to form a base-paired stem region. The amount of complementarity between the first and the third segment can be calculated as a percentage of the entire segment. Thus, the first and the third segment of the hairpin RNA generally share at least 50%, 60%, 70%, 80%, 85%, 90%, 91%, 92%, 93%, 94%, 95%, 96%, 97%, 98%, 99%, up to and including 100% complementarity.

The first and the third segment are at least about 1000, 500, 475, 450, 425, 400, 375, 350, 325, 300, 250, 225, 200, 175, 150, 125, 100, 75, 60, 50, 40, 30, 25, 22, 20, 19, 18, 17, 16, 15 or 10 nucleotides in length. In certain embodiments, the length of the first and/or the third segment is about 10-100 nucleotides, about 10 to about 75 nucleotides, about 10 to about 50 nucleotides, about 10 to about 40 nucleotides, about 10 to about 35 nucleotides, about 10 to about 30 nucleotides, about 10 to about 25 nucleotides, about 10 to about 19 nucleotides, about 10 to about 20 nucleotides, about 19 to about 50 nucleotides, about 50 nucleotides to about 100 nucleotides, about 100 nucleotides to about 150 nucleotides, about 100 nucleotides to about 300 nucleotides, about 150 nucleotides to about 200 nucleotides, about 200 nucleotides to about 250 nucleotides, about 250 nucleotides to about 300 nucleotides, about 300 nucleotides to about 350 nucleotides, about 350 nucleotides to about 400 nucleotides, about 400 nucleotide to about 500 nucleotides, about 600 nt, about 700 nt, about 800 nt, about 900 nt, about 1000 nt, about 1100 nt, about 1200 nt, 1300 nt, 1400 nt, 1500 nt, 1600 nt, 1700 nt, 1800 nt, 1900 nt, 2000 nt or longer. In other embodiments, the length of the first and/or the third segment comprises at least 10-19 nucleotides, 10-20 nucleotides; 19-35 nucleotides, 20-35 nucleotides; 30-45 nucleotides; 40-50 nucleotides; 50-100 nucleotides; 100-300 nucleotides; about 500-700 nucleotides; about 700-900 nucleotides; about 900-1100 nucleotides; about 1300-1500 nucleotides; about 1500-1700 nucleotides; about 1700-1900 nucleotides; about 1900-2100 nucleotides; about 2100-2300 nucleotides; or about 2300-2500 nucleotides. See, for example, International Publication No. WO 02/00904.

The disclosed hairpin molecules or double-stranded RNA molecules may have more than one disclosed sequence or active fragments or variants, or complements thereof, found in the same portion of the RNA molecule. For example, in a chimeric hairpin structure, the first segment of a hairpin molecule comprises two polynucleotide sections, each with a different disclosed sequence. For example, reading from one terminus of the hairpin, the first segment is composed of sequences from two separate genes (A followed by B). This first segment is followed by the second segment, the loop portion of the hairpin. The loop segment is followed by the third segment, where the complementary strands of the sequences in the first segment are found (B* followed by A*) in forming the stem-loop, hairpin structure, the stem contains SeqA-A* at the distal end of the stem and SeqB-B* proximal to the loop region.

In certain embodiments, the first and the third segment comprise at least 20 nucleotides having at least 85% complementary to the first segment. In still other embodiments, the first and the third segments which form the stem-loop structure of the hairpin comprise 3' or 5' overhang regions having unpaired nucleotide residues.

In certain embodiments, the sequences used in the first, the second, and/or the third segments comprise domains that are designed to have sufficient sequence identity to a target polynucleotide of interest and thereby have the ability to decrease the level of expression of the target polynucleotide. The specificity of the inhibitory RNA transcripts is therefore generally conferred by these domains of the silencing element. Thus, in some embodiments, the first, second and/or third segment of the silencing element comprise a domain having at least 10, at least 15, at least 19, at least 20, at least 21, at least 22, at least 23, at least 24, at least 25, at least 30, at least 40, at least 50, at least 100, at least 200, at least 300, at least 500, at least 1000, or more than 1000 nucleotides that share sufficient sequence identity to the target polynucleotide to allow for a decrease in expression levels of the target polynucleotide when expressed in an appropriate cell. In other embodiments, the domain is between about 15 to 50 nucleotides, about 19-35 nucleotides, about 20-35 nucleotides, about 25-50 nucleotides, about 19 to 75 nucleotides, about 20 to 75 nucleotides, about 40-90 nucleotides about 15-100 nucleotides, 10-100 nucleotides, about 10 to about 75 nucleotides, about 10 to about 50 nucleotides, about 10 to about 40 nucleotides, about 10 to about 35 nucleotides, about 10 to about 30 nucleotides, about 10 to about 25 nucleotides, about 10 to about 20 nucleotides, about 10 to about 19 nucleotides, about 50 nucleotides to about 100 nucleotides, about 100 nucleotides to about 150 nucleotides, about 150 nucleotides to about 200 nucleotides, about 200 nucleotides to about 250 nucleotides, about 250 nucleotides to about 300 nucleotides, about 300 nucleotides to about 350 nucleotides, about 350 nucleotides to about 400 nucleotides, about 400 nucleotide to about 500 nucleotides or longer. In other embodiments, the length of the first and/or the third segment comprises at least 10-20 nucleotides, at least 10-19 nucleotides, 20-35 nucleotides, 30-45 nucleotides, 40-50 nucleotides, 50-100 nucleotides, or about 100-300 nucleotides.

In certain embodiments, a domain of the first, the second, and/or the third segment has 100% sequence identity to the target polynucleotide. In other embodiments, the domain of the first, the second and/or the third segment having homology to the target polynucleotide have at least 50%, 60%, 70%, 80%, 85%, 90%, 91%, 92%, 93%, 94%, 95%, 96%, 97%, 98%, 99%, or greater sequence identity to a region of the target polynucleotide. The sequence identity of the domains of the first, the second and/or the third segments complementary to a target polynucleotide need only be sufficient to decrease expression of the target polynucleotide of interest. See, for example, Chuang and Meyerowitz (2000) *Proc. Natl. Acad. Sci. USA* 97:4985-4990; Stoutjesdijk et al. (2002) *Plant Physiol.* 129:1723-1731; Waterhouse and Helliwell (2003) *Nat. Rev. Genet.* 4:29-38; Pandolfini et al. *BMC Biotechnology* 3:7, and U.S. Patent Publication No. 20030175965; each of which is herein incorporated by reference. A transient assay for the efficiency of hpRNA constructs to silence gene expression in vivo has been described by Panstruga et al. (2003) *Mol. Biol. Rep.* 30:135-140.

The amount of complementarity shared between the first, second, and/or third segment and the target polynucleotide or the amount of complementarity shared between the first segment and the third segment (i.e., the stem of the hairpin structure) may vary depending on the organism in which gene expression is to be controlled. Some organisms or cell types may require exact pairing or 100% identity, while other organisms or cell types may tolerate some mismatching. In some cells, for example, a single nucleotide mismatch in the targeting sequence abrogates the ability to suppress gene expression. In these cells, the disclosed suppression cassettes can be used to target the suppression of mutant genes, for example, oncogenes whose transcripts comprise point mutations and therefore they can be specifically targeted using the methods and compositions disclosed herein without altering the expression of the remaining wild-type allele. In other organisms, holistic sequence variability may be tolerated as long as some 22 nt region of the sequence is represented in 100% homology between target polynucleotide and the suppression cassette.

Any region of the target polynucleotide can be used to design a domain of the silencing element that shares sufficient sequence identity to allow expression of the hairpin transcript to decrease the level of the target polynucleotide. For instance, a domain may be designed to share sequence identity to the 5' untranslated region of the target polynucleotide(s), the 3' untranslated region of the target polynucleotide(s), exonic regions of the target polynucleotide(s), intronic regions of the target polynucleotide(s), and any combination thereof. In certain embodiments, a domain of the silencing element shares sufficient identity, homology, or is complementary to at least about 15, 16, 17, 18, 19, 20, 22, 25 or 30 consecutive nucleotides from about nucleotides 1-50, 25-75, 75-125, 50-100, 125-175, 175-225, 100-150, 150-200, 200-250, 225-275, 275-325, 250-300, 325-375, 375-425, 300-350, 350-400, 425-475, 400-450, 475-525, 450-500, 525-575, 575-625, 550-600, 625-675, 675-725, 600-650, 625-675, 675-725, 650-700, 725-825, 825-875, 750-800, 875-925, 925-975, 850-900, 925-975, 975-1025, 950-1000, 1000-1050, 1025-1075, 1075-1125, 1050-1100, 1125-1175, 1100-1200, 1175-1225, 1225-1275, 1200-1300, 1325-1375, 1375-1425, 1300-1400, 1425-1475, 1475-1525, 1400-1500, 1525-1575, 1575-1625, 1625-1675, 1675-1725, 1725-1775, 1775-1825, 1825-1875, 1875-1925, 1925-1975, 1975-2025, 2025-2075, 2075-2125, 2125-2175, 2175-2225, 1500-1600, 1600-1700, 1700-1800, 1800-1900, 1900-2000 of the target sequence. In some instances to optimize the siRNA sequences employed in the hairpin, the synthetic oligodeoxyribonucleotide/RNAse H method can be used to determine sites on the target mRNA that are in a conformation that is susceptible to RNA silencing. See, for example, Vickers et al. (2003) *J. Biol. Chem* 278:7108-7118 and Yang et al. (2002) *Proc. Natl. Acad. Sci. USA* 99:9442-9447, herein incorporated by reference. These studies indicate that there is a significant correlation between the RNase-H-sensitive sites and sites that promote efficient siRNA-directed mRNA degradation.

The hairpin silencing element may also be designed such that the sense sequence or the antisense sequence do not correspond to a target polynucleotide. In this embodiment, the sense and antisense sequence flank a loop sequence that comprises a nucleotide sequence corresponding to all or part of the target polynucleotide. Thus, it is the loop region that determines the specificity of the RNA interference. See, for example, WO 02/00904.

In addition, transcriptional gene silencing (TGS) may be accomplished through use of a hairpin suppression element where the inverted repeat of the hairpin shares sequence identity with the promoter region of a target polynucleotide to be silenced. See, for example, Aufsatz et al. (2002) *PNAS* 99 (Suppl. 4):16499-16506 and Mette et al. (2000) *EMBO J* 19(19):5194-5201.

In other embodiments, the silencing element can comprise a small RNA (sRNA). sRNAs can comprise both micro RNA (miRNA) and short-interfering RNA (siRNA) (Meister and Tuschl (2004) *Nature* 431:343-349 and Bonetta et al. (2004) *Nature Methods* 1:79-86). miRNAs are regulatory agents comprising about 19 to about 24 ribonucleotides in length which are highly efficient at inhibiting the expression of target polynucleotides. See, for example Javier et al. (2003) *Nature* 425: 257-263. For miRNA interference, the silencing element can be designed to express a dsRNA molecule that forms a hairpin structure or partially base-paired structure containing a 19, 20, 21, 22, 23, 24 or 25 nucleotide sequence that is complementary to the target polynucleotide of interest. The miRNA can be synthetically made, or transcribed as a longer RNA which is subsequently cleaved to produce the active miRNA. Specifically, the miRNA can comprise 19 nucleotides of the sequence having homology to a target polynucleotide in sense orientation and 19 nucleotides of a corresponding antisense sequence that is complementary to the sense sequence. The miRNA can be an "artificial miRNA" or "amiRNA" which comprises a miRNA sequence that is synthetically designed to silence a target sequence.

When expressing an miRNA the final (mature) miRNA is present in a duplex in a precursor backbone structure, the two strands being referred to as the miRNA (the strand that will eventually base pair with the target) and miRNA*(star sequence). It has been demonstrated that miRNAs can be transgenically expressed and target genes of interest for efficient silencing (Highly specific gene silencing by artificial microRNAs in *Arabidopsis* Schwab R, Ossowski S, Riester M, Warthmann N, Weigel D. Plant Cell. 2006 May; 18(5):1121-33. Epub 2006 Mar. 10; and Expression of artificial microRNAs in transgenic *Arabidopsis thaliana* confers virus resistance. Niu Q W, Lin S S, Reyes J L, Chen K C, Wu H W, Yeh S D, Chua N H. Nat Biotechnol. 2006 November; 24(11):1420-8. Epub 2006 Oct. 22. Erratum in: Nat Biotechnol. 2007 February; 25(2):254.).

The silencing element for miRNA interference comprises a miRNA primary sequence. The miRNA primary sequence comprises a DNA sequence having the miRNA and star sequences separated by a loop as well as additional sequences flanking this region that are important for processing. When expressed as an RNA, the structure of the primary miRNA is such as to allow for the formation of a hairpin RNA structure that can be processed into a mature miRNA. In some embodiments, the miRNA backbone comprises a genomic or cDNA miRNA precursor sequence, wherein said sequence comprises a native primary in which a heterologous (artificial) mature miRNA and star sequence are inserted.

As used herein, a "star sequence" is the sequence within a miRNA precursor backbone that is complementary to the miRNA and forms a duplex with the miRNA to form the stem structure of a hairpin RNA. In some embodiments, the star sequence can comprise less than 100% complementarity to the miRNA sequence. Alternatively, the star sequence can comprise at least 99%, 98%, 97%, 96%, 95%, 90%, 85%, 80% or lower sequence complementarity to the miRNA sequence as long as the star sequence has sufficient complementarity to the miRNA sequence to form a double stranded structure. In still further embodiments, the star sequence comprises a sequence having 1, 2, 3, 4, 5 or more mismatches with the miRNA sequence and still has sufficient complementarity to form a double stranded structure with the miRNA sequence resulting in production of miRNA and suppression of the target sequence.

The miRNA precursor backbones can be from any plant. In some embodiments, the miRNA precursor backbone is from a monocot. In other embodiments, the miRNA precursor backbone is from a dicot. In further embodiments, the backbone is from maize or soybean. MicroRNA precursor backbones have been described previously. For example, US20090155910A1 (WO 2009/079532) discloses the following soybean miRNA precursor backbones: 156c, 159, 166b, 168c, 396b and 398b, and US20090155909A1 (WO 2009/079548) discloses the following maize miRNA precursor backbones: 159c, 164h, 168a, 169r, and 396h.

Thus, the primary miRNA can be altered to allow for efficient insertion of heterologous miRNA and star sequences within the miRNA precursor backbone. In such instances, the miRNA segment and the star segment of the miRNA precursor backbone are replaced with the heterologous miRNA and the heterologous star sequences, designed to target any sequence of interest, using a PCR technique and cloned into an expression construct. It is recognized that there could be alterations to the position at which the artificial miRNA and star sequences are inserted into the backbone. Detailed methods for inserting the miRNA and star sequence into the miRNA precursor backbone are described in, for example, US Patent Applications 20090155909A1 and US20090155910A1.

When designing a miRNA sequence and star sequence, various design choices can be made. See, for example, Schwab R, et al. (2005) Dev Cell 8: 517-27. In non-limiting embodiments, the miRNA sequences disclosed herein can have a "U" at the 5'-end, a "C" or "G" at the 19th nucleotide position, and an "A" or "U" at the 10th nucleotide position. In other embodiments, the miRNA design is such that the miRNA have a high free delta-G as calculated using the ZipFold algorithm (Markham, N. R. & Zuker, M. (2005) Nucleic Acids Res. 33: W577-W581.) Optionally, a one base pair change can be added within the 5' portion of the miRNA so that the sequence differs from the target sequence by one nucleotide.

The methods and compositions disclosed herein employ DNA constructs that when transcribed "form" a silencing element, such as a dsRNA molecule. The methods and compositions also may comprise a host cell comprising the DNA construct encoding a silencing element. In another embodiment, The methods and compositions also may comprise a transgenic plant comprising the DNA construct encoding a silencing element. Accordingly, the heterologous polynucleotide being expressed need not form the dsRNA by itself, but can interact with other sequences in the plant cell or in the pest gut after ingestion to allow the formation of the dsRNA. For example, a chimeric polynucleotide that can selectively silence the target polynucleotide can be generated by expressing a chimeric construct comprising the target sequence for a miRNA or siRNA to a sequence corresponding to all or part of the gene or genes to be silenced. In this embodiment, the dsRNA is "formed" when the target for the miRNA or siRNA interacts with the miRNA present in the cell. The resulting dsRNA can then reduce the level of expression of the gene or genes to be silenced. See, for example, US Application Publication 2007-0130653, entitled "Methods and Compositions for Gene Silencing". The construct can be designed to have a target for an endogenous miRNA or alternatively, a target for a heterologous and/or synthetic miRNA can be employed in the construct. If a heterologous and/or synthetic miRNA is employed, it can be introduced into the cell on the same nucleotide construct as the chimeric polynucleotide or on a separate construct. As discussed elsewhere herein, any method can be used to introduce the construct comprising the heterologous miRNA.

IV. Variants and Fragments

By "fragment" is intended a portion of the polynucleotide or a portion of the amino acid sequence and hence protein encoded thereby. Fragments of a polynucleotide may encode protein fragments that retain the biological activity of the native protein. Alternatively, fragments of a polynucleotide that are useful as a silencing element do not need to encode fragment proteins that retain biological activity. Thus, fragments of a nucleotide sequence may range from at least about 10, about 15, about 16, about 17, about 18, about 19, nucleotides, about 20 nucleotides, about 22 nucleotides, about 50 nucleotides, about 75 nucleotides, about 100 nucleotides, 200 nucleotides, 300 nucleotides, 400 nucleotides, 500 nucleotides, 600 nucleotides, 700 nucleotides and up to and including one nucleotide less than the full-length polynucleotide employed. Alternatively, fragments of a nucleotide sequence may range from 1-50, 25-75, 75-125, 50-100, 125-175, 175-225, 100-150, 100-300, 150-200, 200-250, 225-275, 275-325, 250-300, 325-375, 375-425, 300-350, 350-400, 425-475, 400-450, 475-525, 450-500, 525-575, 575-625, 550-600, 625-675, 675-725, 600-650, 625-675, 675-725, 650-700, 725-825, 825-875, 750-800, 875-925, 925-975, 850-900, 925-975, 975-1025, 950-1000, 1000-1050, 1025-1075, 1075-1125, 1050-1100, 1125-1175, 1100-1200, 1175-1225, 1225-1275, 1200-1300, 1325-1375, 1375-1425, 1300-1400, 1425-1475, 1475-1525, 1400-1500, 1525-1575, 1575-1625, 1625-1675, 1675-1725, 1725-1775, 1775-1825, 1825-1875, 1875-1925, 1925-1975, 1975-2025, 2025-2075, 2075-2125, 2125-2175, 2175-2225, 1500-1600, 1600-1700, 1700-1800, 1800-1900, 1900-2000 of any one of SEQ ID NOS.: 1-53 or 107-254, or variants and fragments thereof, and complements thereof. Methods to assay for the activity of a desired silencing element are described elsewhere herein.

"Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. A variant of a polynucleotide that is useful as a silencing element will retain the ability to reduce expression of the target polynucleotide and, in some embodiments, thereby control a plant insect pest of interest. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the disclosed polypeptides. Variant polynucleotides also include synthetically derived polynucleotide, such as those generated, for example, by using site-directed mutagenesis, but continue to retain the desired activity. Generally, variants of a particular disclosed polynucleotide (i.e., a silencing element) will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular disclosed polynucleotide (i.e., the reference polynucleotide) can also be evaluated by comparison of the percent sequence identity between the polypeptide encoded by a variant polynucleotide and the polypeptide encoded by the reference polynucleotide. Percent sequence identity between any two polypeptides can be calculated using sequence alignment programs and parameters described elsewhere herein. Where any given pair of disclosed polynucleotides employed is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

The following terms are used to describe the sequence relationships between two or more polynucleotides or polypeptides: (a) "reference sequence", (b) "comparison window", (c) "sequence identity", and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

A method is further provided for identifying a silencing element from the target polynucleotides set forth in SEQ ID NOS.: 1-53 or 107-254, or variants and fragments thereof, and complements thereof. Such methods comprise obtaining a candidate fragment of any one of SEQ ID NOS.: 1-53 or 107-254, or variants and fragments thereof, and complements thereof, which is of sufficient length to act as a silencing element and thereby reduce the expression of the target polynucleotide and/or control a desired pest; expressing said candidate polynucleotide fragment in an appropriate expression cassette to produce a candidate silencing element and determining is said candidate polynucleotide fragment has the activity of a silencing element and thereby reduce the expression of the target polynucleotide and/or controls a desired pest. Methods of identifying such candidate fragments based on the desired pathway for suppression, in light of the teachings provided herein, are known. For example, various bioinformatics programs can be employed to identify the region of the target polynucleotides that could be exploited to generate a silencing element. See, for example, Elbahir et al. (2001) *Genes and Development* 15:188-200, Schwartz et al. (2003) *Cell* 115:199-208, Khvorova et al. (2003) *Cell* 115:209-216. See also, siRNA at Whitehead (jura.wi.mit.edu/bioc/siRNAext/) which calculates the binding energies for both sense and antisense siRNAs. See, also genscript.com/ssl-bin/app/rnai?op=known; Block-iT™ RNAi designer from Invitrogen and GenScript siRNA Construct Builder. In various aspects, it is to be understand that the term " . . . SEQ ID NOS.: 1-53 or 107-254, or variants or fragments thereof, or complements thereof . . . " is intended to mean that the disclosed sequences comprise SEQ ID NOS.: 1-53 or 107-254, and/or fragments of SEQ ID NOS.: 1-53 or 107-254, and/or variants of SEQ ID NOS.: 1-53 or 107-254, and/or the complements of SEQ ID NOS.: 1-53 or 107-254, the variants of SEQ ID NOS.: 1-53 or 107-254, and/or the fragments of SEQ ID NOS.: 1-53 or 107-254, individually (or) or inclusive of some or all listed sequences.

V. DNA Constructs

The use of the term "polynucleotide" is not intended to be limiting to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The disclosed polynucleotides also encompass all forms of sequences including, but not limited to, single-stranded forms, double-stranded forms, hairpins, stem-and-loop structures, and the like.

The polynucleotide encoding the silencing element or in certain embodiments employed in the disclosed methods and compositions can be provided in expression cassettes for expression in a plant or organism of interest. It is recognized that multiple silencing elements including multiple identical silencing elements, multiple silencing elements targeting different regions of the target sequence, or multiple silencing elements from different target sequences can be used. In this embodiment, it is recognized that each silencing element may be encoded by a single or separate cassette, DNA construct, or vector. As discussed, any means of providing the silencing element is contemplated. A plant or plant cell can be transformed with a single cassette comprising DNA encoding one or more silencing elements or separate cassettes encoding a silencing element can be used to transform a plant or plant cell or host cell. Likewise, a plant transformed with one component can be subsequently transformed with the second component. One or more DNA constructs encoding silencing elements can also be brought together by sexual crossing. That is, a first plant comprising one component is crossed with a second plant comprising the second component. Progeny plants from the cross will comprise both components.

The expression cassette can include 5' and 3' regulatory sequences operably linked to the polynucleotide of the invention. "Operably linked" is intended to mean a functional linkage between two or more elements. For example, an operable linkage between a polynucleotide of the invention and a regulatory sequence (i.e., a promoter) is a functional link that allows for expression of the polynucleotide disclosed herein. Operably linked elements may be contiguous or non-contiguous. When used to refer to the joining of two protein coding regions, by operably linked is intended that the coding regions are in the same reading frame. The cassette may additionally contain at least one additional polynucleotide to be cotransformed into the organism. Alternatively, the additional polypeptide(s) can be provided on multiple expression cassettes. Expression cassettes can be provided with a plurality of restriction sites and/or recombination sites for insertion of the polynucleotide to be under the transcriptional regulation of the regulatory regions. The expression cassette may additionally contain selectable marker genes.

The expression cassette can include in the 5'-3' direction of transcription, a transcriptional and translational initiation region (i.e., a promoter), a polynucleotide encoding the silencing element employed in the methods and compositions of the invention, and a transcriptional and translational termination region (i.e., termination region) functional in plants. In other embodiment, the double stranded RNA is expressed from a suppression cassette. Such a cassette can comprise two convergent promoters that drive transcription of an operably linked silencing element. "Convergent promoters" refers to promoters that are oriented on either terminus of the operably linked polynucleotide encoding the silencing element such that each promoter drives transcription of the silencing element in opposite directions, yielding two transcripts. In such embodiments, the convergent promoters allow for the transcription of the sense and anti-sense strand and thus allow for the formation of a dsRNA. Such a cassette may also comprise two divergent promoters that drive transcription of one or more operably linked polynucleotides encoding the silencing elements. "Divergent promoters" refers to promoters that are oriented in opposite directions of each other, driving transcription of the one or more polynucleotides encoding the silencing elements in opposite directions. In such embodiments, the divergent promoters allow for the transcription of the sense and antisense strands and allow for the formation of a dsRNA. In such embodiments, the divergent promoters also allow for the transcription of at least two separate hairpin RNAs. In another embodiment, one cassette comprising two or more polynucleotides encoding the silencing elements under the control of two separate promoters in the same orientation is present in a construct. In another embodiment, two or more individual cassettes, each comprising at least one polynucleotide encoding the silencing element under the control of a promoter, are present in a construct in the same orientation.

The regulatory regions (i.e., promoters, transcriptional regulatory regions, and translational termination regions) and/or the polynucleotides disclosed herein may be native/analogous to the host cell or to each other. Alternatively, the regulatory regions and/or the polynucleotide disclosed herein may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

The termination region may be native with the transcriptional initiation region, may be native with the operably linked polynucleotide encoding the silencing element, may be native with the plant host, or may be derived from another source (i.e., foreign or heterologous) to the promoter, the polynucleotide encoding the silencing element, the plant host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, tissue-preferred, inducible, or other promoters for expression in the host organism.

Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Depending on the desired outcome, it may be beneficial to express the gene from an inducible promoter. An inducible promoter, for instance, a pathogen-inducible promoter could also be employed. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819.

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; winl and wing (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like.

Additionally, pathogen-inducible promoters may be employed in the methods and nucleotide constructs of the embodiments. Such pathogen-inducible promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) Neth. J. Plant Pathol. 89: 245-254; Uknes et al. (1992) Plant Cell 4: 645-656; and Van Loon (1985) Plant Mol. Virol. 4: 111-116. See also WO 99/43819.

Of interest are promoters that are expressed locally at or near the site of pathogen infection. See, for example, Marineau et al. (1987) Plant Mol. Biol. 9:335-342; Matton et al. (1989) Molecular Plant-Microbe Interactions 2:325-

331; Somsisch et al. (1986) Proc. Natl. Acad. Sci. USA 83:2427-2430; Somsisch et al. (1988) Mol. Gen. Genet. 2:93-98; and Yang (1996) Proc. Natl. Acad. Sci. USA 93:14972-14977. See also, Chen et al. (1996) Plant J. 10:955-966; Zhang et al. (1994) Proc. Natl. Acad. Sci. USA 91:2507-2511; Warner et al. (1993) Plant J. 3:191-201; Siebertz et al. (1989) Plant Cell 1:961-968; U.S. Pat. No. 5,750,386 (nematode-inducible). Of particular interest is the inducible promoter for the maize PRms gene, whose expression is induced by the pathogen *Fusarium moniliforme* (see, for example, Cordero et al. (1992) Physiol. Mol. Plant Path. 41:189-200).

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-la promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156).

Tissue-preferred promoters can be utilized to target enhanced expression within a particular plant tissue. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen Genet.* 254 (3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol.* Biol. 23(6):1129-1138; and Matsuoka et al. (1993) *Proc. Natl. Acad. Sci. USA* 90(20):9586-9590.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see Plant Science (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

Seed-preferred" promoters include both "seed-specific" promoters (those promoters active during seed development such as promoters of seed storage proteins) as well as "seed-germinating" promoters (those promoters active during seed germination). See Thompson et al. (1989) BioEssays 10:108. Such seed-preferred promoters include, but are not limited to, Cim1 (cytokinin-induced message); cZ19B1 (maize 19 kDa zein); and milps (myo-inositol-1-phosphate synthase) (see U.S. Pat. No. 6,225,529, herein incorporated by reference). Gamma-zein and Glob-1 are endosperm-specific promoters. For dicots, seed-specific promoters include, but are not limited to, bean □-phaseolin, napin, □-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also WO 00/12733, where seed-preferred promoters from end1 and end2 genes are disclosed. A promoter that has "preferred" expression in a particular tissue is expressed in that tissue to a greater degree than in at least one other plant tissue. Some tissue-preferred promoters show expression almost exclusively in the particular tissue.

In an embodiment, the plant-expressed promoter is a vascular-specific promoter such as a phloem-specific promoter. A "vascular-specific" promoter, as used herein, is a promoter which is at least expressed in vascular cells, or a promoter which is preferentially expressed in vascular cells. Expression of a vascular-specific promoter need not be exclusively in vascular cells, expression in other cell types or tissues is possible. A "phloem-specific promoter" as used herein, is a plant-expressible promoter which is at least expressed in phloem cells, or a promoter which is preferentially expressed in phloem cells.

Expression of a phloem-specific promoter need not be exclusively in phloem cells, expression in other cell types or tissues, e.g., xylem tissue, is possible. In one embodiment of this invention, a phloem-specific promoter is a plant-expressible promoter at least expressed in phloem cells, wherein the expression in non-phloem cells is more limited (or absent) compared to the expression in phloem cells. Examples of suitable vascular-specific or phloem-specific promoters in accordance with this invention include but are not limited to the promoters selected from the group consisting of: the SCSV3, SCSV4, SCSV5, and SCSV7 promoters (Schunmann et al. (2003) *Plant Functional Biology* 30:453-60; the rolC gene promoter of *Agrobacterium rhizogenes* (Kiyokawa et al. (1994) *Plant Physiology* 104:801-02; Pandolfini et al. (2003) *BioMedCentral* (*BMC*) *Biotechnology* 3:7, (www.biomedcentral.com/1472-6750/3/7); Graham et al. (1997) *Plant Mol. Biol.* 33:729-35; Guivarc'h et al. (1996); Almon et al. (1997) *Plant Physiol.* 115:1599-607; the rolA gene promoter of *Agrobacterium rhizogenes* (Dehio et al. (1993) *Plant Mol. Biol.* 23:1199-210); the promoter of the *Agrobacterium tumefaciens* T-DNA gene 5 (Korber et al. (1991) *EMBO J.* 10:3983-91); the rice sucrose synthase RSs1 gene promoter (Shi et al. (1994) *J. Exp. Bot.* 45:623-31); the CoYMV or *Commelina* yellow mottle badnavirus promoter (Medberry et al. (1992) *Plant Cell* 4:185-92; Zhou et al. (1998) *Chin. J. Biotechnol.* 14:9-16); the CFDV or coconut foliar decay virus promoter (Rohde et al. (1994) *Plant Mol. Biol.* 27:623-28; Hehn and Rhode (1998) *J. Gen. Virol.* 79:1495-99); the RTBV or rice tungro bacilliform virus promoter (Yin and Beachy (1995) *Plant J.* 7:969-80; Yin et al. (1997) *Plant J.* 12:1179-80); the pea glutamin synthase GS3A gene (Edwards et al. (1990) *Proc. Natl. Acad. Sci. USA* 87:3459-63; Brears et al. (1991) *Plant J.* 1:235-44); the inv CD111 and inv CD141 promoters of the potato invertase genes (Hedley et al. (2000) *J. Exp. Botany* 51:817-21); the promoter isolated from *Arabidopsis* shown to have phloem-specific expression in tobacco by Kertbundit et al. (1991) *Proc. Natl. Acad. Sci. USA* 88:5212-16); the VAHOX1 promoter region (Tornero et al. (1996) *Plant J.* 9:639-48); the pea cell wall invertase gene promoter (Zhang et al. (1996) *Plant Physiol.* 112:1111-17); the promoter of the endogenous cotton protein related to chitinase of US published patent application 20030106097, an acid invertase gene promoter from carrot (Ramloch-Lorenz et al. (1993) *The Plant J.* 4:545-54); the promoter of the sulfate transporter gene, Sultr1; 3 (Yoshimoto et al. (2003) *Plant Physiol.* 131:1511-17); a promoter of a sucrose synthase gene (Nolte and Koch (1993) *Plant Physiol.* 101:899-905); and the promoter of a tobacco sucrose transporter gene (Kuhn et al. (1997) *Science* 275-1298-1300).

Possible promoters also include the Black Cherry promoter for Prunasin Hydrolase (PH DL1.4 PRO) (U.S. Pat. No. 6,797,859), Thioredoxin H promoter from cucumber and rice (Fukuda A et al. (2005). *Plant Cell Physiol.* 46(11): 1779-86), Rice (RSs1) (Shi, T. Wang et al. (1994). *J. Exp.* Bot. 45(274): 623-631) and maize sucrose synthase-1 promoters (Yang., N-S. et al. (1990) *PNAS* 87:4144-4148), PP2 promoter from pumpkin Guo, H. et al. (2004) *Transgenic Research* 13:559-566), At SUC2 promoter (Truernit, E. et al. (1995) *Planta* 196(3):564-70., At SAM-1 (S-adenosylmethionine synthetase) (Mijnsbrugge K V. et al. (1996) *Plant Cell. Physiol.* 37(8): 1108-1115), and the Rice tungro bacilliform virus (RTBV) promoter (Bhattacharyya-Pakrasi et al. (1993) *Plant J.* 4(1):71-79).

Where low level expression is desired, weak promoters will be used. Generally, the term "weak promoter" as used herein refers to a promoter that drives expression of a coding sequence at a low level. By low level expression at levels of about 1/1000 transcripts to about 1/100,000 transcripts to about 1/500,000 transcripts is intended. Alternatively, it is recognized that the term "weak promoters" also encompasses promoters that drive expression in only a few cells and not in others to give a total low level of expression. Where a promoter drives expression at unacceptably high levels, portions of the promoter sequence can be deleted or modified to decrease expression levels.

Such weak constitutive promoters include, for example the core promoter of the Rsyn7 promoter (WO 99/43838 and U.S. Pat. No. 6,072,050), the core 35S CaMV promoter, and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142; and 6,177,611.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Sci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Bairn et al. (1991) *Proc. Natl. Acad. Sci. USA* 88:5072-5076; Wyborski et al. (1991) *Nucleic Acids* Res. 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. The above list of selectable marker genes is not meant to be limiting. Any selectable marker gene can be used with the compositions and methods described herein.

VI. Compositions Comprising Silencing Elements

One or more of the polynucleotides comprising the silencing element may be provided as an external composition such as a spray or powder to the plant, plant part, seed, a plant insect pest, or an area of cultivation. In another example, a plant is transformed with a DNA construct or expression cassette for expression of at least one silencing element. In either composition, the silencing element, when ingested by an insect, can reduce the level of a target pest sequence and thereby control the pest (i.e., a Coleopteran plant pest including a *Diabrotica* plant pest, such as, *D. virgifera virgifera, D. barberi, D. virgifera zeae, D. speciosa*, or *D. undecimpunctata howardi*). It is recognized that the composition may comprise a cell (such as plant cell or a bacterial cell), in which a polynucleotide encoding the silencing element is stably incorporated into the genome and operably linked to promoters active in the cell. Compositions comprising a mixture of cells, some cells expressing at least one silencing element are also encompassed. In other embodiments, compositions comprising the silencing elements are not contained in a cell. In such embodiments, the composition can be applied to an area inhabited by a plant insect pest. In one embodiment, the composition is applied externally to a plant (i.e., by spraying a field or area of cultivation) to protect the plant from the pest. Methods of applying nucleotides in such a manner are known to those of skill in the art.

A composition disclosed herein may further be formulated as bait. In this embodiment, the compositions comprise a food substance or an attractant which enhances the attractiveness of the composition to the pest.

A composition comprising the silencing element may be formulated in an agriculturally suitable and/or environmentally acceptable carrier. Such carriers may be any material that the animal, plant or environment to be treated can tolerate. Furthermore, the carrier must be such that the composition remains effective at controlling a plant insect pest. Examples of such carriers include water, saline, Ringer's solution, dextrose or other sugar solutions, Hank's solution, and other aqueous physiologically balanced salt solutions, phosphate buffer, bicarbonate buffer and Tris buffer. In addition, the composition may include compounds that increase the half-life of a composition. Various insecticidal formulations can also be found in, for example, US Publications 2008/0275115, 2008/0242174, 2008/0027143, 2005/0042245, and 2004/0127520.

It is recognized that the polynucleotides comprising sequences encoding the silencing element may be used to transform organisms to provide for host organism production of these components, and subsequent application of the host organism to the environment of the target pest(s). Such host organisms include baculoviruses, bacteria, and the like. In this manner, the combination of polynucleotides encoding the silencing element may be introduced via a suitable vector into a microbial host, and said host applied to the environment, or to plants or animals.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be stably incorporated into the genome of the cell (e.g., chromosome, plasmid, plastid, or mitochondrial DNA), converted into an autonomous replicon, or transiently expressed (e.g., transfected mRNA).

Microbial hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, provide for stable maintenance and expression of the sequences encoding the silencing element, and desirably, provide for improved protection of the components from environmental degradation and inactivation.

Such microorganisms include bacteria, algae, and fungi. Of particular interest are microorganisms such as bacteria, e.g., *Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc*, and *Alcaligenes*, fungi, particularly yeast, e.g., *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agro bacteria, Rhodopseudomonas spheroides, Xanthomonas campestris, Rhizobium melioti, Alcaligenes entrophus, Clavibacter xyli* and *Azotobacter vinlandir*, and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae*, and *Aureobasidium pollulans*. Of particular interest are the pigmented microorganisms.

A number of ways are available for introducing the polynucleotide comprising the silencing element into the microbial host under conditions that allow for stable maintenance and expression of such nucleotide encoding sequences. For example, expression cassettes can be constructed which include the nucleotide constructs of interest operably linked with the transcriptional and translational regulatory signals for expression of the nucleotide constructs, and a nucleotide sequence homologous with a sequence in the host organism, whereby integration will occur, and/or a replication system that is functional in the host, whereby integration or stable maintenance will occur.

Transcriptional and translational regulatory signals include, but are not limited to, promoters, transcriptional initiation start sites, operators, activators, enhancers, other regulatory elements, ribosomal binding sites, an initiation codon, termination signals, and the like. See, for example, U.S. Pat. Nos. 5,039,523 and 4,853,331; EP 0480762A2; Sambrook et al. (2000); *Molecular Cloning: A Laboratory Manual* (3rd edition; Cold Spring Harbor Laboratory Press, Plainview, N.Y.); Davis et al. (1980) *Advanced Bacterial Genetics* (Cold Spring Harbor Laboratory, Cold Spring Harbor, N.Y.); and the references cited therein.

Suitable host cells include the prokaryotes and the lower eukaryotes, such as fungi. Illustrative prokaryotes, both Gram-negative and Gram-positive, include Enterobacteriaceae, such as *Escherichia, Erwinia, Shigella, Salmonella*, and *Proteus*; Bacillaceae; Rhizobiceae, such as *Rhizobium*; Spirillaceae, such as photobacterium, *Zymomonas, Serratia, Aeromonas, Vibrio, Desulfovibrio, Spirillum*; Lactobacillaceae; Pseudomonadaceae, such as *Pseudomonas* and *Acetobacter*; Azotobacteraceae and Nitrobacteraceae. Among eukaryotes are fungi, such as Phycomycetes and Ascomycetes, which includes yeast, such as *Saccharomyces* and *Schizosaccharomyces*; and Basidiomycetes yeast, such as *Rhodotorula, Aureobasidium, Sporobolomyces*, and the like.

Characteristics of particular interest in selecting a host cell may include ease of introducing the coding sequence into the host, availability of expression systems, efficiency of expression, stability in the host, and the presence of auxiliary genetic capabilities. Characteristics of interest for use as a pesticide microcapsule include protective qualities, such as thick cell walls, pigmentation, and intracellular packaging or formation of inclusion bodies; leaf affinity; lack of mammalian toxicity; attractiveness to pests for ingestion; and the like. Other considerations include ease of formulation and handling, economics, storage stability, and the like.

Host organisms of particular interest include yeast, such as *Rhodotorula* spp., *Aureobasidium* spp., *Saccharomyces* spp., and *Sporobolomyces* spp., phylloplane organisms such as *Pseudomonas* spp., *Erwinia* spp., and *Flavobacterium* spp., and other such organisms, including *Pseudomonas aeruginosa, Pseudomonas fluorescens, Saccharomyces cerevisiae, Bacillus thuringiensis, Escherichia coli, Bacillus subtilis*, and the like.

The sequences encoding the silencing elements encompassed by the invention may be introduced into microorganisms that multiply on plants (epiphytes) to deliver these components to potential target pests. Epiphytes, for example, can be gram-positive or gram-negative bacteria.

A silencing element may be fermented in a bacterial host and the resulting bacteria processed and used as a microbial spray in the same manner that *Bacillus thuringiensis* strains have been used as insecticidal sprays. Any suitable microorganism can be used for this purpose. By way of example, *Pseudomonas* has been used to express *Bacillus thuringiensis* endotoxins as encapsulated proteins and the resulting cells processed and sprayed as an insecticide Gaertner et al. (1993), in *Advanced Engineered Pesticides*, ed. L. Kim (Marcel Decker, Inc.).

Alternatively, the components of the invention are produced by introducing heterologous genes into a cellular host. Expression of the heterologous sequences results, directly or indirectly, in the intracellular production of a silencing element. These compositions may then be formulated in accordance with conventional techniques for application to the environment hosting a target pest, e.g., soil, water, and foliage of plants. See, for example, EPA 0192319, and the references cited therein.

A transformed microorganism can be formulated with an acceptable carrier into separate or combined compositions that are, for example, a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

Such compositions disclosed above may be obtained by the addition of a surface-active agent, an inert carrier, a preservative, a humectant, a feeding stimulant, an attractant, an encapsulating agent, a binder, an emulsifier, a dye, a UV protectant, a buffer, a flow agent or fertilizers, micronutrient donors, or other preparations that influence plant growth. One or more agrochemicals including, but not limited to, herbicides, insecticides, fungicides, bactericides, nematicides, molluscicides, acaracides, plant growth regulators, harvest aids, and fertilizers, can be combined with carriers, surfactants or adjuvants customarily employed in the art of formulation or other components to facilitate product handling and application for particular target pests. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients (i.e., at least one silencing element) are normally applied in the form of compositions and can be applied to the crop area, plant, or seed to be treated. For example, the compositions may be applied to grain in preparation for or during storage in a grain bin or silo, etc. The compositions may be applied simultaneously or in succession with other compounds. Methods of applying an active ingredient or a composition that contains at least one silencing element include, but are not limited to, foliar application, seed coating, and soil application. The number of applications and the rate of application depend on the intensity of infestation by the corresponding pest.

Suitable surface-active agents include, but are not limited to, anionic compounds such as a carboxylate of, for example, a metal; carboxylate of a long chain fatty acid; an N-acylsarcosinate; mono- or di-esters of phosphoric acid with fatty alcohol ethoxylates or salts of such esters; fatty alcohol sulfates such as sodium dodecyl sulfate, sodium octadecyl sulfate, or sodium cetyl sulfate; ethoxylated fatty alcohol sulfates; ethoxylated alkylphenol sulfates; lignin sulfonates; petroleum sulfonates; alkyl aryl sulfonates such as alkyl-benzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitan fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include, but are not limited to, inorganic minerals such as kaolin, phyllosilicates, carbonates, sulfates, phosphates, or botanical materials such as cork, powdered corncobs, peanut hulls, rice hulls, and walnut shells.

The compositions comprising a silencing element may be in a suitable form for direct application or as a concentrate of primary composition that requires dilution with a suitable quantity of water or other dilutant before application.

The compositions (including the transformed microorganisms) may be applied to the environment of an insect pest (such as a Coleoptera plant pest or a *Diabrotica* plant pest) by, for example, spraying, atomizing, dusting, scattering, coating or pouring, introducing into or on the soil, introducing into irrigation water, by seed treatment or general application or dusting at the time when the pest has begun to appear or before the appearance of pests as a protective measure. For example, the composition(s) and/or transformed microorganism(s) may be mixed with grain to protect the grain during storage. It is generally important to obtain good control of pests in the early stages of plant growth, as this is the time when the plant can be most severely damaged. The compositions can conveniently contain another insecticide if this is thought necessary. In an embodiment of the invention, the composition(s) is applied directly to the soil, at a time of planting, in granular form of a composition of a carrier and dead cells of a *Bacillus* strain or transformed microorganism of the invention. Another embodiment is a granular form of a composition comprising an agrochemical such as, for example, an herbicide, an insecticide, a fertilizer, in an inert carrier, and dead cells of a *Bacillus* strain or transformed microorganism of the invention.

VII. Plants, Plant Parts, and Methods of Introducing Sequences into Plants

In one embodiment, the methods of the invention involve introducing a polynucleotide into a plant. "Introducing" is intended to mean presenting to the plant the polynucleotide in such a manner that the sequence gains access to the interior of a cell of the plant. The methods of the invention do not depend on a particular method for introducing a sequence into a plant, only that the polynucleotide or polypeptides gains access to the interior of at least one cell of the plant. Methods for introducing polynucleotides into plants are known in the art including, but not limited to, stable transformation methods, transient transformation methods, and virus-mediated methods.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055 and 5,981,840), direct gene transfer (Paszkowski et al. (1984) *EMBO J.* 3:2717-2722), and ballistic particle acceleration (see, for example, U.S. Pat. Nos. 4,945,050; 5,879,918; 5,886,244; and, 5,932,782; Tomes et al. (1995) in Plant Cell, Tissue, and Organ Culture: Fundamental Methods, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*).

In certain embodiments, a silencing element disclosed herein may be provided to a plant using a variety of transient transformation methods. Such transient transformation methods include, but are not limited to, the introduction of the protein or variants or fragments thereof directly into the plant or the introduction of the transcript into the plant. Such methods include, for example, microinjection or particle bombardment. See, for example, Crossway et al. (1986) Mol Gen. Genet. 202:179-185; Nomura et al. (1986) Plant Sci. 44:53-58; Hepler et al. (1994) Proc. Natl. Acad. Sci. 91: 2176-2180 and Hush et al. (1994) The Journal of Cell Science 107:775-784, all of which are herein incorporated by reference. Alternatively, polynucleotides can be transiently transformed into the plant using techniques known in the art. Such techniques include viral vector systems and the precipitation of the polynucleotide in a manner that precludes subsequent release of the DNA. Such methods include the use of particles coated with polyethylimine (PEI; Sigma # P3143).

In other embodiments, the polynucleotides disclosed herein may be introduced into plants by contacting plants with a virus or viral nucleic acids. Generally, such methods involve incorporating a nucleotide construct of the invention within a viral DNA or RNA molecule. Further, it is recognized that promoters may also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853. Briefly, the polynucleotides disclosed herein may be contained in transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the compositions and methods described herein provide transformed seeds (also referred to as "transgenic seed") having a polynucleotide disclosed herein, for example, an expression cassette, stably incorporated into their genome.

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The compositions and methods described herein may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (Citrus spp.), cocoa (*Theobroma cacao*), tea (*Camellia sinensis*), banana (Musa spp.), avocado (*Persea americana*), fig (*Ficus casica*), guava (*Psidium guajava*), mango (*Mangifera indica*), olive (*Olea europaea*), *papaya* (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), *hydrangea* (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and *chrysanthemum.*

Conifers that may be employed in practicing the compositions and methods described herein include, for example, pines such as loblolly pine (*Pinus taeda*), slash pine (*Pinus elliotii*), *ponderosa* pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In certain embodiments, the compositions and methods described herein can be used with plants such as crop plants (for example, corn, alfalfa, sunflower, *Brassica*, soybean, cotton, safflower, peanut, sorghum, wheat, millet, tobacco, etc.). In other embodiments, corn and soybean plants and sugarcane plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

VIII. Stacking of Traits in Transgenic Plant

Transgenic plants may comprise a stack of one or more target polynucleotides as set forth in SEQ ID NOS.: 1-53 or 107-254, or variants or fragments thereof, or complements thereof, as disclosed herein with one or more additional polynucleotides resulting in the production or suppression of multiple polypeptide sequences. Transgenic plants comprising stacks of polynucleotide sequences can be obtained by either or both of traditional breeding methods or through genetic engineering methods. These methods include, but are not limited to, breeding individual lines each comprising a polynucleotide of interest, transforming a transgenic plant comprising an expression construct comprising various target polynucleotides as set forth in SEQ ID NOS.: 1-53 or 107-254, or encoding silencing elements directed to such target sequence variants or fragments thereof, or complements thereof, as disclosed herein with a subsequent gene and co-transformation of genes into a single plant cell. As used herein, the term “stacked” includes having the multiple traits present in the same plant (i.e., both traits are incorporated into the nuclear genome, one trait is incorporated into the nuclear genome and one trait is incorporated into the genome of a plastid or both traits are incorporated into the genome of a plastid). In one non-limiting example, “stacked traits” comprise a molecular stack where the sequences are physically adjacent to each other. A trait, as used herein, refers to the phenotype derived from a particular sequence or groups of sequences. Co-transformation of polynucleotides can be carried out using single transformation vectors comprising multiple polynucleotides or polynucleotides carried separately on multiple vectors. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. It is further recognized that polynucleotide sequences can be stacked at a desired genomic location using a site-specific recombination system. See, for example, WO 1999/25821, WO 1999/25854, WO 1999/25840, WO 1999/25855 and WO 1999/25853.

In some embodiments the various target polynucleotides as set forth in SEQ ID NOS.: 1-53 or 107-254, silencing elements directed to such target sequences, and variants or fragments thereof, or complements thereof, as disclosed herein, alone or stacked with one or more additional insect resistance traits can be stacked with one or more additional input traits (e.g., herbicide resistance, fungal resistance, virus resistance, stress tolerance, disease resistance, male sterility, stalk strength, and the like) or output traits (e.g., increased yield, modified starches, improved oil profile, balanced amino acids, high lysine or methionine, increased digestibility, improved fiber quality, drought resistance, and the like). Thus, the polynucleotide embodiments can be used to provide a complete agronomic package of improved crop quality with the ability to flexibly and cost effectively control any number of agronomic pests.

Transgenes useful for stacking include, but are not limited to, to those as described herein below.

i. Transgenes that Confer Resistance to Insects or Disease (A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example, Jones, et al., (1994) Science 266:789 (cloning of the tomato Cf-9 gene for resistance to *Cladosporium fulvum*); Martin, et al., (1993) Science 262: 1432 (tomato Pto gene for resistance to *Pseudomonas syringae* pv. tomato encodes a protein kinase); Mindrinos, et al., (1994) Cell 78:1089 (*Arabidopsis* RSP2 gene for resistance to *Pseudomonas syringae*), McDowell and Woffenden, (2003) Trends Biotechnol. 21(4):178-83 and Toyoda, et al., (2002) Transgenic Res. 11(6):567-82. A plant resistant to a disease is one that is more resistant to a pathogen as compared to the wild type plant.

(B) Genes encoding a *Bacillus thuringiensis* protein, a derivative thereof or a synthetic polypeptide modeled thereon. See, for example, Geiser, et al., (1986) *Gene* 48:109, who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC® Accession Numbers 40098, 67136, 31995 and 31998. Other non-limiting examples of *Bacillus thuringiensis* transgenes being genetically engineered are given in the following patents and patent applications and hereby are incorporated by reference for this purpose: U.S. Pat. Nos. 5,188,960; 5,689,052; 5,880,275; 5,986,177; 6,023,013, 6,060,594, 6,063,597, 6,077,824, 6,620,988, 6,642,030, 6,713,259, 6,893,826, 7,105,332; 7,179,965, 7,208,474; 7,227,056, 7,288,643, 7,323,556, 7,329,736, 7,449,552, 7,468,278, 7,510,878, 7,521,235, 7,544,862, 7,605,304, 7,696,412, 7,629,504, 7,705,216, 7,772,465, 7,790,846, 7,858,849 and WO 1991/14778; WO 1999/31248; WO 2001/12731; WO 1999/24581 and WO 1997/40162.

Genes encoding pesticidal proteins may also be stacked including but are not limited to: insecticidal proteins from *Pseudomonas* sp. such as PSEEN3174 (Monalysin, (2011) *PLoS Pathogens,* 7:1-13), from *Pseudomonas protegens* strain CHAO and Pf-5 (previously *fluorescens*) (Pechy-Tarr, (2008) *Environmental Microbiology* 10:2368-2386: GenBank Accession No. EU400157); from *Pseudomonas Taiwanensis* (Liu, et al., (2010) *J. Agric. Food Chem.* 58:12343-12349) and from *Pseudomonas* pseudoalcligenes (Zhang, et al., (2009) *Annals of Microbiology* 59:45-50 and Li, et al., (2007) *Plant Cell Tiss. Organ Cult.* 89:159-168); insecticidal proteins from *Photorhabdus* sp. and *Xenorhabdus* sp. (Hinchliffe, et al., (2010) *The Open Toxinology Journal* 3:101-118 and Morgan, et al., (2001) *Applied and Envir. Micro.* 67:2062-2069), U.S. Pat. Nos. 6,048,838, and 6,379,946; a PIP-1 polypeptide of US Patent Publication US20140007292; an AfIP-1A and/or AfIP-1B polypeptide of US Patent Publication US20140033361; a PHI-4 polypeptide of US Patent Publication US20140274885 and US20160040184; a PIP-47 polypeptide of PCT Publication Number WO2015/023846, a PIP-72 polypeptide of PCT Publication Number WO2015/038734; a PtIP-50 polypeptide and a PtIP-65 polypeptide of PCT Publication Number WO2015/120270; a PtIP-83 polypeptide of PCT Publication Number WO2015/120276; a PtIP-96 polypeptide of PCT Serial Number PCT/US15/55502; and δ-endotoxins including, but not limited to, the Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry 28, Cry 29, Cry 30, Cry31, Cry32, Cry33, Cry34, Cry35, Cry36, Cry37, Cry38, Cry39, Cry40, Cry41, Cry42, Cry43, Cry44, Cry45, Cry 46, Cry47, Cry49, Cry 51 and Cry55 classes of δ-endotoxin genes and the *B. thuringiensis* cytolytic Cyt1 and Cyt2 genes. Members of these classes of *B. thuringiensis* insecticidal proteins include, but are not limited to Cry1Aa1 (Accession # AAA22353); Cry1Aa2 (Accession # Accession # AAA22552); Cry1Aa3 (Accession # BAA00257); Cry1Aa4 (Accession # CAA31886); Cry1Aa5 (Accession # BAA04468); Cry1Aa6 (Accession # AAA86265); Cry1Aa7 (Accession # AAD46139); Cry1Aa8 (Accession #126149); Cry1Aa9 (Accession # BAA77213); Cry1Aa10 (Accession # AAD55382); Cry1Aa11 (Accession # CAA70856); Cry1Aa12 (Accession # AAP80146); Cry1Aa13 (Accession # AAM44305); Cry1Aa14 (Accession # AAP40639); Cry1Aa15 (Accession # AAY66993); Cry1Aa16 (Accession # HQ439776); Cry1Aa17 (Accession # HQ439788); Cry1Aa18 (Accession # HQ439790); Cry1Aa19 (Accession # HQ685121); Cry1Aa20 (Accession # JF340156); Cry1Aa21 (Accession # JN651496); Cry1Aa22 (Accession # KC158223); Cry1Ab1 (Accession # AAA22330); Cry1Ab2 (Accession # AAA22613); Cry1Ab3 (Accession # AAA22561); Cry1Ab4 (Accession # BAA00071); Cry1Ab5 (Accession # CAA28405); Cry1Ab6 (Accession # AAA22420); Cry1Ab7 (Accession # CAA31620); Cry1Ab8 (Accession # AAA22551); Cry1Ab9 (Accession # CAA38701); Cry1Ab10 (Accession # A29125); Cry1Ab11 (Accession #112419); Cry1Ab12 (Accession # AAC64003); Cry1Ab13 (Accession # AAN76494); Cry1Ab14 (Accession # AAG16877); Cry1Ab15 (Accession # AAO13302); Cry1Ab16 (Accession # AAK55546); Cry1Ab17 (Accession # AAT46415); Cry1Ab18 (Accession # AAQ88259); Cry1Ab19 (Accession # AAW31761); Cry1Ab20 (Accession # ABB72460); Cry1Ab21 (Accession # ABS18384); Cry1Ab22 (Accession # ABW87320); Cry1Ab23 (Accession # HQ439777); Cry1Ab24 (Accession # HQ439778); Cry1Ab25 (Accession # HQ685122); Cry1Ab26 (Accession # HQ847729); Cry1Ab27 (Accession # JN135249); Cry1Ab28 (Accession # JN135250); Cry1Ab29 (Accession # JN135251); Cry1Ab30 (Accession # JN135252); Cry1Ab31 (Accession # JN135253); Cry1Ab32 (Accession # JN135254); Cry1Ab33 (Accession # AAS93798); Cry1Ab34 (Accession # KC156668); Cry1Ab-like (Accession # AAK14336); Cry1Ab-like (Accession # AAK14337); Cry1Ab-like (Accession # AAK14338); Cry1Ab-like (Accession # ABG88858); Cry1Ac1 (Accession # AAA22331); Cry1Ac2 (Accession # AAA22338); Cry1Ac3 (Accession # CAA38098); Cry1Ac4 (Accession # AAA73077); Cry1Ac5 (Accession # AAA22339); Cry1Ac6 (Accession # AAA86266); Cry1Ac7 (Accession # AAB46989); Cry1Ac8 (Accession # AAC44841); Cry1Ac9 (Accession # AAB49768); Cry1Ac10 (Accession # CAA05505); Cry1Ac11 (Accession # CAA10270); Cry1Ac12 (Accession #112418); Cry1Ac13 (Accession # AAD38701); Cry1Ac14 (Accession # AAQ06607); Cry1Ac15 (Accession # AAN07788); Cry1Ac16 (Accession # AAU87037); Cry1Ac17 (Accession # AAX18704); Cry1Ac18 (Accession # AAY88347); Cry1Ac19 (Accession # ABD37053); Cry1Ac20 (Accession # ABB89046); Cry1Ac21 (Accession # AAY66992); Cry1Ac22 (Accession # ABZ01836); Cry1Ac23 (Accession # CAQ30431); Cry1Ac24 (Accession # ABL01535); Cry1Ac25 (Accession # FJ513324); Cry1Ac26 (Accession # FJ617446); Cry1Ac27 (Accession # FJ617447); Cry1Ac28 (Accession # ACM90319); Cry1Ac29 (Accession # DQ438941); Cry1Ac30 (Accession

GQ227507); Cry1Ac31 (Accession # GU446674); Cry1Ac32 (Accession # HM061081); Cry1Ac33 (Accession # GQ866913); Cry1Ac34 (Accession # HQ230364); Cry1Ac35 (Accession # JF340157); Cry1Ac36 (Accession # JN387137); Cry1Ac37 (Accession # JQ317685); Cry1Ad1 (Accession # AAA22340); Cry1Ad2 (Accession # CAA01880); Cry1Ae1 (Accession # AAA22410); Cry1Af1 (Accession # AAB82749); Cry1Ag1 (Accession # AAD46137); Cry1Ah1 (Accession # AAQ14326); Cry1Ah2 (Accession # ABB76664); Cry1Ah3 (Accession # HQ439779); Cry1Ai1 (Accession # AA039719); Cry1Ai2 (Accession # HQ439780); Cry1A-like (Accession # AAK14339); Cry1Ba1 (Accession # CAA29898); Cry1Ba2 (Accession # CAA65003); Cry1Ba3 (Accession # AAK63251); Cry1Ba4 (Accession # AAK51084); Cry1Ba5 (Accession # ABO20894); Cry1Ba6 (Accession # ABL60921); Cry1Ba7 (Accession # HQ439781); Cry1Bb1 (Accession # AAA22344); Cry1Bb2 (Accession # HQ439782); Cry1Bc1 (Accession # CAA86568); Cry1Bd1 (Accession # AAD10292); Cry1Bd2 (Accession # AAM93496); Cry1Be1 (Accession # AAC32850); Cry1Be2 (Accession # AAQ52387); Cry1Be3 (Accession # ACV96720); Cry1Be4 (Accession # HM070026); Cry1Bf1 (Accession # CAC50778); Cry1Bf2 (Accession # AAQ52380); Cry1Bg1 (Accession # AA039720); Cry1Bh1 (Accession # HQ589331); Cry1Bi1 (Accession # KC156700); Cry1Ca1 (Accession # CAA30396); Cry1Ca2 (Accession # CAA31951); Cry1Ca3 (Accession # AAA22343); Cry1Ca4 (Accession # CAA01886); Cry1Ca5 (Accession # CAA65457); Cry1Ca6 [1] (Accession # AAF37224); Cry1Ca7 (Accession # AAG50438); Cry1Ca8 (Accession # AAM00264); Cry1Ca9 (Accession # AAL79362); Cry1Ca10 (Accession # AAN16462); Cry1Ca11 (Accession # AAX53094); Cry1Ca12 (Accession # HM070027); Cry1Ca13 (Accession # HQ412621); Cry1Ca14 (Accession # JN651493); Cry1Cb1 (Accession # M97880); Cry1Cb2 (Accession # AAG35409); Cry1Cb3 (Accession # ACD50894); Cry1Cb-like (Accession # AAX63901); Cry1Da1 (Accession # CAA38099); Cry1Da2 (Accession #176415); Cry1Da3 (Accession # HQ439784); Cry1Db1 (Accession # CAA80234); Cry1Db2 (Accession # AAK48937); Cry1Dc1 (Accession # ABK35074); Cry1Ea1 (Accession # CAA37933); Cry1Ea2 (Accession # CAA39609); Cry1Ea3 (Accession # AAA22345); Cry1Ea4 (Accession # AAD04732); Cry1Ea5 (Accession # A15535); Cry1Ea6 (Accession # AAL50330); Cry1Ea7 (Accession # AAW72936); Cry1Ea8 (Accession # ABX11258); Cry1Ea9 (Accession # HQ439785); Cry1Ea10 (Accession # ADR00398); Cry1Ea11 (Accession # JQ652456); Cry1Eb1 (Accession # AAA22346); Cry1Fa1 (Accession # AAA22348); Cry1Fa2 (Accession # AAA22347); Cry1Fa3 (Accession # HM070028); Cry1Fa4 (Accession # HM439638); Cry1Fb1 (Accession # CAA80235); Cry1Fb2 (Accession # BAA25298); Cry1Fb3 (Accession # AAF21767); Cry1Fb4 (Accession # AAC10641); Cry1Fb5 (Accession # AA013295); Cry1Fb6 (Accession # ACD50892); Cry1Fb7 (Accession # ACD50893); Cry1Ga1 (Accession # CAA80233); Cry1Ga2 (Accession # CAA70506); Cry1Gb1 (Accession # AAD10291); Cry1Gb2 (Accession # AA013756); Cry1Gc1 (Accession # AAQ52381); Cry1Ha1 (Accession # CAA80236); Cry1Hb1 (Accession # AAA79694); Cry1Hb2 (Accession # HQ439786); Cry1H-like (Accession # AAF01213); Cry1Ia1 (Accession # CAA44633); Cry1Ia2 (Accession # AAA22354); Cry1Ia3 (Accession # AAC36999); Cry1Ia4 (Accession # AAB00958); Cry1Ia5 (Accession # CAA70124); Cry1Ia6 (Accession # AAC26910); Cry1Ia7 (Accession # AAM73516); Cry1Ia8 (Accession # AAK66742); Cry1Ia9 (Accession # AAQ08616); Cry1Ia10 (Accession # AAP86782); Cry1Ia11 (Accession # CAC85964); Cry1Ia12 (Accession # AAV53390); Cry1Ia13 (Accession # ABF83202); Cry1Ia14 (Accession # ACG63871); Cry1Ia15 (Accession # FJ617445); Cry1Ia16 (Accession # FJ617448); Cry1Ia17 (Accession # GU989199); Cry1Ia18 (Accession # ADK23801); Cry1Ia19 (Accession # HQ439787); Cry1Ia20 (Accession # JQ228426); Cry1Ia21 (Accession # JQ228424); Cry1Ia22 (Accession # JQ228427); Cry1Ia23 (Accession # JQ228428); Cry1Ia24 (Accession # JQ228429); Cry1Ia25 (Accession # JQ228430); Cry1Ia26 (Accession # JQ228431); Cry1Ia27 (Accession # JQ228432); Cry1Ia28 (Accession # JQ228433); Cry1Ia29 (Accession # JQ228434); Cry1Ia30 (Accession # JQ317686); Cry1Ia31 (Accession # JX944038); Cry1Ia32 (Accession # JX944039); Cry1Ia33 (Accession # JX944040); Cry1Ib1 (Accession # AAA82114); Cry1Ib2 (Accession # ABW88019); Cry1Ib3 (Accession # ACD75515); Cry1Ib4 (Accession # HM051227); Cry1Ib5 (Accession # HM070028); Cry1Ib6 (Accession # ADK38579); Cry1Ib7 (Accession # JN571740); Cry1Ib8 (Accession # JN675714); Cry1Ib9 (Accession # JN675715); Cry1Ib10 (Accession # JN675716); Cry1Ib11 (Accession # JQ228423); Cry1Ic1 (Accession # AAC62933); Cry1Ic2 (Accession # AAE71691); Cry1Id1 (Accession # AAD44366); Cry1Id2 (Accession # JQ228422); Cry1Ie1 (Accession # AAG43526); Cry1Ie2 (Accession # HM439636); Cry1Ie3 (Accession # KC156647); Cry1Ie4 (Accession # KCI56681); Cry1If1 (Accession # AAQ52382); Cry1Ig1 (Accession # KC156701); Cry1I-like (Accession # AAC31094); Cry1I-like (Accession # ABG88859); Cry1Ja1 (Accession # AAA22341); Cry1Ja2 (Accession # HM070030); Cry1Ja3 (Accession # JQ228425); Cry1Jb1 (Accession # AAA98959); Cry1Jc1 (Accession # AAC31092); Cry1Jc2 (Accession # AAQ52372); Cry1Jd1 (Accession # CAC50779); Cry1Ka1 (Accession # AAB00376); Cry1Ka2 (Accession # HQ439783); Cry1La1 (Accession # AAS60191); Cry1La2 (Accession # HM070031); Cry1Ma1 (Accession # FJ884067); Cry1Ma2 (Accession # KC156659); Cry1Na1 (Accession # KC156648); Cry1Nb1 (Accession # KC156678); Cry1-like (Accession # AAC31091); Cry2Aa1 (Accession # AAA22335); Cry2Aa2 (Accession # AAA83516); Cry2Aa3 (Accession # D86064); Cry2Aa4 (Accession # AAC04867); Cry2Aa5 (Accession # CAA10671); Cry2Aa6 (Accession # CAA10672); Cry2Aa7 (Accession # CAA10670); Cry2Aa8 (Accession # AA013734); Cry2Aa9 (Accession # AA013750); Cry2Aa10 (Accession # AAQ04263); Cry2Aa11 (Accession # AAQ52384); Cry2Aa12 (Accession # ABI83671); Cry2Aa13 (Accession # ABL01536); Cry2Aa14 (Accession # ACF04939); Cry2Aa15 (Accession # JN426947); Cry2Ab1 (Accession # AAA22342); Cry2Ab2 (Accession # CAA39075); Cry2Ab3 (Accession # AAG36762); Cry2Ab4 (Accession # AA013296); Cry2Ab5 (Accession # AAQ04609); Cry2Ab6 (Accession # AAP59457); Cry2Ab7 (Accession # AAZ66347); Cry2Ab8 (Accession # ABC95996); Cry2Ab9 (Accession # ABC74968); Cry2Ab10 (Accession # EF157306); Cry2Ab11 (Accession # CAM84575); Cry2Ab12 (Accession # ABM21764); Cry2Ab13 (Accession # ACG76120); Cry2Ab14 (Accession # ACG76121); Cry2Ab15 (Accession # HM037126); Cry2Ab16 (Accession # GQ866914); Cry2Ab17 (Accession # HQ439789); Cry2Ab18 (Accession # JN135255); Cry2Ab19 (Accession # JN135256); Cry2Ab20 (Accession # JN135257); Cry2Ab21 (Accession

JN135258); Cry2Ab22 (Accession # JN135259); Cry2Ab23 (Accession # JN135260); Cry2Ab24 (Accession # JN135261); Cry2Ab25 (Accession # JN415485); Cry2Ab26 (Accession # JN426946); Cry2Ab27 (Accession # JN415764); Cry2Ab28 (Accession # JN651494); Cry2Ac1 (Accession # CAA40536); Cry2Ac2 (Accession # AAG35410); Cry2Ac3 (Accession # AAQ52385); Cry2Ac4 (Accession # ABC95997); Cry2Ac5 (Accession # ABC74969); Cry2Ac6 (Accession # ABC74793); Cry2Ac7 (Accession # CAL18690); Cry2Ac8 (Accession # CAM09325); Cry2Ac9 (Accession # CAM09326); Cry2Ac10 (Accession # ABN15104); Cry2Ac11 (Accession # CAM83895); Cry2Ac12 (Accession # CAM83896); Cry2Ad1 (Accession # AAF09583); Cry2Ad2 (Accession # ABC86927); Cry2Ad3 (Accession # CAK29504); Cry2Ad4 (Accession # CAM32331); Cry2Ad5 (Accession # CA078739); Cry2Ae1 (Accession # AAQ52362); Cry2Af1 (Accession # AB030519); Cry2Af2 (Accession # GQ866915); Cry2Ag1 (Accession # ACH91610); Cry2Ah1 (Accession # EU939453); Cry2Ah2 (Accession # ACL80665); Cry2Ah3 (Accession # GU073380); Cry2Ah4 (Accession # KC156702); Cry2Ai1 (Accession # FJ788388); Cry2Aj (Accession #); Cry2Ak1 (Accession # KC156660); Cry2Ba1 (Accession # KC156658); Cry3Aa1 (Accession # AAA22336); Cry3Aa2 (Accession # AAA22541); Cry3Aa3 (Accession # CAA68482); Cry3Aa4 (Accession # AAA22542); Cry3Aa5 (Accession # AAA50255); Cry3Aa6 (Accession # AAC43266); Cry3Aa7 (Accession # CAB41411); Cry3Aa8 (Accession # AAS79487); Cry3Aa9 (Accession # AAW05659); Cry3Aa10 (Accession # AAU29411); Cry3Aa11 (Accession # AAW82872); Cry3Aa12 (Accession # ABY49136); Cry3Ba1 (Accession # CAA34983); Cry3Ba2 (Accession # CAA00645); Cry3Ba3 (Accession # JQ397327); Cry3Bb1 (Accession # AAA22334); Cry3Bb2 (Accession # AAA74198); Cry3Bb3 (Accession #115475); Cry3Ca1 (Accession # CAA42469); Cry4Aa1 (Accession # CAA68485); Cry4Aa2 (Accession # BAA00179); Cry4Aa3 (Accession # CAD30148); Cry4Aa4 (Accession # AFB18317); Cry4A-like (Accession # AAY96321); Cry4Ba1 (Accession # CAA30312); Cry4Ba2 (Accession # CAA30114); Cry4Ba3 (Accession # AAA22337); Cry4Ba4 (Accession # BAA00178); Cry4Ba5 (Accession # CAD30095); Cry4Ba-like (Accession # ABC47686); Cry4Ca1 (Accession # EU646202); Cry4Cb1 (Accession # FJ403208); Cry4Cb2 (Accession # FJ597622); Cry4Cc1 (Accession # FJ403207); Cry5Aa1 (Accession # AAA67694); Cry5Ab1 (Accession # AAA67693); Cry5Ac1 (Accession #134543); Cry5Ad1 (Accession # ABQ82087); Cry5Ba1 (Accession # AAA68598); Cry5Ba2 (Accession # ABW88931); Cry5Ba3 (Accession # AFJ04417); Cry5Ca1 (Accession # HM461869); Cry5Ca2 (Accession # ZP_04123426); Cry5Da1 (Accession # HM461870); Cry5Da2 (Accession # ZP_04123980); Cry5Ea1 (Accession # HM485580); Cry5Ea2 (Accession # ZP_04124038); Cry6Aa1 (Accession # AAA22357); Cry6Aa2 (Accession # AAM46849); Cry6Aa3 (Accession # ABH03377); Cry6Ba1 (Accession # AAA22358); Cry7Aa1 (Accession # AAA22351); Cry7Ab1 (Accession # AAA21120); Cry7Ab2 (Accession # AAA21121); Cry7Ab3 (Accession # ABX24522); Cry7Ab4 (Accession # EU380678); Cry7Ab5 (Accession # ABX79555); Cry7Ab6 (Accession # ACI44005); Cry7Ab7 (Accession # ADB89216); Cry7Ab8 (Accession # GU145299); Cry7Ab9 (Accession # ADD92572); Cry7Ba1 (Accession # ABB70817); Cry7Bb1 (Accession # KC156653); Cry7Ca1 (Accession # ABR67863); Cry7Cb1 (Accession # KC156698); Cry7Da1 (Accession # ACQ99547); Cry7Da2 (Accession # HM572236); Cry7Da3 (Accession # KC156679); Cry7Ea1 (Accession # HM035086); Cry7Ea2 (Accession # HM132124); Cry7Ea3 (Accession # EEM19403); Cry7Fa1 (Accession # HM035088); Cry7Fa2 (Accession # EEM19090); Cry7Fb1 (Accession # HM572235); Cry7Fb2 (Accession # KC156682); Cry7Ga1 (Accession # HM572237); Cry7Ga2 (Accession # KC156669); Cry7Gb1 (Accession # KC156650); Cry7Gc1 (Accession # KC156654); Cry7Gd1 (Accession # KC156697); Cry7Ha1 (Accession # KC156651); Cry7Ia1 (Accession # KC156665); Cry7Ja1 (Accession # KC156671); Cry7Ka1 (Accession # KC156680); Cry7Kb1 (Accession # BAM99306); Cry7La1 (Accession # BAM99307); Cry8Aa1 (Accession # AAA21117); Cry8Ab1 (Accession # EU044830); Cry8Ac1 (Accession # KC156662); Cry8Ada (Accession # KC156684); Cry8Ba1 (Accession # AAA21118); Cry8Bb1 (Accession # CAD57542); Cry8Bc1 (Accession # CAD57543); Cry8Ca1 (Accession # AAA21119); Cry8Ca2 (Accession # AAR98783); Cry8Ca3 (Accession # EU625349); Cry8Ca4 (Accession # ADB54826); Cry8Da1 (Accession # BAC07226); Cry8Da2 (Accession # BD133574); Cry8Da3 (Accession # BD133575); Cry8Db1 (Accession # BAF93483); Cry8Ea1 (Accession # AAQ73470); Cry8Ea2 (Accession # EU047597); Cry8Ea3 (Accession # KC855216); Cry8Fa1 (Accession # AAT48690); Cry8Fa2 (Accession # HQ174208); Cry8Fa3 (Accession # AFH78109); Cry8Ga1 (Accession # AAT46073); Cry8Ga2 (Accession # ABC42043); Cry8Ga3 (Accession # FJ198072); Cry8Ha1 (Accession # AAW81032); Cry8Ia1 (Accession # EU381044); Cry8Ia2 (Accession # GU073381); Cry8Ia3 (Accession # HM044664); Cry8Ia4 (Accession # KC156674); Cry8Ib1 (Accession # GU325772); Cry8Ib2 (Accession # KC156677); Cry8Ja1 (Accession # EU625348); Cry8Ka1 (Accession # FJ422558); Cry8Ka2 (Accession # ACN87262); Cry8Kb1 (Accession # HM123758); Cry8Kb2 (Accession # KC156675); Cry8La1 (Accession # GU325771); Cry8Ma1 (Accession # HM044665); Cry8Ma2 (Accession # EEM86551); Cry8Ma3 (Accession # HM210574); Cry8Na1 (Accession # HM640939); Cry8Pa1 (Accession # HQ388415); Cry8Qa1 (Accession # HQ441166); Cry8Qa2 (Accession # KC152468); Cry8Ra1 (Accession # AFP87548); Cry8Sa1 (Accession # JQ740599); Cry8Ta1 (Accession # KC156673); Cry8-like (Accession # FJ770571); Cry8-like (Accession # ABS53003); Cry9Aa1 (Accession # CAA41122); Cry9Aa2 (Accession # CAA41425); Cry9Aa3 (Accession # GQ249293); Cry9Aa4 (Accession # GQ249294); Cry9Aa5 (Accession # JX174110); Cry9Aa like (Accession # AAQ52376); Cry9Ba1 (Accession # CAA52927); Cry9Ba2 (Accession # GU299522); Cry9Bb1 (Accession # AAV28716); Cry9Ca1 (Accession # CAA85764); Cry9Ca2 (Accession # AAQ52375); Cry9Da1 (Accession # BAA19948); Cry9Da2 (Accession # AAB97923); Cry9Da3 (Accession # GQ249293); Cry9Da4 (Accession # GQ249297); Cry9Db1 (Accession # AAX78439); Cry9Dc1 (Accession # KC156683); Cry9Ea1 (Accession # BAA34908); Cry9Ea2 (Accession # AA012908); Cry9Ea3 (Accession # ABM21765); Cry9Ea4 (Accession # ACE88267); Cry9Ea5 (Accession # ACF04743); Cry9Ea6 (Accession # ACG63872); Cry9Ea7 (Accession # FJ380927); Cry9Ea8 (Accession # GQ249292); Cry9Ea9 (Accession # JN651495); Cry9Eb1 (Accession # CAC50780); Cry9Eb2 (Accession # GQ249298); Cry9Eb3 (Accession # KC156646); Cry9Ec1 (Accession # AAC63366); Cry9Ed1 (Accession # AAX78440); Cry9Ee1

(Accession # GQ249296); Cry9Ee2 (Accession # KC156664); Cry9Fa1 (Accession # KC156692); Cry9Ga1 (Accession # KC156699); Cry9-like (Accession # AAC63366); Cry10Aa1 (Accession # AAA22614); Cry10Aa2 (Accession # E00614); Cry10Aa3 (Accession # CAD30098); Cry10Aa4 (Accession # AFB18318); Cry10A-like (Accession # DQ167578); Cry11Aa1 (Accession # AAA22352); Cry11Aa2 (Accession # AAA22611); Cry11Aa3 (Accession # CAD30081); Cry11Aa4 (Accession # AFB18319); Cry11Aa-like (Accession # DQ166531); Cry11Ba1 (Accession # CAA60504); Cry11Bb1 (Accession # AAC97162); Cry11Bb2 (Accession # HM068615); Cry12Aa1 (Accession # AAA22355); Cry13Aa1 (Accession # AAA22356); Cry14Aa1 (Accession # AAA21516); Cry14Ab1 (Accession # KC156652); Cry11Aa1 (Accession # AAA22333); Cry16Aa1 (Accession # CAA63860); Cry11Aa1 (Accession # CAA67841); Cry11Aa1 (Accession # CAA67506); Cry18Ba1 (Accession # AAF89667); Cry18Ca1 (Accession # AAF89668); Cry19Aa1 (Accession # CAA68875); Cry19Ba1 (Accession # BAA32397); Cry19Ca1 (Accession # AFM37572); Cry20Aa1 (Accession # AAB93476); Cry20Ba1 (Accession # ACS93601); Cry20Ba2 (Accession # KC156694); Cry20-like (Accession # GQ144333); Cry21Aa1 (Accession #132932); Cry21Aa2 (Accession #166477); Cry21Ba1 (Accession # BAC06484); Cry21Ca1 (Accession # JF521577); Cry21Ca2 (Accession # KC156687); Cry21Da1 (Accession # JF521578); Cry22Aa1 (Accession #134547); Cry22Aa2 (Accession # CAD43579); Cry22Aa3 (Accession # ACD93211); Cry22Ab1 (Accession # AAK50456); Cry22Ab2 (Accession # CAD43577); Cry22Ba1 (Accession # CAD43578); Cry22Bb1 (Accession # KC156672); Cry23Aa1 (Accession # AAF76375); Cry24Aa1 (Accession # AAC61891); Cry24Ba1 (Accession # BAD32657); Cry24Ca1 (Accession # CAJ43600); Cry25Aa1 (Accession # AAC61892); Cry26Aa1 (Accession # AAD25075); Cry27Aa1 (Accession # BAA82796); Cry28Aa1 (Accession # AAD24189); Cry28Aa2 (Accession # AAG00235); Cry29Aa1 (Accession # CAC80985); Cry30Aa1 (Accession # CAC80986); Cry30Ba1 (Accession # BAD00052); Cry30Ca1 (Accession # BAD67157); Cry30Ca2 (Accession # ACU24781); Cry30Da1 (Accession # EF095955); Cry30Db1 (Accession # BAE80088); Cry30Ea1 (Accession # ACC95445); Cry30Ea2 (Accession # FJ499389); Cry30Fa1 (Accession # ACI22625); Cry30Ga1 (Accession # ACG60020); Cry30Ga2 (Accession # HQ638217); Cry31Aa1 (Accession # BAB11757); Cry31Aa2 (Accession # AAL87458); Cry31Aa3 (Accession # BAE79808); Cry31Aa4 (Accession # BAF32571); Cry31Aa5 (Accession # BAF32572); Cry31Aa6 (Accession # BAI44026); Cry31Ab1 (Accession # BAE79809); Cry31Ab2 (Accession # BAF32570); Cry31Ac1 (Accession # BAF34368); Cry31Ac2 (Accession # AB731600); Cry31Ad1 (Accession # BAI44022); Cry32Aa1 (Accession # AAG36711); Cry32Aa2 (Accession # GU063849); Cry32Ab1 (Accession # GU063850); Cry32Ba1 (Accession # BAB78601); Cry32Ca1 (Accession # BAB78602); Cry32Cb1 (Accession # KC156708); Cry32Da1 (Accession # BAB78603); Cry32Ea1 (Accession # GU324274); Cry32Ea2 (Accession # KC156686); Cry32Eb1 (Accession # KC156663); Cry32Fa1 (Accession # KC156656); Cry32Ga1 (Accession # KC156657); Cry32Ha1 (Accession # KC156661); Cry32Hb1 (Accession # KC156666); Cry32Ia1 (Accession # KC156667); Cry32Ja1 (Accession # KC156685); Cry32Ka1 (Accession # KC156688); Cry32La1 (Accession # KC156689); Cry32Ma1 (Accession # KC156690); Cry32Mb1 (Accession # KC156704); Cry32Na1 (Accession # KC156691); Cry32Oa1 (Accession # KC156703); Cry32Pa1 (Accession # KC156705); Cry32Qa1 (Accession # KC156706); Cry32Ra1 (Accession # KC156707); Cry32Sa1 (Accession # KC156709); Cry32Ta1 (Accession # KC156710); Cry32Ua1 (Accession # KC156655); Cry33Aa1 (Accession # AAL26871); Cry34Aa1 (Accession # AAG50341); Cry34Aa2 (Accession # AAK64560); Cry34Aa3 (Accession # AAT29032); Cry34Aa4 (Accession # AAT29030); Cry34Ab1 (Accession # AAG41671); Cry34Ac1 (Accession # AAG50118); Cry34Ac2 (Accession # AAK64562); Cry34Ac3 (Accession # AAT29029); Cry34Ba1 (Accession # AAK64565); Cry34Ba2 (Accession # AAT29033); Cry34Ba3 (Accession # AAT29031); Cry35Aa1 (Accession # AAG50342); Cry35Aa2 (Accession # AAK64561); Cry35Aa3 (Accession # AAT29028); Cry35Aa4 (Accession # AAT29025); Cry35Ab1 (Accession # AAG41672); Cry35Ab2 (Accession # AAK64563); Cry35Ab3 (Accession # AY536891); Cry35Ac1 (Accession # AAG50117); Cry35Ba1 (Accession # AAK64566); Cry35Ba2 (Accession # AAT29027); Cry35Ba3 (Accession # AAT29026); Cry36Aa1 (Accession # AAK64558); Cry37Aa1 (Accession # AAF76376); Cry38Aa1 (Accession # AAK64559); Cry39Aa1 (Accession # BAB72016); Cry40Aa1 (Accession # BAB72018); Cry40Ba1 (Accession # BAC77648); Cry40Ca1 (Accession # EU381045); Cry40Da1 (Accession # ACF15199); Cry41Aa1 (Accession # BAD35157); Cry41Ab1 (Accession # BAD35163); Cry41Ba1 (Accession # HM461871); Cry41Ba2 (Accession # ZP_04099652); Cry42Aa1 (Accession # BAD35166); Cry43Aa1 (Accession # BAD15301); Cry43Aa2 (Accession # BAD95474); Cry43Ba1 (Accession # BAD15303); Cry43Ca1 (Accession # KC156676); Cry43Cb1 (Accession # KC156695); Cry43Cc1 (Accession # KC156696); Cry43-like (Accession # BAD15305); Cry44Aa (Accession # BAD08532); Cry45Aa (Accession # BAD22577); Cry46Aa (Accession # BAC79010); Cry46Aa2 (Accession # BAG68906); Cry46Ab (Accession # BAD35170); Cry47Aa (Accession # AAY24695); Cry48Aa (Accession # CAJ18351); Cry48Aa2 (Accession # CAJ86545); Cry48Aa3 (Accession # CAJ86546); Cry48Ab (Accession # CAJ86548); Cry48Ab2 (Accession # CAJ86549); Cry49Aa (Accession # CAH56541); Cry49Aa2 (Accession # CAJ86541); Cry49Aa3 (Accession # CAJ86543); Cry49Aa4 (Accession # CAJ86544); Cry49Ab1 (Accession # CAJ86542); Cry50Aa1 (Accession # BAE86999); Cry50Ba1 (Accession # GU446675); Cry50Ba2 (Accession # GU446676); Cry51Aa1 (Accession # ABI14444); Cry51Aa2 (Accession # GU570697); Cry52Aa1 (Accession # EF613489); Cry52Ba1 (Accession # FJ361760); Cry53Aa1 (Accession # EF633476); Cry53Ab1 (Accession # FJ361759); Cry54Aa1 (Accession # ACA52194); Cry54Aa2 (Accession # GQ140349); Cry54Ba1 (Accession # GU446677); Cry55Aa1 (Accession # ABW88932); Cry54Ab1 (Accession # JQ916908); Cry55Aa2 (Accession # AAE33526); Cry56Aa1 (Accession # ACU57499); Cry56Aa2 (Accession # GQ483512); Cry56Aa3 (Accession # JX025567); Cry57Aa1 (Accession # ANC87261); Cry58Aa1 (Accession # ANC87260); Cry59Ba1 (Accession # JN790647); Cry59Aa1 (Accession # ACR43758); Cry60Aa1 (Accession # ACU24782); Cry60Aa2 (Accession # EAO57254); Cry60Aa3 (Accession # EEM99278); Cry60Ba1 (Accession # GU810818); Cry60Ba2 (Accession # EAO57253); Cry60Ba3 (Accession # EEM99279); Cry61Aa1 (Accession # HM035087); Cry61Aa2 (Accession # HM132125); Cry61Aa3 (Accession # EEM19308); Cry62Aa1 (Accession # HM054509); Cry63Aa1 (Accession # BAI44028); Cry64Aa1 (Accession # BAJ05397); Cry65Aa1 (Accession # HM461868);

Cry65Aa2 (Accession # ZP_04123838); Cry66Aa1 (Accession # HM485581); Cry66Aa2 (Accession # ZP_04099945); Cry67Aa1 (Accession # HM485582); Cry67Aa2 (Accession # ZP_04148882); Cry68Aa1 (Accession # HQ113114); Cry69Aa1 (Accession # HQ401006); Cry69Aa2 (Accession # JQ821388); Cry69Ab1 (Accession # JN209957); Cry70Aa1 (Accession # JN646781); Cry70Ba1 (Accession # ADO51070); Cry70Bb1 (Accession # EEL67276); Cry71Aa1 (Accession # JX025568); Cry72Aa1 (Accession # JX025569).

Examples of δ-endotoxins also include but are not limited to Cry1A proteins of U.S. Pat. Nos. 5,880,275 and 7,858,849; a DIG-3 or DIG-11 toxin (N-terminal deletion of α-helix 1 and/or α-helix 2 variants of Cry proteins such as Cry1A) of U.S. Pat. Nos. 8,304,604 and 8,304,605, Cry1B of U.S. patent application Ser. No. 10/525,318; Cry1C of U.S. Pat. No. 6,033,874; Cry1F of U.S. Pat. Nos. 5,188,960, 6,218,188; Cry1A/F chimeras of U.S. Pat. Nos. 7,070,982; 6,962,705 and 6,713,063); a Cry2 protein such as Cry2Ab protein of U.S. Pat. No. 7,064,249); a Cry3A protein including but not limited to an engineered hybrid insecticidal protein (eHIP) created by fusing unique combinations of variable regions and conserved blocks of at least two different Cry proteins (US Patent Application Publication Number 2010/0017914); a Cry4 protein; a Cry5 protein; a Cry6 protein; Cry8 proteins of U.S. Pat. Nos. 7,329,736, 7,449,552, 7,803,943, 7,476,781, 7,105,332, 7,378,499 and 7,462,760; a Cry9 protein such as such as members of the Cry9A, Cry9B, Cry9C, Cry9D, Cry9E, and Cry9F families; a Cry15 protein of Naimov, et al., (2008) *Applied and Environmental Microbiology* 74:7145-7151; a Cry22, a Cry34Ab1 protein of U.S. Pat. Nos. 6,127,180, 6,624,145 and 6,340,593; a CryET33 and CryET34 protein of U.S. Pat. Nos. 6,248,535, 6,326,351, 6,399,330, 6,949,626, 7,385,107 and 7,504,229; a CryET33 and CryET34 homologs of US Patent Publication Number 2006/0191034, 2012/0278954, and PCT Publication Number WO 2012/139004; a Cry35Ab1 protein of U.S. Pat. Nos. 6,083,499, 6,548,291 and 6,340,593; a Cry46 protein, a Cry 51 protein, a Cry binary toxin; a TIC901 or related toxin; TIC807 of US 2008/0295207; ET29, ET37, TIC809, TIC810, TIC812, TIC127, TIC128 of PCT US 2006/033867; TIC1100, TIC 860, a TIC867, a TIC868, TIC869, and TIC836 of US Patent Publication Number 2016/0108428. AXMI-027, AXMI-036, and AXMI-038 of U.S. Pat. No. 8,236,757; AXMI-031, AXMI-039, AXMI-040, AXMI-049 of U.S. Pat. No. 7,923,602; AXMI-018, AXMI-020, and AXMI-021 of WO 2006/083891; AXMI-010 of WO 2005/038032; AXMI-003 of WO 2005/021585; AXMI-008 of US 2004/0250311; AXMI-006 of US 2004/0216186; AXMI-007 of US 2004/0210965; AXMI-009 of US 2004/0210964; AXMI-014 of US 2004/0197917; AXMI-004 of US 2004/0197916; AXMI-028 and AXMI-029 of WO 2006/119457; AXMI-007, AXMI-008, AXMI-0080rf2, AXMI-009, AXMI-014 and AXMI-004 of WO 2004/074462; AXMI-150 of U.S. Pat. No. 8,084,416; AXMI-205 of US20110023184; AXMI-011, AXMI-012, AXMI-013, AXMI-015, AXMI-019, AXMI-044, AXMI-037, AXMI-043, AXMI-033, AXMI-034, AXMI-022, AXMI-023, AXMI-041, AXMI-063, and AXMI-064 of US 2011/0263488; AXMI-R1 and related proteins of US 2010/0197592; AXMI221Z, AXMI222z, AXMI223z, AXMI224z and AXMI225z of WO 2011/103248; AXMI218, AXMI219, AXMI220, AXMI226, AXMI227, AXMI228, AXMI229, AXMI230, and AXMI231 of WO11/103247; AXMI-115, AXMI-113, AXMI-005, AXMI-163 and AXMI-184 of U.S. Pat. No. 8,334,431; AXMI-001, AXMI-002, AXMI-030, AXMI-035, and AXMI-045 of US 2010/0298211; AXMI-066 and AXMI-076 of US20090144852; AXMI128, AXMI130, AXMI131, AXMI133, AXMI140, AXMI141, AXMI142, AXMI143, AXMI144, AXMI146, AXMI148, AXMI149, AXMI152, AXMI153, AXMI154, AXMI155, AXMI156, AXMI157, AXMI158, AXMI162, AXMI165, AXMI166, AXMI167, AXMI168, AXMI169, AXMI170, AXMI171, AXMI172, AXMI173, AXMI174, AXMI175, AXMI176, AXMI177, AXMI178, AXMI179, AXMI180, AXMI181, AXMI182, AXMI185, AXMI186, AXMI187, AXMI188, AXMI189 of U.S. Pat. No. 8,318,900; AXMI079, AXMI080, AXMI081, AXMI082, AXMI091, AXMI092, AXMI096, AXMI097, AXMI098, AXMI099, AXMI100, AXMI101, AXMI102, AXMI103, AXMI104, AXMI107, AXMI108, AXMI109, AXMI110, AXMI111, AXMI112, AXMI114, AXMI116, AXMI117, AXMI118, AXMI119, AXMI120, AXMI121, AXMI122, AXMI123, AXMI124, AXMI1257, AXMI1268, AXMI127, AXMI129, AXMI164, AXMI151, AXMI161, AXMI183, AXMI132, AXMI138, AXMI137 of US 2010/0005543; and Cry proteins such as Cry1A and Cry3A having modified proteolytic sites of U.S. Pat. No. 8,319,019; a Cry1Ac, Cry2Aa and Cry1Ca toxin protein from *Bacillus thuringiensis* strain VBTS 2528 of US Patent Application Publication Number 2011/0064710, and an IP1B of PCT publication number WO 2016/061197. Other Cry proteins are well known to one skilled in the art (see, Crickmore, et al., "*Bacillus thuringiensis* toxin nomenclature" (2011), at lifesci.sussex.ac.uk/home/Neil_Crickmore/Bt/which can be accessed on the world-wide web using the "www" prefix). The insecticidal activity of Cry proteins is well known to one skilled in the art (for review, see, van Frannkenhuyzen, (2009) *J. Invert. Path.* 101:1-16). The use of Cry proteins as transgenic plant traits is well known to one skilled in the art and Cry-transgenic plants including but not limited to Cry1Ac, Cry1Ac+Cry2Ab, Cry1Ab, Cry1A.105, Cry1F, Cry1Fa2, Cry1F+Cry1Ac, Cry2Ab, Cry3A, mCry3A, Cry3Bb1, Cry34Ab1, Cry35Ab1, Vip3A, mCry3A, Cry9c and CBI-Bt have received regulatory approval (see, Sanahuja, (2011) *Plant Biotech Journal* 9:283-300 and the CERA (2010) GM Crop Database Center for Environmental Risk Assessment (CERA), ILSI Research Foundation, Washington D.C. at cera-gmc.org/index.php?action=gm_crop_database which can be accessed on the world-wide web using the "www" prefix). More than one pesticidal proteins well known to one skilled in the art can also be expressed in plants such as Vip3Ab & Cry1Fa (US2012/0317682), Cry1BE & Cry1F (US2012/0311746), Cry1CA & Cry1AB (US2012/0311745), Cry1F & CryCa (US2012/0317681), Cry1DA & Cry1BE (US2012/0331590), Cry1DA & Cry1Fa (US2012/0331589), Cry1AB & Cry1BE (US2012/0324606), and Cry1Fa & Cry2Aa, Cry1I or Cry1E (US2012/0324605)); Cry34Ab/35Ab and Cry6Aa (US20130167269); Cry34Ab/VCry35Ab & Cry3Aa (US20130167268); Cry3A and Cry1Ab or Vip3Aa (US20130116170); and Cry1F, Cry34Ab1, and Cry35Ab1 (PCT/US2010/060818). Pesticidal proteins also include insecticidal lipases including lipid acyl hydrolases of U.S. Pat. No. 7,491,869, and cholesterol oxidases such as from *Streptomyces* (Purcell et al. (1993) *Biochem Biophys Res Commun* 15:1406-1413). Pesticidal proteins also include VIP (vegetative insecticidal proteins) toxins of U.S. Pat. Nos. 5,877,012, 6,107,279, 6,137,033, 7,244,820, 7,615,686, and 8,237,020, and the like. Other VIP proteins are well known to one skilled in the art (see, lifesci.sussex.ac.uk/home/Neil_Crickmore/Bt/vip.html which can be accessed on the world-wide web using the "www" prefix). Pesticidal proteins also include toxin complex (TC) proteins, obtainable from organisms such as

*Xenorhabdus, Photorhabdus* and *Paenibacillus* (see, U.S. Pat. Nos. 7,491,698 and 8,084,418). Some TC proteins have "stand alone" insecticidal activity and other TC proteins enhance the activity of the stand-alone toxins produced by the same given organism. The toxicity of a "stand-alone" TC protein (from *Photorhabdus, Xenorhabdus* or *Paenibacillus*, for example) can be enhanced by one or more TC protein "potentiators" derived from a source organism of a different genus. There are three main types of TC proteins. As referred to herein, Class A proteins ("Protein A") are stand-alone toxins. Class B proteins ("Protein B") and Class C proteins ("Protein C") enhance the toxicity of Class A proteins. Examples of Class A proteins are TcbA, TcdA, XptA1 and XptA2. Examples of Class B proteins are TcaC, TcdB, XptB1Xb and XptC1Wi. Examples of Class C proteins are TccC, XptC1Xb and XptB1Wi. Pesticidal proteins also include spider, snake and scorpion venom proteins. Examples of spider venom peptides include but are not limited to lycotoxin-1 peptides and mutants thereof (U.S. Pat. No. 8,334,366).

(C) A polynucleotide encoding an insect-specific hormone or pheromone such as an ecdysteroid and juvenile hormone, a variant thereof, a mimetic based thereon or an antagonist or agonist thereof. See, for example, the disclosure by Hammock, et al., (1990) Nature 344:458, of baculovirus expression of cloned juvenile hormone esterase, an inactivator of juvenile hormone.

(D) A polynucleotide encoding an insect-specific peptide which, upon expression, disrupts the physiology of the affected pest. For example, see the disclosures of, Regan, (1994) J. Biol. Chem. 269:9 (expression cloning yields DNA coding for insect diuretic hormone receptor); Pratt, et al., (1989) Biochem. Biophys. Res. Comm 163:1243 (an allostatin is identified in *Diploptera puntata*); Chattopadhyay, et al., (2004) Critical Reviews in Microbiology 30(1):33-54; Zjawiony, (2004) J Nat Prod 67(2):300-310; Carlini and Grossi-de-Sa, (2002) Toxicon 40(11):1515-1539; Ussuf, et al., (2001) Curr Sci. 80(7):847-853 and Vasconcelos and Oliveira, (2004) Toxicon 44(4):385-403. See also, U.S. Pat. No. 5,266,317 to Tomalski, et al., who disclose genes encoding insect-specific toxins.

(E) A polynucleotide encoding an enzyme responsible for a hyperaccumulation of a monoterpene, a sesquiterpene, a steroid, hydroxamic acid, a phenylpropanoid derivative or another non-protein molecule with insecticidal activity.

(F) A polynucleotide encoding an enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See, PCT Application WO 1993/02197 in the name of Scott, et al., which discloses the nucleotide sequence of a callase gene. DNA molecules which contain chitinase-encoding sequences can be obtained, for example, from the ATCC under Accession Numbers 39637 and 67152. See also, Kramer, et al., (1993) Insect Biochem. Molec. Biol. 23:691, who teach the nucleotide sequence of a cDNA encoding tobacco hookworm chitinase and Kawalleck, et al., (1993) Plant Molec. Biol. 21:673, who provide the nucleotide sequence of the parsley ubi4-2 polyubiquitin gene, and U.S. Pat. Nos. 6,563,020; 7,145,060 and 7,087,810.

(G) A polynucleotide encoding a molecule that stimulates signal transduction. For example, see the disclosure by Botella, et al., (1994) Plant Molec. Biol. 24:757, of nucleotide sequences for mung bean calmodulin cDNA clones, and Griess, et al., (1994) Plant Physiol. 104:1467, who provide the nucleotide sequence of a maize calmodulin cDNA clone.

(H) A polynucleotide encoding a hydrophobic moment peptide. See, PCT Application WO 1995/16776 and U.S. Pat. No. 5,580,852 disclosure of peptide derivatives of Tachyplesin which inhibit fungal plant pathogens) and PCT Application WO 1995/18855 and U.S. Pat. No. 5,607,914 (teaches synthetic antimicrobial peptides that confer disease resistance).

(I) A polynucleotide encoding a membrane permease, a channel former or a channel blocker. For example, see the disclosure by Jaynes, et al., (1993) Plant Sci. 89:43, of heterologous expression of a cecropin-beta lytic peptide analog to render transgenic tobacco plants resistant to *Pseudomonas solanacearum*.

(J) A gene encoding a viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., (1990) Ann. Rev. Phytopathol. 28:451. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(K) A gene encoding an insect-specific antibody or an immunotoxin derived therefrom. Thus, an antibody targeted to a critical metabolic function in the insect gut would inactivate an affected enzyme, killing the insect. Cf. Taylor, et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(L) A gene encoding a virus-specific antibody. See, for example, Tavladoraki, et al., (1993) Nature 366:469, who show that transgenic plants expressing recombinant antibody genes are protected from virus attack.

(M) A polynucleotide encoding a developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See, Lamb, et al., (1992) Bio/Technology 10:1436. The cloning and characterization of a gene which encodes a bean endopolygalacturonase-inhibiting protein is described by Toubart, et al., (1992) Plant J. 2:367.

(N) A polynucleotide encoding a developmental-arrestive protein produced in nature by a plant. For example, Logemann, et al., (1992) Bio/Technology 10:305, have shown that transgenic plants expressing the barley ribosome-inactivating gene have an increased resistance to fungal disease.

(O) Genes involved in the Systemic Acquired Resistance (SAR) Response and/or the pathogenesis related genes. Briggs, (1995) Current Biology 5(2), Pieterse and Van Loon, (2004) Curr. Opin. Plant Bio. 7(4):456-64 and Somssich, (2003) *Cell* 113(7):815-6.

(P) Antifungal genes (Cornelissen and Melchers, (1993) Pl. Physiol. 101:709-712 and Parijs, et al., (1991) Planta 183:258-264 and Bushnell, et al., (1998) Can. J. of Plant Path. 20(2):137-149. Also see, U.S. patent application Ser. Nos. 09/950,933; 11/619,645; 11/657,710; 11/748,994; 11/774,121 and U.S. Pat. Nos. 6,891,085 and 7,306,946. LysM Receptor-like kinases for the perception of chitin fragments as a first step in plant defense response against fungal pathogens (US 2012/0110696).

(Q) Detoxification genes, such as for fumonisin, beauvericin, moniliformin and zearalenone and their structurally related derivatives. For example, see, U.S. Pat. Nos. 5,716,820; 5,792,931; 5,798,255; 5,846,812; 6,083,736; 6,538,177; 6,388,171 and 6,812,380.

(R) A polynucleotide encoding a Cystatin and cysteine proteinase inhibitors. See, U.S. Pat. No. 7,205,453.

(S) Defensin genes. See, WO 2003/000863 and U.S. Pat. Nos. 6,911,577; 6,855,865; 6,777,592 and 7,238,781.

(T) Genes conferring resistance to nematodes. See, e.g., PCT Application WO 1996/30517; PCT Application WO 1993/19181, WO 2003/033651 and Urwin, et al., (1998) Planta 204:472-479, Williamson, (1999) Curr Opin Plant Bio. 2(4):327-31; U.S. Pat. Nos. 6,284,948 and 7,301,069 and miR164 genes (WO 2012/058266).

(U) Genes that confer resistance to *Phytophthora* Root Rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker, et al., *Phytophthora* Root Rot Resistance Gene Mapping in Soybean, Plant Genome IV Conference, San Diego, Calif. (1995).

(V) Genes that confer resistance to Brown Stem Rot, such as described in U.S. Pat. No. 5,689,035 and incorporated by reference for this purpose.

(W) Genes that confer resistance to *Colletotrichum*, such as described in US Patent Application Publication US 2009/0035765 and incorporated by reference for this purpose. This includes the Rcg locus that may be utilized as a single locus conversion.

(X) Some embodiments relate to down-regulation of expression of target genes in insect pest species by interfering ribonucleic acid (RNA) molecules. PCT Publication WO 2007/074405 describes methods of inhibiting expression of target genes in invertebrate pests including Colorado potato beetle. PCT Publication WO 2005/110068 describes methods of inhibiting expression of target genes in invertebrate pests including in particular Western corn rootworm as a means to control insect infestation. Furthermore, PCT Publication WO 2009/091864 describes compositions and methods for the suppression of target genes from insect pest species including pests from the *Lygus* genus.

Nucleic acid molecules including silencing elements for targeting the vacuolar ATPase H subunit, useful for controlling a coleopteran pest population and infestation as described in US Patent Application Publication 2012/0198586. PCT Publication WO 2012/055982 describes ribonucleic acid (RNA or double stranded RNA) that inhibits or down regulates the expression of a target gene that encodes: an insect ribosomal protein such as the ribosomal protein L19, the ribosomal protein L40 or the ribosomal protein S27A; an insect proteasome subunit such as the Rpn6 protein, the Pros 25, the Rpn2 protein, the proteasome beta 1 subunit protein or the Pros beta 2 protein; an insect β-coatomer of the COPI vesicle, the γ-coatomer of the COPI vesicle, the β'-coatomer protein or the ζ-coatomer of the COPI vesicle; an insect Tetraspanine 2 A protein which is a putative transmembrane domain protein; an insect protein belonging to the actin family such as Actin 5C; an insect ubiquitin-5E protein; an insect Sec23 protein which is a GTPase activator involved in intracellular protein transport; an insect crinkled protein which is an unconventional myosin which is involved in motor activity; an insect crooked neck protein which is involved in the regulation of nuclear alternative mRNA splicing; an insect vacuolar H+-ATPase G-subunit protein and an insect Tbp-1 such as Tat-binding protein. PCT publication WO 2007/035650 describes ribonucleic acid (RNA or double stranded RNA) that inhibits or down regulates the expression of a target gene that encodes Snf7. US Patent Application publication 2011/0054007 describes polynucleotide silencing elements targeting RPS10. US Patent Application publication 2014/0275208 and US2015/0257389 describe polynucleotide silencing elements targeting RyanR and PAT3. PCT publications WO 2016/060911, WO 2016/060912, WO 2016/060913, and WO 2016/060914 describe polynucleotide silencing elements targeting COPI coatomer subunit nucleic acid molecules that confer resistance to Coleopteran and Hemipteran pests. US Patent Application Publications 2012/029750, US 20120297501, and 2012/0322660 describe interfering ribonucleic acids (RNA or double stranded RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene. US Patent Application Publication 2012/0164205 describe potential targets for interfering double stranded ribonucleic acids for inhibiting invertebrate pests including: a Chd3 Homologous Sequence, a Beta-Tubulin Homologous Sequence, a 40 kDa V-ATPase Homologous Sequence, a EF1α Homologous Sequence, a 26S Proteosome Subunit p28 Homologous Sequence, a Juvenile Hormone Epoxide Hydrolase Homologous Sequence, a Swelling Dependent Chloride Channel Protein Homologous Sequence, a Glucose-6-Phosphate 1-Dehydrogenase Protein Homologous Sequence, an Act42A Protein Homologous Sequence, a ADP-Ribosylation Factor 1 Homologous Sequence, a Transcription Factor IIB Protein Homologous Sequence, a Chitinase Homologous Sequences, a Ubiquitin Conjugating Enzyme Homologous Sequence, a Glyceraldehyde-3-Phosphate Dehydrogenase Homologous Sequence, an Ubiquitin B Homologous Sequence, a Juvenile Hormone Esterase Homolog, and an Alpha Tubuliln Homologous Sequence.

ii. Transgenes that Confer Resistance to a Herbicide.

(A) A polynucleotide encoding resistance to a herbicide that inhibits the growing point or meristem, such as an imidazolinone or a sulfonylurea. Exemplary genes in this category code for mutant ALS and AHAS enzyme as described, for example, by Lee, et al., (1988) EMBO J. 7:1241 and Mild, et al., (1990) Theor. Appl. Genet. 80:449, respectively. See also, U.S. Pat. Nos. 5,605,011; 5,013,659; 5,141,870; 5,767,361; 5,731,180; 5,304,732; 4,761,373; 5,331,107; 5,928,937 and 5,378,824; U.S. patent application Ser. No. 11/683,737 and International Publication WO 1996/33270.

(B) A polynucleotide encoding a protein for resistance to Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. U.S. Pat. No. 5,627,061 to Barry, et al., also describes genes encoding EPSPS enzymes. See also, U.S. Pat. Nos. 6,566,587; 6,338,961; 6,248,876 B1; 6,040,497; 5,804,425; 5,633,435; 5,145,783; 4,971,908; 5,312,910; 5,188,642; 5,094,945, 4,940,835; 5,866,775;

6,225,114 B1; 6,130,366; 5,310,667; 4,535,060; 4,769,061; 5,633,448; 5,510,471; Re. 36,449; RE 37,287 E and 5,491,288 and International Publications EP 1173580; WO 2001/66704; EP 1173581 and EP 1173582.

Glyphosate resistance is also imparted to plants that express a gene encoding a glyphosate oxido-reductase enzyme as described more fully in U.S. Pat. Nos. 5,776,760 and 5,463,175. In addition glyphosate resistance can be imparted to plants by the over expression of genes encoding glyphosate N-acetyltransferase. See, for example, U.S. Pat. Nos. 7,462,481; 7,405,074 and US Patent Application Publication Number US 2008/0234130. A DNA molecule encoding a mutant aroA gene can be obtained under ATCC Accession Number 39256, and the nucleotide sequence of the mutant gene is disclosed in U.S. Pat. No. 4,769,061 to Comai. EP Application Number 0 333 033 to Kumada, et al., and U.S. Pat. No. 4,975,374 to Goodman, et al., disclose nucleotide sequences of glutamine synthetase genes which confer resistance to herbicides such as L-phosphinothricin. The nucleotide sequence of a phosphinothricin-acetyl-transferase gene is provided in EP Application Numbers 0 242 246 and 0 242 236 to Leemans, et al.; De Greef, et al., (1989) Bio/Technology 7:61, describe the production of transgenic plants that express chimeric bar genes coding for phosphinothricin acetyl transferase activity. See also, U.S. Pat. Nos. 5,969,213; 5,489,520; 5,550,318; 5,874,265; 5,919,675; 5,561,236; 5,648,477; 5,646,024; 6,177,616 B1 and 5,879,903. Exemplary genes conferring resistance to phenoxy proprionic acids and cyclohexones, such as sethoxydim and haloxyfop, are the Acc1-S1, Acc1-S2 and Acc1-S3 genes described by Marshall, et al., (1992) *Theor. Appl. Genet.* 83:435.

(C) A polynucleotide encoding a protein for resistance to herbicide that inhibits photosynthesis, such as a triazine (psbA and gs+ genes) and a benzonitrile (nitrilase gene). Przibilla, et al., (1991) Plant Cell 3:169, describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC Accession Numbers 53435, 67441 and 67442. Cloning and expression of DNA coding for a glutathione S-transferase is described by Hayes, et al., (1992) Biochem. J. 285:173.

(D) A polynucleotide encoding a protein for resistance to Acetohydroxy acid synthase, which has been found to make plants that express this enzyme resistant to multiple types of herbicides, has been introduced into a variety of plants (see, e.g., Hattori, et al., (1995) Mol Gen Genet. 246:419). Other genes that confer resistance to herbicides include: a gene encoding a chimeric protein of rat cytochrome P4507A1 and yeast NADPH-cytochrome P450 oxidoreductase (Shiota, et al., (1994) Plant Physiol 106:17), genes for glutathione reductase and superoxide dismutase (Aono, et al., (1995) Plant Cell Physiol 36:1687) and genes for various phosphotransferases (Datta, et al., (1992) Plant Mol Biol 20:619).

(E) A polynucleotide encoding resistance to a herbicide targeting Protoporphyrinogen oxidase (protox) which is necessary for the production of chlorophyll. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306 B1; 6,282,837 B1 and 5,767,373 and International Publication WO 2001/12825.

(F) The aad-1 gene (originally from *Sphingobium herbicidovorans*) encodes the aryloxyalkanoate dioxygenase (AAD-1) protein. The trait confers tolerance to 2,4-dichlorophenoxyacetic acid and aryloxyphenoxypropionate (commonly referred to as "fop" herbicides such as quizalofop) herbicides. The aad-1 gene, itself, for herbicide tolerance in plants was first disclosed in WO 2005/107437 (see also, US 2009/0093366). The aad-12 gene, derived from *Delftia acidovorans*, which encodes the aryloxyalkanoate dioxygenase (AAD-12) protein that confers tolerance to 2,4-dichlorophenoxyacetic acid and pyridyloxyacetate herbicides by deactivating several herbicides with an aryloxyalkanoate moiety, including phenoxy auxin (e.g., 2,4-D, MCPA), as well as pyridyloxy auxins (e.g., fluoroxypyr, triclopyr).

(G) A polynucleotide encoding a herbicide resistant dicamba monooxygenase disclosed in US Patent Application Publication 2003/0135879 for imparting dicamba tolerance.

(H) A polynucleotide molecule encoding bromoxynil nitrilase (Bxn) disclosed in U.S. Pat. No. 4,810,648 for imparting bromoxynil tolerance.

(I) A polynucleotide molecule encoding phytoene (crtl) described in Misawa, et al., (1993) Plant J. 4:833-840 and in Misawa, et al., (1994) Plant J. 6:481-489 for norflurazon tolerance.

iii. Transgenes that Confer or Contribute to an Altered Grain Characteristic (A) Altered fatty acids, for example, by (1) Down-regulation of stearoyl-ACP to increase stearic acid content of the plant. See, Knultzon, et al., (1992) Proc. Natl. Acad. Sci. USA 89:2624 and WO 1999/64579 (Genes to Alter Lipid Profiles in Corn); (2) Elevating oleic acid via FAD-2 gene modification and/or decreasing linolenic acid via FAD-3 gene modification (see, U.S. Pat. Nos. 6,063,947; 6,323,392; 6,372,965 and WO 1993/11245); (3) Altering conjugated linolenic or linoleic acid content, such as in WO 2001/12800; (4) Altering LEC1, AGP, Dekl, Superall, mil ps, various Ipa genes such as Ipa1, Ipa3, hpt or hggt. For example, see, WO 2002/42424, WO 1998/22604, WO 2003/011015, WO 2002/057439, WO 2003/011015, U.S. Pat. Nos. 6,423,886, 6,197,561, 6,825,397 and US Patent Application Publication Numbers US 2003/0079247, US 2003/0204870 and Rivera-Madrid, et al., (1995) Proc. Natl. Acad. Sci. 92:5620-5624; (5) Genes encoding delta-8 desaturase for making long-chain polyunsaturated fatty acids (U.S. Pat. Nos. 8,058,571 and 8,338,152), delta-9 desaturase for lowering saturated fats (U.S. Pat. No. 8,063,269), Primula delta 6-desaturase for improving omega-3 fatty acid profiles; (6) Isolated nucleic acids and proteins associated with lipid and sugar metabolism regulation, in particular, lipid metabolism protein (LMP) used in methods of producing transgenic plants and modulating levels of seed storage compounds including lipids, fatty acids, starches or seed storage proteins and use in methods of modulating the seed size, seed number, seed weights, root length and leaf size of plants (EP 2404499); (7) Altering expression of a High-Level Expression of Sugar-Inducible 2 (HSI2) protein in the plant to increase or decrease expression of HSI2 in the plant. Increasing expression of HSI2 increases oil content while decreasing expression of HSI2 decreases abscisic acid sensitivity and/or increases drought resistance (US Patent Application Publication Number 2012/0066794); (8) Expression of cytochrome b5 (Cb5) alone or with FAD2 to modulate oil content in plant seed, particularly to increase the levels of omega-3 fatty acids and improve the ratio of omega-6 to omega-3 fatty acids (US Patent Application Publication Number 2011/0191904); and (9) Nucleic acid molecules encoding wrinkled1-like polypeptides for modulating sugar metabolism (U.S. Pat. No. 8,217,223).

(B) Altered phosphorus content, for example, by the (1) introduction of a phytase-encoding gene would enhance breakdown of phytate, adding more free phosphate to the transformed plant. For example, see, Van Hartingsveldt, et al., (1993) Gene 127:87, for a disclosure of the nucleotide sequence of an *Aspergillus niger* phytase gene; and (2) modulating a gene that reduces phytate content. In maize, this, for example, could be accomplished, by cloning and then re-introducing DNA associated with one or more of the alleles, such as the LPA alleles, identified in maize mutants characterized by low levels of phytic acid, such as in WO 2005/113778 and/or by altering inositol kinase activity as in WO 2002/059324, US Patent Application Publication Number 2003/0009011, WO 2003/027243, US Patent Application Publication Number 2003/0079247, WO 1999/05298, U.S. Pat. Nos. 6,197,561, 6,291,224, 6,391,348, WO 2002/059324, US Patent Application Publication Number 2003/0079247, WO 1998/45448, WO 1999/55882, WO 2001/04147.

(C) Altered carbohydrates affected, for example, by altering a gene for an enzyme that affects the branching pattern of starch or, a gene altering thioredoxin such as NTR and/or TRX (see, U.S. Pat. No. 6,531,648. which is incorporated by reference for this purpose) and/or a gamma zein knock out or mutant such as cs27 or TUSC27 or en27 (see, U.S. Pat. No. 6,858,778 and US Patent Application Publication Number 2005/0160488, US Patent Application Publication Number 2005/0204418, which are incorporated by reference for this purpose). See, Shiroza, et al., (1988) J. Bacteriol. 170:810 (nucleotide sequence of *Streptococcus* mutant fructosyltransferase gene), Steinmetz, et al., (1985) Mol. Gen. Genet. 200:220 (nucleotide sequence of *Bacillus subtilis* levansucrase gene), Pen, et al., (1992) Bio/Technology 10:292 (production of transgenic plants that express *Bacillus licheniformis* alpha-amylase), Elliot, et al., (1993) Plant Molec. Biol. 21:515 (nucleotide sequences of tomato invertase genes), Sogaard, et al., (1993) J. Biol. Chem. 268:22480 (site-directed mutagenesis of barley alpha-amylase gene) and Fisher, et al., (1993) Plant Physiol. 102:1045 (maize endosperm starch branching enzyme II), WO 1999/10498 (improved digestibility and/or starch extraction through modification of UDP-D-xylose 4-epimerase, Fragile 1 and 2, Ref1, HCHL, C4H), U.S. Pat. No. 6,232,529 (method of producing high oil seed by modification of starch levels (AGP)). The fatty acid modification genes mentioned herein may also be used to affect starch content and/or composition through the interrelationship of the starch and oil pathways.

(D) Altered antioxidant content or composition, such as alteration of tocopherol or tocotrienols. For example, see, U.S. Pat. No. 6,787,683, US Patent Application Publication Number 2004/0034886 and WO 2000/68393 involving the manipulation of antioxidant levels and WO 2003/082899 through alteration of a homogentisate geranyl geranyl transferase (hggt).

(E) Altered essential seed amino acids. For example, see, U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO 1999/40209 (alteration of amino acid compositions in seeds), WO 1999/29882 (methods for altering amino acid content of proteins), U.S. Pat. No. 5,850,016 (alteration of amino acid compositions in seeds), WO 1998/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO 1998/56935 (plant amino acid biosynthetic enzymes), WO 1998/45458 (engineered seed protein having higher percentage of essential amino acids), WO 1998/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO 1996/01905 (increased threonine), WO 1995/15392 (increased lysine), US Patent Application Publication Number 2003/0163838, US Patent Application Publication Number 2003/0150014, US Patent Application Publication Number 2004/0068767, U.S. Pat. No. 6,803,498, WO 2001/79516.

iv. Genes that Control Male-Sterility

There are several methods of conferring genetic male sterility available, such as multiple mutant genes at separate locations within the genome that confer male sterility, as disclosed in U.S. Pat. Nos. 4,654,465 and 4,727,219 to Brar, et al., and chromosomal translocations as described by Patterson in U.S. Pat. Nos. 3,861,709 and 3,710,511. In addition to these methods, Albertsen, et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing or turning "on", the promoter, which in turn allows the gene that confers male fertility to be transcribed. Non-limiting examples include: (A) Introduction of a deacetylase gene under the control of a tapetum-specific promoter and with the application of the chemical N—Ac-PPT (WO 2001/29237); (B) Introduction of various stamen-specific promoters (WO 1992/13956, WO 1992/13957); and (C) Introduction of the barnase and the barstar gene (Paul, et al., (1992) Plant Mol. Biol. 19:611-622). For additional examples of nuclear male and female sterility systems and genes, see also, U.S. Pat. Nos. 5,859,341; 6,297,426; 5,478,369; 5,824,524; 5,850,014 and 6,265,640.

v. Genes that Create a Site for Site Specific DNA Integration.

This includes the introduction of FRT sites that may be used in the FLP/FRT system and/or Lox sites that may be used in the Cre/Loxp system. For example, see, Lyznik, et al., (2003) Plant Cell Rep 21:925-932 and WO 1999/25821. Other systems that may be used include the Gln recombinase of phage Mu (Maeser, et al., (1991) Vicki Chandler, The Maize Handbook ch. 118 (Springer-Verlag 1994), the Pin recombinase of *E. coli* (Enomoto, et al., 1983) and the R/RS system of the pSRi plasmid (Araki, et al., 1992).

vi. Genes that Affect Abiotic Stress Resistance

Including but not limited to flowering, ear and seed development, enhancement of nitrogen utilization efficiency, altered nitrogen responsiveness, drought resistance or tolerance, cold resistance or tolerance and salt resistance or tolerance and increased yield under stress. Non-limiting examples include: (A) For example, see: WO 2000/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801,104, WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 199809521; (B) WO 199938977 describing genes, including CBF genes and transcription factors effective in mitigating the negative effects of freezing, high salinity and drought on plants, as well as conferring other positive effects on plant phenotype; (C) US Patent Application Publication Number 2004/0148654 and WO 2001/36596 where abscisic acid is altered in plants resulting in improved plant phenotype such as increased yield and/or increased tolerance to abiotic stress; (D) WO 2000/006341, WO 2004/090143, U.S. Pat. Nos. 7,531,723 and 6,992,237 where cytokinin expression is modified resulting in plants with increased stress tolerance, such as drought tolerance, and/or increased yield. Also see, WO 2002/02776, WO 2003/052063, JP 2002/281975, U.S. Pat. No. 6,084,153, WO 2001/64898, U.S. Pat. No. 6,177,275 and U.S. Pat. No. 6,107,547 (enhancement of nitrogen utilization and altered nitrogen responsiveness); (E) For ethylene alteration, see, US Patent Application Publication Number 2004/0128719, US Patent Application Publication Number 2003/0166197 and WO 2000/32761; (F) For plant transcription factors or transcriptional regulators of abiotic stress, see, e.g., US Patent Application Publication Number 2004/0098764 or US Patent Application Publication Number 2004/0078852; (G) Genes that increase expression of vacuolar pyrophosphatase such as AVP1 (U.S. Pat. No. 8,058,515) for increased yield; nucleic acid encoding a HSFA4 or a HSFA5 (Heat Shock Factor of the class A4 or A5) polypeptides, an oligopeptide transporter protein (OPT4-like) polypeptide; a plastochron2-like (PLA2-like) polypeptide or a Wuschel related homeobox 1-like (WOX1-like) polypeptide (U. Patent Application Publication Number US 2011/0283420); (H) Down regulation of polynucleotides encoding poly (ADP-ribose) polymerase (PARP) proteins to modulate programmed cell death (U.S. Pat. No. 8,058,510) for increased vigor; (I) Polynucleotide encoding DTP21 polypeptides for conferring drought resistance (US Patent Application Publication Number US 2011/0277181); (J) Nucleotide sequences encoding ACC Synthase 3 (ACS3) proteins for modulating development, modulating response to stress, and modulating stress tolerance (US Patent Application Publication Number US 2010/0287669); (K) Polynucleotides that encode proteins that confer a drought tolerance phenotype (DTP) for conferring drought resistance (WO 2012/058528); (L) Tocopherol cyclase (TC) genes for conferring drought and salt tolerance (US Patent Application Publication Number 2012/0272352); (M) CAAX amino terminal family proteins for stress tolerance (U.S. Pat. No. 8,338,661); (N) Mutations in the SALT encoding gene have increased stress tolerance, including increased drought resistant (US Patent Application Publication Number 2010/0257633); (O) Expression of a nucleic acid sequence encoding a polypeptide selected from the group consisting of: GRF polypeptide, RAA1-like polypeptide, SYR polypeptide, ARKL polypeptide, and YTP polypeptide increasing yield-related traits (US Patent Application Publication Number 2011/0061133); and (P) Modulating expression in a plant of a nucleic acid encoding a Class III Trehalose Phosphate Phosphatase (TPP) polypeptide for enhancing yield-related traits in plants, particularly increasing seed yield (US Patent Application Publication Number 2010/0024067).

Other genes and transcription factors that affect plant growth and agronomic traits such as yield, flowering, plant growth and/or plant structure, can be introduced or introgressed into plants, see e.g., WO 1997/49811 (LHY), WO 1998/56918 (ESD4), WO 1997/10339 and U.S. Pat. No. 6,573,430 (TFL), U.S. Pat. No. 6,713,663 (FT), WO 1996/14414 (CON), WO 1996/38560, WO 2001/21822 (VRN1), WO 2000/44918 (VRN2), WO 1999/49064 (GI), WO 2000/46358 (FR1), WO 1997/29123, U.S. Pat. Nos. 6,794,560, 6,307,126 (GAI), WO 1999/09174 (D8 and Rht) and WO 2004/076638 and WO 2004/031349 (transcription factors).

vii. Genes that Confer Increased Yield

Non-limiting examples of genes that confer increased yield are: (A) A transgenic crop plant transformed by a 1-AminoCyclopropane-1-Carboxylate Deaminase-like Polypeptide (ACCDP) coding nucleic acid, wherein expression of the nucleic acid sequence in the crop plant results in the plant's increased root growth, and/or increased yield, and/or increased tolerance to environmental stress as compared to a wild type variety of the plant (U.S. Pat. No. 8,097,769); (B) Over-expression of maize zinc finger protein gene (Zm-ZFP1) using a seed preferred promoter has been shown to enhance plant growth, increase kernel number and total kernel weight per plant (US Patent Application Publication Number 2012/0079623); (C) Constitutive over-expression of maize lateral organ boundaries (LOB) domain protein (Zm-LOBDP1) has been shown to increase kernel number and total kernel weight per plant (US Patent Application Publication Number 2012/0079622); (D) Enhancing yield-related traits in plants by modulating expression in a plant of a nucleic acid encoding a VIM1 (Variant in Methylation 1)-like polypeptide or a VTC2-like (GDP-L-galactose phosphorylase) polypeptide or a DUF1685 polypeptide or an ARF6-like (Auxin Responsive Factor) polypeptide (WO 2012/038893); (E) Modulating expression in a plant of a nucleic acid encoding a Ste20-like polypeptide or a homologue thereof gives plants having increased yield relative to control plants (EP 2431472); and (F) Genes encoding nucleoside diphosphatase kinase (NDK) polypeptides and homologs thereof for modifying the plant's root architecture (US Patent Application Publication Number 2009/0064373).

IX. Methods of Use

Methods disclosed herein comprise methods for controlling a plant insect pest, such as a Coleopteran, Hemiptera, or Lepidopteran plant pest, including a *Diabrotica, Leptinotarsa, Phyllotreta, Acyrthosiphan, Bemisia, Halyomorpha, Nezara*, or *Spodoptera* plant pest. In one embodiment, the method comprises feeding or applying to a plant insect pest a composition comprising a silencing element disclosed herein, wherein said silencing element, when ingested or contacted by a plant insect pest (i.e., but not limited to, a Coleopteran plant pest including a *Diabrotica* plant pest, such as, *D. virgifera virgifera, D. barberi, D. virgifera zeae, D. speciosa*, or *D. undecimpunctata howardi*), reduces the level of a target polynucleotide of the pest and thereby controls the pest. The pest can be fed the silencing element in a variety of ways. The silencing element may be fed to male, female, or both sexes of a pest. For example, in an embodiment, a polynucleotide encoding a silencing element, i.e., a silencing element targeting one or more polynucleotides as set forth in SEQ ID NOS.: 1-53 or 107-254, is introduced into a plant. As the plant pest feeds on the plant or part thereof expressing these sequences, the silencing element is delivered to the pest at larval, adult, or at any or all developmental stages. In one embodiment, the methods and compositions described herein further comprise a transgenic plant comprising a silencing element disclosed herein, wherein the silencing element has sterilization activity at larval, adult or at any or all developmental stages. When the silencing element is delivered to the plant in this manner, it is recognized that the silencing element can be expressed constitutively or alternatively, it may be produced in a stage-specific manner by employing the various inducible or tissue-preferred or developmentally regulated promoters that are discussed elsewhere herein. In certain embodiments, the silencing element is expressed in the roots, stalk or stem, leaf including pedicel, xylem and phloem, fruit or reproductive tissue, silk, flowers and all parts therein or any combination thereof. Sterile insects may result from exposure to silencing elements in this manner and hence sterilize insects of opposite the sex through competitive mating or SIT.

In another method, a composition comprising at least one silencing element disclosed herein is applied to a plant. In such embodiments, the silencing element may be formulated in an agronomically suitable and/or environmentally acceptable carrier, which is preferably, suitable for dispersal in fields. In some embodiments, silencing elements targeting different insect stages, pathways, and sexes may be combined for sterility and insecticidal activities. In one embodiment, the silencing elements disclosed herein may be mixed with pesticidal chemicals by tank mix. In addition, the carrier may also include compounds that increase the half-life of the composition. In certain embodiments, the composition comprising the silencing element is formulated in such a manner such that it persists in the environment for a length of time sufficient to allow it to be delivered to a plant insect pest. In such embodiments, the composition can be applied to an area inhabited by a plant insect pest. In one embodiment, the composition is applied externally to a plant (i.e., by spraying a field) to protect the plant from pests. Sterile insects that result from exposure to silencing elements may sterilize insects of opposite sex through competitive mating or SIT.

In certain embodiments, the disclosed polynucleotides or constructs can be stacked with any combination of polynucleotide sequences of interest in order to create plants with a desired trait. A trait, as used herein, refers to the phenotype derived from a particular sequence or groups of sequences. For example, the polynucleotides described herein may be stacked with any other polynucleotides encoding polypeptides having pesticidal and/or insecticidal activity, such as other *Bacillus thuringiensis* toxic proteins (described in U.S. Pat. Nos. 5,366,892; 5,747,450; 5,737,514; 5,723,756; 5,593,881; and Geiser et al. (1986) *Gene* 48:109), lectins (Van Damme et al. (1994) *Plant Mol. Biol.* 24:825, pentin (described in U.S. Pat. No. 5,981,722), and the like. The combinations generated may also include multiple copies of any one of the polynucleotides of interest. The polynucleotides described herein can also be stacked with any other gene or combination of genes to produce plants with a variety of desired trait combinations including, but not limited to, traits desirable for animal feed such as high oil genes (e.g., U.S. Pat. No. 6,232,529); balanced amino acids (e.g., hordothionins (U.S. Pat. Nos. 5,990,389; 5,885,801; 5,885,802; and 5,703,409); barley high lysine (Williamson et al. (1987) *Eur. J. Biochem.* 165:99-106; and WO 98/20122) and high methionine proteins (Pedersen et al. (1986) *J. Biol. Chem.* 261:6279; Kirihara et al. (1988) *Gene* 71:359; and Musumura et al. (1989) *Plant Mol. Biol.* 12:123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)).

Disclosed polynucleotides can also be stacked with traits desirable for disease or herbicide resistance (e.g., fumonisin detoxification genes (U.S. Pat. No. 5,792,931); avirulence and disease resistance genes (Jones et al. (1994) *Science* 266:789; Martin et al. (1993) *Science* 262:1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)); the disclosures of which are herein incorporated by reference. One could also combine the polynucleotides with polynucleotides providing agronomic traits such as male sterility (e.g., see U.S. Pat. No. 5,583,210), stalk strength, drought resistance (e.g., U.S. Pat. No. 7,786,353), flowering time, or transformation technology traits such as cell cycle regulation or gene targeting (e.g., WO 99/61619, WO 00/17364, and WO 99/25821).

These stacked combinations can be created by any method including, but not limited to, cross-breeding plants by any conventional or TopCross methodology, or genetic transformation. If the sequences are stacked by genetically transforming the plants (i.e., molecular stacks), the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853.

X. Insect Resistance Management Methods

Methods disclosed herein comprise methods for controlling a plant insect pest, such as a Coleopteran, Hemiptera, or Lepidopteran plant pest, including a *Diabrotica, Leptinotarsa, Phyllotreta, Acyrthosiphan, Bemisia, Halyomorpha, Nezara*, or *Spodoptera* plant pest, such as insect resistance management. Insect resistance management (IRM) is the term used to describe practices aimed at reducing the potential for insect pests to become resistant to a pesticide. Maintenance of Bt (or other pesticidal protein, chemical, or biological) IRM is of great importance because of the threat insect resistance poses to the future use of Bt plant-incorporated protectants and Bt technology as a whole. Specific IRM strategies, such as the high dose/structured refuge strategy, delay insect resistance to specific Bt proteins produced in corn, cotton, and potatoes. However, such strategies result in portions of crops being left susceptible to one or more pests in order to ensure that non-resistant insects develop and become available to mate with any resistant pests produced in protected crops. Accordingly, from a farmer/producer's perspective, it is highly desirable to have as small a refuge as possible and yet still manage insect resistance, in order that the greatest yield be obtained while still maintaining the efficacy of the pest control method used, whether Bt, chemical, some other method, or combinations thereof.

An often used IRM strategy is the planting of a refuge (a portion of the total acreage using non-Bt/pesticidal trait seed), as it is commonly-believed that this will delay the development of insect resistance to pesticidal traits by maintaining insect susceptibility. The theoretical basis of the refuge strategy for delaying resistance hinges on the assumption that the frequency and recessiveness of insect resistance is inversely proportional to pest susceptibility; resistance will be rare and recessive only when pests are very susceptible to the toxin, and conversely resistance will be more frequent and less recessive when pests are not very susceptible. Furthermore, the strategy assumes that resistance to Bt is recessive and is conferred by a single locus with two alleles resulting in three genotypes: susceptible homozygotes (SS), heterozygotes (RS), and resistant homozygotes (RR). It also assumes that there will be a low initial resistance allele frequency and that there will be extensive random mating between resistant and susceptible adults. Under ideal circumstances, only rare RR individuals will survive a pesticidal toxin produced by the crop. Both SS and RS individuals will be susceptible to the pesticidal toxin. A structured refuge is a non-Bt/pesticidal trait portion of a grower's field or set of fields that provides for the production of susceptible (SS) insects that may randomly mate with rare resistant (RR) insects surviving the pesticidal trait crop, which may be a Bt trait crop, to produce susceptible RS heterozygotes that will be killed by the Bt/pesticidal trait crop. An integrated refuge is a certain portion of randomly planted non-Bt/pesticidal trait portion of a grower's field or set of fields that provides for the production of susceptible (SS) insects that may randomly mate with rare resistant (RR) insects surviving the pesticidal trait crop to produce susceptible RS heterozygotes that will be killed by the pesticidal trait crop Each refuge strategy will remove resistant (R) alleles from the insect populations and delay the evolution of resistance.

Another strategy to reduce the need for refuge is the pyramiding of traits with different modes of action against a target insect pest. For example, Bt toxins that have different modes of action stacked in one transgenic plant are able to have reduced refuge requirements. Different modes of action in a stacked combination also maintains the durability of each trait, as resistance is slower to develop to each trait.

Currently, the size, placement, and management of the refuge are often considered critical to the success of refuge strategies to mitigate insect resistance to the Bt/pesticidal trait produced in corn, cotton, soybean, and other crops. Because of the decrease in yield in refuge planting areas, some farmers choose to eschew the refuge requirements, and others do not follow the size and/or placement requirements. These issues result in either no refuge or less effective refuge, and a corresponding risk of the increase in the development of resistance pests.

Accordingly, there remains a need for methods for managing pest resistance in a plot of pest resistant crop plants. It would be useful to provide an improved method for the protection of plants, especially corn or other crop plants, from feeding damage by pests. It would be particularly useful if such a method would reduce the required application rate of conventional chemical pesticides, and also if it would limit the number of separate field operations that were required for crop planting and cultivation. In addition, it would be useful to have a method of deploying a transgenic refuge that eliminates the above-described problems with regard to compliance that dilute or remove the efficacy of many resistance management strategies.

One embodiment relates to a method of reducing the development of resistant pests comprising providing a plant protection composition to a plant (Bt toxin, transgenic insecticidal protein, other insecticidal proteins, chemical insecticides, insecticidal biological entomopathogens, etc.) and contacting the plant pest with a silencing element, i.e., of a silencing element targeting one or more polynucleotides as set forth in SEQ ID NOS.: 1-53 or 107-254, wherein the silencing element, i.e., of a silencing element targeting one or more polynucleotides as set forth in SEQ ID NOS.: 1-53 or 107-254, produces a decrease in expression of one or more of the sequences in the target pest and controls the pest and pest population by insect sterilization or SIT.

A further embodiment relates to a method of increasing the durability of plant pest compositions comprising providing a plant protection composition to a plant (Bt toxin, transgenic insecticidal protein, other insecticidal proteins, chemical insecticides, insecticidal biological entomopathogens etc.) and contacting a plant pest with the sterilization silencing element, i.e., of one or more polynucleotides as set forth in SEQ ID NOS.: 1-53 or 107-254, or complements thereof, an expression construct comprising a sequence as set forth in SEQ ID NOS.: 1-53 or 107-254, or complements thereof, or silencing elements targeting said polynucleotides, produces a decrease in expression of one or more of the sequences in the target pest and controls the pest and pest population by insect sterilization or sterile insect technique. In another embodiment, the refuge planted as a strip, a block, or integrated with the trait seed comprises a plant further comprising a sterilization silencing element (for example, a silencing element targeting one or more polynucleotides as set forth in SEQ ID NOS.: 1-53 or 107-254).

In a still further embodiment, the refuge required may be reduced or eliminated by the presence of a sterilization silencing element applied to the non-refuge plants. In another embodiment, the refuge or non-refuge may include a silencing element, i.e., of one or more polynucleotides as set forth in SEQ ID NOS.: 1-53 or 107-254, or complements thereof, an expression construct comprising a sequence as set forth in SEQ ID NOS.: 1-53 or 107-254, or complements thereof, or silencing elements targeting said polynucleotides, as a spray, bait, lure, or as a different transgenic plant.

In a further embodiment, a pest insect is feed a diet comprising one or more polynucleotides as set forth in SEQ ID NOS.: 1-53 or 107-254, or complements thereof, an expression construct comprising a sequence as set forth in SEQ ID NOS.: 1-53 or 107-254, or complements thereof, or silencing elements targeting said polynucleotides, and said insects are released onto plants at 1, 2, 3, 4, 5, 6, 7, 8, 9, or 10 days following feeding. In a still further embodiment, the pest insect is a female pest insect. In a yet further embodiment, the pest insect is a pest insect, and the pest insect is fed during a larval or adult stage. Insect sterilization may result from male or female sterility, mating of sterile insects, reduction of sperm count, egg production or viability.

In certain embodiments, the compositions and methods disclosed herein, targeting a sterile gene via RNAi technology, and stacking a polynucleotide encoding a silencing element disclosed herein with an insecticidal protein in a transgenic plant may provide effective control of Coleoptera and potentially extend the durability of Coleopteran insecticidal traits. The extended durability may be a consequence of minimizing the transmission of resistance alleles from Coleopteran beetles that were able to complete their developmental life cycle while feeding on transgenic roots expressing a stack of an insecticidal protein(s) and a RNAi sterility trait disclosed herein.

Current IRM strategy requires a high dose of Bt toxins to minimize insect resistance development. Due to phytotoxicity, it can be difficult to achieve the required high dose. Integrated pest management (IPM) by different means of insect control may be used to delay insect resistance exposed to a sub-optimal dose of protein toxin, such as a Bt toxin. RNAi mediated SIT may be deployed as part of an IPM strategy.

As used herein, the term "pesticidal" is used to refer to a toxic effect against a pest (e.g., CRW), and includes activity of either, or both, an externally supplied pesticide and/or an agent that is produced by the crop plants. As used herein, the term "different mode of pesticidal action" includes the pesticidal effects of one or more resistance traits, whether introduced into the crop plants by transformation or traditional breeding methods, such as binding of a pesticidal toxin produced by the crop plants to different binding sites (i.e., different toxin receptors and/or different sites on the same toxin receptor) in the gut membranes of corn rootworms or through RNA interference.

XI. Application Methods

In one embodiment, one or more polynucleotides as set forth in SEQ ID NOS.: 1-53 or 107-254, or complements thereof, an expression construct comprising a sequence as set forth in SEQ ID NOS.: 1-53 or 107-254, or complements thereof, or silencing elements targeting said polynucleotide sequences, and compositions comprising said sequences can be applied directly to the seed. For example, one or more polynucleotides as set forth in SEQ ID NOS.: 1-53 or 107-254, or complements thereof, an expression construct comprising a sequence as set forth in SEQ ID NOS.: 1-53 or 107-254, or complements thereof, or silencing elements targeting said polynucleotide sequences, used in the compositions and methods disclosed herein can be applied without additional components and without having been diluted.

In one embodiment, sprays, baits, lures, attractants, and seed treatments can comprise one or more polynucleotides as set forth in SEQ ID NOS.: 1-53 or 107-254, or complements thereof, an expression construct comprising a sequence as set forth in SEQ ID NOS.: 1-53 or 107-254, or complements thereof, or silencing elements targeting said polynucleotide sequences, and compositions comprising said sequences.

In another embodiment, one or more polynucleotides as set forth in SEQ ID NOS.: 1-53 or 107-254, or complements thereof, an expression construct comprising a sequence as set forth in SEQ ID NOS.: 1-53 or 107-254, or complements thereof, or silencing elements targeting said polynucleotide sequences, and compositions comprising said sequences are applied to the seed in the form of a suitable formulation. Suitable formulations and methods for the treatment of seed are known to the person skilled in the art and are described, for example, in the following documents: U.S. Pat. Nos. 4,272,417 A, 4,245,432 A, 4,808,430 A, 5,876,739 A, US 2003/0176428 A1, WO 2002/080675 A1, WO 2002/028186 A2.

The one or more polynucleotides as set forth in SEQ ID NOS.: 1-53 or 107-254, or complements thereof, an expression construct comprising a sequence as set forth in SEQ ID NOS.: 1-53 or 107-254, or complements thereof, or silencing elements targeting said polynucleotide sequences, and compositions comprising said sequences can be converted into customary seed dressing formulations, such as solutions, emulsions, suspensions, powders, foams, slurries or other coating materials for seed, and also ULV formulations. These formulations are prepared in a known manner by mixing the one or more polynucleotides as set forth in SEQ ID NOS.: 1-53 or 107-254, or complements thereof, an expression construct comprising a sequence as set forth in SEQ ID NOS.: 1-53 or 107-254, or complements thereof, or silencing elements targeting said polynucleotide sequences, and compositions comprising said sequences with customary additives, such as, for example, customary extenders and also solvents or diluents, colorants, wetting agents, dispersants, emulsifiers, defoamers, preservatives, secondary thickeners, adhesives, gibberellins and water as well.

In another embodiment, suitable colorants that may be present in the seed dressing formulations include all colorants customary for such purposes. Use may be made both of pigments, of sparing solubility in water, and of dyes, which are soluble in water. Examples that may be mentioned include the colorants known under the designations Rhodamine B, C.I. Pigment Red 112, and C.I. Solvent Red 1

In another embodiment, suitable wetting agents that may be present in the seed dressing formulations include all substances that promote wetting and are customary in the formulation of active agrochemical substances. With preference it is possible to use alkylnaphthalene-sulphonates, such as diisopropyl- or diisobutylnaphthalene-sulphonates.

In still another embodiment, suitable dispersants and/or emulsifiers that may be present in the seed dressing formulations include all nonionic, anionic, and cationic dispersants that are customary in the formulation of active agrochemical substances. In one embodiment, nonionic or anionic dispersants or mixtures of nonionic or anionic dispersants can be used. In one embodiment, nonionic dispersants include but are not limited to ethylene oxide-propylene oxide block polymers, alkylphenol polyglycol ethers, and tristyrylphenol polyglycol ethers, and their phosphated or sulphated derivatives.

In still another embodiment, defoamers that may be present in the seed dressing formulations to be used according to the invention include all foam-inhibiting compounds that are customary in the formulation of agrochemically active compounds including, but not limited, to silicone defoamers, magnesium stearate, silicone emulsions, long-chain alcohols, fatty acids and their salts and also organofluorine compounds and mixtures thereof.

In still another embodiment, secondary thickeners that may be present in the seed dressing formulations include all compounds which can be used for such purposes in agrochemical compositions, including but not limited to cellulose derivatives, acrylic acid derivatives, polysaccharides, such as xanthan gum or Veegum, modified clays, phyllosilicates, such as attapulgite and bentonite, and also finely divided silicic acids.

Suitable adhesives that may be present in the seed dressing formulations to be used according to the invention include all customary binders which can be used in seed dressings. Polyvinylpyrrolidone, polyvinyl acetate, polyvinyl alcohol and tylose may be mentioned as being preferred.

In another embodiment, one or more polynucleotides as set forth in SEQ ID NOS.: 1-53 or 107-254, or complements thereof, or an expression construct comprising a sequence as set forth in SEQ ID NOS.: 1-53 or 107-254, or complements thereof, or silencing elements targeting said polynucleotide sequences, and compositions comprising said sequences is applied to soil in a first application step, applied to seed in a second application, and to applied to the foliar region of a plant in a third application.

As used herein, applying one or more polynucleotides as set forth in SEQ ID NOS.: 1-53 or 107-254, or a complement thereof, an expression construct comprising a sequence as set forth in SEQ ID NOS.: 1-53 or 107-254, or a complement thereof, or silencing elements targeting said polynucleotide sequences, and compositions comprising said sequences to a seed, a plant, or plant part includes contacting the seed, plant, or plant part directly and/or indirectly with the one or more polynucleotides as set forth in SEQ ID NOS.: 1-53 or 107-254, or complements thereof, an expression construct comprising a sequence as set forth in SEQ ID NOS.: 1-53 or 107-254, or complements thereof, or silencing elements targeting said polynucleotide sequences, and compositions comprising said sequences. In one embodiment, one or more polynucleotides as set forth in SEQ ID NOS.: 1-53 or 107-254, or complements thereof, an expression construct comprising a sequence as set forth in SEQ ID NOS.: 1-53 or 107-254, or complements thereof, or silencing elements targeting said polynucleotide sequences, and compositions comprising said sequences can be directly applied as a spray, a rinse, or a powder, or any combination thereof.

In another aspect, one or more polynucleotides as set forth in SEQ ID NOS.: 1-53 or 107-254, or complements thereof, an expression construct comprising a sequence as set forth in SEQ ID NOS.: 1-53 or 107-254, or complements thereof, or silencing elements targeting said polynucleotide sequences, and compositions comprising said sequences can be applied directly to a plant or plant part as a powder. As used herein, a powder is a dry or nearly dry bulk solid composed of a large number of very fine particles that may flow freely when shaken or tilted. A dry or nearly dry powder composition disclosed herein preferably contains a low percentage of water, such as, for example, in various aspects, less than 5%, less than 2.5%, or less than 1% by weight.

In a further embodiment, one or more polynucleotides as set forth in SEQ ID NOS.: 1-53 or 107-254, or complements thereof, an expression construct comprising a sequence as set forth in SEQ ID NOS.: 1-53 or 107-254, or complements thereof, or silencing elements targeting said polynucleotide sequences, may be introduced in a bacteria, a yeast, or fungus by transformation techniques known to the skilled artisan, and said transformed bacteria, yeast, or fungus applied to a plant, soil that the plant is growing in, to a hydroponic medium, seed, or any applied per any of the foregoing application methods as described herein above.

In one embodiment, the one or more polynucleotides as set forth in SEQ ID NOS.: 1-53 or 107-254, or complements thereof, an expression construct comprising a sequence as set forth in SEQ ID NOS.: 1-53 or 107-254, or complements thereof, or silencing elements targeting said polynucleotide sequences, and compositions comprising said sequences may be formulated by encapsulation technology to improve stability. In one embodiment the encapsulation technology may comprise a bead polymer for timed release over time. In one embodiment, the encapsulated one or more polynucleotides as set forth in SEQ ID NOS.: 1-53 or 107-254, or complements thereof, an expression construct comprising a sequence as set forth in SEQ ID NOS.: 1-53 or 107-254, or complements thereof, or silencing elements targeting said polynucleotide sequences, and compositions comprising said sequences may be applied in a separate application of beads in-furrow to the seeds. In another embodiment, the encapsulated one or more polynucleotides as set forth in SEQ ID NOS.: 1-53 or 107-254, or complements thereof, an expression construct comprising a sequence as set forth in SEQ ID NOS.: 1-53 or 107-254, or complements thereof, or silencing elements targeting said polynucleotide sequences, and compositions comprising said sequences may be co-applied along with seeds simultaneously.

The coating agent usable for the sustained release microparticles of an encapsulation embodiment may be a substance which is useful for coating the microgranular form with the substance to be supported thereon. Any coating agent which can form a coating difficulty permeable for the supported substance may be used in general, without any particular limitation. For example, higher saturated fatty acid, wax, thermoplastic resin, thermosetting resin and the like may be used.

Examples of useful higher saturated fatty acid include stearic acid, zinc stearate, stearic acid amide and ethylenebis-stearic acid amide; those of wax include synthetic waxes such as polyethylene wax, carbon wax, Hoechst wax, and fatty acid ester; natural waxes such as carnauba wax, bees wax and Japan wax; and petroleum waxes such as paraffin wax and petrolatum. Examples of thermoplastic resin include polyolefins such as polyethylene, polypropylene, polybutene and polystyrene; vinyl polymers such as polyvinyl acetate, polyvinyl chloride, polyvinylidene chloride, polyacrylic acid, polymethacrylic acid, polyacrylate and polymethacrylate; diene polymers such as butadiene polymer, isoprene polymer, chloroprene polymer, butadiene-styrene copolymer, ethylene-propylene-diene copolymer, styrene-isoprene copolymer, MMA-butadiene copolymer and acrylonitrile-butadiene copolymer; polyolefin copolymers such as ethylene-propylene copolymer, butene-ethylene copolymer, butene-propylene copolymer, ethylene-vinyl acetate copolymer, ethylene-acrylic acid copolymer, styreneacrylic acid copolymer, ethylene-methacrylic acid copolymer, ethylene-methacrylic ester copolymer, ethylene-carbon monoxide copolymer, ethylene-vinyl acetate-carbon monoxide copolymer, ethylene-vinyl acetate-vinyl chloride copolymer and ethylene-vinyl acetate-acrylic copolymer; and vinyl chloride copolymers such as vinyl chloride-vinyl acetate copolymer and vinylidene chloride-vinyl chloride copolymer. Examples of thermosetting resin include polyurethane resin, epoxy resin, alkyd resin, unsaturated polyester resin, phenolic resin, urea-melamine resin, urea resin and silicone resin. Of those, thermoplastic acrylic ester resin, butadienestyrene copolymer resin, thermosetting polyurethane resin and epoxy resin are preferred, and among the preferred resins, particularly thermosetting polyurethane resin is preferred. These coating agents can be used either singly or in combination of two or more kinds.

In one embodiment, one or more polynucleotides as set forth in SEQ ID NOS.: 1-53 or 107-254, or complements thereof, an expression construct comprising a sequence as set forth in SEQ ID NOS.: 1-53 or 107-254, or complements thereof, or silencing elements targeting said polynucleotide sequences, and compositions comprising said sequences can be formulated to further comprise an entomopathogen. The methods and compositions of the disclosure, in one embodiment relate to a composition comprising one or more one or more polynucleotides as set forth in SEQ ID NOS.: 1-53 or 107-254, or complements thereof, an expression construct comprising a sequence as set forth in SEQ ID NOS.: 1-53 or 107-254, or complements thereof, or silencing elements targeting said polynucleotide sequences, and compositions comprising said sequences and one or more biocontrol agents. As used herein, the term "biocontrol agent" ("BCA") includes one or more bacteria, fungi or yeasts, protozoas, viruses, entomopathogenic nematodes, and botanical extracts, or products produced by microorganisms including proteins or secondary metabolite, and innoculants that have one or both of the following characteristics: (1) inhibits or reduces plant infestation and/or growth of pathogens, pests, or insects, including but not limited to pathogenic fungi, bacteria, and nematodes, as well as arthropod pests such as insects, arachnids, chilopods, diplopods, or that inhibits plant infestation and/or growth of a combination of plant pathogens, pests, or insects; (2) improves plant performance; (3) improves plant yield; (4) improves plant vigor; and (5) improves plant health.

XII. Knockout of Target Genes Using Cas/CRISPR

In one embodiment, one or more polynucleotides as set forth in SEQ ID NOS.: 1-53 or 107-254, or complements thereof, an expression construct comprising a sequence as set forth in SEQ ID NOS.: 1-53 or 107-254, or complements thereof, or silencing elements targeting said polynucleotides, and compositions comprising said sequences, can be can be introduced into the genome of a plant using genome editing technologies, or previously introduced polynucleotides encoding a silencing element disclosed herein in the genome of a plant may be edited using genome editing technologies. For example, the disclosed polynucleotides can be introduced into a desired location in the genome of a plant through the use of double-stranded break technologies such as TALENs, meganucleases, zinc finger nucleases, CRISPR-Cas, and the like. For example, the disclosed polynucleotides can be introduced into a desired location in a genome using a CRISPR-Cas system, for the purpose of site-specific insertion. The desired location in a plant genome can be any desired target site for insertion, such as a genomic region amenable for breeding or may be a target site located in a genomic window with an existing trait of interest. Existing traits of interest could be either an endogenous trait or a previously introduced trait.

In another aspect, where the disclosed polynucleotide encoding a silencing element has previously been introduced into a genome, genome editing technologies may be used to alter or modify the introduced polynucleotide sequence. Site specific modifications that can be introduced into the disclosed polynucleotide encoding a silencing element compositions include those produced using any method for introducing site specific modification, including, but not limited to, through the use of gene repair oligonucleotides (e.g. US Publication 2013/0019349), or through the use of double-stranded break technologies such as TALENs, meganucleases, zinc finger nucleases, CRISPR-Cas, and the like. Such technologies can be used to modify the previously introduced polynucleotide through the insertion, deletion or substitution of nucleotides within the introduced polynucleotide. Alternatively, double-stranded break technologies can be used to add additional nucleotide sequences to the introduced polynucleotide. Additional sequences that may be added include, additional expression elements, such as enhancer and promoter sequences. In another embodiment, genome editing technologies may be used to position additional insecticidally-active proteins in close proximity to the disclosed polynucleotide compositions disclosed herein within the genome of a plant, in order to generate molecular stacks of insecticidally-active proteins. An "altered target site," "altered target sequence." "modified target site," and "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

In one embodiment, the methods comprise creating an insect, or colony thereof, wherein the target gene is edited so that it is no longer function, thereby creating a sterile insect. The polynucleotide sequence of the target gene can be used to knockout the target gene polynucleotide in an insect by means known to those skilled in the art, including, but not limited to TALENs, meganucleases, zinc finger nucleases, CRISPR-Cas, and the like. See Ma et al (2014), *Scientific Reports,* 4: 4489; Daimon et al (2013), *Development, Growth, and Differentiation,* 56(1): 14-25; and Eggleston et al (2001) *BMC Genetics,* 2:11. One embodiment comprises an insect with an edited polynucleotide of one or more polynucleotides as set forth in SEQ ID NOS.: 1-53 wherein the edit produces a decrease in expression of or a nonfunctional polypeptide and controls the pest and pest population by insect sterilization and sterile insect technique.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing embodiments have been described in some detail by way of illustration and example for purposes of clarity of understanding, certain changes and modifications may be practiced within the scope of the appended claims.

The following examples are offered by way of illustration and not by way of limitation.

EXPERIMENTAL

Example 1: Nucleic Acid Sequences

Nucleic acid sequences disclosed herein comprise the following nucleic acid sequences. Certain sequences are exemplary and were shown to have insect sterilization activity against corn rootworms using the assay methods described in Examples 2, 3, and 6 as set forth below. Such sequences or their complements can be used in the methods as described herein above and below. Methods for making inhibitory sequences are known in the art. DNA constructs, vectors, transgenic cells, plants, seeds or products described herein may comprise one or more of the following nucleic acid or amino acid sequences, or a portion of one or more of the disclosed sequences. Non-limiting examples of target polynucleotides are set forth below in Table 1, or variants and fragments thereof, and complements thereof, including, for example, SEQ ID NOS.: 1-53 or 107-254, and variants and fragments thereof, and complements thereof. The list of sequences referred to herein, SEQ ID NOS.: 1-53 and 107-254, is included herein below.

TABLE 1

VgR RNAi target fragments.

| SEQ ID NO. | Species | Common name | Fragment ID |
|---|---|---|---|
| 1 | *Diabrotica virgifera virgifera* | Western Corn Rootworm | Transcript* |
| 2 | *Diabrotica virgifera virgifera* | Western Corn Rootworm | ORF** |
| 3 | *Diabrotica virgifera virgifera* | Western Corn Rootworm | DV-VGR-Frag1 |
| 4 | *Diabrotica virgifera virgifera* | Western Corn Rootworm | DV-VGR-Frag2 |
| 5 | *Diabrotica virgifera virgifera* | Western Corn Rootworm | DV-VGR-Frag3 |
| 6 | *Diabrotica virgifera virgifera* | Western Corn Rootworm | DV-VGR-Frag4 |
| 7 | *Diabrotica virgifera virgifera* | Western Corn Rootworm | DV-VGR-Frag5 |
| 8 | *Diabrotica virgifera virgifera* | Western Corn Rootworm | DV-VGR-Frag6 |
| 9 | *Diabrotica virgifera virgifera* | Western Corn Rootworm | DV-VGR-Frag7 |
| 10 | *Diabrotica virgifera virgifera* | Western Corn Rootworm | DV-VGR-Frag8 |
| 11 | *Diabrotica virgifera virgifera* | Western Corn Rootworm | DV-VGR-Frag9 |
| 12 | *Diabrotica virgifera virgifera* | Western Corn Rootworm | DV-VGR-Frag10 |
| 13 | *Diabrotica virgifera virgifera* | Western Corn Rootworm | DV-VGR-Frag11 |
| 14 | *Diabrotica virgifera virgifera* | Western Corn Rootworm | DV-VGR-Frag12 |
| 15 | *Diabrotica virgifera virgifera* | Western Corn Rootworm | DV-VGR-Frag13 |
| 16 | *Diabrotica virgifera virgifera* | Western Corn Rootworm | DV-VGR-Frag14 |
| 17 | *Diabrotica virgifera virgifera* | Western Corn Rootworm | DV-VGR-Frag15 |
| 18 | *Diabrotica virgifera virgifera* | Western Corn Rootworm | DV-VGR-Frag16 |
| 19 | *Diabrotica undecimpunctata* | Southern Corn Rootworm | ORF |
| 20 | *Diabrotica undecimpunctata* | Southern Corn Rootworm | Transcript |
| 21 | *Leptinotarsa decemlineata* | Colorado Potato Beetle | ORF |
| 22 | *Leptinotarsa decemlineata* | Colorado Potato Beetle | Transcript |
| 23 | *Phyllotreta striolata* | Striped Flea Beetle | ORF |
| 24 | *Phyllotreta striolata* | Striped Flea Beetle | Transcript |
| 25 | *Halyomorpha halys* | Brown Marmorated Stink Bug | ORF |
| 26 | *Halyomorpha halys* | Brown Marmorated Stink Bug | Transcript |
| 27 | *Acyrthosiphon pisum* | Pea Aphid | ORF |
| 28 | *Acyrthosiphon pisum* | Pea Aphid | Transcript |
| 29 | *Bemisia tabaci* | Silverleaf Whitefly | ORF |
| 30 | *Bemisia tabaci* | Silverleaf Whitefly | Transcript |
| 31 | *Spodoptera litura* | Cotton Leafworm | ORF |
| 32 | *Spodoptera litura* | Cotton Leafworm | Transcript |
| 33 | *Phyllotreta cruciferae* | Crucifer Flea Beetle | ORF |
| 34 | *Phyllotreta cruciferae* | Crucifer Flea Beetle | Transcript |
| 35 | *Nezara viridula* | Southern Green Stink Bug | ORF |
| 36 | *Diabrotica virgifera virgifera* | Western Corn Rootworm | DV-CUL3 |
| 37 | *Diabrotica virgifera virgifera* | Western Corn Rootworm | DV-NCLB |
| 38 | *Diabrotica virgifera virgifera* | Western Corn Rootworm | DV-MAEL |
| 39 | *Diabrotica virgifera virgifera* | Western Corn Rootworm | DV-GUDU |
| 40 | *Diabrotica virgifera virgifera* | Western Corn Rootworm | DV-GSKT |
| 41 | *Diabrotica virgifera virgifera* | Western Corn Rootworm | DV-WTS |
| 42 | *Diabrotica virgifera virgifera* | Western Corn Rootworm | DV-CASP |
| 43 | *Diabrotica virgifera virgifera* | Western Corn Rootworm | DV-CYCA |

TABLE 1-continued

VgR RNAi target fragments.

| SEQ ID NO. | Species | Common name | Fragment ID |
|---|---|---|---|
| 44 | *Diabrotica virgifera virgifera* | Western Corn Rootworm | DV-CUL3-FRAG1 |
| 45 | *Diabrotica virgifera virgifera* | Western Corn Rootworm | DV-NCLB-FRAG1 |
| 46 | *Diabrotica virgifera virgifera* | Western Corn Rootworm | DV-MAEL-FRAG1 |
| 47 | *Diabrotica virgifera virgifera* | Western Corn Rootworm | DV-GUDU-FRAG1 |
| 48 | *Diabrotica virgifera virgifera* | Western Corn Rootworm | DV-GSKT-FRAG1 |
| 49 | *Diabrotica virgifera virgifera* | Western Corn Rootworm | DV-WTS-FRAG1 |
| 50 | *Diabrotica virgifera virgifera* | Western Corn Rootworm | DV-CASP-FRAG1 |
| 51 | *Diabrotica virgifera virgifera* | Western Corn Rootworm | DV-CYCA-FRAG1 |
| 52 | *Spodoptera frugiperda* | Fall Armyworm | ORF |
| 53 | *Spodoptera frugiperda* | Fall Armyworm | Transcript |
| 107 | *Diabrotica virgifera virgifera* | Western Corn Rootworm | DV-ADE2 |
| 108 | *Diabrotica virgifera virgifera* | Western Corn Rootworm | DV-HANG |
| 109 | *Diabrotica virgifera virgifera* | Western Corn Rootworm | DV-KL3 |
| 110 | *Diabrotica virgifera virgifera* | Western Corn Rootworm | DV-PORIN |
| 111 | *Diabrotica virgifera virgifera* | Western Corn Rootworm | DV-SU(VAR)205 |
| 112 | *Diabrotica virgifera virgifera* | Western Corn Rootworm | DV-PARK |
| 113 | *Diabrotica virgifera virgifera* | Western Corn Rootworm | DV-POE |
| 114 | *Diabrotica virgifera virgifera* | Western Corn Rootworm | DV-MBD-LIKE |
| 115 | *Diabrotica virgifera virgifera* | Western Corn Rootworm | DV-PGLYM78 |
| 116 | *Diabrotica virgifera virgifera* | Western Corn Rootworm | DV-HIRA |
| 117 | *Diabrotica virgifera virgifera* | Western Corn Rootworm | DV-PUF |
| 118 | *Diabrotica virgifera virgifera* | Western Corn Rootworm | DV-TUD |
| 119 | *Diabrotica virgifera virgifera* | Western Corn Rootworm | DV-FAF |
| 120 | *Diabrotica virgifera virgifera* | Western Corn Rootworm | DV-NUP44A |
| 121 | *Diabrotica virgifera virgifera* | Western Corn Rootworm | DV-GEK |
| 122 | *Diabrotica virgifera virgifera* | Western Corn Rootworm | DV-HTS |
| 123 | *Diabrotica virgifera virgifera* | Western Corn Rootworm | DV-CDK7 |
| 124 | *Diabrotica virgifera virgifera* | Western Corn Rootworm | DV-DLG1 |
| 125 | *Diabrotica virgifera virgifera* | Western Corn Rootworm | DV-DM |
| 126 | *Diabrotica virgifera virgifera* | Western Corn Rootworm | DV-EGG |
| 127 | *Diabrotica virgifera virgifera* | Western Corn Rootworm | DV-HRG |
| 128 | *Diabrotica virgifera virgifera* | Western Corn Rootworm | DV-MR |
| 129 | *Diabrotica virgifera virgifera* | Western Corn Rootworm | DV-CG17083 |
| 130 | *Diabrotica virgifera virgifera* | Western Corn Rootworm | DV-CG3565 |
| 131 | *Diabrotica virgifera virgifera* | Western Corn Rootworm | DV-CYCB |
| 132 | *Diabrotica virgifera virgifera* | Western Corn Rootworm | DV-KNRL |
| 133 | *Diabrotica virgifera virgifera* | Western Corn Rootworm | DV-MEI |
| 134 | *Diabrotica virgifera virgifera* | Western Corn Rootworm | DV-TWE |

TABLE 1-continued

VgR RNAi target fragments.

| SEQ ID NO. | Species | Common name | Fragment ID |
|---|---|---|---|
| 135 | *Diabrotica virgifera virgifera* | Western Corn Rootworm | DV-BOULE |
| 136 | *Diabrotica virgifera virgifera* | Western Corn Rootworm | DV-ADE2-FRAG1 |
| 137 | *Diabrotica virgifera virgifera* | Western Corn Rootworm | DV-HANG-FRAG1 |
| 138 | *Diabrotica virgifera virgifera* | Western Corn Rootworm | DV-KL3-FRAG1 |
| 139 | *Diabrotica virgifera virgifera* | Western Corn Rootworm | DV-PORIN-FRAG1 |
| 140 | *Diabrotica virgifera virgifera* | Western Corn Rootworm | DV-SU(VAR)205-FRAG1 |
| 141 | *Diabrotica virgifera virgifera* | Western Corn Rootworm | DV-PARK-FRAG1 |
| 142 | *Diabrotica virgifera virgifera* | Western Corn Rootworm | DV-POE-FRAG1 |
| 143 | *Diabrotica virgifera virgifera* | Western Corn Rootworm | DV-MBD-LIKE-FRAG1 |
| 144 | *Diabrotica virgifera virgifera* | Western Corn Rootworm | DV-PGLYM78-FRAG1 |
| 145 | *Diabrotica virgifera virgifera* | Western Corn Rootworm | DV-HIRA-FRAG1 |
| 146 | *Diabrotica virgifera virgifera* | Western Corn Rootworm | DV-PUF-FRAG1 |
| 147 | *Diabrotica virgifera virgifera* | Western Corn Rootworm | DV-TUD-FRAG1 |
| 148 | *Diabrotica virgifera virgifera* | Western Corn Rootworm | DV-FAF-FRAG1 |
| 149 | *Diabrotica virgifera virgifera* | Western Corn Rootworm | DV-NUP44A-FRAG1 |
| 150 | *Diabrotica virgifera virgifera* | Western Corn Rootworm | DV-GEK-FRAG1 |
| 151 | *Diabrotica virgifera virgifera* | Western Corn Rootworm | DV-HTS-FRAG1 |
| 152 | *Diabrotica virgifera virgifera* | Western Corn Rootworm | DV-CDK7-FRAG1 |
| 153 | *Diabrotica virgifera virgifera* | Western Corn Rootworm | DV-DLG1-FRAG1 |
| 154 | *Diabrotica virgifera virgifera* | Western Corn Rootworm | DV-DM-FRAG1 |
| 155 | *Diabrotica virgifera virgifera* | Western Corn Rootworm | DV-EGG-FRAG1 |
| 156 | *Diabrotica virgifera virgifera* | Western Corn Rootworm | DV-HRG-FRAG1 |
| 157 | *Diabrotica virgifera virgifera* | Western Corn Rootworm | DV-MR-FRAG1 |
| 158 | *Diabrotica virgifera virgifera* | Western Corn Rootworm | DV-CG17083-FRAG1 |
| 159 | *Diabrotica virgifera virgifera* | Western Corn Rootworm | DV-CG3565-FRAG1 |
| 160 | *Diabrotica virgifera virgifera* | Western Corn Rootworm | DV-CYCB-FRAG1 |
| 161 | *Diabrotica virgifera virgifera* | Western Corn Rootworm | DV-KNRL-FRAG1 |
| 162 | *Diabrotica virgifera virgifera* | Western Corn Rootworm | DV-MEI-FRAG1 |
| 163 | *Diabrotica virgifera virgifera* | Western Corn Rootworm | DV-TWE-FRAG1 |
| 164 | *Diabrotica virgifera virgifera* | Western Corn Rootworm | DV-BOULE-FRAG1 |
| 165 | *Diabrotica virgifera virgifera* | Western Corn Rootworm | DV-REPH |
| 166 | *Diabrotica virgifera virgifera* | Western Corn Rootworm | DV-ARMI |
| 167 | *Diabrotica virgifera virgifera* | Western Corn Rootworm | DV-LOQS |
| 168 | *Diabrotica virgifera virgifera* | Western Corn Rootworm | DV-SCNY |
| 169 | *Diabrotica virgifera virgifera* | Western Corn Rootworm | DV-AGO3 |
| 170 | *Diabrotica virgifera virgifera* | Western Corn Rootworm | DV-DIA |
| 171 | *Diabrotica virgifera virgifera* | Western Corn Rootworm | DV-DNC |

TABLE 1-continued

VgR RNAi target fragments.

| SEQ ID NO. | Species | Common name | Fragment ID |
|---|---|---|---|
| 172 | *Diabrotica virgifera virgifera* | Western Corn Rootworm | DV-CHI |
| 173 | *Diabrotica virgifera virgifera* | Western Corn Rootworm | DV-SXL |
| 174 | *Diabrotica virgifera virgifera* | Western Corn Rootworm | DV-SLGA |
| 175 | *Diabrotica virgifera virgifera* | Western Corn Rootworm | DV-PAPLA1 |
| 176 | *Diabrotica virgifera virgifera* | Western Corn Rootworm | DV-REPH-FRAG1 |
| 177 | *Diabrotica virgifera virgifera* | Western Corn Rootworm | DV-ARMI-FRAG1 |
| 178 | *Diabrotica virgifera virgifera* | Western Corn Rootworm | DV-LOQS-FRAG1 |
| 179 | *Diabrotica virgifera virgifera* | Western Corn Rootworm | DV-SCNY-FRAG1 |
| 180 | *Diabrotica virgifera virgifera* | Western Corn Rootworm | DV-AGO3-FRAG1 |
| 181 | *Diabrotica virgifera virgifera* | Western Corn Rootworm | DV-DIA-FRAG1 |
| 182 | *Diabrotica virgifera virgifera* | Western Corn Rootworm | DV-DNC-FRAG1 |
| 183 | *Diabrotica virgifera virgifera* | Western Corn Rootworm | DV-CHI-FRAG1 |
| 184 | *Diabrotica virgifera virgifera* | Western Corn Rootworm | DV-SXL-FRAG1 |
| 185 | *Diabrotica virgifera virgifera* | Western Corn Rootworm | DV-SLGA-FRAG1 |
| 186 | *Diabrotica virgifera virgifera* | Western Corn Rootworm | DV-PAPLA1-FRAG1 |
| 187 | *Diabrotica undecimpunctata* | Southern Corn Rootworm | DU-BOULE |
| 188 | *Leptinotarsa decemlineata* | Colorado Potato Beetle | LD-BOULE |
| 189 | *Phyllotreta cruciferae* | Crucifer Flea Beetle | PC-BOULE |
| 190 | *Phyllotreta striolata* | Striped Flea Beetle | PS-BOULE |
| 191 | *Vibidia duodecimguttata* | 12-Spotted Ladybeetle | VD-BOULE |
| 192 | *Orius insidiosus* | Insidious Flower Bug | OI-BOULE |
| 193 | *Lygus hesperus* | Western Plant Bug | LH-BOULE |
| 194 | *Megacopta cribraria* | Kudzu Bug | MC-BOULE |
| 195 | *Euschistus servus* | Brown Stink Bug | ES-BOULE |
| 196 | *Nezara viridula* | Southern Green Stink Bug | NV-BOULE |
| 197 | *Helicoverpa zea* | Corn Earworm | HZ-BOULE |
| 198 | *Ostrinia nubilalis* | European Corn Borer | ON-BOULE |
| 199 | *Spodoptera frugiperda* | Fall Armyworm | SF-BOULE |
| 200 | *Diabrotica undecimpunctata* | Southern Corn Rootworm | DU-MAEL |
| 201 | *Leptinotarsa decemlineata* | Colorado Potato Beetle | LD-MAEL |
| 202 | *Phyllotreta striolata* | Striped Flea Beetle | PS-MAEL |
| 203 | *Phyllotreta cruciferae* | Crucifer Flea Beetle | PC-MAEL |
| 204 | *Epilachna varivestis* | Mexican Bean Beetle | EV-MAEL |
| 205 | *Tribolium castaneum* | Red Flour Beetle | TC-MAEL |
| 206 | *Vibidia duodecimguttata* | 12-Spotted Ladybeetle | VD-MAEL |
| 207 | *Helicoverpa zea* | Corn Earworm | HZ-MAEL |
| 208 | *Megacopta cribraria* | Kudzu Bug | MC-MAEL |
| 209 | *Nezara viridula* | Southern Green Stink Bug | NV-MAEL |
| 210 | *Euschistus servus* | Brown Stink Bug | ES-MAEL |
| 211 | *Orius insidiosus* | Insidious Flower Bug | OI-MAEL |
| 212 | *Manduca sexta* | Hornworm | MS-MAEL |
| 213 | *Spodoptera frugiperda* | Fall Armyworm | SF-MAEL |
| 214 | *Ostrinia nubilalis* | European Corn Borer | ON-MAEL |
| 215 | *Lygus hesperus* | Western Plant Bug | LH-MAEL |
| 216 | *Pectinophora gossypiella* | Pink Bollworm | PG-MAEL |
| 217 | *Diabrotica barberi* | Northern Corn Rootworm | DB-NCLB |
| 218 | *Diabrotica undecimpunctata* | Southern Corn Rootworm | DU-NCLB |
| 219 | *Phyllotreta striolata* | Striped Flea Beetle | PS-NCLB |
| 220 | *Phyllotreta cruciferae* | Crucifer Flea Beetle | PC-NCLB |
| 221 | *Leptinotarsa decemlineata* | Colorado Potato Beetle | LD-NCLB |
| 222 | *Tribolium castaneum* | Red Flour Beetle | TC-NCLB |
| 223 | *Epilachna varivestis* | Mexican Bean Beetle | EV-NCLB |
| 224 | *Vibidia duodecimguttata* | 12-Spotted Ladybeetle | VD-NCLB |
| 225 | *Pectinophora gossypiella* | Pink Bollworm | PG-NCLB |

TABLE 1-continued

VgR RNAi target fragments.

| SEQ ID NO. | Species | Common name | Fragment ID |
|---|---|---|---|
| 226 | *Spodoptera frugiperda* | Fall Armyworm | SF-NCLB |
| 227 | *Ostrinia nubilalis* | European Corn Borer | ON-NCLB |
| 228 | *Manduca sexta* | Hornworm | MS-NCLB |
| 229 | *Helicoverpa zea* | Corn Earworm | HZ-NCLB |
| 230 | *Megacopta cribraria* | Kudzu Bug | MC-NCLB |
| 231 | *Nezara viridula* | Southern Green Stink Bug | NV-NCLB |
| 232 | *Diabrotica virgifera virgifera* | Western Corn Rootworm | DV-BOULE-FRAG2 |
| 233 | *Diabrotica virgifera virgifera* | Western Corn Rootworm | DV-BOULE-FRAG3 |
| 234 | *Diabrotica virgifera virgifera* | Western Corn Rootworm | DV-BOULE-FRAG4 |
| 235 | *Diabrotica virgifera virgifera* | Western Corn Rootworm | DV-BOULE-FRAG5 |
| 236 | *Diabrotica virgifera virgifera* | Western Corn Rootworm | DV-BOULE-FRAG6 |
| 237 | *Diabrotica virgifera virgifera* | Western Corn Rootworm | DV-BOULE-FRAG7 |
| 238 | *Diabrotica virgifera virgifera* | Western Corn Rootworm | DV-BOULE-FRAG8 |
| 239 | *Diabrotica virgifera virgifera* | Western Corn Rootworm | DV-BOULE-FRAG9 |
| 240 | *Diabrotica virgifera virgifera* | Western Corn Rootworm | DV-MAEL-FRAG2 |
| 241 | *Diabrotica virgifera virgifera* | Western Corn Rootworm | DV-MAEL-FRAG3 |
| 242 | *Diabrotica virgifera virgifera* | Western Corn Rootworm | DV-MAEL-FRAG4 |
| 243 | *Diabrotica virgifera virgifera* | Western Corn Rootworm | DV-MAEL-FRAG5 |
| 244 | *Diabrotica virgifera virgifera* | Western Corn Rootworm | DV-MAEL-FRAG6 |
| 245 | *Diabrotica virgifera virgifera* | Western Corn Rootworm | DV-MAEL-FRAG7 |
| 246 | *Diabrotica virgifera virgifera* | Western Corn Rootworm | DV-MAEL-FRAG8 |
| 247 | *Diabrotica virgifera virgifera* | Western Corn Rootworm | DV-MAEL-FRAG9 |
| 248 | *Diabrotica virgifera virgifera* | Western Corn Rootworm | DV-MAEL-FRAG10 |
| 249 | *Diabrotica virgifera virgifera* | Western Corn Rootworm | DV-NCLB-FRAG2 |
| 250 | *Diabrotica virgifera virgifera* | Western Corn Rootworm | DV-NCLB-FRAG3 |
| 251 | *Diabrotica virgifera virgifera* | Western Corn Rootworm | DV-NCLB-FRAG4 |
| 252 | *Diabrotica virgifera virgifera* | Western Corn Rootworm | DV-NCLB-FRAG5 |
| 253 | *Diabrotica virgifera virgifera* | Western Corn Rootworm | DV-NCLB-FRAG6 |
| 254 | *Diabrotica virgifera virgifera* | Western Corn Rootworm | DV-RPS10 |

*"Transcipt" indicates that the sequence is a full-length mRNA transcript sequence.

**"ORF" indicates that the sequence corresponds to the open reading frame sequence.

Example 2: Western Corn Rootworm (WCRW) Adult Sterilization by VgR dsRNA

Artificial diet for WCRW adults was prepared using a modified protocol (Rangasamy M et al. (2012). Pest Manag. Sci. 68(4):587-91; and Nowatzki T M, et al. (2006) J Econ. Entomol. 99(3):927-30). The modified diet was designed for use in the diet incorporated bioassay described herein below (25 μl test sample:75 μl prepared diet) and was produced using standard 96-well micro-titer plates. WCRW adults consumed significant proportions of the diet within 24 hours, and control mortality remains <15% during the 2-3 week study period. For all the bioassays described herein, WCRW life stages (adults and larvae) were kept under standard conditions, for example, Jackson, J. J. (1986), pp 25-48. In Krysan J. L. and Miller T. A. (eds): Methods for the Study of pest Diabrotica. Springer-Verlag, New York. 260 pp, and Branson, T. F., et al. (1988), J. Econ. Entomal. 81(1): 410-414 (1988).

Beetles from the same batch were categorized in to two groups. The first test group consisted of male and females of <10 days old (range 2-5 days old) (hereinafter referred to as "younger females"). The younger females were in their preoviposition period (the period before oviposition of the first eggs). The second group consisted of >11 days old and mated females (hereinafter referred to as "older females") and they were in oviposition period (females are ready to lay eggs). For the younger female group 100 beetles (50 females and 50 males) and for the older female group 50 mated females were arranged for each treatment. The following three treatments were compared 1) sterile DI water (control); 2) GFP dsRNA (negative control, GenBank Accession # AY233272.1; SEQ ID NO: 104 herein); and 3) VgR dsRNA fragment 2 (SEQ ID NO: 4). The bioassay was carried out using a diet incorporation methodology. Test samples of GFP dsRNA and VgR dsRNA were prepared separately and 25 μl of the respective samples were incorporated into 75 μl of modified WCRW adult artificial diet per well in 96-well micro-titer plates for a final concentration of 100 ppm. For control 25 μl of sterile DI water was incorporated into 75 μl of modified WCRW adult artificial diet per well.

The effects on individual WCRW adult beetle were confined using individual wells of 32 cell trays (C-D International, Pitman, N.J.) provided with single diet pill (mixture of 25 μl test sample and 75 μl of modified WCRW adult artificial diet) for 24 hours. After 24 hour, treated adults were collected, counted and transferred to their respective holding cages and provided standard SCRW dry adult diet and water source until the end of the study period (22-25 days).

WCRW eggs were collected daily for 13-14 days starting from 24 hour or 7 days after exposure for the older and younger female group, respectively. Eggs were collected using oviposition dish. Collected eggs were incubated in a heat and humidity controlled growth chamber (25° C., 65%±5% relative humidity (RH)) with controlled light/dark cycles (16 hr light:8 hr darkness) for 12-14 days before processing.

Several small aliquots of egg-agar suspensions were dispensed onto a hatch plate (petri-dish containing 2% water agar and two layers of filter paper) for counting and/or hatch test depending on the number of eggs obtained for a given day. For the egg hatch test, samples (1-6) each containing 25 μl of egg-agar suspension were dispensed onto the hatch plate as described above and the lids secured with micropore tape to avoid larval escape. Total number of eggs in each 25 μl sample was counted prior incubation. Egg hatch plates were then incubated in a heat and humidity controlled growth chamber (25° C., 65%±5% RH) with controlled light/dark cycles (16 hr light:8 hr darkness) for three days. Egg hatch was counted over three days period by counting the number of eggs showing larval emergence hole. For each treatment, four treated female and male beetles (younger female group) and four females (older female group) were sampled for gene suppression at 4 and 8 days after exposure for the older and younger female group respectively.

For dsRNA in vitro transcript ("IVT") production, PCR was performed using target specific forward and reverse primers (see Table 2 below) with a T7 promoter sequence at the 5' end of each primer. The dsRNA samples were produced from PCR template using Ambion Megascript High Yield Transcription Kit (Thermo Fisher Scientific, Grand Island, N.Y.). An agarose gel was run to check for yield and product size. For real time qRTPCR assay, total RNA was extracted with MirVana miRNA Isolation Kit, treated by TURBO DNase Kit, assayed by SuperScript® III Platinum® One-Step qRT-PCR Kit with ROX according to manufacturer's instructions (Thermo Fisher Scientific). Relative expression was derived by delta delta Ct method (Livak, K. J. and T. D. Schmittgen (2001). *Methods* 25(4): 402-408) using WCRW RPS10 as reference (i.e., SEQ ID NO: 8 in US 2011/0054007; also SEQ ID NOs.: 102 and 103, ORF and transcript, respectively, herein).

TABLE 2

Primer Sequences IVT Production.

| Fragment ID | Forward Primer SEQ ID NO. | Reverse Primer SEQ ID NO. |
|---|---|---|
| DV-VGR-FRAG1 | 54 | 55 |
| DV-VGR-FRAG2 | 56 | 57 |
| DV-VGR-FRAG3 | 58 | 59 |
| DV-VGR-FRAG4 | 60 | 61 |
| DV-VGR-FRAG5 | 62 | 63 |
| DV-VGR-FRAG6 | 64 | 65 |
| DV-VGR-FRAG7 | 66 | 67 |
| DV-VGR-FRAG8 | 68 | 69 |
| DV-VGR-FRAG9 | 70 | 71 |
| DV-VGR-FRAG10 | 72 | 73 |
| DV-VGR-FRAG11 | 74 | 75 |
| DV-VGR-FRAG12 | 76 | 77 |
| DV-VGR-FRAG13 | 78 | 79 |
| DV-VGR-FRAG14 | 80 | 81 |
| DV-VGR-FRAG15 | 82 | 83 |
| DV-VGR-FRAG16 | 84 | 85 |
| GFP | 86 | 87 |
| GUS | 88 | 89 |

Figure 1B:
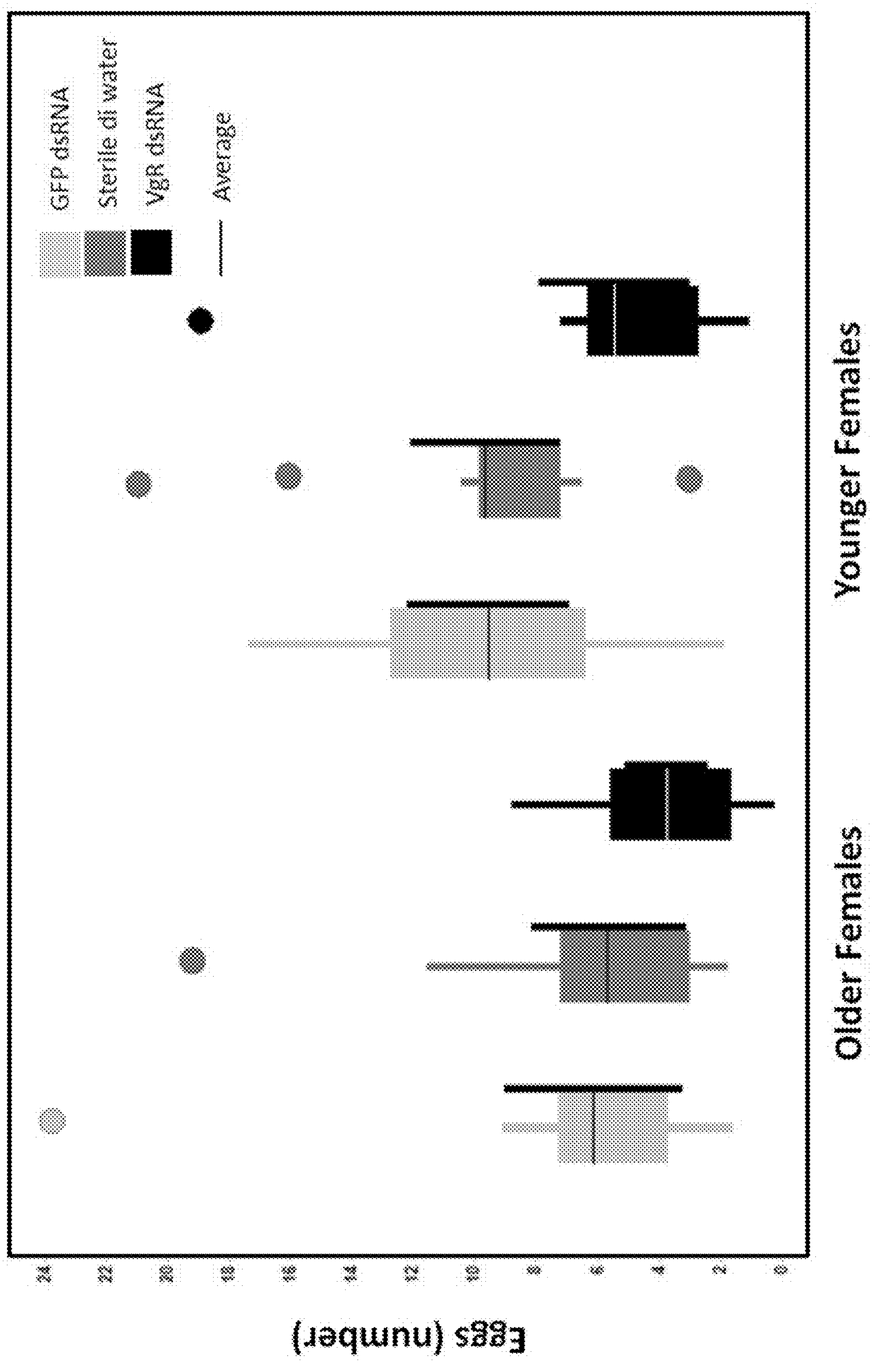
Figure 1C:
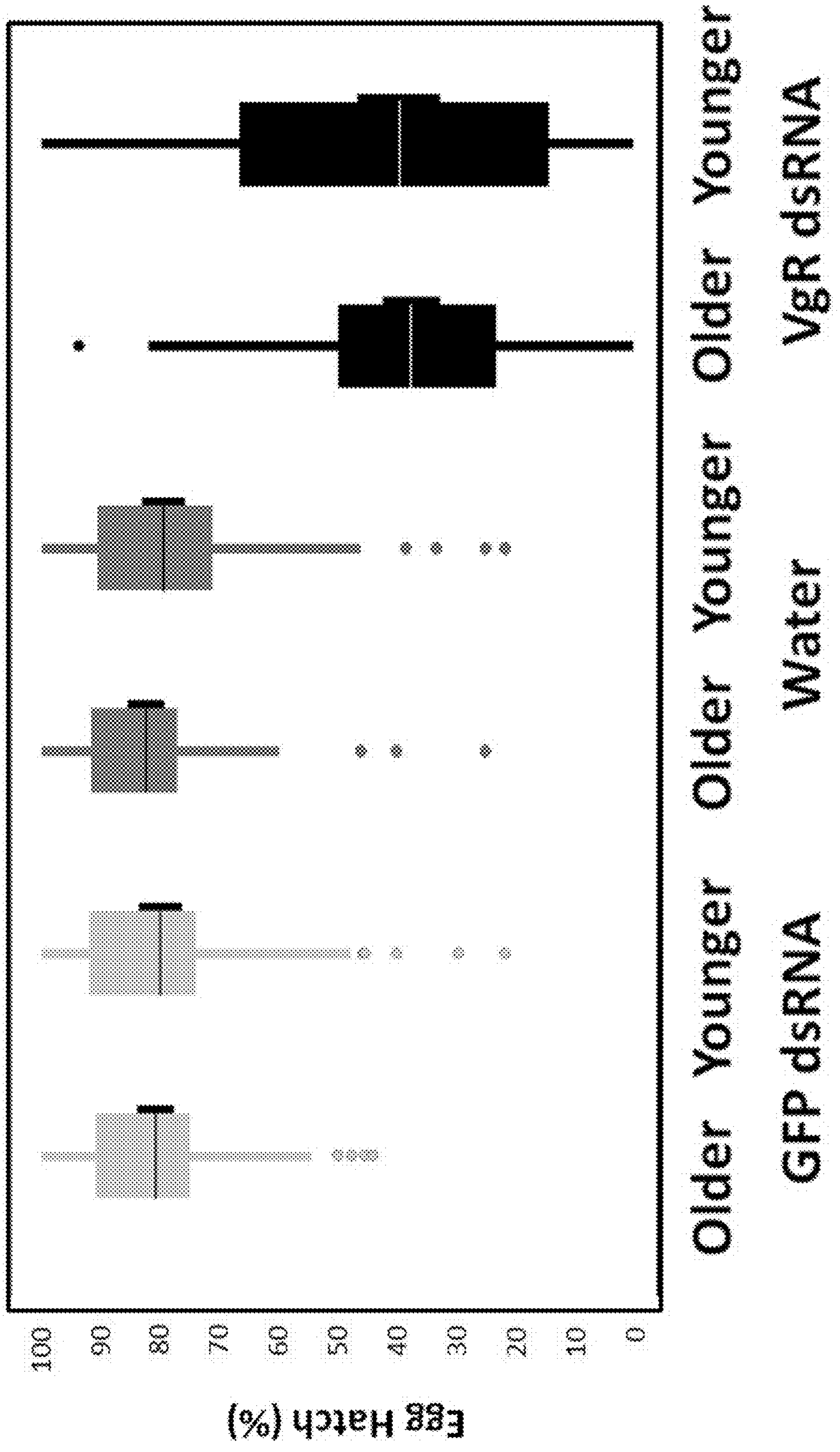
Figure 1D:
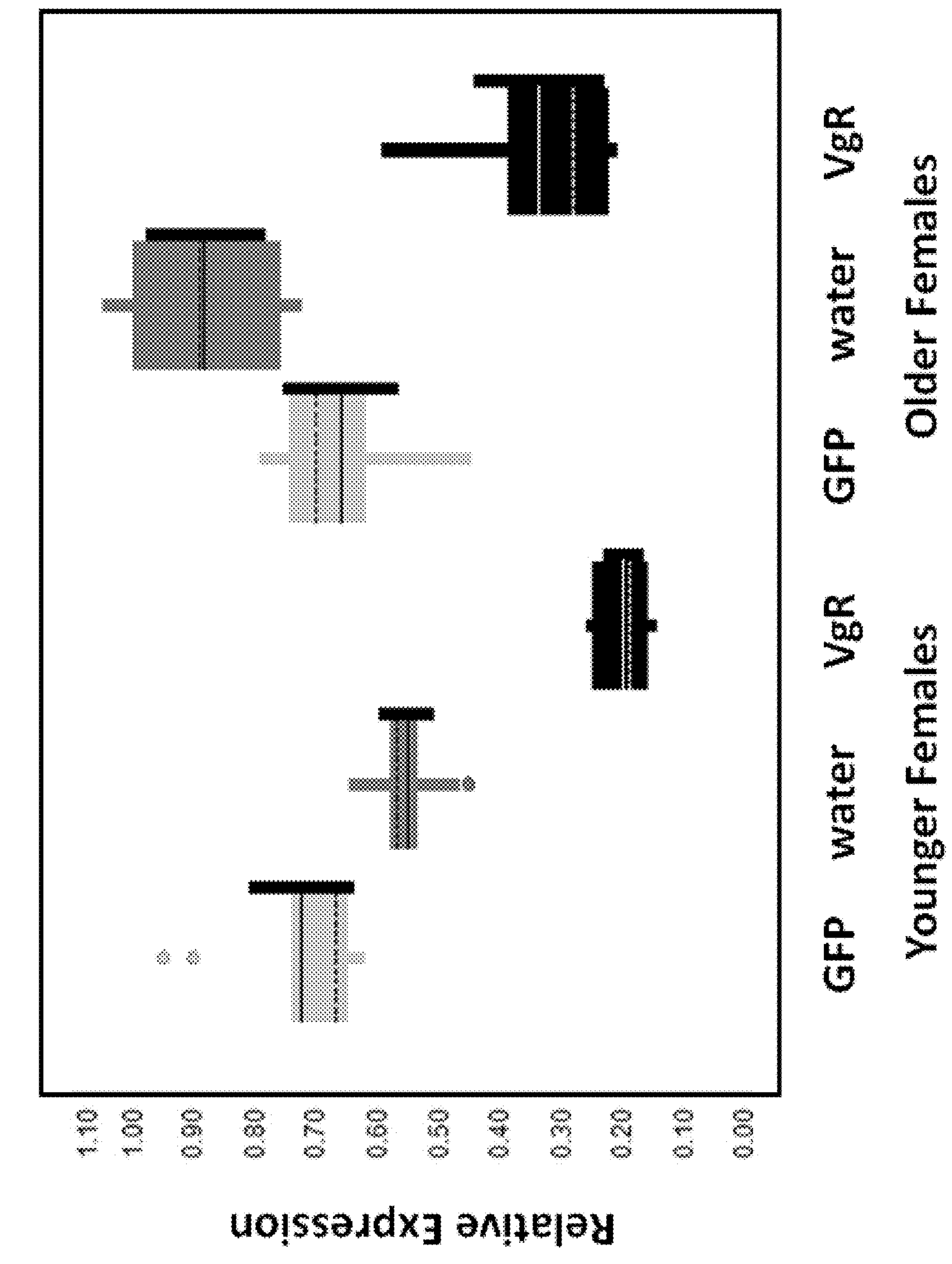

Data obtained using these methods are shown in FIGS. 1A-1D. In particular, FIG. 1A shows the total number of eggs produced within 13-14 days by treatment and age group. In the experiment shown in FIG. 1A, the younger female group contained 50 pairs of male and female beetles, whereas the older female group had 50 mated female beetles. The data in FIG. 1A show that ingestion of the VgR dsRNA significantly reduced the total number of eggs produced during the test period. FIG. 1B shows the average number of eggs produced per female/day during 13-14 day oviposition period by treatment and age group. The box plot shows 4 quartiles, average, and 95% confidence interval of the mean. The data show that in both younger and older females, ingestion of the VgR dsRNA reduced the average number of eggs produced per day. FIG. 1C shows the effect of various treatments on overall average egg hatch rate. Data represents 13-14 days egg collection period; n=6 replication/treatment/day; 5-45 eggs/replication depending on the day ($p<0.001$). Gene suppression analysis is shown in FIG. 1D for analysis carried out on WCRW adult beetles 8 days after treatment of female and male insects for younger age group and 4 days after treatment of female insects for older age group. Relative expression of VgR is shown from 4 individual insects for each treatment using WCRW RPS10 gene as reference and untreated older beetle as normalizer. The box plot shows 4 quartiles, average, median, and 95% confidence interval of the mean by treatment and age group.

Example 3: WCRW Sterilization by Treatment of 3rd Instar Larvae with VgR dsRNA The effect of treatment of larva on WCRW sterilization by VgR dsRNA (VgR dsRNA fragment 2) was assessed. The study was carried out using 3rd instar larvae that were harvested from corn mats and acclimatized on standard WCRW larval diet for 24 h. About 192 larvae were exposed to water and 75 ppm VgR dsRNA fragment 2 (SEQ ID NO: 4) for 1 day using the diet incorporation method described above (25 μl dsRNA and 75 μl artificial WCRW larval diet). Treated larvae were placed in pupation medium for 15 days. Emerged adults were collected, counted, and transferred to their respective holding cages and provided standard SCRW dry adult diet with a water source until the end of the study period (22-25 days). Beetle holding cages were kept at room temperature (usually from 22-25° C.) with no RH control.

No intentional light/dark control but cages were getting roughly 16:8 Dark and light condition. Beetle holding cages were cleaned maintained twice a week and each time the beetles received new food and water agar. Adult beetles were kept for a total of 26 days. Each cage received oviposition dishes after 10 days preoviposition period and eggs were collected over a period of for 16 days oviposition period, and processed following the method described above.

Figure 2A:
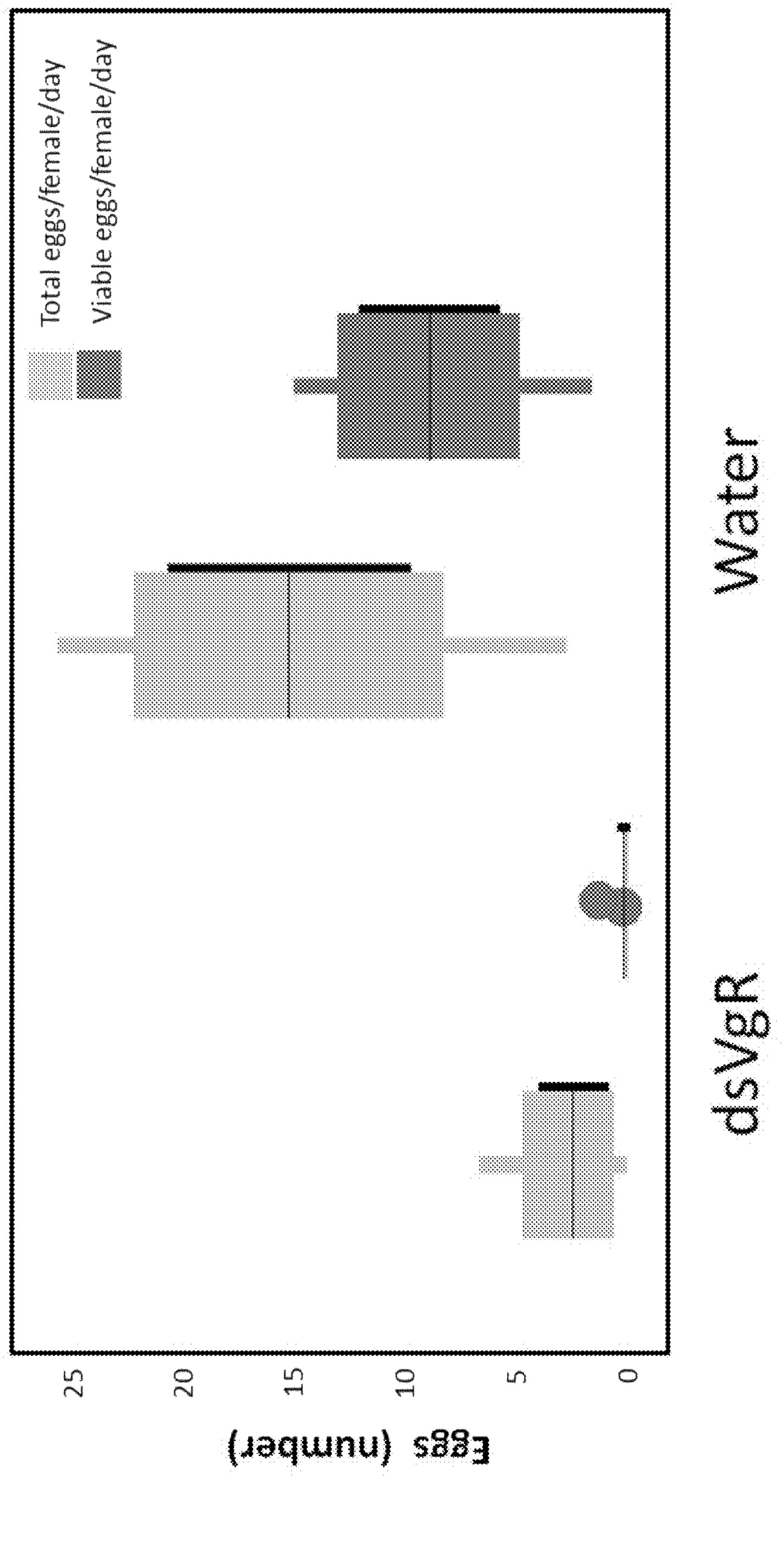
FIGS. 2A-2B show representative data pertaining to sterilization of WCRW following feeding $3^{rd}$ instar larvae with an artificial diet comprising a dsRNA construct comprising a target nucleotide sequence of SEQ ID NO.: 4.
Figure 2B:
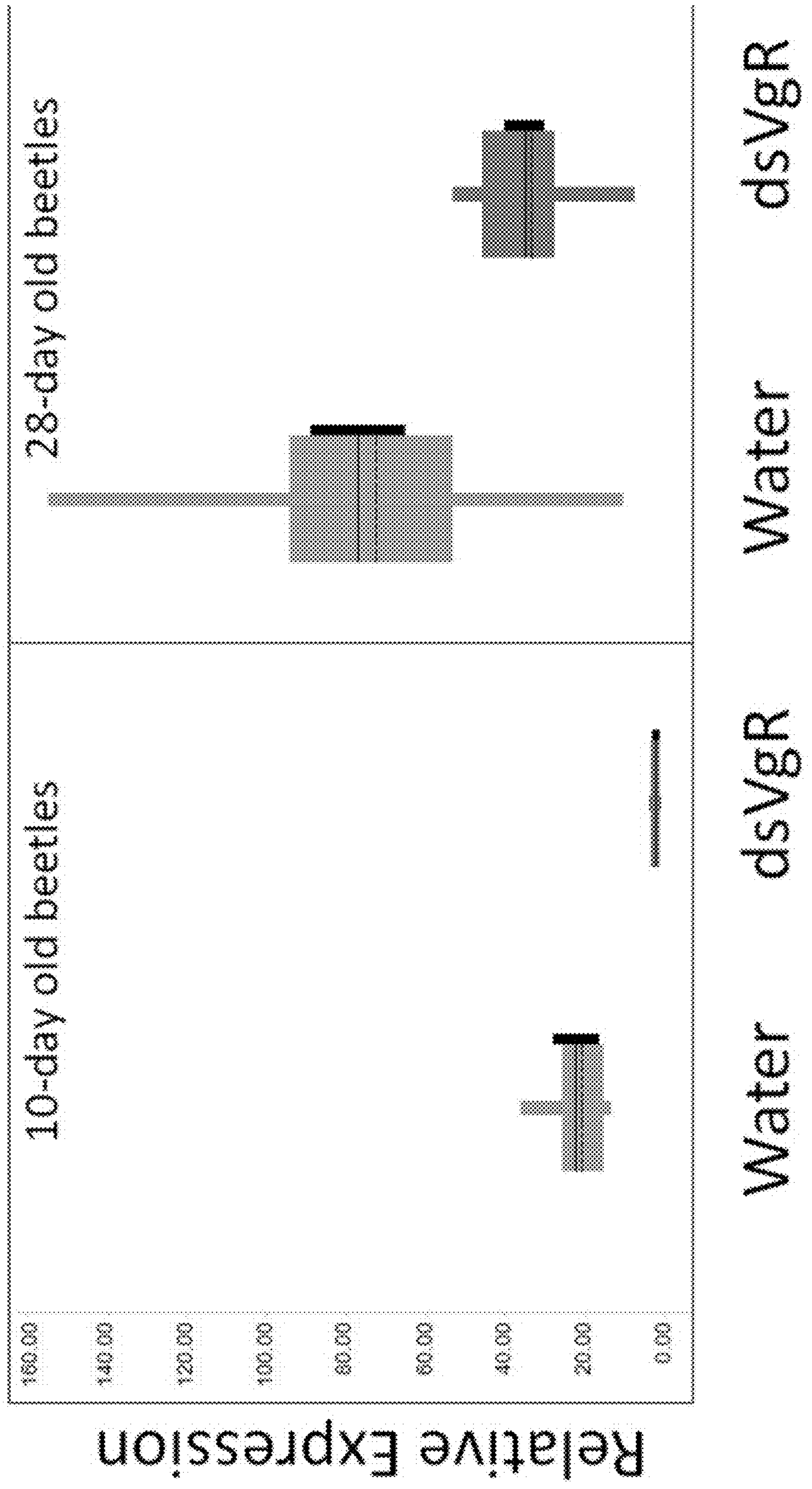

Representative data for this study are shown in FIGS. 2A and 2B. The average total number of eggs produced per female and the average number of viable eggs produced per female are shown in FIG. 2A. Eggs from 15-42 female adult beetles were counted for each indicated treatment. The box plot of shows 4 quartiles, average, median, and 95% confidence interval of the mean for each treatment. The data show that for the VgR dsRNA exposed group, the viable egg production remained very low throughout the study period. It should be noted that treatment with VgR dsRNA did not affect adult emergence, and that mortality of adult beetles in the VgR dsRNA group was negligible.

Representative data for VgR gene suppression analysis is shown in FIG. 2B. The data were obtained for 10-day old (n=4) and 28-day old (n=15) beetles, which represents day 40 and day 58, respectively, following treatment of the $3^{rd}$ instar larvae. The box plot of relative expression by qRT-PCR shows 4 quartiles, average, median, and 95% confidence interval of the mean for each treatment in 10 and 28 day old beetles. The data were normalized to untreated 3rd instar larvae. The data show decreasesd relative expression of VgR in both age groups.

Example 4: Dose Response of WCRW Sterilization and Gene Suppression by VgR dsRNA Treatment The dose response effect of dsRNA treatment was determined in younger and older adult females. The older female group (>11 days old) was collected and exposed VgR dsRNA using the diet incorporation methodology described above. The treatment groups were exposed for 24 hours. The VgR dsRNA was complementary to SEQ ID NO: 3, and the concentrations tested were as follows: 0, 0.01 ppm, 0.1 ppm, 1 ppm, 10 ppm and 75 ppm. The treatment groups consisted of about 40-48 females for each dose level. Egg production was assessed starting 24 hours after exposure and continued for 18 days. For each treatment, the total number of female beetles used for egg production varies from 40-48 (days 1-6) and 20-28 (days 7-18). Eggs were handled and processed following the methods described above. Six day after exposure 20 treated females were retrieved from each treatment and were used for gene suppression analysis.

Figure 3B:
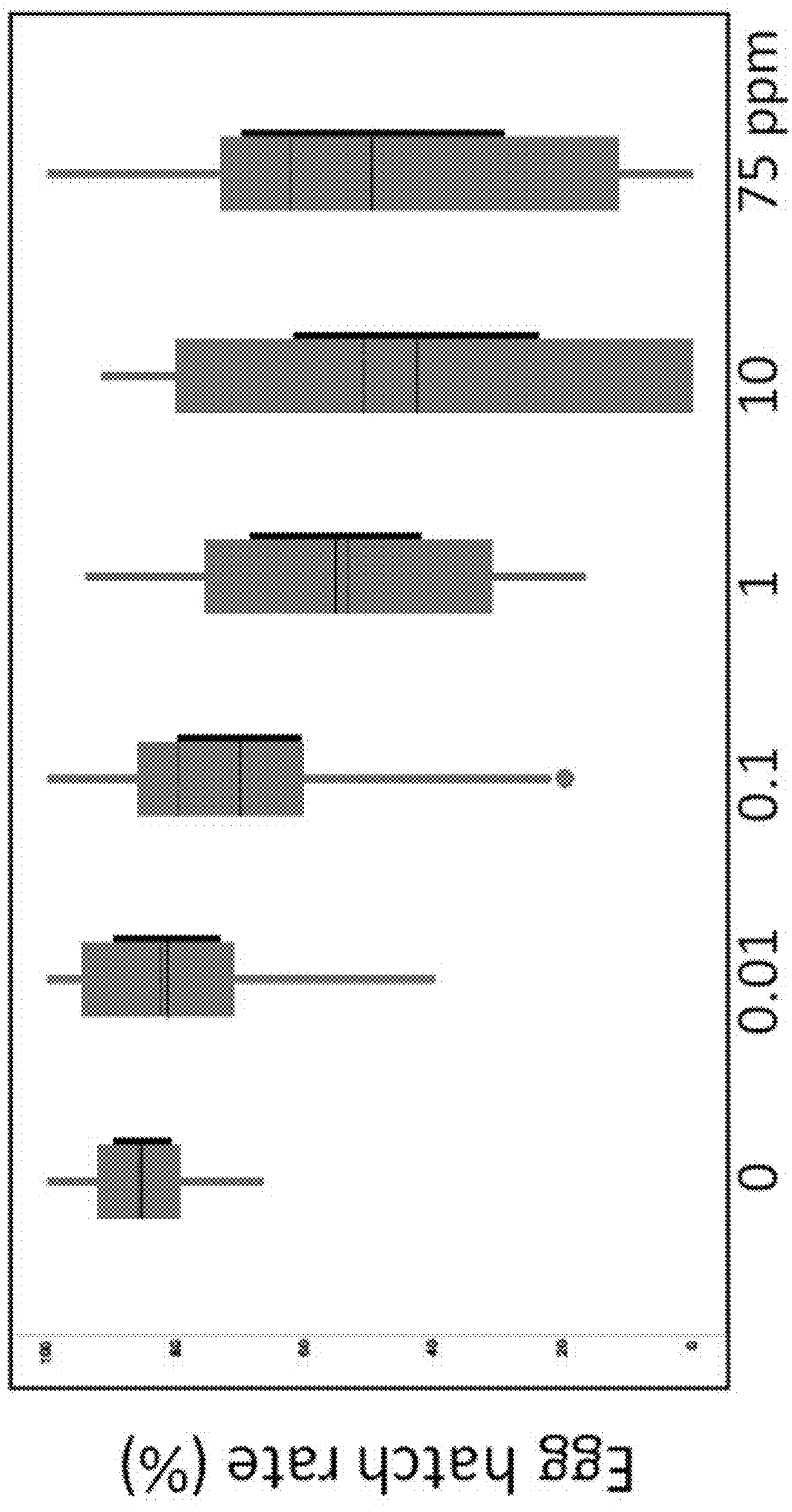
Figure 3C:
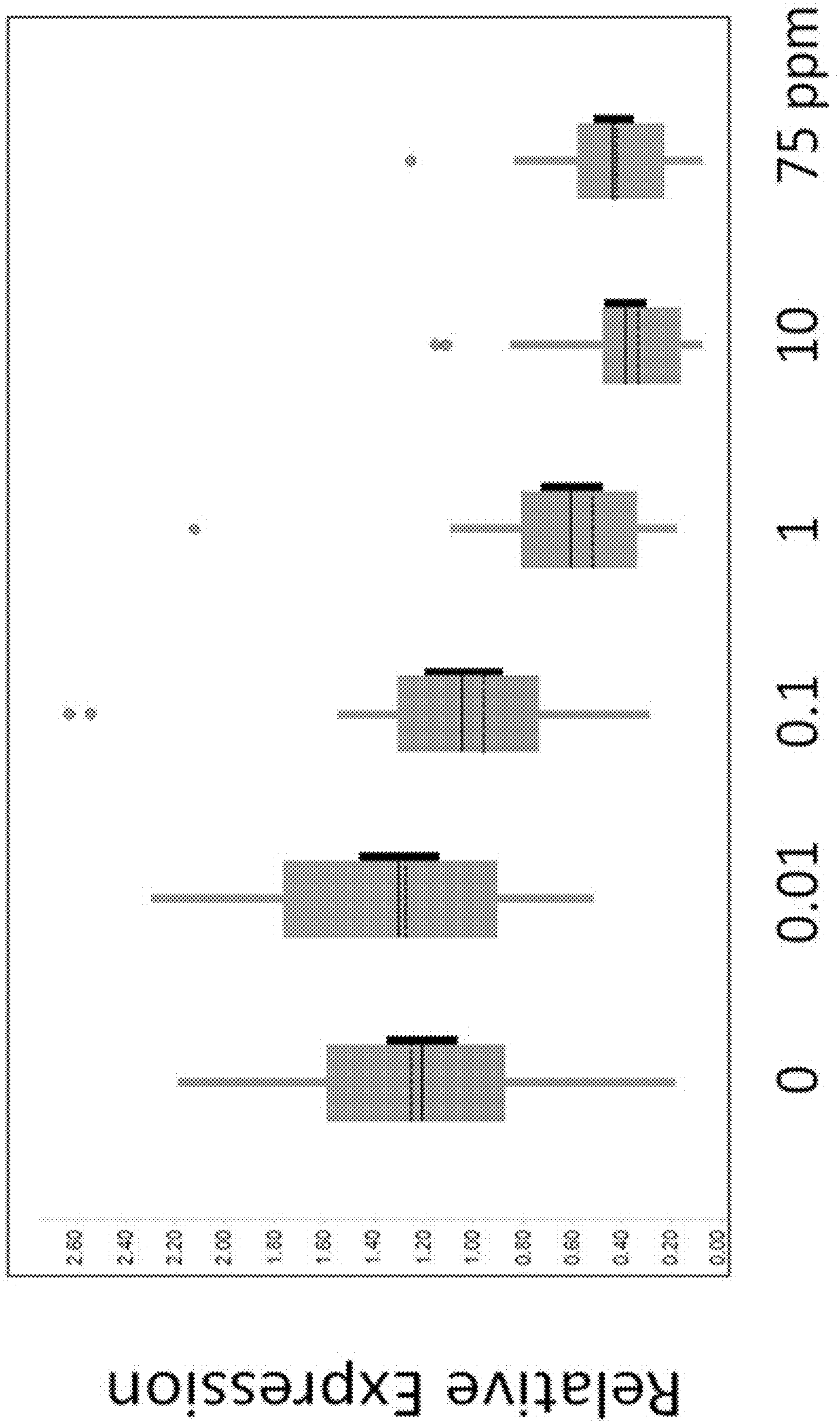

The details for each dose treatment group (e.g. number of total eggs analyzed, number of viable eggs, and net reduction in fecundity) are given in FIG. 3A. Eggs were collected and counted over the 18 day oviposition period. The net reduction in fecundity (NRF) of VgR dsRNA-treated females relative to control (water exposed females) was estimated using the following formula:

$$NRF\ (\%)=[1-(NVEt/NVEwc)]*100,$$

where "NRF" represents the net reduction in fecundity as a percent; "NVEt" represents the number of viable eggs in the treatment group; and "NVEwc" represents the number of viable eggs in water (control) treated group. The data show a significant reduction in egg production after 10 days of exposure to the VgR dsRNA (see eggs/female day 10-18 in FIG. 3A). The data further show that egg production and viability of eggs were negatively correlated with VgR dsRNA doses. The net reduction in fecundity was positively correlated with increased vgR dsRNA doses. FIG. 3B shows a box plot of percentage of overall egg hatch rates by dose for the 18 day egg collection period; n=1-4 replication/treatment/day; 5-478 eggs/replication depending on the day and availability of eggs. The data in FIG. 3C show a box plot of relative expression of VgR at day 6 after VgR dsRNA treatment at different doses. The data in FIG. 3C show the correlation of increasing dose with a larger decrease in expression of VgR. The treatment group data were normalized to the expression for untreated beetles.

Example 5: Gene Suppression Analysis of VgR Fragments

Figure 4A:
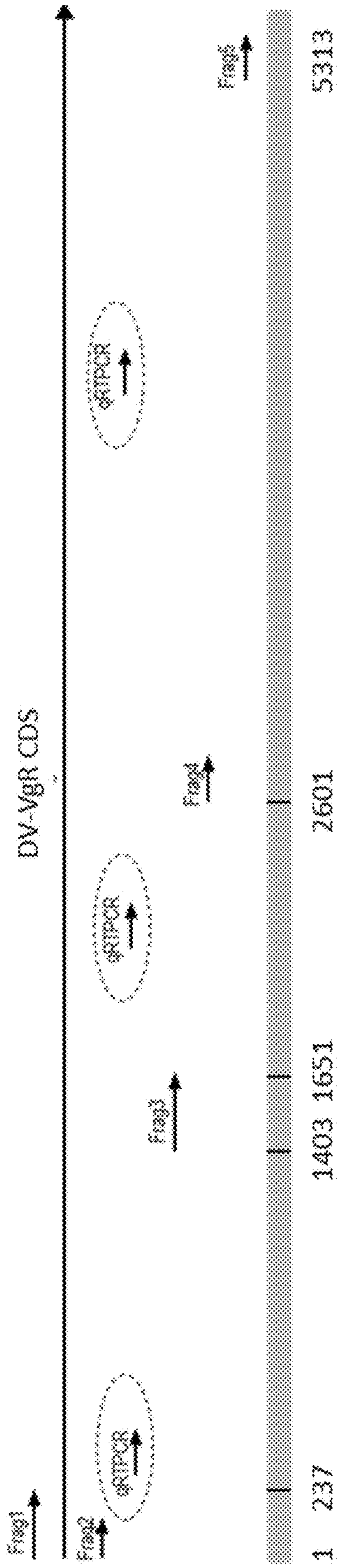
FIGS. 4A-4B show data pertaining to VgR gene suppression following ingestion of various VgR dsRNA fragments.
Figure 4B:
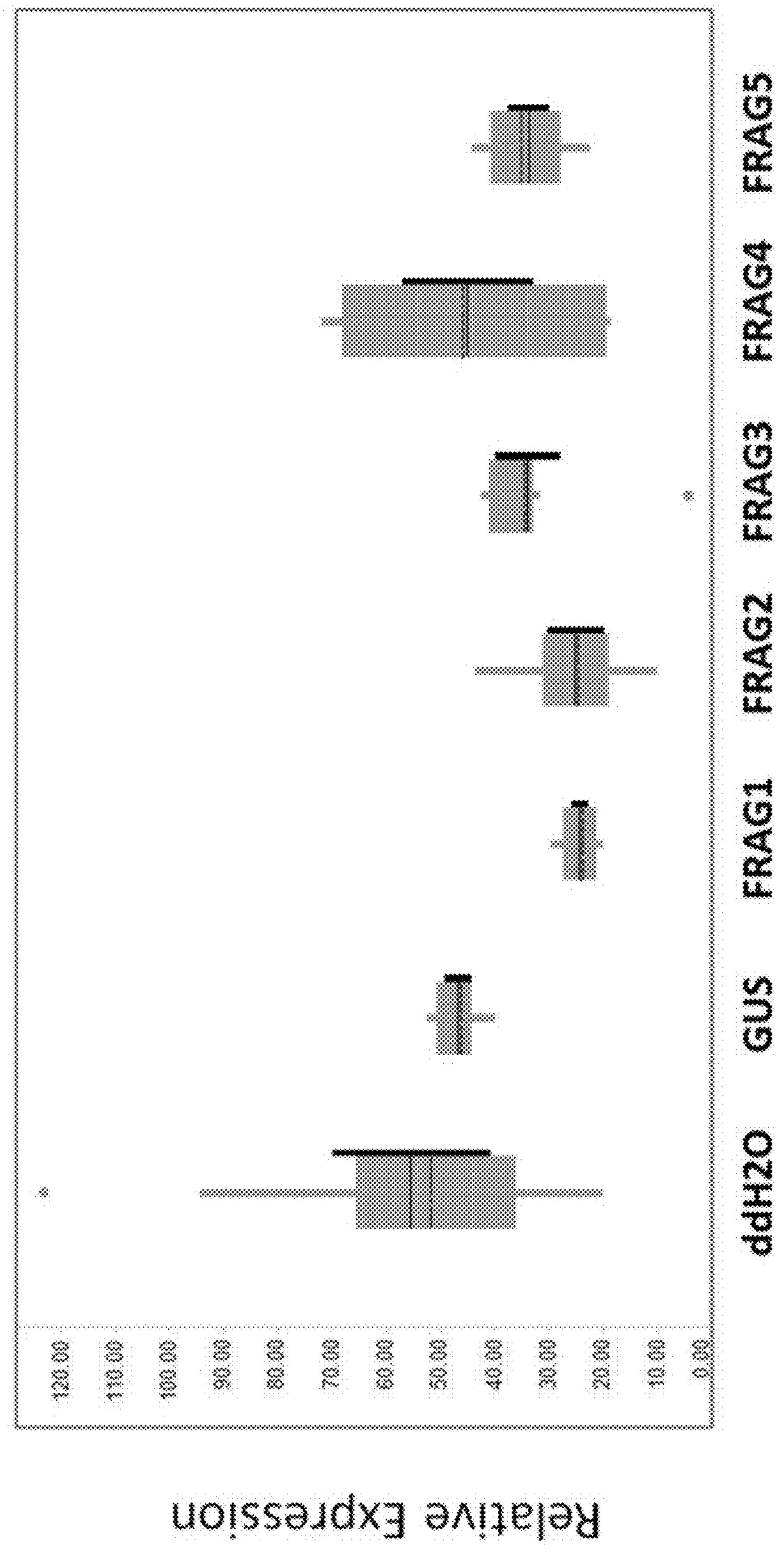

The effect of five distinct VgR dsRNA target fragments was assessed. FIG. 4A shows schematically the relative position of the different fragments tested aligned against SEQ ID NO: 2. The target fragments tested were as follows: Frag1 is VgR fragment 1 (SEQ ID NO: 3); Frag2 is VgR fragment 2 (SEQ ID NO: 4); Frag3 is VgR fragment 3 (SEQ ID NO: 5); Frag4 is VgR fragment 4 (SEQ ID NO: 6); and Frag5 is VgR fragment 5 (SEQ ID NO: 7). Each VgR dsRNA fragment was tested using the diet incorporation methodology described above with WCRW female beetles with the VgR dsRNA at 100 ppm in the diet plug. The beetles were treated individually for one day and fed with standard diet with no dsRNA for an additional six days. The individual beetles were then collected and flash frozen in liquid nitrogen. For the qRTPCR assays, at least 3 insects were used for each treatment group using the primer sequences indicated in Table 3 below. FIG. 4B shows a box plot of the relative VgR expression at day 6 after treatment with the indicated dsVgR fragments or control treatment (i.e., ddH2O and dsGUS (SEQ ID NO: 105, herein), as indicated, replacing the VgR dsRNA in the diet) using 5' qRTPCR assay. The box plot shows four quartiles: average (horizontal solid line), median (horizontal dash line), and 95% confidence interval of the mean are shown. Similar results were also obtained with Mid- and 3'-qRTPCR assays. The data in the treatment groups were normalized to data obtained from qRTPCR from untreated 3rd instar larvae.

TABLE 3

Primer Sequences Gene Suppression Analysis.

| qRTPCR Assay ID | Forward Primer SEQ ID NO. | Reverse Primer SEQ ID NO. | Amplicon SEQ ID NO. | Amplicon Length (nc) |
|---|---|---|---|---|
| DV-VgR 5' | 90 | 91 | 92 | 147 |
| DV-VgR mid | 93 | 94 | 95 | 140 |
| DV-VgR 3' | 96 | 97 | 98 | 78 |
| DV-RPS10 | 99 | 100 | 101 | 77 |

Example 6: WCRW VgR Fragment Screen by Gene Suppression Analysis

Figure 5A:
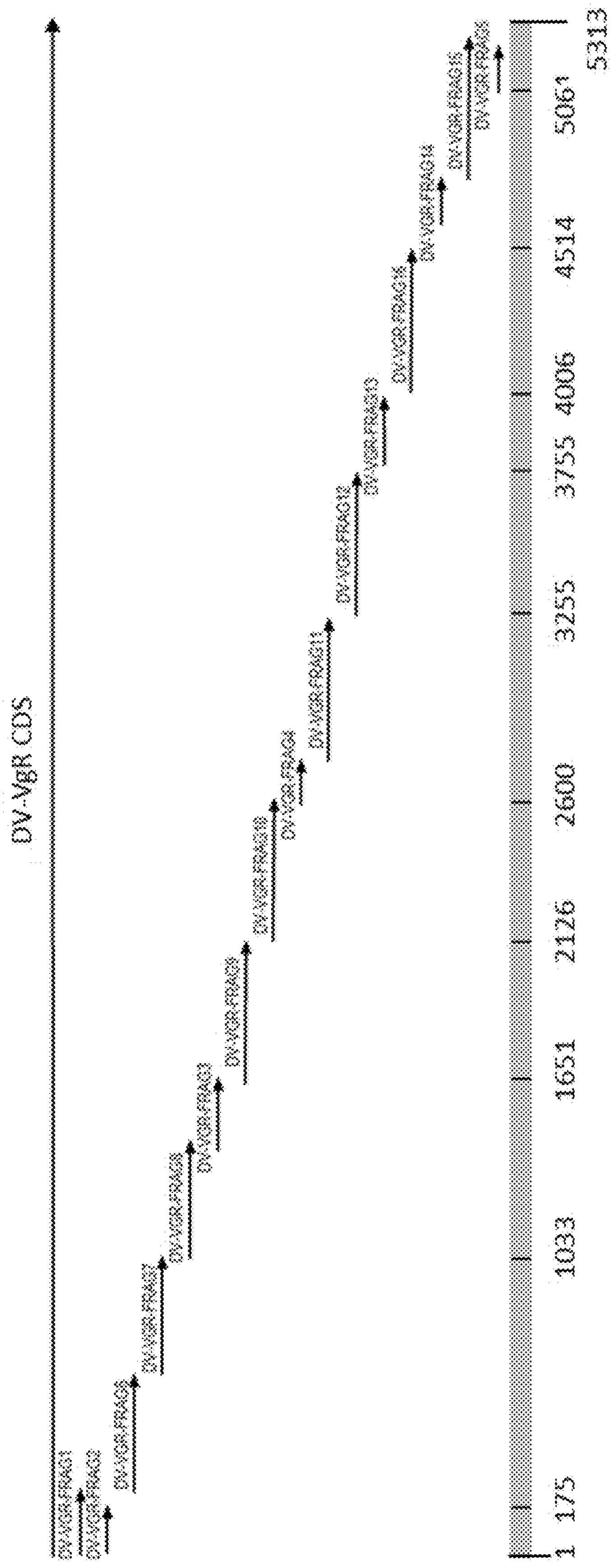
FIGS. 5A-5D show data pertaining to VgR fragment screen using gene suppression analysis.
Figure 5B:
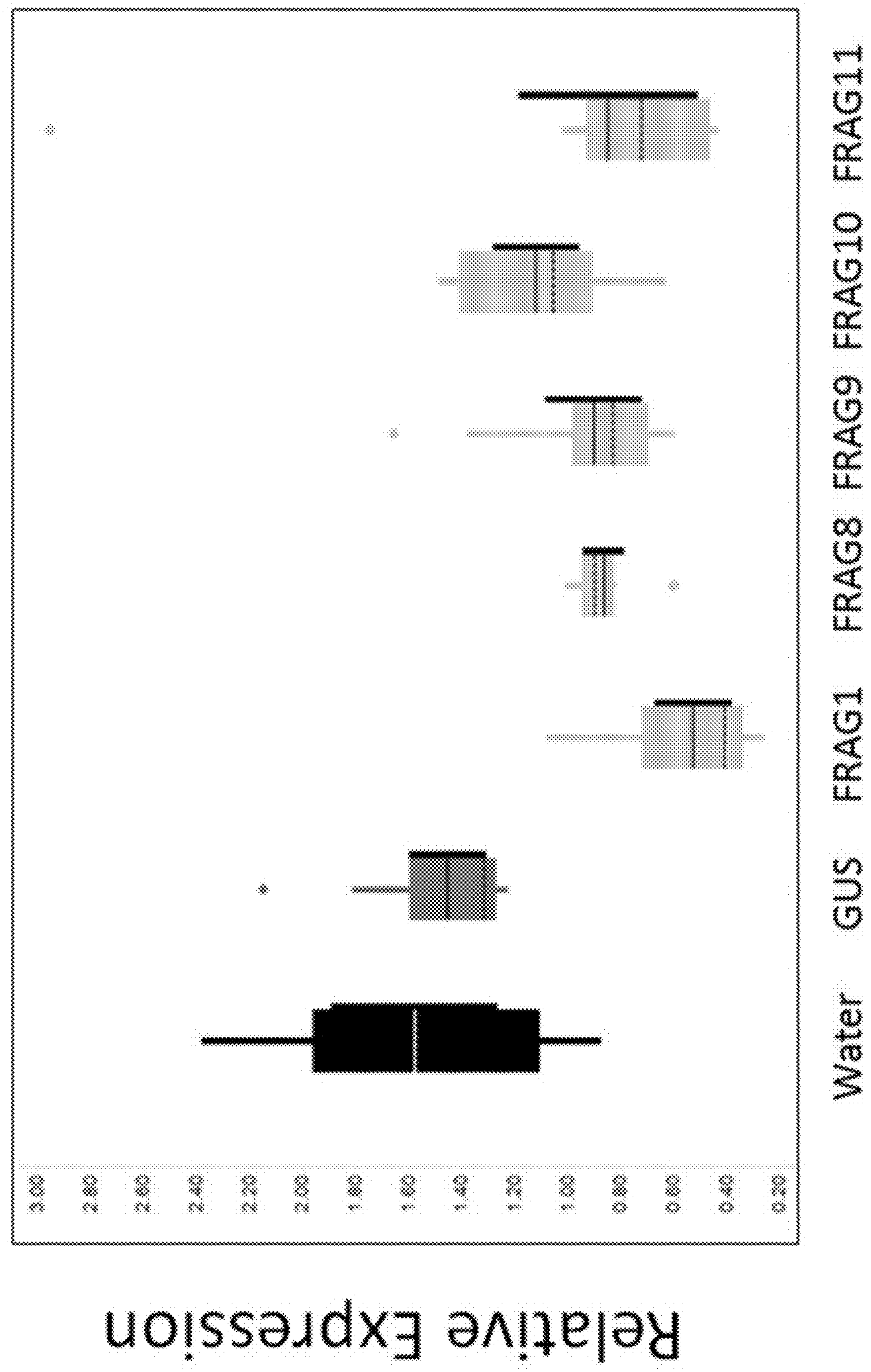
Figure 5C:
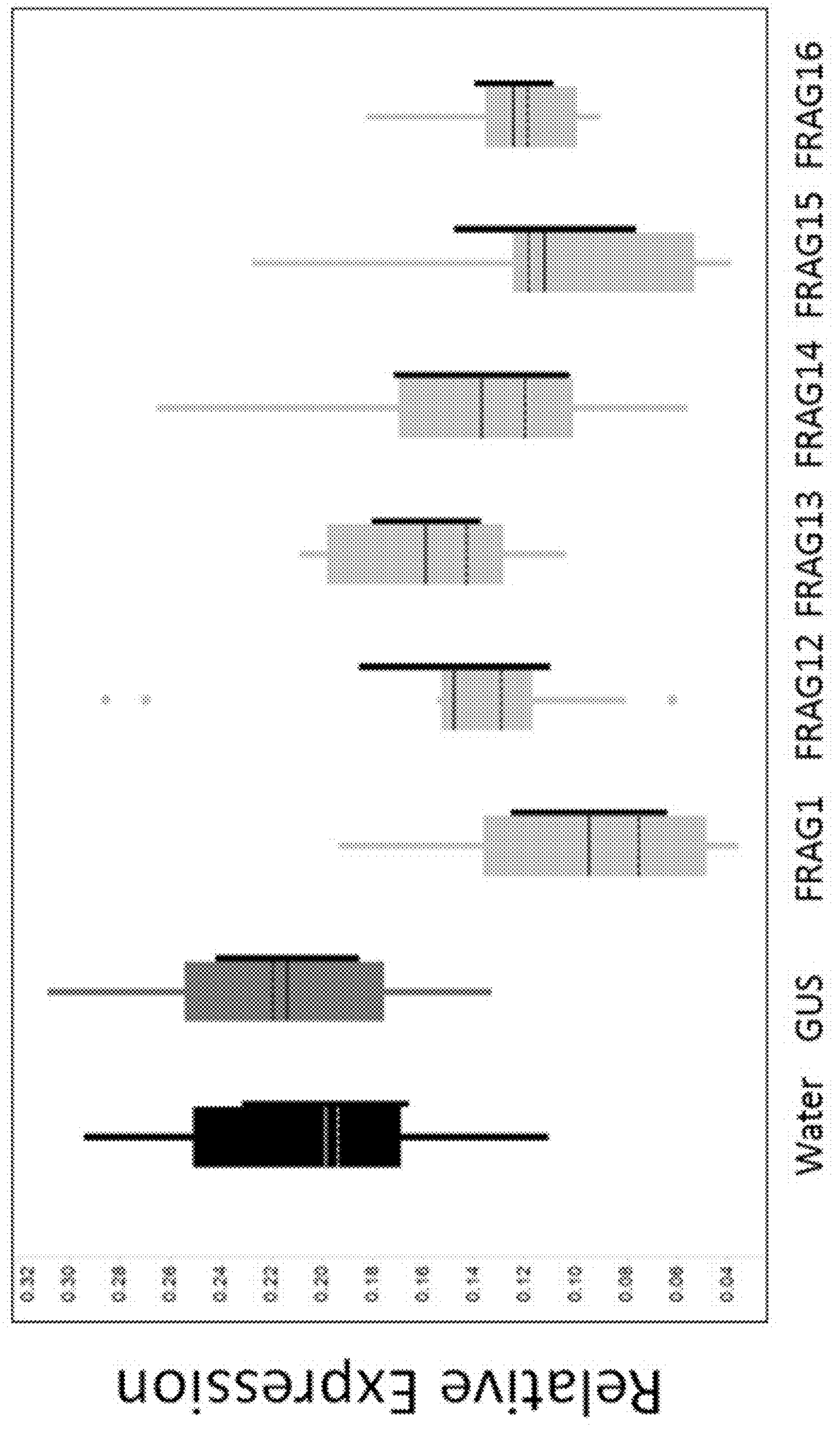
Figure 5D:
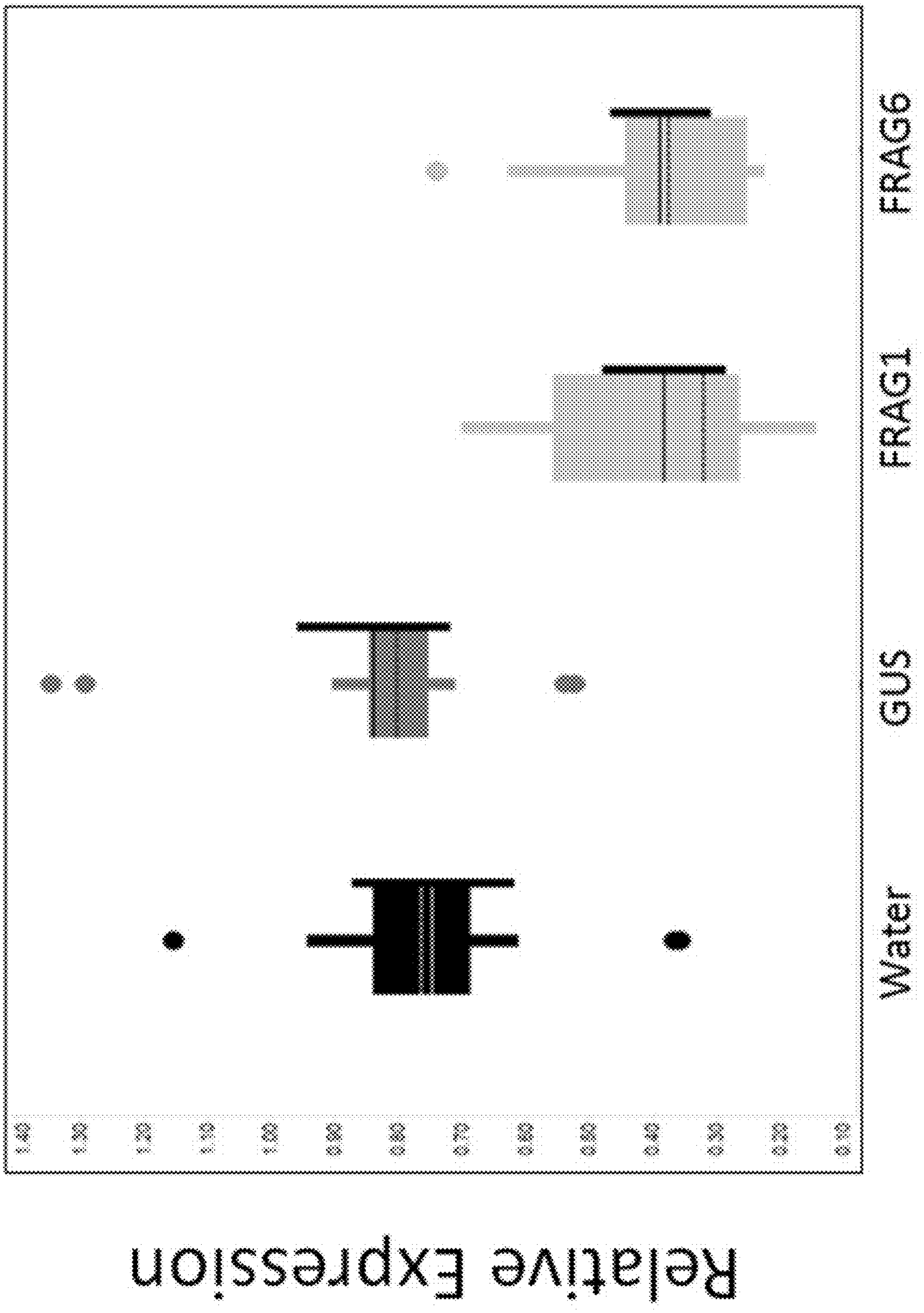

Additional VgR dsRNA fragments covering the entirety of the coding DNA sequence of SEQ ID NO: 2 were assessed for ability to suppress expression of VgR. The fragments tested are shown aligned against SEQ ID NO: 2 in FIG. 5A, and the various sequence names correspond to the fragment ID shown in Table 1. Each VgR dsRNA fragment was tested using the diet incorporation methodology described above with WCRW female beetles with the VgR dsRNA at 100 ppm in the diet plug. The beetles were treated individually for one day and fed with standard diet with no dsRNA for 6 additional days. The individual beetles were then collected and flash frozen in liquid nitrogen. For the qRTPCR assays, at least 6 insects were used for each treatment group. FIGS. 5B-5D box plots of the relative VgR expression at day 6 after treatment with the indicated dsVgR fragments or control treatment (i.e., ddH2O and dsGUS, as indicated, replacing the VgR dsRNA in the diet) using 5' qRTPCR assay. The data in the treatment groups were normalized to data obtained from qRTPCR from water treated beetles. Two qRTPCR assays (5'- and Mid-qRTPCR assays) were used to avoid overlapping of VgR fragment and PCR amplicon.

Example 7: *Agrobacterium*-Mediated Transformation of Maize

For *Agrobacterium*-mediated transformation of maize with a silencing element of the invention, the method of Zhao is employed (U.S. Pat. No. 5,981,840, and PCT patent publication WO98/32326; the contents of which are hereby incorporated by reference). Such as a construct can, for example, express a long double stranded RNA of the target sequence set forth in table 1. Such a construct can be linked to a promoter. Briefly, immature embryos are isolated from maize and the embryos contacted with a suspension of *Agrobacterium*, where the bacteria are capable of transferring the polynucleotide comprising the silencing element to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step). The immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). The immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants.

Example 8: WCRW VgR Transgenic Feeding Bioassay

Figure 6A:
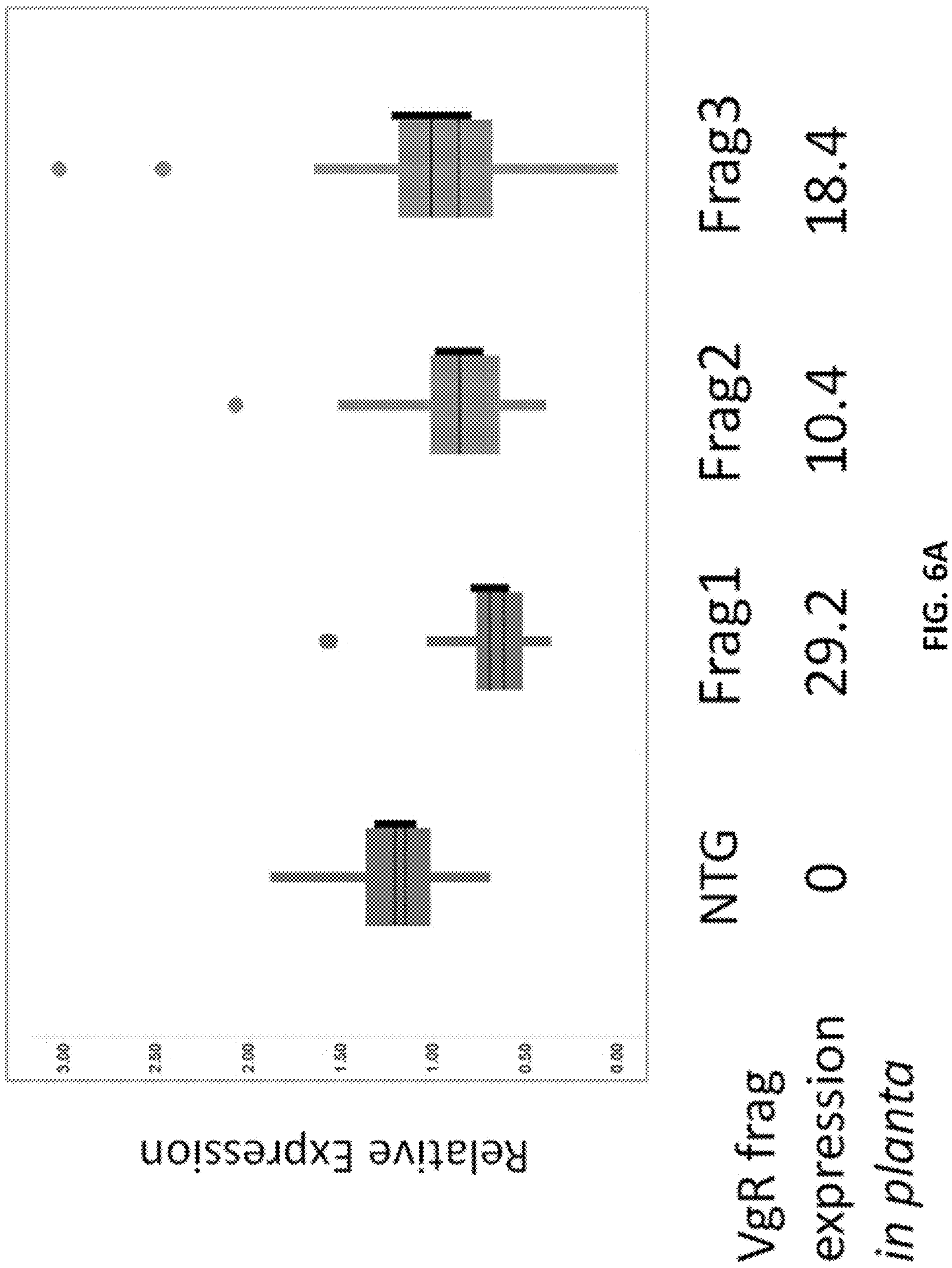
FIGS. 6A-6B show data pertaining to VgR gene suppression in beetles ingesting transgenic plants expressing VgR dsRNA constructs as indicated in the figure. VgR expression in planta is indicated at the bottom of each figure.
Figure 6B:
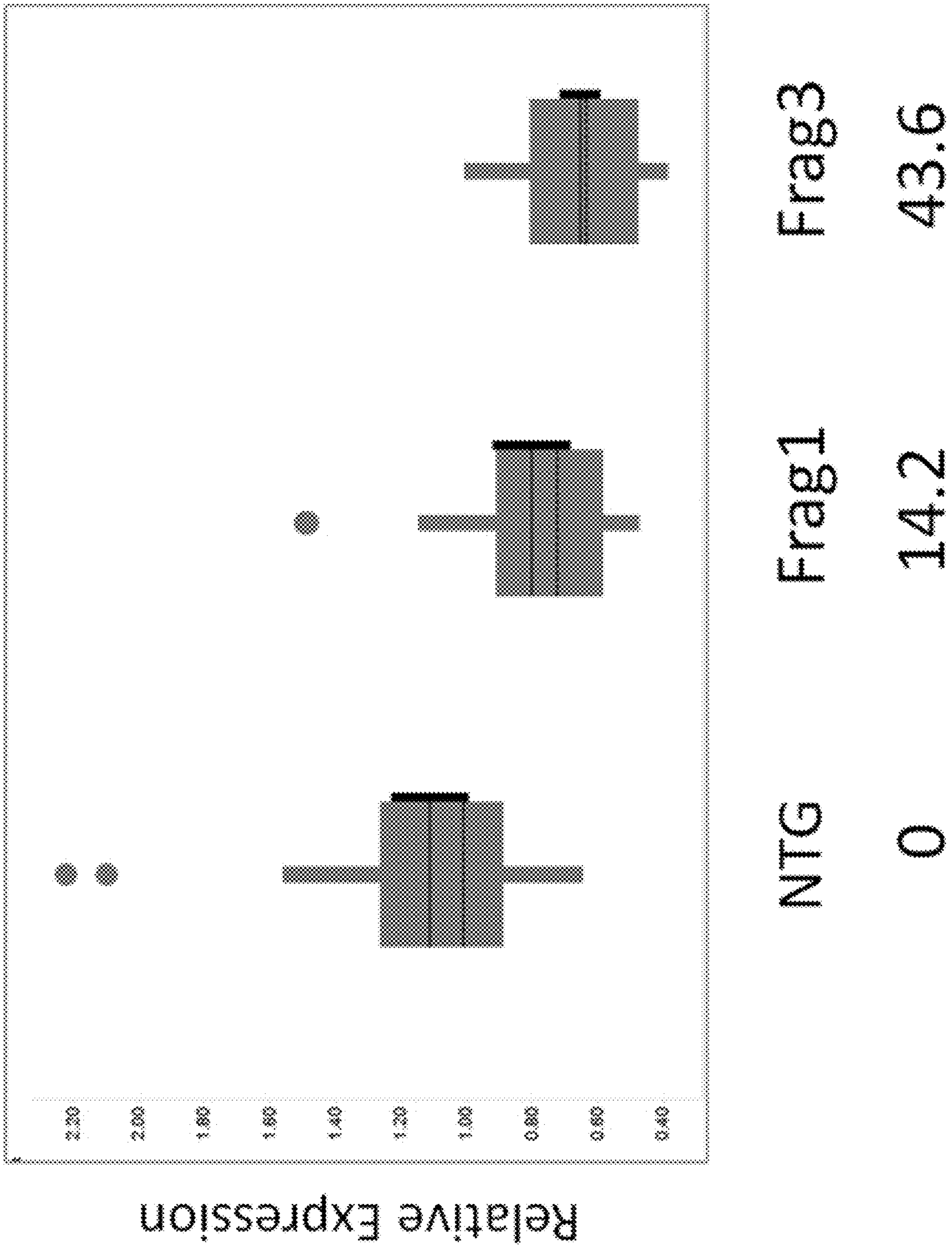

Transgenic maize plants for VgR Frag1, Frag2 and Frag3 were generated using the methods described herein above and used in adult feeding bioassays for gene suppression analysis in WCRW beetles as described herein above. The expression levels of the VgR fragments in planta were determined in leaf samples using in vitro transcription (IVT) products as controls. The expression analyses were carried out according to manufacturer's instruction (Quantigene 2.0 Assay, Affymetrix, Santa Clara, Calif. 95051). The average VgR fragment expression level (pg VgR fragment/mg fresh plant weight) in leaves is indicated at below each graph in FIGS. 6A and 6B. FIG. 6A shows data obtained from three young plants at about the V4 growth stage for either a non-transgenic control (NTG) or the indicated transgenic planted expressing the indicated fragment VgR Frag1 (SEQ ID NO: 3), Frag2 (SEQ ID NO: 4), and Frag3 (SEQ ID NO: 5). The test plants were infested with at least 14 young female beetles in cages. The beetles were collected at 8 days after feeding and used for gene suppression analysis. Data were normalized to expression levels obtained in beetles exposed NTG plants. FIG. 6B shows results obtained using either non-transgenic control plants or transgenic plants expressing the indicated VgR dsRNA fragment. The individual R1 maize plants were infested with at least 6 young female beetles in cages. Beetles were collected 12 days after feeding for VgR expression analysis. Each fragment and control is represented by 2 plants used for feeding and more than 12 insects used in gene suppression analysis, and data were normalized to data obtained from non-transgenic control plants exposed under similar conditions.

Example 9: WCRW Adult VgR Transgenic Exposure Bioassay

At least 32 pairs of newly emerged adult beetles were exposed to 8 days to above ground plant part of T1 transgenic events or non-transgenic (NTG) control plants. Beetles were recollected and at least 13-37 female beetles were arranged in a cage for each treatment and maintained for 15 days for fecundity assessment. Transgenic constructs expressed VgR Frag1 (SEQ ID NO: 3), Frag2 (SEQ ID NO: 4), or Frag3 (SEQ ID NO: 5). For each construct 2-4 events were tested (FIG. 7). Each cage received oviposition dish daily and/or at interval of 2-4 days and eggs were processed following the method described in Example 2.

Example 10: WCRW Larval VgR Transgenic Exposure Bioassay

Maize T1 plants expressing silencing elements (targeting SEQ ID NOs: 3, 4, and 5) were transplanted from culture plates into greenhouse flats containing Fafard Superfine potting mix. Three positive individual plants (of same event) were transplanted and maintained in a greenhouse (80° F., 15 hr light:9 hr darkness) and watered as needed. When the plants reached the V2 leaf stage, each pot was infested with 200 non-diapausing *D. virgifera virgifera* eggs. Plants were monitored daily for first beetle emergence. The number of adult *D. virgifera virgifera* that emerged from each pot was determined in the greenhouse in a similar manner as described by Meihls et al. (2008) PNAS 105: 19177-19182. Adult beetles emerged from T1 transgenic events and non-transgenic (NTG) control plants as in Example 9 were collected every 2 or 3 days and maintained for 15 days for fecundity assessment. For each event three replicate cages containing at least 8-14 pairs of male and female beetles were arranged. Each cage received oviposition dish every 5 days and eggs were processed following the method described in Example 2 (FIG. 8).

Figure 9B:
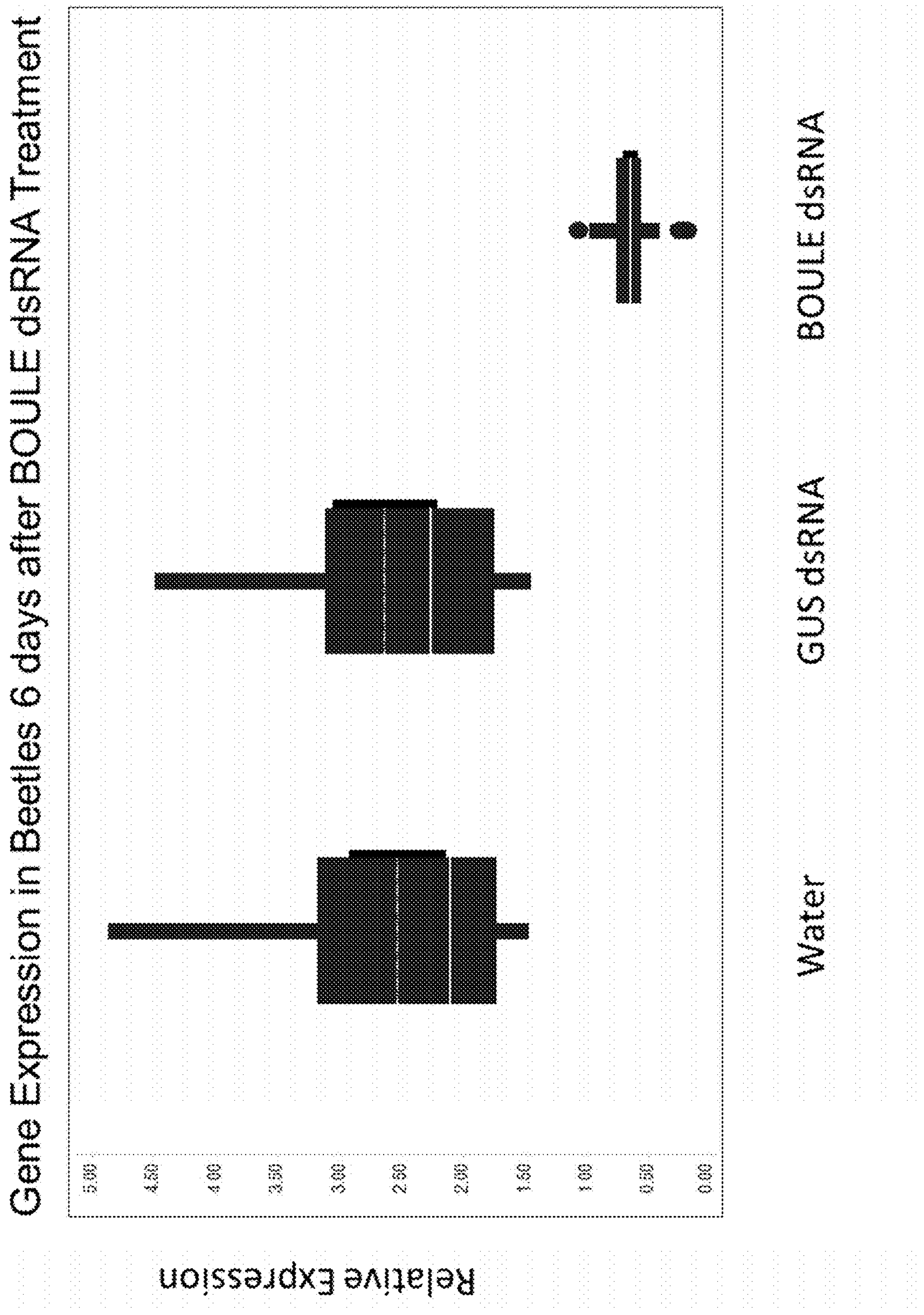

Example 11: WCRW Adult Exposed Sterilization Bioassay and Gene Suppression by Treatment of dsRNA Targeting BOULE Virgin adult beetles were obtained by rearing $3^{rd}$ instar larvae individually in a 50 mL falcon tube containing the pupation medium. Beetles were sexed upon emergence; starved for 24 hours and exposed at 100 ppm of dsRNA targeting the BOULE target gene (DV-BOULE-FRAG1, SEQ ID NO: 164) or controls (sterile water or GUS dsRNA) using diet incorporated method for one day. Treated beetles were provided untreated diet and kept in solitary confinement for additional 5 days. At least 12 treated beetles of mixed sex were collected in liquid nitrogen for gene suppression analysis. At least 14 pairs (male and female) were arranged for each treatment for subsequent mating and fecundity assessment. Due to delay in mating, oviposition was begun 19 days after emergence and egg production was assessed for 10 days. As shown in FIG. 9A, high dose adult exposure to dsRNA targeting BOULE (BOULE dsRNA, SEQ ID NO: 164) did not affect egg production and hatch rate of the eggs. FIG. 9B shows gene expression in beetles after BOULE dsRNA (SEQ ID NO: 164) treatment. Relative expression by qRTPCR assay was performed as in previous examples.

Figure 10:
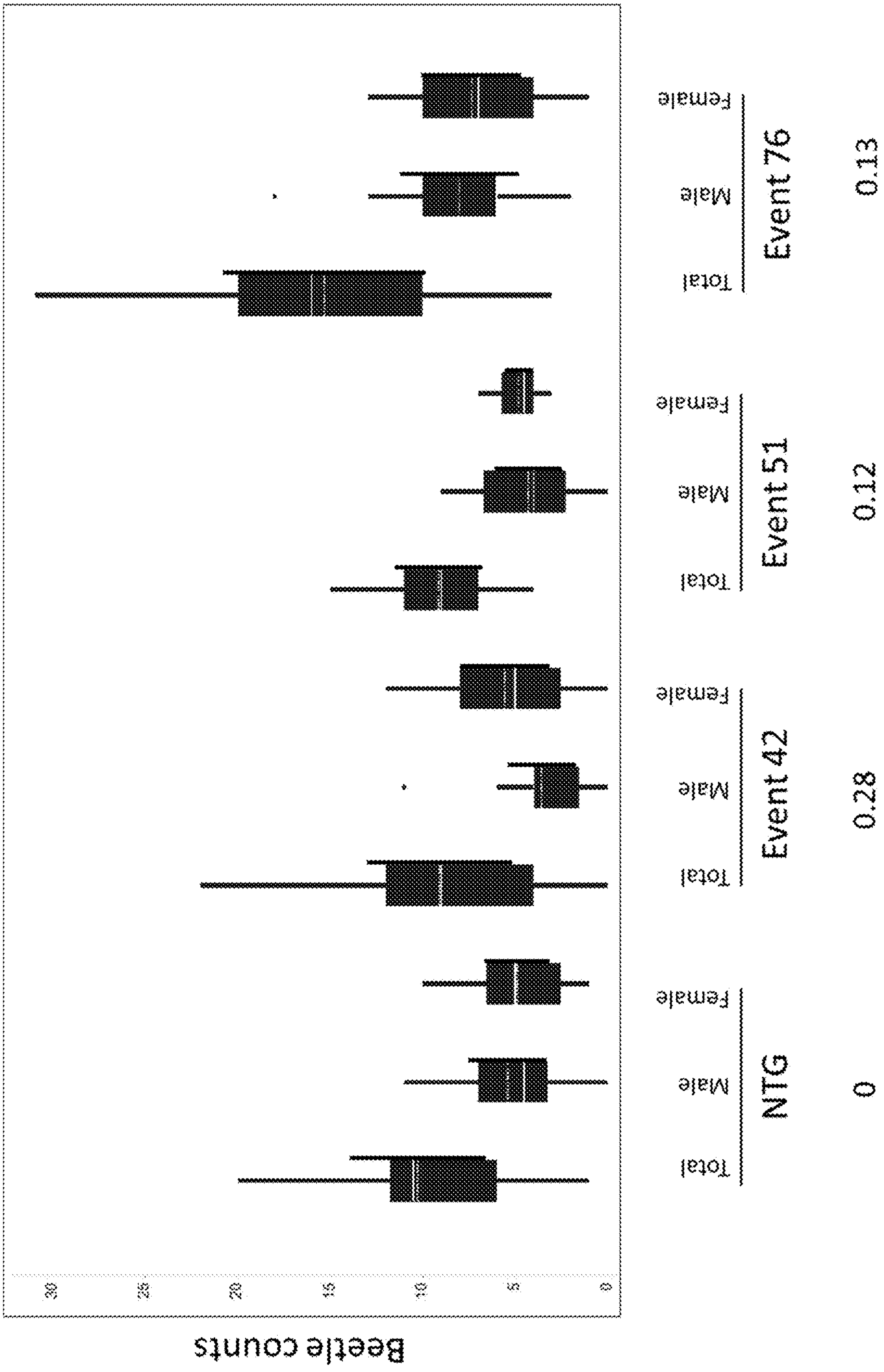
FIG. 10 shows data pertaining to beetle counts from larval exposure to BOULE FRAG1 (SEQ ID NO: 164) dsRNA-expressing T1 transgenic plants. The box plot shows four quartiles, average (horizontal dash line), median (horizontal solid line), and 95% confidence interval of the mean. Average expression levels of the BOULE dsRNA fragment in planta for each event were determined in root samples using in vitro transcription (IVT) product as control.

Example 12: WCRW Beetle Counts from Larval Exposure to T1 Transgenic Plants Expressing dsRNA Targeting BOULE Three maize seedlings of V2 leaf stage T1 transgenic events expressing dsRNA targeting BOULE using DV-BOULE-FRAG1 (SEQ ID NO: 164) and non-transgenic (NTG) control plants were infested with 200 WCR eggs per pot in greenhouse. Approximately one month after infestation, beetles emerged from each pot were captured every 2 or 3 days over 10 days. Average beetle numbers for the total and each sex (Male and Female) from at least 9 pots per event and 10 NTG control pots are shown. The box plot shows four quartiles, average (horizontal dash line), median (horizontal solid line), and 95% confidence interval of the mean. The results suggest that exposure of WCRW larvae to transgenic events expressing DV-BOULE FRAG1 (SEQ ID NO: 164) dsRNA did not affect adult emergence pattern when compared to NTG plants (FIG. 10). Average expression levels of the BOULE fragment in planta for each event were determined in root samples using in vitro transcription (IVT) product as control as described in Example 8.

Figure 11A:
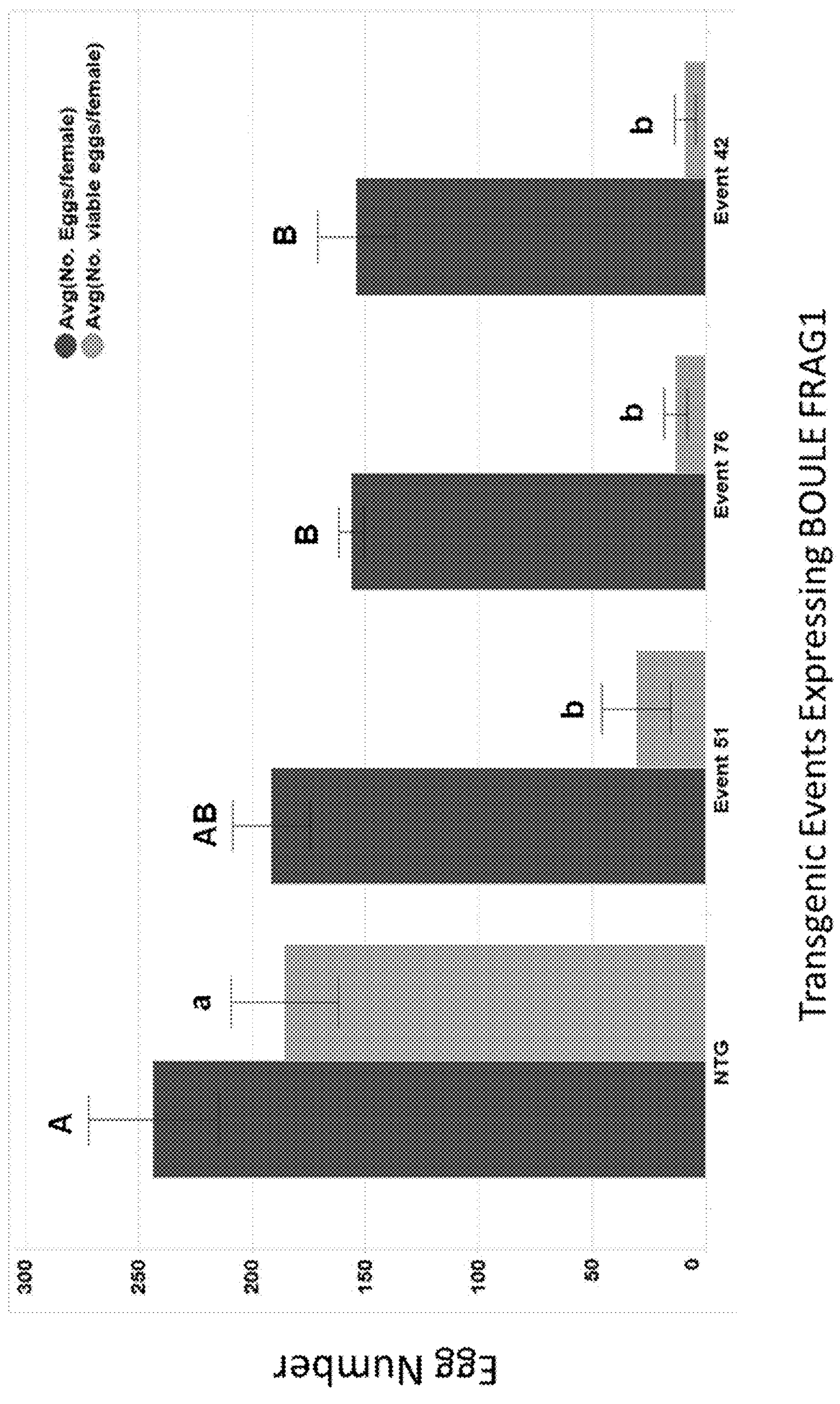
FIGS. 11A-11C show data pertaining to WCRW larval exposure to BOULE transgenic T1 plants causing adult sterilization.
Figure 11B:
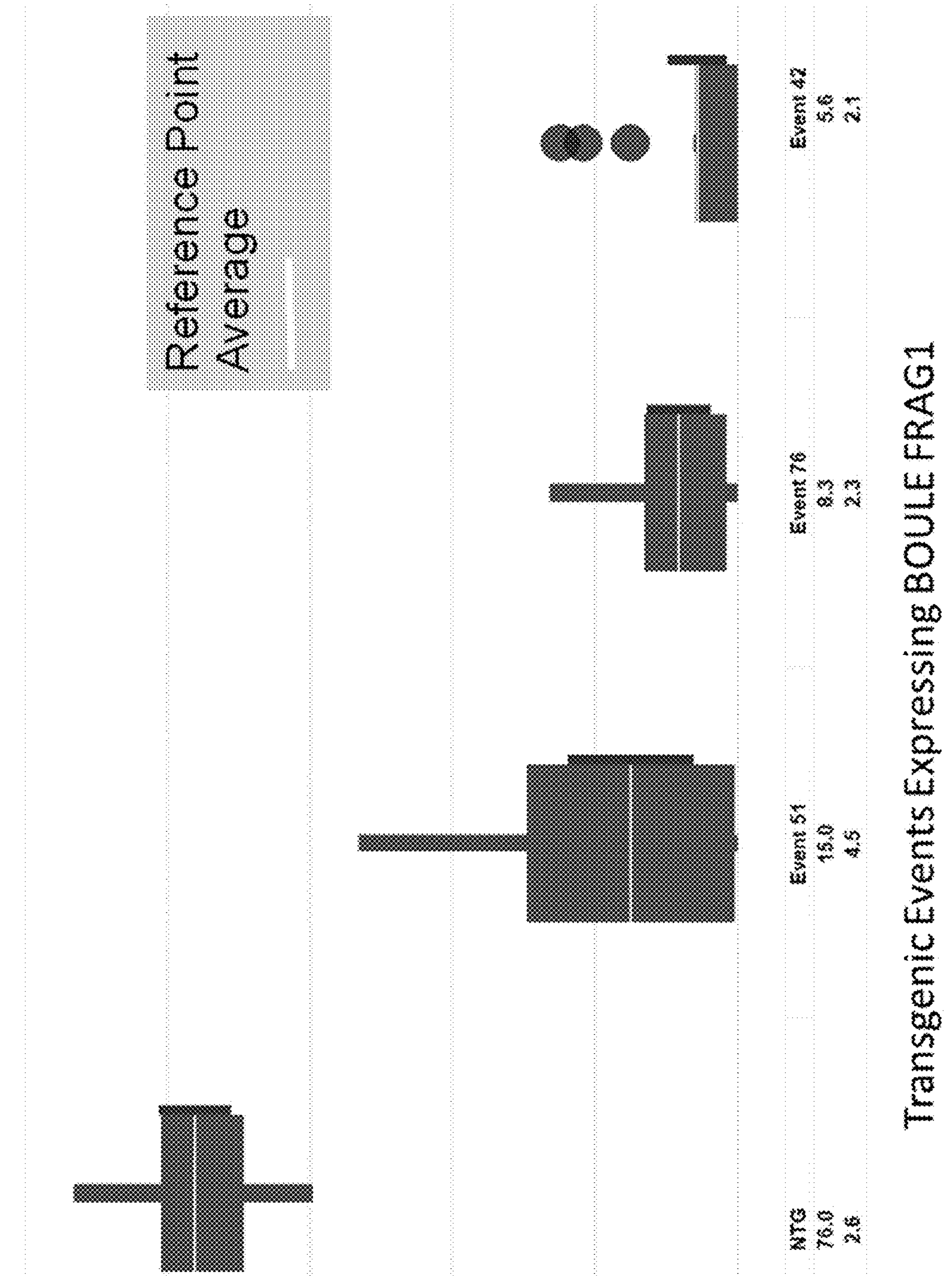
Figure 11C:
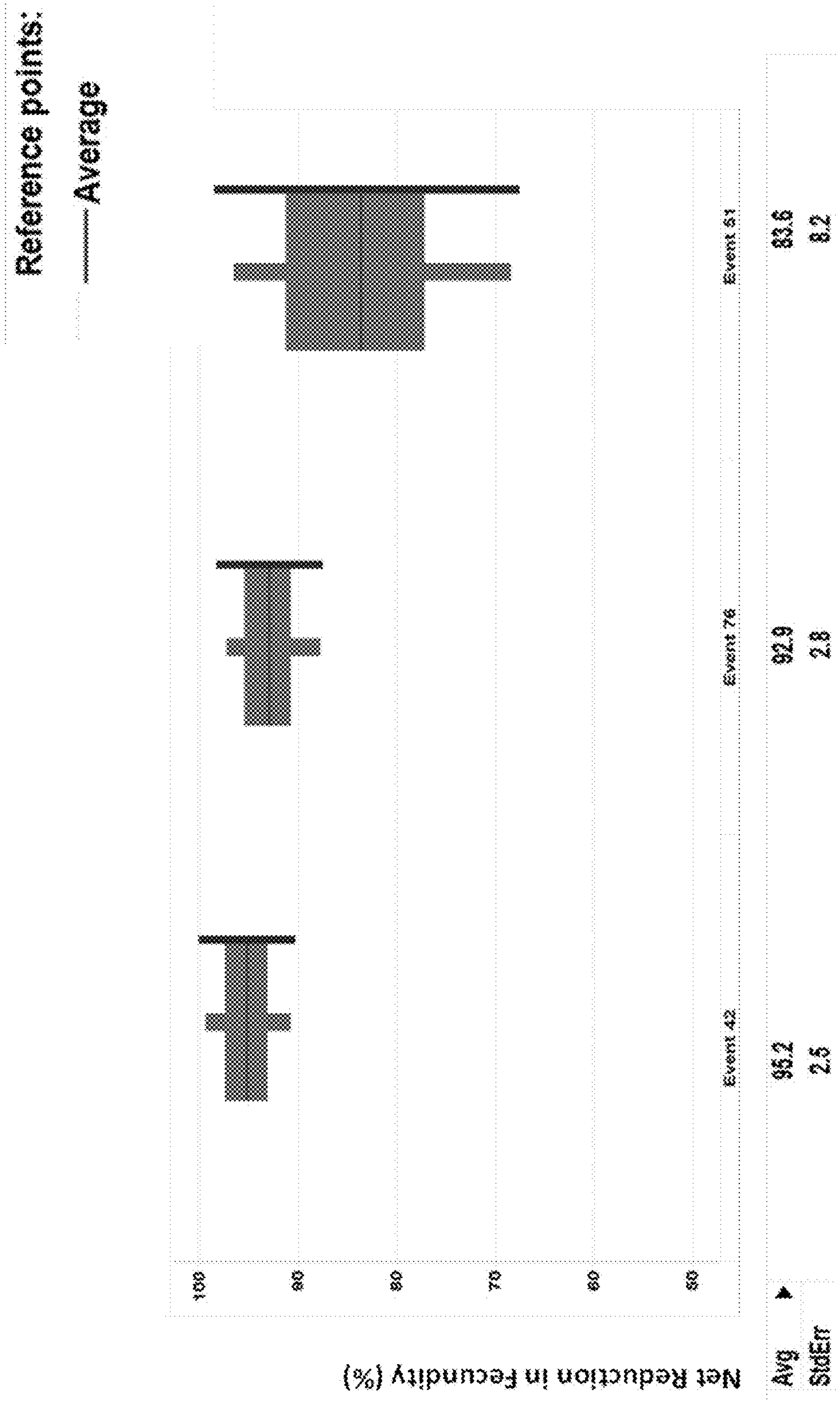

Example 13: WCRW Larval Exposure to Transgenic T1 Plants Expressing dsRNA Targeting BOULE Caused Adult Sterilization Beetles emerged from T1 transgenic events expressing DV-BOULE-FRAG1 (SEQ ID NO: 164) dsRNA and non-transgenic (NTG) control plants were maintained for 25 days for fecundity assessment. For each event three replicate cages containing at least 8-14 pairs of male and female beetles were arranged. Each cage received oviposition dish every 5 days and eggs were processed following the method described in Example 2 except that egg hatch duration was extended up to 8 days. FIG. 11A shows the effect of larval exposure to transgenic plants expressing DV-BOULE-FRAG1 (SEQ ID NO: 164) dsRNA on the overall average egg production per female and average viable eggs produced per female from emerged beetles. FIG. 11B shows the effect of larval exposure to transgenic plants expressing DV-BOULE-FRAG1 (SEQ ID NO: 164) dsRNA on hatch rate of eggs obtained from the emerged beetles. FIG. 11C indicates the effect of larval exposure to transgenic plants expressing DV-BOULE-FRAG1 (SEQ ID NO: 164) dsRNA on net reduction in fecundity of emerged adult beetles relative to NTG control.

Example 14: WCRW 3$^{rd}$ Instar Sterilization Bioassay of Exposure to dsRNA Targeting MAEL, NCLB and CUL3 at 1 ppm Over 400 3rd instar larvae were exposed to 1 ppm of the respective dsRNA samples (DV-MAEL-FRAG1, SEQ ID NO: 46; DV-NCLB-FRAG1, SEQ ID NO: 45; and DV-CUL3-FRAG1, SEQ ID NO: 44) following the method described on Example 3. Water and GUS treatment were included as experimental controls. Treated larvae were separated into four groups, each containing about 95 to 100 treated larvae and placed in pupation medium for 15 days. Emerged adults were collected, counted, and transferred to their respective holding cages and handled as described in Example 3. After 10 days of oviposition period the number beetles in each replicate cage was adjusted to at least 12-16 pairs (male and female) and fecundity was assessed for 15 days. At least 2-3 replicate cages were setup for each treatment. The average total number of eggs produced per female, the average number of viable eggs produced per female, the average egg hatch rate; average reduction in egg production and net reduction in fecundity (both relative to water control) are shown in FIG. 12.

Example 15: WCRW Sterile Gene Screening by 3$^{rd}$ Instar Sterilization Bioassay at 50 ppm The effect of treatment of larvae on WCRW sterilization by dsRNA targeting various genes of interest (GOI) was assessed using 3$^{rd}$ instar. A set of 8-14 dsRNA samples including water and GUS control was tested at a time. The study was carried out using 10 day old 3rd instar larvae that were harvested from corn mats and acclimatized on standard WCRW larval diet for 24 hours. Diet incorporation method was used for exposing larvae to 50 ppm final concentration of the respective test dsRNA samples in 2 mL per well of 6-well plate. A total of three 6-well plates were prepared for each sample and about 312 larvae were exposed to water or 50 ppm of target dsRNA fragment (GOI) for 1 day (~104 larvae/plate; 16-18 larvae/well). After exposure, ~10 3$^{rd}$ instar larvae were sampled for gene suppression analysis and the remaining treated larvae were placed in pupation medium for 15 days. Emerged adults were collected, counted, and transferred to their respective holding cages and provided standard SCRW dry adult diet with a water source (water agar) until the end of the study period (~26 days). Beetle holding cages were kept at room temperature (usually from 22-25° C.); 16:8 dark and light condition with no relative humidity control. After 10 days of preoviposition period, for each treatment the number of male and female pairs was adjusted to 16-20 pairs depending on beetle density and each cage received oviposition dishes and eggs were collected over a period of for 15 days oviposition period, and processed following the method described in Example 2. A set of three males and three females were sampled 10 and 25 days after emergence for gene suppression. Table 4 shows a consolidated summary of egg production, egg hatch and reduction in egg production and fecundity for active WCRW gene targets. Column 1 indicates GOI (gene of interest), column 2 and 3 indicate total egg production/female and total viable eggs/female respectively during the 15 days egg production period; column 4-5 indicate cumulative average egg hatch (±SEM); column 6 and 7 indicates average reduction in egg production (%) (±SEM); column 8 and 9 indicate average net reduction in fecundity (%) (±SEM). Note that values for controls (water and GUS) are cumulative average of 11 independent experiments, each run for the duration of 15 days of egg production period.

TABLE 4

WCRW sterile gene screening by 3rd instar sterilization bioassay at 50 ppm*

| Target Gene | Total No. Eggs/female | Total No. fertile Eggs/ female | Avg. Egg hatch (%) ± (SEM) | | Reduction in egg production (%) ± (SEM) | | Net reduction in fecundity (%) ± (SEM) | | SEQ ID NO: |
|---|---|---|---|---|---|---|---|---|---|
| MEI | 0 | 0 | 0.0 | 0.0 | 100.0 | 0.0 | 100.0 | 0.0 | 133 |
| KNRL | 96 | 0 | 0.5 | 0.3 | 59.6 | 9.4 | 99.6 | 0.1 | 132 |
| TUD | 7 | 1 | 15.0 | 0.8 | 95.5 | 0.8 | 98.6 | 0.2 | 118 |
| CG3565 | 172 | 2 | 1.4 | 0.4 | 28.0 | 10.7 | 98.0 | 0.3 | 130 |
| CG17083 | 160 | 3 | 1.7 | 0.6 | 32.8 | 20.5 | 97.7 | 0.7 | 129 |
| DM | 96 | 8 | 8.7 | 2.7 | 73.5 | 6.0 | 95.7 | 1.0 | 125 |
| CYCA | 26 | 8 | 29.9 | 7.6 | 89.5 | 2.1 | 93.6 | 1.3 | 43 |
| HIRA | 63 | 5 | 7.6 | 1.8 | 57.5 | 6.5 | 93.1 | 1.1 | 116 |
| Poe | 41 | 8 | 16.8 | 2.9 | 74.2 | 7.2 | 91.9 | 2.2 | 113 |
| EGG | 52 | 20 | 38.7 | 2.9 | 85.8 | 4.7 | 89.8 | 3.4 | 126 |
| MR | 45 | 21 | 45.9 | 3.5 | 87.6 | 2.2 | 89.4 | 1.8 | 128 |
| HANG | 129 | 22 | 17.3 | 2.6 | 54.0 | 6.2 | 84.3 | 2.1 | 108 |
| HTS | 125 | 14 | 10.8 | 2.5 | 23.5 | 13.0 | 81.9 | 3.1 | 122 |
| GSKT | 82 | 26 | 32.3 | 3.4 | 67.7 | 4.8 | 80.6 | 2.9 | 40 |
| ADE2 | 70 | 28 | 40.3 | 8.3 | 75.1 | 7.0 | 80.1 | 5.6 | 107 |
| DLG1 | 202 | 39 | 19.3 | 4.8 | 44.3 | 7.1 | 79.9 | 2.6 | 124 |
| SU(VAR)205 | 132 | 32 | 24.3 | 4.7 | 52.7 | 9.3 | 77.3 | 4.4 | 111 |
| CDK7 | 148 | 45 | 30.1 | 3.6 | 59.2 | 7.0 | 77.1 | 3.9 | 123 |
| HRG | 200 | 50 | 25.2 | 4.5 | 45.0 | 9.4 | 74.2 | 4.4 | 127 |
| MBD-like | 85 | 17 | 20.4 | 3.4 | 41.2 | 11.9 | 74.0 | 5.3 | 114 |
| 11NUP44A | 112 | 29 | 26.1 | 2.8 | 46.2 | 12.5 | 70.4 | 6.9 | 120 |
| CASP | 150 | 27 | 18.0 | 4.8 | 13.4 | 12.4 | 70.2 | 4.3 | 42 |
| FAF | 101 | 30 | 29.8 | 3.5 | 51.5 | 7.9 | 69.5 | 5.0 | 119 |
| TWE | 257 | 38 | 14.9 | 1.7 | −7.6 | 10.3 | 67.4 | 3.1 | 134 |
| PORIN | 105 | 46 | 44.2 | 4.8 | 62.5 | 4.6 | 67.1 | 4.0 | 110 |
| PARK | 64 | 31 | 46.3 | 4.0 | 60.1 | 6.4 | 66.8 | 5.4 | 112 |
| PGLYM78 | 80 | 22 | 27.8 | 4.4 | 44.5 | 13.5 | 66.5 | 8.2 | 115 |
| WTS | 103 | 46 | 44.7 | 3.6 | 59.5 | 5.9 | 66.4 | 4.9 | 41 |
| PUF | 89 | 25 | 28.3 | 3.9 | 40.3 | 8.3 | 64.2 | 5.0 | 117 |
| KL3 | 130 | 55 | 42.4 | 7.8 | 53.4 | 8.7 | 60.8 | 7.3 | 109 |
| GUDU | 211 | 55 | 26.2 | 3.0 | 16.9 | 6.2 | 59.6 | 3.0 | 39 |
| CYCB | 214 | 49 | 22.7 | 2.6 | 10.2 | 6.9 | 58.6 | 3.2 | 131 |
| GEK | 136 | 36 | 26.2 | 2.3 | 17.4 | 9.9 | 52.6 | 5.7 | 121 |
| REPH | 183 | 72 | 39.2 | 4.0 | 27.7 | 12.5 | 47.3 | 9.1 | 165 |
| ARMI | 316 | 108 | 34.2 | 4.4 | 12.9 | 10.9 | 44.5 | 7.0 | 166 |
| loqs | 148 | 42 | 28.4 | 3.9 | 9.8 | 15.8 | 44.1 | 9.8 | 167 |
| SCNY | 165 | 72 | 43.5 | 3.2 | 31.0 | 5.1 | 39.0 | 4.5 | 168 |
| AGO3 | 186 | 46 | 24.9 | 2.5 | −13.7 | 14.0 | 38.1 | 7.6 | 169 |
| DIA | 288 | 124 | 43.0 | 4.9 | 20.8 | 9.9 | 36.5 | 7.9 | 170 |
| DNC | 274 | 101 | 37.0 | 3.3 | 9.5 | 21.5 | 36.1 | 15.2 | 171 |
| Chi | 269 | 103 | 38.2 | 3.8 | 11.3 | 18.3 | 35.3 | 13.3 | 172 |
| SXL | 188 | 66 | 35.2 | 3.6 | 10.2 | 13.7 | 33.3 | 10.2 | 173 |
| SLGA | 199 | 94 | 47.1 | 3.9 | 21.5 | 8.1 | 31.3 | 7.1 | 174 |
| PAPLA1 | 150 | 53 | 35.4 | 2.7 | 8.7 | 11.6 | 29.4 | 8.9 | 175 |
| GUS* | 187 | 88 | 43.8 | 1.3 | 12.1 | 4.3 | 16.8 | 5.1 | |
| H20* | 217 | 110 | 50.0 | 1.0 | | | | | |

*Column 1 indicates GOI (gene of interest), column 2 and 3 indicate total egg production/female and total viable eggs/female respectively during the 15 days egg production period; column 4-5 indicate cumulative average egg hatch (± SEM); column 6 and 7 indicates average reduction in egg production (%) (± SEM); column 8 and 9 indicate average net reduction in fecundity (%) (± SEM). Note that values for controls (water and GUS) are cumulative average of 11 independent experiments, each run for the duration of 15 days of egg production period.

The invention claimed is:

1. A silencing element comprising at least one double-stranded RNA region, at least one strand of which comprises a polynucleotide that is complementary to:

(a) the nucleotide sequence comprising SEQ ID NO: 135;
(b) the nucleotide sequence comprising at least 90% sequence identity to SEQ ID NO: 135; or
(c) the nucleotide sequence comprising at least 25 consecutive nucleotides of SEQ ID NO: 135;

wherein the silencing element has sterilization activity against an insect plant pest.

2. The silencing element of claim 1, wherein the insect plant pest is a Coleoptera plant pest.

3. The silencing element of claim 2, wherein the Coleoptera plant pest is a *Diabrotica* plant pest.

4. The silencing element of claim 3, wherein the *Diabrotica* plant pest comprises *D. virgifera virgifera, D. virgifera zeae, D. speciosa, D. barberi, D. virgifera zeae*, or *D. undecimpunctata howardi.*

5. The silencing element of claim 1, wherein the silencing element comprises a hairpin loop.

6. A composition comprising the silencing element of claim 1.

7. The composition of claim 6, further comprising an agriculturally acceptable carrier.

8. The composition of claim 6, further comprising a herbicide compound, an insecticide, a fungicide, a nematocide, an agriculturally-acceptable carrier, and/or a bacteria, or combinations thereof.

9. The composition of claim 6, wherein the composition is in liquid form, solid form, or gel form.

10. The composition of claim 9, wherein the solid form is a pellet, a powder, an aggregate, or a molded article.

11. A plant cell having stably incorporated into its genome a heterologous polynucleotide encoding a silencing element, wherein the polynucleotide comprises:

a. the nucleotide sequence comprising SEQ ID NO: 135;
b. the nucleotide sequence comprising at least 90% sequence identity to SEQ ID NO: 135; or
c. the nucleotide sequence comprising at least 25 consecutive nucleotides of SEQ ID NO: 135;

wherein the silencing element decreases the fertility of an insect plant pest.

12. The plant cell of claim 11, wherein the insect plant pest is a Coleoptera plant pest.

13. The plant cell of claim 12, wherein the Coleoptera plant pest is a *Diabrotica* plant pest.

14. The plant cell of claim 13, wherein the *Diabrotica* plant pest comprises *D. virgifera virgifera, D. virgifera zeae, D. speciosa, D. barberi, D. virgifera zeae*, or *D. undecimpunctata howardi.*

15. The plant cell of claim 11, wherein the plant cell further comprises an expression cassette, wherein the expression cassette comprises the heterologous polynucleotide encoding a silencing element.

16. The plant cell of claim 11, wherein the silencing element comprises a double stranded RNA.

17. The plant cell of claim 11, wherein the silencing element compises a hairpin RNA.

18. The plant cell of claim 11, wherein the polynucleotide is operably linked to a heterologous promoter.

19. The plant cell of claim 11, wherein the plant cell is from a monocot.

20. The plant cell of claim 19, wherein the monocot is maize, barley, millet, wheat or rice.

21. The plant cell of claim 11, wherein the plant cell is from a dicot.

22. The plant cell of claim 21, wherein the dicot is kale, cauliflower, broccoli, mustard plant, cabbage, pea, clover, alfalfa, broad bean, tomato, cassava, soybean, canola, alfalfa, sunflower, safflower, tobacco, *Arabidopsis*, or cotton.

23. A plant or plant part comprising the plant cell of claim 11.

24. A transgenic seed from the plant of claim 23.

25. A method for controlling a plant insect pest comprising feeding to a plant insect pest a composition comprising a silencing element, wherein the silencing element controls the plant pest, wherein the silencing element comprises a sequence complementary to:

a. the nucleotide sequence comprising SEQ ID NO: 135;
b. the nucleotide sequence comprising at least 90% sequence identity to SEQ ID NO: 135; or the nucleotide sequence comprising at least 25 consecutive nucleotides of SEQ ID NO: 135; wherein the silencing element has insect sterilization activity against the plant pest.

26. The method of claim 25, wherein the composition comprises a plant or plant part having stably incorporated into its genome a polynucleotide encoding the silencing element.

27. The method of claim 25, wherein the silencing element comprises a double stranded RNA.

28. The method of claim 25, wherein the silencing element comprises a hairpin RNA.

29. The method of claim 26, wherein the polynucleotide encoding silencing element is operably linked to a heterologous promoter.

30. The method of claim 25, wherein the plant is a monocot.

31. The method of claim 30, wherein the monocot is maize, barley, millet, wheat or rice.

32. The method of claim 25, wherein the plant is a dicot.

33. The method of claim 32, wherein the dicot is kale, cauliflower, broccoli, mustard plant, cabbage, pea, clover, alfalfa, broad bean, tomato, cassava, soybean, canola, alfalfa, sunflower, safflower, tobacco, *Arabidopsis*, or cotton.

* * * * *

SEQUENCE LISTING

<160> NUMBER OF SEQ ID NOS: 254

<210> SEQ ID NO 1
<211> LENGTH: 5612
<212> TYPE: DNA
<213> ORGANISM: Diabrotica virgifera

<400> SEQUENCE: 1

```
tggtcagttc gtcctttaaa actgtgcgtg ttaaactttt tgaatatctt gtaaagtatg      60

ttaattttgt tctttgtgct ttcaacgtta ttaaatgcag tcgtttcaac gaataataat     120

gattgccctc cacatcagtt tagatgcaca aattcaaaat gtatagactt tcaacaaaga     180

tgtgatggtt ccgacaattg tggagatgga tcggatgaac tggattgtga tcataaatgt     240
```

-continued

```
catgaacatt ttttcaattg tcgaaatgga agatgtataa gcgaagcatt cctgtgtgat    300
ggtgaaaatg attgtaataa ctttttggat gaaaaagact gtaagggtca aacggtgcta    360
actctcgaaa ctgatggcca ttgcgaagat ggtcattgga agtgtgccga taaattgtgt    420
attccacttg acatggtatg taatggcgca cctgaatgtt tggatggatc agatgaaact    480
attggatgca gtaacaagat cgtttgtgat ggatttaaat gtaaaaatgg ccattgcata    540
ccaactgaat gggcttgcga cggtcttgat gattgtggtg ataaaactga tgaacaagat    600
tgcgcaaacc acgtaccact tgatcaatgc actttggata aaagaaaatt cttgtgtagt    660
aacaataaaa cttgcataga tcttcactcg gtctgtgata ataagttaga ttgtcccgat    720
tattctgatg aaggaaaaca gtgcaattcg tctgcaatat catgtaacaa taacaaatgt    780
tctcatacat gtatatcact tccaacgggt ccaaaatgtc tgtgtccgaa tggttaccat    840
acgcttgatg attcgaattg tttggatatt aatgaatgta caacttatgg aatttgtgac    900
caaaaatgta gaaatcttcc tggatcatac gaatgctact gtgatgataa gtacacactc    960
caagccgata aaaaaacatg taaagcaact ggcggaagcg gaataatgat ctttagttcc   1020
aagcaggaaa ttcgagcttt aaccttagat tctttagatt attttacagt ggctaaagat   1080
ttaaatcaag tagtgggaat agcatacgat ggacatcata tttactggac agacgtattt   1140
actggacatg aaactatatc gaggtctatt gaagatggat cggaaaggga ggtattggta   1200
acatctggac tcagtctacc agaggatcta gcgtatgatt ggttaactgg taatatttat   1260
ttcaccgatg ctctcaaaca acatgttgga gtgtgttcca atgatggtca ccattgtaca   1320
gttctagtca acaaagatat tcgaaaacca cgtgggattg ttgttaatgt ggaagctgga   1380
gatatgtatt ggtctgattg gggtgtacca gcagcaattg gatattcact tatggatgga   1440
tcccaggaca aaccgttcgt caccaataat atacactggc ccaatggttt ggctctagat   1500
caacctaact ctagacttta ttggactgat gctaaaaaga tgacactaga aagtattaat   1560
ttagacggaa ctgatcaaag gatcgttttg gaaggaatag tgaaacatcc atatgccatc   1620
gctgtgtttg aaaacaaact ttattggtca gattgggact cccataccat tcaaacttgt   1680
gataagttta atggtaaaaa tcatcataca ctcgtggaag aacataaaaa tttaatctat   1740
ggaatcagta tttttcacta tgctctcgaa aagcgtctag tgaatccttg tgagcatgct   1800
tcctgtagtg acatttgttt attgaaggct cagtcatatg cttgtgcgtg cccagagaat   1860
aaagttttgg atacggatgg tcatacgtgc aaagaagtac aaccaacgca agcacttgta   1920
ggaggaactg gacacgtgtt ggtatcaatt aaacatcaat ttctaggcaa acacgatgta   1980
acattcctac cagacctggc gaaacacgta ggaagcttag catttgatag ttataaaaac   2040
attttgtatg taagcgattt ggaaacaaaa agtatagttg cgcttaacat gaacatcgga   2100
attagcaaaa ctcttgagat cgacggtctt ggcaaagtta cttcaatgga ttttgatcca   2160
aaaagtaata atttatacat ttgcgatacg gagaggctag tcgtagaaat aattgatatg   2220
aataatctag aaagaaaaat aattgtccat gacacatttg gagaaactcc tgaaagcatt   2280
gcgttggtac cggaagatgg gatcatgttt gttagcttta aacaagggaa attgggaaat   2340
agccacatcg accgtttttt catggatggt actggaagaa ctcacgtcat cgaaaacggt   2400
ttagtgggcc cagttcgtgt agtatacgac cgcagtcttt atagaatttt ctttgccgat   2460
ctaagtactg ggtaataga atctactagc gcggccggtg acgatagaca tcattttcgt   2520
actctgacta cccatccagt aagtatagca gttttgaaag atgacctatt gtggacaaat   2580
cttgactcca aggatttata ttggtctgaa aaaagatcta gcgagtctta tgagaagaaa   2640
```

-continued

```
attacgatag gttttaaaga ggataacgtc aacatccact tagtgtcagt aacacgtaaa   2700
caattagaaa tcaatagctg tcgtgttaat aataatggat gtagtcatct ttgtcttcaa   2760
tcccataaat cgatagtttg tgcatgtcca gctggatggg agctatcggc aaatggtttt   2820
acatgtaata aaagggtaac ctgcgacaat aaagagatgc tttgtcctca ttccaatact   2880
tgcgttctga agagcttaag gtgcaatggt tttaaagact gcgcatttgg tgaagatgaa   2940
tgggactgcc aaactgtttc ccaatgttta cctggccagt ataaatgcga cgatggacag   3000
tgcatcagtg aagatttggt ctgcaatcat agttatgact gtaaagataa gtctgatgag   3060
tatggatgtg cagataaaaa caaaaaacta ggatgtcctc ccggacattt tacctgtaaa   3120
agctccgaat gcatatctga acgctttgta tgtgatgctt tccatgattg cgatgatgga   3180
tcagatgaac taaactgcga aaataatatt tgtttggaat ctcagtttag gtgtgatgtc   3240
ggaacttgca taccaaaaga ttgggaatgt gatggagaat atgactgtac tgatagttca   3300
gatgagcatt gttcttcaga agtttgtcag tctaactatt ttaagtgtga caacaacaga   3360
tgtatcgatc ctaagcttca gtgcgatggg tttgatgact gcggtgatca ctctgatgaa   3420
aaattcgaga aatgtttgca tcactcgaaa gcaccaaaat gtacattgga agaattcgcg   3480
tgtattacta atacttccat ttgtcttcca aaatcagcta aatgtaacgg aacgtcagaa   3540
tgtccgaata acgaagacga aaaggattgt tcaaaatgtg aagaagatga atttgagtgc   3600
aagcataagc attatagaga atgtattcct aggtcctgga tatgtgatgg tacagatgat   3660
tgcggtgata atagtgatga gagtatggaa acctgttctt caaaacttaa acctgcggca   3720
gataactttg ctgttactga ctcgtgtcta accggatata gatgtcatag cggtgcatgc   3780
ataaatatga cctcagtatg caataataac cacgattgtt ttgatggctc tgatgaagat   3840
ggcctctgtt cttcatcttg tgtcggtgtg aaaaatcctt gcaatcaaat atgcgtaaaa   3900
acaccatctg gaccaagatg tgaatgtaaa cctggatata agttgttagg agatggaaaa   3960
acttgtattg atgataatga atgccaaacg gatccaccaa tctgtagtca gctatgtcac   4020
aataaagaag gaggctattc ttgcgattgt tacaataatt tcctttttaag ttctaataaa   4080
aaatcttgta aagctcacgg accaagaatg accatatact tagtgattta cggaaaccaa   4140
atccgtcacc taattcctaa atcaaacaca atggctgttc tttacaccaa tccaatgata   4200
aaaatatcca gcttggatac tctggttaaa ccaaaactaa tcttcttcag ttcttatgaa   4260
actcaagcta tttataaact tgataccacc accaacatga tgcactacat cagaaacgta   4320
ggtttcccta gaacaattgc agttgattgg tcaactcaaa acatttatta cttcgatact   4380
gatgttaatg gccggtccat tagtgtttgc agttttgaag aaaagtgcgc taagttgata   4440
aatattgaat cgcctcgaca tgtaactgcc ttagctgttg attccgtcaa taaattgctt   4500
ttctacgttt tgaggaattg gtgggtatta gaaacaccaa gcttcgtaat atacagtgta   4560
aacttggatg gatctaatag acaagaaata gtaaaaacaa caacgggcaa tgttgaagat   4620
ataactttcg atattaacaa gaaactttta tactatacta acaaacaaga tgaaagtata   4680
cacgaagtaa gctacaaagg aggaccggtt aaaactgtat tttcaaatat ctctcaacca   4740
gaaggactta aatttttttga gaaccaatta tactatactg ttgcaactgg ttatatagtc   4800
agttgtaagc tatatggaga cagatcctgc aatcccagat ataaattaca cacgtttgcc   4860
agtggtcaat ttgttattga gcaggaatcg cttcagccta aagtagaaaa tgtttgtact   4920
ggacacaaat gtccatactt atgtgtacca gcagaatcag gatatagatg tctctgtcat   4980
```

-continued

```
aacgggaaag ttagtaatca ttcagaaatt tgtggtgaaa acgatgataa tcagtcagga   5040
aataatcaca aatttgctgt acatactaca ccaatacaga ctgcatccga taaacattca   5100
ggagcagtgg cctcagcaat attaattcca ctactattag tattccttgg agcagtattt   5160
tattatttgc taaaaaggag aggtgatact ggattaaata taagcatgcg attttataac   5220
ccactctacg gaaaacctgt ccgtgaagac caaaaacaaa tccttaaacc aggacaacac   5280
gagtacacaa atccgataat tgtggccgaa gaacatgagg accacgcgaa agatgctagc   5340
agaatgctaa acgatagttg tgtttgttaa gtttgtatct tttgttacg tcattctttg    5400
ttttatgttt tatataatct tataaacgtt gttttaatct tttgaagtgt attaaaagca   5460
aaatgactaa ttccattgtt gaacatagca atctatatta acatcaaaat agatacaaat   5520
tattatttat ctcttatatc aaacagtaga attaaaactt aagaggaaac agtggcgatc   5580
aacaggtggc gaaggcgcgt tccaggattg cg                                 5612
```

<210> SEQ ID NO 2
<211> LENGTH: 5313
<212> TYPE: DNA
<213> ORGANISM: Diabrotica virgifera

<400> SEQUENCE: 2

```
atgttaattt tgttctttgt gctttcaacg ttattaaatg cagtcgtttc aacgaataat     60
aatgattgcc ctccacatca gtttagatgc acaaattcaa aatgtataga ctttcaacaa    120
agatgtgatg gttccgacaa ttgtggagat ggatcggatg aactggattg tgatcataaa    180
tgtcatgaac atttttttcaa ttgtcgaaat ggaagatgta taagcgaagc attcctgtgt   240
gatggtgaaa atgattgtaa taactttttg gatgaaaaag actgtaaggg tcaaacggtg    300
ctaactctcg aaactgatgg ccattgcgaa gatggtcatt ggaagtgtgc cgataaattg    360
tgtattccac ttgacatggt atgtaatggc gcacctgaat gtttggatgg atcagatgaa    420
actattggat gcagtaacaa gatcgtttgt gatggattta aatgtaaaaa tggccattgc    480
ataccaactg aatgggcttg cgacggtctt gatgattgtg gtgataaaac tgatgaacaa    540
gattgcgcaa accacgtacc acttgatcaa tgcactttgg ataaaagaaa attcttgtgt    600
agtaacaata aaacttgcat agatcttcac tcggtctgtg ataataagtt agattgtccc    660
gattattctg atgaaggaaa acagtgcaat tcgtctgcaa tatcatgtaa caataacaaa    720
tgttctcata catgtatatc acttccaacg ggtccaaaat gtctgtgtcc gaatggttac    780
catacgcttg atgattcgaa ttgtttggat attaatgaat gtacaactta tggaatttgt    840
gaccaaaaat gtagaaatct tcctggatca tacgaatgct actgtgatga taagtacaca    900
ctccaagccg ataaaaaaac atgtaaagca actggcggaa gcggaataat gatctttagt    960
tccaagcagg aaattcgagc tttaacctta gattctttag attattttac agtggctaaa   1020
gatttaaatc aagtagtggg aatagcatac gatggacatc atatttactg gacagacgta   1080
tttactggac atgaaactat atcgaggtct attgaagatg gatcggaaag ggaggtattg   1140
gtaacatctg gactcagtct accagaggat ctagcgtatg attggttaac tggtaatatt   1200
tatttcaccg atgctctcaa acaacatgtt ggagtgtgtt ccaatgatgg tcaccattgt   1260
acagttctag tcaacaaaga tattcgaaaa ccacgtggga ttgttgttaa tgtggaagct   1320
ggagatatgt attggtctga ttggggtgta ccagcagcaa ttggatattc acttatggat   1380
ggatcccagg acaaaccgtt cgtcaccaat aatatacact ggcccaatgg tttggctcta   1440
gatcaaccta actctagact ttattggact gatgctaaaa agatgacact agaaagtatt   1500
```

-continued

```
aatttagacg gaactgatca aaggatcgtt ttggaaggaa tagtgaaaca tccatatgcc   1560
atcgctgtgt ttgaaaacaa actttattgg tcagattggg actcccatac cattcaaact   1620
tgtgataagt ttaatggtaa aaatcatcat acactcgtgg aagaacataa aaatttaatc   1680
tatggaatca gtatttttca ctatgctctc gaaaagcgtc tagtgaatcc ttgtgagcat   1740
gcttcctgta gtgacatttg tttattgaag gctcagtcat atgcttgtgc gtgcccagag   1800
aataaagttt tggatacgga tggtcatacg tgcaaagaag tacaaccaac gcaagcactt   1860
gtaggaggaa ctggacacgt gttggtatca attaaacatc aatttctagg caaacacgat   1920
gtaacattcc taccagacct ggcgaaacac gtaggaagct tagcatttga tagttataaa   1980
aacattttgt atgtaagcga tttggaaaca aaaagtatag ttgcgcttaa catgaacatc   2040
ggaattagca aaactcttga gatcgacggt cttggcaaag ttacttcaat ggattttgat   2100
ccaaaaaagta ataatttata catttgcgat acggagaggc tagtcgtaga aataattgat   2160
atgaataatc tagaaagaaa aataattgtc catgacacat ttggagaaac tcctgaaagc   2220
attgcgttgg taccggaaga tgggatcatg tttgttagct ttaaacaagg gaaattggga   2280
aatagccaca tcgaccgttt tttcatggat ggtactggaa gaactcacgt catcgaaaac   2340
ggtttagtgg gcccagttcg tgtagtatac gaccgcagtc tttatagaat tttctttgcc   2400
gatctaagta ctggggtaat agaatctact agcgcggccg gtgacgatag acatcatttt   2460
cgtactctga ctacccatcc agtaagtata gcagttttga aagatgacct attgtggaca   2520
aatcttgact ccaaggattt atattggtct gaaaaaagat ctagcgagtc ttatgagaag   2580
aaaattacga taggttttaa agaggataac gtcaacatcc acttagtgtc agtaacacgt   2640
aaacaattag aaatcaatag ctgtcgtgtt aataataatg gatgtagtca tctttgtctt   2700
caatcccata aatcgatagt ttgtgcatgt ccagctggat gggagctatc ggcaaatggt   2760
tttacatgta ataaaagggt aacctgcgac aataaagaga tgctttgtcc tcattccaat   2820
acttgcgttc tgaagagctt aaggtgcaat ggttttaaag actgcgcatt tggtgaagat   2880
gaatgggact gccaaactgt ttcccaatgt ttacctggcc agtataaatg cgacgatgga   2940
cagtgcatca gtgaagattt ggtctgcaat catagttatg actgtaaaga taagtctgat   3000
gagtatggat gtgcagataa aaacaaaaaa ctaggatgtc ctcccggaca ttttacctgt   3060
aaaagctccg aatgcatatc tgaacgcttt gtatgtgatg ctttccatga ttgcgatgat   3120
ggatcagatg aactaaactg cgaaaataat atttgtttgg aatctcagtt taggtgtgat   3180
gtcggaactt gcataccaaa agattgggaa tgtgatggag aatatgactg tactgatagt   3240
tcagatgagc attgttcttc agaagtttgt cagtctaact attttaagtg tgacaacaac   3300
agatgtatcg atcctaagct tcagtgcgat gggtttgatg actgcggtga tcactctgat   3360
gaaaaattcg agaaatgttt gcatcactcg aaagcaccaa aatgtacatt ggaagaattc   3420
gcgtgtatta ctaatacttc catttgtctt ccaaaatcag ctaaatgtaa cggaacgtca   3480
gaatgtccga ataacgaaga cgaaaaggat tgttcaaaat gtgaagaaga tgaatttgag   3540
tgcaagcata agcattatag agaatgtatt cctaggtcct ggatatgtga tggtacagat   3600
gattgcggtg ataatagtga tgagagtatg gaaacctgtt cttcaaaact taaacctgcg   3660
gcagataact ttgctgttac tgactcgtgt ctaaccggat atagatgtca tagcggtgca   3720
tgcataaata tgacctcagt atgcaataat aaccacgatt gttttgatgg ctctgatgaa   3780
gatggcctct gttcttcatc ttgtgtcggt gtgaaaaatc cttgcaatca aatatgcgta   3840
```

-continued

```
aaaacaccat ctggaccaag atgtgaatgt aaacctggat ataagttgtt aggagatgga   3900

aaaacttgta ttgatgataa tgaatgccaa acggatccac caatctgtag tcagctatgt   3960

cacaataaag aaggaggcta ttcttgcgat tgttacaata atttcctttt aagttctaat   4020

aaaaaatctt gtaaagctca cggaccaaga atgaccatat acttagtgat ttacggaaac   4080

caaatccgtc acctaattcc taaatcaaac acaatggctg ttctttacac caatccaatg   4140

ataaaaatat ccagcttgga tactctggtt aaaccaaaac taatcttctt cagttcttat   4200

gaaactcaag ctatttataa acttgatacc accaccaaca tgatgcacta catcagaaac   4260

gtaggtttcc ctagaacaat tgcagttgat tggtcaactc aaaacattta ttacttcgat   4320

actgatgtta atggccggtc cattagtgtt tgcagttttg aagaaaagtg cgctaagttg   4380

ataaatattg aatcgcctcg acatgtaact gccttagctg ttgattccgt caataaattg   4440

cttttctacg ttttgaggaa ttggtgggta ttagaaacac caagcttcgt aatatacagt   4500

gtaaacttgg atggatctaa tagacaagaa atagtaaaaa caacaacggg caatgttgaa   4560

gatataactt tcgatattaa caagaaactt ttatactata ctaacaaaca agatgaaagt   4620

atacacgaag taagctacaa aggaggaccg gttaaaactg tattttcaaa tatctctcaa   4680

ccagaaggac ttaaattttt tgagaaccaa ttatactata ctgttgcaac tggttatata   4740

gtcagttgta agctatatgg agacagatcc tgcaatccca gatataaatt acacacgttt   4800

gccagtggtc aatttgttat tgagcaggaa tcgcttcagc ctaaagtaga aaatgtttgt   4860

actggacaca aatgtccata cttatgtgta ccagcagaat caggatatag atgtctctgt   4920

cataacggga aagttagtaa tcattcagaa atttgtggtg aaaacgatga taatcagtca   4980

ggaaataatc acaaatttgc tgtacatact acaccaatac agactgcatc cgataaacat   5040

tcaggagcag tggcctcagc aatattaatt ccactactat tagtattcct tggagcagta   5100

ttttattatt tgctaaaaag gagaggtgat actggattaa atataagcat gcgattttat   5160

aacccactct acggaaaacc tgtccgtgaa gaccaaaaac aaatccttaa accaggacaa   5220

cacgagtaca caaatccgat aattgtggcc gaagaacatg aggaccacgc gaaagatgct   5280

agcagaatgc taaacgatag ttgtgtttgt taa                                5313
```

```
<210> SEQ ID NO 3
<211> LENGTH: 236
<212> TYPE: DNA
<213> ORGANISM: Diabrotica virgifera

<400> SEQUENCE: 3

tgttaatttt gttctttgtg ctttcaacgt tattaaatgc agtcgtttca acgaataata     60

atgattgccc tccacatcag tttagatgca caaattcaaa atgtatagac tttcaacaaa    120

gatgtgatgg ttccgacaat tgtggagatg gatcggatga actggattgt gatcataaat    180

gtcatgaaca ttttttcaat tgtcgaaatg gaagatgtat aagcgaagca ttcctg       236
```

```
<210> SEQ ID NO 4
<211> LENGTH: 155
<212> TYPE: DNA
<213> ORGANISM: Diabrotica virgifera

<400> SEQUENCE: 4

gctttcaacg ttattaaatg cagtcgtttc aacgaataat aatgattgcc ctccacatca     60

gtttagatgc acaaattcaa aatgtataga ctttcaacaa agatgtgatg gttccgacaa    120

ttgtggagat ggatcggatg aactggattg tgatc                              155
```

<210> SEQ ID NO 5
<211> LENGTH: 250
<212> TYPE: DNA
<213> ORGANISM: Diabrotica virgifera

<400> SEQUENCE: 5
gtcaccaata atatacactg gcccaatggt ttggctctag atcaacctaa ctctagactt 60
tattggactg atgctaaaaa gatgacacta gaaagtatta atttagacgg aactgatcaa 120
aggatcgttt tggaaggaat agtgaaacat ccatatgcca tcgctgtgtt tgaaaacaaa 180
ctttattggt cagattggga ctcccatacc attcaaactt gtgataagtt taatggtaaa 240
aatcatcata 250

<210> SEQ ID NO 6
<211> LENGTH: 155
<212> TYPE: DNA
<213> ORGANISM: Diabrotica virgifera

<400> SEQUENCE: 6
agaggataac gtcaacatcc acttagtgtc agtaacacgt aaacaattag aaatcaatag 60
ctgtcgtgtt aataataatg gatgtagtca tctttgtctt caatcccata aatcgatagt 120
ttgtgcatgt ccagctggat gggagctatc ggcaa 155

<210> SEQ ID NO 7
<211> LENGTH: 155
<212> TYPE: DNA
<213> ORGANISM: Diabrotica virgifera

<400> SEQUENCE: 7
aatattaatt ccactactat tagtattcct tggagcagta ttttattatt tgctaaaaag 60
gagaggtgat actggattaa atataagcat gcgattttat aacccactct acggaaaacc 120
tgtccgtgaa gaccaaaaac aaatccttaa accag 155

<210> SEQ ID NO 8
<211> LENGTH: 400
<212> TYPE: DNA
<213> ORGANISM: Diabrotica virgifera

<400> SEQUENCE: 8
cctgtgtgat ggtgaaaatg attgtaataa ctttttggat gaaaaagact gtaagggtca 60
aacggtgcta actctcgaaa ctgatggcca ttgcgaagat ggtcattgga agtgtgccga 120
taaattgtgt attccacttg acatggtatg taatggcgca cctgaatgtt tggatggatc 180
agatgaaact attggatgca gtaacaagat cgtttgtgat ggatttaaat gtaaaaatgg 240
ccattgcata ccaactgaat gggcttgcga cggtcttgat gattgtggtg ataaaactga 300
tgaacaagat tgcgcaaacc acgtaccact tgatcaatgc actttggata aaagaaaatt 360
cttgtgtagt aacaataaaa cttgcataga tcttcactcg 400

<210> SEQ ID NO 9
<211> LENGTH: 400
<212> TYPE: DNA
<213> ORGANISM: Diabrotica virgifera

<400> SEQUENCE: 9
gtctgtgata ataagttaga ttgtcccgat tattctgatg aaggaaaaca gtgcaattcg 60

-continued

```
tctgcaatat catgtaacaa taacaaatgt tctcatacat gtatatcact tccaacgggt    120

ccaaaatgtc tgtgtccgaa tggttaccat acgcttgatg attcgaattg tttggatatt    180

aatgaatgta caacttatgg aatttgtgac caaaaatgta gaaatcttcc tggatcatac    240

gaatgctact gtgatgataa gtacacactc caagccgata aaaaaacatg taaagcaact    300

ggcggaagcg gaataatgat ctttagttcc aagcaggaaa ttcgagcttt aaccttagat    360

tctttagatt attttacagt ggctaaagat ttaaatcaag                          400


<210> SEQ ID NO 10
<211> LENGTH: 368
<212> TYPE: DNA
<213> ORGANISM: Diabrotica virgifera

<400> SEQUENCE: 10

tagtgggaat agcatacgat ggacatcata tttactggac agacgtattt actggacatg     60

aaactatatc gaggtctatt gaagatggat cggaaaggga ggtattggta acatctggac    120

tcagtctacc agaggatcta gcgtatgatt ggttaactgg taatatttat ttcaccgatg    180

ctctcaaaca acatgttgga gtgtgttcca atgatggtca ccattgtaca gttctagtca    240

acaaagatat tcgaaaacca cgtgggattg ttgttaatgt ggaagctgga gatatgtatt    300

ggtctgattg ggtgtacca gcagcaattg gatattcact tatggatgga tcccaggaca     360

aaccgttc                                                             368


<210> SEQ ID NO 11
<211> LENGTH: 475
<212> TYPE: DNA
<213> ORGANISM: Diabrotica virgifera

<400> SEQUENCE: 11

cactcgtgga agaacataaa aatttaatct atggaatcag tatttttcac tatgctctcg     60

aaaagcgtct agtgaatcct tgtgagcatg cttcctgtag tgacatttgt ttattgaagg    120

ctcagtcata tgcttgtgcg tgcccagaga ataaagtttt ggatacggat ggtcatacgt    180

gcaaagaagt acaaccaacg caagcacttg taggaggaac tggacacgtg ttggtatcaa    240

ttaaacatca atttctaggc aaacacgatg taacattcct accagacctg gcgaaacacg    300

taggaagctt agcatttgat agttataaaa acattttgta tgtaagcgat ttggaaacaa    360

aaagtatagt tgcgcttaac atgaacatcg gaattagcaa aactcttgag atcgacggtc    420

ttggcaaagt tacttcaatg gattttgatc caaaaagtaa taatttatac atttg         475


<210> SEQ ID NO 12
<211> LENGTH: 474
<212> TYPE: DNA
<213> ORGANISM: Diabrotica virgifera

<400> SEQUENCE: 12

cgatacggag aggctagtcg tagaaataat tgatatgaat aatctagaaa gaaaaataat     60

tgtccatgac acatttggag aaactcctga aagcattgcg ttggtaccgg aagatgggat    120

catgtttgtt agctttaaac aagggaaatt gggaaatagc cacatcgacc gttttttcat    180

ggatggtact ggaagaactc acgtcatcga aaacggttta gtgggcccag ttcgtgtagt    240

atacgaccgc agtctttata gaattttctt tgccgatcta agtactgggg taatagaatc    300

tactagcgcg gccggtgacg atagacatca ttttcgtact ctgactaccc atccagtaag    360

tatagcagtt ttgaaagatg acctattgtg gacaaatctt gactccaagg atttatattg    420
```

gtctgaaaaa agatctagcg agtcttatga gaagaaaatt acgataggtt ttaa 474

<210> SEQ ID NO 13
<211> LENGTH: 500
<212> TYPE: DNA
<213> ORGANISM: Diabrotica virgifera

<400> SEQUENCE: 13
atggttttac atgtaataaa agggtaacct gcgacaataa agagatgctt tgtcctcatt 60
ccaatacttg cgttctgaag agcttaaggt gcaatggttt taaagactgc gcatttggtg 120
aagatgaatg ggactgccaa actgtttccc aatgtttacc tggccagtat aaatgcgacg 180
atggacagtg catcagtgaa gatttggtct gcaatcatag ttatgactgt aaagataagt 240
ctgatgagta tggatgtgca gataaaaaca aaaaactagg atgtcctccc ggacatttta 300
cctgtaaaag ctccgaatgc atatctgaac gctttgtatg tgatgctttc catgattgcg 360
atgatggatc agatgaacta aactgcgaaa ataatatttg tttggaatct cagtttaggt 420
gtgatgtcgg aacttgcata ccaaaagatt gggaatgtga tggagaatat gactgtactg 480
atagttcaga tgagcattgt 500

<210> SEQ ID NO 14
<211> LENGTH: 500
<212> TYPE: DNA
<213> ORGANISM: Diabrotica virgifera

<400> SEQUENCE: 14
tcttcagaag tttgtcagtc taactatttt aagtgtgaca acaacagatg tatcgatcct 60
aagcttcagt gcgatgggtt tgatgactgc ggtgatcact ctgatgaaaa attcgagaaa 120
tgtttgcatc actcgaaagc accaaaatgt acattggaag aattcgcgtg tattactaat 180
acttccattt gtcttccaaa atcagctaaa tgtaacggaa cgtcagaatg tccgaataac 240
gaagacgaaa aggattgttc aaaatgtgaa gaagatgaat ttgagtgcaa gcataagcat 300
tatagagaat gtattcctag gtcctggata tgtgatggta cagatgattg cggtgataat 360
agtgatgaga gtatggaaac ctgttcttca aaacttaaac ctgcggcaga taactttgct 420
gttactgact cgtgtctaac cggatataga tgtcatagcg gtgcatgcat aaatatgacc 480
tcagtatgca ataataacca 500

<210> SEQ ID NO 15
<211> LENGTH: 251
<212> TYPE: DNA
<213> ORGANISM: Diabrotica virgifera

<400> SEQUENCE: 15
cgattgtttt gatggctctg atgaagatgg cctctgttct tcatcttgtg tcggtgtgaa 60
aaatccttgc aatcaaatat gcgtaaaaac accatctgga ccaagatgtg aatgtaaacc 120
tggatataag ttgttaggag atggaaaaac ttgtattgat gataatgaat gccaaacgga 180
tccaccaatc tgtagtcagc tatgtcacaa taaagaagga ggctattctt gcgattgtta 240
caataatttc c 251

<210> SEQ ID NO 16
<211> LENGTH: 140
<212> TYPE: DNA
<213> ORGANISM: Diabrotica virgifera

<400> SEQUENCE: 16
aaagtataca cgaagtaagc tacaaaggag gaccggttaa aactgtattt tcaaatatct 60
ctcaaccaga aggacttaaa ttttttgaga accaattata ctatactgtt gcaactggtt 120
atatagtcag ttgtaagcta 140

<210> SEQ ID NO 17
<211> LENGTH: 500
<212> TYPE: DNA
<213> ORGANISM: Diabrotica virgifera

<400> SEQUENCE: 17
tatggagaca gatcctgcaa tcccagatat aaattacaca cgtttgccag tggtcaattt 60
gttattgagc aggaatcgct tcagcctaaa gtagaaaatg tttgtactgg acacaaatgt 120
ccatacttat gtgtaccagc agaatcagga tatagatgtc tctgtcataa cgggaaagtt 180
agtaatcatt cagaaatttg tggtgaaaac gatgataatc agtcaggaaa taatcacaaa 240
tttgctgtac atactacacc aatacagact gcatccgata aacattcagg agcagtggcc 300
tcagcaatat taattccact actattagta ttccttggag cagtatttta ttatttgcta 360
aaaaggagag gtgatactgg attaaatata agcatgcgat tttataaccc actctacgga 420
aaacctgtcc gtgaagacca aaaacaaatc cttaaaccag gacaacacga gtacacaaat 480
ccgataattg tggccgaaga 500

<210> SEQ ID NO 18
<211> LENGTH: 488
<212> TYPE: DNA
<213> ORGANISM: Diabrotica virgifera

<400> SEQUENCE: 18
tcttgtaaag ctcacggacc aagaatgacc atatacttag tgatttacgg aaaccaaatc 60
cgtcacctaa ttcctaaatc aaacacaatg gctgttcttt acaccaatcc aatgataaaa 120
atatccagct tggatactct ggttaaacca aaactaatct tcttcagttc ttatgaaact 180
caagctattt ataaacttga taccaccacc aacatgatgc actacatcag aaacgtaggt 240
ttccctagaa caattgcagt tgattggtca actcaaaaca tttattactt cgatactgat 300
gttaatggcc ggtccattag tgtttgcagt tttgaagaaa agtgcgctaa gttgataaat 360
attgaatcgc ctcgacatgt aactgcctta gctgttgatt ccgtcaataa attgcttttc 420
tacgttttga ggaattggtg ggtattagaa acaccaagct tcgtaatata cagtgtaaac 480
ttggatgg 488

<210> SEQ ID NO 19
<211> LENGTH: 5313
<212> TYPE: DNA
<213> ORGANISM: Diabrotica undecimpunctata

<400> SEQUENCE: 19
atgttaattt tgtttttgt gctttccacg ttattaaatg cagtcgtttc aacgaataac 60
aatgattgtc ttcaacatca gttcagatgc acaaattcaa aatgtataga ttttcagcaa 120
agatgtgatg gttccgataa ttgtggggat ggatcggatg aactggagtg tgatcataaa 180
tgtcatgaac attttttcga ttgtcgaaat gggagatgta taagcgaagc attcgtatgt 240
gatggtgaaa atgattgtaa taacttttg gatgaaaaag actgtaagga taaaacgcta 300
actctcgaaa ctgatcagca ttgtgaagat ggtcattgga agtgtactga tagattgtgt 360

-continued

```
attccaaatg actgggtgtg taatggcgta cctgaatgtt tggatggatc agatgaaact    420
attggatgta gcagcaagat cgattgtgat gggtttaaat gtaaaaatgg tcattgtata    480
ccaaatgaat ggaattgcga tggtgttgac gattgcggcg ataaaactga tgaacaagat    540
tgtgaagacc acgtgccact tgatcaatgc actttggata aaagaaaatt cttgtgtagc    600
aacaataaaa cttgcatcga tcttcactca gtctgtgata ataagtttga ttgtcccgat    660
tattctgatg aaggaaaact ttgcaattcg tctacagtat tatgtaagaa taacaaatgt    720
tcgcacacat gtatcccact tccaacgggt acaaaatgtc tgtgtccgaa tggataccat    780
acgattgatg attcgaaatg tttggatatt aatgaatgta caatttatgg tatatgcgac    840
caaaaatgtc gaaatcttcc tggatcatac gaatgctact gtgatgataa atacaaactc    900
caagctgata aaagaacttg taaagcaatt ggaggaagcg gaataatgat ctttagttcc    960
aagcaggaaa ttagagcttt aaccttggat tctttagatt attttacagt ggctaaagat   1020
ttaaaacaag tagtcggaat agcatacgat ggaaatcata tttattggac agacgtattt   1080
actggacatg aaactatatc gaggtctatt gaagatggat cacagagaga ggtattggta   1140
acatctggat taagtttacc agaggatcta gcatttgatt ggttaactca taatatttat   1200
tttaccgatg ctctgaaaca acatgttgga gtatgttcca atgatggtaa ccattgtaca   1260
gtactagtca acaaagatat tcgaaaacca cgtgggattg ttgttaatgt ggaagctgga   1320
gatatgtatt ggtctgattg gggagtacca gcagcaattg gatattcact tatggatggt   1380
tcccatgaca gaccgtttgt caccaataat atacactggc ccaatggttt ggctctagat   1440
caacctaact ctagacttta ttggactgat gccaaaaaga tgacattaga aagtattaat   1500
ttagacggaa ctgatcaaag gattgttttg gaaggaatcg tgaaacatcc ctatgccatc   1560
gctgtgtttg aaaacaaatt gtattggtca gattgggact cccatagcat tcaaacttgt   1620
gataagttcg atggtaaaaa tcaccataca ctcgtagaag aacataaaaa tctaatctat   1680
ggaatcagta tctttcacta tgctctcgaa aagcgtctag tgaatccttg tgaccatact   1740
tcctgtagtg atatttgtct attgaaggct cagtcatatg cttgtgcgtg cccggaaaat   1800
aaaattttag atacggatgg tcatacgtgc aaagaaatac aaccaacgca agcacttgtt   1860
ggaggaactg gacatgtttt agtgtcaatc aaacatcaat ttctaggcaa acacgacgta   1920
acattcctac cagacctggt gaaacacgta ggaagcttag cgtatgacag ttataaaaaa   1980
gttttgtatg ttagcgattt ggaaacaaaa agtatagttg agcttaacat ggttacaggc   2040
gttagcaaaa ctcttgatat cagcggtatt ggcagagtta cttcaatgga ttttgatcca   2100
aaaagtaata atttatacat ttgcgatacg gaaaggctgg ttgtagaaat tattgatatg   2160
aatagtcaag aaagaaaaat aattgttcac gacacttttg gagaaagtcc tgaaagcatt   2220
gctttggtac cggaagatgg tatcatgttt gtaagtttta aacaaggaaa atcaggaaat   2280
agtcacatcg atcgtttatt catggatggt accggaagaa ctcacgtcat cgaaagcgga   2340
ttagtgggcc cagtccatgt agtgtatgac cacagtcttt atagaatttt ctttgcggat   2400
ctaagtactg gtgttatcga atctacgagt gtgaccggtg acgatagaca tcattttcgt   2460
actctgacta ctcatccagt aagtttagcg gttttgaaag atgatatatt gtggacaaat   2520
attgactcca aggatttata ttggtctgaa aaaagatcta gtgagtctta tgagaagaaa   2580
attactttag gttttaaaga agataacgtt aatattcact tagtatcagt gacacataaa   2640
caattagaaa ttaatggttg ccgtgttaat aataatggat gcagtcatct ttgtcttcaa   2700
```

-continued

```
tcccacaaat caataatttg tgcatgtcca gctggatggg agctatcggc aaatggtttt   2760
acatgtaata aaaggttaac ctgcgacaat aaagagatgc tttgtcctca ttccaatact   2820
tgcattctaa agagcttaag gtgcaatggt tttaaagact gcgcatttgg tgaagatgaa   2880
tgggattgtc aagctgcttc cgaatgttta cctggtcagt ataaatgcga cgatggacag   2940
tgcatcagtg aagatttggt ctgcaatcat agttatgact gtaaagataa gtcggacgag   3000
tatggatgtg cagataaaaa gaagaaacta gggtgtcctc ccggtcattt tacctgtaag   3060
agctctgaat gtatatcaga acgattttta tgtgatggtt atcatgattg cgatgatgga   3120
tcagatgaat ttaattgcga gaataatatt tgtttggaat ctcagttcag gtgtgatgtc   3180
ggaacttgca taccaaaaga ttgggaatgc gatggagaat atgactgtac tgataattca   3240
gatgagcact gttcttcaga aggttgtcgc tccgactatt tcaagtgtga taacaacaga   3300
tgtatcgatc ctaaacttca ttgcgatggg tttgatgact gcggtgacca ctctgatgaa   3360
aaattcgagc aatgtttgca tcactcgaaa gcaccaaaat gtacattgga ggaattcgca   3420
tgcaccacta atacttccat ttgtcttcca caatcagcta aatgtaacgg aacatcagaa   3480
tgcccgaata aagaagacga aaaggattgt tcaaaatgcg aagaagatga atttgagtgt   3540
aagaataagc attacagaga atgtattcct agatcctggt tatgtgatgg cgcagatgat   3600
tgcggtgata atagtgatga gaatatggaa acatgttctt caaaactcaa aactctggga   3660
aataatactg ctgttgctga tccgtgtcta accggatata gatgtcgcag cggtgcatgc   3720
ataaatatga cttcagtatg caataataaa cacgattgtt atgatggctc tgatgaagat   3780
ggactctgtt cttcatcttg tgtcggtgta aaaaatccct gcaatcaaat atgcgtaaaa   3840
acaccatctg gaccaagatg tgaatgtaga ctgggatata aattgctagg agacggaaaa   3900
acgtgtatcg atgataatga atgccaaacg gatcccccaa tctgtagtca gttatgtcac   3960
aataaagaag gaggttattc ttgtgattgt tacaataatt tcctttttaag ttctaataaa   4020
aaatcttgta aggctcacgg accacgaatg accatatact tagtgattta cggaaacgaa   4080
atccgtcaac taattcctaa atcaaataca atggctgttg tttacaccaa tccaatgata   4140
aaaatctcca gcttggatac tctgattaaa ccaaaactaa tcttctttgg ttcttatgaa   4200
actcaagcta tttataaact ggataccacc acaaacatga tgcactacat cagaaacgta   4260
ggttttccta gaaaaattgc agttgattgg tccactcaaa acatttatta cttcgatact   4320
gattataatg gccggtccat tagtgtttgc agttttgaag aaaagtgtgc taagttaata   4380
aatattgaat cgcctcgaca tgtatctgcc ttagctgttg attccgttaa taaaaaactt   4440
ttctacgttt tgaggaattg gtgggtatta gaaacaccaa gcttcgtaat atacagtgta   4500
aacttggatg gatctaatag acaagaaata gtaaaaacaa caacaggtaa tgttgaagat   4560
ataactttcg atattaacaa gaaactttta tactacacta ataaacaaga tgaaagtata   4620
tatgaagtaa actacaaagg aggacctgtt aaaactgtat tttcaaacat ctctcaacca   4680
gaaggtctta aattttttcga aaatcagtta tactatactg ttgcaactgg ttatatagtc   4740
agttgtaagc tatatggaga caaatcttgt catcccagat ataaattaca cacttttgcc   4800
agtggtcaat ttattattga gcaggaatcg cttcagccta aaaccgaaaa tgtttgtact   4860
ggacacaaat gtccatactt atgtgtacca gcagaaacag gttatagatg tctttgccat   4920
gacgggaaag ttagtaatca ttcagaaatt tgtggcgaaa atgatgataa tcagtcagga   4980
aataatcaca agtttgctgt acacactaca ccattacaaa cggcatccga taaacactct   5040
ggagcagtgg cctcagcaat attaattcca atactcttgg tattccttgg agcagtattt   5100
```

-continued

```
tattatgtgc taaaaaagaa aggtgatact ggcttaaata taagcatgag attttataac   5160

ccactttacg gaaaacctgt cgaagaccaa aaaccaatcc ttcagccagg acaacacgag   5220

tacacaaatc cgatcattgt ggcagaagaa agaagtcaag aggaccatgc gaaagatgct   5280

agcagaatgc taaacgatag ttgtgtttgt taa                                5313
```

```
<210> SEQ ID NO 20
<211> LENGTH: 5730
<212> TYPE: DNA
<213> ORGANISM: Diabrotica undecimpunctata

<400> SEQUENCE: 20

tttggccagt tcatcagtta aaactgtgag tgctacattt tttgaatatc tcgtaaagta     60

tgttaatttt gtttttgtg ctttccacgt tattaaatgc agtcgtttca acgaataaca    120

atgattgtct tcaacatcag ttcagatgca caaattcaaa atgtatagat tttcagcaaa    180

gatgtgatgg ttccgataat tgtggggatg gatcggatga actggagtgt gatcataaat    240

gtcatgaaca ttttttcgat tgtcgaaatg ggagatgtat aagcgaagca ttcgtatgtg    300

atggtgaaaa tgattgtaat aactttttgg atgaaaaaga ctgtaaggat aaaacgctaa    360

ctctcgaaac tgatcagcat tgtgaagatg gtcattggaa gtgtactgat agattgtgta    420

ttccaaatga ctgggtgtgt aatggcgtac ctgaatgttt ggatggatca gatgaaacta    480

ttggatgtag cagcaagatc gattgtgatg ggtttaaatg taaaaatggt cattgtatac    540

caaatgaatg gaattgcgat ggtgttgacg attgcggcga taaaactgat gaacaagatt    600

gtgaagacca cgtgccactt gatcaatgca ctttggataa aagaaaattc ttgtgtagca    660

acaataaaac ttgcatcgat cttcactcag tctgtgataa taagtttgat tgtcccgatt    720

attctgatga aggaaaactt tgcaattcgt ctacagtatt atgtaagaat aacaaatgtt    780

cgcacacatg tatcccactt ccaacgggta caaaatgtct gtgtccgaat ggataccata    840

cgattgatga ttcgaaatgt ttggatatta atgaatgtac aatttatggt atatgcgacc    900

aaaaatgtcg aaatcttcct ggatcatacg aatgctactg tgatgataaa tacaaactcc    960

aagctgataa aagaacttgt aaagcaattg gaggaagcgg aataatgatc tttagttcca   1020

agcaggaaat tagagcttta accttggatt ctttagatta ttttacagtg gctaaagatt   1080

taaaacaagt agtcggaata gcatacgatg gaaatcatat ttattggaca gacgtattta   1140

ctggacatga aactatatcg aggtctattg aagatggatc acagagagag gtattggtaa   1200

catctggatt aagtttacca gaggatctag catttgattg gttaactcat aatatttatt   1260

ttaccgatgc tctgaaacaa catgttggag tatgttccaa tgatggtaac cattgtacag   1320

tactagtcaa caaagatatt cgaaaaccac gtgggattgt tgttaatgtg gaagctggag   1380

atatgtattg gtctgattgg ggagtaccag cagcaattgg atattcactt atggatggtt   1440

cccatgacag accgtttgtc accaataata tacactggcc caatggtttg gctctagatc   1500

aacctaactc tagactttat tggactgatg ccaaaaagat gacattagaa agtattaatt   1560

tagacggaac tgatcaaagg attgttttgg aaggaatcgt gaaacatccc tatgccatcg   1620

ctgtgtttga aaacaaattg tattggtcag attgggactc ccatagcatt caaacttgtg   1680

ataagttcga tggtaaaaat caccatacac tcgtagaaga acataaaaat ctaatctatg   1740

gaatcagtat ctttcactat gctctcgaaa agcgtctagt gaatccttgt gaccatactt   1800

cctgtagtga tatttgtcta ttgaaggctc agtcatatgc ttgtgcgtgc ccggaaaata   1860
```

-continued

```
aaattttaga tacggatggt catacgtgca aagaaataca accaacgcaa gcacttgttg   1920
gaggaactgg acatgtttta gtgtcaatca aacatcaatt tctaggcaaa cacgacgtaa   1980
cattcctacc agacctggtg aaacacgtag gaagcttagc gtatgacagt tataaaaaag   2040
ttttgtatgt tagcgatttg gaaacaaaaa gtatagttga gcttaacatg gttacaggcg   2100
ttagcaaaac tcttgatatc agcggtattg gcagagttac ttcaatggat tttgatccaa   2160
aaagtaataa tttatacatt tgcgatacgg aaaggctggt tgtagaaatt attgatatga   2220
atagtcaaga aagaaaaata attgttcacg acacttttgg agaaagtcct gaaagcattg   2280
ctttggtacc ggaagatggt atcatgtttg taagttttaa acaaggaaaa tcaggaaata   2340
gtcacatcga tcgtttattc atggatggta ccggaagaac tcacgtcatc gaaagcggat   2400
tagtgggccc agtccatgta gtgtatgacc acagtcttta tagaattttc tttgcggatc   2460
taagtactgg tgttatcgaa tctacgagtg tgaccggtga cgatagacat cattttcgta   2520
ctctgactac tcatccagta agtttagcgg ttttgaaaga tgatatattg tggacaaata   2580
ttgactccaa ggatttatat tggtctgaaa aaagatctag tgagtcttat gagaagaaaa   2640
ttactttagg ttttaaagaa gataacgtta atattcactt agtatcagtg acacataaac   2700
aattagaaat taatggttgc cgtgttaata ataatggatg cagtcatctt tgtcttcaat   2760
cccacaaatc aataatttgt gcatgtccag ctggatggga gctatcggca aatggtttta   2820
catgtaataa aaggttaacc tgcgacaata aagagatgct ttgtcctcat tccaatactt   2880
gcattctaaa gagcttaagg tgcaatggtt ttaaagactg cgcatttggt gaagatgaat   2940
gggattgtca agctgcttcc gaatgtttac ctggtcagta taaatgcgac gatggacagt   3000
gcatcagtga agatttggtc tgcaatcata gttatgactg taaagataag tcggacgagt   3060
atggatgtgc agataaaaag aagaaactag ggtgtcctcc cggtcatttt acctgtaaga   3120
gctctgaatg tatatcagaa cgatttttat gtgatggtta tcatgattgc gatgatggat   3180
cagatgaatt taattgcgag aataatattt gtttggaatc tcagttcagg tgtgatgtcg   3240
gaacttgcat accaaaagat tgggaatgcg atggagaata tgactgtact gataattcag   3300
atgagcactg ttcttcagaa ggttgtcgct ccgactattt caagtgtgat aacaacagat   3360
gtatcgatcc taaacttcat tgcgatgggt ttgatgactg cggtgaccac tctgatgaaa   3420
aattcgagca atgtttgcat cactcgaaag caccaaaatg tacattggag gaattcgcat   3480
gcaccactaa tacttccatt tgtcttccac aatcagctaa atgtaacgga acatcagaat   3540
gcccgaataa agaagacgaa aaggattgtt caaaatgcga agaagatgaa tttgagtgta   3600
agaataagca ttacagagaa tgtattccta gatcctggtt atgtgatggc gcagatgatt   3660
gcggtgataa tagtgatgag aatatggaaa catgttcttc aaaactcaaa actctgggaa   3720
ataatactgc tgttgctgat ccgtgtctaa ccggatatag atgtcgcagc ggtgcatgca   3780
taaatatgac ttcagtatgc aataataaac acgattgtta tgatggctct gatgaagatg   3840
gactctgttc ttcatcttgt gtcggtgtaa aaaatccctg caatcaaata tgcgtaaaaa   3900
caccatctgg accaagatgt gaatgtagac tgggatataa attgctagga gacggaaaaa   3960
cgtgtatcga tgataatgaa tgccaaacgg atcccccaat ctgtagtcag ttatgtcaca   4020
ataaagaagg aggttattct tgtgattgtt acaataattt ccttttaagt tctaataaaa   4080
aatcttgtaa ggctcacgga ccacgaatga ccatatactt agtgatttac ggaaacgaaa   4140
tccgtcaact aattcctaaa tcaaatacaa tggctgttgt ttacaccaat ccaatgataa   4200
aaatctccag cttggatact ctgattaaac caaaactaat cttctttggt tcttatgaaa   4260
```

```
ctcaagctat ttataaactg gataccacca caaacatgat gcactacatc agaaacgtag   4320
gttttcctag aaaaattgca gttgattggt ccactcaaaa catttattac ttcgatactg   4380
attataatgg ccggtccatt agtgtttgca gttttgaaga aaagtgtgct aagttaataa   4440
atattgaatc gcctcgacat gtatctgcct tagctgttga ttccgttaat aaaaaacttt   4500
tctacgtttt gaggaattgg tgggtattag aaacaccaag cttcgtaata tacagtgtaa   4560
acttggatgg atctaataga caagaaatag taaaaacaac aacaggtaat gttgaagata   4620
taactttcga tattaacaag aaacttttat actacactaa taaacaagat gaaagtatat   4680
atgaagtaaa ctacaaagga ggacctgtta aaactgtatt ttcaaacatc tctcaaccag   4740
aaggtcttaa atttttcgaa aatcagttat actatactgt tgcaactggt tatatagtca   4800
gttgtaagct atatggagac aaatcttgtc atcccagata taaattacac acttttgcca   4860
gtggtcaatt tattattgag caggaatcgc ttcagcctaa aaccgaaaat gtttgtactg   4920
gacacaaatg tccatactta tgtgtaccag cagaaacagg ttatagatgt ctttgccatg   4980
acgggaaagt tagtaatcat tcagaaattt gtggcgaaaa tgatgataat cagtcaggaa   5040
ataatcacaa gtttgctgta cacactacac cattacaaac ggcatccgat aaacactctg   5100
gagcagtggc ctcagcaata ttaattccaa tactcttggt attccttgga gcagtatttt   5160
attatgtgct aaaaaagaaa ggtgatactg gcttaaatat aagcatgaga ttttataacc   5220
cactttacgg aaaacctgtc gaagaccaaa aaccaatcct tcagccagga caacacgagt   5280
acacaaatcc gatcattgtg gcagaagaaa gaagtcaaga ggaccatgcg aaagatgcta   5340
gcagaatgct aaacgatagt tgtgtttgtt aactttgtat ctttttgtta cgtcattctt   5400
tgttttatgt tttatataat cttataaacg ttgttttaat cttttgaagt gtattaaaag   5460
taaattaatt cttacacttc acaaatatta aattcgttga aaattgaatt gttgaacata   5520
acaatctata ttatacctac atcaaaatag atacaaatga atatttatta taacgctata   5580
tcgagcagta gagtttaacc ttaataccaa taaataggtg taacgggtgc atttgacaat   5640
atcaaattat ttattataga ataggctaaa tgcataatac tttatatttt tataattata   5700
ttttattaaa attttatgaa ctttaaaaaa                                    5730
```

<210> SEQ ID NO 21
<211> LENGTH: 5295
<212> TYPE: DNA
<213> ORGANISM: Leptinotarsa decemlineata

<400> SEQUENCE: 21

```
atgtatgttc ttttggttct gggagctgta gcatcctcat cagctttctt ggaatcgcta     60
atctccctga acgactgccc tccggctcag tttgcttgca ggaatggaaa atgcgtggat    120
aaaactttga gatgcaatgg attcaacaac tgtttggatg gatctgatga aatggattgt    180
gaattgtatt tatgcaaaga gccgagatat tatcgatgta agaataaaag atgtatcagc    240
aaattatttg tttgcgatgg agaaaatgat tgcgaggatt tttctgatga agtcgaatgt    300
gagaacttta agatgtcaga tcacgtgaac acaacatgcg aaaaaggcca ctggcagtgc    360
acagataaac tgtgcatacc aaatgaatgg gtgtgcaatg gagaatcaga ttgtttagat    420
ggatcagatg aaggaatagg gtgcagctcg aaaatagagt gcgatggatt caaatgtaaa    480
aatggtcact gtattcccaa cgaatggata tgcgacaaca acaatgactg tcacgataat    540
agtgacgagg aggattgtga aaatcacgtt cctatcaaca agtgcacact ggataatcga    600
```

-continued

```
aaatttcttt gctctaacaa taaaacctgc attgacctag ttcttacgtg cgatggccat    660
cctaactgcc cggatggatc tgacgaggga cccctttgca aatcggcagt ttcttgccaa    720
aatcacgggt gctctcacga atgtttccct ttgcctacag gaccgttatg tttatgccct    780
cctggatatc ttactgagaa tgataaacgt tgccaggata tcaacgagtg cgaacagttt    840
gatatttgtg atcaaaagtg caggaatctg ccgggatcct atgaatgtta ttgcgatcat    900
aaatatttgc ttaaagaaga taaaagaact tgcaaagctg tgggtggaga agctttaatg    960
gtatttagtt ccaaatccga aataagagca tatgccttgg aatccgagtt atattttccg   1020
atagtacaaa agttgaagca agtagtcggc gttgattatg acggccacca tatctactgg   1080
acggatattt ttgcagagca tgagagtatc gcacgaacca ctgaggatgg atcaaaacga   1140
gagattctga ttacttccgg acttggttta ccagaagatt tagctgttga ttggctcaca   1200
ggaaatattt atttcacgga tgctgaaaag gcgcatatag gcgtttgtaa cagtcatgga   1260
actcactgta ccgttttggt gaacaaagat gtcaatagac ccagaggact ggtactgaat   1320
gttgaagagg gagacatgta ctggtctgat tggggaaaac cgtccaaaat tgctcattct   1380
ctgatggatg gttcaaatga cagagcattc atatctacag atattcattg gcctaatggg   1440
ctagccctgg atcaatctaa ccaaaggctt tattggactg atgctaaaaa aatgaccctg   1500
gaaagcattc gattggacgg aacggataga aggattgtgt tggaaggggt cgtgaaacat   1560
ccttatgcca ttgcggtgtt cgaaaataaa ttgtactggt cagattggtc aactcgttcc   1620
atccaaactt gtgacaaatt tactggcaaa gatcatcaca ctctggttaa agaagataag   1680
tatatatatg gaatcagcat attccattca gctctccaca gaagacttga taatccttgt   1740
gcattgtcct actgtagcga tatttgcttg ctgaagggaa atacctacag ctgtgcctgc   1800
cctgagaata aacttctggg aagtgacaag cattcatgta aagatattgg acccacagaa   1860
acgttgatcg ctgggactca agatagttta gttcatatag agcacaaatt tttgggaaaa   1920
catgatgtca cgtatctgcc cagtatagtt aaaaaaattg gttgcttggc ttatgatagt   1980
attaataact cactactgat cagcgacttg gagttgaaaa aaatcgttaa cttggatttg   2040
gatgatggaa tcaataaagt tcttgaaatt gatggattag gaagtataac agcaatggat   2100
tatgatgcta aaggaaataa cctctatgta tgtgataggg agaaacgaac cttggaagta   2160
atcagtctca atactttgtc aaaaaaaatt cttctgaact tcatgaacgg ggaaattcca   2220
gaagctgtgg ctgtggttcc ggatgaaggg gtgatgtttg tcagtttgag agaagcagaa   2280
ggtacatttt gtcatttgga tcgcttctat atggacggaa cgggaaggac acacacctta   2340
gaagatcatc tgataggccc tatatcacta cgctatgacc atgatttgaa cagagttttc   2400
tttgctgatg ctggtactgg attgatagaa tcaactagtg ttgaaggaga cgatcgacat   2460
gatttccgaa ggctaacaac ccacccctct agcatcacaa ctcttaaaaa tgatctattc   2520
tgggtgaacg aaaactccaa gcgtttgtat tgggcagaga agaaaagcat ttcaatgtat   2580
aacagaaaaa ttaccctaga tctctccaga gaaccagaga aactccatct aatatcagta   2640
acccccagaa aaaatgtgtt gagcgcttgt tggctcaaca acaatggatg cagtcacctt   2700
tgcctcatgt cgcacaagac aacggtttgc gcttgtccaa ctggctacga actatccgac   2760
gaccacagga cttgcatccg acgcgtgcat tgcgactctt ctgaattctt ttgccctcag   2820
tctaacgtct gcgtcatgaa gagcttaaga tgcaattcac atcaggactg tgcatttgga   2880
gaagatgaac tgaactgtga cataaacaga tgcacaaccg ggttcttccg ttgcgataat   2940
ggcgattgca tcaaagaaca gctagtgtgc gaccatcatt acgactgcag ggataaatct   3000
```

-continued

```
gacgaagata attgcgctga gaagaagaaa cacgtgggat gtccgccaaa gcactttaga   3060
tgcgggaatg gagactgcat ttcagataga ttcatatgcg atggttataa agattgtgag   3120
gatagctcgg atgaaaaggg ctgcgagaag atgttctgtt cggataccga atttagatgc   3180
gattctggaa catgtattcc tagtagctgg gagtgcgacc acgaatatga ttgctcagat   3240
tcctccgacg aacatcccgg atgtgcttcc atcacctgtt ctgcaaccat gttcacttgt   3300
ggaaatggca aatgcctcga taaaagtctt gtctgcgaca aaagcgatga ctgtggcgat   3360
aattcagacg aaacgtcctg cttcaaacgc ccctcctctt gccttccgca agaattttct   3420
tgtccttcga atacctctat ctgcgtccct atgtcagcca agtgcaatgg atccgtcgag   3480
tgtcctaagg gagaagacga ggaagaatgt ggcgactgca tgccggatga gttccgctgt   3540
ctcaacaagc aatgcattgc ggcacaatgg atgtgcgatg gcatcaacga ctgtgatgac   3600
ggcagtgatg aaactgctga aggttgctcg cagaagaata aaaccacggg ggagatgtcc   3660
gtggttcata ctgcctgtga aaatggattc aggtgtaaaa atggagattg cttggatatg   3720
aaactggtgt gtaatggaaa tcacgattgt tacgatggtt ctgatgagga tggactgtgt   3780
tcaacttcct gtgaaggatc agccaatcga tgttctcaaa tatgcaataa aactccaatg   3840
ggaccgtctt gcgagtgtag atctgggttt atattgatgg gcaatggggt cagctgcatg   3900
gatttgaatg aatgccagaa tcatccacca gtgtgcagtc aaatttgcca caatcaggac   3960
ggcggtttca aatgcgattg ttatgatggc tttttactga gatccgacaa gaaatcttgc   4020
aaagcagaag gaaatccgat gtcgctcatt ttcagtgaat atgggcaaat aagggaactc   4080
tcgcaattga ctaatatctt gtctgttgta tttgccactc ctgcaccaaa aataactggc   4140
ctagacgtac ttgtcaatcc aagaaccatc tatttcagca tggaggaaac ttccacgatt   4200
cacaaaatcg atatggcatc aaaaacgaga catttcataa ggaatattgg acaacctcag   4260
gacattgctg ttgattggtc tactcacaac atctattact ataacacgga caccaactcg   4320
aaatctatca gtatttgtag tttcgaagaa aagtgcgcga agttgattga tgttgacatg   4380
cacagacaag tggcaggatt ggttgtcgac tctgtcaaca aattttttatt ttatgctttg   4440
aacagttggt acgtgttcaa ttcccccagt tacgttatct acaggtgcaa cttggatgga   4500
actgagaaga cggaaataat gaaaactaca gatgggtttg tatccgacat cacttttgac   4560
cacaacagta ggatattgta ctacatggat atgtacttgg gtcaaataaa taagataacc   4620
tatgatggta gtttcaaaac tccaatttat tccaatatca cccgatcctc agggcttaag   4680
ttcttcgaga accgattata ctattctacg aatgggggat ttgtttcagt ttgcaggtta   4740
tacggatttc tgagatgtga tagtttcagg cttcacaatg atgcaataga tttcttcact   4800
attctacaag agacgcttca gccgagtgtg ggtaatcctt gcaagaacca caattgctcc   4860
aacttatgcg ttccagctca gtttggatat aaatgtctct gccaggatgg aacgcttcta   4920
tctggaccag gaagttgtcc aattaatgag aataccccag agtccgacaa aaaatatact   4980
gttcactcgg tggcgatgac acaggctggt cctgaggagg gaagttcggg tactgtagct   5040
gttgccatca cgatacctct tctggtgata ttatttgctt tgggagccat ttactttatc   5100
aagaaaaagc atgcaggagc tttgaatgtc aggatgagat tttatactcc tcatttcgga   5160
aggaccgttc aagatgaaaa tcctattcta aagcctggtc aacatgaata cacaaaccct   5220
gttcatttta ataaagaaga taatgaatta actctagaaa cagcacctat caaactgaat   5280
gatgcctcga atgtg                                                    5295
```

<210> SEQ ID NO 22
<211> LENGTH: 5690
<212> TYPE: DNA
<213> ORGANISM: Leptinotarsa decemlineata

<400> SEQUENCE: 22
gctctcgtag ttagcccttc tgtgttgtga aaattgtttc attttatcag tattcatcct 60
tagaaattga tattttttc atatggtttt caaccgagat tgattactaa atatttgaga 120
atgtatgttc ttttggttct gggagctgta gcatcctcat cagctttctt ggaatcgcta 180
atctccctga acgactgccc tccggctcag tttgcttgca ggaatggaaa atgcgtggat 240
aaaactttga gatgcaatgg attcaacaac tgtttggatg gatctgatga aatggattgt 300
gaattgtatt tatgcaaaga gccgagatat tatcgatgta agaataaaag atgtatcagc 360
aaattatttg tttgcgatgg agaaaatgat tgcgaggatt tttctgatga agtcgaatgt 420
gagaacttta agatgtcaga tcacgtgaac acaacatgcg aaaaaggcca ctggcagtgc 480
acagataaac tgtgcatacc aaatgaatgg gtgtgcaatg gagaatcaga ttgtttagat 540
ggatcagatg aaggaatagg gtgcagctcg aaaatagagt gcgatggatt caaatgtaaa 600
aatggtcact gtattcccaa cgaatggata tgcgacaaca acaatgactg tcacgataat 660
agtgacgagg aggattgtga aaatcacgtt cctatcaaca agtgcacact ggataatcga 720
aaatttcttt gctctaacaa taaaacctgc attgacctag ttcttacgtg cgatggccat 780
cctaactgcc cggatggatc tgacgaggga ccccttttgca aatcggcagt ttcttgccaa 840
aatcacgggt gctctcacga atgtttccct ttgcctacag gaccgttatg tttatgccct 900
cctggatatc ttactgagaa tgataaacgt tgccaggata tcaacgagtg cgaacagttt 960
gatatttgtg atcaaaagtg caggaatctg ccgggatcct atgaatgtta ttgcgatcat 1020
aaatatttgc ttaaagaaga taaaagaact tgcaaagctg tgggtggaga agctttaatg 1080
gtatttagtt ccaaatccga aataagagca tatgccttgg aatccgagtt atattttccg 1140
atagtacaaa agttgaagca agtagtcggc gttgattatg acggccacca tatctactgg 1200
acggatattt ttgcagagca tgagagtatc gcacgaacca ctgaggatgg atcaaaacga 1260
gagattctga ttacttccgg acttggttta ccagaagatt tagctgttga ttggctcaca 1320
ggaaatattt atttcacgga tgctgaaaag gcgcatatag gcgtttgtaa cagtcatgga 1380
actcactgta ccgttttggt gaacaaagat gtcaatagac ccagaggact ggtactgaat 1440
gttgaagagg gagacatgta ctggtctgat tggggaaaac cgtccaaaat tgctcattct 1500
ctgatggatg gttcaaatga cagagcattc atatctacag atattcattg gcctaatggg 1560
ctagccctgg atcaatctaa ccaaaggctt tattggactg atgctaaaaa aatgaccctg 1620
gaaagcattc gattggacgg aacggataga aggattgtgt tggaaggggt cgtgaaacat 1680
ccttatgcca ttgcggtgtt cgaaaataaa ttgtactggt cagattggtc aactcgttcc 1740
atccaaactt gtgacaaatt tactggcaaa gatcatcaca ctctggttaa agaagataag 1800
tatatatatg gaatcagcat attccattca gctctccaca gaagacttga taatccttgt 1860
gcattgtcct actgtagcga tatttgcttg ctgaagggaa atacctacag ctgtgcctgc 1920
cctgagaata aacttctggg aagtgacaag cattcatgta aagatattgg acccacagaa 1980
acgttgatcg ctgggactca agatagttta gttcatatag agcacaaatt tttgggaaaa 2040
catgatgtca cgtatctgcc cagtatagtt aaaaaaattg gttgcttggc ttatgatagt 2100
attaataact cactactgat cagcgacttg gagttgaaaa aaatcgttaa cttggatttg 2160

-continued

```
gatgatggaa tcaataaagt tcttgaaatt gatggattag gaagtataac agcaatggat   2220
tatgatgcta aaggaaataa cctctatgta tgtgataggg agaaacgaac cttggaagta   2280
atcagtctca atactttgtc aaaaaaaatt cttctgaact tcatgaacgg ggaaattcca   2340
gaagctgtgg ctgtggttcc ggatgaaggg gtgatgtttg tcagtttgag agaagcagaa   2400
ggtacatttt gtcatttgga tcgcttctat atggacggaa cgggaaggac acacacctta   2460
gaagatcatc tgataggccc tatatcacta cgctatgacc atgatttgaa cagagttttc   2520
tttgctgatg ctggtactgg attgatagaa tcaactagtg ttgaaggaga cgatcgacat   2580
gatttccgaa ggctaacaac ccacccctct agcatcacaa ctcttaaaaa tgatctattc   2640
tgggtgaacg aaaactccaa gcgtttgtat tgggcagaga agaaaagcat ttcaatgtat   2700
aacagaaaaa ttaccctaga tctctccaga gaaccagaga aactccatct aatatcagta   2760
acccccagaa aaaatgtgtt gagcgcttgt tggctcaaca acaatggatg cagtcacctt   2820
tgcctcatgt cgcacaagac aacggtttgc gcttgtccaa ctggctacga actatccgac   2880
gaccacagga cttgcatccg acgcgtgcat tgcgactctt ctgaattctt ttgccctcag   2940
tctaacgtct gcgtcatgaa gagcttaaga tgcaattcac atcaggactg tgcatttgga   3000
gaagatgaac tgaactgtga cataaacaga tgcacaaccg ggttcttccg ttgcgataat   3060
ggcgattgca tcaaagaaca gctagtgtgc gaccatcatt acgactgcag ggataaatct   3120
gacgaagata attgcgctga gaagaagaaa cacgtgggat gtccgccaaa gcactttaga   3180
tgcgggaatg gagactgcat ttcagataga ttcatatgcg atggttataa agattgtgag   3240
gatagctcgg atgaaaaggg ctgcgagaag atgttctgtt cggataccga atttagatgc   3300
gattctggaa catgtattcc tagtagctgg gagtgcgacc acgaatatga ttgctcagat   3360
tcctccgacg aacatcccgg atgtgcttcc atcacctgtt ctgcaaccat gttcacttgt   3420
ggaaatggca aatgcctcga taaaagtctt gtctgcgaca aaagcgatga ctgtggcgat   3480
aattcagacg aaacgtcctg cttcaaacgc ccctcctctt gccttccgca agaattttct   3540
tgtccttcga atacctctat ctgcgtccct atgtcagcca agtgcaatgg atccgtcgag   3600
tgtcctaagg gagaagacga ggaagaatgt ggcgactgca tgccggatga gttccgctgt   3660
ctcaacaagc aatgcattgc ggcacaatgg atgtgcgatg gcatcaacga ctgtgatgac   3720
ggcagtgatg aaactgctga aggttgctcg cagaagaata aaaccacggg ggagatgtcc   3780
gtggttcata ctgcctgtga aaatggattc aggtgtaaaa atggagattg cttggatatg   3840
aaactggtgt gtaatggaaa tcacgattgt tacgatggtt ctgatgagga tggactgtgt   3900
tcaacttcct gtgaaggatc agccaatcga tgttctcaaa tatgcaataa aactccaatg   3960
ggaccgtctt gcgagtgtag atctgggttt atattgatgg gcaatggggt cagctgcatg   4020
gatttgaatg aatgccagaa tcatccacca gtgtgcagtc aaatttgcca caatcaggac   4080
ggcggtttca aatgcgattg ttatgatggc tttttactga gatccgacaa gaaatcttgc   4140
aaagcagaag gaaatccgat gtcgctcatt ttcagtgaat atgggcaaat aagggaactc   4200
tcgcaattga ctaatatctt gtctgttgta tttgccactc ctgcaccaaa aataactggc   4260
ctagacgtac ttgtcaatcc aagaaccatc tatttcagca tggaggaaac ttccacgatt   4320
cacaaaatcg atatggcatc aaaaacgaga catttcataa ggaatattgg acaacctcag   4380
gacattgctg ttgattggtc tactcacaac atctattact ataacacgga caccaactcg   4440
aaatctatca gtatttgtag tttcgaagaa aagtgcgcga agttgattga tgttgacatg   4500
```

cacagacaag tggcaggatt ggttgtcgac tctgtcaaca aatttttatt ttatgctttg 4560
aacagttggt acgtgttcaa ttcccccagt tacgttatct acaggtgcaa cttggatgga 4620
actgagaaga cggaaataat gaaaactaca gatgggtttg tatccgacat cacttttgac 4680
cacaacagta ggatattgta ctacatggat atgtacttgg gtcaaataaa taagataacc 4740
tatgatggta gtttcaaaac tccaatttat tccaatatca cccgatcctc agggcttaag 4800
ttcttcgaga accgattata ctattctacg aatgggggat ttgtttcagt ttgcaggtta 4860
tacggatttc tgagatgtga tagtttcagg cttcacaatg atgcaataga tttcttcact 4920
attctacaag agacgcttca gccgagtgtg ggtaatcctt gcaagaacca caattgctcc 4980
aacttatgcg ttccagctca gtttggatat aaatgtctct gccaggatgg aacgcttcta 5040
tctggaccag gaagttgtcc aattaatgag aataccccag agtccgacaa aaaatatact 5100
gttcactcgg tggcgatgac acaggctggt cctgaggagg gaagttcggg tactgtagct 5160
gttgccatca cgatacctct tctggtgata ttatttgctt tgggagccat ttactttatc 5220
aagaaaaagc atgcaggagc tttgaatgtc aggatgagat tttatactcc tcatttcgga 5280
aggaccgttc aagatgaaaa tcctattcta aagcctggtc aacatgaata cacaaaccct 5340
gttcatttta ataaagaaga taatgaatta actctagaaa cagcacctat caaactgaat 5400
gatgcctcga atgtgtgata tttaataagt ttctttgggt tttacttttt atattgttgt 5460
tttatcgttt gtataagttt tatcgatgtt aaatattgaa atgttatatt tttaccgtta 5520
tagttcataa atgaagagga atgcttcaga gtgaatattg aatttgaagt gtgatattga 5580
tagcattgtt atacatttag ctattacaca ggatgaacaa tgtacacatc ctccatatat 5640
ttattatcat tgaaaaatga ataaatcatt ttaatagtac ctactgaaaa 5690

<210> SEQ ID NO 23
<211> LENGTH: 4413
<212> TYPE: DNA
<213> ORGANISM: Phyllotreta striolata

<400> SEQUENCE: 23
atgttactcg tattgctcct gggagcagta acagtctctt cgtcagcagt tttcccaccc 60
aaaggaaatt gcacctccga acaattccaa tgctccgatc gaagatgcat aagcctcaaa 120
gccagatgcg acttgataat ggattgcccg gacggatcgg acgaattgga atgcgatttg 180
cagctctgcg atgagccgga gttcttccgc tgtaaaaata acaaatgcat cagtcacgat 240
ttggtctgcg ataaaatgaa cgattgcgac gacttctccg acgagttgaa ctgccaaagc 300
ttccagtctt tggtggcgtc ggcttgcgag gagggcacct ggaggtgcgc cgataaattg 360
tgcataccca acgattgggt gtgcgacggc acgccggaat gcatcgacgg atccgacgaa 420
accatcggtt gcagcaggca aatcgactgc gacgggttcc gctgcaagaa caagcattgc 480
gtgcccaaag agtgggtctg cgaccatcac aacgattgca tcgataacag cgacgaagag 540
aactgcgagg accacgtccc catcgaccag tgcacgttgg acaagcgcaa gttcctctgc 600
cacaacaacg tgacgtgcat cgatacggaa tcggtttgcg acggacacaa ccactgtccg 660
gacaattcgg acgaatcgcc caattgcaac gcgtccgcca aggcgtgccg gggcgatcac 720
aagtgctcgc acgtttgcat accgctgccc gccggcccca cgtgcctctg ccccctcggc 780
taccacacgc tcgacgagaa gaactgcgag gacatcaacg aatgcgaaac atacggtata 840
tgcgatcaaa tgtgccggaa cacgccgggc tcgtacgagt gctactgcga caaggcgtac 900
catttggcgg atgacaagaa aacctgcaag gccgatggcg aggtgggcgt catggtgttc 960

-continued

```
agttcgaagg atcagatcag agcggtggcg ttgaatttga ccagttacat cctcgtcgct   1020
aagaacttga agaaagtggt gggcgtcgat ttcgacggtc gcagggtcta ctggacggag   1080
atatacgggg gctacgagaa catcgcccgg agcgccgagg acgggtcgca aaaggaggtt   1140
ttagtaacgg ccggtataga tctgccggag gatttggcca tcgactggtt gacgggtaac   1200
atttatttca ccgatggcga gaagaaacac ataggagttt gctcgcccga cgggacccat   1260
tgcgctgttt taatcaataa ggacatcgcg aaacccagag gcatcgttct taacgtcttg   1320
gacggcgaca tgtattggac ggattgggaa gaaccgtcgc gaatcggtta ctcattaatg   1380
gacggatcaa atgataagcc cttcgtagaa aaagacattc attggcccaa cggtttagca   1440
ttggatcatc ctaatagcag actgtactgg acggatgcta agaagatgac gttggaaagc   1500
atccgtttag atggaactga tcgaaggata atattagaag atatcgtaaa gcatccgtac   1560
gccatagcgg tattcgaaga taaattgtac tggtcggatt gggcgacgcg caccatccag   1620
cagtgcgaca aattcgacgg gaagaatcac cggacgatga tcgaagagaa ggaactcatc   1680
tacggtatca gcatatacca tccggcgcaa cagtcgcgca gcgtaaatcc ctgcgagacg   1740
gccctgtgca gcgacctgtg cttgctgaaa ggtacatcgt acagctgcgc ttgtccgcag   1800
aacaaggtcc tacagcccga cggaatgttt tgtaaagaat tgtcgcctat agagagtctc   1860
atagccgctc atcgggacat gttggtacac atcgagcatc cgattctcgg caggcatgtt   1920
gttacagctc taccgggcgc cactggagac attgaaagct tggcattcga tagcttcaaa   1980
aacgtactgt acatcagcga tttcaagact aagagaatca ccactttgca catgaagacc   2040
ggtaccagca aagtaatgga tatacccgat ttgggtagaa tcaacgctat ggatttcgat   2100
tccaaaagca acaatcttta catctgcgat tcggtccgca aagtggtaga agtaatcagt   2160
atcaacacga tggctcggcg aattttaatt cacgacacgt taggagagta cccgcaaagt   2220
atcgcgttag ttcccgacga aggggtgatg tttataagct tcggaggcga gggacgcagc   2280
cacatcgatc gcttcttcat ggacggcacc ggccgaacgc acgccatcga caccaaactg   2340
acggggcccg tcgtgctcgc gtacgacgcc gatttgcaca gggtcttctt cgccgacgcc   2400
gccaacggcg tcatcgaatc caccagcgtc gacggcgacg atcgcatcca cttcagaacc   2460
gtcgacacgc accccaccag cctggtggtc ctcaaagacg acgtgttctg gatgaacgcc   2520
cgctcgaagc agctctactg gacgtcgaag aaagtcccct cgaactacga caagaaaatc   2580
acgctcgcct tccccgacga tccggacaag gtgcacctgg cgtcggtgac gtcgcgccgc   2640
aaggagacca acctctgtcg catcaacaac aacggttgca gccacttgtg cgtccaatcg   2700
cagaaatcga tcgtgtgccg atgtccgatc ggttgggaac tgaaacagga caatcgcacg   2760
tgcgccaagc gagtgggttg catcagcgac gaatttctgt gcgcgcagtc caacgcgtgc   2820
atcgtgaaga gcctgcgttg cgacggccgg aaggattgcc tcttcggcga agacgaggac   2880
gattgcgcgg cgacgaagac gtgcggcgac gggcagttcc gatgcgccga cggcgattgc   2940
atcgccgaag ggctggcgtg caacctgcgc tacgattgca aggataaatc ggacgagcac   3000
ggttgcggcg acgtgatgaa cggcacgcga tgcgcgcccg atcacttcgc ctgctcgaac   3060
ggcgaatgca tcagcgggca tttccactgc gacggcgtct ccgattgcac ggacaatacg   3120
gacgagttgc actgtcagac gaaggagtgc aatgtaacgc agtttaggtg cgattcgggc   3180
gcttgtattc ccaaggagtg ggagtgcgat caggattacg attgcgcgga taattccgat   3240
gaacattgcg atacggtatg cccggcgagc cacttcaaat gcgacaacgg cctgtgcgtg   3300
```

-continued

```
gataagaaat tattgtgcga cggtttcgac aattgcggcg accattccga cgagaagatt   3360
cacatgtgtc accagagggc cccgcacaat tgcaccgcct acgagacggc ctgctcgtcc   3420
aacgcttcca tttgcattcc tttgggagcg aaatgcgacg gcaaatccga ctgtcccaag   3480
cacgaggacg agatcggctg cgccatgtgc gccgacgagg atttcgaatg ccgcagcaaa   3540
cacctcaagg actgcattcc gagattgtgg ttgtgcgacg gcgagaacga ttgcggcgac   3600
aacagcgacg aggacttggt gatgtgcagt aaaaagaaca agaccacgtt cgctccggcc   3660
caacaaccct gcaccgacgg cttcagatgc gacaacggcg tttgcatcaa ctctacgttg   3720
ctctgtaacg gcaaacacga ctgctacgac ggctccgacg aaggaggctc ctgctccggg   3780
tcctgcgacg gccccaagaa tccctgcaac cacgtctgcg tcaagacgcc gaagggaccg   3840
aagtgccggt gcagaccggg ctaccggttg atgggcgacg gtaaaacgtg cgtcgacgtg   3900
aacgagtgcg aggccgatcc gccgatatgc agccaacttt gccgcaacaa agatggcggt   3960
tacacgtgcg attgtttcca aaacttttat ttgaggaaga acatgaaatc gtgcaaagcg   4020
gccggttccg acatgttgat ctacttcaac gtgaacggtg acgaaatcta cgaaatctcg   4080
ccgaagaaca attcgatgag cgtcgtccag gacgggtcga tgttgaagat ctcgagtctg   4140
gccgccgtgg tggactcgaa cgagctgttc tacagcgtac ccgacaccgg cgccgtctac   4200
aagctcgatc cggccaccaa aaccgttcgc tacatcgaga acttgggcga gcccaaactg   4260
atagcggtgg attgggcgac gcgtaatgtt tattattacg acgccgaatc ggacgcgaaa   4320
tcgattggag tgtgcaattt cgaggagaag tgcgtcaaat tgatcgacgt cgatgctcat   4380
cggcaggtgt ccgccttgac cgtggattca taa                                4413
```

<210> SEQ ID NO 24
<211> LENGTH: 5529
<212> TYPE: DNA
<213> ORGANISM: Phyllotreta striolata

<400> SEQUENCE: 24

```
aactcgtgtt acttaccttt gaaaacgatc agtttcacgt ggcctgctcg aaataattga     60
gagaatgtta ctcgtattgc tcctgggagc agtaacagtc tcttcgtcag cagttttccc    120
acccaaagga aattgcacct ccgaacaatt ccaatgctcc gatcgaagat gcataagcct    180
caaagccaga tgcgacttga taatggattg cccggacgga tcggacgaat tggaatgcga    240
tttgcagctc tgcgatgagc cggagttctt ccgctgtaaa aataacaaat gcatcagtca    300
cgatttggtc tgcgataaaa tgaacgattg cgacgacttc tccgacgagt tgaactgcca    360
aagcttccag tctttggtgg cgtcggcttg cgaggagggc acctggaggt gcgccgataa    420
attgtgcata cccaacgatt gggtgtgcga cggcacgccg gaatgcatcg acggatccga    480
cgaaaccatc ggttgcagca ggcaaatcga ctgcgacggg ttccgctgca agaacaagca    540
ttgcgtgccc aaagagtggg tctgcgacca tcacaacgat tgcatcgata acagcgacga    600
agagaactgc gaggaccacg tccccatcga ccagtgcacg ttggacaagc gcaagttcct    660
ctgccacaac aacgtgacgt gcatcgatac ggaatcggtt tgcgacggac acaaccactg    720
tccggacaat tcggacgaat cgcccaattg caacgcgtcc gccaaggcgt gccggggcga    780
tcacaagtgc tcgcacgttt gcataccgct gcccgccggc cccacgtgcc tctgcccccct    840
cggctaccac acgctcgacg agaagaactg cgaggacatc aacgaatgcg aaacatacgg    900
tatatgcgat caaatgtgcc ggaacacgcc gggctcgtac gagtgctact gcgacaaggc    960
gtaccatttg gcggatgaca agaaaacctg caaggccgat ggcgaggtgg gcgtcatggt   1020
```

```
gttcagttcg aaggatcaga tcagagcggt ggcgttgaat ttgaccagtt acatcctcgt   1080
cgctaagaac ttgaagaaag tggtgggcgt cgatttcgac ggtcgcaggg tctactggac   1140
ggagatatac gggggctacg agaacatcgc ccggagcgcc gaggacgggt cgcaaaagga   1200
ggttttagta acggccggta tagatctgcc ggaggatttg gccatcgact ggttgacggg   1260
taacatttat ttcaccgatg gcgagaagaa acacatagga gtttgctcgc ccgacgggac   1320
ccattgcgct gttttaatca ataaggacat cgcgaaaccc agaggcatcg ttcttaacgt   1380
cttggacggc gacatgtatt ggacggattg ggaagaaccg tcgcgaatcg gttactcatt   1440
aatggacgga tcaaatgata agcccttcgt agaaaaagac attcattggc ccaacggttt   1500
agcattggat catcctaata gcagactgta ctggacggat gctaagaaga tgacgttgga   1560
aagcatccgt ttagatggaa ctgatcgaag gataatatta gaagatatcg taaagcatcc   1620
gtacgccata gcggtattcg aagataaatt gtactggtcg gattgggcga cgcgcaccat   1680
ccagcagtgc gacaaattcg acgggaagaa tcaccggacg atgatcgaag agaaggaact   1740
catctacggt atcagcatat accatccggc gcaacagtcg cgcagcgtaa atccctgcga   1800
gacggccctg tgcagcgacc tgtgcttgct gaaaggtaca tcgtacagct gcgcttgtcc   1860
gcagaacaag gtcctacagc ccgacggaat gttttgtaaa gaattgtcgc ctatagagag   1920
tctcatagcc gctcatcggg acatgttggt acacatcgag catccgattc tcggcaggca   1980
tgttgttaca gctctaccgg gcgccactgg agacattgaa agcttggcat tcgatagctt   2040
caaaaacgta ctgtacatca gcgatttcaa gactaagaga atcaccactt tgcacatgaa   2100
gaccggtacc agcaaagtaa tggatatacc cgatttgggt agaatcaacg ctatggattt   2160
cgattccaaa agcaacaatc tttacatctg cgattcggtc cgcaaagtgg tagaagtaat   2220
cagtatcaac acgatggctc ggcgaatttt aattcacgac acgttaggag agtacccgca   2280
aagtatcgcg ttagttcccg acgaaggggt gatgtttata agcttcggag gcgagggacg   2340
cagccacatc gatcgcttct tcatggacgg caccggccga acgcacgcca tcgacaccaa   2400
actgacgggg cccgtcgtgc tcgcgtacga cgccgatttg cacagggtct tcttcgccga   2460
cgccgccaac ggcgtcatcg aatccaccag cgtcgacggc gacgatcgca tccacttcag   2520
aaccgtcgac acgcacccca ccagcctggt ggtcctcaaa gacgacgtgt tctggatgaa   2580
cgcccgctcg aagcagctct actggacgtc gaagaaagtc ccctcgaact acgacaagaa   2640
aatcacgctc gccttccccg acgatccgga caaggtgcac ctggcgtcgg tgacgtcgcg   2700
ccgcaaggag accaacctct gtcgcatcaa caacaacggt tgcagccact tgtgcgtcca   2760
atcgcagaaa tcgatcgtgt gccgatgtcc gatcggttgg gaactgaaac aggacaatcg   2820
cacgtgcgcc aagcgagtgg gttgcatcag cgacgaattt ctgtgcgcgc agtccaacgc   2880
gtgcatcgtg aagagcctgc gttgcgacgg ccggaaggat tgcctcttcg gcgaagacga   2940
ggacgattgc gcggcgacga agacgtgcgg cgacgggcag ttccgatgcg ccgacggcga   3000
ttgcatcgcc gaagggctgg cgtgcaacct gcgctacgat tgcaaggata aatcggacga   3060
gcacggttgc ggcgacgtga tgaacggcac gcgatgcgcg cccgatcact tcgcctgctc   3120
gaacggcgaa tgcatcagcg ggcatttcca ctgcgacggc gtctccgatt gcacggacaa   3180
tacggacgag ttgcactgtc agacgaagga gtgcaatgta acgcagttta ggtgcgattc   3240
gggcgcttgt attcccaagg agtgggagtg cgatcaggat tacgattgcg cggataattc   3300
cgatgaacat tgcgatacgg tatgcccggc gagccacttc aaatgcgaca acggcctgtg   3360
```

-continued

```
cgtggataag aaattattgt gcgacggttt cgacaattgc ggcgaccatt ccgacgagaa   3420
gattcacatg tgtcaccaga gggccccgca caattgcacc gcctacgaga cggcctgctc   3480
gtccaacgct tccatttgca ttcctttggg agcgaaatgc gacggcaaat ccgactgtcc   3540
caagcacgag gacgagatcg gctgcgccat gtgcgccgac gaggatttcg aatgccgcag   3600
caaacacctc aaggactgca ttccgagatt gtggttgtgc gacggcgaga acgattgcgg   3660
cgacaacagc gacgaggact tggtgatgtg cagtaaaaag aacaagacca cgttcgctcc   3720
ggcccaacaa ccctgcaccg acggcttcag atgcgacaac ggcgtttgca tcaactctac   3780
gttgctctgt aacggcaaac acgactgcta cgacggctcc gacgaaggag gctcctgctc   3840
cgggtcctgc gacggcccca agaatccctg caaccacgtc tgcgtcaaga cgccgaaggg   3900
accgaagtgc cggtgcagac cgggctaccg gttgatgggc gacggtaaaa cgtgcgtcga   3960
cgtgaacgag tgcgaggccg atccgccgat atgcagccaa ctttgccgca acaaagatgg   4020
cggttacacg tgcgattgtt tccaaaactt ttatttgagg aagaacatga aatcgtgcaa   4080
agcggccggt tccgacatgt tgatctactt caacgtgaac ggtgacgaaa tctacgaaat   4140
ctcgccgaag aacaattcga tgagcgtcgt ccaggacggg tcgatgttga agatctcgag   4200
tctggccgcc gtggtggact cgaacgagct gttctacagc gtacccgaca ccggcgccgt   4260
ctacaagctc gatccggcca ccaaaaccgt tcgctacatc gagaacttgg gcgagcccaa   4320
actgatagcg gtggattggg cgacgcgtaa tgtttattat tacgacgccg aatcggacgc   4380
gaaatcgatt ggagtgtgca atttcgagga gaagtgcgtc aaattgatcg acgtcgatgc   4440
tcatcggcag gtgtccgcct tgaccgtgga ttcataaatt gatcgacgtc gatgctcatc   4500
gacaggtgtc cgccttggcc gtggattcgt acaacaaggt tttgttctat gtgctgagat   4560
cgtggacgat attcgcatcg cccagttacg ttttgtacaa aaccgatttg gacggtagca   4620
acgtggtgga actgatcaaa acaaatatag gtaacgtgga acacatcacc tacgatttga   4680
acaaacgcca gttgtacttc cacgacgaaa acacccatca aatcaacacg atcggctaca   4740
acgggggcaa cgtcaaaccg ctcttctaca atgtatcatc actgatcgaa gggctcaaac   4800
tgttcgaaga caatttgtac tatctgcgcc aggacgggtt cctcattagg tgtcagttgt   4860
tcgaagaggc cgtctgtcac tacggtttca atttgcacag tctggccagg gacgatttcg   4920
tcatctcgca ccgatccctt cagcccttgg tcgaaaacgt ctgcgacggt cacagttgcc   4980
cttacatgtg cgtggccgga cgagagggct acaagtgcat ttgccacgat ggctcgacta   5040
ctggcgaatg cggtacacca caagacgaca acggtgcgaa caaattcaaa gtaaccacca   5100
ttgaaggaaa atccaattct tcggcgttct tgtcgggctt cggggtggta ctcgtgttac   5160
tcgcttgcgt catgtttata gttgggttgt attacttgct gaagaagaga agcgcagaaa   5220
acagtacagc agatttaagt attgtccgtt ttcaaaatcc gctttacgga agaccggtgg   5280
aagacgagaa accgatcttg gaacccggca agcacgagta cgtgaattgt ttgtacgaac   5340
acaaaacgga tggcggcgaa aacagcaatg cggaacccaa aacgtttaac gtctgtgatg   5400
ataatttgtg ttaatttatt gtttttttta tgttttacgt taattaagtg cattatttga   5460
ttgttaattc tatttataac acattattat gtatatacaa aatttgttaa atatttaata   5520
aatatagag                                                           5529
```

<210> SEQ ID NO 25
<211> LENGTH: 5226
<212> TYPE: DNA
<213> ORGANISM: Halyomorpha halys

<400> SEQUENCE: 25

```
atgctgtcgc cacgatatag gttaaaattt tccaacgatt tgaagttttt gtttgcgact     60
atattaatcg ctttggtcac ttctactgaa cagcatgata cagattgtga tgaaaatttc    120
ttcagatgcc gcaatggtag atgtatatct ctcagcttta tttgcgatgg ttacgaagac    180
tgcggccatg ggacatgtc tgatgaagaa aattgccatt tgaccactac cccagcagtg    240
aaaccgtgca ataaagatga atatcagtgc aaagataggc tgtgcattcc ttcgttatgg    300
gtctgcgatg gtgaatcaga ctgttcggat ggcagcgatg agactcatgg atgtagtgag    360
gcgacctgtg acggttttca gtgccacagc aaatcttgta tccccaaaga gtgggagtgc    420
gatggcgtac gtgattgtcc agataactca gacgaacagt tctgtgctaa gaaaccagtg    480
agcactgaag aatgcaatat tcatgaaaat ggtttcatgt gccatgatag tatgaaatgc    540
attgaactgg aagaagtctg caacagtcac cctgattgcg atgatggttc tgatgaaggt    600
ggtatgtgcc tcaatccgaa caaaacagat ttatgctcta atctgaaatg tcccacaaat    660
caaggctgta taatattacc cgagggcccg gtatgtactg aggtgtgcaa gaaaggatac    720
cacttcgcca gtggttcttg ttttgatatc gatgaatgta taacatttgg aaggtgtgat    780
caaatatgta taaacacaaa tggaggctac aattgctcct gcattgaagg ctatagattt    840
gataatgatt tgaaaaaatg caaagctaga ggaagtgaag gtatactatt tttcacttca    900
aatcaagaaa taagaggata ttatttagac tccgaaatct actttaaagt agttgaaaat    960
ctaccacatg caacaggagt agcatatgat ggtgttaatg tttactggac aacagtagca   1020
gatgaggaag aaacaattgt caaagcagct gaaaatggtg aaaatcagaa aataattgta   1080
acttctggta ttggcagtcc tgaagatcta gcagttgatt gggttacaaa aaatgtatac   1140
ttcacggatt ctaaattaaa gtatgtaggt gtttgttcca atgatggata ctattgcctt   1200
atactccatg aagatcaagt tgagaaacca cgtgctattg ttctgcattc atcagaggga   1260
ctgatgtatt ggtctgactg gggaacagaa cctgccatta tgcgttctgg aatggatgga   1320
tctaatgtta tcaaattcat aaaagataac attcattggc caaatggatt agccattgac   1380
tatgggacaa attatatata ttgggttgat gctaaagaag caaaaattga atgtgtgaaa   1440
ctagatggaa ctgacagaag aaaagtacca tccagtgctg tgaaacatcc cttttctatt   1500
gatatttttg aagatagaat ctactggagt gactgggaca gtgaccaaat tgtatcctgc   1560
aataaatttt ctggtaaaga ttgccataca ataataaagg aaagagatca caagatttat   1620
ggtatccatg tataccatcc tagcatgata aaagaagtta ttaatccatg ctttgatgtt   1680
caatgctctg atatatgctt aatagctcca aaaaatgcag ataatgagtt ggaatattct   1740
tgtgcttgcc catatcacaa aaaacttagc agagatcatc atacatgtat tgaggataaa   1800
ccacttcaaa ctataattgt gggttctgga cagcagatct tcaaaatcca acacaaaaaa   1860
tttggaggat ttgtttcaga ccattttaaa ctaacaatat taaggaaaat aggtgctcta   1920
gcttatgatc caaattcaga taaaatcatt gttagtgatt tggttagacg aaaaattttt   1980
tcagtcgact ggaaaactct agagtcagag ccattaattg aacacaacat tggtagagtt   2040
gttggtatgg atgttgacta ttatgaaaat aatctatatt ggatcgatga tgagaaaaaa   2100
actattgaag ttatgaacct acaaaacaaa caccgattaa cactaatacg agatctaaat   2160
gaaggtctta atgatatagc attagtgtta gaacatgggt ttatgtttgt cgctctttca   2220
acatttgaag gagcacacat tgatagaata tcaatggatg ggcgacatac ttcaaggatt   2280
```

-continued

```
catgttattg aagacaaatt atttggccca ttgtctctca gctatgatcc taaacttgag   2340
cgtctgttct ggtctgacca aatgggaggt gaaatagctt ccacaggtgt tgatgggatt   2400
gatcgacata tttttaaaga aggacattct ggtccagtag atgtggcaat tactgaatcc   2460
gaagtgtttt ggcttggcta tggagccaga aaagtctttt ggtcaaataa gtttgatgga   2520
tcgcttacaa aaagatttct tttagactca cttgatgaaa ctgataatat gaaaatcatt   2580
ggattaaata aaggtttaag aaaggaagca agtgcttgta attccctcgg aaactgcagc   2640
catgtttgtt tgctttcaac acctatgggg atttgtgcat gtcctgatgg aatggagctt   2700
ggatttgata gaaaaacctg ccaaaaattg cttgcatgta aagaaggaca atacaaatgt   2760
accactggag aatgtatttc aaaatccatg cgatgtaatg gtagaccaga ttgtaggctt   2820
ggtgatgatg aagagtattg ttctataatt tgttcaacaa acaagttcgc ttgcatagat   2880
ggttctagtt gtatagaaca atctcaaaaa tgtgattcta aagttgactg caatgatggt   2940
tctgatgaaa aatattgtga atcaaatcga aattgtactg gaaatgaatt ccaatgtacg   3000
tcaggagaat gtgttcctaa agtggcacag tgtgatggca tgagtgattg cagtgatggt   3060
agtgatgaaa gcagttgtaa tactttcact tgcaaaacca attacttccg ttgcaacaca   3120
ggaaattgta taccaagctc atgggaatgt gacagtcaga ttgactgtag cgacggttct   3180
gatgaaggtc ctaaatgttc tgagattgaa ggatgtggtg aggatcagtt tacttgtgat   3240
aatggtcact gcatttcaca tgttttggtg tgtaaccatg aagatgattg tgaagactca   3300
tctgatgaaa aatattgtta ctttccaaaa accaaaaaaa attatgaaaa tgaagaaaat   3360
aagactaagg gcttatcaaa ggattgccag tttttatgtc cttcagattt aaaaatatgt   3420
ttgcctgcat cagggagatg taatggtact tcagaatgcc cagacggaga agatgaactt   3480
cgttgcaaca agtgttcaga ggaagaattc acttgttctt ctagtaagcg atgtttgcca   3540
atgacatggg tttgtgacaa tgtcagtgac tgtgaagacc agtccgatga aatgcattgt   3600
cttaatggaa ccctggctgt acatgatttg tataatcttc agtgtgatgg tttattctgc   3660
aaagataata aaaaatgcat tccattaaat aaactgtgtg attctcatat ggattgtaat   3720
gatgggtctg atgaaaaagg tctttgtggt aagggatgtg aacatgctgc atgtcatcac   3780
aaatgtaaag agacacccat gggacctagg tgtgaatgtt taagtggttt tactctagaa   3840
ggcgatggga gggcatgtaa tgatataaat gaatgtgaaa aactgtcttc ttgctctcaa   3900
tattgccata attctgttgg cagttacagt tgttcatgca tggattataa ctttcaacta   3960
agatctgata agattaggtg caaagcaaaa ggaactgaaa tgaagtatta ctttgccaca   4020
aaaaaagaaa taaaatataa atcacaatcc ttacagcaaa ctgttgtagt atatcaatca   4080
cagcgtgata tggatatgaa aggaatggat tttgatatga atagtgatgt aatattttgg   4140
acttcagaga ttagtggtta tttgtacaaa gttgatatta aatctaaaaa tgtcactcaa   4200
attacaaatc tcattagacc aactaaagta tcatatgact gggttactgg taatatttat   4260
gtccttgaaa acttcaaaat tattagagtt tgtaacttta aagctaaact ttgttcagca   4320
atatacacag ctaagaatgg tataaacata gaaactattg ttcttgatcc aaaatcaaga   4380
atcatgttct ggtctgaaag taaatggtta atgagccaaa caccaaatag tacacttcaa   4440
caggcctcaa tgagtgcaga aaatccaagt gtagtgctaa gttttgattt tagtccagtt   4500
aatgatattg tagttgatca ttttcacaag gttgtttact ggtcaaaccc cattgataat   4560
aaaatagaaa gatgtacata tgatggaaaa gacagaacta tagtagtgcg tagtgagtat   4620
cctccaagag acttggtact atttgaagat tatttgtact gggtaaatga tcaaaaacaa   4680
```

-continued

```
tctcacttta ttcgcccaga agcagaagga actattacta agtatggcct gtatggatca   4740

gtgtacatga aacatgaatc agtaaggctt ttaccttctt catcctataa tgaaattaaa   4800

gctttccaag tttcacagtc tgcactccag cctgaaggaa taaaccactg cagtaaaatt   4860

acttgtaatt acctgtgtat aagcaatgaa agagaaccag tatgtttctg tgaagatggc   4920

ttaaaagtga aacctggtga tatatgctac aatcatactg ggatacattt caaagcttac   4980

gaaacagaaa atgtagcaga gagtagttca gtattgacat ggtttttctg gattgttggg   5040

ttagttctag catctggact tggttatgga agttattatt ttgtagctaa ctacgttcag   5100

aaaaataaaa tacacccacg gttcagtgta ttttttcctg ttggccgttc tgagactcat   5160

agagaacaag gatctcaggt tcatcaattt gaaaatccta cgtatagtga ggtcattgtg   5220

gtataa                                                              5226
```

<210> SEQ ID NO 26
<211> LENGTH: 5718
<212> TYPE: DNA
<213> ORGANISM: Halyomorpha halys

<400> SEQUENCE: 26

```
gctgaacctc tgtaccttgg atcttcagtt cccatttcat tttaccaagg cttccagtta     60

gcttcgaact atgctgtcgc cacgatatag gttaaaattt tccaacgatt tgaagttttt    120

gtttgcgact atattaatcg ctttggtcac ttctactgaa cagcatgata cagattgtga    180

tgaaaatttc ttcagatgcc gcaatggtag atgtatatct ctcagcttta tttgcgatgg    240

ttacgaagac tgcggccatg ggacatgtc tgatgaagaa aattgccatt tgaccactac     300

cccagcagtg aaaccgtgca ataaagatga atatcagtgc aaagataggc tgtgcattcc    360

ttcgttatgg gtctgcgatg gtgaatcaga ctgttcggat ggcagcgatg agactcatgg    420

atgtagtgag gcgacctgtg acggttttca gtgccacagc aaatcttgta tccccaaaga    480

gtgggagtgc gatggcgtac gtgattgtcc agataactca gacgaacagt tctgtgctaa    540

gaaaccagtg agcactgaag aatgcaatat tcatgaaaat ggtttcatgt gccatgatag    600

tatgaaatgc attgaactgg aagaagtctg caacagtcac cctgattgcg atgatggttc    660

tgatgaaggt ggtatgtgcc tcaatccgaa caaaaacagat ttatgctcta atctgaaatg    720

tcccacaaat caaggctgta taatattacc cgagggcccg gtatgtactg aggtgtgcaa    780

gaaaggatac cacttcgcca gtggttcttg ttttgatatc gatgaatgta taacatttgg    840

aaggtgtgat caaatatgta taaacacaaa tggaggctac aattgctcct gcattgaagg    900

ctatagattt gataatgatt tgaaaaaatg caaagctaga ggaagtgaag gtatactatt    960

tttcacttca aatcaagaaa taagaggata ttatttagac tccgaaatct actttaaagt   1020

agttgaaaat ctaccacatg caacaggagt agcatatgat ggtgttaatg tttactggac   1080

aacagtagca gatgaggaag aaacaattgt caaagcagct gaaaatggtg aaaatcagaa   1140

aataattgta acttctggta ttggcagtcc tgaagatcta gcagttgatt gggttacaaa   1200

aaatgtatac ttcacggatt ctaaattaaa gtatgtaggt gtttgttcca atgatggata   1260

ctattgcctt atactccatg aagatcaagt tgagaaacca cgtgctattg ttctgcattc   1320

atcagaggga ctgatgtatt ggtctgactg gggaacagaa cctgccatta tgcgttctgg   1380

aatggatgga tctaatgtta tcaaattcat aaaagataac attcattggc caaatggatt   1440

agccattgac tatgggacaa attatatata ttgggttgat gctaaagaag caaaaattga   1500
```

-continued atgtgtgaaa ctagatggaa ctgacagaag aaaagtacca tccagtgctg tgaaacatcc 1560
cttttctatt gatatttttg aagatagaat ctactggagt gactgggaca gtgaccaaat 1620
tgtatcctgc aataaatttt ctggtaaaga ttgccataca ataataaagg aaagagatca 1680
caagatttat ggtatccatg tataccatcc tagcatgata aaagaagtta ttaatccatg 1740
ctttgatgtt caatgctctg atatatgctt aatagctcca aaaaatgcag ataatgagtt 1800
ggaatattct tgtgcttgcc catatcacaa aaaacttagc agagatcatc atacatgtat 1860
tgaggataaa ccacttcaaa ctataattgt gggttctgga cagcagatct tcaaaatcca 1920
acacaaaaaa tttggaggat ttgtttcaga ccattttaaa ctaacaatat taaggaaaat 1980
aggtgctcta gcttatgatc caaattcaga taaaatcatt gttagtgatt tggttagacg 2040
aaaaattttt tcagtcgact ggaaaactct agagtcagag ccattaattg aacacaacat 2100
tggtagagtt gttggtatgg atgttgacta ttatgaaaat aatctatatt ggatcgatga 2160
tgagaaaaaa actattgaag ttatgaacct acaaaacaaa caccgattaa cactaatacg 2220
agatctaaat gaaggtctta atgatatagc attagtgtta gaacatgggt ttatgtttgt 2280
cgctctttca acatttgaag gagcacacat tgatagaata tcaatggatg ggcgacatac 2340
ttcaaggatt catgttattg aagacaaatt atttggccca ttgtctctca gctatgatcc 2400
taaacttgag cgtctgttct ggtctgacca aatgggaggt gaaatagctt ccacaggtgt 2460
tgatgggatt gatcgacata tttttaaaga aggacattct ggtccagtag atgtggcaat 2520
tactgaatcc gaagtgtttt ggcttggcta tggagccaga aaagtctttt ggtcaaataa 2580
gtttgatgga tcgcttacaa aaagatttct tttagactca cttgatgaaa ctgataatat 2640
gaaaatcatt ggattaaata aaggtttaag aaaggaagca agtgcttgta attccctcgg 2700
aaactgcagc catgtttgtt tgctttcaac acctatgggg atttgtgcat gtcctgatgg 2760
aatggagctt ggatttgata gaaaaacctg ccaaaaattg cttgcatgta aagaaggaca 2820
atacaaatgt accactggag aatgtatttc aaaatccatg cgatgtaatg gtagaccaga 2880
ttgtaggctt ggtgatgatg aagagtattg ttctataatt tgttcaacaa acaagttcgc 2940
ttgcatagat ggttctagtt gtatagaaca atctcaaaaa tgtgattcta aagttgactg 3000
caatgatggt tctgatgaaa aatattgtga atcaaatcga aattgtactg gaaatgaatt 3060
ccaatgtacg tcaggagaat gtgttcctaa agtggcacag tgtgatggca tgagtgattg 3120
cagtgatggt agtgatgaaa gcagttgtaa tactttcact tgcaaaacca attacttccg 3180
ttgcaacaca ggaaattgta taccaagctc atgggaatgt gacagtcaga ttgactgtag 3240
cgacggttct gatgaaggtc ctaaatgttc tgagattgaa ggatgtggtg aggatcagtt 3300
tacttgtgat aatggtcact gcatttcaca tgttttggtg tgtaaccatg aagatgattg 3360
tgaagactca tctgatgaaa aatattgtta ctttccaaaa accaaaaaaa attatgaaaa 3420
tgaagaaaat aagactaagg gcttatcaaa ggattgccag tttttatgtc cttcagattt 3480
aaaaatatgt ttgcctgcat cagggagatg taatggtact tcagaatgcc cagacggaga 3540
agatgaactt cgttgcaaca agtgttcaga ggaagaattc acttgttctt ctagtaagcg 3600
atgtttgcca atgacatggg tttgtgacaa tgtcagtgac tgtgaagacc agtccgatga 3660
aatgcattgt cttaatggaa ccctggctgt acatgatttg tataatcttc agtgtgatgg 3720
tttattctgc aaagataata aaaaatgcat tccattaaat aaactgtgtg attctcatat 3780
ggattgtaat gatgggtctg atgaaaaagg tctttgtggt aagggatgtg aacatgctgc 3840
atgtcatcac aaatgtaaag agacacccat gggacctagg tgtgaatgtt taagtggttt 3900

```
tactctagaa ggcgatggga gggcatgtaa tgatataaat gaatgtgaaa aactgtcttc   3960
ttgctctcaa tattgccata attctgttgg cagttacagt tgttcatgca tggattataa   4020
ctttcaacta agatctgata agattaggtg caaagcaaaa ggaactgaaa tgaagtatta   4080
ctttgccaca aaaaaagaaa taaaatataa atcacaatcc ttacagcaaa ctgttgtagt   4140
atatcaatca cagcgtgata tggatatgaa aggaatggat tttgatatga atagtgatgt   4200
aatattttgg acttcagaga ttagtggtta tttgtacaaa gttgatatta aatctaaaaa   4260
tgtcactcaa attacaaatc tcattagacc aactaaagta tcatatgact gggttactgg   4320
taatatttat gtccttgaaa acttcaaaat tattagagtt tgtaacttta aagctaaact   4380
ttgttcagca atatacacag ctaagaatgg tataaacata gaaactattg ttcttgatcc   4440
aaaatcaaga atcatgttct ggtctgaaag taaatggtta atgagccaaa caccaaatag   4500
tacacttcaa caggcctcaa tgagtgcaga aaatccaagt gtagtgctaa gttttgattt   4560
tagtccagtt aatgatattg tagttgatca ttttcacaag gttgtttact ggtcaaaccc   4620
cattgataat aaaatagaaa gatgtacata tgatggaaaa gacagaacta tagtagtgcg   4680
tagtgagtat cctccaagag acttggtact atttgaagat tatttgtact gggtaaatga   4740
tcaaaaacaa tctcacttta ttcgcccaga agcagaagga actattacta agtatggcct   4800
gtatggatca gtgtacatga aacatgaatc agtaaggctt ttaccttctt catcctataa   4860
tgaaattaaa gctttccaag tttcacagtc tgcactccag cctgaaggaa taaaccactg   4920
cagtaaaatt acttgtaatt acctgtgtat aagcaatgaa agagaaccag tatgtttctg   4980
tgaagatggc ttaaaagtga aacctggtga tatatgctac aatcatactg ggatacattt   5040
caaagcttac gaaacagaaa atgtagcaga gagtagttca gtattgacat ggtttttctg   5100
gattgttggg ttagttctag catctggact tggttatgga agttattatt ttgtagctaa   5160
ctacgttcag aaaaataaaa tacacccacg gttcagtgta ttttttcctg ttggccgttc   5220
tgagactcat agagaacaag gatctcaggt tcatcaattt gaaaatccta cgtatagtga   5280
ggtcattgtg gtataataca atataaatat gatgtttatt taagaaaaaa caaatatatg   5340
catatatata tgtatacact tatatataca catatatatg tatatattta tagatacaca   5400
cattaaatta agttgtttat ctttttctat aggagaactc tgaatttaaa tctttgttaa   5460
acaatgaaat atctgtgaat caagtgtaga aataattgat ttacattgta aacctccgtg   5520
taacaagttt cttattaaca ttatattatt accatatcat ataaatatga atttcctagt   5580
aactgattgt tcttattact atttttgact gattaaagta atgtactctc agtttaaatc   5640
agcaaagagc tatttaagct ctataaaact gtattattat caaatattta atatttgaac   5700
tgtaatttat tgttttaa                                                  5718
```

<210> SEQ ID NO 27
<211> LENGTH: 5307
<212> TYPE: DNA
<213> ORGANISM: Acyrthosiphon pisum

<400> SEQUENCE: 27

```
atggacaatg gcgctgacga agacgattgt gatattagca aaaagccttg cctggcgcca     60
gaatactttg aatgtgataa caagagaaaa tgcattccta aggaatttgt gtgtgataag    120
tcgaatgaat gcatcgacaa gtctgacgaa agtcattgta aagagacgtc atcatcttta    180
acgcagtcat gccgggaagg aaaattcaaa tgctccgatg gcacttgtat tccaatggct    240
```

-continued

```
tggcattgtg acgcggagat tgattgccac gacggtagcg atgaagacgg agaaaaatgt    300
agatacacga cattgtgtac ctctggttat atgtgcaaaa acttcaattg cgtttcaaag    360
acgtggagat gtgacggaaa agatgactgt ggagatggtt cagacgaaac ccattgcgat    420
atccaactgg ttgagccaga aaaatgttta attgaaaatc gtaaatttct atgtcacgat    480
cataaaaaat gtatcgatgt cagaaatgtc tgtgattaca acaatgactg tcttgatgca    540
tcggacgaag gtggtctttg caataataaa actgatttca aaagtgaatg taattcgatg    600
aattgttctg ccgcatttga atgtttaaga aagccacatg gcattatgtg tgtgtgccca    660
aaaggaatgc attatttaaa taataaatgt tctgatatca acgaatgtga acaatatggt    720
atttgtgacc aagtgtgtct taatttggaa ggttcatata cgtgctcctg tgatccacat    780
tatgaactag tagataatca taagtgtaaa ataaaaggcc taaatccgga attattatat    840
tcatcactac gtcaaataaa agtttttaac ttggaattac ttcatagttt tactttgatt    900
gatgatttgc aacatgtcac tggattagct gttgataaat taactttata ctggacactt    960
tatttggatg ggaactcagc tattgttaga gcaaacaagt ctgagcctaa accagaaatt   1020
attgttgact cgggtcttgg atcgcctgag aatctagtta tagatattat tacacataat   1080
ttgtacttca ccgatgcaaa aatgaaacat attggagtgt gcaataatga tggttcagta   1140
tgtacagttc ttcataataa aaacatagac aaaccaagag cagtagctgt ttcaccacta   1200
gatggtctca tgtactggac agattggggt aaaaatccaa tgattggtcg ttctggtatg   1260
gacgggtcaa gaccacaacc gtttgttaca caaaatatac actggccaaa tggtgttcat   1320
gttgattatg tcgggaaaag aatttactgg gtggatgcta agatgcaatt tattgaatcc   1380
attaatttag atgcaactga tcgaagagta attgtaacag aatatgtaga tcatccatat   1440
tcggttactg tgttcgagga taaattgtac tggagtgatt ggtcaagtaa agaaataaaa   1500
gtatgcaaca aatttacggg taaagatagc aagacattga tacgtgaaaa taagaacaga   1560
gtgtatggca tgcaaattaa ccatccctcg ctcttcgagt ctcaaatgcc aaatccttgt   1620
gaacaaggaa aatgcagtga tatatgctta ttagcaccga aacagaaat caattctaaa    1680
ggatactcgt gcgcttgccc cgatgataaa aaactatcgg aagatggaat cttttgtatc   1740
accattgcca tacctcctac gcttattgtg ggtacaccaa caagtattat agaaattgag   1800
caggaacatt taggccgcca aaaagcaaaa aaaatatcgt tgaaaaatga tatatctagc   1860
atatccgcat tgacttataa ttcattatct ggtgacatca tcatctatga ctcaaggtct   1920
aagaaattat tcactttcga ttttgttaag atgaaattat cagatttaga tgtaccagaa   1980
attagttcca tttattctct tgaattcgac aatcatggaa acaatttata ctggtgtgat   2040
aggactagaa aaacattaga tgtgttaagt ctctctacaa aaacacacac aacgatattc   2100
aaagaaattg aaggtcatat cccatttgcc gttactttag ttccagataa aagctttatg   2160
tttgtagcta tgaaagaagg ttcacacata catatcgatc gaattgacat ggatggaagt   2220
attcagtctc tagtacatat ggtggagtat ggattgacag gagatgaaat tgctttacat   2280
tttgatatga ttacaagact gttgtatttt actgactata aaaatggcat tattgatagt   2340
gtcagcgaag atggaacgga tagaagaatt ataaaaaaag caggatttgt aagagatatt   2400
gtttcaattg gttatgacat tgtttgggta tctgaaggtt cgaaaatttt aaactggatt   2460
gataacgttg atgaagaccg agcatctaga gctcttgata tagataattg gaaaactgat   2520
tcaaatttat atttaaccgt agcaaatgga attcacaaaa atatacaaca cccgtgtcaa   2580
caaaataatg gtggttgtag tcatatatgc cttttatctg agaaaggaaa ggtttgtggt   2640
```

-continued

```
tgtccacctg gattagtttt atcaaacaac agcctgaatt gtacatcact aggagagtgt   2700
aaatctgatg aatatcgttg ttacactggt gaatgtattt catctcattc ccgatgtgat   2760
tttataaaag attgtcctcg tggtgacgat gaagacgttg ttaaatgttt gcattacaca   2820
ccaaactcat gtccacaatc tcaattttta tgtcatgata aaacaaagtg cttggataaa   2880
aaacatatgt gtgatagtat taaagactgt agtgatggtt cagatgaaat ggattgttta   2940
cacaagcaca cttgtgattc aactacagaa tatcagtgta catctggaga gtgtattcag   3000
cgcatatttt tatgtgatgg taatcccgac tgtattaatg gacaagacga gttaaattgt   3060
ctgaaccaaa gttgtaataa tattacagaa tttagatgta attctggaaa ctgtatacct   3120
gcaacatggg aatgcgatgg tgaggttgat tgttttgatg gttcggatga acactattca   3180
tgtgctacca aaaaatgtaa agatgatcag ttttcttgca ccaatggtcg atgtatatca   3240
cataaattca cttgtaacgg taaagatgat tgtggtgata gttctgatga aaatggttgt   3300
tcgtcaaatc atgcatacat gacaaaaaga gtttcaaaag tatgtaatga aaaaacagaa   3360
tttgaatgtg aaaacacaat gggacattgt ataccgatca aggctaggtg caacggcaca   3420
tccgagtgca aacatttaga ggacgaattg aattgtggat gtcaaaaatc taattttttc   3480
gaatgtcaga ataagcgttg tgtgttaaaa gattggttat gtgataaaca tgatgattgt   3540
ggcgatgggt cagatgaaag tcaaaaggcg tgtgatatgc tttctgaaca tttatcgaat   3600
tcagtcgttt catcaaaaga ctgtgatgga tatttatgta agaaccaaga atgtatacct   3660
ctagatcaag cttgtaataa gaaaatcaat tgtaaagatg gttcagacga aggagatctt   3720
tgtggtttat cttgtataca catggattgt agtcatactt gtcaagaaac tccaaaaggt   3780
gggaaatgta catgttatca tggctataaa cttgcacaag atggtataac ttgcagagat   3840
attaatgaat gtgaagacga caatttatgt actcaatatt gtacaaattc agatggttca   3900
tatagctgta gttgtttaaa ttctgattac attttgcgtg cagataaaag ttcctgtaaa   3960
gcaattggac ccacaatgga tttagtttat tcgagtgttg atgaaataag aagtacttca   4020
ggagatatta aggaatcaaa attaattttt tcgatgcctg gaatgacaat atcgagcctt   4080
gatatagata ttagaagaaa tcttatttat tggacatcaa aacaagctgg tgttcttatt   4140
tgtatggata tgcaacaaca gcataaattt tacatgacag atttgttaca cccaacttta   4200
gttcgtattg attggttaac agaaaacgtt tactttgtac aaaattttaa agatattgtt   4260
gtatgttatt taaatgctaa acgttgtgcc actatataca gtgcaaacat ccatacaaca   4320
attatggctt ttgaaattga tcctcgttcc ggagtgatgt tctggtcgga aaccatatgg   4380
gcagtatttt caacaccaac aactattatt aggaaatctg attgcagtgg atacaatgta   4440
aaaactataa tccatcaagg gttacagtat gttactgatt tagctataga tccaatcaaa   4500
catatggtct attgggtcga tcaagttaat tcaacaatcg agaggtctaa ttacgacgga   4560
actaaaataa ctgtgttggt caattcgata gaacatttgc cagagaaaat atcattgtac   4620
gaagacaaac tgttttggac caaccatgaa accgggttgt ctatatttaa atgtaaagtt   4680
ctcggttctg aaaatgtcca ctgtgagtct gttcctgttc aagtgtttgc taccatcgag   4740
acattcacga taagtcaaca ggccaaacaa agaaatggat caaatgtttg cattgatgtc   4800
gattgcgatt ttatttgtac ttctggatca aaaggaccga tgtgtgtttg tggagatgga   4860
tctcaagtcg agccaggcaa tatttgtgat gatgctggtc atagaaaatt gcctgttttt   4920
aaagacttag attacaaaaa aaatatgatt tcaatctata tttctatatt tttaattgta   4980
```

-continued atgttgttat tagcgatgtt atattatttt ctattctatt ccaaaaataa atctttgaat 5040
caactagtat ctagattatt tcatcggcca ttaacaactg tcatccaagt aattgaccag 5100
aaagaagatg aaataaattc aagatataat gtttatgaga atcctatgaa cgaagatggg 5160
ttaataaaag accatgcttg tggaagtgaa atcgtcttga actatgatag tgcacgttac 5220
gttaatgcta actgctcaga acctccactt aactcgtttt cagagtacga cgagaacgag 5280
aaaaaaaaac ttattatggt tttataa 5307

<210> SEQ ID NO 28
<211> LENGTH: 5772
<212> TYPE: DNA
<213> ORGANISM: Acyrthosiphon pisum

<400> SEQUENCE: 28
attgaatgtt ttttcagaaa aagaatgtac taaatacgaa ttcaactgcg ggaacggtac 60
ttgtatcaat aagacaagac tttgtgacgg cattgttgac tgtatggaca atggcgctga 120
cgaagacgat tgtgatatta gcaaaaagcc ttgcctggcg ccagaatact ttgaatgtga 180
taacaagaga aaatgcattc ctaaggaatt tgtgtgtgat aagtcgaatg aatgcatcga 240
caagtctgac gaaagtcatt gtaaagagac gtcatcatct ttaacgcagt catgccggga 300
aggaaaattc aaatgctccg atggcacttg tattccaatg gcttggcatt gtgacgcgga 360
gattgattgc cacgacggta gcgatgaaga cggagaaaaa tgtagataca cgacattgtg 420
tacctctggt tatatgtgca aaaacttcaa ttgcgtttca aagacgtgga gatgtgacgg 480
aaaagatgac tgtggagatg gttcagacga aacccattgc gatatccaac tggttgagcc 540
agaaaaatgt ttaattgaaa atcgtaaatt tctatgtcac gatcataaaa aatgtatcga 600
tgtcagaaat gtctgtgatt acaacaatga ctgtcttgat gcatcggacg aaggtggtct 660
ttgcaataat aaaactgatt tcaaaagtga atgtaattcg atgaattgtt ctgccgcatt 720
tgaatgttta agaaagccac atggcattat gtgtgtgtgc ccaaaaggaa tgcattattt 780
aaataataaa tgttctgata tcaacgaatg tgaacaatat ggtatttgtg accaagtgtg 840
tcttaatttg gaaggttcat atacgtgctc ctgtgatcca cattatgaac tagtagataa 900
tcataagtgt aaaataaaag gcctaaatcc ggaattatta tattcatcac tacgtcaaat 960
aaaagttttt aacttggaat tacttcatag ttttactttg attgatgatt tgcaacatgt 1020
cactggatta gctgttgata aattaacttt atactggaca ctttatttgg atgggaactc 1080
agctattgtt agagcaaaca agtctgagcc taaaccagaa attattgttg actcgggtct 1140
tggatcgcct gagaatctag ttatagatat tattacacat aatttgtact tcaccgatgc 1200
aaaaatgaaa catattggag tgtgcaataa tgatggttca gtatgtacag ttcttcataa 1260
taaaaacata gacaaaccaa gagcagtagc tgtttcacca ctagatggtc tcatgtactg 1320
gacagattgg ggtaaaaatc caatgattgg tcgttctggt atggacgggt caagaccaca 1380
accgtttgtt acacaaaata tacactggcc aaatggtgtt catgttgatt atgtcgggaa 1440
aagaatttac tgggtggatg ctaagatgca atttattgaa tccattaatt tagatgcaac 1500
tgatcgaaga gtaattgtaa cagaatatgt agatcatcca tattcggtta ctgtgttcga 1560
ggataaattg tactggagtg attggtcaag taaagaaata aaagtatgca acaaatttac 1620
gggtaaagat agcaagacat tgatacgtga aaataagaac agagtgtatg gcatgcaaat 1680
taaccatccc tcgctcttcg agtctcaaat gccaaatcct tgtgaacaag gaaaatgcag 1740
tgatatatgc ttattagcac cgaaaacaga aatcaattct aaaggatact cgtgcgcttg 1800

-continued

```
ccccgatgat aaaaaactat cggaagatgg aatcttttgt atcaccattg ccatacctcc   1860
tacgcttatt gtgggtacac caacaagtat tatagaaatt gagcaggaac atttaggccg   1920
ccaaaaagca aaaaaaatat cgttgaaaaa tgatatatct agcatatccg cattgactta   1980
taattcatta tctggtgaca tcatcatcta tgactcaagg tctaagaaat tattcacttt   2040
cgattttgtt aagatgaaat tatcagattt agatgtacca gaaattagtt ccatttattc   2100
tcttgaattc gacaatcatg gaaacaattt atactggtgt gataggacta gaaaaacatt   2160
agatgtgtta agtctctcta caaaaacaca cacaacgata ttcaaagaaa ttgaaggtca   2220
tatcccattt gccgttactt tagttccaga taaaagcttt atgtttgtag ctatgaaaga   2280
aggttcacac atacatatcg atcgaattga catggatgga agtattcagt ctctagtaca   2340
tatggtggag tatggattga caggagatga aattgcttta cattttgata tgattacaag   2400
actgttgtat tttactgact ataaaaatgg cattattgat agtgtcagcg aagatggaac   2460
ggatagaaga attataaaaa aagcaggatt tgtaagagat attgtttcaa ttggttatga   2520
cattgtttgg gtatctgaag gttcgaaaat tttaaactgg attgataacg ttgatgaaga   2580
ccgagcatct agagctcttg atatagataa ttggaaaact gattcaaatt tatatttaac   2640
cgtagcaaat ggaattcaca aaaatataca acacccgtgt caacaaaata atggtggttg   2700
tagtcatata tgccttttat ctgagaaagg aaaggtttgt ggttgtccac ctggattagt   2760
tttatcaaac aacagcctga attgtacatc actaggagag tgtaaatctg atgaatatcg   2820
ttgttacact ggtgaatgta tttcatctca ttcccgatgt gattttataa aagattgtcc   2880
tcgtggtgac gatgaagacg ttgttaaatg tttgcattac acaccaaact catgtccaca   2940
atctcaattt ttatgtcatg ataaaacaaa gtgcttggat aaaaaacata tgtgtgatag   3000
tattaaagac tgtagtgatg gttcagatga aatggattgt ttacacaagc acacttgtga   3060
ttcaactaca gaatatcagt gtacatctgg agagtgtatt cagcgcatat ttttatgtga   3120
tggtaatccc gactgtatta atggacaaga cgagttaaat tgtctgaacc aaagttgtaa   3180
taatattaca gaatttagat gtaattctgg aaactgtata cctgcaacat gggaatgcga   3240
tggtgaggtt gattgttttg atggttcgga tgaacactat tcatgtgcta ccaaaaaatg   3300
taaagatgat cagttttctt gcaccaatgg tcgatgtata tcacataaat tcacttgtaa   3360
cggtaaagat gattgtggtg atagttctga tgaaaatggt tgttcgtcaa atcatgcata   3420
catgacaaaa agagtttcaa aagtatgtaa tgaaaaaaca gaatttgaat gtgaaaacac   3480
aatgggacat tgtataccga tcaaggctag gtgcaacggc acatccgagt gcaaacattt   3540
agaggacgaa ttgaattgtg gatgtcaaaa atctaatttt ttcgaatgtc agaataagcg   3600
ttgtgtgtta aaagattggt tatgtgataa acatgatgat tgtggcgatg ggtcagatga   3660
aagtcaaaag gcgtgtgata tgctttctga acatttatcg aattcagtcg tttcatcaaa   3720
agactgtgat ggatatttat gtaagaacca agaatgtata cctctagatc aagcttgtaa   3780
taagaaaatc aattgtaaag atggttcaga cgaaggagat ctttgtggtt tatcttgtat   3840
acacatggat tgtagtcata cttgtcaaga aactccaaaa ggtgggaaat gtacatgtta   3900
tcatggctat aaacttgcac aagatggtat aacttgcaga gatattaatg aatgtgaaga   3960
cgacaattta tgtactcaat attgtacaaa ttcagatggt tcatatagct gtagttgttt   4020
aaattctgat tacattttgc gtgcagataa aagttcctgt aaagcaattg gacccacaat   4080
ggatttagtt tattcgagtg ttgatgaaat aagaagtact tcaggagata ttaaggaatc   4140
```

```
aaaattaatt ttttcgatgc ctggaatgac aatatcgagc cttgatatag atattagaag   4200
aaatcttatt tattggacat caaaacaagc tggtgttctt atttgtatgg atatgcaaca   4260
acagcataaa ttttacatga cagatttgtt acacccaact ttagttcgta ttgattggtt   4320
aacagaaaac gtttactttg tacaaaattt taaagatatt gttgtatgtt atttaaatgc   4380
taaacgttgt gccactatat acagtgcaaa catccataca acaattatgg cttttgaaat   4440
tgatcctcgt tccggagtga tgttctggtc ggaaaccata tgggcagtat tttcaacacc   4500
aacaactatt attaggaaat ctgattgcag tggatacaat gtaaaaacta taatccatca   4560
agggttacag tatgttactg atttagctat agatccaatc aaacatatgg tctattgggt   4620
cgatcaagtt aattcaacaa tcgagaggtc taattacgac ggaactaaaa taactgtgtt   4680
ggtcaattcg atagaacatt tgccagagaa aatatcattg tacgaagaca aactgttttg   4740
gaccaaccat gaaaccgggt tgtctatatt taaatgtaaa gttctcggtt ctgaaaatgt   4800
ccactgtgag tctgttcctg ttcaagtgtt tgctaccatc gagacattca cgataagtca   4860
acaggccaaa caaagaaatg gatcaaatgt ttgcattgat gtcgattgcg attttatttg   4920
tacttctgga tcaaaaggac cgatgtgtgt ttgtggagat ggatctcaag tcgagccagg   4980
caatatttgt gatgatgctg gtcatagaaa attgcctgtt tttaaagact tagattacaa   5040
aaaaaatatg atttcaatct atatttctat atttttaatt gtaatgttgt tattagcgat   5100
gttatattat tttctattct attccaaaaa taaatctttg aatcaactag tatctagatt   5160
atttcatcgg ccattaacaa ctgtcatcca agtaattgac cagaaagaag atgaaataaa   5220
ttcaagatat aatgtttatg agaatcctat gaacgaagat gggttaataa aagaccatgc   5280
ttgtggaagt gaaatcgtct tgaactatga tagtgcacgt tacgttaatg ctaactgctc   5340
agaacctcca cttaactcgt tttcagagta cgacgagaac gagaaaaaaa aacttattat   5400
ggttttataa gcatcataaa attataaact ttgttaagga tgaatattta tttgttaatt   5460
tttattttta taaatacaat tttattttat ttttataata tcaatatgca cattgcacat   5520
agatataaat tattactgaa atttataatt ctgtatacct aaatgattat ttttttagt    5580
ttgttaactt ttacaatagt tccttatttt taatttgttt aattcaaagt tacccggtat   5640
atatatatta ttataataat aaataaaagt tacattaaat tagtgtgatt gtgtcaatat   5700
atcaaaagct aacacttaat ataattcaat gtatattcaa aagatctgcg tgtgtaatga   5760
aattaaatat at                                                       5772
```

<210> SEQ ID NO 29
<211> LENGTH: 5430
<212> TYPE: DNA
<213> ORGANISM: Bemisia tabaci

<400> SEQUENCE: 29

```
atgattcaga gggaatggag ctccatatcc aagggctcat ggtgcacagc attattagta     60
gttatcgcag tcttttgcac atttgtacaa tcatcttcat catatgaatg tgtcggacca    120
tcccatttcg aatgtacaaa tcacaggtgt atatccatgg atttaaggtg cgatggagat    180
gacgattgta atgatggatc cgatgaacac ggttgtaatg tggataaatc aaaaaatgaa    240
acctgtgcta gtacccagtt tgattgcggt cagggccaat gtataccacg gtcctgggtt    300
tgtgatggga atgcagattg tgaggacggt aaagatgaag gagctgtagg ctgcgctgaa    360
agccattgcg cagcgtctga gtgggagtgc cctcataacc atcgctgtat cccgaatgat    420
tatatctgtg atggggatga tgattgtggt gacaattcag atgaagacga ctgtacaggc    480
```

-continued

```
aagaataatt ttacagagtg cacttcagcg tttggaaaat ttctctgcaa aaataggaat    540
cagtgcatcg atgattctct tctgtgcaac gggcaccctg actgtaaaga tgggtcagat    600
gagggtggtc actgtgcttc gaaagctcaa gtagctactg actgtgcaaa gctaaactgt    660
acccactcgt gtgttgaaag cccagatgga ccggtttgcg tctgtggatc aggatatcac    720
cttgaaggaa acgtctgtga agatattaat gagtgcttgg aatggggaac atgtgaccaa    780
atgtgtgaaa acacggtcgg aggttacatc tgtgaatgtg aacctggata caaactggaa    840
agtaacggac gcacatgcaa agcagaagag ggtgaaggac ttctgatcta ttcaagcctc    900
aaaaagatta agtctctata tctgacatct cgcatatcaa tgacagttgc ctctgaggtt    960
ccatatgcga caggtgtgtc ttttgatggt aaacatgtct attggacgac cgtgcttgat   1020
ggagttgaat ctattgttcg ggcaagtgag gatggatctc atgaaaccac cattgttgat   1080
tcaggtgttg gctcccctga agacctagct gtcgactggg tgactggtaa catatacttc   1140
actgatggcg agtaccaaca gatcggcatt tgcacctaca acgaagagct ggttgaaacg   1200
aaatgcgctg tcctccacaa caaagacctg aacaagcccc gcgcaattgt tttaaaccca   1260
gctgatgcgg tcatgtactg gtctgattgg ggctttaaac cactcatcgc ccgttctgga   1320
atggatggca cagacttcta tgagtttgta acgacagagc tccattggcc caatggtctc   1380
acaattgatc acggaaatcg gagagtatat tgggtcgatg cgagactcgg aactgttgaa   1440
actgttgatt ttcaaggccg tgatcggcgg aaaatattaa ctgatctcaa tgatcatcct   1500
ttcgcaatcg ctgtttttga agataaaatc tattggagtg gatggacaaa ccaagaaata   1560
gtagaatgta ataagttcac cgggaaaaac cgagtacaag ttgtcaaaag tcggaaagac   1620
aaaatttacg gtgtgcacat ttttcaccca actttgcaaa atcattcgct accaaatccg   1680
tgcgccggga agtgcagtga catctgtgct ctatctccat cagcttcaag cggaggcaaa   1740
ggctactctt gcttgtgccc tgacaataaa atcttatccc cctctggaga atggtgccaa   1800
gaacagccca aagaatctgt cattgttagc attggaaact ttgttttcca gctgaaagtg   1860
actcttggga agcagtacat tcatccgctg cctgttaata acctccagtc tgtcagtgca   1920
atcgtctaca actcctttga tggctctcta ttaatagctg acccagatgc caaaatgatt   1980
tactcgtatc aactgaacac ggacaccatg gagactctaa ttgatctcaa agtgggctat   2040
gtctcagcat tggcttacga tcccattggc cggaatctct attggtgcga caaagaggcc   2100
ggcactgtag aagtgttcag tttcttctct cacagaagga agttgttgct ccgggaattt   2160
gacgatgaaa aacctttcgc catgactctc ataccagaag aaggcctgat gttcgtcatt   2220
gccaaagccc atgaccacct tcacattgat cggatcaaca tggatggctc actaagcaca   2280
ctgactcaca tgaccagtct caagttgcaa ggaccggatg tagctttgca ctatgacagt   2340
gattctcgca gggtttattg ggctgatcac tcagctggcc tcattgagag caccgatacg   2400
aatggaaacg acaggcaagt ataccgtgac gtatcatcac ctttagctct gaccgatgtg   2460
gatagagacc tttattggac atcagatggt cgcccacacc tgtactactc tgagaaaagc   2520
aatgcaagca tgcccgtcag gaaaatcaac atggaacgat tttgcgatc accaaaggac    2580
cactatcgga tgtttgttac tgcaatcatc cctgataaaa ctactagaga tcatccttgc   2640
caaactaaca atggcaagtg tagccatttt tgcctcctca ccagtcgtaa tccaaagcat   2700
gtatgcagtt gtcctgatgg gatgaagctg gcggataatg gtcaggactg tgaagagatt   2760
gctgcatgtg gagcacatga ataccattgc acgacaggtg aatgcattcc aatgtcgaag   2820
```

-continued aaatgcgacc gaaacaagga ttgcccctat ggcgaagatg agaccttctg cccagcacag 2880
tgtgagactg atcagtttgc gtgctttgat ggacaaaaat gtatcgatgc caaggataga 2940
tgcaacatgc attttgattg tcacgaccac tctgatgagg ctaactgcca aaatgtcacc 3000
tgcgatcaat catacaactt tttgtgccga atcggtgagt gcgtaagtca cgctgtgctg 3060
tgcaataatg aatggaattg caaggacggt agtgatgaag agaactgtac gacttccacg 3120
tgcccttcca gcgagtttcg gtgtcattcc ggaacatgca taccgaagaa ctgggtctgt 3180
gatctggatg ccgattgccc cgaccaatca gatgaaaata actgcagttt ctcaagaaaa 3240
gaaaagtgca ccgaattctt gtgtcagagt ggcatgtgtg tagcacagga acttgtctgt 3300
aacggtcaaa ccgaatgtga cgatggaagt gacgaattca attgcgatga gccggttcca 3360
aaaacggcaa acaaagagga tggttttata gataactgtg atgaagagaa ggagttcatg 3420
tgcgagcctg gcaaatgcat taatcttata ttcaagtgta atggtgttaa agattgcgag 3480
aacggagctg atgagctaaa ctgcataggc tgtgaacaat tcacttgcaa taatgggaaa 3540
tgcatcactt atgatcttgt atgcaatgat gatgatgact gtggtgactc atccgatgaa 3600
agacctctca actcgtgccc agacagcaaa gaaaacccag ctattgtgcc tgctcatatt 3660
cccaatgtgt gccatggatt tgtttgcaag aacggtgaat gccttgatga tttcagtcta 3720
gtctgcaaca aaaagcaaga ttgtaaggac ggctcagatg aaggtggacg atgcggttca 3780
agctgtgatg tgacagcaaa ttgcagtcag atttgtcgtg ataagccaaa tggacatgag 3840
tgtgcgtgtg tccctggctt taaaattgct gaggatggcc gcgattgcga ggatattgat 3900
gagtgcaccg aattggagcc gtgtagccag atgtgtttca acacctatgg aagttacacc 3960
tgtgcctgtc ttggtccaga ttatattaaa aagtcagatg ggtcctgcaa agccactggc 4020
ccaaaattgc agtacgtctt tgctaccggt taccagattc gcactatatc atacctaatg 4080
accgatgtca aagtggcata ctatagtgca gatcttgaag tttcaggatt tgatgtgaac 4140
atgagaacag agcatgtcta ctggtcatct gaaaacaagg gtgtcatcac aaaaatgtca 4200
ttaacgcaca gacacgagcc aaaacatttc atcactggtt tacgccgtcc atcagagctg 4260
gcagtcgatt ggataacaca caacctctac tttgtccaag caaggaacat cattaatgtc 4320
tgtaacttcc accttgaacg ctgcgcacaa attttgaccg ctgaaagtgg cttggagatc 4380
aacagtcttg ccgttgatcc tgtcagaggt gtccttttct ggagtgaaac aagccgcatc 4440
gtctggaata tgcctaagag ctccattaga cgcgcagaca tgaatggaaa aaatattgag 4500
accattgttt cagctaatgt gagctacgca ttggatcttg ctttagatcc aatcctcaat 4560
catgtctatt gggtcgacaa aacattgaag gtcattgaaa gagctaacta tgatggaact 4620
cgccgacgtg tcatcttgac atcaaagttc catccaaaat ctgttgcgct ctttgatggt 4680
tctatctact ggtcggttga gtcgagtgga tccccgatta caaagtgtgc tcttcaagga 4740
ctttccacgg aatcgtactc gtgcaatcaa atcccaatca aagttgtaga tccaataact 4800
cacttcactc tcatgcaacc agctctgcaa agaaacatat caaacgcttg taggaacatg 4860
gagtgcagtc acatgtgcgt tctcagctcg acattaccat catgcatttg tcgcaatgga 4920
aagatagttc ctccaaaaac agcctgtacg gatagcaatt atatgccaga aacccacttt 4980
ttggaaacaa ctggaactgt tgatggtcaa agtcctggat attcttggtc atcaatctgt 5040
gcaacaatca tcttagtcgc tttcatcgga acaactttct atgccttatt ctactactat 5100
aactccaagt acaacatgcg acgtctattt ccatcaattc attttaaaaa tccagccttc 5160
aacctacagt caaaattcca ggctaatggg atgaccggtt tagccagtgg caaccatatg 5220
gctcacttgt catcgaagga ccatcatttc gaaaaccctc tgcaagagag tcgtgaaggt 5280
gaagtgagaa tcgttactcc aaatgaaatc acgattagcc gagccgagac cagttggaca 5340
tcagcccatc tagaagactc aagctctata gaaacagaat acgcagacct tgttgtcgag 5400
acaaacccca aagctaattt gatatcgtga 5430

<210> SEQ ID NO 30
<211> LENGTH: 5774
<212> TYPE: DNA
<213> ORGANISM: Bemisia tabaci
<400> SEQUENCE: 30
atgattcaga gggaatggag ctccatatcc aagggctcat ggtgcacagc attattagta 60
gttatcgcag tcttttgcac atttgtacaa tcatcttcat catatgaatg tgtcggacca 120
tcccatttcg aatgtacaaa tcacaggtgt atatccatgg atttaaggtg cgatggagat 180
gacgattgta atgatggatc cgatgaacac ggttgtaatg tggataaatc aaaaaatgaa 240
acctgtgcta gtacccagtt tgattgcggt cagggccaat gtataccacg gtcctgggtt 300
tgtgatggga atgcagattg tgaggacggt aaagatgaag gagctgtagg ctgcgctgaa 360
agccattgcg cagcgtctga gtgggagtgc cctcataacc atcgctgtat cccgaatgat 420
tatatctgtg atggggatga tgattgtggt gacaattcag atgaagacga ctgtacaggc 480
aagaataatt ttacagagtg cacttcagcg tttggaaaat ttctctgcaa aaataggaat 540
cagtgcatcg atgattctct tctgtgcaac gggcaccctg actgtaaaga tgggtcagat 600
gagggtggtc actgtgcttc gaaagctcaa gtagctactg actgtgcaaa gctaaactgt 660
acccactcgt gtgttgaaag cccagatgga ccggtttgcg tctgtggatc aggatatcac 720
cttgaaggaa acgtctgtga agatattaat gagtgcttgg aatggggaac atgtgaccaa 780
atgtgtgaaa acacggtcgg aggttacatc tgtgaatgtg aacctggata caaactggaa 840
agtaacggac gcacatgcaa agcagaagag ggtgaaggac ttctgatcta ttcaagcctc 900
aaaaagatta agtctctata tctgacatct cgcatatcaa tgacagttgc ctctgaggtt 960
ccatatgcga caggtgtgtc ttttgatggt aaacatgtct attggacgac cgtgcttgat 1020
ggagttgaat ctattgttcg ggcaagtgag gatggatctc atgaaaccac cattgttgat 1080
tcaggtgttg gctcccctga agacctagct gtcgactggg tgactggtaa catatacttc 1140
actgatggcg agtaccaaca gatcggcatt tgcacctaca acgaagagct ggttgaaacg 1200
aaatgcgctg tcctccacaa caaagacctg aacaagcccc gcgcaattgt tttaaaccca 1260
gctgatgcgg tcatgtactg gtctgattgg ggctttaaac cactcatcgc ccgttctgga 1320
atggatggca cagacttcta tgagtttgta acgacagagc tccattggcc caatggtctc 1380
acaattgatc acggaaatcg gagagtatat tgggtcgatg cgagactcgg aactgttgaa 1440
actgttgatt ttcaaggccg tgatcggcgg aaaatattaa ctgatctcaa tgatcatcct 1500
ttcgcaatcg ctgtttttga agataaaatc tattggagtg gatggacaaa ccaagaaata 1560
gtagaatgta ataagttcac cgggaaaaac cgagtacaag ttgtcaaaag tcggaaagac 1620
aaaatttacg gtgtgcacat ttttcaccca actttgcaaa atcattcgct accaaatccg 1680
tgcgccggga agtgcagtga catctgtgct ctatctccat cagcttcaag cggaggcaaa 1740
ggctactctt gcttgtgccc tgacaataaa atcttatccc cctctggaga atggtgccaa 1800
gaacagccca aagaatctgt cattgttagc attggaaact ttgttttcca gctgaaagtg 1860

-continued

```
actcttggga agcagtacat tcatccgctg cctgttaata acctccagtc tgtcagtgca   1920
atcgtctaca actcctttga tggctctcta ttaatagctg acccagatgc caaaatgatt   1980
tactcgtatc aactgaacac ggacaccatg gagactctaa ttgatctcaa agtgggctat   2040
gtctcagcat tggcttacga tcccattggc cggaatctct attggtgcga caaagaggcc   2100
ggcactgtag aagtgttcag tttcttctct cacagaagga agttgttgct ccgggaattt   2160
gacgatgaaa aacctttcgc catgactctc ataccagaag aaggcctgat gttcgtcatt   2220
gccaaagccc atgaccacct tcacattgat cggatcaaca tggatggctc actaagcaca   2280
ctgactcaca tgaccagtct caagttgcaa ggaccggatg tagctttgca ctatgacagt   2340
gattctcgca gggtttattg ggctgatcac tcagctggcc tcattgagag caccgatacg   2400
aatggaaacg acaggcaagt ataccgtgac gtatcatcac ctttagctct gaccgatgtg   2460
gatagagacc tttattggac atcagatggt cgcccacacc tgtactactc tgagaaaagc   2520
aatgcaagca tgcccgtcag gaaaatcaac atggaacgat tttgcgatc accaaaggac    2580
cactatcgga tgtttgttac tgcaatcatc cctgataaaa ctactagaga tcatccttgc   2640
caaactaaca atggcaagtg tagccatttt tgcctcctca ccagtcgtaa tccaaagcat   2700
gtatgcagtt gtcctgatgg gatgaagctg gcggataatg gtcaggactg tgaagagatt   2760
gctgcatgtg gagcacatga ataccattgc acgacaggtg aatgcattcc aatgtcgaag   2820
aaatgcgacc gaaacaagga ttgcccctat ggcgaagatg agaccttctg cccagcacag   2880
tgtgagactg atcagtttgc gtgctttgat ggacaaaaat gtatcgatgc caaggataga   2940
tgcaacatgc attttgattg tcacgaccac tctgatgagg ctaactgcca aaatgtcacc   3000
tgcgatcaat catacaactt tttgtgccga atcggtgagt gcgtaagtca cgctgtgctg   3060
tgcaataatg aatggaattg caaggacggt agtgatgaag agaactgtac gacttccacg   3120
tgcccttcca gcgagtttcg gtgtcattcc ggaacatgca taccgaagaa ctgggtctgt   3180
gatctggatg ccgattgccc cgaccaatca gatgaaaata actgcagttt ctcaagaaaa   3240
gaaaagtgca ccgaattctt gtgtcagagt ggcatgtgtg tagcacagga acttgtctgt   3300
aacggtcaaa ccgaatgtga cgatggaagt gacgaattca attgcgatga gccggttcca   3360
aaaacggcaa acaaagagga tggttttata gataactgtg atgaagagaa ggagttcatg   3420
tgcgagcctg gcaaatgcat taatcttata ttcaagtgta atggtgttaa agattgcgag   3480
aacggagctg atgagctaaa ctgcataggc tgtgaacaat tcacttgcaa taatgggaaa   3540
tgcatcactt atgatcttgt atgcaatgat gatgatgact gtggtgactc atccgatgaa   3600
agacctctca actcgtgccc agacagcaaa gaaaacccag ctattgtgcc tgctcatatt   3660
cccaatgtgt gccatggatt tgtttgcaag aacggtgaat gccttgatga tttcagtcta   3720
gtctgcaaca aaaagcaaga ttgtaaggac ggctcagatg aaggtggacg atgcggttca   3780
agctgtgatg tgacagcaaa ttgcagtcag atttgtcgtg ataagccaaa tggacatgag   3840
tgtgcgtgtg tccctggctt taaaattgct gaggatggcc gcgattgcga ggatattgat   3900
gagtgcaccg aattggagcc gtgtagccag atgtgtttca acacctatgg aagttacacc   3960
tgtgcctgtc ttggtccaga ttatattaaa aagtcagatg ggtcctgcaa agccactggc   4020
ccaaaattgc agtacgtctt tgctaccggt taccagattc gcactatatc atacctaatg   4080
accgatgtca aagtggcata ctatagtgca gatcttgaag tttcaggatt tgatgtgaac   4140
atgagaacag agcatgtcta ctggtcatct gaaaacaagg gtgtcatcac aaaaatgtca   4200
ttaacgcaca gacacgagcc aaaacatttc atcactggtt tacgccgtcc atcagagctg   4260
```

gcagtcgatt ggataacaca caacctctac tttgtccaag caaggaacat cattaatgtc 4320
tgtaacttcc accttgaacg ctgcgcacaa attttgaccg ctgaaagtgg cttggagatc 4380
aacagtcttg ccgttgatcc tgtcagaggt gtccttttct ggagtgaaac aagccgcatc 4440
gtctggaata tgcctaagag ctccattaga cgcgcagaca tgaatggaaa aaatattgag 4500
accattgttt cagctaatgt gagctacgca ttggatcttg ctttagatcc aatcctcaat 4560
catgtctatt gggtcgacaa aacattgaag gtcattgaaa gagctaacta tgatggaact 4620
cgccgacgtg tcatcttgac atcaaagttc catccaaaat ctgttgcgct ctttgatggt 4680
tctatctact ggtcggttga gtcgagtgga tccccgatta caaagtgtgc tcttcaagga 4740
ctttccacgg aatcgtactc gtgcaatcaa atcccaatca aagttgtaga tccaataact 4800
cacttcactc tcatgcaacc agctctgcaa agaaacatat caaacgcttg taggaacatg 4860
gagtgcagtc acatgtgcgt tctcagctcg acattaccat catgcatttg tcgcaatgga 4920
aagatagttc ctccaaaaac agcctgtacg gatagcaatt atatgccaga aacccacttt 4980
ttggaaacaa ctggaactgt tgatggtcaa agtcctggat attcttggtc atcaatctgt 5040
gcaacaatca tcttagtcgc tttcatcgga acaactttct atgccttatt ctactactat 5100
aactccaagt acaacatgcg acgtctattt ccatcaattc attttaaaaa tccagccttc 5160
aacctacagt caaaattcca ggctaatggg atgaccggtt tagccagtgg caaccatatg 5220
gctcacttgt catcgaagga ccatcatttc gaaaaccctc tgcaagagag tcgtgaaggt 5280
gaagtgagaa tcgttactcc aaatgaaatc acgattagcc gagccgagac cagttggaca 5340
tcagcccatc tagaagactc aagctctata gaaacagaat acgcagacct tgttgtcgag 5400 acaaaccccca aagctaattt gatatcgtga tactctttaa tcatttgaaa aatgcagtcg 5460
tgtaaatatg ttgtacagtt tgttttttgt tgaatctttt aatttatcta tgcatttgtt 5520
gtttgtataa atttttatta ccatattttg gtgtcttcgg aactgaagtc agtcaaattt 5580
atcgagtcaa atttcatatc gatcagatca gtttatggtg tttttatatt tgtttaaaga 5640
agattgatcc atttttatca aaagcatctg tcaattatct tccttagaaa aatgatacaa 5700
tctaaatttt ttcaaattta taatacaagg aaaaaaaaaa aacctatagt gaaatcacta 5760
gtggaggatc cgcg 5774

<210> SEQ ID NO 31
<211> LENGTH: 5370
<212> TYPE: DNA
<213> ORGANISM: Spodoptera litura

<400> SEQUENCE: 31
atgaggaaat atagtaacaa aatgaagtat caaggcttgc tattgatagt tagtgtggcg 60
tggtgttcag ctcagctcag cgatgacatg cagatgtttg acccagaata catggcggaa 120
gacaagttcc cctgcatggg tggaggatgt atttcagtgt cacagtactg cgatggaaaa 180
ttggactgtg atgatggcag cgacgagaat ttttgcatcg aacacaagcc gttccaggag 240
ttttgtaacg agatccacca gtacatgtgt cgggactcca cgaagtgtgt tcctttatcc 300
tggctgtgca acaatgagcc ggactgcgat gatggcagcg atgagttcaa ctgcaccgca 360
ctgccggctg taaacgtcaa ttcgacatgc aaaggcttcc aatgtggaga cggcaaatgc 420
atctccttcc tgtgggtgtg tgacggtgtc tacgactgtg aagataaaag cgatgagtat 480
gctgaggaac tctgcaggca cgtatcccgt ccccacgcga tcgtcgacgg ttcatactgt 540

```
caggaattgc acacaatgga cgaccgtaac tacaagtgtc tggacgcctc cttctgcctg    600
cccagcagta tgatgtgcga cggactccag gattgccgcg atggcagcga tgagggacca    660
ttttgcaaaa actggaatac aatgtgcgac aacttcaaat gcatgggtaa cgacacgata    720
tgttccccgg agaggtttgg agcctcctgc ctctgcctgc cctcccactt catgcggcaa    780
tacgattaca tcaccaaaca gtgccaggat gtcaacgagt gcctcatgga gcacccaccc    840
tgctcccata aatgcattaa cgccgatggc cattatattt gtgaatgcga tcctggatac    900
aaacgggatg tgtatggata tctttgttat gctactggtc ccgaagcgat gctgttcttc    960
aatactcgga acgatatcag atacctgaag attaagacta aagaaatggt cacagtggct   1020
accgacatca aagagggtca tggcgtttca ttcgacggga cttacattta ttgggtggag   1080
acagcacagg gacatcagtc catcttcaaa gcacaactcg gagacgtcaa ggatacaaag   1140
gaggtactgg taggtctcgg tctggaggac cctggcgaca tagcagtgga ctacctgggc   1200
gggaacatat acttcagtga tgcggagcga ggaatcatct ccgcttgcag ggtcgacggc   1260
tccatctgca ccacgatcaa gactcatgct aacaacccac gatttgtcac tcttgatcct   1320
aaaaatggta agatgtactg ggcagactgg cacgagcgtc cagtgataat gtcagctcgg   1380
atggacggca gccgacacga tgagctggtg gacaacttgg agaactttgc caccggcctg   1440
gccgtggacg cgccaaacgg gagactgtac ttcgttgaca aaactatcaa agtcgtcatg   1500
attgcggaga aacatgttta tgctttattt gaagagccct tccaccatcc gtactccatc   1560
tcagtgttcg agaacactgt gttctggagt gactggacct ccaacagtat acagacgact   1620
gacaaagtgc acgggaccgc gcagaagagg aatgttctac tcaaacttga tacacctgta   1680
ctaggcatgc acatgtacca tccagtgctg atgaacacga catcgaaccc gtgcagcaac   1740
aacaactgct cgcatctctg cttcgtcacc tccaacgcca cccacgtctg cgcctgcccc   1800
gatggcatgg agattgagaa taatcagtgc catcacgtag gcaactaccg cgccaagtac   1860
ctggtggtgg gaagtgggca gctgttcaca aagatccagt acaacgcgct cggcaacccg   1920
gagtgtcacg ccacgcactt cgaaatcgga cgcgtgcagg ccatggcgta cgatcggtat   1980
agagattcac tattcatata cgacggccag cgacggacca tcaactacat aaacatgagt   2040
gacttcactc tcggtatcac tcacgtgttg atctacaacg gactggagaa cgtcgtcgac   2100
atggattatg attacgtgac agataacctg tacgtgctgg atgcaagtcg tcgtgtcgtt   2160
gaagctgtgt ctctgaggac tcagaagcgc gccatagtac atcgattcga cattcaagaa   2220
ctgcctgtta gcttctgtat tctttcggac tacgggagaa tgttggtggc cgtggtggag   2280
agtgagatgc acaacaccat tcatatcgac agcatcgggc tcgacgggac ccaacggaga   2340
cacgtcatca tgaacaattt gaaaggtcct catattcgat tgcggtacgt gccagatttt   2400
attgggcgcg actggaccca acggagacac gtcatcatga acaatttgaa aggtcctcat   2460
attcgattgc ggtacgtgcc agaaactgag caggtgttca tatccgacga gagcaacggc   2520
atcatcgatt tcatacatcc tgaaggcacc gggcgggaga actatcggga gctgacctcg   2580
acggtgacca gcctcgccat agcagataac tacgtcttct ggacagaccg aaagaccccc   2640
agactcttct ggtctgacat acacgaagcc tcgccgaaga taaggaggat tgatctggca   2700
cttttcccaa acactacgca acttctgatc caagcaacga actcgctccc tgatccaaaa   2760
gaccctcttc tgaaccatcc ctgtctaaag aatccttgtt ctgacgtctg tgtccaactt   2820
ccccatgata ctccagaaga tcacccgaaa ctagcaaact tcgagatgaa gtacaagtgt   2880
ttgtgtcctc ctgggttgtt ggtgaatggt aaccagtgcg ccaaacctgc gacatgtggt   2940
```

```
tcggatgaga tactgtgcca taggagtaat atttgtgtga agcaagatgc caggtgtgat   3000
ggaaaggccg actgtccgaa gaatgaagac gaggaaggtt gtatagtgga tccggcaaac   3060
atatgttcat cagacgaaat attctgtcgc ggcttgtgcg taaacaggga caaagccacg   3120
acgtgttcta ccggagaaaa aactaataaa gcactacctt cgaacaactg cagcagcaca   3180
gaattccagt gcacggacac ctcaatctgc atctctcggt cgcaggtctg tgaccaacac   3240
atcgactgtc ctaatggatc ggatgagcag ctcttagagt gcgacatcta ctcttgtcat   3300
gaaactgagt tcatgtgtgc gtccggctca tgtatagtga aaacgtggac atgtgatgga   3360
gaccgtgact gtaatgatgg atctgatgaa atcaactgcg tgaacatgac ttgcggcctg   3420
ggcttctacc agtgcagaga cagggagtgc gtggagttat cgaagaggtg tgacggacat   3480
cgggattgct cggattactc cgacgaagag gactgtgatg agcctcaaat tgtcgagacg   3540
atagaagaag ccccgaaatg tgctgcgtgg gaatatactt gtgaaaaaaa tactagcatt   3600
tgtttgcctg aaaccgctcg atgcaacatg aagacggact gcccgggtgg cacggatgag   3660
cacggttgcg accaccgctg tgccccgaag ggaatgtttg cgtgcggcca acaggtcact   3720
tgtatcacaa tgaacaaggt ctgcaacgga cgactggatt gtgatgacgg atccgatgag   3780
acgcctgatg cttgttctca ggtgaacagg acctctcacc tgttcccagt agctcggaca   3840
ttcactgaat gtactgaggg ttataagtgt aacaacggac agtgcattga gtggtcacag   3900
ttgtgtgaca agaagaggga ctgcatcgat gggacagatg aaaatggact ttgcgatact   3960
gcatgcgcaa acagcacatg tacgttcatg tgtcagccga ccccattcgg acgtcgctgt   4020
ctgtgcccct ttggcttcca aatttccaag gatcagttct cgtgcgagga catcgacgag   4080
tgcactgaag atgtctgctc tcaagggtgt atcaacgtgc cagggtcctt cctgtgctgg   4140
tgccatcatg gttatgccat caggaggaca gaccgtcgct attgcaaggc gatccgcggc   4200
aacatgtcga tcctgtacgt gtcgggtaac accgtgcggt ctatctcagc agacgggtac   4260
ggtgctatcg agtataccga tactaatgcc tcggccatca ctgatatgga ttataatgtt   4320
cggcagaaga agctatacgt gacctcggaa gcgggtggca agttgttaga agtgaatgag   4380
acgcagaatg tgatcgctgt tacgaacgtt gggaaaccat cgagggtggc agtggactgg   4440
gtgaccggca acgtgtactt cgtggacacg acgccatttg accagcgcat acgagtctgt   4500
catgtcaaga ggaagcgctg cgcttccctg ctgaaacttc cttctgatgc cacggtgaca   4560
gcgttgatag tagagcccag ttccagccgc atgttctact gcgtcactcg gaagctggag   4620
tcggtgatct ggacagcgaa cctggctggc agacacgtga cggatctggc tactgtacgg   4680
aactgcaccg gtctggccgc agactccttc aagaagaagc tgtacgtcgc agagacgggc   4740
ccagcgcata ttattaggat ggattatgag ggggagaatt tcaacaaaat cctctcagat   4800
cacccacgtc tgcaagcacc gcatggacta gaaatattcg aagactacat ctactacttg   4860
gaagccaact cgttccgcct cagccgctgc cagctgtacg gggccaaaca ttgtgaaact   4920
tatgtgtacc gtgtgtttga cgccaacacg ttcgtcattc gccacgagag catccaacgc   4980
gatgacatag tcaacgaatg tgaagatgtc gtttgtgaca acatttgtgc cgtggacgaa   5040
gatgggccca aatgtttgtg tgacgatgga gccttggcca agagtgggaa gtgtcctgtg   5100
gttgataaga aattggtacc tttattcaac ggctggtcgt acgagcagct ggcatcggct   5160
cgcagcatcc ccttcaccgt caccttggga gtactgaccc tgatcgccat ctacctctgc   5220
gtcttcgtat actaccattg tatatacata cccaggaaga gaatgttagc atctgcttac   5280
```

```
actgaagttc ggttccagaa cacacaaaat acgtcctatc ctgaatcaga cccggtagtg   5340

gagatgcatc cctcaaggta tctaccttag                                     5370


<210> SEQ ID NO 32
<211> LENGTH: 5370
<212> TYPE: DNA
<213> ORGANISM: Spodoptera litura

<400> SEQUENCE: 32

atgaggaaat atagtaacaa aatgaagtat caaggcttgc tattgatagt tagtgtggcg     60

tggtgttcag ctcagctcag cgatgacatg cagatgtttg acccagaata catggcggaa    120

gacaagttcc cctgcatggg tggaggatgt atttcagtgt cacagtactg cgatggaaaa    180

ttggactgtg atgatggcag cgacgagaat ttttgcatcg aacacaagcc gttccaggag    240

ttttgtaacg agatccacca gtacatgtgt cgggactcca cgaagtgtgt tcctttatcc    300

tggctgtgca acaatgagcc ggactgcgat gatggcagcg atgagttcaa ctgcaccgca    360

ctgccggctg taaacgtcaa ttcgacatgc aaaggcttcc aatgtggaga cggcaaatgc    420

atctccttcc tgtgggtgtg tgacggtgtc tacgactgtg aagataaaag cgatgagtat    480

gctgaggaac tctgcaggca cgtatcccgt ccccacgcga tcgtcgacgg ttcatactgt    540

caggaattgc acacaatgga cgaccgtaac tacaagtgtc tggacgcctc cttctgcctg    600

cccagcagta tgatgtgcga cggactccag gattgccgcg atggcagcga tgagggacca    660

ttttgcaaaa actggaatac aatgtgcgac aacttcaaat gcatgggtaa cgacacgata    720

tgttccccgg agaggtttgg agcctcctgc ctctgcctgc cctcccactt catgcggcaa    780

tacgattaca tcaccaaaca gtgccaggat gtcaacgagt gcctcatgga gcacccaccc    840

tgctcccata aatgcattaa cgccgatggc cattatattt gtgaatgcga tcctggatac    900

aaacgggatg tgtatggata tctttgttat gctactggtc ccgaagcgat gctgttcttc    960

aatactcgga acgatatcag atacctgaag attaagacta aagaaatggt cacagtggct   1020

accgacatca aagagggtca tggcgtttca ttcgacggga cttacattta ttgggtggag   1080

acagcacagg gacatcagtc catcttcaaa gcacaactcg gagacgtcaa ggatacaaag   1140

gaggtactgg taggtctcgg tctggaggac cctggcgaca tagcagtgga ctacctgggc   1200

gggaacatat acttcagtga tgcggagcga ggaatcatct ccgcttgcag ggtcgacggc   1260

tccatctgca ccacgatcaa gactcatgct aacaacccac gatttgtcac tcttgatcct   1320

aaaaatggta agatgtactg ggcagactgg cacgagcgtc cagtgataat gtcagctcgg   1380

atggacggca gccgacacga tgagctggtg gacaacttgg agaactttgc caccggcctg   1440

gccgtggacg cgccaaacgg gagactgtac ttcgttgaca aaactatcaa agtcgtcatg   1500

attgcggaga aacatgttta tgctttattt gaagagccct tccaccatcc gtactccatc   1560

tcagtgttcg agaacactgt gttctggagt gactggacct ccaacagtat acagacgact   1620

gacaaagtgc acgggaccgc gcagaagagg aatgttctac tcaaacttga tacacctgta   1680

ctaggcatgc acatgtacca tccagtgctg atgaacacga catcgaaccc gtgcagcaac   1740

aacaactgct cgcatctctg cttcgtcacc tccaacgcca cccacgtctg cgcctgcccc   1800

gatggcatgg agattgagaa taatcagtgc catcacgtag gcaactaccg cgccaagtac   1860

ctggtggtgg gaagtgggca gctgttcaca aagatccagt acaacgcgct cggcaacccg   1920

gagtgtcacg ccacgcactt cgaaatcgga cgcgtgcagg ccatggcgta cgatcggtat   1980

agagattcac tattcatata cgacggccag cgacggacca tcaactacat aaacatgagt   2040
```

-continued gacttcactc tcggtatcac tcacgtgttg atctacaacg gactggagaa cgtcgtcgac 2100
atggattatg attacgtgac agataacctg tacgtgctgg atgcaagtcg tcgtgtcgtt 2160
gaagctgtgt ctctgaggac tcagaagcgc gccatagtac atcgattcga cattcaagaa 2220
ctgcctgtta gcttctgtat tctttcggac tacgggagaa tgttggtggc cgtggtggag 2280
agtgagatgc acaacaccat tcatatcgac agcatcgggc tcgacgggac ccaacggaga 2340
cacgtcatca tgaacaattt gaaaggtcct catattcgat tgcggtacgt gccagatttt 2400
attgggcgcg actggaccca acggagacac gtcatcatga acaatttgaa aggtcctcat 2460
attcgattgc ggtacgtgcc agaaactgag caggtgttca tatccgacga gagcaacggc 2520
atcatcgatt tcatacatcc tgaaggcacc gggcgggaga actatcggga gctgacctcg 2580
acggtgacca gcctcgccat agcagataac tacgtcttct ggacagaccg aaagaccccc 2640
agactcttct ggtctgacat acacgaagcc tcgccgaaga taaggaggat tgatctggca 2700
cttttcccaa acactacgca acttctgatc caagcaacga actcgctccc tgatccaaaa 2760
gaccctcttc tgaaccatcc ctgtctaaag aatccttgtt ctgacgtctg tgtccaactt 2820
ccccatgata ctccagaaga tcacccgaaa ctagcaaact tcgagatgaa gtacaagtgt 2880
ttgtgtcctc ctgggttgtt ggtgaatggt aaccagtgcg ccaaacctgc gacatgtggt 2940
tcggatgaga tactgtgcca taggagtaat atttgtgtga agcaagatgc caggtgtgat 3000
ggaaaggccg actgtccgaa gaatgaagac gaggaaggtt gtatagtgga tccggcaaac 3060
atatgttcat cagacgaaat attctgtcgc ggcttgtgcg taaacaggga caaagccacg 3120
acgtgttcta ccggagaaaa aactaataaa gcactacctt cgaacaactg cagcagcaca 3180
gaattccagt gcacggacac ctcaatctgc atctctcggt cgcaggtctg tgaccaacac 3240
atcgactgtc ctaatggatc ggatgagcag ctcttagagt gcgacatcta ctcttgtcat 3300
gaaactgagt tcatgtgtgc gtccggctca tgtatagtga aaacgtggac atgtgatgga 3360
gaccgtgact gtaatgatgg atctgatgaa atcaactgcg tgaacatgac ttgcggcctg 3420
ggcttctacc agtgcagaga cagggagtgc gtggagttat cgaagaggtg tgacggacat 3480
cgggattgct cggattactc cgacgaagag gactgtgatg agcctcaaat tgtcgagacg 3540
atagaagaag ccccgaaatg tgctgcgtgg gaatatactt gtgaaaaaaa tactagcatt 3600
tgtttgcctg aaaccgctcg atgcaacatg aagacggact gcccgggtgg cacggatgag 3660
cacggttgcg accaccgctg tgccccgaag ggaatgtttg cgtgcggcca acaggtcact 3720
tgtatcacaa tgaacaaggt ctgcaacgga cgactggatt gtgatgacgg atccgatgag 3780
acgcctgatg cttgttctca ggtgaacagg acctctcacc tgttcccagt agctcggaca 3840
ttcactgaat gtactgaggg ttataagtgt aacaacggac agtgcattga gtggtcacag 3900
ttgtgtgaca agaagaggga ctgcatcgat gggacagatg aaaatggact ttgcgatact 3960
gcatgcgcaa acagcacatg tacgttcatg tgtcagccga ccccattcgg acgtcgctgt 4020
ctgtgcccct ttggcttcca aatttccaag gatcagttct cgtgcgagga catcgacgag 4080
tgcactgaag atgtctgctc tcaagggtgt atcaacgtgc cagggtcctt cctgtgctgg 4140
tgccatcatg gttatgccat caggaggaca gaccgtcgct attgcaaggc gatccgcggc 4200
aacatgtcga tcctgtacgt gtcgggtaac accgtgcggt ctatctcagc agacgggtac 4260
ggtgctatcg agtataccga tactaatgcc tcggccatca ctgatatgga ttataatgtt 4320
cggcagaaga agctatacgt gacctcggaa gcgggtggca agttgttaga agtgaatgag 4380

```
acgcagaatg tgatcgctgt tacgaacgtt gggaaaccat cgagggtggc agtggactgg   4440
gtgaccggca acgtgtactt cgtggacacg acgccatttg accagcgcat acgagtctgt   4500
catgtcaaga ggaagcgctg cgcttccctg ctgaaacttc cttctgatgc cacggtgaca   4560
gcgttgatag tagagcccag ttccagccgc atgttctact gcgtcactcg gaagctggag   4620
tcggtgatct ggacagcgaa cctggctggc agacacgtga cggatctggc tactgtacgg   4680
aactgcaccg gtctggccgc agactccttc aagaagaagc tgtacgtcgc agagacgggc   4740
ccagcgcata ttattaggat ggattatgag ggggagaatt tcaacaaaat cctctcagat   4800
cacccacgtc tgcaagcacc gcatggacta gaaatattcg aagactacat ctactacttg   4860
gaagccaact cgttccgcct cagccgctgc cagctgtacg ggccaaaaca ttgtgaaact   4920
tatgtgtacc gtgtgtttga cgccaacacg ttcgtcattc gccacgagag catccaacgc   4980
gatgacatag tcaacgaatg tgaagatgtc gtttgtgaca acatttgtgc cgtggacgaa   5040
gatgggccca aatgtttgtg tgacgatgga gccttggcca agagtgggaa gtgtcctgtg   5100
gttgataaga aattggtacc tttattcaac ggctggtcgt acgagcagct ggcatcggct   5160
cgcagcatcc ccttcaccgt caccttggga gtactgaccc tgatcgccat ctacctctgc   5220
gtcttcgtat actaccattg tatatacata cccaggaaga gaatgttagc atctgcttac   5280
actgaagttc ggttccagaa cacacaaaat acgtcctatc ctgaatcaga cccggtagtg   5340
gagatgcatc cctcaaggta tctaccttag                                    5370
```

<210> SEQ ID NO 33
<211> LENGTH: 5341
<212> TYPE: DNA
<213> ORGANISM: Phyllotreta cruciferae

<400> SEQUENCE: 33

```
tcagcagttt tcgcacccga aggaaattgc acctccgacc agttccaatg ctccgaccag     60
cgatgcataa actttaaagc cagatgcgac tcaaaactgg attgcccgga cggatcggac    120
gaattagaat gcgatctgca tcgctgcgat gagccggagt tcttccgctg taaaaataac    180
agatgcatca gtcacgcttt cgtctgcgat aaacagaacg attgcgagga cttctccgac    240
gaggcgaact gcgacagctt ccagtctttg gtgtcttcgg cttgcgaaga gggccactgg    300
aagtgcgccg acaaattgtg catacccaac gattgggtgt gcgacggcac gccggaatgc    360
atcgacggat ccgacgagac catcggctgc agcacccaga tcgcctgcga cgggttccgc    420
tgcaagaaca agcactgcgt gcccaaagag tgggtctgcg acaaccacaa cgattgcatc    480
gataacagcg acgaggagga ctgcgagaac cacatcccca tcgaccagtg cacgctggac    540
aagcgcaagt tcctctgcca caacaacgtg acttgcattg acaccgagtc ggtttgcgat    600
ggagtcaata attgtccaga caattcggac gaatccctgc aatgtaacgc gtcagtgaag    660
gcttgcaaag gcgatcacca gtgctcgcac gtttgcatcc cgctgcccga aggccccaag    720
tgcgtctgtc ccgcggggta ccacacgctc gacgagaaaa actgcgagga tatcaacgaa    780
tgcgaaacat acggtatatg cgatcaaatg tgccggaaca cgccgggttc gtacgaatgc    840
tactgcgaca aggcgtaccg tttggcggag gacaagaaaa cctgcaaggc ggagggcgag    900
gtgggcatca tggtgttcag ctcgaaggat caaatcagag cggtggcgct ggattcgacc    960
agctacatca tcgtcgccaa gaacttgaag aaagtggtgg gcgtcgattt cgacggtcgc   1020
cgggtctact ggacggagat atacggggga tacgagaaca tcgccaggag cgccgaggac   1080
gggtctcaga aggaggtgtt agtaacggct ggcgtagatc taccagagga tttgtccatc   1140
```

-continued gattggttga cgggtaacat ttatttcacc gatggcgaga agcagcacat cggagtttgc 1200
tcgccggacg ggacccattg cgctgtttta atcaataagg acatcaggaa acccagaggg 1260
atcgttctta acgtggtgga cggcgacatg tactggacgg attgggaaga tccggcgcga 1320
atcggttact cgctaatgga cggatcaaat gataagcctt tcgtggaaaa agacatacat 1380
tggcccaacg gtttagcatt ggatcatcct aatagtagat tgtactggac ggatgctagg 1440
aagatgacat tggagagcat acgtttagat ggaactgatc gaaggataat attagaagac 1500
atcgtgaagc atccgtacgc catagcagta ttcgaggata aattgtactg gtcggattgg 1560
gcgacgcgaa ccatccaaca gtgcgacaaa ttcgacggga agaaccacaa aacgttgatc 1620
gaagagaaag agctcatcta cgggatcagc atattccatt cggcgcagca gaagcgcagc 1680
aaaaacccct gcgagatggc gctgtgcagc gacttgtgct tactgaaagg tacatcgtac 1740
agctgcgctt gtccacagaa caaggtctta caatccgacg ggcttttttg taaagaatta 1800
tcgcctacag aaactcttat cgccgctcat cgggatatgc tagtacatat agagcatccg 1860
attcttggta ggcatgttgt tacagctcta cccggcgcca ctgcagacat agaaagcatg 1920
acattcgaca gctataagaa tgtactgtac gtcagcgact tcaagaccag gaggatcagt 1980
actttgcaca tgaagaccgg tagtagcaaa gttatggaca tttccgattt gggtagaatc 2040
agcgctatgg atttcgattc taaaagcaac aatctttaca tctgcgattc ggtacgcaaa 2100
gtggtggaag taatcagtct caacacgatg gcaaggcgga ttttaatcca cgacacgttc 2160
ggagaaatcc cccaaagtat cgcgttagtc cccgacgaag gggtgatgtt tgtaagcttc 2220
ggaggcgagg gacccagcca catcgatcgc ttctccatgg acggtacgga tcgaactcac 2280
tctatagaca ccaaactaac ggggccagtg tcactggcgt acgatcccga tttacacagg 2340
gtgttcttcg ccgacgccac caacggctta atcgaatcca ccaacgtgga cggcgacgat 2400
cgcatccact tcagaaccgt cgattctcac cccatcagct tgctggtgct caaagacgat 2460
gtgttctggg tgaacgtgca ctcgaagcag ctctactgga cctcgaagaa agtcccatcg 2520
aattacgaca agaaaattac gctggcgttc cccgacgatc cggacaaggt gcacttggtg 2580
tcagtaacgt cgcgccatgt agagagcaac ttatgtcgca tcaacaacaa cggttgcagc 2640
catctgtgct tgcagtcgca gaagtccatc gtgtgccagt gcccgatcgg ctgggagctg 2700
aaggaggaca accgcacctg cgccaagaga gtgggttgca tcggcggcga gtttttgtgc 2760
caccactcca acacttgcat tttgaaaagc ctcagatgca acggccacaa ggactgcttg 2820
tttggagaag acgagagcga ttgcgcagct gcagcgaaat gcggaggaag cgagttccaa 2880
tgcgccaacg gcgattgcat agctgcggat ctggcctgca accatcggta tgattgcaag 2940
gataaatctg acgagcacgg ttgcgatgat gttaagaacg gcactcgatg cccgccagat 3000
cacttcacct gctcgaacgg ggattgcatc agccagcatt tccactgcga tggcgtctcc 3060
gattgcacag acaactcaga cgagattcac tgccaggtga acgattgtaa tgcaacgcaa 3120
tttaggtgcg attcgggctc ttgcattccc aaggaatggg agtgcgatca cgattacgat 3180
tgcatggata gttctgatga gcattgcaat gcgctgtgcc cggagagcca cttcaaatgc 3240
gacaacggcc tgtgcgtgga caagaagtta atgtgcgacg gtttcgacaa ctgcggcgac 3300
cactccgacg agaagatgca catgtgccac cagagggccg cgcacaactg caccgcctac 3360
gagacggcct gctcgtccaa cgcctccatt tgcattcctt tggaagcgaa atgcgacggg 3420
aaatccgact gtcccaagca cgaagacgag atcggctgcg ccatgtgcgc cgacgaggat 3480

-continued

```
ttcgagtgcc gcaacaagca tttgaaggac tgcattccga ggatgtggct gtgcgacggc   3540
atgaacgatt gcggggacaa cagcgacgag gacttggtga tgtgcagcaa aaagaacaga   3600
accatgttcg ctccggccca agtaccctgc accgatggct tcaggtgcga taacggcaac   3660
tgcatcaacg catccttgct ctgcaacggg aaacacgact gctatgatgg ctctgacgaa   3720
ggaggcttgt gcaccgggtc ctgcgaaggc tctaagaatc cttgtaatca catctgcatc   3780
aaaacaccga aaggtcctaa atgccagtgc aggtcgggct acaagttgat gggcgatggt   3840
aaaacgtgcg ttgatgagaa cgaatgcgag gtctatcctc ccatatgcag ccaaatttgc   3900
cgcaacagag aaggcggtta cacttgcgat tgcttccaca acttttattt aagaaaggac   3960
atgaaatcct gcaaagcggc gggttccgac atgttgatct acttcaacgt gaacggcaat   4020
caaatctacg aaatcgcgcc gaagaacaat tcgatgagcg tcgtccagga agagtcgatg   4080
ctgaagatca cgagtctgga tactctggtg gactctaagg agctcttctt cagcgtgcag   4140
gacaccggcg ccatctacaa gctggatccg gctacaggaa ccatgcacta catcaagaac   4200
ttgggcgagc cgaagctgat agccgtggat tggtcgacgg ggaatgttta ttatcacaac   4260
gcccaatcgg acgcgaaatc gatcggggtg tgcaattacg aggagaagtg cgccaaattg   4320
atcgacatcg acgcgcatcg acaggtgtcc gcattggctg tggattcttt caacaaagtt   4380
ttgttctatg tggtcagatc gtggacgata ttcgcatcgc ccagctacgt tatatacaaa   4440
accgatttgg acggtagcaa cgtggtggaa ctggtcaaaa caaatatagg caacgtggaa   4500
cacatcacct acgatttgaa caaacgacag ctgtacttcc acgacgagaa cacccagcaa   4560
atcaacgtga tcggctacga agggggccgc accaaatccc tcttctacaa cgtgacttta   4620
atcgaagggc tcagactgtt cgaagataat ttgtactact tgcgccagga cgggttcctc   4680
atcagatgcc agttgttcga agaggccgcc tgtcactacg gtttcaactt gcacagtttg   4740
gctagggacg agttcgtaat ctcgcacaga tcccttcagc ccttcgttgg gcacgtctgc   4800
gatgggcatg cttgccccta catgtgcgtg gctggacaag agggctattt gtgcgtttgc   4860
catgacggct cgaccagtgg cgaatgcggc acaccgcaag acgagaacgg cgagaacaaa   4920
ttcaaagtaa cttccatcga gggaaaatcc agatcttcgg cgtttttgtc cggtttcgcg   4980
gtgtttgggg tactagtagc atgcgtcatg attatacttg gggcttatta catgataaag   5040
aggagaagcg gtgataacag taccgatttg agcatcgtgc gatttcaaaa tccgctttac   5100
ggaagacccg tggaggacga gaaacctatt ttggagcccg ggaagcacga gtacgtgaat   5160
tgtttgtacc aacacaaagc ggatggtggc gaaaatagca atactgaacc caaaacgttc   5220
aacgtctgtg atgataattt gtgttaattt attgtttttt tatgttttac gttaattagg   5280
tgcattattt gattgttaat tctatttata acacattatt atatgtatat acaaattgtt   5340
a                                                                   5341
```

<210> SEQ ID NO 34
<211> LENGTH: 5341
<212> TYPE: DNA
<213> ORGANISM: Phyllotreta cruciferae

<400> SEQUENCE: 34

```
tcagcagttt tcgcacccga aggaaattgc acctccgacc agttccaatg ctccgaccag     60
cgatgcataa actttaaagc cagatgcgac tcaaaactgg attgcccgga cggatcggac    120
gaattagaat gcgatctgca tcgctgcgat gagccggagt tcttccgctg taaaaataac    180
agatgcatca gtcacgcttt cgtctgcgat aaacagaacg attgcgagga cttctccgac    240
```

-continued

```
gaggcgaact gcgacagctt ccagtctttg gtgtcttcgg cttgcgaaga gggccactgg    300
aagtgcgccg acaaattgtg catacccaac gattgggtgt gcgacggcac gccggaatgc    360
atcgacggat ccgacgagac catcggctgc agcacccaga tcgcctgcga cgggttccgc    420
tgcaagaaca agcactgcgt gcccaaagag tgggtctgcg acaaccacaa cgattgcatc    480
gataacagcg acgaggagga ctgcgagaac cacatcccca tcgaccagtg cacgctggac    540
aagcgcaagt tcctctgcca caacaacgtg acttgcattg acaccgagtc ggtttgcgat    600
ggagtcaata attgtccaga caattcggac gaatccctgc aatgtaacgc gtcagtgaag    660
gcttgcaaag gcgatcacca gtgctcgcac gtttgcatcc cgctgcccga aggccccaag    720
tgcgtctgtc ccgcggggta ccacacgctc gacgagaaaa actgcgagga tatcaacgaa    780
tgcgaaacat acggtatatg cgatcaaatg tgccggaaca cgccgggttc gtacgaatgc    840
tactgcgaca aggcgtaccg tttggcggag gacaagaaaa cctgcaaggc ggagggcgag    900
gtgggcatca tggtgttcag ctcgaaggat caaatcagag cggtggcgct ggattcgacc    960
agctacatca tcgtcgccaa gaacttgaag aaagtggtgg gcgtcgattt cgacggtcgc   1020
cgggtctact ggacggagat atacgggga tacgagaaca tcgccaggag cgccgaggac   1080
gggtctcaga aggaggtgtt agtaacggct ggcgtagatc taccagagga tttgtccatc   1140
gattggttga cgggtaacat ttatttcacc gatggcgaga agcagcacat cggagtttgc   1200
tcgccggacg ggacccattg cgctgtttta atcaataagg acatcaggaa acccagaggg   1260
atcgttctta acgtggtgga cggcgacatg tactggacgg attgggaaga tccggcgcga   1320
atcggttact cgctaatgga cggatcaaat gataagcctt tcgtggaaaa agacatacat   1380
tggcccaacg gtttagcatt ggatcatcct aatagtagat tgtactggac ggatgctagg   1440
aagatgacat tggagagcat acgtttagat ggaactgatc gaaggataat attagaagac   1500
atcgtgaagc atccgtacgc catagcagta ttcgaggata aattgtactg gtcggattgg   1560
gcgacgcgaa ccatccaaca gtgcgacaaa ttcgacggga agaaccacaa aacgttgatc   1620
gaagagaaag agctcatcta cgggatcagc atattccatt cggcgcagca gaagcgcagc   1680
aaaaacccct gcgagatggc gctgtgcagc gacttgtgct tactgaaagg tacatcgtac   1740
agctgcgctt gtccacagaa caaggtctta caatccgacg ggcttttttg taaagaatta   1800
tcgcctacag aaactcttat cgccgctcat cgggatatgc tagtacatat agagcatccg   1860
attcttggta ggcatgttgt tacagctcta cccggcgcca ctgcagacat agaaagcatg   1920
acattcgaca gctataagaa tgtactgtac gtcagcgact tcaagaccag gaggatcagt   1980
actttgcaca tgaagaccgg tagtagcaaa gttatggaca tttccgattt gggtagaatc   2040
agcgctatgg atttcgattc taaaagcaac aatctttaca tctgcgattc ggtacgcaaa   2100
gtggtggaag taatcagtct caacacgatg gcaaggcgga ttttaatcca cgacacgttc   2160
ggagaaatcc cccaaagtat cgcgttagtc cccgacgaag gggtgatgtt tgtaagcttc   2220
ggaggcgagg gacccagcca catcgatcgc ttctccatgg acggtacgga tcgaactcac   2280
tctatagaca ccaaactaac ggggccagtg tcactggcgt acgatcccga tttacacagg   2340
gtgttcttcg ccgacgccac caacggctta atcgaatcca ccaacgtgga cggcgacgat   2400
cgcatccact tcagaaccgt cgattctcac cccatcagct tgctggtgct caaagacgat   2460
gtgttctggg tgaacgtgca ctcgaagcag ctctactgga cctcgaagaa agtcccatcg   2520
aattacgaca agaaaattac gctggcgttc cccgacgatc cggacaaggt gcacttggtg   2580
```

-continued

```
tcagtaacgt cgcgccatgt agagagcaac ttatgtcgca tcaacaacaa cggttgcagc   2640
catctgtgct tgcagtcgca gaagtccatc gtgtgccagt gcccgatcgg ctgggagctg   2700
aaggaggaca accgcacctg cgccaagaga gtgggttgca tcggcggcga gtttttgtgc   2760
caccactcca acacttgcat tttgaaaagc ctcagatgca acggccacaa ggactgcttg   2820
tttggagaag acgagagcga ttgcgcagct gcagcgaaat gcggaggaag cgagttccaa   2880
tgcgccaacg gcgattgcat agctgcggat ctggcctgca accatcggta tgattgcaag   2940
gataaatctg acgagcacgg ttgcgatgat gttaagaacg gcactcgatg cccgccagat   3000
cacttcacct gctcgaacgg ggattgcatc agccagcatt tccactgcga tggcgtctcc   3060
gattgcacag acaactcaga cgagattcac tgccaggtga acgattgtaa tgcaacgcaa   3120
tttaggtgcg attcgggctc ttgcattccc aaggaatggg agtgcgatca cgattacgat   3180
tgcatggata gttctgatga gcattgcaat gcgctgtgcc cggagagcca cttcaaatgc   3240
gacaacggcc tgtgcgtgga caagaagtta atgtgcgacg gtttcgacaa ctgcggcgac   3300
cactccgacg agaagatgca catgtgccac cagagggccg cgcacaactg caccgcctac   3360
gagacggcct gctcgtccaa cgcctccatt tgcattcctt tggaagcgaa atgcgacggg   3420
aaatccgact gtcccaagca cgaagacgag atcggctgcg ccatgtgcgc cgacgaggat   3480
ttcgagtgcc gcaacaagca tttgaaggac tgcattccga ggatgtggct gtgcgacggc   3540
atgaacgatt gcggggacaa cagcgacgag gacttggtga tgtgcagcaa aaagaacaga   3600
accatgttcg ctccggccca agtaccctgc accgatggct tcaggtgcga taacggcaac   3660
tgcatcaacg catccttgct ctgcaacggg aaacacgact gctatgatgg ctctgacgaa   3720
ggaggcttgt gcaccgggtc ctgcgaaggc tctaagaatc cttgtaatca catctgcatc   3780
aaaacaccga aaggtcctaa atgccagtgc aggtcgggct acaagttgat gggcgatggt   3840
aaaacgtgcg ttgatgagaa cgaatgcgag gtctatcctc ccatatgcag ccaaatttgc   3900
cgcaacagag aaggcggtta cacttgcgat tgcttccaca acttttattt aagaaaggac   3960
atgaaatcct gcaaagcggc gggttccgac atgttgatct acttcaacgt gaacggcaat   4020
caaatctacg aaatcgcgcc gaagaacaat tcgatgagcg tcgtccagga agagtcgatg   4080
ctgaagatca cgagtctgga tactctggtg gactctaagg agctcttctt cagcgtgcag   4140
gacaccggcg ccatctacaa gctggatccg gctacaggaa ccatgcacta catcaagaac   4200
ttgggcgagc cgaagctgat agccgtggat tggtcgacgg ggaatgttta ttatcacaac   4260
gcccaatcgg acgcgaaatc gatcggggtg tgcaattacg aggagaagtg cgccaaattg   4320
atcgacatcg acgcgcatcg acaggtgtcc gcattggctg tggattcttt caacaaagtt   4380
ttgttctatg tggtcagatc gtggacgata ttcgcatcgc ccagctacgt tatatacaaa   4440
accgatttgg acggtagcaa cgtggtggaa ctggtcaaaa caaatatagg caacgtggaa   4500
cacatcacct acgatttgaa caaacgacag ctgtacttcc acgacgagaa cacccagcaa   4560
atcaacgtga tcggctacga aggggggccgc accaaatccc tcttctacaa cgtgacttta   4620
atcgaagggc tcagactgtt cgaagataat ttgtactact tgcgccagga cgggttcctc   4680
atcagatgcc agttgttcga agaggccgcc tgtcactacg gtttcaactt gcacagtttg   4740
gctagggacg agttcgtaat ctcgcacaga tcccttcagc ccttcgttgg gcacgtctgc   4800
gatgggcatg cttgccccta catgtgcgtg gctggacaag agggctattt gtgcgtttgc   4860
catgacggct cgaccagtgg cgaatgcggc acaccgcaag acgagaacgg cgagaacaaa   4920
ttcaaagtaa cttccatcga gggaaaatcc agatcttcgg cgtttttgtc cggtttcgcg   4980
```

```
gtgtttgggg tactagtagc atgcgtcatg attatacttg gggcttatta catgataaag   5040
aggagaagcg gtgataacag taccgatttg agcatcgtgc gatttcaaaa tccgctttac   5100
ggaagacccg tggaggacga gaaacctatt ttggagcccg ggaagcacga gtacgtgaat   5160
tgtttgtacc aacacaaagc ggatggtggc gaaaatagca atactgaacc caaaacgttc   5220
aacgtctgtg atgataattt gtgttaattt attgtttttt tatgttttac gttaattagg   5280
tgcattattt gattgttaat tctatttata acacattatt atatgtatat acaaattgtt   5340
a                                                                   5341

<210> SEQ ID NO 35
<211> LENGTH: 5186
<212> TYPE: DNA
<213> ORGANISM: Nezara viridula

<400> SEQUENCE: 35

ctggaacgag tttaatttat tgtttgtcac aacactaatc attctggtca cttctagcga     60
acaacatgag acagaatgcg atgataattt cttcagatgt cgctcaggca gatgtatatc    120
tatgagcttc atttgcgatg gatatgaaga ttgcggccat ggggacatgt cggatgaaga    180
gaattgtcat atgaccacta ccccaggaac gaaaccatgt aataaggatg aataccagtg    240
ccaagatagg ctatgcattc cttcgttatg ggtctgcgac ggtgaagcgg actgtttgga    300
tggcagcgat gagactcatg gatgtactgc ggggacatgt gacggttttc tgtgccacag    360
caagacttgt atccccaaag agtgggaatg cgatggcgta agggattgtc ctgataattc    420
agacgaattg ttctgtacta agaaaccagt gaactcagaa gaatgcagta ttcatgaaaa    480
tggtttcttg tgtcgtgatc aaatgaaatg tattgaattg aaagaagtct gcaccctgat    540
tgtgatgata gttctgatga aggtggcgtg tgcctcgttt caaacaaaac agatacatgt    600
actaatctga aatgttctac taaccaaggc tgcataaatat tacctgaggg gcctgtatgt    660
actgaggtgt gcatgaaagg ataccacttc actggtggtt cttgtttcga tatagatgaa    720
tgtttatcat ttggaagttg tgaccaaata tgtatgaaca caattggagg ctacaattgc    780
tcctgtattg aaggctataa atttaatatt gatttgaaca aatgcaaagc taaaggaagt    840
gaaggcatat tatttttcac ttcaaaccaa gaaataagag gatattattt agactctgaa    900
gtctacttta aagtagtaga aaatctacca catgcaacag gagtaacata tgatggtgtt    960
aatgtttatt ggacaacagt agcagatgag gaagaaacaa ttgtcaaagc agctgaaaat   1020
ggtgaaaatc aaaaaataat tgtaacttct ggtattggca gacctgaaga tctggcagtt   1080
gattggatta caaaaaatgt atacttcaca gattctaaat taaagtatgt aggtgtttgt   1140
tccaatgatg gatactattg ccttatgctc cacgaagatc aagtggaaaa accacgtgct   1200
attgtcctgc attcatcaga aggattgatg tattggtcag attggggaac agaacctgcc   1260
attatgcgtt caatataata aaatttataa aagatgacat tcattggcca aatggtctag   1320
ccatcgacca tggaacaaat tatttatatt gggtagatgc taaagaagca agaattgaat   1380
gtgtaaaact agatggaacc gacagaagaa aagtaccatc cactgctgta aaacatccct   1440
tttccattga tatttttgaa gatagaatct tctggagtga ctgggacagt gaccaaatcg   1500
tatcctgcaa taaattttct ggcaaagatt gccatacaat aataaaagaa agagaccata   1560
agatttatgg tatccatgtc taccatccta gtaaaggaag ttattaatcc ttgccttgat   1620
gttcaatgct ctgatatatg cctaatttct ccgaaaaata tggatgatga tttgcaatat   1680
```

-continued

```
acttgtgctt gtccttatca taaaaaactt agcagagatc atcatacatg tattgaggat   1740
aagccacttc aaaccataat tgtgggttct ggacagcaga tcattaaaat acaacataaa   1800
aaatttggag gatttagttc agatcatttc aaactaacag tattaaggaa aataggtgct   1860
ctagcttatg atccaaattc agatagaatc attgtaagtg acttagttag acgtaaaata   1920
ttttcattca acgttaaaag tttcgaatca gagatattaa ttgaacacaa tattggaaaa   1980
gttgttggta tggatgttga ctattatgaa aataatctat attggataga tgatgagaaa   2040
aaaactattg aagttatgaa tttgcaaaac aaacatcgat taacactcat acgagatcta   2100
aatgaaggtc tcaatgatat agcattggtg tttatgtttg ttgcactttc aacatttgag   2160
ggtgcacaca ttgacaggat atcaatggat gggcgacaaa cttccagaat tcatgtaatt   2220
gaagagaaac tatttggccc tttgtctctt agctatgatc ctaaacttga gcgactgttc   2280
tggtctgatc aaatgggagg tgaaatagct tccacagctg ttgaaggact tgatcgacat   2340
atttttaaag acggacattc cggtccagta gatgttgcag ttactgagtc agaagtattt   2400
tggcttggtt atggagctac gaaggttttt tggtcaaata agtttgatgg atctcttaca   2460
aaaagattta ttttagacaa gcttgaagaa actgataaca tgaaaatcat tggattaaat   2520
aaaggtttaa ggaaggaagc aagtgcttgc aatgcccttg gaaactgcag tcatgtctgt   2580
ttgatttcta cacatatggg gatttgtgca tgccctgacg gaatggagct tggatttgat   2640
agaaaaacct gccaaaaatt acttgcctgt aaagaaggac aatacaaatg taccactggt   2700
gaatgtattt caaagtctct acgatgtaat ggtagatcag attgtaggct tggtgatgat   2760
gaagaatatt gttctataat ttgttcacca gaccagcttg cttgcttaga tggttctagt   2820
tgtattgaaa aatctaaaaa atgtgattct aaagttgact gcaatgacgg ttctgatgaa   2880
aaatattgtg aatctactcg gaattgtact ggaaatgaat tccaatgcac atcaggagaa   2940
tgtgtttcca aagtagcaca atgtgatggc atgaatgact gcaacgatgg cagtgatgaa   3000
agcagttgta atgctttcac ttgtaaaact aatgagttcc gctgcaatac aggaaactgt   3060
ataccaaatt catgggtatg tgacagtcag attgactgta atgatggttc tgatgaaggt   3120
ccaaaatgtt ctgaaattga aggatgcgat gaagatcagt ttacttgtga caatggtcac   3180
tgtatttctc atgttttggt ctgtaaccat gaagatgatt gtgaagattc atctgatgaa   3240
aaatattgtt actttccaaa aagcaaaaaa aaatatgata atgaggaaaa taagactcag   3300
gattcatcaa aagactgcca atttttatgc ccttcagatt taaaaaatatg tttgccttca   3360
tcagggagat gtaatggaac ttcagagtgt ccagacggag aagatgagct tcgttgcaac   3420
aagtgctctg aggaagaatt cacttgttct tcgagtaagc gatgtttgcc aatgacatgg   3480
gtttgtgata atgtcagtga ttgtgaagac cagtctgatg aaatgcattg ccttaatgga   3540
accttggctg tacacgatat gtttatttca gacaatcttc tatgtgatgg tttattctgc   3600
aaagatagta agaaatgtat tcccttaagt aaactgtgtg attctcttat ggattgtact   3660
gatgggtcag atgaaaaagg cctttgcggt aagggatgtg aacacgctgc atgtcatcac   3720
aaatgtaaag agacacctat gggacctagg tgtgaatgct taagtggtta tactctagga   3780
ggtgatggta ggacttgcag tgacatcaac gaatgtgaga aaatgtcttc ttgctctcaa   3840
tattgccata atactgttgg cagttatagt tgttcatgca tggatgataa ttttcaacta   3900
agatctgata aaataagatg caaagcaaaa ggaactgaaa tgaagtatta ctttgccacg   3960
aaaaaagaaa ttaaatataa atcccaatcc ttacagcaaa cagttgtagt gtatcaatca   4020
cagcgtgata tggatatgaa aggaatggat tttgatatga ataatgatat aatattttgg   4080
```

```
acttcagaga ttagtggtta tttgtacaaa gttgatatta aatctaaaaa catcactcaa   4140

attacaaacc tcataagacc aacaaaaata tcatatgact gggttactgg taatgtttat   4200

gtccttgaaa acttcaaaat tataagagtt tgcaattttg aagctaaact ttgttcagca   4260

ttgtacacag ctaagaatgg tatcaacatt gaaaccattg ctcttgatcc aaaatcgaga   4320

atcatgttct ggtctgaaag taaatggtta ataaatcaaa cacccaatag tacacttcag   4380

ctggcatcaa tgagtgcaga taatccttgg gcagtgctaa gttttgattt tagtccagtt   4440

actgatattg tagttgatca ttttcacaaa gttgtttatt ggtcaaactt agcagaaaat   4500

aaaattgaaa gatgtagtta tgatggaaaa gacagatctg tattattgcg tagtgagtat   4560

cctccaagag acttggtact gtttgaagat tatttatact gggtaaatga tcaaaaacaa   4620

tctcacatta ttcgtccaga agcagaagga actattacta aatatgggct gtatggatct   4680

gtgtatatga agcatgaatc agtaaggctt ttaccttctt catcctacaa tgaaattaaa   4740

gctttccggg tttcacagtc tgcactccag cctgaaggag tgaatcattg tagcaaaatc   4800

acttgtaatt acttgtgcat aagcaatgaa aacgaaccaa tatgttactg tgaagatggc   4860

tcaaaagtga aacccggaga tatatgcaac aatcatactg gaatacattt caaaacctat   4920

gaaacagaaa atgtatcagg gagtagttca gtattagctt ggtttttctg gattggtggg   4980

ttagttatag cagctggact tggttatgca agttatcatt ttgtagctaa ctatgttcaa   5040

aaaaataaaa tacacccaag gttcagtgta tttttttcctg ttggccgttc tgaggctcag   5100

agagaacaag gatcacaggt tcatcagttt gaaaacccta catatagtga ggtcattgtg   5160

gtataatgaa atatgaagtt aattta                                        5186
```

<210> SEQ ID NO 36
<211> LENGTH: 3378
<212> TYPE: DNA
<213> ORGANISM: Diabrotica virgifera

<400> SEQUENCE: 36

```
agaatgacgg attgaattga aaaagaaaca gctgaacaag aattaactgt ctacgaatga     60

tgaaagtaaa ttgatgaagt ataaaactta gaaattagat aacagaagta gtcaactgca    120

tccaaattca gctgatttag ggcatttacg ggaacctttt accttttggg aagtgaaagt    180

ggccgtgata tcgaattagt ataaccgaac tgaaaatgac ccatgtagta caaacacaaa    240

aacaagtcat tcgttaattg gtaaaagtgc ctaaggtcct attttcatct tgtaactatg    300

aaggattgtt taaagtgttg ataagttagt aatgtaccct aaaattaatt gtgtgtaatg    360

aatacctgct agtaattacc gaatttggag cgagaaaaga gaaagaaaat gtcatcgata    420

aaaagtggag gtctaaccaa aaaggaaggc aagatgagga tcagagcctt cccaatgact    480

atggatgaaa aatatgtaga aagtatatgg gctttattaa agaatgctat acaagaaatt    540

caaaagaaaa ataactcagg tttaagtttt gaagaattat atcgaaatgc atacaccatg    600

gtattacaca aacatggtga acgcctttat acaggattaa aggaagtggt cacccaacat    660

ttagaagtga aggttagaga agatgtgtta cgatctttac ataataattt ccttatgact    720

ttgaatcaag cttggaatga tcatcagacc tccatggtta tgattagaga tatactcatg    780

tatatggaca gggtctatgt ccaacaaaac gatgttgata atgtatataa tttgggactt    840

atcattttta gagatcaggt ggtacgttat ggctgtatta gagatcatct tcgagagact    900

ttattagata tggtaatgcg agaacgtaga ggagaaaaag ttgatagaat ttcaattaaa    960
```

-continued aatgcgtgtc aaatgttaat ggtacttgga atcaactccc gagttgtcta tgaagaagac 1020
tttgaacggc ctttttgca acagtctgca gaattttata aggtggaaag tcaacggttt 1080
ctggctgaaa atagcgcatc agtgtatata aacaaagtag aagcgcgaat caatgaggaa 1140
tccgatcgtg cgaaacacta tttagataaa tcaacagaat ctcgaattgt tgaagtagta 1200
gaagaagaac tgatcaaaaa acacatgaag actatcgtag agatggaaaa ctctggtgtg 1260
gtacacatgc tgaagcacca aaagaccgaa gatctatgct gtatgtacaa actgttcggt 1320
cgcgtaacag atggtttgaa aacaatggca gattgcgtca gtttgtatct tagagaacaa 1380
ggtaaagccc tcgtccagga agaagaacac cagccggcca ccaatgctat ctccttcgtg 1440
cagtcattgc tcgatctcaa agacggcttc gaccatttcc tccagaattc ctttaacaat 1500
gataaaatat ttaaacagat gatagcgtct gattttgaac atttcctcaa tttgaatccc 1560
aaatcgccgg agtatttgtc gctgtttatt gatgataagc tcaagaaagg tgtaaaaggc 1620
atgaaatctt ctaaccttga aagattcctc aatttgagcc ccacatcgtc agaatatttg 1680
acgctgttta gtgacgatta cctcaagaaa ggtgtagaaa tcatgaccga acaagagata 1740
gaacaagtat tggataagtc aatggtttta tttaggttcc tccaagagaa agacgttttc 1800
gaaaggtatt acaagcagca tcttgccaaa cggttgttgt tgaataaatc tgtcagtgat 1860
gattatgaaa agaatatgat ctctaagtta aagacggagt gtggatgcca atttacttct 1920
aagttagaag gaatgtttaa agatatgact gtttccaata cgattatgga tgaatttaaa 1980
gaacatgtta cgaagtctga gacaaattta ggtggaatag atttattaat gcgagtgctg 2040
acaactggct tttggcccac acaaaacgca accccaaaat gtcatatacc agctgtacca 2100
ctagctgcct tcgaatgttt taggagattt tatttagcca aacacagcgg ccggcaactt 2160
acgttgcaac ctcaacttgg aagtgccgac ttgaacgcta tcttctacgg cccgaagaaa 2220
gacgatagcg acaaggatgg cgcttgttct tcctcgacaa caatagtctc gatgaggtca 2280
gggcctagga agcacatcat acaagtgtcc acttatcaaa tggtagtttt gatgttgttt 2340
aataatcacg ataagttgac atatgaagag atccttaatg agtctgatat accagaaagg 2400
gatctaatta gggcgttaca gtcgctggca atgggtaaag caacgcaaag agttctcata 2460
aaaaatccca ggaataaaga aatagaatct aatcatgaat tctatgttaa cgaatcgttt 2520
agttctaaac ttcatcgagt gaagattcaa accgtagctg caaagggaga gaacgagccc 2580
gaaagacgag aaactaggaa caaggtcgac gaagatagaa aacacgaaat tgaggcagct 2640
atcgttcgga taatgaaatc gcgtaaacgc atggcgcaca acatcctcgt cacagaagtg 2700
acagaacaac tcaagagccg tttccttcct tctcccgtca taataaagaa aaggatagaa 2760
ggtctcatag agagggagta tctggcccgt acgcccgaag acagaaaagt gtacacatac 2820
gtggcatgaa ctttaacaag gatcattatg agactttgga tagtggtcca gtgatcttca 2880
atagatgaat atttacataa atgtaattat taattattaa attattccaa caggttcttt 2940
ttgtctaatt tcttcaagtt gttgaagaaa aataatgtat ttgtggaaag ataacttccg 3000
gaccatatta acaattttca atttatttat aataattttg tgatagattg attgacaaga 3060
taattttaga ttttcagttt gcaataaata atgtagagtg tgtttgatga tatattaaat 3120
ctcgatttgg acttttcgga aaattaacac gttgatggac agaacgtata ggcgtctaat 3180
ttccattgat gtaatgtgac acaacgtcta ttataatttt taaaataacg agttgtaaca 3240
aaaaatccat gtcagaaaat atcacatttc atctacagag gcacattgtt tccataaatt 3300
aaaagcgtta aaagaaattc agcaattttc ctattctact ttgcaaaata caaggtgatt 3360
cagtgaaacg gtacgatt 3378

<210> SEQ ID NO 37
<211> LENGTH: 1786
<212> TYPE: DNA
<213> ORGANISM: Diabrotica virgifera

<400> SEQUENCE: 37
caccggctta cgtaataatt aatttattcc tttcatttgc accatactat atattattta 60
ttgagtggac aaatgttaaa aagtaagtct ggcagcgaac gtgttaatga aacctagtaa 120
aaggctccaa catttgacac ttcttcatgc aacatgttct gttctgtgtc aatctaacct 180
aacctaacat tttcaaatac gaatatggaa acatttcacc acatcaacac gtgaattaat 240
attcgaaaat ggagtacgaa aatacacaac aaaatataaa cttcgtaccg tgtgtaagat 300
gggttaaacg aggagtggcc aattcaagcc cagtaaaatt gcaactgtcg aaaaacgagc 360
tggctcaaat tattaatgac accaagatta aattacaaga atccaatgaa aatgaagatg 420
agcctatgga agaaggtgaa acgtctcaaa cagatgagtt tgccttagag gattacgata 480
aagaagacga aaatgaggac actgcaaatg ctttaggaat tggatcattg gcagaactcg 540
ataatgatgc tgcagacaat ttttctgagt cagacgattc tgaaaaagaa gatgataaaa 600
tcaaaccatc tgacaatctc atactagtag gacatgtaga aggggatgca agtctattgg 660
aagtctacat atacaatgaa caagaagagt cattgtatgt tcatcatgat attatgttat 720
catcctttcc tctgtgttta gaaccgctaa actatgaacc gaagatgccc aaaggaaatt 780
attgtgcagt gggatcaatg tcacctgtta tagaggtctg ggatgtagat attatgaatg 840
ttattgaacc ttcatttact ttagggagac ctgctagtaa aaagaagaac aaggaacata 900
taggccatac ggatgcagtg ctttcattag cttggaacaa aacctttgaa catgtgttgg 960
ctagtggatc tgtagatcaa acaatacact tgtgggatat ggaaatcaaa aaaccaagta 1020
caaccattaa atccttccaa gaaaaagttc aatgtctcga atggcatcct ttagaggcac 1080
aaacactttt aggtggaggt tgtgacaaat ctgcaagagt atttgatggc aggacccctg 1140
aaacccacca aacttggcta cttgatggag aagctgaaag gctatgctgg aacccattag 1200
aacctttcac atttttagca ggtaccagca gtgggtctgt acagtgtttc gactgtagaa 1260
aaggacagct atggtcagtt aaagcacaca gcaaggaagt aacagggtta gtccttagca 1320
aacaatgcca aggattgttg attacttctt ctacagatga aacagttaaa atttgggact 1380
tggctacact ggaagctgaa cctaagcttg ttaatgaaaa ggagtttaat atggggaata 1440
ttcactgttt ggatttatgt ccagacttgc cgtttgttat atctgtaggt ggagataaga 1500
agtcaaataa ttttactgtt tttgatgtac agaatattga tgttgttaaa cacacatttg 1560
ggccaagagg attggtacag ctagttccag atacagaaga aaatactaat acgttttatt 1620
gtttaataaa gtttttattt tatttatttg taataatttc atgcttcttc tttaagtacc 1680
gtgcccaaat attagtcatt ggtagattcc ttgacaattt gccgatactg ttttcgatta 1740
ctgaacaatt catcttctga tgagccagtc cattgacaaa ggtttc 1786

<210> SEQ ID NO 38
<211> LENGTH: 3948
<212> TYPE: DNA
<213> ORGANISM: Diabrotica virgifera
<220> FEATURE:
<221> NAME/KEY: misc_feature
<222> LOCATION: (3773)..(3795)

-continued

```
<223> OTHER INFORMATION: n is a, c, g, or t

<400> SEQUENCE: 38

tggttcttac caacttccag acattttttt ttggtggtta aggcccatct aaaatgccca     60
aatcaaataa atctagaaat gcgttttact actttatgga ggattttaaa caaagacaag    120
gatttgcttg taaatcgatg aaggatgtag cagatgctgc aggtccccat tgggctagga    180
tgtctaaagc agaaagaaga ccttatgaag agagggcaaa caaagagaag ggaggtttga    240
gatatacttg ggatggtcaa tgcgttgaag atatagaaag gaggaacaaa gctgaggaca    300
ataaaattgc taagatgaaa gatgatatcg actgcacctt gaaatttgcc aaagaaaatt    360
gtcgactccg agatgaaatg ttcttcataa tccatatcaa tactttctgt taccatgcca    420
gtggtgatcg gtattatccc gctgaaattg ccatttcatg cttcagcttg gaggatggcg    480
ttttgcctca aaatgtgttt cataaaatta ttaagccagg tagactacca ctggggtatg    540
ctagtgacgc aaaaaagcaa tctgaagatt cacatcaact gcctatcccc ttaactggtg    600
acgacgacga caatgtggaa gaagtttata cagagatgaa agaatttata ttatctaaaa    660
ccggagatac taagaaattc cctcccttgt atgctaagaa agatattgtt aaaatgttgc    720
aacatgtgtt agacacttgg tgcgctgatt ttgatgagcc gccattattt aaagtttatt    780
atttacaata tatgtttcaa gtattaaaaa actcggtagc taacgataac gtatggccct    840
tatattcaat ggcagaaacg gaactggata aggatcttta ttcccatact gttggaatat    900
gttgtgaatt ccattctgtt agtgaagctt gtcaattttg cagcaagtca gtggcagtac    960
gacttgcata cacaatttgt gataattgct gttcgttcct agatattcct atagagcctg   1020
gaagacacgt acctgatcaa gcttttacag catccagttt gagctcaaga gcttcatcaa   1080
aagctagttt gtatacaggt tccagtaaat cttctaagaa gcagtcagtt cgtgaagatg   1140
acaaagacac tgttttatcg ttttctagtg cctctcagtg ggagagcgaa tctgtagtgt   1200
cagactcctc tacagctact ttcaataata gctttccagg tctgaaatcg aaatggacat   1260
taagcaattc tcaacctgta gaaactgact caatgagcca aatgtcaggt cagagctatg   1320
caagtgctat gggaactaga agacagtttt ctagtgcaat gggaaataga ggatctcaaa   1380
gagagtcctc taacaattcc aacaatggtg acactagtga ttcgaatacc gattatttta   1440
acagtcaatc atttccggct cttggaaggg gaagaggtat ggccagaaat cgaagaaatt   1500
gatcattttt gactgcaatg ggtcttgttc cacttcatga gattgttaaa tgagtatgta   1560
actgattaca ttaggcgaca atattttttt tagtgtcaga ttatttgatg taattgtcct   1620
tttgacaatt ctttaatcat tgatgttttc ttctattgtg gtgtttttag atgtcatatt   1680
tttatgtatg taaattggtt ttttatctaa gtatagaata ttacatttta gtttaataag   1740
ataccagtaa agtatattgg tttaccagtc gcctaatgta aactagtata tacataccta   1800
tattattttt ctttaatagt tttaagtcaa ttttgataca gatcacgaga cagatatttt   1860
ttccgtctag tccgaattgc gttccgtttc ttgggccttg tcgaattgcg tcccaaatat   1920
tttgcttacc tggccaccga taacgtctag tccgaattgc gtttcatttc ttaattagcc   1980
aacccaattg cggtcagaag atagcttaat aaatattagt taagcaggga aatacaatca   2040
acgtaatatc aactaacagt ttatttttat tttagcaccg aatttataac taacacattt   2100
aacgaaattg tatcttgaaa tttcacccct gttatactgg ttaattttct gttcgagaaa   2160
aatatatttg ctggaggtag ctttatctac atttctagaa atattttgtt taacagaatt   2220
tatttttata taagaatcgg tttgaatgcg ctttaatgtt tcaacaaaca aaaaaatatt   2280
```

```
aggatgtgga gacaaacaat aatttttaaa ttttgaatga aatcactcac aagaattagt   2340
tgttctatat atagatgcgc tattctttgc ccaaatttgt ggaggaaatg tgtagtcctc   2400
ttcgatatac ctttcaacta gatagtttgc aaatgcgtca actcgatgat catctggttt   2460
ttcaggcata aaatcttcca caaaacaatc tccaacttgg ctcggaggaa gatacattag   2520
gccaaaaata tgcttcagcc atttacctat ttctgagttc tcgttcttat actcagaact   2580
caaccccata ttttgtactt tacgccacct gtaacaagat tatagaataa attctttatt   2640
tcagaaagta cttgcattca agaaaaagtt tgaaacaggt cagattttat aaaaaaaata   2700
catctttaaa aaataatgag aatatttagg agccaatttt ttgacagagg ttatgacgac   2760
atcttttttt tatgtcaaaa atttgaagat attttaccta caattcttgt tttaacttat   2820
atcaaatgct gttttttgta aaaaaaaatt gaaaaaagaa attacagtga agtttgaaat   2880
aaacatattg aaatgtttag ttttacagca aaaaaaatag gatgacgtca taactcaagt   2940
ttttcttaac aatctactat ttgccagtta cattgccata cgtattactt accaagcttg   3000
agcaagatga agtcgataac caacaacatt tgcttccgga aaaacttctc gtacgctgga   3060
gtggatacct aattcgtaat caatcactat tttcgttgga tttaaattgc atcccaaatc   3120
ttgacatttt ttctttaata attcgaataa tgatttgtaa gtgaattttt gcttattagg   3180
taacaaacaa aatgcaaccg gaacataagt gtcattaatc aatgtatgta atgtaaacat   3240
ttaaaaaaaa attgtgcaat aatcgaatgt tccatccata aataaagtgg aattgttaca   3300
cataaatgaa agattagaca ttcatgaaaa aacaaaaata ttaaactgtt catcattaat   3360
caacaaaaac tgttcatttt tgatagtaaa tatttcaatt tgttccaaaa attcttgaac   3420
atccttggct gattttggca attttggaac cgttttcaat cgcgtgcgat taatgttctt   3480
tttttatgta ttggacatct tttgttgaca gagaggtaag tacttcgctt tgcttttcga   3540
tttccttgtg taacaacttc gcaggtcgtt ccgcaatatc ttctgttgct tttcttttaa   3600
gagaattgtt aactttctgg cgaattaata cttcttcagc aagctcatga ttgtgttcac   3660
cactaacttt tgaaaacaca ttatttaatg tatatagttt tgctttacac tttttgaagt   3720
tatacttctt taggcgcgat tgagtaatta tttattatta atctgcgcgc atnnnnnnnn   3780
nnnnnnnnnn nnnnnggttg ctaatctttc aaattatgta tcagcgcaaa taagccatta   3840
aaataatata ttagtgtttt ttagtaaatg tattatttat tatcattttt gtgtctttgg   3900
atttgttttc ctttggcgta aaataataaa atatctattt ttatattt                3948
```

<210> SEQ ID NO 39
<211> LENGTH: 2088
<212> TYPE: DNA
<213> ORGANISM: Diabrotica virgifera

<400> SEQUENCE: 39

```
caatcaagtg tcaaattgtt tttaaaaaat aatgacagag gaatcagtta cagcaatttc     60
cgaacgagaa gaactagaac cagaacttcc cccaccacca ccgataactc tgaaggaagt    120
ctttgtacaa gaacatgaag atagtcctga ttcgtctatt tccgggtccg atgaagaaag    180
aaaaacagac aaacccagag ctgatatacc tcccgaatac tggcacatac aaaaattgat    240
taaatattta aaaactggca atcaaacggc tacagtggtt gcattatgtt gtttaagaga    300
ccatgactta actacagaaa ccagtcagct tgcaatccaa gaaataggcg gcctggaaat    360
attaataaac ctgctagaga caaaagacct caaatgcaaa ctaggtgcct tgggcgtttt    420
```

-continued

```
atcagagctg tctacaaata tagatatacg caaatccata gccgatttgg gtggagtgga    480

gttattggta cagaatttag ctgagccagc tagagatctt caagtacttg tagccgaaac    540

tatatacaat gttgctcaaa tccgaaaagc taggaaacac attcgaaagt gtaatggaat    600

acctaggttg gtcgactttt tagatgtgaa ggagtctcta ttgaagacgc cgaaagatca    660

gttgaatgag tatgatgctg aacaggtaaa catagcaaaa gctgccacca gagccttatg    720

gtccgtttct aaaagtaaga agaatattcg cgtaatgatg aaaagtggtt ccgtgcccct    780

actagccaga ctgcttaaat cagaccatat ggatgtggtg gtaccaacta tcggaacgat    840

ctcccaatgt gccatcgatc ccacttatca attggccatc cagactgaag gaatgattaa    900

ggatatagtt ttgcatctat tttctgagga atatccagct ctcagaagat actgctcaga    960

aactatattt agatgtggag aaaatgctct gattagagat atggtaagag aagctggtgg   1020

tctggatcct ttgatcaaga tggtaaggga tccgaaaaca aaggaagaca aaccgctatt   1080

ggcggcagtg actggagcta tctggaaact ggctataagt ccgcagaatg tagaacgctt   1140

cgatcagtta aaaacggttg agagcctagt aacattattg gaaaacgtcg aggaagacga   1200

gggcgttctt agcaacgttg ttggtgctct tggagaatgc ctaaagtttg aacacaatcg   1260

acacaacctg cttagagcta atggtatacc tcatttagta aatctgctaa attataccta   1320

tccccctctt ctcgaaaacg ttccaatggt tttaagggaa tgcgctgaag attatgactc   1380

gatgcgtgtt atagaagaac tggacggagt aaggctgatt tggtcattgt taagaaatga   1440

ctcgcagaag gttcaagcta acgcggcttg gtcccttgtt ccttgtgtca gatacgccac   1500

agactcagga gaaatggttc gctgcttcgt tggaggatta gaactcatcg tgaatctatt   1560

gaaatccaac gataaccacg ttctagcatg cgtgtgtgcg gctgtttctg aggtagctaa   1620

agacatcgaa aatctggcag ttatgaccga ccatggggta gttccgctat tggttaatct   1680

ggtgaataca gatgatgtgg agttgagaca gcatttggct tcagctattg cttattgctg   1740

tgcgtgggga accaactgca aaatgtttgg aagattgggt gccattactc ctctagttca   1800

atacatggcc gacgatgacg ccaatgtcca cagaaccaca gctctagcct tgttccacct   1860

ttctaagaat ccgttcaatt gcattacgat gcacgaaagc ggagtagtga cttttcttct   1920

aagagcagtg tcttccaaag actgggagct acaagaagct gctgcggggt gccttgctaa   1980

tatcaggaaa ttggcattgg aagctgaaac tgtgcatctt attagaaata gggacgacac   2040

ttctgatgag gacaattagg gatacgcttt ttgtggattt ttatatac                2088
```

<210> SEQ ID NO 40
<211> LENGTH: 2198
<212> TYPE: DNA
<213> ORGANISM: Diabrotica virgifera

<400> SEQUENCE: 40

```
cgaactaagc taaaattaat cgtgaagtga aatccatttt aagaaaaaaa tggtttaata     60

agaataattt atacaaaagt gatatttata tattttcgtt gacgcgttga ggatattgtg    120

aaatatatca aatagtgtca acatttgaac aaatgactat atatgtgtaa aagactgtag    180

tgatcaccag atccaaaaaa gggtgtcttc aagaaatgtg ttaaacccat gaatctttag    240

aaaagagtta aattgaagat atgagtggcc gaccaagaac tacttctttt gcagagggca    300

acaagcaagc taagaatcca cctttggggg gtatgaaaat cagcaataaa atttaaaatg    360

gcgtcgaaaa gtaaaagagg aaaaagtaaa gaaatggaag atgatattag taaacttgta    420

tctacactca aagttaggcc aggtaaggat ggaagcaaag tgactacagt agttgcgacg    480
```

-continued cccggccaag gaccagacag acctcaggag gtatcataca ctgacaccaa agttatcggc 540
aatggcagct tcggtgtggt ctatcaggcg aaattgtgcg aaacttcaga attggtagcg 600
attaagaaag tactgcagga caaacggttt aagaatcggg agttacaaat catgcgaaaa 660
ttagaacatt gtaatatagt gaaacttaaa tatttctttt actctagtgg agataagaaa 720
gacgaggtgt acctgaattt ggttttggaa tacatccctg agacggtata taaagttgca 780
cgacactaca gcaaatcgaa gcaaactata ccaattagct tcatcaagtt atacatgtac 840
cagttgtttc ggtcactagc atacattcac tctttaggga tatgccatag ggacataaaa 900
ccgcaaaact tgttgttaga tccagagact ggagtgttaa aattgtgtga tttcggaagt 960
gcaaaacacc tcgtcaaagg tgaacctaac gtagcttata tttgcagtag atattatagg 1020
gcaccggagt taatttttgg tgctatcgat tacaccacga aaattgacgt gtggagtgct 1080
ggctgtgttt tagcagagct tttattaggt ctgcccatat ttcctggtga ttcaggcgta 1140
gaccaattag tcgagattat caaggtgttg ggaacaccta ccaaagaaca gatcaaggaa 1200
atgaatccca actacaccga gttcaagttt cctcaaatca aatcacaccc ttggcaacag 1260
gtattcagag ctagaacacc tcctgaagca attgaactag tagcaagatt attagagtat 1320
acccccttctt ctagaattag tccgttacag gcttgtgcac attctttttt caatgaactt 1380
agagaaccaa atactcgact tccgaatgga aacaagctac cacctttatt taattttacc 1440
gaacaagagt taagcattca accagcattg aacagtatat tgttgccgag aggaacgcag 1500
gaggcagcta atcctcagga gagtacgtca gctgctagtc aggaagcctc cgaggcgaca 1560
gcaactatcc aagcagcggc tgcttctggt atagcttagt taatagttag tttattcgtg 1620
ctagaatgtt taaatttaca cttgtcaaat ataataccta aaatacttca ctctactgta 1680
ggggtcgacc catttatgtt tatttgtttg tcgatttaga taatttcaag gctgatgtat 1740
cactttatag gtctattggc caccatttga tatgttttag tttaaataat cgatatacac 1800
atatggcttg gtttgaaaac acctatataa tctttatata cagaagcata tatagtatat 1860
atagtttaag tcaaatttat cactgtaaaa ttcttgtaat tggggcaatc tagttaaata 1920
aatttatcaa gttagttaat gtatttgtaa ttctttagat tcagtatata ggccagcagt 1980
ttacctcgca aaagatgcct agcaataaaa tacagtgata ctactaataa ctgacaaaat 2040
aaagcaaaag atggaaaaca taaaagttgt gagataaaaa gaaaagaaac tagcagagat 2100
ggtaaattta gttataaaaa cctataaact tgaattctac ttaatgtttc ccaccttaga 2160
catatcagag ctatatgtca actaaaactg tcactgtt 2198

<210> SEQ ID NO 41
<211> LENGTH: 3910
<212> TYPE: DNA
<213> ORGANISM: Diabrotica virgifera

<400> SEQUENCE: 41
tttagcaaca tttacacggc ggcggtagtt aggaagcaag cgctcgaagc gtcgcaatat 60
agaacgtcaa taacgacgac gacggatagc tagtgcaaca ggtgattccg cgtatttctg 120
ttagttagca gcgagcgaga aattacacaa cgcggtgaaa agggaaaagg ggaggtcgca 180
acacaacgtg ttaatacttt tccttagaag attcgaacga ttcgttttta gtgccgtttc 240
acttcaaaaa tgttttagga aaaaaagtgc gtttaagtgt catgtgtgca gtttattgtt 300
gaatgtcccc ttacagtaga taccggcctt taccaggccc tgatggattg gttctgcaaa 360

-continued

```
catcacccgg gtgtagacct tcaccgacca gtgcttgcag atttttgcgg tggatatcca    420
aattgagtcc ccagcccgtt aataaacaag gattaggggt cctggacatg accgccacgg    480
agaacaccat ccgttttagt gtccataccc tggacaaagc aaccaaagca aaagttactt    540
tagaaaatta ttacagtaat cttatagccc aacatgtaga acgaaagcag aggttagcaa    600
aattagaaga atccttaaaa gacgacagtc tctctgagga gcagaaacat gaaaagaggc    660
tacaacatgc ccaaaaagaa accgaatttc ttaggttaaa acgatctcga ctaggcgttg    720
aagacttcga acccctcaaa gtgataggta gaggggcctt cggagaagtt agattagtgc    780
agaagaaaga tactggccac gtttatgcga tgaaaattct caggaaagca gacatgttag    840
aaaaagaaca ggtggcgcat gtgagagcag aacgggatat tttagtagaa gccgatcatc    900
agtgggtagt aaaaatgtat tatagtttcc aagatcccat taatctatat ttaataatgg    960
aatttctacc gggaggtgat atgatgaccc tactcatgaa aaaagacacc ctttctgaag   1020
atagtacgca gttttatata acagaaacag cactagccat tgattcgatt cataaactcg   1080
gtttcattca tagagatatc aaaccggata atttattgtt agacgccaaa ggacatttga   1140
agttgtctga tttcggatta tgcactggtt taaagaaatc ccatcggacg gatttttata   1200
gggacttaag tcaagcaaag ccttcggatt ttattattac ctcaagtccg atggatagta   1260
aacgcagagc ggaaagctgg aagaaaaata ggagagccct ggcctatagt acagtaggca   1320
cacctgatta catagcacca gaagtattca tgcaaacggg atacggacct gcttgcgatt   1380
ggtggtcact aggtgttatt atgtatgaaa tgttgatagg ttatcctccg ttctgttcgg   1440
aaaaccctca agatacatac acaaaagtga tgaattggag ggatacgttg gttttccccg   1500
ctgaagtacc gatctctgaa gaggccaaag atacaatcat taaattctgt tgtgaagcag   1560
acagaagact gggatctcaa aaaggtctag aagacctaaa attaaatcag tttttccgag   1620
gcgtcgattg ggagcatata agggaaaggc cagcagccat accagtagaa gttaagtcaa   1680
ttgatgacac atcaaacttt gatgattttc ctgatgttaa acttgaaatt ccttctgcgc   1740
cccttcctca agacggcgag atcaattata aagattgggt cttcatcaac tacacattca   1800
aaagattcga gggactcacc cagagaggta ctccaacgaa gaaatagttg tttgttaata   1860
gtttttacca cgataaagat atactaggca gttgaatgcc cagcacttat ttttagaaaa   1920
taaagtcatt taagagatgt ttatattaat tatattaaat aaaaagtagt aagtttcggt   1980
aaagacaaat tccacaatat ctttacatgc catcgatcat tccgtttatt attaattttt   2040
atttctttat tatttgattt ttaaaactat gctatttgtt tcatcgtgtt cttttaattt   2100
ttaactattg caccatcaac tcaaacggtt tatacaaggt tggaaatcca agacatgaat   2160
gaatatacag tggataaatt ttgccacact gcaagtgtag tctacttcta ctcatttctt   2220
tctgataaag tcactacagc ggttttaaag agtttggtgt catttgctct ataaataacc   2280
aaatatgttt tgtaagttgt gttcgtatag tgaaatttaa cattattttt cctatatcaa   2340
taaactatat tctttctaat ctgctctaca tttgagacaa ataatttttt ggtcatttta   2400
ttgcaaattg gattcttatt aaatatctta cttatgtttt tataaaacac gacataccgt   2460
ttttgattac acgtaaatcc tgaagtaata ctattaactg aaaaaaaaac tcgaaatcga   2520
taaaatgcct tgtattgtat ctgctttttt tatctccgta acattcttaa cgatgttcca   2580
tttgaatcct tgattccagt tcttcacgtt ccaatactgt ttcaattttt tatttactga   2640
ttttaattta tcaattaaat tatctttaaa ttaactgctt aatcaataat gtatattagg   2700
tctctctaat ttaagattaa ataaaatata ttagataaat agagtatatt actaaaattg   2760
```

```
aaaatacaaa aggaatttct tagcttcata gatatattat taataatttt aaaaaataca   2820
ttaaacagtt gaagttactg actcgttagc aaactaaata aaaataaaac atgtggaatt   2880
tgtttgtgcc gaaatcgtta aatgttctat cgattgcgct gtattgtttt ctaaaaataa   2940
gctattttgt gtattatagg tctgaagcag ttttgcactg ttttgctttt ttaagagctg   3000
tgaaaactgt atcttgcatt gttctcgacg ctatacttct agaagtatcg tacacttcaa   3060
aattatttaa ttcattataa gcacttttcc tgtacaagac ttacatcgtt tcgtcaaata   3120
ttaaatatac attacgctta cacgattaac aattttacat tttaacttat gtgatcagtt   3180
atgttacaat ttttattttt tacaataata gatttttatt tcctattttt taatgtaaag   3240
atctgctttt tatatttaaa cattattaaa gatttttggt tttatacttt cattctattt   3300
aaatgagaaa tttgatgtga ttatcaaaat gatcgaaatg gtaatttgaa aaaaactaat   3360
atttttgatt cggattatta caagagaact gacaacttta tcattaaaaa gagtacctaa   3420
ataattgtac tttctcgctt tttctcactc gttagaagca tagatttggt tttgtttatg   3480
tttagtgtag tccatattcc tcactatctt ccatgactgt attgatacgc gcctgtaggt   3540
atttgaagtg ttccgactat catcactgta tcatctgcat atctcagatt gttaactcgg   3600
cttccgttaa ttttaacgct atatatattc ttgaccactc aatgttttat tcattcctcc   3660
gagttcatat tgaacaggat tgcgaaagca cacaactctg acgaaatccc ttctgtgttt   3720
ctatattttc agttgaattt tcttcttttt gtactaattt tagagttctc gaagtctaga   3780
gttttcctgt atcatttatc tgattacttt cacattgatt atcgtaaatg agccataata   3840
aataaatatc cacaaggaaa aagttttcct tgtatggggc tgtgggtttt cctgtagttg   3900
gctgtaatcc                                                          3910
```

<210> SEQ ID NO 42
<211> LENGTH: 2386
<212> TYPE: DNA
<213> ORGANISM: Diabrotica virgifera

<400> SEQUENCE: 42

```
aaattttgac attgcatgat agcatgtgaa actatcatta gctcataatg tttgtcagtt     60
tttgactttg acaagagttg acaatctaaa aggtgatcaa agaaagattt taataaaagg    120
ttaaaaacac atttgttctt tgtaagcttt gttcttaaat tttgttaaaa aatgtcagaa    180
aatagagaag aaattttagc tgattttcaa gcttgcactg gaattgaaga tgttgctgaa    240
gctatttatc acctggatga ggccaactgg gacttattgc gtgctgtgag tagagtaatg    300
ccaccagata ctcaaagttt tcgtccacca gctgtagagc ctgtagatcc agatgtcatg    360
atagtagaag atgatgctga tataccaagt gcagtaactg cagacgcagc atcagatatg    420
gtagtagtag gcaacagttt gggccattcg tctacagtaa cgaaaaaagc aaatacacct    480
gatgacagct ttccatccac ttctgctgga aaaagtggat cacgaatgtt aaaatttaat    540
gtgcagtact gtgatagagt tgtcaaagtt gaattaccag agtctgcaac cgttagtgat    600
ataaacatta atcttttaga ctgtaatgaa gaattcgtgg aagagtataa aagtatcatg    660
aatgatctga aactaaagtt gcaccgagaa gtgaaagtaa atccttgcag acagcttctt    720
tccagttggg ctcgattagc acagtatgaa gatactccgt tttcgaagct catgttacca    780
aatgacaatt cgcttcattt aacagtaaaa ccaagcgatg gagctttcac ctcagacgaa    840
gaaaatgccg tatctgaaaa attaagaggt acttacactc taaacgtaaa atatgagaat    900
```

-continued

```
aagacattta atttaaaata tcaaggaaca aaaactattt tggaagtaaa aggtgacgtt    960

tacacgttaa cgaatataca tgtgcgtaat caagtatgga gtgggtggcc tcctaatata   1020

gacgacaata cagtactcgc actcagtgga ataaactatc ctgaacatga tctatcagtg   1080

cgacgaagca cacagagtgt tagagagaaa aaaagtatgc ccgtggttca aattgacagt   1140

gacgatgacg aatttgaaga tgcctccgaa agttttacag ttgatgatga gtattttgtt   1200

gacaatgaag gagcaaatgc aaaaagaaca gacccattaa ttccagagga tgtagaagat   1260

gaaattgtag gctgtataac atttgcagaa cagtttacga caagatacgg tcctgtccat   1320

cctgccttct atcagggaac attagacgat gctatcaaag aagcatgctc aaaacctgcc   1380

aaagaccgaa aaattttggc tatatactta caccacgacg ctagtgttct tacaaatgtt   1440

ttttgcacac aactgttagg ttttgaaagt gtaatgcaaa tgttcgaaaa caactttgtc   1500

ctttggggtt gggatattac ttttgaaagt aatagacgca ggttgcagca atcggttacg   1560

acatctttgg gtgctacagc agcaatgagt ttacgaaata taccagtaga tagattacct   1620

gtcattatac ttataacaaa aattcgatcg acaattgaga tttttagtgt agtgtatgga   1680

aatgttggtg taaatgagct tttgtcaagt ctgatagaat gtgtagaagt atttttagaa   1740

catcaacgag tagaaataaa ggaagaggag gaaagagccg aaagagaaat ggttaaatta   1800

gagcaagatt tagcatatcg tgaaagttta gaagcagata gagcaaaaga agaggccaag   1860

cggttacaag agaaaaaaga aactgaaacc aggaaacgac tggaaagtga aaaggcactc   1920

tcggaagcaa aaaaagaggc ctttaggaaa caagtcgaag cagatttacc tcccgagcca   1980

tctctagaac aaggcgacag tattactaaa atacgattta ggttgccaaa aggagaacat   2040

ttggaaaggc ggtttcagac gactacacct ttgaaagtgc tgttagactt tttaatagtg   2100

aaaggatatc ctacggaaga attcaaagtt atatctagct ggcctaggag agacttgact   2160

tcattagata aaagccaaac actgaaagaa ctgaagctat atcctcaaga aactgtgata   2220

ttagaagagc gatagttttg atcacacatt ccccaaccaa gggttaggtt tttataccag   2280

catttaagcg ttgtaaagtt atttaatata tttttaattt cacgtagtgt atgattaatt   2340

taaatgtatg cagtccgatg aatatacatt acataaaaaa gaaaaa                 2386
```

<210> SEQ ID NO 43
<211> LENGTH: 2657
<212> TYPE: DNA
<213> ORGANISM: Diabrotica virgifera

<400> SEQUENCE: 43

```
atcgtctgtc gtgtttgtca ttttgttccc gcataaacct taacgttctt gttgtcatgg     60

ttcatgtgtg atgaccgtta aaaatttgcc gggatatttt gcttaagttc ggccggaagt    120

gattgattat ttatatattt tacaaacgat tatagttcta cataatggag acaattcaaa    180

acgaaaacaa ggagaatttc gtacatgaaa tgcaaaagca aagcgccatg gccgttcctc    240

aaaaacgacc attgggccag aggaatacca acgtggatcc gcaaccagtt caattgaaag    300

aaaaacaacc acttacagta cccagttcat ttaatgcatt taaagaacaa tttgaaagga    360

acaaatataa aggaacaaaa aatacaaata aagaaaatta ttgccaaaaa ggaaataaga    420

acatagttaa tccagttata ccctgcaacc agtttaaaga ctttaaagta ttcgaagatg    480

aacagtatcc ggaagaaaaa cttaaaaatc ttgcggctaa aaatccaccc aaagtacaag    540

tacacgaaga taccaaggaa gagacaaaag atgaagtgaa agcgccagaa aagatagtag    600

aaaaggaaaa tataaagcaa gattcggaat cactcagtct aaagacatcc gatgcacatt    660
```

-continued

```
tattcatgac tatagatgat aattataaaa aagaccatga aattccgtca acaaaacgta    720
tgaaagatat tttctttgaa atggaagaat acagatctga tatttatcac tatctaagag    780
aacatgagtt acgaaatcga ccaaaacctg gatatatgaa gaaacaacca gacgtttcat    840
ctaatatgag gacaatattg gtagattggt tagtagaagt agctgaagag tacaaattac    900
acacagaaac cctgtatctt gcagtaaatt atatagaccg atttttgagc tatatgtccg    960
ttgtaagggc caagttgcaa ttggttggaa ctgcagcaat gtttatcgct tcgaaatacg   1020
aggaaatata tccaccagag atcagcgaat ttgtatatat tactgacgac acttacacga   1080
aaaaacaagt actacgaatg gagcagttga ttttgaaagt tttaagtttc gatctctcaa   1140
tacctactcc actaacattt atcacagcaa tgtgtgttag caacaatttg agtgataaaa   1200
ctatgtatct tgccatgtat ttgagcgagt tggcgttact taacggtgac atctacctgg   1260
agttcttacc atcagttata gccgccgcag caatagcgct tgcccgccat actttatgcg   1320
aagaagcttg gcctaaagaa ctcgttcaat ctacaggcta cgaaggtctt caaatcagat   1380
ctggcatctc gtttttatac cagatgtttg tttccgctat gactttacct caacacgcca   1440
tacaagacaa atacaagacc aggaaatgta tgcacgtatc tactttgaaa cctcgcgatg   1500
tggcgttaga gttataattt aattagtaat atttgtaata ggcttaagtc tgccaagggg   1560
atcgaaaatt ttatggctag tttaatcgaa aaaggttcca tgccccgact tcgaagaggc   1620
aataaatgct cgaatgtcaa tggtgcgcgg atgcgctgtt gccaaatcta cggaatgaaa   1680
ttaaattttg ttctatcttg tattaataaa taaaacacgg ttgcatatga catatatgaa   1740
atgaaattac aaacaaaata gttgtagatt tcggtccttg gcaaatgaca agtattgata   1800
attaccgact gaatattatt taatcaacat taataattta tcgtaaattt atttagttca   1860
ataattacaa gacatgatta aaagacgatt agaatcataa tcaaaccaaa ttacacttcg   1920
tcaagaatag taatgtactt atcattgact tgacttcgtc aataatagta aaggattttt   1980
aataaattca tatgcctacc cccttttaa acttttaaag aaaatttaag ttcattccgt   2040
aaacttggca acagcgcatc tgagcgcaat tagcttttga gtattcattg cttcttctag   2100
cttggggcat ggaacctttt tggattaaaa ctgcaataaa attttccacc cctcttggtg   2160
gacgttaacc tttgtaatat atttttatat ttagtttaat ttttaaggga caatttttac   2220
tgaaatgtga cgttccgttt tacagtattt ttaagagctt tttcctattt gttcgactga   2280
atttacacaa cattatacat tgccttttaa aagtttttct gtaacatttt ttagattttt   2340
tcaacgaagt atgtggtcca agcatgagta aagggtgttc caaaatttac gaaagattta   2400
aatttaatag gaaacgctgt tttgtttttc tttagattgt aattttttat tgcatcataa   2460
agtacgtaga ggtggtgtga atttttgttg aatctcaccc caacagtcgc gaaaggggtt   2520
taattattac cttttgccta attagacatg ggtgaatatt ttacgactac acgcatctgt   2580
cccaaagcag agagtccttc gatattaaca aactagtgaa cttttagggc gactggttct   2640
gagaatttat ttggtcg                                                  2657
```

<210> SEQ ID NO 44
<211> LENGTH: 155
<212> TYPE: DNA
<213> ORGANISM: Diabrotica virgifera

<400> SEQUENCE: 44

```
tgtcatcgat aaaaagtgga ggtctaacca aaaaggaagg caagatgagg atcagagcct     60
```

-continued

```
tcccaatgac tatggatgaa aaatatgtag aaagtatatg ggctttatta aagaatgcta    120

tacaagaaat tcaaaagaaa aataactcag gttta                               155


<210> SEQ ID NO 45
<211> LENGTH: 155
<212> TYPE: DNA
<213> ORGANISM: Diabrotica virgifera

<400> SEQUENCE: 45

cgattctgaa aaagaagatg ataaaatcaa accatctgac aatctcatac tagtaggaca     60

tgtagaaggg gatgcaagtc tattggaagt ctacatatac aatgaacaag aagagtcatt    120

gtatgttcat catgatatta tgttatcatc ctttc                               155


<210> SEQ ID NO 46
<211> LENGTH: 155
<212> TYPE: DNA
<213> ORGANISM: Diabrotica virgifera

<400> SEQUENCE: 46

atggaggatt ttaaacaaag acaaggattt gcttgtaaat cgatgaagga tgtagcagat     60

gctgcaggtc cccattgggc taggatgtct aaagcagaaa gaagacctta tgaagagagg    120

gcaaacaaag agaagggagg tttgagatat acttg                               155


<210> SEQ ID NO 47
<211> LENGTH: 275
<212> TYPE: DNA
<213> ORGANISM: Diabrotica virgifera

<400> SEQUENCE: 47

tgatgaaaag tggttccgtg cccctactag ccagactgct taaatcagac cacatggatg     60

tggtggtacc aactatcgga acgatctccc aatgtgccat cgatcccact tatcaattgg    120

ctatccagac tgaaggaatg attaaggata tagttttgca tctattttct gaggaatatc    180

cagctctcag aagatactgc tcagaaacta tatttagatg tggagaaaat gctctgatta    240

gagatatggt aagagaagct ggtggtctgg atcct                               275


<210> SEQ ID NO 48
<211> LENGTH: 275
<212> TYPE: DNA
<213> ORGANISM: Diabrotica virgifera

<400> SEQUENCE: 48

tgcgaaaatt agaacattgt aatatagtga aacttaaata tttcttttac tctagtggag     60

ataagaaaga cgaggtgtac ctgaatttgg ttttggaata catccctgag acggtatata    120

aagttgcacg acactacagc aaatcgaagc aaactatacc aattagcttc atcaagttat    180

acatgtacca gttgtttcgg tcactagcat acattcactc tttagggata tgccataggg    240

acataaaacc gcaaaacttg ttgttagatc cagag                               275


<210> SEQ ID NO 49
<211> LENGTH: 275
<212> TYPE: DNA
<213> ORGANISM: Diabrotica virgifera

<400> SEQUENCE: 49

tgaaaattct caggaaagca gacatgttag aaaaagaaca ggtggcgcat gtgagagcag     60

aacgggatat tttagtagaa gccgatcatc agtgggtagt aaaaatgtat tatagtttcc    120
```

aagatcccat taatctatat ttaataatgg aatttctacc gggaggtgat atgatgaccc 180
tactcatgaa aaaagacacc ctttctgaag atagtacgca gttttatata acagaaacag 240
cactagccat tgattcgatt cataaactcg gtttc 275

<210> SEQ ID NO 50
<211> LENGTH: 276
<212> TYPE: DNA
<213> ORGANISM: Diabrotica virgifera

<400> SEQUENCE: 50
atgacgaatt tgaagatgcc tccgaaagtt tttacagttg atgatgagta ttttgttgac 60
aatgaaggag caaatgcaaa aagaacagac ccattaattc cagaggatgt agaagatgaa 120
attgtaggct gtataacatt tgcagaacag tttacgacaa gatacggtcc tgtccatcct 180
gccttctatc agggaacatt agacgatgct atcaaagaag catgctcaaa acctgccaaa 240
gaccgaaaaa ttttggctat atacttacac cacgac 276

<210> SEQ ID NO 51
<211> LENGTH: 275
<212> TYPE: DNA
<213> ORGANISM: Diabrotica virgifera

<400> SEQUENCE: 51
tcggggcatg gaaccttttt cgattaaact agccataaaa ttttcgatcc ccttggcaga 60
cttaagccta ttacaaatat tactaattaa attataactc taacgccaca tcgcgaggct 120
tcaaagtaga tacgtgcata catttcctgg tcttgtattt gtcttgtatg gcgtgttgag 180
gtaaagtcat agcggaaaca aacatctggt ataaaaacga gatgccagat ctgatttgaa 240
gaccttcgta gcctgtagat tgaacgagtt cttta 275

<210> SEQ ID NO 52
<211> LENGTH: 5385
<212> TYPE: DNA
<213> ORGANISM: Spodoptera frugiperda

<400> SEQUENCE: 52
atgaagtatc aaagcttggt attgatagtt agtgtggcgt ggtgctcggc tcagctcacg 60
gatgacatgc agatgtttga gccggagtgc atgacggagg ataagttccc ctgcatggga 120
ggagggtgta tctcggtgtc tcagtactgt gacgggaacc tggactgtga agatggcagt 180
gacgagaatt tttgcatcga acacaagccg ttccaagagt tctgtaacga gactcatcag 240
tacatgtgtc aggactccac gaagtgtgtt cctctgtcct ggctgtgcaa caacgagccg 300
gactgtgatg acggcagcga tgagttcaac tgcaccgcgc tgccggctgt caatgttaat 360
tcaacatgca aaggcttcca atgtggagac ggcaagtgta tctctttcct gtgggtctgc 420
gacggcgtgt acgactgcga agataaaagc gatgagtatg ctgaggagct ctgcaggcac 480
gtgtcccgtc cccacgccat tgtcgacggc tcgtactgcc aggagctgca cacgatggat 540
gaccggaact acaaatgtct ggacgcctcc ttctgcctgc caagcagcat gatgtgcgat 600
ggactgcagg actgccgcga tggcagcgat gagggacctt tttgcaagga ctggaacaca 660
atgtgcgaca acttcaaatg catgggtaac gacacgcgat gctccccgga gaggtacggg 720
cccacctgcc tgtgcctgcc gtcccacttc atgcgccagt acgactacat caccaagcaa 780
tgccaggacg tcaacgagtg cctgatggaa cgtcccccgt gctcccacaa atgtatcaac 840

-continued

```
gctgacggtc actatatttg cgaatgtgat cctgggtaca agagggatgt gtatggatac    900
ctttgttatg ctactggtcc cgaagcgatg ctgttcttta atactcggaa cgatatcaga    960
tacctgaaaa tcaagagtaa agaaatggtc acagtggcta ccgatatcat agagggtcac   1020
ggcgtatcat tcgatggcac ttacatttac tgggtggaga cggcacaggg acatcagtct   1080
atcttcaaag cgcagctcgg agacgtcaag gatacaaagg aggtgctggt aggtctcggt   1140
ctggaggacc ctggcgacat agcagtggac tacttaggcg ggaacatata cttcagtgat   1200
gcggagcgag ggaccatctc cgcctgcagg gtcgacggct ccatctgcac caccatcaag   1260
acctatgcta aaaacccacg attcgtcaca cttgatccta agaatggtaa gatgtactgg   1320
gcggactggc acgagcggcc ggtgataatg tcagctcgca tggacggtag ccaccacgac   1380
acgctggtgg acaccttgga gaacttcgcc accggcctgg cagtggacgc gcccaacggg   1440
aggctgtact tcgtcgacaa aactgtcaaa gtcgtcatga ttgcagagaa acatgtttat   1500
tctttatttg aagagccgtt ccaccacccg tactccatct ccgtgttcga gaacacggtg   1560
ttctggagcg actggacctc caacagcata cagacgactg acaaagtgca cgggaccgcg   1620
cagaagagga acgttctact caaacttgat acgcctgtac tagggatgca catgtaccac   1680
ccggtgttga tgaacacgac atcgaaccct tgcagcaaca acaactgctc gcacctctgc   1740
ttcgtcacct ccaacgccac gcacgtctgc gcctgccccg acggcatgga gatcgagaat   1800
aatcagtgtc atcatgtagg gaactaccgt gccaagtacc tggtggtggg aagtggacag   1860
ctgttcacca agatccagta caacgcgctc ggcaacccgg agtgccacgc cacgcacttc   1920
gacatcggac gcgtgcaggc catggcttat gatcggtaca gagattctct attcatatac   1980
gacggccagc ggcggaccat caactacatc aacatgagtg acttcacgct cggcgtcacg   2040
cacttgttga tctacaacgg gctggaaaat gtcgtcgaca tggattatga ttatgtgact   2100
gataacctgt acgttttgga cgcgagtcgt cgtgtggtgg aagctgtgtc tctgaggact   2160
cagaagcgcg ccatagtgca tcggttcgac attcaagaac tgcctattag cttctgtatt   2220
ctttccgact acgggaggat gttggtggct gtggtggaga gtgagatgca caataccata   2280
cacattgaca gcatcgggct cgacgggaac cagcggagac acgtcctcat gaacaatttg   2340
aaaggtcccc acattagatt gcggtacgtg gcagaaacgg aacaggtatt catatccgat   2400
gagagcaacg gcatcatcga cttcatacat cctgaaggaa ccgggcgaga gaactatcgg   2460
gagctcacct cgacggtgac cagcctcgcc atagcagaca actacgtctt ctggacagac   2520
cgaaagaccc ccaggctctt ctggtctgac atacacgagg cctcaccgaa gataaggagg   2580
atggatctgg ccctttttccc aaacaccacg cagctcctaa tccaagccac aaactcgcta   2640
cctgatccga aagacccccct tctgaaccat ccttgtctga agaacccttg ttctgacgtc   2700
tgtgtccaac ttccccatga aactccacaa gatcacccga aactggcaaa cttcgagatg   2760
aagtacaagt gtttgtgccc acctggatta ctggttaacg gtaaccagtg cgccaaacct   2820
gcggcgtgtg gttcggatga gatactgtgc cacaggagca atatttgcgt gaagcaagat   2880
gctaggtgtg atggaaaggt ggactgtcct aagagtgaag acgaggaagg ttgtatagtg   2940
gatccggcaa acatatgtac atcagatgag atattttgtc gcggcttgtg cataaataag   3000
gagaaagcct ccatgtgttc tactggtgaa aaacctaata aagcgctacc ttcgaacaac   3060
tgcagcagca cagaattcca atgcacggac acgtctatct gcatctctcg gttgcaagtc   3120
tgcgaccaac acgtcgactg ccccaatgga tcggatgaac atctctccga gtgtgacacc   3180
tacgcttgtc acgaaactga gttcatgtgt gcgtccggct cgtgtatatt caagacgtgg   3240
```

-continued

```
acatgtgatg gagaccgcga ctgtaacgat ggatctgatg aaatcaactg cgtgaacatg   3300

acttgcggcc ctggtttcta ccagtgcaga gacagggagt gcgtagaact atcgaaaagg   3360

tgtgatggac gccgggactg ttcggattac tccgacgaag aagactgtga tgaggctcaa   3420

gttatcgaga aagtagaaga agccccaaaa tgtgctgcgt gggagtatac ttgtgaaaaa   3480

aatactagca tttgcttgcc tgaaactgct cggtgcaaca tgaagacaga ctgcccaggt   3540

ggcacggatg agcacggttg cgacctgcgc tgcgccccaa aaggaatgtt tgcgtgtggg   3600

caacaggtta cgtgtataac cttgaacaaa gtctgcaacg gccgtctgga ctgtgatgat   3660

gggtccgacg agacgcctga tgcttgttct cgggtgaaca ggacctccca cttattccca   3720

gtgtcccgta cattcagcga ctgtacggag ggttacaagt gcaacaacgg tcagtgcatt   3780

gaatggtcac aggtgtgtga caagaagagg gactgtgtcg acggtacaga tgaaaacgga   3840

ctctgtgata ctgcatgtgc aaacagcaca tgtaccttca tgtgtcagcc gaccccattc   3900

ggacggcgct gtctctgccc cttcggcttc caagtgtccc aggatcagtt ctcgtgcgag   3960

gacatcgacg agtgcactga agacgtctgc tcccaaggtt gtatcaacgt gccaggatca   4020

ttcctgtgct ggtgccatca tggttatgcc atcaggaggt cagaccgtcg ctcctgcaag   4080

gcgatccgcg gcaacatgtc cattctatac gtgtcgggta actccgtgcg gtctatctca   4140

gcggacgggt atgggtctat agagtacacc gatactgacg cctcggccat cactgatatg   4200

gattataatg ttaggcagaa gaagctatac gtggcttcgg aagagggcag caagttattg   4260

gaagtgaatg agacgcagaa tgtgatcgca gtcaccaacg ttgggaaacc atcgcgggtg   4320

gcagtggact gggtgacagg caacgtgtac ttcgtggaca cgactccgta cgaccagcgc   4380

atacgagtct gccacgtcaa gaggaagcgc tgcgcctccc tgctgaaact gccgtctgat   4440

gccacggtca cagcattgat agtggaacct agttctagcc gaatgttcta ctgcgtcact   4500

cggaagctgg agtcagtgat ctggacagct aacctggctg gcagacacgt gactgacctg   4560

gctactgtgc ggaactgcac cggactggcc gcagactctt tcaagaagaa gttgtatgtt   4620

gcagagacgg gcccagcaca tatcattagg atggattatg aaggggagaa tttcaacaag   4680

atcctctcag atcacccacg tcttcaagcg ccacatggac tagtaatctt cgaagactac   4740

atttactact tggaagccaa ctccttccgc ctcagccgct gccagctata tggagccaag   4800

cattgtgaaa catatgtgta tcgcgtgttt gacgccaaca catttgtcat tcgccacgag   4860

agcatccaac gtgatgacat cgtcaatgag tgtgaagatg tggtctgtga caatatttgc   4920

gccgtggacg aagatgggcc caaatgtctg tgtgatgatg gagctttggc gaagcgtggg   4980

aagtgtcccg aggttgataa gaaactggta ccattattca acggctggtc gtacgaggaa   5040

ctgaaatcag ctcacagcgt ctccttcacc atcatcgttg gagtgctgag cctaatcgct   5100

atataccttg gcgtgttcgt gtattaccac ttcgtatacc tacccaggaa gagaatgcta   5160

gctgccactt acactgaagt gcggttccag aacacaaata gttcgcccta tcccgaatca   5220

gacccaactg tggagatgca tccctcaagt tccgtttcac acgagttcat aaaccctctt   5280

cagttcgtaa gaaacatgtg gtatgggccc tttaggaaag atagacgacc aaattttagg   5340

aaagatagac gaccaaatgt aagtttaaac accacttggc attaa                   5385
```

<210> SEQ ID NO 53
<211> LENGTH: 7020
<212> TYPE: DNA
<213> ORGANISM: Spodoptera frugiperda

<400> SEQUENCE: 53

```
tctctacgtt ctcaatttcc gttccgttgc tcttccgccg tgccagcaac cacgtgtatc     60
aattaaaata ataattaatc aatttattaa tttaataaat caattttaat aattaaacaa    120
tcgttatttt ttttacttat taagtatcaa tgaaggaaat ataaataatg aagtatcaaa    180
gcttggtatt gatagttagt gtggcgtggt gctcggctca gctcacggat gacatgcaga    240
tgtttgagcc ggagtgcatg acggaggata agttcccctg catgggagga gggtgtatct    300
cggtgtctca gtactgtgac gggaacctgg actgtgaaga tggcagtgac gagaattttt    360
gcatcgaaca caagccgttc caagagttct gtaacgagac tcatcagtac atgtgtcagg    420
actccacgaa gtgtgttcct ctgtcctggc tgtgcaacaa cgagccggac tgtgatgacg    480
gcagcgatga gttcaactgc accgcgctgc cggctgtcaa tgttaattca acatgcaaag    540
gcttccaatg tggagacggc aagtgtatct ctttcctgtg ggtctgcgac ggcgtgtacg    600
actgcgaaga taaaagcgat gagtatgctg aggagctctg caggcacgtg tcccgtcccc    660
acgccattgt cgacggctcg tactgccagg agctgcacac gatggatgac cggaactaca    720
aatgtctgga cgcctccttc tgcctgccaa gcagcatgat gtgcgatgga ctgcaggact    780
gccgcgatgg cagcgatgag ggaccttttt gcaaggactg gaacacaatg tgcgacaact    840
tcaaatgcat gggtaacgac acgcgatgct ccccggagag gtacgggccc acctgcctgt    900
gcctgccgtc ccacttcatg cgccagtacg actacatcac caagcaatgc caggacgtca    960
acgagtgcct gatggaacgt cccccgtgct cccacaaatg tatcaacgct gacggtcact   1020
atatttgcga atgtgatcct gggtacaaga gggatgtgta tggatacctt tgttatgcta   1080
ctggtcccga agcgatgctg ttctttaata ctcggaacga tatcagatac ctgaaaatca   1140
agagtaaaga aatggtcaca gtggctaccg atatcataga gggtcacggc gtatcattcg   1200
atggcactta catttactgg gtggagacgg cacagggaca tcagtctatc ttcaaagcgc   1260
agctcggaga cgtcaaggat acaaaggagg tgctggtagg tctcggtctg gaggaccctg   1320
gcgacatagc agtggactac ttaggcggga acatatactt cagtgatgcg gagcgaggga   1380
ccatctccgc ctgcagggtc gacggctcca tctgcaccac catcaagacc tatgctaaaa   1440
acccacgatt cgtcacactt gatcctaaga atggtaagat gtactgggcg gactggcacg   1500
agcggccggt gataatgtca gctcgcatgg acggtagcca ccacgacacg ctggtggaca   1560
ccttggagaa cttcgccacc ggcctggcag tggacgcgcc caacgggagg ctgtacttcg   1620
tcgacaaaac tgtcaaagtc gtcatgattg cagagaaaca tgtttattct ttatttgaag   1680
agccgttcca ccacccgtac tccatctccg tgttcgagaa cacggtgttc tggagcgact   1740
ggacctccaa cagcatacag acgactgaca aagtgcacgg gaccgcgcag aagaggaacg   1800
ttctactcaa acttgatacg cctgtactag ggatgcacat gtaccacccg gtgttgatga   1860
acacgacatc gaacccttgc agcaacaaca actgctcgca cctctgcttc gtcacctcca   1920
acgccacgca cgtctgcgcc tgccccgacg gcatggagat cgagaataat cagtgtcatc   1980
atgtagggaa ctaccgtgcc aagtacctgg tggtgggaag tggacagctg ttcaccaaga   2040
tccagtacaa cgcgctcggc aacccggagt gccacgccac gcacttcgac atcggacgcg   2100
tgcaggccat ggcttatgat cggtacagag attctctatt catatacgac ggccagcggc   2160
ggaccatcaa ctacatcaac atgagtgact tcacgctcgg cgtcacgcac ttgttgatct   2220
acaacgggct ggaaaatgtc gtcgacatgg attatgatta tgtgactgat aacctgtacg   2280
ttttggacgc gagtcgtcgt gtggtggaag ctgtgtctct gaggactcag aagcgcgcca   2340
```

```
tagtgcatcg gttcgacatt caagaactgc ctattagctt ctgtattctt tccgactacg   2400
ggaggatgtt ggtggctgtg gtggagagtg agatgcacaa taccatacac attgacagca   2460
tcgggctcga cgggaaccag cggagacacg tcctcatgaa caatttgaaa ggtccccaca   2520
ttagattgcg gtacgtggca gaaacggaac aggtattcat atccgatgag agcaacggca   2580
tcatcgactt catacatcct gaaggaaccg ggcgagagaa ctatcgggag ctcacctcga   2640
cggtgaccag cctcgccata gcagacaact acgtcttctg gacagaccga aagaccccca   2700
ggctcttctg gtctgacata cacgaggcct caccgaagat aaggaggatg gatctggccc   2760
ttttcccaaa caccacgcag ctcctaatcc aagccacaaa ctcgctacct gatccgaaag   2820
acccccttct gaaccatcct tgtctgaaga acccttgttc tgacgtctgt gtccaacttc   2880
cccatgaaac tccacaagat cacccgaaac tggcaaactt cgagatgaag tacaagtgtt   2940
tgtgcccacc tggattactg gttaacggta accagtgcgc caaacctgcg gcgtgtggtt   3000
cggatgagat actgtgccac aggagcaata tttgcgtgaa gcaagatgct aggtgtgatg   3060
gaaaggtgga ctgtcctaag agtgaagacg aggaaggttg tatagtggat ccggcaaaca   3120
tatgtacatc agatgagata ttttgtcgcg gcttgtgcat aaataaggag aaagcctcca   3180
tgtgttctac tggtgaaaaa cctaataaag cgctaccttc gaacaactgc agcagcacag   3240
aattccaatg cacggacacg tctatctgca tctctcggtt gcaagtctgc gaccaacacg   3300
tcgactgccc caatggatcg gatgaacatc tctccgagtg tgacacctac gcttgtcacg   3360
aaactgagtt catgtgtgcg tccggctcgt gtatattcaa gacgtggaca tgtgatggag   3420
accgcgactg taacgatgga tctgatgaaa tcaactgcgt gaacatgact tgcggccctg   3480
gtttctacca gtgcagagac agggagtgcg tagaactatc gaaaaggtgt gatggacgcc   3540
gggactgttc ggattactcc gacgaagaag actgtgatga ggctcaagtt atcgagaaag   3600
tagaagaagc cccaaaatgt gctgcgtggg agtatacttg tgaaaaaaat actagcattt   3660
gcttgcctga aactgctcgg tgcaacatga agacagactg cccaggtggc acggatgagc   3720
acggttgcga cctgcgctgc gccccaaaag gaatgtttgc gtgtgggcaa caggttacgt   3780
gtataacctt gaacaaagtc tgcaacggcc gtctggactg tgatgatggg tccgacgaga   3840
cgcctgatgc ttgttctcgg gtgaacagga cctcccactt attcccagtg tcccgtacat   3900
tcagcgactg tacggagggt tacaagtgca acaacggtca gtgcattgaa tggtcacagg   3960
tgtgtgacaa gaagagggac tgtgtcgacg gtacagatga aaacggactc tgtgatactg   4020
catgtgcaaa cagcacatgt accttcatgt gtcagccgac cccattcgga cggcgctgtc   4080
tctgcccctt cggcttccaa gtgtcccagg atcagttctc gtgcgaggac atcgacgagt   4140
gcactgaaga cgtctgctcc caaggttgta tcaacgtgcc aggatcattc ctgtgctggt   4200
gccatcatgg ttatgccatc aggaggtcag accgtcgctc ctgcaaggcg atccgcggca   4260
acatgtccat tctatacgtg tcgggtaact ccgtgcggtc tatctcagcg gacgggtatg   4320
ggtctataga gtacaccgat actgacgcct cggccatcac tgatatggat tataatgtta   4380
ggcagaagaa gctatacgtg gcttcggaag agggcagcaa gttattggaa gtgaatgaga   4440
cgcagaatgt gatcgcagtc accaacgttg ggaaaccatc gcgggtggca gtggactggg   4500
tgacaggcaa cgtgtacttc gtggacacga ctccgtacga ccagcgcata cgagtctgcc   4560
acgtcaagag gaagcgctgc gcctccctgc tgaaactgcc gtctgatgcc acggtcacag   4620
cattgatagt ggaacctagt tctagccgaa tgttctactg cgtcactcgg aagctggagt   4680
```

-continued

```
cagtgatctg gacagctaac ctggctggca gacacgtgac tgacctggct actgtgcgga   4740
actgcaccgg actggccgca gactctttca agaagaagtt gtatgttgca gagacgggcc   4800
cagcacatat cattaggatg gattatgaag ggagagaattt caacaagatc ctctcagatc  4860
acccacgtct tcaagcgcca catggactag taatcttcga agactacatt tactacttgg   4920
aagccaactc cttccgcctc agccgctgcc agctatatgg agccaagcat tgtgaaacat   4980
atgtgtatcg cgtgtttgac gccaacacat ttgtcattcg ccacgagagc atccaacgtg   5040
atgacatcgt caatgagtgt gaagatgtgg tctgtgacaa tatttgcgcc gtggacgaag   5100
atgggcccaa atgtctgtgt gatgatggag ctttggcgaa gcgtgggaag tgtcccgagg   5160
ttgataagaa actggtacca ttattcaacg gctggtcgta cgaggaactg aaatcagctc   5220
acagcgtctc cttcaccatc atcgttggag tgctgagcct aatcgctata taccttggcg   5280
tgttcgtgta ttaccacttc gtatacctac ccaggaagag aatgctagct gccacttaca   5340
ctgaagtgcg gttccagaac acaaatagtt cgccctatcc cgaatcagac ccaactgtgg   5400
agatgcatcc ctcaagttcc gtttcacacg agttcataaa ccctcttcag ttcgtaagaa   5460
acatgtggta tgggcccttt aggaaagata gacgaccaaa ttttaggaaa gatagacgac   5520
caaatgtaag tttaaacacc acttggcatt aaatgaccat aagtagacag ggtattcaag   5580
gtctattgaa aatttctagt actcattact tgtgtccaac cgatactgga tttttgccaa   5640
aaccgaaacc gaactttggg ccatggtttg gtcgtggtgg ttatataatc ttaatctaga   5700
aaaacaataa gcatcttcat aaaatcattc atgtatcttt aatcataaca aatcaaagca   5760
ttaaactgaa gcatacattt gtcttatatt ttttactttt agccgaaact ataccgaggc   5820
cgaaacttag gatccggttt cggccagaaa tccaatttca gtagacgcta cataataagt   5880
acttttgaaa ttttcttgtc acacaatcca ggcctatttg aatttaaata atcgttattt   5940
tgtataaaat aaatgtaatt tgttgcaggt catctccggt ctaccagtca ccacgcccgc   6000
atccccgccg caaccagatt tctccgacac agaatccgac ttagacgata aagagagtca   6060
gagaatttta aaatataatt aattttattc aatgagccta caaaataatt taatttttaa   6120
tctgtagcac gtttattttt attcacttga ttaatgatca agctaagaat tattttgtaa   6180
ttattatttt tattgcttta ttttttatgt tttaataatt taattattat gattgtgtgt   6240
aattgaatta tgtgttttat attatgttag tataaaatgt acaaagttta atttattgaa   6300
attaaaatta atgtaatttt tcatagtcca atcatttggt attggtgatt atacattttg   6360
ataatattat tcaccatcaa tagcctgtgt ggcagttcac tgctgaacat tgagggttag   6420
ccacgatctc ttttcgaatc tcatctttat tcattcatat cctggccagt tcggcaagaa   6480
ttcatattat ccacactacc ttaaaatgga taaacttttt aaactatctt tttcatacaa   6540
aatgactgga ctatgaatac tgaaataatt ataattgtat tgttatttat gaattattta   6600
ttcgatttgc agagttatag ataatacaaa tcaataaatt ggtgtgccat cgagtaagta   6660
attaatactt attccaataa aagtatcgcg tggaacagtt tttgttattt tcacattata   6720
aagacacacg gatgccttgc gacttactca cttatttaat ttatcacgaa aatagaaacg   6780
aacattttac actcacaata tgcaatacaa attgctattt ttacaaaaac atttacgtaa   6840
ctaaaaaaac gcgccaaatt atccataacg gaagtaggga gtctagtgtt gtccacacat   6900
atgactatca aactaaatac gatcactaat tatttatata tttgcaacca atagattttt   6960
tcaactattc aacgttgtgt taaatgtgaa taaattaatt taatttaatt agtcaaaaaa   7020
```

-continued

<210> SEQ ID NO 54
<211> LENGTH: 40
<212> TYPE: DNA
<213> ORGANISM: Artificial Sequence
<220> FEATURE:
<223> OTHER INFORMATION: Primer

<400> SEQUENCE: 54
tgttaatttt gttctttgtg ctttcaacgt tattaaatgc 40

<210> SEQ ID NO 55
<211> LENGTH: 40
<212> TYPE: DNA
<213> ORGANISM: Artificial Sequence
<220> FEATURE:
<223> OTHER INFORMATION: Primer

<400> SEQUENCE: 55
caggaatgct tcgcttatac atcttccatt tcgacaattg 40

<210> SEQ ID NO 56
<211> LENGTH: 39
<212> TYPE: DNA
<213> ORGANISM: Artificial Sequence
<220> FEATURE:
<223> OTHER INFORMATION: Primer

<400> SEQUENCE: 56
ctttcaacgt tattaaatgc agtcgtttca acgaataat 39

<210> SEQ ID NO 57
<211> LENGTH: 39
<212> TYPE: DNA
<213> ORGANISM: Artificial Sequence
<220> FEATURE:
<223> OTHER INFORMATION: Primer

<400> SEQUENCE: 57
atcacaatcc agttcatccg atccatctcc acaattgtc 39

<210> SEQ ID NO 58
<211> LENGTH: 39
<212> TYPE: DNA
<213> ORGANISM: Artificial Sequence
<220> FEATURE:
<223> OTHER INFORMATION: Primer

<400> SEQUENCE: 58
tcaccaataa tatacactgg cccaatggtt tggctctag 39

<210> SEQ ID NO 59
<211> LENGTH: 40
<212> TYPE: DNA
<213> ORGANISM: Artificial Sequence
<220> FEATURE:
<223> OTHER INFORMATION: Primer

<400> SEQUENCE: 59
tatgatgatt tttaccatta aacttatcac aagtttgaat 40

<210> SEQ ID NO 60
<211> LENGTH: 40
<212> TYPE: DNA
<213> ORGANISM: Artificial Sequence
<220> FEATURE:
<223> OTHER INFORMATION: Primer

<400> SEQUENCE: 60
agaggataac gtcaacatcc acttagtgtc agtaacacgt 40

<210> SEQ ID NO 61
<211> LENGTH: 40
<212> TYPE: DNA
<213> ORGANISM: Artificial Sequence
<220> FEATURE:
<223> OTHER INFORMATION: Primer

<400> SEQUENCE: 61
ttgccgatag ctcccatcca gctggacatg cacaaactat 40

<210> SEQ ID NO 62
<211> LENGTH: 40
<212> TYPE: DNA
<213> ORGANISM: Artificial Sequence
<220> FEATURE:
<223> OTHER INFORMATION: Primer

<400> SEQUENCE: 62
aatattaatt ccactactat tagtattcct tggagcagta 40

<210> SEQ ID NO 63
<211> LENGTH: 40
<212> TYPE: DNA
<213> ORGANISM: Artificial Sequence
<220> FEATURE:
<223> OTHER INFORMATION: Primer

<400> SEQUENCE: 63
ttgccgatag ctcccatcca gctggacatg cacaaactat 40

<210> SEQ ID NO 64
<211> LENGTH: 40
<212> TYPE: DNA
<213> ORGANISM: Artificial Sequence
<220> FEATURE:
<223> OTHER INFORMATION: Primer

<400> SEQUENCE: 64
cctgtgtgat ggtgaaaatg attgtaataa ctttttggat 40

<210> SEQ ID NO 65
<211> LENGTH: 40
<212> TYPE: DNA
<213> ORGANISM: Artificial Sequence
<220> FEATURE:
<223> OTHER INFORMATION: Primer

<400> SEQUENCE: 65
cgagtgaaga tctatgcaag ttttattgtt actacacaag 40

<210> SEQ ID NO 66
<211> LENGTH: 40
<212> TYPE: DNA
<213> ORGANISM: Artificial Sequence
<220> FEATURE:
<223> OTHER INFORMATION: Primer

<400> SEQUENCE: 66
gtctgtgata ataagttaga ttgtcccgat tattctgatg 40

<210> SEQ ID NO 67
<211> LENGTH: 40

<212> TYPE: DNA
<213> ORGANISM: Artificial Sequence
<220> FEATURE:
<223> OTHER INFORMATION: Primer

<400> SEQUENCE: 67
cttgatttaa atctttagcc actgtaaaat aatctaaaga 40

<210> SEQ ID NO 68
<211> LENGTH: 40
<212> TYPE: DNA
<213> ORGANISM: Artificial Sequence
<220> FEATURE:
<223> OTHER INFORMATION: Primer

<400> SEQUENCE: 68
tagtgggaat agcatacgat ggacatcata tttactggac 40

<210> SEQ ID NO 69
<211> LENGTH: 40
<212> TYPE: DNA
<213> ORGANISM: Artificial Sequence
<220> FEATURE:
<223> OTHER INFORMATION: Primer

<400> SEQUENCE: 69
gaacggtttg tcctgggatc catccataag tgaatatcca 40

<210> SEQ ID NO 70
<211> LENGTH: 40
<212> TYPE: DNA
<213> ORGANISM: Artificial Sequence
<220> FEATURE:
<223> OTHER INFORMATION: Primer

<400> SEQUENCE: 70
cactcgtgga agaacataaa aatttaatct atggaatcag 40

<210> SEQ ID NO 71
<211> LENGTH: 40
<212> TYPE: DNA
<213> ORGANISM: Artificial Sequence
<220> FEATURE:
<223> OTHER INFORMATION: Primer

<400> SEQUENCE: 71
caaatgtata aattattact ttttggatca aaatccattg 40

<210> SEQ ID NO 72
<211> LENGTH: 40
<212> TYPE: DNA
<213> ORGANISM: Artificial Sequence
<220> FEATURE:
<223> OTHER INFORMATION: Primer

<400> SEQUENCE: 72
cgatacggag aggctagtcg tagaaataat tgatatgaat 40

<210> SEQ ID NO 73
<211> LENGTH: 40
<212> TYPE: DNA
<213> ORGANISM: Artificial Sequence
<220> FEATURE:
<223> OTHER INFORMATION: Primer

<400> SEQUENCE: 73

-continued ttaaaaccta tcgtaatttt cttctcataa gactcgctag 40

<210> SEQ ID NO 74
<211> LENGTH: 40
<212> TYPE: DNA
<213> ORGANISM: Artificial Sequence
<220> FEATURE:
<223> OTHER INFORMATION: Primer

<400> SEQUENCE: 74
atggttttac atgtaataaa agggtaacct gcgacaataa 40

<210> SEQ ID NO 75
<211> LENGTH: 40
<212> TYPE: DNA
<213> ORGANISM: Artificial Sequence
<220> FEATURE:
<223> OTHER INFORMATION: Primer

<400> SEQUENCE: 75
acaatgctca tctgaactat cagtacagtc atattctcca 40

<210> SEQ ID NO 76
<211> LENGTH: 40
<212> TYPE: DNA
<213> ORGANISM: Artificial Sequence
<220> FEATURE:
<223> OTHER INFORMATION: Primer

<400> SEQUENCE: 76
tcttcagaag tttgtcagtc taactatttt aagtgtgaca 40

<210> SEQ ID NO 77
<211> LENGTH: 40
<212> TYPE: DNA
<213> ORGANISM: Artificial Sequence
<220> FEATURE:
<223> OTHER INFORMATION: Primer

<400> SEQUENCE: 77
tggttattat tgcatactga ggtcatattt atgcatgcac 40

<210> SEQ ID NO 78
<211> LENGTH: 40
<212> TYPE: DNA
<213> ORGANISM: Artificial Sequence
<220> FEATURE:
<223> OTHER INFORMATION: Primer

<400> SEQUENCE: 78
cgattgtttt gatggctctg atgaagatgg cctctgttct 40

<210> SEQ ID NO 79
<211> LENGTH: 40
<212> TYPE: DNA
<213> ORGANISM: Artificial Sequence
<220> FEATURE:
<223> OTHER INFORMATION: Primer

<400> SEQUENCE: 79
ggaaattatt gtaacaatcg caagaatagc ctccttcttt 40

<210> SEQ ID NO 80
<211> LENGTH: 40
<212> TYPE: DNA
<213> ORGANISM: Artificial Sequence
<220> FEATURE:
<223> OTHER INFORMATION: Primer

<400> SEQUENCE: 80
gaaagtatac acgaagtaag ctacaaagga ggaccggtta 40

<210> SEQ ID NO 81
<211> LENGTH: 40
<212> TYPE: DNA
<213> ORGANISM: Artificial Sequence
<220> FEATURE:
<223> OTHER INFORMATION: Primer

<400> SEQUENCE: 81
tagcttacaa ctgactatat aaccagttgc aacagtatag 40

<210> SEQ ID NO 82
<211> LENGTH: 40
<212> TYPE: DNA
<213> ORGANISM: Artificial Sequence
<220> FEATURE:
<223> OTHER INFORMATION: Primer

<400> SEQUENCE: 82
tatggagaca gatcctgcaa tcccagatat aaattacaca 40

<210> SEQ ID NO 83
<211> LENGTH: 40
<212> TYPE: DNA
<213> ORGANISM: Artificial Sequence
<220> FEATURE:
<223> OTHER INFORMATION: Primer

<400> SEQUENCE: 83
tcttcggcca caattatcgg atttgtgtac tcgtgttgtc 40

<210> SEQ ID NO 84
<211> LENGTH: 40
<212> TYPE: DNA
<213> ORGANISM: Artificial Sequence
<220> FEATURE:
<223> OTHER INFORMATION: Primer

<400> SEQUENCE: 84
tcttgtaaag ctcacggacc aagaatgacc atatacttag 40

<210> SEQ ID NO 85
<211> LENGTH: 40
<212> TYPE: DNA
<213> ORGANISM: Artificial Sequence
<220> FEATURE:
<223> OTHER INFORMATION: Primer

<400> SEQUENCE: 85
ccatccaagt ttacactgta tattacgaag cttggtgttt 40

<210> SEQ ID NO 86
<211> LENGTH: 40
<212> TYPE: DNA
<213> ORGANISM: Artificial Sequence
<220> FEATURE:
<223> OTHER INFORMATION: Primer

<400> SEQUENCE: 86
cgccatgcct gagggctaca tccaggagcg caccatcttc 40

<210> SEQ ID NO 87
<211> LENGTH: 40
<212> TYPE: DNA
<213> ORGANISM: Artificial Sequence
<220> FEATURE:
<223> OTHER INFORMATION: Primer

<400> SEQUENCE: 87
ccaggatgtt gccatcctcc ttgaaatcgg tgccggtcag 40

<210> SEQ ID NO 88
<211> LENGTH: 40
<212> TYPE: DNA
<213> ORGANISM: Artificial Sequence
<220> FEATURE:
<223> OTHER INFORMATION: Primer

<400> SEQUENCE: 88
atgttacgtc ctgtagaaac cccaacccgt gaaatcaaaa 40

<210> SEQ ID NO 89
<211> LENGTH: 40
<212> TYPE: DNA
<213> ORGANISM: Artificial Sequence
<220> FEATURE:
<223> OTHER INFORMATION: Primer

<400> SEQUENCE: 89
ttaaaactgc ctggcacagc aattgcccgg ctttcttgta 40

<210> SEQ ID NO 90
<211> LENGTH: 20
<212> TYPE: DNA
<213> ORGANISM: Diabrotica virgifera

<400> SEQUENCE: 90
aactctcgaa actgatggcc 20

<210> SEQ ID NO 91
<211> LENGTH: 23
<212> TYPE: DNA
<213> ORGANISM: Diabrotica virgifera

<400> SEQUENCE: 91
caaacgatct tgttactgca tcc 23

<210> SEQ ID NO 92
<211> LENGTH: 147
<212> TYPE: DNA
<213> ORGANISM: Diabrotica virgifera

<400> SEQUENCE: 92
aactctcgaa actgatggcc attgcgaaga tggtcattgg aagtgtgccg ataaattgtg 60
tattccactt gacatggtat gtaatggcgc acctgaatgt ttggatggat cagatgaaac 120
tattggatgc agtaacaaga tcgtttg 147

<210> SEQ ID NO 93
<211> LENGTH: 20
<212> TYPE: DNA
<213> ORGANISM: Diabrotica virgifera

<400> SEQUENCE: 93
tgggaaatag ccacatcgac 20

<210> SEQ ID NO 94
<211> LENGTH: 22
<212> TYPE: DNA
<213> ORGANISM: Diabrotica virgifera

<400> SEQUENCE: 94
cccagtactt agatcggcaa ag 22

<210> SEQ ID NO 95
<211> LENGTH: 140
<212> TYPE: DNA
<213> ORGANISM: Diabrotica virgifera

<400> SEQUENCE: 95
tgggaaatag ccacatcgac cgttttttca tggatggtac tggaagaact cacgtcatcg 60
aaaacggttt agtgggccca gttcgtgtag tatacgaccg cagtctttat agaattttct 120
ttgccgatct aagtactggg 140

<210> SEQ ID NO 96
<211> LENGTH: 18
<212> TYPE: DNA
<213> ORGANISM: Diabrotica virgifera

<400> SEQUENCE: 96
acacgtttgc cagtggtc 18

<210> SEQ ID NO 97
<211> LENGTH: 25
<212> TYPE: DNA
<213> ORGANISM: Diabrotica virgifera

<400> SEQUENCE: 97
tgtgtccagt acaaacattt tctac 25

<210> SEQ ID NO 98
<211> LENGTH: 78
<212> TYPE: DNA
<213> ORGANISM: Diabrotica virgifera

<400> SEQUENCE: 98
acacgtttgc cagtggtcaa tttgttattg agcaggaatc gcttcagcct aaagtagaaa 60
atgtttgtac tggacaca 78

<210> SEQ ID NO 99
<211> LENGTH: 23
<212> TYPE: DNA
<213> ORGANISM: Diabrotica virgifera

<400> SEQUENCE: 99
ctaactctgg catcgaatac ctc 23

<210> SEQ ID NO 100
<211> LENGTH: 20
<212> TYPE: DNA
<213> ORGANISM: Diabrotica virgifera

<400> SEQUENCE: 100
tgggcgtttc aaggtagatg 20

<210> SEQ ID NO 101

<211> LENGTH: 77
<212> TYPE: DNA
<213> ORGANISM: Diabrotica virgifera

<400> SEQUENCE: 101
ctaactctgg catcgaatac ctccgcacat tcttacactt acctggagaa attgtcccat 60
ctaccttgaa acgccca 77

<210> SEQ ID NO 102
<211> LENGTH: 474
<212> TYPE: DNA
<213> ORGANISM: Diabrotica virgifera

<400> SEQUENCE: 102
atgttgatgc caaaaaagaa tagagtatgt atttacgaat acctcttcaa agagggagtc 60
atggtagcta aaaaagatta ccatgcccca aaacacctcg aactagaaac tatccctaac 120
cttcaagtaa ttaaggcttt acaatcactt aaatcaaaag gttacgtaaa ggaacaattc 180
gcctggaggc attattattg gtatttgact aactctggca tcgaatacct ccgcacattc 240
ttacacttac ctggagaaat tgtcccatct accttgaaac gcccagcaag gacagaaacc 300
acccgtccta gaccagctgc tctcagatct gagacatcta aaccttcaga agaccgtgca 360
ggatacagaa ggactcctgg aggccctgga gctgacaaga aagctgatgt tggtccagga 420
actggagatg ttgagttcag gcaaggattc ggacgtggac gggcaccaca ataa 474

<210> SEQ ID NO 103
<211> LENGTH: 570
<212> TYPE: DNA
<213> ORGANISM: Diabrotica virgifera

<400> SEQUENCE: 103
ggggctttct gatttttgac agcttctata gaagtttatc aagatgttga tgccaaaaaa 60
gaatagagta tgtatttacg aatacctctt caaagaggga gtcatggtag ctaaaaaaga 120
ttaccatgcc ccaaaacacc tcgaactaga aactatccct aaccttcaag taattaaggc 180
tttacaatca cttaaatcaa aaggttacgt aaaggaacaa ttcgcctgga ggcattatta 240
ttggtatttg actaactctg gcatcgaata cctccgcaca ttcttacact tacctggaga 300
aattgtccca tctaccttga aacgcccagc aaggacagaa accacccgtc ctagaccagc 360
tgctctcaga tctgagacat ctaaaccttc agaagaccgt gcaggataca gaaggactcc 420
tggaggccct ggagctgaca agaaagctga tgttggtcca ggaactggag atgttgagtt 480
caggcaagga ttcggacgtg gacgggcacc acaataaatt tattgataag ttaattttta 540
taaattgatc agccaataaa aagtttggtt 570

<210> SEQ ID NO 104
<211> LENGTH: 155
<212> TYPE: DNA
<213> ORGANISM: Artificial Sequence
<220> FEATURE:
<223> OTHER INFORMATION: Primer

<400> SEQUENCE: 104
cgccatgcct gagggctaca tccaggagcg caccatcttc ttcgaggatg acggcaacta 60
caagtcgcgc gccgaggtga agttcgaggg cgataccctg gtgaatcgca tcgagctgac 120
cggcaccgat ttcaaggagg atggcaacat cctgg 155

<210> SEQ ID NO 105
<211> LENGTH: 155
<212> TYPE: DNA
<213> ORGANISM: Artificial Sequence
<220> FEATURE:
<223> OTHER INFORMATION: Primer

<400> SEQUENCE: 105
atgttacgtc ctgtagaaac cccaacccgt gaaatcaaaa aactcgacgg cctgtgggca 60
ttcagtctgg atcgcgaaaa ctgtggaatt gatcagcgtt ggtgggaaag cgcgttacaa 120
gaaagccggg caattgctgt gccaggcagt tttaa 155

<210> SEQ ID NO 106
<211> LENGTH: 1770
<212> TYPE: PRT
<213> ORGANISM: Diabrotica virgifera

<400> SEQUENCE: 106

Met Leu Ile Leu Phe Phe Val Leu Ser Thr Leu Leu Asn Ala Val Val
1 5 10 15

Ser Thr Asn Asn Asn Asp Cys Pro Pro His Gln Phe Arg Cys Thr Asn
20 25 30

Ser Lys Cys Ile Asp Phe Gln Gln Arg Cys Asp Gly Ser Asp Asn Cys
35 40 45

Gly Asp Gly Ser Asp Glu Leu Asp Cys Asp His Lys Cys His Glu His
50 55 60

Phe Phe Asn Cys Arg Asn Gly Arg Cys Ile Ser Glu Ala Phe Leu Cys
65 70 75 80

Asp Gly Glu Asn Asp Cys Asn Asn Phe Leu Asp Glu Lys Asp Cys Lys
85 90 95

Gly Gln Thr Val Leu Thr Leu Glu Thr Asp Gly His Cys Glu Asp Gly
100 105 110

His Trp Lys Cys Ala Asp Lys Leu Cys Ile Pro Leu Asp Met Val Cys
115 120 125

Asn Gly Ala Pro Glu Cys Leu Asp Gly Ser Asp Glu Thr Ile Gly Cys
130 135 140

Ser Asn Lys Ile Val Cys Asp Gly Phe Lys Cys Lys Asn Gly His Cys
145 150 155 160

Ile Pro Thr Glu Trp Ala Cys Asp Gly Leu Asp Asp Cys Gly Asp Lys
165 170 175

Thr Asp Glu Gln Asp Cys Ala Asn His Val Pro Leu Asp Gln Cys Thr
180 185 190

Leu Asp Lys Arg Lys Phe Leu Cys Ser Asn Asn Lys Thr Cys Ile Asp
195 200 205

Leu His Ser Val Cys Asp Asn Lys Leu Asp Cys Pro Asp Tyr Ser Asp
210 215 220

Glu Gly Lys Gln Cys Asn Ser Ser Ala Ile Ser Cys Asn Asn Asn Lys
225 230 235 240

Cys Ser His Thr Cys Ile Ser Leu Pro Thr Gly Pro Lys Cys Leu Cys
245 250 255

Pro Asn Gly Tyr His Thr Leu Asp Asp Ser Asn Cys Leu Asp Ile Asn
260 265 270

Glu Cys Thr Thr Tyr Gly Ile Cys Asp Gln Lys Cys Arg Asn Leu Pro
275 280 285

Gly Ser Tyr Glu Cys Tyr Cys Asp Asp Lys Tyr Thr Leu Gln Ala Asp
290 295 300

```
Lys Lys Thr Cys Lys Ala Thr Gly Gly Ser Gly Ile Met Ile Phe Ser
305                 310                 315                 320

Ser Lys Gln Glu Ile Arg Ala Leu Thr Leu Asp Ser Leu Asp Tyr Phe
                325                 330                 335

Thr Val Ala Lys Asp Leu Asn Gln Val Val Gly Ile Ala Tyr Asp Gly
            340                 345                 350

His His Ile Tyr Trp Thr Asp Val Phe Thr Gly His Glu Thr Ile Ser
        355                 360                 365

Arg Ser Ile Glu Asp Gly Ser Glu Arg Glu Val Leu Val Thr Ser Gly
    370                 375                 380

Leu Ser Leu Pro Glu Asp Leu Ala Tyr Asp Trp Leu Thr Gly Asn Ile
385                 390                 395                 400

Tyr Phe Thr Asp Ala Leu Lys Gln His Val Gly Val Cys Ser Asn Asp
                405                 410                 415

Gly His His Cys Thr Val Leu Val Asn Lys Asp Ile Arg Lys Pro Arg
            420                 425                 430

Gly Ile Val Val Asn Val Glu Ala Gly Asp Met Tyr Trp Ser Asp Trp
        435                 440                 445

Gly Val Pro Ala Ala Ile Gly Tyr Ser Leu Met Asp Gly Ser Gln Asp
    450                 455                 460

Lys Pro Phe Val Thr Asn Asn Ile His Trp Pro Asn Gly Leu Ala Leu
465                 470                 475                 480

Asp Gln Pro Asn Ser Arg Leu Tyr Trp Thr Asp Ala Lys Lys Met Thr
                485                 490                 495

Leu Glu Ser Ile Asn Leu Asp Gly Thr Asp Gln Arg Ile Val Leu Glu
            500                 505                 510

Gly Ile Val Lys His Pro Tyr Ala Ile Ala Val Phe Glu Asn Lys Leu
        515                 520                 525

Tyr Trp Ser Asp Trp Asp Ser His Thr Ile Gln Thr Cys Asp Lys Phe
    530                 535                 540

Asn Gly Lys Asn His His Thr Leu Val Glu Glu His Lys Asn Leu Ile
545                 550                 555                 560

Tyr Gly Ile Ser Ile Phe His Tyr Ala Leu Glu Lys Arg Leu Val Asn
                565                 570                 575

Pro Cys Glu His Ala Ser Cys Ser Asp Ile Cys Leu Leu Lys Ala Gln
            580                 585                 590

Ser Tyr Ala Cys Ala Cys Pro Glu Asn Lys Val Leu Asp Thr Asp Gly
        595                 600                 605

His Thr Cys Lys Glu Val Gln Pro Thr Gln Ala Leu Val Gly Gly Thr
    610                 615                 620

Gly His Val Leu Val Ser Ile Lys His Gln Phe Leu Gly Lys His Asp
625                 630                 635                 640

Val Thr Phe Leu Pro Asp Leu Ala Lys His Val Gly Ser Leu Ala Phe
                645                 650                 655

Asp Ser Tyr Lys Asn Ile Leu Tyr Val Ser Asp Leu Glu Thr Lys Ser
            660                 665                 670

Ile Val Ala Leu Asn Met Asn Ile Gly Ile Ser Lys Thr Leu Glu Ile
        675                 680                 685

Asp Gly Leu Gly Lys Val Thr Ser Met Asp Phe Asp Pro Lys Ser Asn
    690                 695                 700

Asn Leu Tyr Ile Cys Asp Thr Glu Arg Leu Val Val Glu Ile Ile Asp
705                 710                 715                 720
```

-continued

```
Met Asn Asn Leu Glu Arg Lys Ile Ile Val His Asp Thr Phe Gly Glu
                725                 730                 735

Thr Pro Glu Ser Ile Ala Leu Val Pro Glu Asp Gly Ile Met Phe Val
            740                 745                 750

Ser Phe Lys Gln Gly Lys Leu Gly Asn Ser His Ile Asp Arg Phe Phe
        755                 760                 765

Met Asp Gly Thr Gly Arg Thr His Val Ile Glu Asn Gly Leu Val Gly
    770                 775                 780

Pro Val Arg Val Val Tyr Asp Arg Ser Leu Tyr Arg Ile Phe Phe Ala
785                 790                 795                 800

Asp Leu Ser Thr Gly Val Ile Glu Ser Thr Ser Ala Ala Gly Asp Asp
                805                 810                 815

Arg His His Phe Arg Thr Leu Thr Thr His Pro Val Ser Ile Ala Val
            820                 825                 830

Leu Lys Asp Asp Leu Leu Trp Thr Asn Leu Asp Ser Lys Asp Leu Tyr
        835                 840                 845

Trp Ser Glu Lys Arg Ser Ser Glu Ser Tyr Glu Lys Lys Ile Thr Ile
    850                 855                 860

Gly Phe Lys Glu Asp Asn Val Asn Ile His Leu Val Ser Val Thr Arg
865                 870                 875                 880

Lys Gln Leu Glu Ile Asn Ser Cys Arg Val Asn Asn Asn Gly Cys Ser
                885                 890                 895

His Leu Cys Leu Gln Ser His Lys Ser Ile Val Cys Ala Cys Pro Ala
            900                 905                 910

Gly Trp Glu Leu Ser Ala Asn Gly Phe Thr Cys Asn Lys Arg Val Thr
        915                 920                 925

Cys Asp Asn Lys Glu Met Leu Cys Pro His Ser Asn Thr Cys Val Leu
    930                 935                 940

Lys Ser Leu Arg Cys Asn Gly Phe Lys Asp Cys Ala Phe Gly Glu Asp
945                 950                 955                 960

Glu Trp Asp Cys Gln Thr Val Ser Gln Cys Leu Pro Gly Gln Tyr Lys
                965                 970                 975

Cys Asp Asp Gly Gln Cys Ile Ser Glu Asp Leu Val Cys Asn His Ser
            980                 985                 990

Tyr Asp Cys Lys Asp Lys Ser Asp  Glu Tyr Gly Cys Ala  Asp Lys Asn
        995                 1000                1005

Lys Lys  Leu Gly Cys Pro Pro  Gly His Phe Thr Cys  Lys Ser Ser
    1010                1015                1020

Glu Cys  Ile Ser Glu Arg Phe  Val Cys Asp Ala Phe  His Asp Cys
    1025                1030                1035

Asp Asp  Gly Ser Asp Glu Leu  Asn Cys Glu Asn Asn  Ile Cys Leu
    1040                1045                1050

Glu Ser  Gln Phe Arg Cys Asp  Val Gly Thr Cys Ile  Pro Lys Asp
    1055                1060                1065

Trp Glu  Cys Asp Gly Glu Tyr  Asp Cys Thr Asp Ser  Ser Asp Glu
    1070                1075                1080

His Cys  Ser Ser Glu Val Cys  Gln Ser Asn Tyr Phe  Lys Cys Asp
    1085                1090                1095

Asn Asn  Arg Cys Ile Asp Pro  Lys Leu Gln Cys Asp  Gly Phe Asp
    1100                1105                1110

Asp Cys  Gly Asp His Ser Asp  Glu Lys Phe Glu Lys  Cys Leu His
    1115                1120                1125

His Ser  Lys Ala Pro Lys Cys  Thr Leu Glu Glu Phe  Ala Cys Ile
```

```
    1130                1135                1140

Thr Asn  Thr Ser Ile Cys Leu  Pro Lys Ser Ala Lys  Cys Asn Gly
    1145                1150                1155

Thr Ser  Glu Cys Pro Asn Asn  Glu Asp Glu Lys Asp  Cys Ser Lys
    1160                1165                1170

Cys Glu  Glu Asp Glu Phe Glu  Cys Lys His Lys His  Tyr Arg Glu
    1175                1180                1185

Cys Ile  Pro Arg Ser Trp Ile  Cys Asp Gly Thr Asp  Asp Cys Gly
    1190                1195                1200

Asp Asn  Ser Asp Glu Ser Met  Glu Thr Cys Ser Ser  Lys Leu Lys
    1205                1210                1215

Pro Ala  Ala Asp Asn Phe Ala  Val Thr Asp Ser Cys  Leu Thr Gly
    1220                1225                1230

Tyr Arg  Cys His Ser Gly Ala  Cys Ile Asn Met Thr  Ser Val Cys
    1235                1240                1245

Asn Asn  Asn His Asp Cys Phe  Asp Gly Ser Asp Glu  Asp Gly Leu
    1250                1255                1260

Cys Ser  Ser Ser Cys Val Gly  Val Lys Asn Pro Cys  Asn Gln Ile
    1265                1270                1275

Cys Val  Lys Thr Pro Ser Gly  Pro Arg Cys Glu Cys  Lys Pro Gly
    1280                1285                1290

Tyr Lys  Leu Leu Gly Asp Gly  Lys Thr Cys Ile Asp  Asp Asn Glu
    1295                1300                1305

Cys Gln  Thr Asp Pro Pro Ile  Cys Ser Gln Leu Cys  His Asn Lys
    1310                1315                1320

Glu Gly  Gly Tyr Ser Cys Asp  Cys Tyr Asn Asn Phe  Leu Leu Ser
    1325                1330                1335

Ser Asn  Lys Lys Ser Cys Lys  Ala His Gly Pro Arg  Met Thr Ile
    1340                1345                1350

Tyr Leu  Val Ile Tyr Gly Asn  Gln Ile Arg His Leu  Ile Pro Lys
    1355                1360                1365

Ser Asn  Thr Met Ala Val Leu  Tyr Thr Asn Pro Met  Ile Lys Ile
    1370                1375                1380

Ser Ser  Leu Asp Thr Leu Val  Lys Pro Lys Leu Ile  Phe Phe Ser
    1385                1390                1395

Ser Tyr  Glu Thr Gln Ala Ile  Tyr Lys Leu Asp Thr  Thr Thr Asn
    1400                1405                1410

Met Met  His Tyr Ile Arg Asn  Val Gly Phe Pro Arg  Thr Ile Ala
    1415                1420                1425

Val Asp  Trp Ser Thr Gln Asn  Ile Tyr Tyr Phe Asp  Thr Asp Val
    1430                1435                1440

Asn Gly  Arg Ser Ile Ser Val  Cys Ser Phe Glu Glu  Lys Cys Ala
    1445                1450                1455

Lys Leu  Ile Asn Ile Glu Ser  Pro Arg His Val Thr  Ala Leu Ala
    1460                1465                1470

Val Asp  Ser Val Asn Lys Leu  Leu Phe Tyr Val Leu  Arg Asn Trp
    1475                1480                1485

Trp Val  Leu Glu Thr Pro Ser  Phe Val Ile Tyr Ser  Val Asn Leu
    1490                1495                1500

Asp Gly  Ser Asn Arg Gln Glu  Ile Val Lys Thr Thr  Thr Gly Asn
    1505                1510                1515

Val Glu  Asp Ile Thr Phe Asp  Ile Asn Lys Lys Leu  Leu Tyr Tyr
    1520                1525                1530
```

```
Thr Asn  Lys Gln Asp Glu Ser  Ile His Glu Val Ser  Tyr Lys Gly
    1535                 1540                 1545

Gly Pro  Val Lys Thr Val Phe  Ser Asn Ile Ser Gln  Pro Glu Gly
    1550                 1555                 1560

Leu Lys  Phe Phe Glu Asn Gln  Leu Tyr Tyr Thr Val  Ala Thr Gly
    1565                 1570                 1575

Tyr Ile  Val Ser Cys Lys Leu  Tyr Gly Asp Arg Ser  Cys Asn Pro
    1580                 1585                 1590

Arg Tyr  Lys Leu His Thr Phe  Ala Ser Gly Gln Phe  Val Ile Glu
    1595                 1600                 1605

Gln Glu  Ser Leu Gln Pro Lys  Val Glu Asn Val Cys  Thr Gly His
    1610                 1615                 1620

Lys Cys  Pro Tyr Leu Cys Val  Pro Ala Glu Ser Gly  Tyr Arg Cys
    1625                 1630                 1635

Leu Cys  His Asn Gly Lys Val  Ser Asn His Ser Glu  Ile Cys Gly
    1640                 1645                 1650

Glu Asn  Asp Asp Asn Gln Ser  Gly Asn Asn His Lys  Phe Ala Val
    1655                 1660                 1665

His Thr  Thr Pro Ile Gln Thr  Ala Ser Asp Lys His  Ser Gly Ala
    1670                 1675                 1680

Val Ala  Ser Ala Ile Leu Ile  Pro Leu Leu Leu Val  Phe Leu Gly
    1685                 1690                 1695

Ala Val  Phe Tyr Tyr Leu Leu  Lys Arg Arg Gly Asp  Thr Gly Leu
    1700                 1705                 1710

Asn Ile  Ser Met Arg Phe Tyr  Asn Pro Leu Tyr Gly  Lys Pro Val
    1715                 1720                 1725

Arg Glu  Asp Gln Lys Gln Ile  Leu Lys Pro Gly Gln  His Glu Tyr
    1730                 1735                 1740

Thr Asn  Pro Ile Ile Val Ala  Glu Glu His Glu Asp  His Ala Lys
    1745                 1750                 1755

Asp Ala  Ser Arg Met Leu Asn  Asp Ser Cys Val Cys
    1760                 1765                 1770
```

<210> SEQ ID NO 107
<211> LENGTH: 5498
<212> TYPE: DNA
<213> ORGANISM: Diabrotica virgifera

<400> SEQUENCE: 107

```
taccacagtc gacatctgac agtttctaca gtatagttgc agtgttcagt ggaaaatatt     60
caattaagga acctatatat tgttgactct gctacgcccg tcatgttggc acaactctcg    120
attatgttcc gaacagtgtt tgtgggattc tgaaaaacca gagcatcgtg aacgttcagg    180
acaatagtat tctctcttgg tgaatagaca gacttactga ctgtacgcaa tagcaccggt    240
gtaaaacttg atgacgttga tgatgatgaa gccatcgcaa gcaataacaa aaacaagcac    300
gaacgaaagg ttaattacaa tagcactgat agtatcgttt cttggtgatt catgtatgat    360
tgtgactaat cggtttgata gaaagaaaga tttattgtaa ctcctttcct catcgacctt    420
aaaaagtata tactacaatc aaaatcgttt tcaaagaact caaagggact ggcgagcttt    480
ggccgttgta gccgtgttct gttttatggc gttctatcgt ttataatgaa cagtttgcta    540
taaacgacat tacactagtt acaaatcagt tcgttgtaag tttatgatgc aaaatggaaa    600
gatgtatatt gcaggactat gtgctaatag aactgaagta cttcggaaaa taagcaagaa    660
```

-continued ttagctcaga gtcataacag gtttccttac aagacaagtc aagttcccct atgggaaaag 720
aagtttgaaa ataacgaaac ctggtggtgg tcaaagaagt tcaataaaaa gaaaaagaga 780
agagaaaact atataaacag tggcaagaaa atagatcgca catagagagg aagcgaaagc 840
agcaaaagct aaagcagatg tgtgtacaac tctatacgat caacttgaca tcagttagaa 900
gtaagaagtt tacgtcagag agattgtaat ttttctatga agaaattgtt tttcgtatca 960
ttagtttagt ttgttcagtg aaagagaaaa tgaaaaaaca aggtggaatt ttaaggttat 1020
accgcacacc tggttgtaca gcagcaaaaa agtttgaaat tgtccagaaa cttcagcaaa 1080
catgtaaaaa tctaaaggat attcaaaccg aaatatgttt tcatatcgaa tcaacaagtg 1140
ccttggaagc aaaagacgtt aagattttga aatgggttct tcaagatcct ctccatcccc 1200
aaaatttaag cgaaaaggga acgctggtag cgaaaaatgg tacggctttg gttgaggtag 1260
gacctagatt taatttttcc acatcaagtt ccacaaatgc tgtttctatt tgccaaaatc 1320
tcggcttggt ccaagtaacc agattagagg tctcacgtcg ctatctttta gtgtttaatc 1380
aaggtacaaa acttacacct caaattgaga ataatctagc atctttactc tatgatagaa 1440
tgactgaatg caggtatact ccagaaaata tacctaaagt tagctttaat gaaaaacttg 1500
tcaaaaagga ggatataaaa gagattgata tattgggtaa aggtgcagaa gctttaaaag 1560
ccattgataa agaacttggt ctggcgttcg atgaagcaga tatagtatat tacacaaatt 1620
tgtttaaaaa tgttcttaag aggaatccca ctaatgttga atgctttgac ttggctcaat 1680
ctaacagtga acacagtaga cattggtttt ttaagggaaa aatggttatt gatggtgtag 1740
agcataagca atcactgata gatatgatta ttgaaactca agaacacaca aatcccaaca 1800
atgttataaa attcagtgat aatagtagtg caattaaggg attcttacac cgaagcttaa 1860
ggcctgtaac agcaggttct ctcagtgagc ttaagcaagt accagtagaa tctcatctta 1920
ttttcactgc agaaactcac aatttcccga ctggtgtagc tcctttcagt ggagccacta 1980
caggaactgg aggaagaatt agggatgtgc aaagtgtggg aaggggtggt tattgcatag 2040
ctggtactgc tggttattct gtaggcaatc ttcagattcc agattatgat ctaccatggg 2100
aagacaaaaa cttctcttat ccatcaaact ttgctccacc tttagaagtt ctagttgaag 2160
ccagtaacgg agcctcggat tatggtaaca agttcggtga acccttgatt tccggcttcg 2220
tacggtcctt tggtcttgtt gacgcggctg gagagagaaa agaatggatt aaacctatca 2280
tgtttagtgg aggtattggc agcatggaag ccgatatgac tgagaagctg ccacctaaat 2340
taggacacca aatcatcaaa attggaggac ctgtatacag aattggtgta ggtggaggat 2400
ctgctagttc agtcgaggta caaggggaca acaaagtaga gttagacttt aatgctgtac 2460
aaagaggtga tgccgaaatg gaaaacaaat tgaacagagt cgtacgtgct tgcttggaac 2520
taggttccaa aaaccctatc gtcagtattc atgaccaagg agctggaggc aatggaaatg 2580
ttttgaaaga attagtagaa ccagtaggag gaattatata cgccaataaa tttgatttag 2640
gtgatccgac aataaacgtt cttgagttgt ggggagccga atatcaagaa aataatgcgt 2700
tgttgtgtaa aaaagaagat cttcctcgtc ttaagagtat ttgtgcaaga gaaagatgcc 2760
ctgttaacgt tgtaggtgaa gtaactgata caggaagagt agttctggct ttagacgaaa 2820
gcaaggctgt tacaccgttt aatttggaat tggaacatgt attaggaaaa atgccacaga 2880
aagtcttcaa gttaaacagg cacaaagtag ccagtaaacc actagaattc ccaaaagccc 2940
tttcaatcta ccaatctctg ctgagagtat taaggttgcc atctattgga agcaagcggt 3000
acttaacaaa caaagtagat cggtgtgtta caggtttgat agctcagcag caatgtgtgg 3060

-continued

```
gaccactaca tacaccttta gctgatgttg ctgttacggc tctttctcat tttggacatg   3120
aaggtatagc gtcatctatt ggagagcaac ctatcaaagg tttagtgaac actgcagccg   3180
gtgctagaat gacggtagtc gaagctttaa gcaacctcgt attcgccggt atcaccagtt   3240
tacgcgacgt caaatgcagt ggtaactgga tgtgggctgc caagctccct ggcgaaggag   3300
cagctctgta tgacgcatgc aaagctatgt gtgacctcat gagcgagtta ggaatcgcca   3360
tcgatggtgg aaaggattct ttgagtatgg cagctagagt tggaaaagac actgtcaaag   3420
ctccaggaac cttagtagtt tctacttatg ctccttgtcc tgatattaga aaagttgtga   3480
cccctgattt caaagcgcct tctatgggaa aaacaggaac cattctgttc gtagatcttt   3540
cccgaagtga cagtagactt ggtggttcgg cattagctca agcatttggt caacttggag   3600
aggaatctcc cgatcttcat agcgctgaag aattagtaaa tgcatttaat gcaacacaac   3660
agttaataaa agatgattca attttggcag gacacgatat cagcgatggt ggcttaatcg   3720
tatgcctatt agaaatgtgc ttcgcaggaa tatgtggtat ggaagttgat gttcaacata   3780
gacaaggcaa accacttaat attttgtttg ctgaagaagt tggatgggta ctggaagttt   3840
tggatgaaga tgttgctcac tgcctgaatg tgttttcgaa tcacaacgtc ccagtattca   3900
aaataggaaa gactgttgga tatggagtta aatctaaatt tggaataata gccaaccatg   3960
cttgcctaga aagtacaatt ctacctttga tgaagctttg ggaagagact agttataggt   4020
tagaactaca tcagactatt aaatcctgtg ccgattcgga attccatagt cttccaagcc   4080
gaactggacc caaatacaca cttacattcg accctgatca cgatcagact gtaaaagacg   4140
aattagttcc cgtagctgtg ataagagaag aaggaacaaa cggagatagg gaaatggctg   4200
ctgcgttgat aagagccggg ttcaaagtgt gggatattac tatgcaagat ctgttgagcg   4260
gtgtggccac tttggatagg tttaggggcg tgatattccc tggaggtttc agttatgcag   4320
atgtcttggg ttctgctaaa ggctgggcgg ccagtattct attcaacaaa accgtccgag   4380
aacagttcga caaattcttt gccagaagag acacgttcag tttgggagta tgtaacggat   4440
gccaattgat ggctcttatc ggttgggttg gaacacctgt taatgaaggt actaaaccag   4500
acataatgtt ggaacataat ttgtctgaaa gattcgaatg ccggtggagc actatcaaga   4560
tagaaaaatc caaagctata atgatgaagg gtatggaagg gtcttcattt ggtgtgtggg   4620
tcgctcatgg agaaggtcga ttcacgttca aatcagacac catctacgac caattgaaat   4680
ccgaagaact cgtcgccttg cgttacgtag acgataacgg aaaaccgact gaaatctatc   4740
ccatgaatcc caatggaagt attgagggat tggcgggagt gtgctccgaa gacggaagac   4800
acttagcgat gatgccgcat cccgaaagat gcgttcaacc attccaatgg ccgtacatgc   4860
cacaaagctg ggtacactac aagaagagtc catgggagaa gatgtttaga aacgcttatg   4920
aatggtgcag aagcaataaa ttccataatg tttattatta agttaaaaga aatattgtaa   4980
atatttcaat gatctagctc aaattttata atgtttatac acattttgaa gttattctat   5040
tttagatata gcagtttcga atgtagagtt gagtccatgg atatttaccc gtgcgtcatc   5100
atttacagca tacgaaataa gtcggaaatt tacttaacgc aacagcaagt gacagaaagt   5160
ggctactgct ccgatgacgg atattataaa atttgacatt atcaaataaa tagaatgtaa   5220
aatgttagtt ttgctttaaa attttggtgc agaattaaca ctacatttga agtagcttaa   5280
taaattattt taatatcatt actgattaat aaatacttaa ataacaattt ttaaaaaatt   5340
taatgaaata tatattttg ttatttcttt cacttttgcg gaaacttaaa taaaaccatt   5400
```

-continued

```
ccttaactgt gtgaatgagg ttaactttgt atgtaaatta atggcaaaat aaaatacact   5460

taccataaaa tttcaaactc caatataaaa ttagttgt                           5498


<210> SEQ ID NO 108
<211> LENGTH: 1875
<212> TYPE: DNA
<213> ORGANISM: Diabrotica virgifera

<400> SEQUENCE: 108

ctccgtttag cgagcggaat aacggcgtcg aatcaaacgg aaagacaaga gattgacctc     60

tctaaataat ccatctgctt gctatcagcc agcgagcaag ctacacacgg cccaagacga    120

aagaacgaag aaccttcgcc ttctctcctt cgccagttca gtatcccttc agcgacgctg    180

tgcatcgttg ctggtttaca acagtcgttg tagttcttcc caccttttca atcgctaact    240

caacggttga aaaccgacga tatatcctgc ctctgccttt gcctcatcga gtggggagaa    300

atacgggcag acaacgatct gtgtaatggc aatggcgttg tacagactat cagaactgaa    360

atcatggcct agttcccttt aaaagttcag aaaacagtga attcgcgtgg atagtgaaac    420

tggtgtaaat gagtgataaa aatttaataa ttctacgatg gctgaagcag aaaacatcga    480

tttccaagca tgttgcagac tgtgtctcag cgaaatggtg gattctttaa agtccatttt    540

cgacgaaact cctgaagatg aaagtctctc ccaaaagatt ttacaatcag tggctattga    600

ggtcagttcg gcagacaaat tatccaccaa gatctgcaaa gagtgcgtag aaaaagtaac    660

tgactggtct tcgtacaaag aacgatgtct ccaaaaccaa aagaaattaa cggagttgtt    720

agttgcgaaa gaaggtccag aagttttggt tgtacctgaa attatacccg aacccgaagc    780

accacttcct gtaaatggaa ttgaatcaga aactccttct gatgacgaca ttcatgaaaa    840

ccaagtggat cctgcctctt tgttggacct tagcttgcaa attaaagaag aaccagcaga    900

ccacactgaa cagaacgaac acgataaccc atatctagca tatttgggtt atcgtgttcg    960

ttctgttcag tgtggtctgc tggttcttct ttaatttgca agctaaggtc caacaaagag   1020

gcaggatcca cttggttttc atgaatgtcg tcatcagaag gagtttctga ttcaattcca   1080

tttacaggaa gtggtgcttc gggttcgggt ataatttcag gtacaaccaa aacttctgga   1140

ccttctttcg caactaacaa ctccgttaat ttcttttggt tttggagaca tcgttctttg   1200

tacgaagacc agtcagttac tttttctacg cactctttgc agatcttggt ggataatttg   1260

tctgccgaac tgacctcaat agccactgat tgtaaaatct tttgggagag actttcatct   1320

tcaggagttt cgtcgaaaat ggactttaaa gaatccacca tttcgctgag acacagtctg   1380

caacatgctt ggaaatcgat gttttctgct tcagccatcg tagaattatt aaatttttat   1440

cactcattta caccagtttc actatccacg cgaattcact gttttctgaa cttttaaagg   1500

gaactaggcc atgatttcag ttctgatagt ctgtacaacg ccattgccat tacacagatc   1560

gttgtctgcc cgtatttctc cccactcgat gaggcaaagg cagaggcagg atatatcgtc   1620

ggttttcaac cgttgagtta gcgattgaaa aggtgggaag aactacaacg actgttgtaa   1680

accagcaacg atgcacagcg tcgctgaagg gatactgaac tggcgaagga gagaaggcga   1740

aggttcttcg ttctttcgtc ttgggccgtg tgtagcttgc tcgctggctg atagcaagca   1800

gatggattat ttagagaggt caatctcttg tctttccgtt tgattcgacg ccgttattcc   1860

gctcgctaaa cggag                                                    1875


<210> SEQ ID NO 109
<211> LENGTH: 3249
```

<212> TYPE: DNA
<213> ORGANISM: Diabrotica virgifera

<400> SEQUENCE: 109

```
tgattttgat gaaaaaaaat ctgatgaaat agtagccatg aactctgacc tgggagaaaa     60
aatattattc gaaaaaactg taacatgcca gggaggtgtc gaaatttggc tgaaccatct    120
tcttaatgcc gtcagagaca ccgtcaaaaa cgtctgtgct atgcaggctc agtgttttaa    180
tgatcctgaa tacgacttca tatctggatt cgttcatttt tgtggacagg ctggactagt    240
tggtatacaa atattgtgga caaaagaatc cgaaattgct attaagaaag caagagtaga    300
tagaatggct atgaaaatta caaataaacg atttctcgac ctcttaaatg ctctcattga    360
tcttacatca aaagatttaa caaaaatgca aagaataaga tttgaaacca tggttactat    420
ccacgttcat caacgagaca ttttcgacaa catttacaag ttaaaagtta agtcattatt    480
ggattttgaa tgggcttgcc agacaaggtt ttactatgat gaagagacgg atgatataac    540
tgtgaaaatt acagacgtca tctttttata ccaaaacgaa tatttaggaa taacagagag    600
gctggcgatc accccttttaa ctgacagatg ttacataact ttggctcagg ctatttggat    660
taatatggga ggagcacccg ctggccctgc tggaacagga aagacagaaa cagtcaaaga    720
tatgggaaga actctgggaa aatttgtagt tgtattcaac tgctctgacc aaatggattt    780
tagaggactt ggtcgaattt tcaagggact tgctcaatca ggaacctggg gatgcttcga    840
cgaattcaac agaattgagc tacctgtgtt atcagtagct gctcaacaga tctacatagt    900
tttagaagca agaaaagcac gcaagccatc gtttatcttc atggatggag acaacgttag    960
tatgaatata gagtttggta tattcctcac gatgaatcct gggtacgcag gaagacaaga   1020
attgccagag aatctgaaaa ttatgttccg aagtgttgct atgatggtcc ctgatagaca   1080
gatcatcatc agagttaaac tagcttcctg cggctttaaa gaaaatgttc acttgtccaa   1140
gaagttcttt accttgtatc agttatgtga agaacaactt tctaaacagg tgcattatga   1200
ttttggcctt cgaaatattt tatcagtgtt gagaacactt ggagcacaaa agcgagcaaa   1260
tccaaatgaa actgaagaag tcgtagtaat gagagtttta agagatatga atttgagcaa   1320
actaattgac gaagatgaac ctcttttcct ttccctaata gaagatatgt tccctggtat   1380
taaactaact acaaaagctt ggaaagacct gcaaaaagct atcacgcata tatgccaaga   1440
gcttggtttc gtcaattatc cttcgtggaa tcttaaggtt gtgcaattgt atgaaacctc   1500
tttggtacgg cacggactaa tggttatggg tcccacgggt gcgggaaaaa caaaatgcat   1560
gttaactcta atgaagtcta tgacagaaat gggtatgcct catagagaac ttcgaatgaa   1620
tccgaaagca atcacggctc cccaaatgtt tggaagattg gatgttgcca cgaacgactg   1680
gacggatgga atcttctcaa ctttgtggag aagaactctt aaatttaaga aaacagacta   1740
ttgttggtta attttggatg gtcctgtaga tgcagtatgg atagaaaacc taaactcagt   1800
tttagacgat aacaaaactt taactctagc caatggcgac agaatagtga tggcaaataa   1860
ctgtaaattg gtattcgaac cggacaatgt tgataacgca agcccagcca ctgtatcccg   1920
aatgggtatg gtattcatga gttcttcggt ccttccttgg tcaccgatct tagaggcttg   1980
gttgaaaact agatcagcgc aagaagctga ttctatcaga aatcatttta acagatgcta   2040
tgatgacctt cacgttttcg tgcagaccag attaaaagcc aagatgtttg taagggaagc   2100
tctgtacgta agacagtgtt acgatgtttt acaaggggta ttagatatct ttgaagaacc   2160
aaaaacatgg agtgatagac aaatagaacg attggtacta ttctcaataa tgtggtcctt   2220
```

-continued

```
gggagcactg ttagagttag acgacagaca aaaacttgaa gaatttgctt taacccaccc   2280

gtccaaaatg gattggccaa aagctcagga aggagaaacc atttttgaat ttgtagttaa   2340

tccagacaat ggaagatggg aacactggaa atccagagtt gaaccctttg tatatcctac   2400

agataccgtg ctagaattta cttcgatatt ggtacctaat gttgacaacg ttagaacagc   2460

ctttttaata catacgatag ccaaacaggg taaagctgta ttgctaattg gtgaacccgg   2520

aactgccaaa accgttatga ttaagggtta ttgctcaact tttgatcctg aatataaact   2580

gaacaaatgc tttaattttt cttctgctac tactccaaac atggttcagc gtatcataga   2640

atcttatgtc gataagagag ttggtacaac ctacggacct cctgccggaa aaactttaac   2700

catatttata gacgacatta atatgcctgt aattaatgat tggggtgatc aaatcacaaa   2760

cgaaatcgta agacagtgca tggaaactgg aggattctat agtttggata aaccaggcga   2820

tttttcagta attgctgacg ttatgtttct gtctgctatg attcatcctg gaggtggtag   2880

aaatgatatt ccccaccgtc tcaaaaggca gtttagtata ttcaactgta cactgccaag   2940

tacttctgct atggatgtta tattcagtca aattgcttgc ggctactttt gtctagaaag   3000

gtttaacgaa gaaatggcag agtttattcc aaagctagta ccacttacgc gacatgtatg   3060

gcagaatacg aagaaaaaaa tgttacccac tccagccaaa ttccattatg tatttaatct   3120

acgagatctt tctagaatat ggcaaggaat attgacagtc caagtgcttg agtgtccgac   3180

taagaatatg gctcttaagc tctggagaca cgagtgtact agagtaattt cagataggtt   3240

tactgaagc                                                           3249
```

<210> SEQ ID NO 110
<211> LENGTH: 1370
<212> TYPE: DNA
<213> ORGANISM: Diabrotica virgifera

<400> SEQUENCE: 110

```
cttaaacata accttcaatt tgtaatgtgg ttttaaaatt cattccttaa ctttaaattt     60

atttattttc aattaggaaa attaggctat aacgtcgaaa aatgtccaaa aaacgctata    120

attggaaagc taggcaaaat gttgaaactc tggttgataa tactcataaa gaaaaggaaa    180

tggctcctcc accatacgca gacctcggca aaagagcaag agacgtattc ggcaacggtt    240

atcactttgg cctaattaaa ttaaattgca aaaccaaaac agccagtggg gtccaattta    300

gtacaggtgg tagttcagac catgaatctg gaaaagtgtc tggatctttg gagagcaaat    360

acaccgtcaa agattatgga ttgactttca cagaaaaatg gaatacaaat aatactttgg    420

ggactgagat cgccatttca gaccaaggta ttaagggact caaggtctct ggtaatgtta    480

acttctcccc acaagaagga taccagtcag gagttgtgaa gtctgaatac ggcaacgaaa    540

gaatacacct caacgccgat gttgacttaa atagtaacgg acctgtcgta agaggttcgg    600

ctgtcgtggg ctatcaagga tggttggctg gttaccaggc tgcctttgac gttcaaaact    660

caaaattggc caagagcaat tttgcattag gattttcaac atcagacttt gttctccata    720

catgtgttaa cgacggccaa acgtttggcg gttccatcta ccaaaaaatc aaccccaaat    780

tggaaacagc catcaacttg tcttgggcag ctagcggaga aaagaccgac ttcggtttgg    840

gctgcaagta tgacttggac gccgacgcat ctcttcgcgc taagattaac aacgccagtc    900

aaatcggttt aggataccaa caaaaactac gtgatggtgt aactctaact ttgtctaccc    960

tcatcgacgg caagaacttc aatcaaggtg gtcacaagat tggtttggcc ttggacctgg   1020

aggcttaaat atgttattac atcttgttcc acaaatacat attagcgccc atttaatata   1080
```

```
tttaagaatc ctgtattgta gataataatt atttaaacgg gactttagtg ttatacttta   1140

ttactcccgt tgtgtttatt tcagttgctc ctcccaatta ctcctttttt acacgctata   1200

cgtatatatt gtttttatta ttaaactctg aaaggcgcgc ttttctggat attttcaaag   1260

attgatgtca agttaggagc atatgcattt tatgtcaaaa aattagattg ggattgtggg   1320

tcttagatgg ctacaatccg ctttgtgtag ttttgcaatt ttgcaaaaaa              1370
```

```
<210> SEQ ID NO 111
<211> LENGTH: 1194
<212> TYPE: DNA
<213> ORGANISM: Diabrotica virgifera

<400> SEQUENCE: 111

acccattggg gaacgcacgc attttgttta gttccggcgt ctttgctcaa gttttgcccg     60

gttgttgctg tgtttggttt gttggtgcat tttattatta taacaagttc attacaatgg    120

gcaaaaagaa ggtagaagag agtgaaagtg aagaggagta ttctgtagag aaaattattg    180

ataggagagt tgtagatgga aaagtagaat attatctaaa atggaaagga tattcagaag    240

atgataacac ttgggaacct gaggacaatc tagattgtcc tgaacttatt tctgagtttg    300

agaggaatcg taaaagtaag aaggctgctg gcaaagaaaa gaaaagaaca agagataatt    360

ctacatcttc cgtggattca aacaattcat ccactaaaga aaaagaaaaa aagaaaaaga    420

aaggccgttc tccatcaccc gagtctgaaa gtgaacccag ctctaaaaaa tcaaaaatag    480

atgattcaga tgatgacaaa aagagcaaaa agaagtcgtc atcaaaagat gctgattccg    540

atgatgataa aggaaaaaag tcaaagaaga aagacaaaag tgctttagat gatgactctg    600

acgatgagaa gtcaaaaaag tcaaaaaaaa agattctgat tcagaagatg aaaaaaagaa    660

aaagaagaga aaaagtggtc ctaaatctcg taaagctgcc gtttcagatg actcagatga    720

agatgaagcc ccaaaaaaga aaactgaaag tcgggcgaaa aaagatgatg aaaaatccaa    780

gaaaaaagct gatgattctg atgatgaaga tgatccgaag aagagcaaaa aagttgacaa    840

caaggaaaaa aagggtgcta aacctaaaga caaagagaag tctgcatttg acaaaggttt    900

agaagctgat aaaattattg gagcatctga cactagtggt caattgatgt tcttgatgaa    960

atggaagggt acagatgata ctgatttagt ttatgcaaga caagccaatt tgaaatgccc   1020

acaggtggtc attaaatttt atgaagaaag aattgcgtgg catacgccag acgactttta   1080

attttactta gtgataagat ttgttgtaga tttaatttct tacttttaaa taggtagagt   1140

tcttatatta ttaatccata tgtatttttt ttaaatggaa gaaaccacga cttg         1194
```

```
<210> SEQ ID NO 112
<211> LENGTH: 1802
<212> TYPE: DNA
<213> ORGANISM: Diabrotica virgifera

<400> SEQUENCE: 112

gggggagaaa acatatgatt gcccagactg acagtaattc gatattttga attaattgaa     60

ctgaacactt ctattattaa aactaatcaa aacactcgaa acagatacgt aatgcagtta    120

taatgagttt tataattatt gcttttaaaa atttcctaca taccatgttg cagttattat    180

cttttggtaa aaaaactatt acaaatagtt tgagtgtgta tgtaaaaact attggtggca    240

acactttaac tgtagatcta gatcctacat gggacattaa aaatgttaag gaaatagtgg    300

caccacaact tggattagaa ccagatgaag taaagatcat ttttgctgga aaggaattgg    360
```

-continued

```
gagacgaaat taaaattgag gaatgtgatt taggtcagaa aagtattctc catgctgtaa    420
aaattagagg aaagaggagt aagcttattc aacctacaaa tagtagtgta atagaggaaa    480
atgaagatcc aagtagcaag ccattgagtg aggttttaga tgatagtatg ttctctcatg    540
aagacagcaa ttcttttaat agtacaactg aaaggcggtc atctcaatca gaaagtggtt    600
taattaagtc aaaagtacat ttctatgtat tctgtccaac atgtaaggca atgaagtcag    660
gaaaaataag agtaaggtgc catttttgta aaagtggagc gatcactgta catgctgatc    720
cccaaaactg gaatgatgtt ctaatatcaa aacaaattac aggaacatgt gaaaatagtc    780
cagaattatg ttctaaccta ttaaaaaacg tagagcctac ttttgctgag ttttacttca    840
aatgttctga acatacatca ttaggggaac aagatggagc agtgccacta gatctaataa    900
ggccaaattt aagggacatt ccctgtttag cctgtgcgga tgttagcgat cctgttcttg    960
tctttccttg tcaagaaaaa catgttacat gcctggattg ctttcgccaa tattgtgtga   1020
ccagattaat ggaaagacag ttctggcaac atccagagct gggatacacg ttggcttgtc   1080
cagctggttg cctagactcg tttataaaag aagtccatca ttttagattg ctcacagatg   1140
ctcaatatgc gcaatatcaa cgtttcggaa ccgaagaatt cgtcctcaga tccggcggag   1200
tactgtgccc tcaaccgggt tgtggaatgg ggattttagt tgattccagt tgtaacaagg   1260
tggcgtgtat aaacggttgt ggttacgtat tttgtcggtt atgtttacaa ggctatcata   1320
tcggcgagtg tcgaccatcc gatatggaca gttctgcagg tggtgaagga tgtttgtaca   1380
gcgtagaccc aaatcgagca tcggacgcaa ggtgggacga agcttcgaga gttaccatta   1440
aagtttccac gaaaccttgt cctaaatgta ggacacctac tgaaagagat ggcggctgta   1500
tgcacatggt atgtactaga gcagggtgtg agttccattg gtgttgggtg tgccaaactg   1560
catggaccag agattgtatg ggaagccatt ggtttggtta agacattgaa aaatatgtga   1620
tattaataaa ctaaaaaatg tgtgttcttt tgattgtaca gttgtgtttc acttaacaaa   1680
ggttgtttgg ttattttttg ctatgtttga atcaacagac cttaaaatgc cgttctgtgt   1740
catacaaaag agaccacaga gtacagaaga agaatcatca gatctattat agatatagaa   1800
ta                                                                  1802
```

<210> SEQ ID NO 113
<211> LENGTH: 15730
<212> TYPE: DNA
<213> ORGANISM: Diabrotica virgifera

<400> SEQUENCE: 113

```
agcaaatggc atggcagatt acaatggcag cgagcagtgg cggagtagat tggacgactg     60
tcttaaaacc attcttatct aaaaattatg agacttctaa tacagcagaa ctgatagaac    120
tatgttcagc tattgtaaaa agcgaatccg aaatcttgcg acacaaagag agtaataaga    180
atttcttcaa ttcctttgcg gttctagctt cagattatat tagcagtagt actagtggtt    240
tacttgcgag tcaactagaa acggtaaacg ctgcatgtcg tatactatta aagtatctgc    300
ttagtgctct cagtagcgca tgtagcgaaa ccaatccgag cagtgcccaa atcgaacgat    360
atttaaatgc tattaaagta ctttgcatag gtactggact gctgtccacc acggaggtca    420
ccgtcctcgt cgacagtatg aagggagaaa atttacccca acagaaccca gtgccttcag    480
gaaatgaaaa agatgtcagt aacaaacagg aatcgtctaa aaatcgatcg gatttatcag    540
tcagcattta cgaacaatta acactaccat taagagatgg ccgctcagta tctctcgata    600
ctggcgctag cggttcctca actgtacccg aagtgacacc tggtagcgat ccttcatcag    660
```

```
aaattaatcg tttgttttta aaggcaaaca cagaaagttt acaatcgtta agggccggtg    720
acactttgat agatctgtgt cttagtttac catccatcaa aaaagccaaa ggcaaagttg    780
aagatgcttt ggccggaaaa cctttttgta tacctaccaa tcatgcagaa gcgacaactc    840
ttagaaatac actatcgtca accctatctg acattaacct agccatgtcg gctataaacc    900
taccggtctt agaaccgtta acctcgagca aactagacaa attgtgtagc ctagctatgg    960
cagttctaca ctgcgccctt agtcaagcct cagcagctgc ggttctttct atgggctcag   1020
tggtttcacc taagtgctca aatcaacagt cacaagctgg tttgaaagaa gacgatttag   1080
attcaaacgc agtggcttta gtcgaagaga ctctaaatat gtataatttt attggaaatg   1140
ttattaaaac ttctacgagg gcaggaggtc atgtgtatca aaattattta cttgctgggg   1200
catgggtgct catttcgggt ctccaaacgc atctcacctc cagtacgtct gcggaaaaat   1260
caccacatct tagagaaagg gaggaaaaag gtagaagccc ttgtaaaagt cgagacggaa   1320
atactgccag atctggatta caaaaatttc agcagtcttt tggagtactt tcggtagctc   1380
tggcttctag ggctcttagt ttgttatccg aattgtttga cgatttatat ttagaagtgt   1440
gtggtggagc agggagcata gtccaggttg aacctgctcc cttagcaata atgggccagt   1500
tcacagcatt gcagagaatt tctaggatat tgaatgcggc tcccttaaat cacctttgt   1560
tttatctagc aatagtcagt tatagaaaag catgtacact taaaagatta catccgccag   1620
agggcgacac ctttagccaa tcagattcaa cgacatatta tgaagatatg atcatgtgct   1680
ccgacgatag ttcaacggat gaagacgatg atagtgagcc catcttagga caatggtttg   1740
aagaaaccct tgcgccccca gaaacaaccg agtccaaatc accaacttct gaaaatggag   1800
aaactaaaac tgtccaaaac gaacgatctc gatcgatggt cccggaaaaa ggagaagctc   1860
acggatttat cgctctttca actagtgttt ttgagttctt aaataaacac tttctgtgta   1920
cgaaaagtac ttttatatcg aggtacgtca aaaatggctt aacggaacag caaatgatta   1980
ttttggctgc gatcattaga gacttggaca gggagacagc gagaactgaa ataggaacaa   2040
tttcagtgta tttcggccaa gcactaggtc agctttattg cgaattctcc ggagcactaa   2100
ctagattcgc acacaactta gtaacaaacg gaaatttgag taatttacaa gcttgccttt   2160
taaatcatct aggagtatct ccctggaata ccgatgtccc tcacgcgtgg cccttacaag   2220
tatatccaag gacattggct gtcttagctc aggttttgct tttgagacca cagaacgaga   2280
aagaggcatc tgtaattagt atatggcata ggttggtgaa tacactcata gaaaatgttc   2340
ttaacaatcc tcattctgtc gttgaatcag aaaatgaaga tttaaatgtg gaacatgccc   2400
aagtgctcct ctatttattt cattcattga acttgatgca gaagaaatca gtcgtgttac   2460
ttatggctgg tggtgtttta agatgttccg agatagcaag aggtccactt aaagattcac   2520
agttgctaca cttatctaga gtattgctat tattcgatta tattatgaag cacctatacg   2580
atccacctac gtcgttgtta gaacagattc aatggaacct cttctacttg acaaacctga   2640
attccgacaa agaaaaagaa aatacaatga cccgtatgta caccgcttgg caggacatag   2700
aagacaacta caggaaaata tcggcagttg atgaattcgc catgaaacct cggttctacg   2760
ttttgacaaa tttggaagtg aacaatcaag atgctccgaa actggacggt ttggcgtgta   2820
attttatctt gggaaccccca gataaactac gatatccttt gttgttggat gctctaattg   2880
aaattttgaa cgtaacacac atcacttcag gtgctaacgc gtcgaaaatg agtttcctgg   2940
gactttgtgc tacacaatac tgtttcacta tttgctggag gctattacag ctactcccgc   3000
```

catcagcgtc atatatggaa cgcttggcga caggcgaaaa tttgacggct ggccccttat 3060
tacttcattc tctagtctgg gggcctagag cgtcccacaa gaatttcagt agatggctga 3120
aggactgtct agttaagcaa gggatgtaca cgcaacacac agacaaatta ttaaaggaag 3180
tgtccgaagc agttaacaat attaaataca atataacgaa tgctaaaaat tgtattatgt 3240
cgcttactcc tgatgtcaaa aaaggaatgg taaccaaaga aaaccttcca ccattatggc 3300
atttattttt actcgacgct cttatgacaa acgtacaagt ggctttagaa gagcccgaag 3360
ggagcactga aagtacttca atcactgtat ctaacggaac ctacgtccag gatttattac 3420
cccacgtttt aaggttaact caagcaatac tgcactgtac aagatggtcc ttactacata 3480
ctattgctga ccaaaatccg tcgtgtgaaa aattctcatt gcagaacttt gaaggactac 3540
aagatgtcct tgcaatagct tctacaaaga atacactaac gatgtcgtta tcttctgagc 3600
taaccactct tttgccttca tgtgtaagct ctgcccagtt gcagaattat aagacaattt 3660
tagaagatgt ttcattgagt gcttatcaaa acgacataat cccatcagaa agcgccattt 3720
taaaagtagt agacgcacat gtagctactc tttccatggg cagcccatac agcatcaact 3780
tgtcacttcg acgtttatta caatgcctag tcaaatttat ttgtgatcat gcccctaaaa 3840
cagaaaatac agacacgaag aacaaagcga ttgaactact agtttcaatc actttagatc 3900
taaggaccga atttttgaat gacactgtga ctaaaacgtt agacaaaatg attggcgata 3960
ccgaaataga cgaacatcaa aaacgagtct acctgagggt tttagatcat acttataaac 4020
tcataataaa ttacacgtca ggtaactcag agacgtatag tgctaatatt gatgaaaaaa 4080
tacttcacca ctgtttgaaa ttctacgaaa aaatcatcga gaaatcttca ggcagacaag 4140
ctttagaaat cttctttact ggagataggg atttggtgaa agtgctgatg tctgtatcta 4200
gtccgcaaat gtcgcaacat tatggtacca gagtactgca tttcttcaat aaactgttcc 4260
aagcagccga gaagagctct acagatccaa gcctgaacta cttatgttca agtatgagta 4320
aactggcaaa cgtagatagc gaaaagctgc aaacctggtt gcgtcaaatc atcatcggta 4380
caagtagtat tgaacccgtc gtgacaacta cagttaccat caataaagaa gaatctcctg 4440
cgacatctac caacggaaaa tggactataa ccacggttga aagtaaagag gctaattctc 4500
caacatctaa cgacgatcaa aagtccttgg tgcaagagaa cagtcagctg ttgcaagctt 4560
taactagttt tattgttaaa caaaacagta atgtttccga agaagtttcg ataacaatat 4620
tgaaggcgct gatccaactt ggaaaacatc tgttatcgcc tactctggaa ggtactggtt 4680
ttactgattt aatggtggat atgatcatgt tagcagatgc tggttcagga aagggacaca 4740
gttatttatt ccctgctaca gcagaatgga tagaactgtg caacaaacgc atctcagaaa 4800
aagatgttat agataaatta actagtaatc ctgattcctt gaagaaaaat gctatgctgg 4860
aagcctcttc tagtattcta gactacgtta gcgatgttat atcaactatt attgcccagc 4920
atcctcaaac gataagacct cttagtcctc cttgggaaag tgagtctcct ttagagttgg 4980
aatctgagtg gcaagacttc gcgaacgatg acgatgatag cggtgaagat agcgacgagg 5040
attctttatg caacaaactt tgcaccttca ccgtaaccca aaaagaattc atgaatcagc 5100
attggtatca ctgtcacact tgcaaaatgt tagatggcgt tggtgtatgc tctatctgtg 5160
ccagagtttg tcacaaaggg cacgatttga gttacgccaa gtatggtaac tttttctgtg 5220
attgtggcgc caaagaggat ggaagttgtc aagcgttggt aaagagaagt ccccaaacca 5280
acgaaaccaa taatgcaaca actggaaaca actctgaaca tatgttaacc agttctttaa 5340
gaagaaagac ttcaagtccc atcccagctg acaagattat ttataaggag cgaaaaaatt 5400

-continued

```
cgaacactgt caaacagtta gatggttcaa aagaattcat catcaactac ttaggatcaa   5460
gtttggtggc aggatctctt ttagaattcc tacaatcttt aatcccagct attgaagaaa   5520
actgtcgtag aaattcactt gtaggatgcc acttacgcgg tattaaggcc ttggatcaac   5580
tatactcaaa cgaaaagaaa tatgtacata ctgatcaact tatggtacca actttaggtt   5640
ctcaagaagg agcttttgaa aatgttagaa tgagttatgc tggtgaacaa ggacagacca   5700
taagacagtt gctttcggcg catatagtac gaaggattgc gatgtgttgt atgacgtcta   5760
cccaaggtcg tagacagcac ttagcagtat cacatgaaaa gggcaaaata accgtattac   5820
aactgtcagc tttacttaaa caagctgatt cgtctactag aaagttgaca ttaacaagac   5880
tatctacagc accaatacct tttactgtac tatcgctatc aagtaatctt tgtaacgaag   5940
actttttggc agtctgtgga ttgaaggatt gccatgtact cacattcacc tctgggggat   6000
cagtttgtga tcatttagtc ttgcatcccc aattagaaac tggaaatttc atcataaaag   6060
ctatatggct gcctggttct caaaccaaat tagctctcgt aacagcagac tttgtcaaaa   6120
tctacgactt agccacggat gcattaagtc ctcagtacta ctttttggta ccgagtggaa   6180
agatacggga ttgtacgttc atgtacgatg aaggcactta tcacatttta ttaatgtctt   6240
caccgggaca catatacacc gaaattttaa atgatgattc ctctacgaag tatggttcat   6300
tttatgtgac gaatacctta gaagtttttc atttagaagc agcggatgtc attgggcaag   6360
tagccggagg tggagtatcc atctattact cacatactct tggtctccta ttctatagct   6420
acgcccaagg aaaaagtttc atatctccca tcaatcccaa aagcaacagt ctaccgttag   6480
tatttgccat aaacctaccg caaaccaata acaccacttc aaaaagcaat ggttcgaaaa   6540
attctgccaa ccaaccgtta tgccaatgga ccgagatccc aaaccatccc ggtttgattt   6600
gttgcgccat gcaatcgaat aacaatcctg ttattttgat gcttaagcca gacactattt   6660
tgatacagga gattagagtc ttaccagcca aagtaagat tatggatatg gttgccatta   6720
gacacagttc cggaaatgag ttgagaacaa ctttgattct gctgtgcgaa gatggtagct   6780
taaaaatgta tatggctaat atggatcaaa caggtttttg gatgtcgtca agcattcaag   6840
ctaacattac caactcgtcc gtaaaaccga aaaagaagaa aataataaaa tcggggaaga   6900
ctacaaattc cgtaaacttc ccagtggact tctttgaaca ttgcacaatt ttgaccgaga   6960
ttgaactggg cggtaatgac gttttgcaaa tttataacca ggcacaactg aaaaatcgac   7020
tgaacactac tggtttatac atagcttgta ataaaccact aggtttttct ctcgatgtaa   7080
ctaataatga tccgaacatt gttatggtag gactgagagt attagttgga agtcaagatg   7140
tcataaggat cccatctttt gtagagatat ttggacgtac aattcctata acagcaactc   7200
gcagccgctg gtatgacatt gcattctcaa gagaagaagc tcttcaatca gacaagaaag   7260
tcacaattct atttggtcct tctcaagatc ctgaaactgt tactatggtc gactgtgtaa   7320
aaatttatgg aaaaactaag gattcatttg gatggcctga agaaagtgac gaaaatgtag   7380
ctgctggtgg tacgggaagt tcccaacagg ctgcttccaa ttcagatagt gatcagagtt   7440
caggaaataa aactcaatta acgaaacttg aaaagcttgt ggttggcata cttgaatcac   7500
tcgatggcag cttctctctg cattcaactg aagacaaact ggctaccttc aagacaccaa   7560
cacttaaagt tgcaacgtcc ttgttgaccc ttcccaccca gccgtcagta caaatccatt   7620
ctaaggctct tttatcatct cttcactcta caaggctact gtatcataat tacaaagacc   7680
aagcgttact tcaacatgtt ttgacaactt tgacggaaat gacaagtacc aacattaaag   7740
```

-continued

```
atttagatgc cgagagctat tatagactgg ttttgattgt aagaggaatc gctgttgcta   7800
gaccacagaa tttggtgaaa tttgctgata gccatacttc gatacaagat gttgtcctgg   7860
aagatcctct ggaaaatatt ataagagaaa agcaaggttc aacgtccaaa gaagtcaaac   7920
catttgaacg taaacaacat agtcagcatc ttcttcttca gctaatggag gttctttggc   7980
tattgcactc tctgaatcct gaaattcctt cattgtccct agtagtttca caaggactca   8040
agcacaccga acaaattgtt catgcacttg ttgaaatagt gcacgccttt aatagctgtg   8100
atacatacag caatgtcact atagcagtgt atcttcaact gttattgtgc aatgatcctc   8160
tgattgcatt tagtgctaaa caagctctta gcatagtgct taaaccaaag acgaagagaa   8220
gaaaggtttt catacctagt cctcctcatt gcgtttcacc gcctcttcag aagaccacag   8280
atgataggtc taagactcct cccgctatac aacaatcggt tagtcatgaa gaagagatgc   8340
aagcaagaca cccaaatcaa tatgatgtgg acgccattga agctattgga ttactagaac   8400
agcctggtca acagcaagac aaccacaatg ttaatgcttt ggaagcttta cttggtggtg   8460
gcgtaggctt tcctccattg ctggatattc caccagatgc tgatgacgaa gctatggtag   8520
aattggcaat tgcattaagc ctacaggatc atgaaattgg aggtgaacaa aatcagaccc   8580
tgcaaagtct tcaagttcaa ttaggtcaag atgtgcttgg cgcccaccaa ggccaaaatg   8640
cgcaagcgca agaatctgct aattttagcg acacaacagc ttcggcagct ggatcagatg   8700
atgaaggttc aacagctgca actgatggtt caactttgag gacttcacct gcagaacaag   8760
ctgggtctga aagtggcggt agtggagttg aaagtattac tggagaacac aatgtttctg   8820
gaaggtcttc cgcatatgga gataatatgc aagaagcaat caatctagtt tctagatcag   8880
ataccagttc gattgctaac acggttgccg gtatggttga ggctgatgcc cagcacgaag   8940
aagttgaact ggaaactgaa agtagcagta gattacacgt tctcaggctg caactcctgg   9000
agaaactggt ggagtatctt ccgaaattga aaaacgttga tggagtcaga gtaataccct   9060
tcttacaagt ggtactccag ttaactgcag atatcgatgg ccattctgag cgagaccgag   9120
tatgtttaaa ttcactttta acaacaataa ttagtgaatt acaactaaca aatgataatt   9180
ttgctgacgt ttgcacacga accacccaac gcgaagttca gttgatactt ttgcgattac   9240
tcagtgtatt aatgcaaaga tgtaaaacat catcaacgtc aacatctagc aaaaccccaa   9300
taccagacag cactaccttt gtttctcgca ccacagcaac agctcttcac aaagctgaca   9360
ttatcaacta ctgcaataaa ctccttcaag ctttgttgag ctactggcga aactctacaa   9420
atgaggatga ttcggtcagc atcacaggaa atcttcttaa agaacgattg cctcatccgc   9480
cacctgatat gacaccattt ttccagaggc agtttgttaa agacaatcaa gacgtattcc   9540
atacatatcc acaacttttg acagaaatag ctttgaggtt gccttaccaa gtgcacaggc   9600
attcggatgt ttcagagcct atcagtgccg cgttccatgt gtcatggtac aagcatctct   9660
gtgattatat gatgacacca cagacacctt ttgtaagaag acaagtacgt aaattactca   9720
tgttcatttg tggaaataag gaaacatata ggcaattgag agacttacac ggattaagaa   9780
accatatgaa gagagtaatg gaatgctgta ccaaggctgg ataccaacct gctactgaca   9840
ttcagcatgc tttgagcctg ccgtatgatg ccctggttga attaattgaa catttgaaat   9900
attgtgttga ggtcgctcaa agtcgcaccg gtaactggca acgcttctgc ataaaagaag   9960
aagacgtaat ccaattcttg atacgtatca gttttctttt ggatgatggt gttgcaccta  10020
ccgttcttca gcttcttcaa agcgcaatag tagttaactc accggcaaag aagcccgatc  10080
catcgaaaac agcctccagg aaagatcgag aaaagtctga cgattctagt accgaagccg  10140
```

```
tgttcgaaga atctaactct gtaattttag tagaacagat caccaagcat atatctaaag  10200
aagtgtttgc gcgttttgta aagacattta tgctagaaac taatataacc tctgtaagat  10260
ggcaggcgca tgcgttgacg ctagccattt ataaaaactg taaacctaaa gatcaagaag  10320
ccatactaga ccttttgtgg cagttatggc cattgctacc ggcttatggg agaaaagctg  10380
cccagttcgt cgatttgctc ggttactttt cactgagata tacggagaaa accgaaggtg  10440
ttgaagctat tcccgaatat gtcgaacgag cattcagtgt tcttaaagca cagaacgaaa  10500
tgttagcaca tcacccaaat gcaaacctat atgctcacat gggccaattt gtagatctgg  10560
atggatatta cttggaatca gaaccttgcc ttgtttgtaa caacccagaa gtttcgttta  10620
ctgtcattaa attgagttca atcaagattg attcaaagtt tacaacaact acacaaatcg  10680
taaagctact gtccagtcac acaattagta aaatcactat aagaatagca gatttaaaac  10740
gaacgaagat ggttagaaca gtcaatattt actataacaa tagatctgta caagcagtag  10800
ttgagcttaa aaataaacct gcactatggc ataaagcaaa gaaggttact ttacaatctg  10860
gtcaaactga agttaaaatc gagtttcctc taccaattgt agcctgcaat ttaatggtgg  10920
agtacgcaga tttttatgaa aacattcagg cttcatccga aacgttacag tgtccgagat  10980
gtagtgcctc ggtaccggct aacccaggag tatgcgccaa ctgtggtgaa aatgttttcc  11040
aatgtcacaa atgtcgtgct atcaactacg acgaaaagga tcctttcctg tgccatgcat  11100
gtggattctg caaatatgct aagttcgact ttagcttact ggcgaaacct tgttgcgctg  11160
tggagcctat agaaagcgac gaagatcgca aaaagaccgt ttctagtata aattcttttt  11220
tggaaaaagc cgatagagtt tacaaacaac tcatcgcgaa taaacctact ttggaatcgc  11280
tggttgttaa gattacagag cacagacccg ataaaaaaga agatgctgtt tcgacttcgt  11340
cggcaccgac tgcaggtggc gctgcagcag cagctgctgg tgctggagcc cagttgaaag  11400
tgaacaaaac aatacaaatg ctggctcaac aatactgtaa tgagtgcaag acttcgtttg  11460
aggagctcag caaaattata cagaaggtgt tggtgtcgcg gaaagaattg gtggcttatg  11520
acaggaaaca cagagatatg gaattgccga aatctacacc ggtccttagc gaaaatctgg  11580
tcaattttcc ttgcgttaac aatcgttgtt acggttgttc caccgctgcc acagaacact  11640
gcttgacttt gctaagagca ttggcacaca atcctacaac cagagaagtt ctatgttcac  11700
aaggactcat ccaagaacta gtatggaaca atctaagaaa tggaagcatt cacagtcaag  11760
aggaggtgag acaattactt tgcgttctga ctaaggataa caggactgcc acggaagaac  11820
tctgcaacct tttaatggag aggataagtt tgagtttgaa tggccacatc agttctgcag  11880
acttgggtac gagtgttagg catgaaattg ctctcttggc agcgatggtt caaaaagaag  11940
atgactgctg ggagctgaaa ctcaggtgta tgatgaatct gttcctgaaa gcatgtgaag  12000
gatcgagaag tcccttggtg atggaatcta tcattttacc atgtttaaaa atactgcaaa  12060
gtttaatgaa aattccggaa cctggatcta agaaaactaa ggaaaaacca gctccttcct  12120
tgcaactaag cgtgcaactt gaatctccgt atggtgcgat ggttgacctc aataaatttt  12180
tggataaaga cgatgctcat acttttaatg ggtggaaatc aagattccct aaggcacaag  12240
aggcctctgc ctcggccaaa ctcagcaaag aggagaacag aaaatactat ttggctgaaa  12300
aatactgccg caaatggaga agacacatta agaacctata tatccgcgac ggactcaatt  12360
tcgacgatac ctcatggctc aaagccgtca ttttcaaccc aagttctcga ttagcccgac  12420
aagtcgcatg taacatcata gaaatcatgt gcagcagttt cgaacgcaag cgcgacatgc  12480
```

```
tcgatctgct aactcatttc ttagcagagt taaatactgc aggcgaaagt gctgccgagt   12540

tccttgccat ttaccaagaa cttatcgcgg agacgccttg gaaacagtat ttaactgtta   12600

acggcgtact tacagtgctc gcgcaccttA tcaccatcga gatagagcaa cttcacaggc   12660

tcgaagagac aactttgacg tcagatcttg cacaaggata tgcattgaat cagattacgg   12720

agttgctgtc atatttctta gatgacgtgg ctattagaag acaatacaaa agcagacttg   12780

ttggagcggt gttgaatgga tacctgtctt taaggaggct tgttgtacag agaactaggt   12840

tgatagatga tacacaggaa aaattattgg aactactgga agaaatgact acaggtacgg   12900

aagaggaaac caaagctttt atgtcagtgt gcattcaaac agtagaacga tacagtcttc   12960

aagacatttt aactccggtg ttcatctttg aacgtctttg ttccattata tatcccgagg   13020

agaatgatgt aggagagttc ttcttgactc tggaaaaaga tcctcaacag gaagatttcc   13080

ttcaaggccg aatgttaggc aatccttatt gcagtctgga agctggattg gggcctttga   13140

tgagggatgt caagaacaag atctgtcaag attgcgaatt ggtggctctt cttgaggacg   13200

acaatggtat ggagctcttg gtcaacaaca aaatcatgag tttagattta caagtgaaag   13260

atgtatataa aaagatctgg ttggcagaag gaagtgacca tgaaccgatg aggattgtgt   13320

acagaatgag ggggctcctt ggtgatgcta ccgaagaatt tgtagaaagt cttagtaata   13380

aatcccaaag tgatgtagat aatgaagagg tctataaaat ggccaatgag ttagccgatt   13440

gtggaggact tcaggttatg gtaactagat tgggagcgat accgagcgtc accagagcta   13500

gaccgttgtt acaagtgtta ttaaaattat ttaggttatg tgtgaaagtt aatcgttgtc   13560

aagaggtttt aataaagccg gagttgaagt ccatggaagt atttttacgc acgttgcaac   13620

tttgtttaga tagcgataaa gattctagtc aaactggcgt taccgaacaa ctattagata   13680

ttatggaaac gatcttgtcg aaagcaacga gtgaatccga agaaaacttc accgagttct   13740

cacaaactct aggtagtgcc gaatacgtca aatctttact gtcatgtact aatcagcagg   13800

tagtgaagaa cagttccgtt ctagtccatt taaccagggt attagccgct ttggtttacg   13860

gcaacaaaga gaaaatgaag attttacttg accatttcag ttccgtcctg gatttcaaca   13920

aatatgacat ggaacataac tcagacgatc aacaaaaact cgagatgttc tgtgttttaa   13980

ccaacagcat cgagaagaat gccatcggca gcacgttaaa agattacata atcgctttgg   14040

aaatagtcaa aaatgcctta gaatacataa ctatgcacgc accttgtgtc aaaccgactt   14100

tattaagggt agacagcgac gagttgaaag atttcatatc caaaccggct ttgaagtaca   14160

tcttgagatt tttaactgga ttagctcata gtcacgaaaa aacgcaacta gcaatagctg   14220

ctgcggaaac tattccgatc attcatcgtc tggaacaggt gtcttcagat gaacacgtcg   14280

gatccctagc tgaaaacttg ttagaagcac tctgcacgaa tccggatgtc gcaaagcaga   14340

ttgacgccgt cagagagttt acaagatctg agaagaaacg tctcgccatg gcaatgaggg   14400

aaaagcaact tggtcagttg ggaatgagaa ccaacgataa aggccaagtc actgcaaagt   14460

ctaatatact ccaacaaatt gaagaattgg gcgaggaatc cggtttggtg tgttgcatat   14520

gtcgtgaagg atataaatat caaccaacca aagttttggg gctgtacacg tttacaaaaa   14580

gatgtaatgt tgaagaattc gaaggcaaac caagaaaaac tgttggatac actactgtca   14640

gccacttcaa catcgttcat atcgattgtc atatgagtgc agtgaggttg gcacgggctc   14700

gtgacgaatg ggaatctgcg gcccttcaaa acgccaacac caaatgcaac ggactcttgc   14760

cgctatgggg tccacaagta cccgaatcat catttgccag ttgtcttgcc agacacaaca   14820

catacttgca ggaaagcacg aatcacagag atataggaca caattcaact attcacgatt   14880
```

```
tgaagctttt gctgttgagg tttgcacaag agaaatcttt tcatgaagat acgggaggcg  14940

gtggaccaca aagtaatatg catttaatac catatctgat acacgttgct ttatatgtga  15000

taaatactac aagagtgaat aaaagggaag aagccaacct tatgtcgtac atcgaagcta  15060

ctaatgcaga aaaatggata gaaacagcgt atgatgctga aggtcctcta tattggataa  15120

cgatgtccat tttacttcac tccagacaac agtggcaagc acatcggctt tctcacttca  15180

aacggttaat ggttttggca caagtgcgac attgtcaacc gtccggacct gtcaaaactg  15240

tatcagacaa atcagtaaaa gattataata tctataaacc gtacttgttg ttctttgggc  15300

ttatcgatgg aatctataac catttcttca agaatgtggg aggtccagac gaacaatggt  15360

caaccaactt agcagactac attcgccaca atgatgaagc tttgatgaaa tcttcagaaa  15420

agctcttggc tgattataca gatgaatttt taccttgtac ttccttttca gaattctgtg  15480

atgtggcagg tttactcgac attataacca cgccggatag gtatttaagt gacctgctga  15540

atggattacc ttaatgtgta taaaatgttt ccgaatttta aaatgtaaac aaaggctgta  15600

cactgttttt actaatcgct tgctgctagg ttgtaatcta aataaatgta gtatatattt  15660

gcttgttgtt ggagttttag aaaaactaaa ttattgtaat tacgattgat taattattat  15720

ttgaattaaa                                                         15730
```

<210> SEQ ID NO 114
<211> LENGTH: 852
<212> TYPE: DNA
<213> ORGANISM: Diabrotica virgifera

<400> SEQUENCE: 114

```
aagaaacaaa ttgaaattga aaataaacaa aaataaaaaa taaccagtcc aaaattaaat     60

ggcaaatatt acaatagtaa aaaacaaaat atgaatgtgc tccagtctca aaacgttgcc    120

agagagatga tgttttacgt aagaccggtc tgactgttgg aaaggtagat ttatattatg    180

gaagaggcgt ccgaaatgat ggatctcttg tacccccgat tagacaaact gcaagtattt    240

ttaaacagcc cgtaactgtc tataagctac aagagagtaa agtaaaaaat gattataaaa    300

acgggaatca agagaaacca aagcaactaa tttgggagaa aagattggaa ggtttaaggg    360

cttgtgatat ggatggcttt gagttcgaag ctatggaact gccaaaaggt ttaaaaccag    420

tgggacctaa tgtaactgaa gacaccatta tccagagtgt tgctacagca ctccatgttt    480

cttctcaacc agtgacaggc cagacaagta caaaaacact acttgaaaaa aatccaggag    540

tatttctcga tcccaaacaa ccattagtac acgctgtaaa tatatcagag gatgatatca    600

aacgtcaaga ggagagagtt gcattagcga ggaagaagtt acaagaggct ctaaagggca    660

acctataaga tataagtatt ttgagtaatg ttttatatgt acatgtcata attattagat    720

tgtaagttac aaattaaatc gttccaatcc tgtaaattat aaccaattgg taaataaaat    780

aagtttcttc agtcatatac aaaaattata ctttttaata ataagaatgt caaagacttt    840

atatgtgtga ac                                                        852
```

<210> SEQ ID NO 115
<211> LENGTH: 1099
<212> TYPE: DNA
<213> ORGANISM: Diabrotica virgifera

<400> SEQUENCE: 115

```
ctaacaaatt tatacgtata gaaatatacc ctgtgatgag agatgttagt ttagacaaat     60
```

-continued

```
agaacaacat agggataaaa ctcttctcgc tccggggtaa cggcagagct ttcacaaccc    120

gaaatgttac ctcggttaaa ataataataa tggcaccctt taaaattgtt atggttcgtc    180

atggagaatc agaatggaat gaaaagaatc tattttgtgg ctggtttgat gcaaatttaa    240

gtgaaaaagg taaacaagaa gccattaatg ccggaaaagc actaaaaaat gcaggataca    300

aatttgacat tgcatataca tctgtcctta caagagctca gaacacactt aattcaataa    360

tcaaagaaat tggccaagag aatttggaaa ctataaaaac ttggagactc aatgaaagac    420

attatggtgg cctcactggc ttaaataaag cagaaacagc agcaaaatat ggagatgagc    480

aggtagctat ttggcggcgc agttttgaca ttccacctcc accaatggaa cctgaccatg    540

cttattatga taccattgta aaagatgccc gatatgctga tggtcctgca ccagatcagt    600

ttcctaaatt tgaatcctta aagctaacaa ttgagcgtac tttacccttc tggaatgaaa    660

ctgttgttcc acaaattaag gctggaaaac agatcttaat tgcagcacat ggtaacagtt    720

tgagaggaat tgtaaagcat ctagaccagc ttactgatga ccaaattatg cagttgaatt    780

tgccaacagg aattccattt gtctacacat tagatgaaaa tttgaaacca ataaagagtt    840

tagaattcct aggagatcca gaaactgtga aaaaggctat ggaagctgta gctgcccaag    900

gaaaagccaa ataagcatta tttattattt attgttttaa tttatatcaa aatcatttat    960

tgttagatat ttgatgtgta atgaataaat ggttaggctg aattgtaaaa ctcagcagaa   1020

atgttatgtg caagacatta aagcatattc ttagataaga aaaacatgtc tgaggatgat   1080

aaaatataaa aaaaaaaaa                                                1099
```

<210> SEQ ID NO 116
<211> LENGTH: 523
<212> TYPE: DNA
<213> ORGANISM: Diabrotica virgifera

<400> SEQUENCE: 116

```
caactagcgt gttaagactc tcttggtctc ctgatggtca gtatttagtg tcagcccatg     60

ctatgaatgg tggaggacct acagcgcaaa tcgtagaaag agaggggtgg aaacatgata    120

aagattttgt tggacacagg aaagctgtca cttgtgtgag gttcaactcc aacattctcc    180

aaaaacaaga aaagaacaac tctaaaccca ctcaatattg ttgttgtgcc attggatcaa    240

gggacagatc tatcagtgtt tggttaactt cattaaaaag acctcgtgtg gtcataaaag    300

acttatttaa taatagtgta ttagatatgt catggagtag caatggactc tatttgatgg    360

catgctcttg ggatggttct gtagcatgta ttgtgtttgg acatgcagaa attggaacac    420

ccttgactat ggatgagaag aatgaattat atgaaaaaaa tgtaccacaa atcatttcaa    480

aaaaagttgg aatcgtaatt ttggtacgtc ccaaatcatc gaa                      523
```

<210> SEQ ID NO 117
<211> LENGTH: 531
<212> TYPE: DNA
<213> ORGANISM: Diabrotica virgifera

<400> SEQUENCE: 117

```
attcccaaga aaatagaacg aaatctggtg aaacatggat aaggataatc acccaaggtc     60

aggaagtgac tattgactgc gatgaaaaga ctttagcaga aatgggattt aaagataacc    120

agatcgttta tatatcgata ggcatgtcga ggaatatgaa gaaacgggag tttatggatg    180

caccatcttt acacccgcct cctcctcggg aatgtttacc aacattactt cttctacagc    240

caaattactt tgagcagcta ttttccttaa tgcacacact tagttcaatg aaaattcaaa    300
```

```
ttaaaggagg gtgccaatta ccacatacaa gagcccaagt tctcagcaga agagtatggg    360

atattcttag cttattacca accagtccca aacttcttcg tggtttcaaa tacttggata    420

tccctcttcc agaattgtta gatccttcaa gtgctcaaaa attaatgtat tctttgtata    480

ttgtcgaatc tttaagcgcc aaaatgtacc gaggaaagta ttcagatgag g             531


<210> SEQ ID NO 118
<211> LENGTH: 4324
<212> TYPE: DNA
<213> ORGANISM: Diabrotica virgifera

<400> SEQUENCE: 118

gtagaaaagg caactgtcac aatcgatatg agaagcgctt tcaaaaagtt cgtagacact     60

agattattgc atatgaaggt tttaccatcg cctactagaa cagctttacc caaatgcgaa    120

ctgtgggatc cagaaactat gaccagtgca ctcgatgtcg taattagagc agcaaaacac    180

tcgtatcccg agccagtaat gttagtgaga ggttttagcc agccagtcaa agttagtttt    240

gtgtatagtt gtaaccgatt ctatgttcag ttagtaaaaa aagaacagga actaacaact    300

cttatggaag agcttcaaag tttatgtcta gaaagtgctt ttatggactt ttcttccgtt    360

aaaccaggaa ttccatgttg tgcccaatac agcgaagacc agatgtggta tagatcgcaa    420

gttacagaag tacaaggaaa tgtagtcaca gttcgctaca tagactacgg aaacgaggaa    480

tcagtggcta tagaccagct gaaaaacatc gaaggcgaaa ttctaactgt tcttaaacct    540

caagccattg aatgttgtct gaatggatac caaaagatgg aacctgatct ccaaagggat    600

ggtttacttg aggaactgct attggaaaac acatttacaa tgaaagttgt ggatatgtgc    660

gacaaaaagg cattggttga cttatttgat gaaaatgaat acaacgtttc ttccttgttg    720

ctggtcaaat tatctgaagc tagttcacag gtcagtcccg tattggtaca agcaggcaac    780

aaactagaac atagaaaatc atatacacaa caaagggaac agaatttcaa gggggacaga    840

agcccaaaca ccggacgtga acaaaaacct tgggaaaaac ctggagacag gaacgaaaag    900

tcttggagac aagatagtcg agataataga gataatcgaa atttcgaaaa aaatacgaac    960

gacaacgata gatcttggcg tcaaaataac aaagattaca gtgtaaatag tcgactggac   1020

aaatacaaac aaaacgatac cgggaacagt aacgactata acagtaacag taacgatgcc   1080

aattggaatg acaatcagac cagcgagagt tggaacgacg gcgccgaaaa taatcccacc   1140

gaagaaccaa aagacgaatg ggtaactggt tcgaacgata acaatgaagg tggatccagt   1200

tggagaaaca acgataacag aggcgataga aagaacagag gggggtctca tagtgacaga   1260

ggtggtagag atggtttcaa gagagacaga gatggaggtg gttataacaa cgatagaggc   1320

ggtcgtggag attataacag cgataggggg gatcgtggag gatttaacag tgatagaggc   1380

gaacgtggag gatttaagag tgatagaggc gatcgtggag attttaacag cgatagaggc   1440

gatcgaggat ttaaaagcga tagaggcgat cgaggattta acagtgatag gagttataac   1500

aacgataggg gcgacagaga cgattttaac agcgataggg gagatcgtgg aggatttaga   1560

aatgatagag gaggaagagg tggaggacgt ggaggtttca acgatagagg aagccaaaga   1620

gatggaggat ataaaagaga ttataataaa aaggatggat ctgaggatgg ttctgagaaa   1680

ggcttccaaa gaggaaacag atcgaattcc cgctatgatc gaggaggtag accccctaga   1740

gacttcgaca aagccaggaa tttcgatgac aacaatgctg gtagagattc atggaactcc   1800

acaccgaaag caccggccat agattctgtt cccgtctcta ccacattcca gtcatacgaa   1860
```

-continued gtcgttggta ctgaagcgaa gattacagtc agttggttcc ataatcctga actattccat 1920
tgccagttag tagactatca agaaacattc aagaccatga tggaagaaat ccacgacttt 1980
tacaaagaca gaaaacccga attggtagtt tgcggtgcac ctgtagttgc tctgtttccc 2040
gaagacaatg ttctgtatcg cgcaagagta ttggaagttg taggtatcga ttacaaagta 2100
tatttcgtcg attttggcaa cgtatccata gtttccaaga cgtttcctat cgataagaag 2160
tttatgaacc ttcctgctca agctatagca tgttccttga acggcgtaag tcccgttggt 2220
gaagattggg cagatccaga tacatatagc ggatattttg ataaggacgc ttttgtttgc 2280
aattttatta aaaccgttga tgaaaaagct tatgtaaata taacctacga atcccaaagt 2340
atcgctgacc tattagtcag agacggcttg gccctgtcgg ccgcatctgg tccgtcggac 2400
ggagatgtag atatcaacgt gctactcggc cagcaattta gagctactat catcagcgta 2460
aatgatctga acgacttcat cgtgggactg gattgtggta aaatcatcac ctgcaccatg 2520
cataacttgg aaactgcgac tgaaactttt aaagacgacc ttaagggtct cttgcaacag 2580
gctgtgatta tatatgtcga taatgtctta gaagataata agttagaaat taccctttat 2640
gatactgaag gaaataaaca cgttatagtt aaccctgatg aaggtgcata cgacacttta 2700
gatcttcctt gtccaacgct gatattacgt tcaaacataa ccggttacgt acctttcggc 2760
agcgaatcat cagtttttat ccaaccaaac gaatacctcg aaaccataaa ttcccttctc 2820
gatctgttgt ttgaaactta cgacagtaaa ccaaacgaga acacaataat tcccgaaact 2880
gattccatat atgcggtaca tagtgaagat ggaaactggt atcgaggcaa agtgactgat 2940
ttcgatgatg aactggctac ggtttcgttt atagattatg gcaactctga gcaagtggcg 3000
ttttctgcgt taagagagct tgaaaaagca tttttggaca ttcctatttt gtgcgttgag 3060
gttaatattg gcgttgacgg taccccgttc gttgacagtg aagtaacagc caaagtcttt 3120
tatggtgaaa ctggctggga aggtactctg cagcccccgg agtcttctgc tccagaggcc 3180
gcttcagtac cagaaccgca ggaaaattat gtcgaaagta cacaggaaac tgttgcctat 3240
actgaagaga taccacaaga gaatatttcg aatgatcaac cattacatgg tcaaatagtt 3300
gaaacaggat catctgctga agcagcatca gctgttgatg aaccattaaa aggaactgtt 3360
gtttatatga gtcatattga ctccccaagc gatttttacc tgcagtttgc caaaaacaag 3420
gaagatatcg aaatccttca aaatgaatta caaactatgg tagaagaaat ggaggttctc 3480
gaaaatccag cacatggtgc tttgtgcgct gctccctatt ccgtggacca atagtggtac 3540
cgagcagaag tgttggatgc tgatgaggat attaccacgg tgcgattcgt tgattttggt 3600
aacactgatg tcatcgataa taacacaaca aaagtaaaaa ctcttcctcc aaagcttcta 3660
tcactagcga tctacgcaac gagatgtgcc cttaaagttg agcccttggg agaggaatgg 3720
gacgctttag caatgacagc ttttgagaat cttaccaata tcgaccttaa tttaacggcc 3780
gagattataa atcaggatga aaaatgcacg tatgtggaac tgtacagtga tggtacggat 3840
gttcgggcag ctttggtgaa tgacaacctg gttaaaccaa ttgcagaaac gaccgaaaca 3900
agacagactg gtttcgtaag ccacttaaac tcaccgtccg aattctggat ccaactggag 3960
agttgcatag acgaactcga atggattgcc gaacagctca gctcagctga gacattcccc 4020
gacgtaacgg atttgactcc cggcacttta tgtgcagctc ttttcccaga cgatcaaatg 4080
tggtacagag ctagaattct atctgacact gtggcaggtc tagaacttat tttcatcgat 4140
tatggcaact cgtgcgtctg cacggatttg aagcagcttc cagaagattt ggtcatgact 4200
gcgccacttg cgatgaagtg tagtctgcag aagaacgacg gtattcccac atggacgcca 4260
gaggccgctg ctaagttttc ggatatatcc gccgaaggcc agacgatttt taccgttaaa 4320
aaaa 4324

<210> SEQ ID NO 119
<211> LENGTH: 7780
<212> TYPE: DNA
<213> ORGANISM: Diabrotica virgifera

<400> SEQUENCE: 119
aaaaaataaa agtgtcgggc gataaaaagt cattttatgt actttttaag acgtcctttc 60
ctctagaaac ccacaaagtt ggtcaaatta tgagtataga gttgaaccta caatgttaat 120
gtaaaaacga atcaaaatat gactattgca actagggcac aaggattgac aggagatagt 180
gttgaacctc aaggatcttc tcctggacca tctgagaaca acgtcgtcga ggaaatccaa 240
gatgaaaact tcgaaccgga gttccccaaa gataaattag cgtcactgga tgaaaaaata 300
tcgagcttgc gatgggtggt gccagtcctg gccgaccagg agctagaatg tctactgaaa 360
gtctccatag acttggcccg aaaaaatctc gatacaagat ccgaatcttg ccagaggttc 420
ttcagggagg gattgacggt gtctttcacg aagatattga cggacgatgc agtgtccagt 480
tggaaaccga atattcacgc ctgcatttat caaaactgcc tgaaactcat agagctgtgc 540
gtggtgaagc tgcctcaaga ctggtaccct ctattggatt tactcgccat ggttcttaat 600
ccgaataaca agttccacag cttcaattct tctagacaga gcgaaacggc cggtccgaat 660
tgtaatttat cggaagagga gctcttcgct agaccatcga gcgacttgag gaatcccaga 720
gggtggttgg tggaccttat caacaaattc ggagagttgg gcggtttcca agttttatta 780
gatagattcc aatcggggaa aaatttaagt atttctatag tgttcgcttt actgaggcct 840
tttgggtttt gctttgaatt tttgacggtt cacagtatca acaagtatat attgcctata 900
ttagaaatga ttcctggtat attagataaa ttatcggacg aagaattgaa gaaggaagcg 960
aaaaatgaac aaaaaagcga tatcgtctcg gctattataa aatcgtctaa gaatttggca 1020
tctagagtac ccaatcaaga agaacttatt agaactttag aaggatttag attgactatg 1080
atattaagac agttgcaaat ctccagcttt aacggaaaga tgaacgcttt aaatgaaatc 1140
aataaagtta tttcgagcgt tatttattac ccgaatcgac accacggaat ggaagaggag 1200
gaatatctca cgcctgaacg tatggccaag tggattaatg aaaataaagt attagaaata 1260
gtgttaaggg attcgctaca ccagccgcag tacgtagaga aactcgagaa gatactgagg 1320
ttcgtcatca aagagagggc gctaagtttg cacgatttgg acgccgtttg ggcagctcaa 1380
gtcggaaaac acgaagccat agttaaaaac gtccacgatt tgttggctaa actcgcttgg 1440
gacttcagcg ccgaacaatt agaccattta tttgagtgtt tccaaaacaa ctggacttcg 1500
gcgtcgaagc gacagagaga aagactttta gaactgatac gtcgattggc ggaggacgac 1560
aaagacggcg tcatggcgca caaagttttg acgctgtttt ggaatctggc acacgccgaa 1620
gatgtcccaa ccgaaataat ggatcaagct ttagctgctc atgttaagat attggattat 1680
agttgttcgc aggagcggga cgcccaaaag acagtttggt tggataaatg tgtggaagaa 1740
ctgaagaacg gagaaatgtg ggcgcttccg gctctcaagc agatccgtga gatttgcacg 1800
ttatacgaac agaacacgaa cggcagccac actcaacgta cccaccacat ttactacaga 1860
caagaagtga tagaacgatt gcaaaaccag cattctctag ttatattagt aaccaacagc 1920
ctttgtagtt atatggatag attaagagaa ttaatcaaag agaacccgga attgaccagc 1980

-continued gagacctaca tacccgacgg acggtacggc cacacgctgc aagtccagga aagactgaat 2040
tttcttagat tcctcttaaa agacggacaa ttgtggctat gcgccgaaca agcgaagcaa 2100
atatggcagt gtctcgccga gaacgcggtt ttccagagcg acagagaagc ctgtttcaag 2160
tggttctcta aattaatggg agacgagcct gatctagatc ccggcatcaa caaagacttc 2220
ttcgaaaaca acatattaca gatagatccg atattgctca cagaaagcgg gatcagatgc 2280
ttcgaacgat ttttcaaagc ggttaacgtg aaggaaggca aagtgaaata caaaagaagg 2340
tcccttctaa cggaagatcc cgatctaata ggtctcgatt atctatggaa agtagttact 2400
ttgtgcccaa acgatatcgc taccagagcg atcgagcttc ttaaagaagt cagtaccaac 2460
ctcggtccta gattgaccca agcgcagttg gtgttccacg aaaactacat caccgaatgc 2520
tacgacaggc ttcgagctca ctacgacacg ttaagtatct tgcaaaaatc gaccaacgac 2580
aaagaattcg actccgagca acttcaaaac cgcattaagt cggaagccgt gaaaatatgc 2640
agggtactga aggttctaca cgagtacatc agcgaatgcg acaacagctt cgtgggggaa 2700
cgtaaaattc ttccgttgca cagagcttgt tacggcaaac acattactct gatcgtgcgg 2760
ttctctagtc ccaacaggca agtcgaagac ttggaactgt acacgcattc gaacgatact 2820
ctagcctctt tgagaaaata cattttgaaa cgaatcaagc ctggtatata ttgcaagctc 2880
gaattgttca tcaacggcga gcctttggag cccgccgagg acaagaaact tctttcgcag 2940
atacccatca gggacaaaat gttaatatca gcaaaaatag ttcaaatgaa ctcgaatatg 3000
gcgtcgtccc aggacagtag ttcggacagt tcgacctctt ccccccacca cccgtacgac 3060
ggtccaaacg tcgaagcgga gaatctgtta ccgggcgttc tgatgtccca acaaccgttc 3120
tacgcccaat tcttctgcca gttgatgaac gtaggaagca cgttgccgtt tgcgatgttg 3180
agagatatgg ggcacgcgct tcttcagttg atgccttgca atctgatgac gatggagaaa 3240
ctgaggattt tgtttttctgc gccgggagag cagaacattt cgatggatag catgtttttc 3300
agcgcctcgc cttctgaagt attatacaac ttggaagtcc tctacactat gttaatgcca 3360
gccatagacg ccatctccga aaaatcgtac gaattccagt acagcttcat gatatccgga 3420
gaagcccacc tcttcctcga gatgttgacg aagaataact tcatgtcgag cgccgataac 3480
gttaccagac gttcggcgta tctagttgtc ctgaaaatat gtaaattgat actgacatct 3540
gtcgcgcacg tcctggtaag actgagtgaa gatcacactc ctccagaaaa tgaggctttc 3600
aacgaaaata ccactccacc gggaaccttt ttgagacagg cattacgaaa tgttcctgga 3660
cactcggatc atttactgcg acaagtttcc atgaaactag ctcaaggttt agcgcaattg 3720
atggtatccg aaacgggaaa caccggccaa gctcaagcac tgttcagtca agcgttgaat 3780
tgggaactgc cagacttagc cacgacgttg gctttggtgc ggctggtttg ggcagcgagc 3840
agcaacaatc tcggcgctgt caacgcctcg ttggaaaact tgcactcttt atccgaagcc 3900
agcaacaaga aaaagtcgga actagtcaac gacgacgtgc tcctctgcaa agaagctctg 3960
gaactgctca gtaccgccgt agtgctcaac ccccagcagtt tgcagcactt gtaccaggac 4020
aattggtggc cttacttcgt tacggacttg gtgctagtca atccgaattg ttccataaga 4080
gtcgcagctg ccgaacagat gatcattata tgttcttgcg gcgctagcag tcaaatggct 4140
ttgcacgtca tcatgccgtt gctcttttct ctcatcaata ccatcgtagt cgaacacgcc 4200
aacacgtccc acgagttttt tcaactgttg tgccgtttag tcaatgtagc gtaccttacc 4260
ggatgtccca tcaacggtgt ggagaccctta ctgtcaaatg aggttgcgtg gttacgaaaa 4320
gccagagaca aacacgaagt actgatagaa ggccatctcc ttctcgccaa agagctcctt 4380

-continued

```
ttgctgatct cctcagaaca gaagtgcgaa ctgggtagtg ctgagtccgg cagtctgatt   4440
aaagaattgc tcgaagactt cctgtttccc gccagcaagt tgatgttgag attacacaaa   4500
acgggtcagc tgggcgaaga cccggccatt cctatttgtg atactcccca aactcaggcc   4560
gcagcattcg atctgttggt atcactgtgc atgaactgtg tacaaaacta caaacagctg   4620
gttaatatgc tcacggagat gttttacaac gatcctgaca ctgcaatctc ggaatgggac   4680
taccttccgg cagtagggcc gcgtccattc caaggtttcg taggtttgaa gaacgccgga   4740
gctacttgtt acatgaactc agtcttgcag caactctaca tggtcgacag tattaaagaa   4800
ggcattttgg cagcagaagg agcagctacg gaccctaacg aggatttcac cggtgaagag   4860
agactggata tggacgtgga ttgcactgat gataggaata gtttggacga taataggaag   4920
gactacaacg ttgggatttt gaagcaggtc caggctattt tcggccattt ggcctgttct   4980
cgccttcaat attacgtgcc taggggactg tggagacatt tcaaacttca aggcgagcct   5040
gtgaatctga gagagcagca ggatgccgtg gagttcttca tgtcgttagt ggagagtctg   5100
gacgaagctt taaaaacatt gggacacgag cagatcatgt cgaaaattct tggaggttcc   5160
tactccgatc agaagatctg caaaggctgt cctcatcgtt attccaaaga agaaccgttt   5220
agtgtgatta gtgtagatat taggaaccac agtagtttgc cggattcgat ggagcaatat   5280
gtcaaaggtg aattattgga aggcgccgac gcttaccact gtgaaaaatg cgcgaagaaa   5340
gtagtgactg ttaaacgact gtgcgtgaaa aaacttcccc cgattctagg tatccaattg   5400
aaacgattcg aatacgattt cgaacgagta tgcgcgatca aattcaacga ctacttcgag   5460
tttccgcgcg aactcgacat ggaaccgtac accgtgtccg gtttggccaa aatcgaaggg   5520
gaaattatag actgtgatct tcaacctacc tccaccgagg tctgtaccaa gtatcgtcta   5580
tctggtatcg tcgtccattc tggacaagct tcaggtggac attattattc gtatattaga   5640
agtagagatc cctcgggaga cgtcagatgg tacaaattcg atgacggcga cgtgtcggag   5700
tgtcgaatgg gcgaagacga ggaaatgaag gtgcaatgct ttggcggcga ttatatgggt   5760
gaagttttcg atcccatgtt gaagaggact acgtatagga gacagaaaag gtggtggaac   5820
gcctatatgt tgttttatac caggcatgat gttgaggagg agagtgcctt gaagatgatg   5880
aaccaattga cgatttccgg tacgagaaaa gaaacacatc tcaagatgcc gatagccata   5940
gaaaacagta taagaaagca aaatatcaaa tttctacacc ataggagtca attttctttg   6000
gaatatttca cgttcatcag aaaactggcg acgagttcag ctcagggcaa tactagactt   6060
agtcaaccgt tgccaaacga tcaattagaa caacagtatc tactcagtgt tcaactagtc   6120
agcaaattcc tttttcatac tgggtggcat acgaagaaga atctacgagg acctgccatg   6180
gaatggtgtg acgtcctatg tttgcatctg cgcacctcgc ctgtgatacg ttcctggttc   6240
gcacactgca tgctcttcga gcacatgagc cgtttctgcg aatacctgct gagttgtcct   6300
agcaacgaag tccgttctgc atttatcaag atcgtggtat tgctcgcgca cttctccatc   6360
aacgacggac cgtcggcttc tccggcggcc ctcaacagca ccgccactgg ctctttgagt   6420
gatcacatcc tgtgggcgtt gctcagtctg ctgcagaggg aggtcagcga gcacgggcgg   6480
catttgccgc actattgtac ggtgtttcac atgtacgcca atcaaggtat tcaagaaaag   6540
acgcagctgc tgaggatgaa cgtgccggcg acctttatga tggtcgctct agacgaaggt   6600
cccggaccag ccataaaata tcaattcacc gaattaggaa aacttaatca attagtcgct   6660
tgtttaattc gatgctgtga tgtaagcagt aagtgccaga acagtaccaa cggtccagtt   6720
```

-continued

```
ttacccaatc cctacaaaga tcccaccata caggaataca tcatgccaat ctcctcgcct   6780

gccgccgaaa tcctattcaa caggaacgta tacgtcaaga aagtgatcga agatacgaat   6840

ctgactgaag acgcgatcaa attcttgcag ttctgttcgt gggaaaatcc tcatttctcc   6900

agggcggtat tatcggagct cctgtggcag atagcctacg cctattgcca agaacttaga   6960

caccacatag agatcttatt gtcaattttg ttaatagaag attcctggca gaatcataga   7020

atacataatg ccattaaagg tgttccggaa gagcgggaag gtcttctgga aaccatcgtc   7080

cgtgccaaga atcactacca gaagagggcg taccagtgca tcaagtgcat ggtggcgttg   7140

ttcagtcgtt cgtcggcggc tcaagctatg ctgttgagac aggccgaagt gaggcgatcg   7200

tggacctcag cagtagcttg gttacaggac gagctggaga ggaagtaccc cccaaatgct   7260

cagtactcct acaacacgtg gtcgccaccg gcacaaagca acgaaagctc caatggatat   7320

tttcttgaaa gatcaaacag tgcccgcaag acgttagaga aggcgctaga actgatgcct   7380

gagaccgaaa gagaagagga agtggaagag acgcactcgc aagaggagcc gtcgccgccc   7440

tccgagcagc attcgcagca gcacacgatc gcgcagccgc aaaatgtcga taacaacgcg   7500

ccgtcagagc tgccggatgt aacacagcac tgcgaaaacc agcaggacag gtaaaagaaa   7560

tgacggacgg gacggcggtt gtcgagcatt tcatccactt ctataagctt tgcacgttat   7620

ataaaacggg cgataggaat gtgatatgta tgtatatatt ataaaaaaaa aaaaaaaaaa   7680

caggttatat tggctgggaa gcatttttct cttgagcatg ttcctcatat ttttttggtt   7740

tttaatccgc aagtctaaat gtaaataccg aggcaaaaaa                         7780
```

<210> SEQ ID NO 120
<211> LENGTH: 1219
<212> TYPE: DNA
<213> ORGANISM: Diabrotica virgifera
<220> FEATURE:
<221> NAME/KEY: misc_feature
<222> LOCATION: (1198)..(1200)
<223> OTHER INFORMATION: n is a, c, g, or t

<400> SEQUENCE: 120

```
gtttggttta catcttagtt tttaaaataa aaaaatgttt gaagctcaag aaattcacgc     60

agaacataaa gatctcattc acgatgtcgc ttatgattat tatgggagga gaatggccac    120

ctgttcaagt gatcaatttg tgaaggtttg ggatcaaaca tctgatggaa agtgggtgtt    180

aacatcaagt tggaaagcac acagtggatc tgtatggaaa gtaacttggg cccatcctga    240

atttgggcaa gttttagcca cttgctcctt tgacagaaca gcagctgttt gggaagaaat    300

agttggagaa ttaccaggac caggcgaaag aggtaccaga cattgggtaa ggagaacaaa    360

tctagtggat tcccgcactt cagtaacaga tgtcaagttt ggaccaaaat ctcaaggact    420

ccagttagct acttgttcag cagaaggaat tataagaatt tatgaagctc cagacgttat    480

gaatttgagt cagtggacat tacagcacga agtccaatgc aagctgccat gcagttgttt    540

atcatggaat cctagtttgt ctaaaatgca cccccaaatg atagcagtgg gaagcgacga    600

tccaaatcca gcaaatggcg gcaaagtgtt catctatgaa tacaatgaga acagtagacg    660

atggacaaaa ttagaaacta taagttcagt agtggatcct gtacatgaca ttgccttctc    720

gccaaatttg ggaagaagct atcacattct tgctgtcgct accaaagatg ttaggattat    780

taatttgaca cctgtaaacg atgaacagag cattcagagt ggagtaacta aattggatgt    840

agaaaccatt gcacagtttg aagatcacaa cagtttagta tggagagtat gctggaatct    900

aactggtaca gttctgtgtt caactggaga tgatgggtgt gtcagaatgt tcaaaatgat    960
```

ttacattaac tcatggaaac ctgtagccgt attgaaaggg gactcctctc aatcctcgta 1020
cgatcaaaga accaccagct caacgaacaa cggaagtacc atcataccat tttaccaaac 1080
tgctagatat atcaagttag gatctatagc acagacgagg gaggcaccgt ggcactgaat 1140
ttattataac ttatttatat tgttaactga tgattttaat ataataaaca ttttaagnnn 1200
taaaaaaaaa aaaaaaaaa 1219

<210> SEQ ID NO 121
<211> LENGTH: 680
<212> TYPE: DNA
<213> ORGANISM: Diabrotica virgifera
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (506)..(506)
<223> OTHER INFORMATION: n is a, c, g, or t
<220> FEATURE:
<221> NAME/KEY: misc_feature
<222> LOCATION: (585)..(585)
<223> OTHER INFORMATION: n is a, c, g, or t

<400> SEQUENCE: 121
tcaaaaggtg ctaatgtcat nttcaaatga gtgaaaagag cgtgggaacc atgcaggggg 60
tttcgggcga acgccggttg cgccaactgg aaatgttgtt tcttggcggg cctgtgctag 120
ccaaagaaca aagttttagt atcgaaaccc tcatagatat attacttgtt ctctacgatg 180
aatgttgcaa ttcgagttta aggaaagaaa aaacagtttc agattttata gaacaagtta 240
agcctgtagc cagcacagta aaatctttaa gattgactcg tgaagatttc gagataatca 300
aggtgatagg tagaggagct tttggcgaag tgtgcgtagt caaatttaag ggcaccgaaa 360
aggttttcgc catgaaaatt ctcaataaat gggaaatgct caaaagggca gaaacggcgt 420
gttttaaaga agaacgcgat gttttagtct atggtgatag aagatggata acgcatcttc 480
attatgcgtt tcaggatgta tctaanttat atttagtgat ggattatcac tgtggtggtg 540
atttgttaac tttattaagc aaattcgaag atcgtcttcc agaanaaatg gctcggttct 600
atatagttga aatggtctta gccattgatt caatacataa tcttaaatat gtacacagag 660
atatcaaacc tgacaatgtt 680

<210> SEQ ID NO 122
<211> LENGTH: 5553
<212> TYPE: DNA
<213> ORGANISM: Diabrotica virgifera

<400> SEQUENCE: 122
tgaagagtgc acagtggtgt atggagaaaa ctgctgtggg tacgcggatt gaatgacttt 60
tatgtccctt ttctgtaaat gagtgttttt tttgtataaa gtaacctaag ggaactaacc 120
gttgttgttg actaaatcgt atttgtgata taactcgacc acatgaggcg tatcctcctc 180
aagcatcagt gattaagttt tacctatcga attattggtg gatcaagacc cggagaacca 240
tttgtagcgg ttggctatta ttttgggtta atcattatca cgatctcata atatgacgga 300
tacgagtcag gcggagcaac cgccccaaac gaacggcatt tccgacttgg aagacgatga 360
cagggccaaa atgagaccag tagacataga cgccgatgtg agagaaatgg aacgaaggaa 420
acgagtagag atgataatga acagtaaact attcaaagaa gaactggaaa ggatcttaga 480

-continued

```
ctcacagctg aaagatggat caggaccaag cgggcttctc caacaaattt cggacatggt    540
aggcgtcaac agacaaggcg gaaacgtttt taagagttcg agctgtgtga ttcccgttaa    600
cgacattaga ggaatcgagt cgatgggata tggcaaggga gaaaagattc ttagatgtaa    660
attggcctgc ctctacaggt tgatcgactt gtacggctgg gcctacggct caagtacact    720
cataactgcc aggttgaacc aggatgacga acaattcttg gtcaaccctt acggaatgct    780
cttccacgaa gtgacagctt ccagtctgat taaagtagac atgcagggcg cggtcctcga    840
acaaggcaca accaacttct ccgtcaacat taccgcatat tcactccacg cagcagtaca    900
ttccgctaga ccagacatca aatgcatcat ccacgttcac actccttccg tagtagctgt    960
atcttcgtta aaacaaggac tgatgccttt gagccaggag tctgttgtca taggtgaagt   1020
aagtacacac atgtacttag gcggtcatct agatccagaa gaaaaggaca aaatcgcaag   1080
gaacctagga ccgaacaata aagtcctcct actgaccaac caaggagcat tatgttgtgg   1140
aacgaccatt gaagaagcct tcttcaatgc cagaaatacc gttttagcct ctgaatcaca   1200
gctcaaactt cttcctgtag gcattgataa tttagttttg ataaatgatg aagtaaggaa   1260
aaaaatatac gacgcagcgc acaaagcacc agaaagtact ccccgaccgg accaaccctc   1320
tattttggag ggcaaagtag aaagaaagtg gcgtgtaggc ggtgtagaat tcgaagcttt   1380
gatgaggatg ttggacaacg caggattcag gacaggctac atctacaggc atccattagt   1440
taagggcgaa ccaccgaaac caaagaacga cgttgaggta cccccagcag tttcctccct   1500
tggatatttg ttggaagagg aggagttata tagacaagga ctctggagaa aacttgaagg   1560
tggtaggaaa ggcaacgatc gcagcagatg gttgaattcg cccaacacct atcaaaaagt   1620
ggaaattttg gaaaccggaa cacccgaccc caagaaaatc acaaagtggg tagccgaagg   1680
atcacctagc cattcgagca gcacaccagt taaaattgaa tcggctcttc agttcgtacc   1740
aacaggtact aatccaaagg aattcaaaca aaaacaacaa cagatcaaag attacagacg   1800
agcagacaaa atttctgccg gtcctcaatc ccacattttg gaaggtgtaa cgtgggagga   1860
agctaaaaaa atgcaggacg ctacagtaac tcaaacaggc gaccatgtag tgctaatggg   1920
agctgcttca aagggcatta tccagagagg gcaccaacac aacgccatgg tatacaaatc   1980
gccttacgcc aagaatcctt tcgatagcat cacagacgaa gaactcaacg aatacaagaa   2040
agtcgtagaa aagaaagcta agggtgaata tgacactgac tacagtgaat cagaaggtct   2100
ttcgtcagca gctttgaaca aaagaattga agatatgcaa attaggtctc caacttctgt   2160
tactagtgag acagaggaag aaagtagaga cgaacctcaa atcttacgga tagaaacgaa   2220
gaccgttccc aaacctagtc aaccagaagt tgtattaagc gacggacgaa ctcgaagaga   2280
actatataga actaacaact atgcaggttt tcccaaagga tcatttttgg agcctaaccc   2340
cttgcatttc cacttagtca gagaaagcca gatcgctgtt agacagcgcc ctctaaagat   2400
atctttgact actaataata gatcttcaga ttcccgttct gttgtcgtta accttgataa   2460
ttctaggtgt atatctgtaa acatgccttc cagtacattc gagggcttta ttgttccgtt   2520
tgcatcagca ttgaactcaa gaaatcttcc tatgatcaag gaacaagctt cacaaaccag   2580
ctatgttaac gtagtgaatt atactccttt atatattagt caatatagaa catgtctgac   2640
agaacccgac aatacaaatt cattcgagag aaatattttg atgaacatgc acgagcagat   2700
gctggaagat ttgaacgata gctcagattc tgagtatgag tctttaaata acaccaaaca   2760
gcaatactgt gaatctacca gaagggatat tgttgagttt gatgaaaatg atcagtgcga   2820
caatgagagt ttggttgaag taacagcaga ggtacaggaa atgatgttaa atatagaaag   2880
```

cagcactgat ttaaatgaag atggtccacg tgagaaccaa cgttcggttg cagtagctgc 2940
agaattatca gaaacgactc cacctacaga aagtttttct tctgtttatg ttgaatatga 3000
cgaaaatgat caatttgaga atgaaagttc tgttggggga accacagagt catcagaaat 3060
tctgactaat gtagaaagtt gtactaattc ggaaactgta ggaatatttg ttgatgtagt 3120
caagcaagca tttgtaatga cagaagactt cttaagtgga gccaaagata ttttaatgaa 3180
aattcctaat gacagatata ttgtcaaaga aaactctgat gaaggaattg tggattgtac 3240
ttttacgaac aaaaccttca gtatcgacga tgataatgaa aatacaactg tattggaaaa 3300
aactgagtat gagtatgttc aagatttgac acaactgata gtggactatt taatagagca 3360
gtgtatggag gttaaagagc ttattctatt cccagaggtt ctacatgatt ctaacttgca 3420
taaattgctt gaaaagatga aattaatata ttatgacgcc tttaaggacc agttatgtga 3480
agataaaaat gagctaagac tttctttagc ttcatcagtt ctaaggagac tggaactcga 3540
agaaaagtta aacaattctg gagattctgt aacctcgaac acagtttccg ataaaatctt 3600
tacgatttca gagtttttga acgatatttt ggaccatttc tttgacaaca tcgatttaag 3660
gcagtttaac aacttcagtc aggagttaat tgcgaacagt gatcttgaag tacattctac 3720
accaaaactg aaaagaagag atataaatgg caacgttgag ccattcgaag tgaatacctt 3780
tcatcaacag accttgtcaa agtcgggctc tgaaatattt tggatttctg tgtctcctgg 3840
tacttctgct aacaatgaac aacctcgtag aaaaattatt aatgttgatg atattccttt 3900
gagacctcct gttgacctga ttagtaaaga agtgttggac cctatatctc aacctcctgt 3960
tgacttgatt agtaacaaaa tgttggctgc tatacctgaa gaagtttgtt tagatttatt 4020
taacacttcg tcaattgaag aaggatttaa accagttgat gataattcca ctttagtaaa 4080
aggacttcag acgcaaaaag gagataatac ttgtgtcaac gtagagaaaa aaaaagttac 4140
taaaattttg actaaccaag tgagttttta taggagccaa agtgtaaata gtactgatta 4200
tgttagtgta aaaagagcag tatggaacaa caatactgaa aataaggaaa atgacccctt 4260
gaacgattct ggagattgga tgggttacga cactgcaatg ttttgaattg aatttcattt 4320
tgtatatcct ttaccaagtt ttatttatat ttgatatatt tctcgttttt aaatacattt 4380
ttatatcaaa gtgtatattt ttcttcgtat gggggaagtt tttaggggag attaaggttt 4440
gaacacaatg tatagtaatg cacaataaat aaatccacta acattgaata tagacatgta 4500
tacaacacat tttttaatca aaatcactaa tcagtatcat caagaaaagt ttcgacctaa 4560
tttcatcatc aggaatcatc tacctcatgt aagaaaatct aaaattatag ttaatttata 4620
tcctccctct aaagttatgt cttcgtgtcg attttgataa caatttataa atataaagtg 4680
aaataattta tcacatttat ttacaaaaat tatatcaaca cactgtaact ttttcgacag 4740
aaacatttta ttgagtaata tttggtcctc tcactccttc atgccatctc tcttgaggtg 4800
gtaaacagta cggaaacggc tgttctcttt ttcatatata ccacgttttc cttcaatttt 4860
tacacagtta aactaaactg tggttttatt tttcacaagg cgattacaaa catttggccc 4920
ttctctgttc tttcatttat aagttgaatt ttttctattt ttcttttaag ttggactttt 4980
ctttttacat attcctgttt gtttacgttt tttatcaaaa tgtccccatc ttttgcgtct 5040
gatagtatac caaagtacta agaataaatt attgtaatca atttttgaaa acacactgat 5100
atgaaggata aactgttttt tctgttttgt gcatttttttg tttgtactgt atacaatttc 5160
ggatacaaaa tcatttcttt tatcggtgtt taaatctatt taatgtttta ctgtaagctc 5220

-continued

```
aatctcctgc ttggttttat ttagtttata gttttttctt ttcaaattaa aataaataga   5280

taaaaatcag ctgagcctta accactttct tgcattttcc taatttattt gtagtttagt   5340

agtctagaat aattgtttga ttaatcttta aaaattgatc agttagtaaa ttttgtgttc   5400

acgccttaag gtgtatatta ataatgtata taatgtaaaa gttattgacc ttataacttc   5460

tcttttattg tatttaacga ggaaactgta ttttaaacaa tgtttactat gtaaaatctt   5520

attcactaat aaaatatttt tcgtcaatta aaa                                5553
```

<210> SEQ ID NO 123
<211> LENGTH: 978
<212> TYPE: DNA
<213> ORGANISM: Diabrotica virgifera

<400> SEQUENCE: 123

```
cggaatcatg ttatcaatgg aaaataaact aaagaaatac gaaaaaatta aatttttagg     60

agaagggcaa tttgcaacag tatatcaagc tcgagatgta gacacggaca atatagtggc    120

tgtgaaaaaa attaaaatag gtagtcgaca agaggcccaa gatggaatca atagaacggc    180

tcttagagaa attaaactac tccaagaact gcatcatacg aatataatcg gtcttctaga    240

tgtttttgga catatgtcca atgtgtcatt agttttcgat tttatggata cagatcttga    300

ggttattatt aaagacaata ctattattct cactactgcg aatattaagt cttacatact    360

tcaaaccctt catgggttgg aatatcttca tttgaactgg gttctacata gggatttgaa    420

accaaataat ttgttagtta attcaagtgg catcttaaaa gtaggtgatt ttggtttagc    480

taaattgtat ggatctccca ataggataaa tactcatcaa gtcgtcacaa ggtggtacag    540

agcaccggag cttctttttg gagccaaaca gtacagtacc tgtatagata tgtgggctgt    600

aggttgtatt ttagcagaat tgctgctcag ggtacctcta tttcaaggag aatcagatct    660

ggatcaattg acaaagattt ttgatgtatt tggaaatccc acagaagaaa actggcctgg    720

gctaaagaca ctatcagact tcatcgagtt caaaccattc aacgccattc cactgaagtt    780

gatcttcacg gcagctggtg acgatttgtt agaactaata cagggtttat tagtgttaaa    840

tccaatcaaa agaaaaacat gttcagaatg tttgcagatg cctttcttta gcaataagcc    900

cgctcccact attggtacca aactaccact tccacagagc ttaaggaata acagagataa    960

tgataaacct actgcctt                                                  978
```

<210> SEQ ID NO 124
<211> LENGTH: 1132
<212> TYPE: DNA
<213> ORGANISM: Diabrotica virgifera

<400> SEQUENCE: 124

```
cctttcatgc tctgttatac tcaagaggat gctaacgcag aaggcaacga ggaaaacgtt     60

ctatcgtacg aaccagtcca acagttgcat attaattata cgagacctgt tattgtactg    120

ggtcctctaa aggatcgtat caatgatgac ttgatatctg agtttcctga caagttcgga    180

agttgtgtac cacataccac aagacctaaa agggaatatg aagtcgacgg tagagactac    240

cacttcgtcg catccaggga acaaatggaa agagatattc aaaatcatct attcattgaa    300

gcgggacagt acaatgacaa tttgtatgga acttctgtag catctgtacg tgaagtcgct    360

gacaagggta aacattgtat cctggatgtt agcggtaatg caataaaaag gctgcaagtg    420

gcgcagttgt atcccatcgc tgtttttgtc aagccaaaat cggtcgaatc cataatggaa    480

atgaataaaa gaatgacaga agagcaagcc aagaagactt ttgaaagagc aatcaagatg    540
```

-continued

```
gaacaagaat tcggcgaata cttcacagct gttgtgcaag gcgacactcc cgaagacatc    600

tataaccaag tcaaagaagt aattaaggaa caatcaggac caaacatatg ggtaccggcc    660

aaggagaaac tgtgaccttt ggccccaccc atatggactc ttccgtctcg tccacaacgg    720

ctgcactgaa gacgccacta tttaaactaa tataagatcc ccaaaatccc cctgtagcga    780

atgagcgcta aaagttttca aaattgcgca ctgatttttg atcaaaaatt gtcctcagga    840

gtatttgttt attcatgaag tattcttttg aaatttgttc tgtctactta tagtttattt    900

cactttgttt ttgattttgt tttattattt tagattcata tcggtaattc ttagtttggg    960

taaattagtt tccagaaatc tctaagagat tgaaagacat tcatttttac atatttctgg   1020

gaaaatttgt ctattataat ctttctcttt agaaagtgcg tattttgaaa tttacagttg   1080

gtcgaatcga tcggttattc tcttcgtgtc cgctacgtat ttacgatctc cc           1132
```

```
<210> SEQ ID NO 125
<211> LENGTH: 1151
<212> TYPE: DNA
<213> ORGANISM: Diabrotica virgifera

<400> SEQUENCE: 125

aagaggagga agaagttgaa attaagattg aagaacatga tgtgaaacct agcgtcagca     60

gactttacca tgctgccgag agcgatcata gctaccacaa gggcaagcag agtgccatgc    120

agatggctac ctttggaatc gagactcctt ctgattcaga ggaggaaata gatgttgtca    180

atgtcaacaa cgagaagttc ccgttcaata aaacggcggt gttttcgttc cccaataatc    240

catcgacgaa agatcgccaa cagatccaga tgcgtatggc aactgctata tccaagaagc    300

gaatacaagc ccaagctcaa ggcatcaaga ctatcatgcc cgttaggaaa acagccacac    360

cggaggcgtc acctatcaaa aggaaacccg tggaaaccac aaggagtggg aaaaaaactc    420

ggcaatacag aacaccggtg agcactccat acaaacgtag acaatacggc aacagcagcg    480

atagcgaacc agaaccatcc gagaagagaa gtttacacaa caacatggag aggcagcgaa    540

gaatagactt gcgcaatgcc tttgaagatc tgcgagtatt ggttcccgaa gttagcagaa    600

agagagagcc gccaaagtgg tgatcctcag ggaggcagct caatattgcg atttcctcac    660

caacacctcc acaaaatatt cgaaacactt cgatgaatta aaaaagaagc aggaattcct    720

taggcggaga gtgtcacaac ttcgaaggaa tttagcagca aatcgttaag taaatataga    780

atttgtaaga aataatgcga tttgtagtaa agggtgtgtt tagaattgta tagaaaaatt    840

ccgagtatcg gagagactaa tgagtgactc aaaagagcga aacatctcag ttatttgtta    900

tatttttggt ttcaaaaaac agaacttgtt ctagcaacat tatatacatt atcttaaatt    960

ttcagtctcg aaagcactaa taggcaaaag caggttgttt tatcctgcga tcattgtgga   1020

tagctgaagt gatcctgagt tcaaaaatac aacaaacaaa aagatgttac gtttaccagt   1080

cgtattttat accttacatt aattgtaatt gatttttgaa tgccgttttt gtttttttcga   1140

aatttggtca c                                                        1151
```

```
<210> SEQ ID NO 126
<211> LENGTH: 1529
<212> TYPE: DNA
<213> ORGANISM: Diabrotica virgifera

<400> SEQUENCE: 126

ccgcctgatc ccgcagatct ttccaaggga atggaacaaa ctcctattcc ggttgtgaat     60
```

-continued

```
ggaatcaata gagaaatgtt agacttttgt aattattcaa ttaaacgagt tcctatggaa    120
ggcgttgata tgaatctcga tccagactat ctgtgcggct gtgattgcga tgacgattgc    180
attgataaga cgaagtgcgc ttgctggaag ctcactttag agggagcaaa gtataccgga    240
aaagatgtaa atcctacatc ggtcggatat atttatcgaa ggttgcccga acaagttatt    300
acaggaatat atgaatgtaa ctccaggtgc aaatgttcat cgacgtgtct aaacagagtg    360
gtgcagaacc ctatgagttt gaaacttcaa gtatttagaa ctcacaatcg cggttggggt    420
atcaggtgtc tcaatgacgt tcctccaggc agctttatct gtatttatgc tggtacaata    480
cacactgaag ctatggcgaa tgtggatggt gtggcgttcg gagatgaata ctttgcagaa    540
ttggattata tcgaaaccgt tgaaaaatat aaagaagatt acgaagcgga agtcatggag    600
gaggaggaag aacaaaataa gaataaacgt cgaaaggaac ccgaagagga agaggaagaa    660
gaagaggaat ccgtagcggt gatctctaac agcaaataca aaaggtacaa ttatgctgca    720
gataacgatt ttacacctag tcatcccgac aggattgttg cgggagatgc accaattaga    780
acgcgtctaa gaaagagaaa caaagatgac gctaaagatg aagagaacga agtgaaagga    840
caaaaaagaa gactcaagga atgaaatgat agaaaataaa acaagaaata tacaaataaa    900
aataattaca gagtctaatc aatcaatgaa ggcattaatc gaaggactgt ctgataatat    960
cgaaactgtt accataagcg acgaagaaga tgagggaaga gaagtattaa gttttaatcc   1020
acaagcgagt aacttggacg acaaagcacc caattacacc tctgtccgag atctctacgg   1080
aaaagacgaa tctgtttatg tgatggatgc aaaaaacgct ggaaacattg gaagattttt   1140
gaatcattcc tgttcgccaa acgtgttcgt ccagaacgtt ttcgttgata ctcatgatcc   1200
ccgtttcccg tgggtatcat tcttttcgtt gcaccatatc agagcaggaa cagaactgac   1260
gtggaattac aattatgaca ttggcagcgt tcccggtaaa atgttgacct gtcattgtgc   1320
ctcaggagaa tgtaaagggc gtttattgta atctgacaga atttgtactg ttctgcaggc   1380
aatggagatg tattatttca tacattacgt aattatttat accgtttata atagtgtgct   1440
gtattttatt aatttcgtgt atcaaaattc aatatttcgt tcattgattt tgtctttcat   1500
tgtgctaagt attagaataa tatataatt                                      1529
```

<210> SEQ ID NO 127
<211> LENGTH: 2613
<212> TYPE: DNA
<213> ORGANISM: Diabrotica virgifera

<400> SEQUENCE: 127

```
aaacctactg tgtaggttcc tttgtttttg ttaatgagaa caagtggtgt tgtattgagt     60
gaacaagtga aaaatattga gtataattaa ttattcacat acaactggtt tttgttttca    120
caactggaat acatatctta ttctttaagt taataatcaa gttcaacaat gtggcaaacg    180
caggcagtcc atattaccac aaacaataag gagaaccact ttcaaaaaag tgaagataag    240
ttaactcttg gaatgacttc tgctatatca acagcagaac caaaaccagt tgatttggta    300
aaaacaaggg aattaataga ggctctgaaa ccttttgatg tattcgaaag tgaacaagaa    360
ttaaacaaga ggatgcacat tttagggaaa ctgtttagtc tagttaaaca atggataaag    420
gaggtttcac tttcaaaaaa tatgccagag agtgttgctg agcaagttgg cggtaaagtt    480
tatacattcg gaagttacag attaggggtt cataataagg gggctgatat tgatgcactc    540
tgtgtagctc caaggcatat tcataggtcc gatttctttt cctcctttta tgaccttctt    600
aagcaacagc cagaagttac tgatctcagg gcagtagaag aagcatatgt gcctgttata    660
```

aaaatggact tcgatggtat agaaattgat atgctctttg cacagttatt acttaaagaa 720
attccagaat caatggattt gagagatgat atgcttctta aacatttaga acctaaatgc 780
gtgcggagtc tgaatggttg tcgagtgaca gacgagattt taagactggt accaaatatt 840
gaaaacttca gaatggctct tcgagctatt aagctttggg caaaacgaca tggtatatac 900
agtaacgtat tgggttactt gggtggtgta tcctgggcga tgctagttgc aagaacatgc 960
cagttgtatc caaacgcaac atcatctaca cttgttaata aattcttcct tatattttcg 1020
aaatggcaat ggcctcaacc agttctacta aaacaaccat ctaacgtcaa cttaggattt 1080
gtggtgtggg atccgagggt aaatgttcaa gatagatacc atctcatgcc aatcattacg 1140
ccagcttatc cacaacagaa ttccacattc aacgtttcac aatcgaccag aacgattatg 1200
gttgaagaat tcaaacaagg tctgcttatt accgacgaca taatagtagg caagtacgga 1260
tgggataagc tgttcgaaca accgccattt ttcactaaat ataaacattt cattttactt 1320
ctggttatgg cagataattc cgatgatcat ttggaatggt gtggacttgt ggagagtaag 1380
gcgaggttac tagtaggtca gctggaaaga aaccaataca taaccctagc acacataaat 1440
cccgagagct atgccatgct tgaatccgcc atggaacccc atacattatg ttccatgtgg 1500
ttcataggac ttgagtttgc caaaactgaa ggtatcagcg tcgatctaac aagagacatt 1560
cagacattta cggaacaagt caataaccat gctatcaata tcaagatgct gaaggatgga 1620
atgaggttag acgccaggca tgtcaaaagg aaacagctgt cacaatatct tgctccggga 1680
gtgacttaaa agagaaagga aattgagtat cagtaagaac ggggttacac cggaacaaaa 1740
tagaaagagg cagtcttcgg aagctactca agaacacaac gatgctccaa gtaaaaagac 1800
gaggttgtca gaggatatcg cgtcacaaga gttcgatgaa tgctccaaca cgtcaataca 1860
catagattcc agcagtaatt taagtctaga atcagagagt aacattagtt gtacatcccc 1920
ggcctcaact ccctcccata taaatacaaa ttccaccacc acaaacgtac cagaaacggt 1980
gtgtacgtga caacctacaa ctgatgtata tgtgagtcgt ccattcgttg ctgtcaaata 2040
aaataatttt tattgtaggt ttcttccaag aaacaacagt ttatgtggtg ttcacgtatg 2100
tattaaatta cttttccaaa aacagacaga aaaacttttt tgaggtaaaa tattatcgca 2160
aagagtgcaa tgttcttatt ttaaggctta atgtgtttat tgtgagtgtg cgttaaaaat 2220
tatcctgtat atacaccaaa aggattcctc cgtcgtcaag gaaagataat ttgtaggcag 2280
atagaccgac tgcacatgaa agcggatgat ctaaaatcca acgaaaatac acaggatgta 2340
tcacttgtaa aatgttcgtt tatttgttta tcagtttaag gattctttaa tggtttagat 2400
ggatctagcg atttagttaa cctatggagt aatttataat tgaaaacata agtttatgag 2460
gagtttaaag gtattgtctc attttcttct atttttagtt gtataccatg gagtctgata 2520
ttttttcggt ttctcgtcca ataactaaat tgtcgttcta tatttccctt tagtttcgtc 2580
aacactcata acagtctgcc ctcttgtgtt taa 2613

<210> SEQ ID NO 128
<211> LENGTH: 450
<212> TYPE: DNA
<213> ORGANISM: Diabrotica virgifera

<400> SEQUENCE: 128
atgaggatag atcaactatt taatatcatt atagaatacc cagaatctct accggcttta 60
gaagacctac gaatatgtct tcctagaaca gatctaaagc ctatgctaac taagaaacta 120

-continued

```
caaaaagcaa tggaaacacg attactacac cctggtgtaa gtacacctga tgttctaaca    180
gcttacgttg ctgccattag gtctttaagg gtgcttgatc ctacaggact attgctcgaa    240
actgtcacgc aaccggttca tgaatacttg aggagtagag aagatacagt aaggtgtgta    300
gtcaccagtt taactgagga tggtcctaat gatctagcag aggagttggt gagaggagag    360
gccgttcaag ttgatgaaaa tacaccactg gacgaagata atgaagactg ggaaacttgg    420
gtgccagatc ccatcgatac agtaccaaat                                     450
```

<210> SEQ ID NO 129
<211> LENGTH: 1812
<212> TYPE: DNA
<213> ORGANISM: Diabrotica virgifera

<400> SEQUENCE: 129

```
ttgatcagaa gagacaatat atcacatgaa tagaataaga agaaagtgaa tgatatgaat     60
acgtccctga cgtttataaa atttgacatt ttacaggaat tttgcacgaa tttactagaa    120
acatggtttt aaataacgtt aaagaactaa ccgaagaaga aaaattcgat attcagctgc    180
aagctgagca ggaactgggc agactagtca gaacttatac gatcctagaa agaaaccgag    240
cccaaaaatg tgatacaggt ggtaaacttc tcaaacaacg aaaagtgctg gacattttca    300
agaaggaaca aaaaaatatt ctcacggatc ttgctgtagc gtctgccgat gctagaagag    360
tggaggacga aaagaagtcc aaggaattga aggatttact tagagagcac gacgatttcg    420
acgctgaaat cactcaacaa aaatcacata ttagtgagat cgatggacag attcgaatga    480
ccaagaaaaa ggttcttgac ttaaggtcga agcaaattac agacgaaatg tatcaacaaa    540
gagtaattgc aggagaaaag acggttcaaa ctttagaaaa caaactggaa gtccaaataa    600
agaaattttg ctcaatatca gccgagaata tcaagttaag agaagaaatt gatcatttac    660
ttttagaaag aaacgatttt aacaaaattt gggacagcct tatcaacaat ttagctgtcg    720
gaaagaagtt catgttggac ttaatagaac aagcaactat agcttatgat caaagggaag    780
agtgggtgtc caagctacag attttaagaa caaaagccca caatgatctg attaatcaca    840
ttcaggaaat gagggtgttg caaagaaaaa tggacgacga tcagaaacta caagagtttt    900
tctcagtgaa atgccaaaaa agaatcatga gacaactaga agaaaaagaa aaaaacaaaa    960
ggatgctcaa taaagaaaat atggaaaaga aattggaacg ttacttacaa attttaatta   1020
cgattaagga atttaccgga gaagaaaaag ttacgacgat tgccaacaat tttgtaaccc   1080
aagaagaaga aaattttgcg atgtttaaat atattaatca tttgaacaaa gaaatggaag   1140
atcttacgga cagtctagca aaattgcaac tcaaaattgg cgagcaggag gcactaaatg   1200
aattgcgtaa gcaccaacaa gaaactaggc tggaaaagct gaataaagat tttgaagatg   1260
ctaaacagat cacgagtcaa aaatctgaag agctgaaagt aattgatcaa aagttgagaa   1320
cgattataaa tggcatcggc caattgttta gaatgtttag atgcaaaaat gatcctctaa   1380
taaagttatt aggtgaaaat caaaacatac attattataa tgtactgctg tatctggaaa   1440
ttttggaaaa caacatcgaa gaggcaatgg tttctgtcaa tttcaaggag acccaaactt   1500
tggaaagaac aaaacacaag gaacccaaaa taacaacttt gagacacgtg aaatgtccac   1560
ccatgatcga acccatcgag agaatagtcg ctactaatcc ttgccctttg tgcgttgaac   1620
atgagcatgt cagtgatgtc atagatgtac tgcaattcgc gcttaccaaa gaagagatcc   1680
aggagaggct taagatcaaa atcgataaaa cagaggcaga cgacaagttg cataatgtat   1740
ccgcctgtca tctgccgaaa tccagacaaa ttatacaaaa aagatatcaa taaaaattat   1800
```

aaagtgatca ct 1812

<210> SEQ ID NO 130
<211> LENGTH: 830
<212> TYPE: DNA
<213> ORGANISM: Diabrotica virgifera

<400> SEQUENCE: 130
tttttttcat ttttgacacc gactttgtca tttatttaac aattatatac taattttaat 60
attacgattt taattgatat aattatatct aaaattcaat aatggctaga tacgatttga 120
cattgaatcc catggaagaa accaggtttc ttaaaaaaca tagagtactg gctttaagtt 180
tggcaagaca ggtccatttt agctttcagg aggttgaagc cattctcatt atatattaca 240
agatacaaaa atacgacact tacgatccaa aaggtattac gagagacgtt ctgatggaag 300
ttttccattg ctgtttagat atgacggata tggaaaaagt gattcgaata ataacttgcc 360
tagacgagaa agctcgagat gtctacatat caaaagagct ttggtgcaac atgttatcgt 420
tatttttaag aggaacgatt gaagaaaaaa tggcattttg tttcaaagtc tatgattaca 480
gtggaagcgg acatctcatg aaggaaaatc tttttaagct tttagtggga tctttgaaga 540
gcaacatcgg cgaatcagat gcggaagaag ccgtgaagga tatggtggaa gttataatga 600
agaaaatgga tgcagaccgg gacggcaaga tttcctttaa tgactaccga tataacgttc 660
tccgccaacc agacctgttg gagtttttgg gccagtgtct tccagacaga catacggttc 720
acaaattttt gtgtaccttt actgaaaata ctaagatccg attctataag ttaaaattag 780
gcacaagtat aatgtgaaat taggaagtaa acgattaaaa gttaaaaaaa 830

<210> SEQ ID NO 131
<211> LENGTH: 2072
<212> TYPE: DNA
<213> ORGANISM: Diabrotica virgifera

<400> SEQUENCE: 131
gttaaatatg atacatcaca ccaattcgag gattataaca actacaggtt aactttacgt 60
taaagataac ttcggtcatc catcacacgg ctgattagct atctattgac aggttgtgta 120
tatagagcag ttccttgtaa cacgacttgt ctcttctatt ataatgtttg tctcactatt 180
ccaatcagtt ttgaagagtt tttaagccca cacttcataa catttggtag atgaattcct 240
caatttaact atgaggataa aagtacgcat aaagtcacaa aaaatttccc cgcttttccg 300
tgacatcctt attccgcaag ttatattgtt tctgcgcttc ctatagacat gggatttgga 360
ctaggagtcg agctcatcga gctcaaagta tcttctttca acctcaactt attcggatcc 420
ttctcctttt tttctttatc cttatgttta tgttcgtgtt tgtgtttatt aacgctaaaa 480
gacgtactat tttaccgaaa tgatgttatt actacaataa gttaatgatt tttgaacaaa 540
aaataagttt gtttggtgtg ccttctacat aatttttaat tataagtttc atatagaaat 600
aaatttttaa tcatggccgc gccaaggaga gccgcacaga ccgtaaatca agaaaacgta 660
aattcccgtc ttgctgtgaa atcaaacgta aatgcgccat tagaaccgct aaaaagacca 720
gcacttggcg aactcggcaa tacactacaa gacacccaaa aagcacaaaa cggtcttgct 780
ccaacaaaag atggttttaa aaaacctgaa ggtactttgc aacccaaaaa agagacaatc 840
aaaactttga ctaacaagga aaaggcaatt ccgatcaaac ctagaactat cctaaaaaga 900
caggaaagtt tagtaaaacc gttacaagga aaatgtacac agcctaaaga agtaccacgc 960

```
acatcgacac tagtaaacaa aaaactgtct atcgttgacc cagacgaaag tagcaaaaat   1020
gatcctcaga tggtaaccga gtatgtaatg gatatcttca aatatcttag agacatggaa   1080
ttgaaattag ctatcaaaga taacttcctc aaagaccacg aaactacttc caggatgcgt   1140
gcaatactcg ttaattggtt agtcgacgta cacgcaaact ttaaagccac gcttgatact   1200
ttgcatatat gcattggaat cgtggataga tatttacagg cgaacaaaaa agtaggaaga   1260
aatacgcttc agttagtagg ggcctcagca atgttgatag catgtaagta tgaagaaata   1320
tatgttccag aattagacga ctttgaatat gtatgtgatc acacatttac aaaacgacaa   1380
attcttcaaa tggaaaggga aatactgaag ggttagatt ttagtttagg tcgaccgatt   1440
tcggtgcagt ttctccgtag atatacaaaa gtgactcaat ctcgcgtgga gcaccataac   1500
ttaggtaaat atatgttgga attggtatta ctcgaaagcg atctagtgca cgtaagacct   1560
tccctactgg cagccgcagc ttgttgcttg tcaataggaa tattgaacga aactatggat   1620
ttgccgaaac tgtggaaccc cacctgtgta cagtacacgt cctacaatta caacgacttc   1680
aaatcgataa taacggaact cgcttatctc ttagtcaaaa gcgaacagtc gaaattccaa   1740
gcaataagaa gaaaatacgc cctagcaaaa ttcggcaaaa ttagtcttaa tgttaaatta   1800
aatggtcctc ttgtgagaaa gttgacagcg gggaaaaagt gatatttcca ttttatcttt   1860
taaccgaatt tttatatttt atatcagttt tatatttagt gtcattttta tttacgtttt   1920
agtacatttt aataaattag attcaagcta aagactatta aaagccttca atatcaattt   1980
ttgttagtca gtttttattt gacggaatgt gaagcaacaa tggagcaata aagttaagta   2040
gtccaggctg tttgctcgcc cccgtcaggt aa                                 2072
```

<210> SEQ ID NO 132
<211> LENGTH: 1517
<212> TYPE: DNA
<213> ORGANISM: Diabrotica virgifera

<400> SEQUENCE: 132

```
gacagttaat acgcgaaaaa gaactaatac accgatgaaa ctatcgtatt aaaataaagt     60
ttaaagtttt taaattatgt gtggattagt ttagtgttta gtgttatgtt gtgttagtgt    120
ttttttctg tgactaagcc tacaataatt tcttcgagca acaggaaaaa atttaaaacg    180
gagaggttct gaacatttgt atctgaaata aattaataaa gatgaatcaa acgtgtaaag    240
tgtgtggaga accagcagct ggtttccatt ttggtgcttt tacctgtgaa ggatgcaagt    300
cattcttcgg acgctcctac aacaacctaa gctcaatatc agaatgcaag aacaacggcg    360
aatgtgtcat caacaagaag aaccgcacag cttgcaaagc atgtcggctt cggaaatgtc    420
ttttagtggg tatgtccaag agcgggtccc gatacggtag acggtccaat tggttcaaga    480
ttcattgctt actgcaagaa caacaacagc aacaacaagc ccatttagcg aatgtttcac    540
agaacatgaa accaccacag aagacgccac cattacatcc gcagccgcca ctaggtatgg    600
gccttcttgg aatgaattcc tttcaaccgc cacttttaca tttacccaaa acaaaggaag    660
agttaatttt attgggcttg gatgaataca aacactcagc ctctcctcaa gtcagttctc    720
ccgaatcaca caattcagac tcatcaatag aactaagcga tgctaggagg ttacctttgt    780
ttcctggact attacctcct acattcctgc cacctcctgg tctcctttc cctccaggat    840
acccccctct ataccctggc ttactgcaac ctgccaataa caacagactt atgagaaacc    900
acaatcatgg tgtcgaagca tttaacaagc gagtgttcct ggatgcagtc cttaaatctc    960
agcggtcgcc aactcccgaa gaaagaataa ctcccatatc cactgaaacc ataatccaag   1020
```

aagatcctat cgatctcagc atgaaaacga acagcgatag ggggtcttct ccagctcata 1080
gcgaccaatc gggctcagga acggagcgag gaaatggtag cgaagccgat gaagaaagtg 1140
attgcgagtc agatagagaa atcaaaagga tgaaactcca caggcccacg ccgctagatc 1200
tcacgacgaa agtatgatgg aacatatttt tcatattact gatattgctt tcggagtacc 1260
tgaataatct agataaaaga ttttcaggtc actgatcagt ttctgggcca gtcttgaagc 1320
tatctggatt tccgtttcga aactgtcgat ataatgcaga tcgaaaatga aagtgttcaa 1380
tcttttactc aagaagtcac ttggcggttt tcttaataat atttagattt aaaatggaaa 1440
aagtaaaaag aaccagtaga atattaagtg tttacatttc attgctaaac tgattttggt 1500
tatttgtgat tgatttt 1517

<210> SEQ ID NO 133
<211> LENGTH: 3192
<212> TYPE: DNA
<213> ORGANISM: Diabrotica virgifera

<400> SEQUENCE: 133
tacacgtttt gctacttttt gtattatttt ttccaagtgt attaaggata aacctttcac 60
gggattaaaa tttcgtgaca aacaggccta ctattacaag aaacttcagt gttgtgttta 120
cttcactata caagtttgca actatgggta caaatactaa ggacgacttt tcagaatcaa 180
aagaatacgg cgtaaaatct gaggaattcg aagacttttc tgagactatg ttagatggaa 240
gcgataagaa atcattagag gacggctcat tgtcagatcc tgataactgt ggcatgtgtg 300
gtggcccatt ggttatacct cgaatgctgc actgtttaca tacattttgc gaagaatgcc 360
taggcaaaaa gcttgtcggg gaagctggag atgctggatc cacagacact tcaatccaat 420
gcccgatctg taactattca accctggttg gaacaaagaa gttagctgct ctaccgcttg 480
atgtctcaaa gacaaatgtt accgacgttt ccaactcccc cgatttgcat tgcacttcct 540
gcactgccaa agaaatggcc aagtccaaat gtaacacctg ccaacacctt ctatgcaaca 600
attgtgacaa ggctcatcat tttatgagat gtttcgagtc acacaaggtt gttgctctcg 660
aggacatggt taaatctggt attaagatca cagttcacaa gcctctagta tgcgatttcc 720
atcctggcga aaatctcatc ttctattgct tggtgtgcag tgtaacagct tgcacggagt 780
gtattaaagt tgatcataaa ggccaccagt ttgaggggat actcgactct gaaccaagag 840
ttagacaaga gatggagggt ttggttaaga aaggcaaaga aaaaatcgaa aacctcacca 900
aagcttctgc tactttgaac aataacatgg aagaactttc ccaccagcgc tccaccgcta 960
gagatcttat caatgaatca tatcagagtt acaaggctgt tcttgagaaa tgtaaggatg 1020
atattttaga agagctgact ggattgtatc atgaacgtga gctagtcctc atgcaagaga 1080
gtaatgagtt gggcaatacc attgttaact tagaagatgc ctgtaaatgc acttccagct 1140
tattggaagg cggtactgca caagagatga tgtatttaag aacagcactt gctactaggt 1200
tgatgacttt aaaccacaaa tcacccaaac tggaaaaatc attcagtatt gagttcaaat 1260
ctgacttgga taagtttgaa tatgctatca ggagtaattt cggaaagttt gctacagagg 1320
aagatgtcat cgtgaaaaca tcacagtctt ctccagtttt acctgaattg gctcccttga 1380
acatcaacgg gatcaatgga atcaacaact caccacctgc tatcgtcaca aacggttgta 1440
gcgcaccttc ggtaacaaca accagtccaa tttctttacc cacatccatg caatcttcat 1500
tcgacgggga acttggaaac aatttacaaa tgttgatggc tcagagtcct cccttacccc 1560

```
acgtcaattc aaaccaaggg ttttcccaag ggtttttctag tattgccgag tacaatatag   1620

cacaactagc cactttagca gaaaacacaa acagtgctgc cacgtcacca actacagctc   1680

cgttcaatat tgccgatatt ttgaacaatg atactgcctt caagaatatt gcaacgttag   1740

ttaagctggc aggaaccaat actactccgt cgattcctag atccaacaaa gttagtccta   1800

tgcagatccg ctgcaagttt ggccagttgg gacccggcaa ggggcagttc aattctccac   1860

atggattttg cttgggattg gaagaggaca ttatcgttgc cgatacaaat aatcatagaa   1920

ttcagatctt tgaaaaaacc ggaacattca agtttcaatt tggcatccca ggtaaagacg   1980

aaggtcagct gtggtatccc aggaaagtag cagttatgcg caataccggc aaatacgtcg   2040

tatgcgatcg tggcaacgaa cgctccagga tgcagatctt cactaaaaac ggccatttct   2100

tgaaaaagat agctatacgt tacatcgaca tagtcgctgg cctagcagtc actgtcaatg   2160

gtgagattgt cgccgttgac agcgtcagtc cgacagtatt catcataggg gagagtggag   2220

atctgctgcg ttggttcgat tgcagtgatt atatgagaga gccatccgat atcgctattc   2280

atgggaagga attttacgtt tgtgacttca aagggcacaa cgtggtagta tttaacgacg   2340

acgggcaatt tttgcgtaga atcggatgtg agaacctaac caactttccc aacggaattg   2400

atatatcaga tgcaggagac gtattgattg gagattccca tggaaatcga ttccacgttg   2460

cagtcttttc acgcgatggg ggcttgattt cggaattcga atgtccatat gtaaaggtct   2520

ccagatgttg tggattgaaa atcacatccg aaggttacgt agtaaccctc gccaaaaaca   2580

atcatcatgt tctggtattg aatacgttat acatcctgta aaccccgaat aatatagcgt   2640

cgtcgacgaa tattttgacc ttagtccctc ttcccgacca actgtttcat gaatatgttg   2700

tgttagttga catcctctga cacatgttgt gttagttgac aaccctgaca cattctcacc   2760

cgaccctcgc ctgttgagct gtggcattta acaatttttg ataaaaatat ttttatgtat   2820

ttaatcttca cagttcgtac ccagaaatag actaagaact ccccgtaaaa atatgagtag   2880

ataaggtatc ggtacgacac aaatcaaaat gtgcgtagaa gaaagttaac attgtgttga   2940

aacttacgct ggtcacggct tttgttacca gctgctcaaa taattatgct tatattcgta   3000

ttaacgttta cactgttctt taaaaactat ttaaacattg atataaggtt tgttccaaca   3060

gaacgaggaa ccgtcatgta acgattatgc tcatgcgcag taagcaaaat atcccattgg   3120

aacgtattat tttgtttact gcgcagtaaa gcgtcattgt cacatgacga tttttcgttg   3180

tgttggaaca aa                                                        3192
```

<210> SEQ ID NO 134
<211> LENGTH: 1578
<212> TYPE: DNA
<213> ORGANISM: Diabrotica virgifera

<400> SEQUENCE: 134

```
tatttttaaa cacagatttg aaatgtggga ctcttttact attgatgatt gtcaaacatg     60

tccgtataat agcactacaa atatatatga ccaaatggaa gttccacact tggacaagga    120

aaatattcag ccgttcaatc acataaaaaa tgacgagctg tctctatacg acaatggagg    180

cagtatcaca aaataccgcg aagcaccttt gtctcatact caccgacccc tagaagaaca    240

cgactcaaat tcgcaagatt ctggctacag tgcaagctac catggagaaa aatttttgtc    300

ttatgcctct ccagtacgaa ctgcaagcac atcctttggc tctatggtct ctatggaaga    360

tgaatatttt gatttctctg atgttgaacc tttggagaaa ccaaacttac ctcacgattt    420

caataagctc ataacaaatc ctttgattaa cagaactaaa cctgaagtag tctcatctcc    480
```

-continued

```
aaaagacact atcataagac cacttttcag aagggcttta tcacttcagc ctatcagtga    540

gaacacacct aatagtagaa gggtccgaac aagtttattt agaggtgaac atgaaatcag    600

atcatttaaa agacctgaac ctccgaatga tctagacagt acaattgtga aaaggtcaaa    660

gatatttaac gataatgatg atagtgattg tgaagcttca gttcctgtag ccaggaccag    720

acctatacta caacgcgcat tctctgctac agaagacagt attatgtgcg cagtgcaaag    780

atctgcaatt gaacctgacc ttattggaga ttttacaaag aacttcagtc ttccgttaac    840

aatcagtcga caccaagatt taaaagccat cacggcagat acactagctt cactgatgag    900

gggagagttt agtgatgctg tggattctta caaagtcatt gactgcaggt atccttacga    960

gtttgatggg ggccacatta acgatgcact taacttctac accaaagagc aatgcatgca   1020

actactaaac tcaacacctg atgttgctga aggttcccac gcaagacata tattggtttt   1080

ccattgcgag ttctccagcg aacgtggccc taatctatac cgatttttgc ggaaagaaga   1140

tagaaacaaa aacgaaagtg tatatccttc tcttaacttt ccagaaatct acctcctgga   1200

aggtggatat aagaagttct ttgagactca tccagagttc tgcactccag ttgcatacaa   1260

agaaatgctg catcctgatc acgaagatga atataggcac tttcgatcca aatcaaaaac   1320

gtggaactgt gattcacgcc aacgtctatt gaagaaaagg ttaggtgtgt aaaacttgtt   1380

taggatgcca tataacttta tagtacaaat aattagctta tctatttggt tcagttcata   1440

gtacctgttg tcaaaaacac gagatatatt attttaatca ttcagacagt tcatgtctga   1500

tgaaccaaaa tctccacacc acttagtggt ctaggtgaag tgccttttac tattatttgt   1560

tgcctgatac cagaagaa                                                 1578
```

<210> SEQ ID NO 135
<211> LENGTH: 2465
<212> TYPE: DNA
<213> ORGANISM: Diabrotica virgifera

<400> SEQUENCE: 135

```
cgtttagtag tacatagaga aatcgctttt agttttaatc ttttctgtgt tggaatattg     60

aacaaattct aatgattcgt aaaataacac ttctgttaaa aaccaaaact gatagtttgt    120

tcaaaaaaag tacaattttt ctgggcttgc tactgaaata atgtgccata ctctaattgt    180

ggaacaaatt gtaggtatat gttgaaagtg aacaaataac taatgcttac aataatgtcg    240

acatcaagtc aaaataatgg taaaaagagt tcaagcagct ctattgttaa cacccccttcc    300

agtactccca ttaccaatct tgcaaatggt agtagtagta cccaaggaac agcacatagt    360

tcacctccac ctaataacaa tgctccaaag tatggtaccc tagtgcctaa cagaatattc    420

gtgggaggaa tatcagctaa cacaacagaa ggagaattga tgcaactttt tagcaactat    480

ggtactgtta aagctgctaa aattatacag gacagggctg gtgtgtcaaa aggatatggt    540

ttcatcacct ttgagagtga agatgatgct aaaaggcctc ttagagaagc tgaaaacata    600

gtgctaagag aaagaaaact taatatagca cccgctatta aaaaacagcc ttttagtcga    660

gcatttgatg catccagtcc acctgctgtt gctgcaaata gtgccagtca attctttttt    720

cctccgggtg ctgccgtgcc atattttcag agtggagtta catattatac tcagccagct    780

cctgctgcac ctggagatcc cactgctcaa caacctgttt atcaaccccc tccaatgtat    840

cccacgcaaa ctggtcctcc acaggcagct acataccctt ctatgatgtt tcctgctcaa    900

actatatata tgccgcaaca gtatcccatg cctattccgt acgagtacaa cttctaccag    960
```

```
ggtaacggac cgtcgctgcc aactcagtat ctggccggag gccaaagcgg tccgggaaac    1020

tctcattgca cctcattacc atcatcaaac agtccaccca gacccaattg ttatggtcaa    1080

caggtgcctg cctataattc aggagatccc gtgtactaca acttgccaat atacggagcc    1140

actttggaag gtccgccatt atacgctgat gccttcgatc taagcgctag tggagcttat    1200

gcggaggaaa cctacagcgg catgattact caagaaaatg tagaagcttc tcttggatca    1260

tcggtaaatt caactcgtgc aacttccgat aattttacgc aacatatgga tcaatctctc    1320

gttgagtctg attcaaatat tgttaatgtt ggaggtaaac caccagcaca taaatcttca    1380

gagacaattg tttctactcc ttcccagcct caggaggaga gaaactcaca cacgcctatt    1440

gtttcactac tttccataga tcatcaacag gaaaaagact attcatcaat gcaaagcggt    1500

cgtagacgga aacttctgat tcaaagcaat caaaataacg tacccatgta tcctacaaac    1560

ggatacgtca accagtttgt cggatataat cctcaacaac catccccacc ttcattcggt    1620

ccacctctct ataacaacgg ctacggttat tctgaatatc gtcgatttaa cggataccca    1680

gatctcaggt caaataataa tagtaataaa ccgaggagac gaatatacga aaataggcgg    1740

tcgaacgatc attctagccg ttccagtctt cgcacagact caaactcatc ggctagttgt    1800

gttgacgaaa ataaaaacga agaaaaaact tttcgaacta ctgttaacac tcctccacct    1860

gccccatact cacctatgac caatcatcaa ttcaaattta ttaattacac taacacgaaa    1920

aacgtttata atcataagta cgctcacacg tttataatca taagtacgct aacaacaata    1980

attattataa tagaacagct acacacaatg accgatttaa acataccgaa cctttagcga    2040

ataaaaacaa taacagttcc atttacccat taacaaataa tttcctaaat aatagccata    2100

cccaaagtaa ttctgattcc cttccctccc aaaattccca ggtacatgtg acgactacgg    2160

gtcagagctt cgtcccggcg gctatccaag ctcagacgaa acgcaacaag cgttctttga    2220

gaagaagcgg tgccagtgcc ggaggcatca acgaaatcgg cgccggtgac gccccttttac   2280

caggcgaaga atgcgaagat gtctacaaga agctggaaac gcttaagttg taacgaaaaa    2340

gtggtatctt tcttgtata tttttttcta tttatttaag actgtacaat aatgtaaaat    2400

actagaaatt taatgtaaac taaagaggaa aaatatataa tacatattta ttgaagatga    2460

aaaaa                                                                2465
```

<210> SEQ ID NO 136
<211> LENGTH: 275
<212> TYPE: DNA
<213> ORGANISM: Diabrotica virgifera

<400> SEQUENCE: 136

```
caaggtggaa ttttaaggtt ataccgcaca cctggttgta cagcagcaaa aaagtttgaa    60

attgtccaga aacttcagca aacatgtaaa aatctaaagg atattcaaac cgaaatatgt    120

tttcatatcg aatcaacaag tgccttggaa gcaaaagacg ttaagatttt gaaatgggtt    180

cttcaagatc ctctccatcc ccaaaattta agcgaaaagg gaacgctggt agcgaaaaat    240

ggtacggctt tggttgaggt aggacctaga tttaa                                275
```

<210> SEQ ID NO 137
<211> LENGTH: 275
<212> TYPE: DNA
<213> ORGANISM: Diabrotica virgifera

<400> SEQUENCE: 137

```
atggtggatt ctttaaagtc cattttcgac gaaactcctg aagatgaaag tctctcccaa    60
```

-continued

```
aagattttac aatcagtggc tattgaggtc agttcggcag acaaattatc caccaagatc    120

tgcaaagagt gcgtagaaaa agtaactgac tggtcttcgt acaaagaacg atgtctccaa    180

aaccaaaaga aattaacgga gttgttagtt gcgaaagaag gtccagaagt tttggttgta    240

cctgaaatta tacccgaacc cgaagcacca cttcc                               275
```

<210> SEQ ID NO 138
<211> LENGTH: 275
<212> TYPE: DNA
<213> ORGANISM: Diabrotica virgifera

<400> SEQUENCE: 138

```
aatgatcctg aatacgactt catatctgga ttcgttcatt tttgtggaca ggctggacta     60

gttggtatac aaatattgtg gacaaaagaa tccgaaattg ctattaagaa agcaagagta    120

gatagaatgg ctatgaaaat tacaaataaa cgatttctcg acctcttaaa tgctctcatt    180

gatcttacat caaaagattt aacaaaaatg caaagaataa gatttgaaac catggttact    240

atccacgttc atcaacgaga cattttcgac aacat                               275
```

<210> SEQ ID NO 139
<211> LENGTH: 275
<212> TYPE: DNA
<213> ORGANISM: Diabrotica virgifera

<400> SEQUENCE: 139

```
tggctcctcc accatacgca gacctcggca aaagagcaag agacgtattc ggcaacggtt     60

atcactttgg cctaattaaa ttaaattgca aaaccaaaac agccagtggg gtccaattta    120

gtacaggtgg tagttcagac catgaatctg gaaaagtgtc tggatctttg gagagcaaat    180

acaccgtcaa agattatgga ttgactttca cagaaaaatg gaatacaaat aatactttgg    240

ggactgagat cgccatttca gaccaaggta ttaag                               275
```

<210> SEQ ID NO 140
<211> LENGTH: 280
<212> TYPE: DNA
<213> ORGANISM: Diabrotica virgifera

<400> SEQUENCE: 140

```
tgggcaaaaa gaaggtagaa gagagtgaaa gtgaagagga gtattctgta gagaaaatta     60

ttgataggag agttgtagat ggaaaagtag aatattatct aaaatggaaa ggatattcag    120

aagatgataa cacttgggaa cctgaggaca atctagattg tcctgaactt atttctgagt    180

ttgagaggaa tcgtaaaagt aagaaggctg ctggcaaaga aaagaaaaga acaagagata    240

attctacatc ttccgtggat tcaaacaatt catccactaa                          280
```

<210> SEQ ID NO 141
<211> LENGTH: 275
<212> TYPE: DNA
<213> ORGANISM: Diabrotica virgifera

<400> SEQUENCE: 141

```
tgagttttat aattattgct tttaaaaatt tcctacatac catgttgcag ttattatctt     60

ttggtaaaaa aactattaca aatagtttga gtgtgtatgt aaaaactatt ggtggcaaca    120

ctttaactgt agatctagat cctacatggg acattaaaaa tgttaaggaa atagtggcac    180

cacaacttgg attagaacca gatgaagtaa agatcatttt tgctggaaag gaattgggag    240
```

acgaaattaa aattgaggaa tgtgatttag gtcag 275

<210> SEQ ID NO 142
<211> LENGTH: 275
<212> TYPE: DNA
<213> ORGANISM: Diabrotica virgifera

<400> SEQUENCE: 142
tgaagggaga aaatttaccc caacagaacc cagtgccttc aggaaatgaa aaagatgtca 60
gtaacaaaca ggaatcgtct aaaaatcgat cggatttatc agtcagcatt tacgaacaat 120
taacactacc attaagagat ggccgctcag tatctctcga tactggcgct agcggttcct 180
caactgtacc cgaagtgaca cctggtagcg atccttcatc agaaattaat cgtttgtttt 240
taaaggcaaa cacagaaagt ttacaatcgt taagg 275

<210> SEQ ID NO 143
<211> LENGTH: 271
<212> TYPE: DNA
<213> ORGANISM: Diabrotica virgifera

<400> SEQUENCE: 143
atggaactgc caaaaggttt aaaaccagtg ggacctaatg taactgaaga caccattatc 60
cagagtgttg ctacagcact ccatgtttct tctcaaccag tgacaggcca gacaagtaca 120
aaaacactac ttgaaaaaaa tccaggagta tttctcgatc ccaaacaacc attagtacac 180
gctgtaaata tatcagagga tgatatcaaa cgtcaagagg agagagttgc attagcgagg 240
aagaagttac aagaggctct aaagggcaac c 271

<210> SEQ ID NO 144
<211> LENGTH: 275
<212> TYPE: DNA
<213> ORGANISM: Diabrotica virgifera

<400> SEQUENCE: 144
atggttcgtc atggagaatc agaatggaat gaaaagaatc tattttgtgg ctggtttgat 60
gcaaatttaa gtgaaaaagg taaacaagaa gccattaatg ccggaaaagc actaaaaaat 120
gcaggataca aatttgacat tgcatataca tctgtcctta caagagctca gaacacactt 180
aattcaataa tcaaagaaat tggccaagag aatttggaaa ctataaaaac ttggagactc 240
aatgaaagac attatggtgg cctcactggc ttaaa 275

<210> SEQ ID NO 145
<211> LENGTH: 269
<212> TYPE: DNA
<213> ORGANISM: Diabrotica virgifera

<400> SEQUENCE: 145
tgaatggtgg aggacctaca gcgcaaatcg tagaaagaga ggggtggaaa catgataaag 60
attttgttgg acacaggaaa gctgtcactt gtgtgaggtt caactccaac attctccaaa 120
aacaagaaaa gaacaactct aaacccactc aatattgttg ttgtgccatt ggatcaaggg 180
acagatctat cagtgtttgg ttaacttcat taaaaagacc tcgtgtggtc ataaaagact 240
tatttaataa tagtgtatta gatatgtca 269

<210> SEQ ID NO 146
<211> LENGTH: 269
<212> TYPE: DNA
<213> ORGANISM: Diabrotica virgifera

<400> SEQUENCE: 146
tgggatttaa agataaccag atcgtttata tatcgatagg catgtcgagg aatatgaaga 60
aacgggagtt tatggatgca ccatctttac acccgcctcc tcctcgggaa tgtttaccaa 120
cattacttct tctacagcca aattactttg agcagctatt ttccttaatg cacacactta 180
gttcaatgaa aattcaaatt aaaggagggt gccaattacc acatacaaga gcccaagttc 240
tcagcagaag agtatgggat attcttagc 269

<210> SEQ ID NO 147
<211> LENGTH: 270
<212> TYPE: DNA
<213> ORGANISM: Diabrotica virgifera

<400> SEQUENCE: 147
tgaaggtttt accatcgcct actagaacag ctttacccaa atgcgaactg tgggatccag 60
aaactatgac cagtgcactc gatgtcgtaa ttagagcagc aaaacactcg tatcccgagc 120
cagtaatgtt agtgagaggt tttagccagc cagtcaaagt tagttttgtg tatagttgta 180
accgattcta tgttcagtta gtaaaaaaag aacaggaact aacaactctt atggaagagc 240
ttcaaagttt atgtctagaa agtgctttta 270

<210> SEQ ID NO 148
<211> LENGTH: 273
<212> TYPE: DNA
<213> ORGANISM: Diabrotica virgifera

<400> SEQUENCE: 148
tgtcgagcgc cgataacgtt accagacgtt cggcgtatct agttgtcctg aaaatatgta 60
aattgatact gacatctgtc gcgcacgtcc tggtaagact gagtgaagat cacactcctc 120
cagaaaatga ggctttcaac gaaaatacca ctccaccggg aaccttttg agacaggcat 180 tacgaaatgt tcctggacac tcggatcatt tactgcgaca agtttccatg aaactagctc 240
aaggtttagc gcaattgatg gtatccgaaa cgg 273

<210> SEQ ID NO 149
<211> LENGTH: 275
<212> TYPE: DNA
<213> ORGANISM: Diabrotica virgifera

<400> SEQUENCE: 149
tgtttgaagc tcaagaaatt cacgcagaac ataaagatct cattcacgat gtcgcttatg 60
attattatgg gaggagaatg gccacctgtt caagtgatca atttgtgaag gtttgggatc 120
aaacatctga tggaaagtgg gtgttaacat caagttggaa agcacacagt ggatctgtat 180
ggaaagtaac ttgggcccat cctgaatttg ggcaagtttt agccacttgc tcctttgaca 240
gaacagcagc tgtttgggaa gaaatagttg gagaa 275

<210> SEQ ID NO 150
<211> LENGTH: 275
<212> TYPE: DNA
<213> ORGANISM: Diabrotica virgifera

<400> SEQUENCE: 150
tgagtgaaaa gagcgtggga accatgcagg gggtttcggg cgaacgccgg ttgcgccaac 60
tggaaatgtt gtttcttggc gggcctgtgc tagccaaaga acaaagtttt agtatcgaaa 120

-continued

```
ccctcataga tatattactt gttctctacg atgaatgttg caattcgagt ttaaggaaag    180

aaaaaacagt ttcagatttt atagaacaag ttaagcctgt agccagcaca gtaaaatctt    240

taagattgac tcgtgaagat ttcgagataa tcaag                               275


<210> SEQ ID NO 151
<211> LENGTH: 271
<212> TYPE: DNA
<213> ORGANISM: Diabrotica virgifera

<400> SEQUENCE: 151

tgggatatgg caagggagaa aagattctta gatgtaaatt ggcctgcctc tacaggttga     60

tcgacttgta cggctgggcc tacggctcaa gtacactcat aactgccagg ttgaaccagg    120

atgacgaaca attcttggtc aacccttacg gaatgctctt ccacgaagtg acagcttcca    180

gtctgattaa agtagacatg cagggcgcgg tcctcgaaca aggcacaacc aacttctccg    240

tcaacattac cgcatattca ctccacgcag c                                   271


<210> SEQ ID NO 152
<211> LENGTH: 274
<212> TYPE: DNA
<213> ORGANISM: Diabrotica virgifera

<400> SEQUENCE: 152

tggaaaataa actaaagaaa tacgaaaaaa ttaaattttt aggagaaggg caatttgcaa     60

cagtatatca agctcgagat gtagacacgg acaatatagt ggctgtgaaa aaaattaaaa    120

taggtagtcg acaagaggcc caagatggaa tcaatagaac ggctcttaga gaaattaaac    180

tactccaaga actgcatcat acgaatataa tcggtcttct agatgttttt ggacatatgt    240

ccaatgtgtc attagttttc gattttatgg atac                                274


<210> SEQ ID NO 153
<211> LENGTH: 275
<212> TYPE: DNA
<213> ORGANISM: Diabrotica virgifera

<400> SEQUENCE: 153

tgctctgtta tactcaagag gatgctaacg cagaaggcaa cgaggaaaac gttctatcgt     60

acgaaccagt ccaacagttg catattaatt atacgagacc tgttattgta ctgggtcctc    120

taaaggatcg tatcaatgat gacttgatat ctgagtttcc tgacaagttc ggaagttgtg    180

taccacatac cacaagacct aaaagggaat atgaagtcga cggtagagac taccacttcg    240

tcgcatccag ggaacaaatg gaaagagata ttcaa                               275


<210> SEQ ID NO 154
<211> LENGTH: 274
<212> TYPE: DNA
<213> ORGANISM: Diabrotica virgifera

<400> SEQUENCE: 154

tgcagatggc tacctttgga atcgagactc cttctgattc agaggaggaa atagatgttg     60

tcaatgtcaa caacgagaag ttcccgttca ataaaacggc ggtgttttcg ttccccaata    120

atccatcgac gaaagatcgc caacagatcc agatgcgtat ggcaactgct atatccaaga    180

agcgaataca agcccaagct caaggcatca agactatcat gcccgttagg aaaacagcca    240

caccggaggc gtcacctatc aaaaggaaac ccgt                                274
```

<210> SEQ ID NO 155
<211> LENGTH: 272
<212> TYPE: DNA
<213> ORGANISM: Diabrotica virgifera

<400> SEQUENCE: 155
tggaacaaac tcctattccg gttgtgaatg gaatcaatag agaaatgtta gacttttgta 60
attattcaat taaacgagtt cctatggaag gcgttgatat gaatctcgat ccagactatc 120
tgtgcggctg tgattgcgat gacgattgca ttgataagac gaagtgcgct tgctggaagc 180
tcactttaga gggagcaaag tataccggaa aagatgtaaa tcctacatcg gtcggatata 240
tttatcgaag gttgcccgaa caagttatta ca 272

<210> SEQ ID NO 156
<211> LENGTH: 272
<212> TYPE: DNA
<213> ORGANISM: Diabrotica virgifera

<400> SEQUENCE: 156
tgtggcaaac gcaggcagtc catattacca caaacaataa ggagaaccac tttcaaaaaa 60
gtgaagataa gttaactctt ggaatgactt ctgctatatc aacagcagaa ccaaaaccag 120
ttgatttggt aaaaacaagg gaattaatag aggctctgaa accttttgat gtattcgaaa 180
gtgaacaaga attaaacaag aggatgcaca ttttagggaa actgtttagt ctagttaaac 240
aatggataaa ggaggtttca ctttcaaaaa at 272

<210> SEQ ID NO 157
<211> LENGTH: 270
<212> TYPE: DNA
<213> ORGANISM: Diabrotica virgifera

<400> SEQUENCE: 157
tgaggataga tcaactattt aatatcatta tagaataccc agaatctcta ccggctttag 60
aagacctacg aatatgtctt cctagaacag atctaaagcc tatgctaact aagaaactac 120
aaaaagcaat ggaaacacga ttactacacc ctggtgtaag tacacctgat gttctaacag 180
cttacgttgc tgccattagg tctttaaggg tgcttgatcc tacaggacta ttgctcgaaa 240
ctgtcacgca accggttcat gaatacttga 270

<210> SEQ ID NO 158
<211> LENGTH: 275
<212> TYPE: DNA
<213> ORGANISM: Diabrotica virgifera

<400> SEQUENCE: 158
tggttttaaa taacgttaaa gaactaaccg aagaagaaaa attcgatatt cagctgcaag 60
ctgagcagga actgggcaga ctagtcagaa cttatacgat cctagaaaga aaccgagccc 120
aaaaatgtga tacaggtggt aaacttctca aacaacgaaa agtgctggac attttcaaga 180
aggaacaaaa aaatattctc acggatcttg ctgtagcgtc tgccgatgct agaagagtgg 240
aggacgaaaa gaagtccaag gaattgaagg attta 275

<210> SEQ ID NO 159
<211> LENGTH: 274
<212> TYPE: DNA
<213> ORGANISM: Diabrotica virgifera

<400> SEQUENCE: 159
tggctagata cgatttgaca ttgaatccca tggaagaaac caggtttctt aaaaaacata 60
gagtactggc tttaagtttg gcaagacagg tccattttag ctttcaggag gttgaagcca 120
ttctcattat atattacaag atacaaaaat acgacactta cgatccaaaa ggtattacga 180
gagacgttct gatggaagtt ttccattgct gtttagatat gacggatatg gaaaaagtga 240
ttcgaataat aacttgccta gacgagaaag ctcg 274

<210> SEQ ID NO 160
<211> LENGTH: 274
<212> TYPE: DNA
<213> ORGANISM: Diabrotica virgifera

<400> SEQUENCE: 160
tggtaaccga gtatgtaatg gatatcttca aatatcttag agacatggaa ttgaaattag 60
ctatcaaaga taacttcctc aaagaccacg aaactacttc caggatgcgt gcaatactcg 120
ttaattggtt agtcgacgta cacgcaaact ttaaagccac gcttgatact ttgcatatat 180
gcattggaat cgtggataga tatttacagg cgaacaaaaa agtaggaaga aatacgcttc 240
agttagtagg ggcctcagca atgttgatag catg 274

<210> SEQ ID NO 161
<211> LENGTH: 272
<212> TYPE: DNA
<213> ORGANISM: Diabrotica virgifera

<400> SEQUENCE: 161
tgaatcaaac gtgtaaagtg tgtggagaac cagcagctgg tttccatttt ggtgctttta 60
cctgtgaagg atgcaagtca ttcttcggac gctcctacaa caacctaagc tcaatatcag 120
aatgcaagaa caacggcgaa tgtgtcatca acaagaagaa ccgcacagct tgcaaagcat 180
gtcggcttcg gaaatgtctt ttagtgggta tgtccaagag cgggtcccga tacggtagac 240
ggtccaattg gttcaagatt cattgcttac tg 272

<210> SEQ ID NO 162
<211> LENGTH: 271
<212> TYPE: DNA
<213> ORGANISM: Diabrotica virgifera

<400> SEQUENCE: 162
tggctcagag tcctccctta ccccacgtca attcaaacca agggttttcc caagggtttt 60
ctagtattgc cgagtacaat atagcacaac tagccacttt agcagaaaac acaaacagtg 120
ctgccacgtc accaactaca gctccgttca atattgccga tattttgaac aatgatactg 180
ccttcaagaa tattgcaacg ttagttaagc tggcaggaac caatactact ccgtcgattc 240
ctagatccaa caaagttagt cctatgcaga t 271

<210> SEQ ID NO 163
<211> LENGTH: 272
<212> TYPE: DNA
<213> ORGANISM: Diabrotica virgifera

<400> SEQUENCE: 163
tgtgggactc ttttactatt gatgattgtc aaacatgtcc gtataatagc actacaaata 60
tatatgacca aatggaagtt ccacacttgg acaaggaaaa tattcagccg ttcaatcaca 120
taaaaaatga cgagctgtct ctatacgaca atggaggcag tatcacaaaa taccgcgaag 180
cacctttgtc tcatactcac cgacccctag aagaacacga ctcaaattcg caagattctg 240
gctacagtgc aagctaccat ggagaaaaat tt 272

<210> SEQ ID NO 164
<211> LENGTH: 155
<212> TYPE: DNA
<213> ORGANISM: Diabrotica virgifera

<400> SEQUENCE: 164
gctccaaagt atggtaccct agtgcctaac agaatattcg tgggaggaat atcagctaac 60
acaacagaag gagaattgat gcaacttttt agcaactatg gtactgttaa agctgctaaa 120
attatacagg acagggctgg tgtgtcaaaa ggata 155

<210> SEQ ID NO 165
<211> LENGTH: 1624
<212> TYPE: DNA
<213> ORGANISM: Diabrotica virgifera

<400> SEQUENCE: 165
ggggagtagt acgtagtacg gccggttcta aggtaggcgg ttcgttgtgg tcgtgtggta 60
gtatgccaac cggttggaga aaaatctgtt tttcaccctt tagttctcaa tagaatgaaa 120
tcgtgagttc tgtgacaaat ttcaacaaaa atcgtttata aaaccatcaa agtggcggcc 180
aatacaggat ctcgcacctc caaggataat atgctcaaat ttctcaccca caaattaaga 240
actcattcta taaatgagga taactatgca gggaaggccg atgaagacca tgattctggt 300
acggaatcag atgaagagat tgatgctcca gtatcaggat cagcatcctg ttcagaacgc 360
gtttgtaacg tatcaccggc agacacagga tgttcgatgg aaagtccagc tcctgatcaa 420
cacgatgctc acagctccga agaagagttg gaagttatca atagcaatag taaaatgagg 480
cgatcaacgg cacctcccag gccgctgagg gctgcgtcag tttgtctagc tgaaaaacga 540
aagtggtctc aaattggaga cgcgcagaat cgaaggtata cacccgaaaa cgaagagaac 600
atgtcccact atagtaatct atctccgtct ccttgttcgc cgttccatat aaaatgttgt 660
agcgaagatg gtggacacca tattgaacat tccggctcgt cggatgatga ggtgcaccac 720
ttcttgtaca cacgggctac tcctgtacag ttccgcactt ctcctccttt agaagcggta 780
aaacctgaac gaagatcaat tgtaacgagc aagggtcggt cgacgagccc gcctgccaaa 840
ctacttcact acgaagattc cccaagaaaa agaaccaagc acatgaaaca tgcacatatc 900
cagaggccat accttgattt ttgaaaaaat gcaacagatg aaaacgaggt cagtaacggc 960
ctggcgccac accgctgacc acacaggaga gctgtccgtt tactgttggt gagatcagct 1020
taaggggcgg actccgtcgc cctccgactt aagtaatcac cccatggagg gctgcagttc 1080
gtcatcctca tcatggcctg ataatccttc atagtctaca aaataactct aaccgaaact 1140
aaaactacta aagaattgct gcatagaagc actgaattgg tacacgtggt ttttggaccg 1200
acggttttgg atttgggtag ttggcgtaga ctggaatact tcaaatggaa tagacgtgcg 1260
ttgaagatct tgcgtcgaaa gcatttcgca gactatatag ttttgtaatt ttatatggac 1320
tcattaattg caataaatat tttccactca aatttgaagg cagaatacag gaatggtact 1380
aaaacgggta caactcttaa gatttcttaa ttaactcaac aagatgttcc taaatactcg 1440
gctagaaatc aagtgaatat aggtacgctg aatattgttt gaacccaaca gtaatgcccg 1500
gtttcacaaa cagctgttaa ttgccttatt cattatgaaa gttaactgtg acagctatta 1560
ttaaaggtca tataaatata ttgtatgacc aaaattccgc agaattttgt agtcaatcgg 1620
tata 1624

<210> SEQ ID NO 166
<211> LENGTH: 1348
<212> TYPE: DNA
<213> ORGANISM: Diabrotica virgifera

<400> SEQUENCE: 166
aaagaataca aagagaatga tagtttgaac atttctgaca atgaaaacat aagagaagga 60
gttactttgg aatggtttaa taagaattta aatgacaccc agaaaaatgc tgtaatgcag 120
gttctttggg gtactgctag acctcttcca tatattattt ttggacctcc aggtactgga 180
aaaacaatta ctcttgttga aacaatttta cagttaacac gattaattcc ttcatctaga 240
ttattagtaa ctgcaccatc caatagtgca gcaaatttaa tagctctgag acttattgat 300
tcaggagtac ttttaccagg agatcttgtt agattaattt catataatta tgctttaaaa 360
gaaactattc ctgataagtt attaccctat tgtgccactg caggcttggc tagagaagat 420
actgttgttt cagaagtaaa taacccaaat ggaatacaat ttggtagcaa tatgtctact 480
ttaggccgaa gtagaataac tgttgcaacc tgtagttgtg caggaacgtt tttccagttg 540
agcattccca gaggtcattt tactcatata gttgtgacga agcagcacaa gctggagaac 600
ctcatgttat gattccttta tcttttgtaa ataaaaattc tggccaaatt atattagcag 660
gtgatcctat gcagctaggg cctgttatat tatctaaagt tgctaccgaa tgtggactag 720
cagagtctta tttggaacga attatgagca gatttccata ttgtcgtgat ccagaaggat 780
ttccagaaac gtctggattt gatccaagat ttgtaacgaa attattatat aattacagag 840
cccttccgga cattcttact ttgtacagta cactctttta tcataatgag ttgataccga 900
ctattgacga tgaaactagc aatgaagcaa aactgctaac ttctcttcaa gatttcttac 960
cagtcaaacg tgataagcta acccgaatac tatttcatgg agtaattggt gaaaactatc 1020
aaacagcaga ttctccatct tggtataatc cccaggaagt agcccaagtg ttttattatg 1080
ttaatcagtt ttacaggctt ggagtaaaat ctggtggtat aggtattgtc accccttata 1140
ttaaacaggc taaagaatta cgaacagttt tcacggaagc agaatttgaa gtaccaaaaa 1200
tcgggactat agaagaattt caaggtcaag aattcgacat cgtcattata tccacggtac 1260
gttcatctaa agattttatc aaatcggatc ttacttacca cttgggcttc gttgcacacc 1320
ccaaaagatt gaacgttgcg atttcgag 1348

<210> SEQ ID NO 167
<211> LENGTH: 6699
<212> TYPE: DNA
<213> ORGANISM: Diabrotica virgifera

<400> SEQUENCE: 167
gttagattct ttgacaggtc taattgatta tcgagtgctt tctttgaaaa gctcgacatg 60
gagtcccaaa acatgaccat gatgcactcg gccggaccga ttcagccccc accaagggaa 120
ggggcggccc ccatcccaac agaaggggta accgcaaggg gcacggacca cttcacggaa 180
atctaccgac agagaggtta tccttggggg aagaagccaa attgctctac tctcaagaaa 240
tggcctccat gccgagcaag actcccgtca gcgtcctcca ggagttgctg agccgtcgcg 300
gcatcactcc caaatacgaa ctggtccaaa tcgagggcgc catccacgag ccaatcttcc 360
gctaccgcgt gttccttaac aacgatctgg tggccaccgg aaccggaaga tcgaagaaag 420
acgccaaaca ttcggcagcc aagaacttgc tggatctctt ggtcggaaaa gtgactcccg 480

-continued

```
aacaagccaa tcagaccaac ggaacgcccg gagcggctga tatcaccaat caggtggtga    540
catcgttcga tgacaaagtg atgggcaatc ccattggctg gctccaagag atgtgcatgt    600
cccgcagatg gccaccacca ttctatgaaa tggaacacga agagggacta ccacacgaaa    660
ggcagttcac catcgcttgt catgtgttga aattccgcga aattggcact ggcaagtcaa    720
agaagctagc caagagaatg gcggctcaca agatgtggca atccttgcag gatttacccg    780
tggagggtaa caatctgcct tctacatttg cgagtgacga agagactctc agcttcaacg    840
ccaaggactt caactttgtt cagttcttgc aggagatcgc tagcgaacaa tccttcgagg    900
taacctacgt ggacatcgaa gaaaaaacat tgaccaatcg ccaccaatgc ttggtgcagc    960
tatccacttt gccagtggcc gtctgctacg gaacaggcaa aactccgaag gaagccaagg   1020
gctcggctgc tcatcatgcc ctcgagtacc tcaaaatcat gaccaaaaag tgaacagcta   1080
tcgatacaca gtcatagatc caatcctata attatccatt tcctgtaatt ctggtttctc   1140
tatagttttg tcatacgttt ttgaggcagc aaatttctca agggcacacg gcaacaaaaa   1200
gtgataatgg atacaaattt gactactgta tagctttctt ctcttggtga acacatactt   1260
tattcgtcat cgctccccac gagcgtttct ttagtctgta tattttcttg tatcacttat   1320
tgcgtctttg ctttggtcac tttacgcgcg aaaaccatta tgttttacta atttttcaat   1380
aaagtacact ttatttaaga acaggggaga aaagtcacga gaatttgaaa agcgagcttc   1440
atgatcccct gaagaatata tcttgaagaa ctattatttt ttaatttttc atcacagtga   1500
tgtttgtttc agaacaaacc gggaaaagta ttatgagaat atgaaattta aaagaaaatt   1560
tgaaaagtat catgagtttt gtgattctcc gaagagtatg tctcgaaaga cttcgacttt   1620
ttactatttt tgtatgcaca aaattcgttc tacatatgaa acatgtcagt tatatattca   1680
cctttatatg tcacattttg tggttcttta acgaaatgtc aagagcataa agtatgtcta   1740
gaacgatttt acctttgcgc gaaaagtgac cacaagcaat gtcaaagaga aggatagcaa   1800
ctaattttac aagctatact ttgcatagaa ttagtggttt ttttctaaaa tcaatttaca   1860
tattattttt gacttgaata aatttttaaa tttaaaaatg cgtgtgtgca ggtatattta   1920
tcacatcatt cgtcgtgtac cacatctcgg atcttgctac taatattcga ttcgataggt   1980
gctttgtctg gttaacttta gtgggaaggt ttaggtattt gtggtatctg tcgatgttgc   2040
cagaacgtaa gatatcctaa actcactttt ttccgaaaaa atatcgcaat agctcaaaag   2100
ggaacaattt ttgtcgagtt attgatttcg aggaataata cgaacttcca tagattcaaa   2160
tgaagtaaac aacatacgtt tttcatttaa aatgaactca catatgcaat gcattcaaca   2220
ttccatagat tcagtgaaaa cacgccatcg ggttctattt tgcgcttagg ccttcacctc   2280
gtttcaaggc tatccttaac atcttatctc gtctatgata tatcttctcc aagtttgtgc   2340
tgggcaaatc aatcaatttg cctcgaaatc taaggttata ttacttttat gaatcgtgat   2400
aacatgcata aaatataata aaaatttata gtttttttgca tttttattcg gcttattgta   2460
atattcctcc atagttctta catccttgtt tatttccctt tttgtggaga ggtactatgt   2520
gtgtttggct agattctgtt tgacattcga aaagtaaacg tcagtttgcg tttcaatgca   2580
tcgataagac gaatggtaaa gctgctaaaa aagcaggaaa agcccagaag aacgttcgac   2640
tttcacttca ttctatcggc ctttcttctc tttgccgtat tttattttgt aaggtgaggt   2700
atttgtacat gaagttgtct gcccctttct taatcggttc tgcatgaatg ccatctgggc   2760
ccggggctct gtgatttctt agtgtcaata gtgctgccgt tacttcctca agcgctggta   2820
```

-continued

```
acgctttatc gggttctgct aagtggtaag tagaaggtaa gccacttaag cacacatgtt   2880
acataaatgt caaaatttcg caaatatata tcacataatt tgtttgtgga cataaaggaa   2940
agaaaaaaat gtcaaaattt tgcaaattat gtggcatttt gacatttatg tgacataatt   3000
tgcgacattt gacgtacggt tcaagtagct gaagtaaaag tgtgctccat tggtttatcc   3060
tctactgtac aactgtttac ctgtgtatga taaataaact tttttcgggt ttggaaaaat   3120
ttcaaattgt tcaggtaaaa tcttgcttca tgattgaaaa tttgcaaggt ttggaggagt   3180
tgtactaatt tgtgtaattg aagttcgtat tatttcctcg aaatcaataa tgcaatgtgt   3240
ttaaattttt gtcgagtcaa aagcgaagaa tatttgaaaa tttctaatat tgcgatattt   3300
ttttatcgat ctggcttcaa tgtttgaatg atgattatat aacgagtaga tagctttaga   3360
ggtaatacac tattattagg cactagttat taattataat catcaatatt atctatcgat   3420
actgaatgta attttttata tagtgccccg atgatatgat atgtatttat tatattgtga   3480
aaagggagca tttatttgat gcaaagtata gaggttgtac ccaaactttt cggggtgcaa   3540
tcttcttttc cggaaaatgc tcgaaaactc aattggcgca cattcagcag gtttttttaac   3600
agtttgaaaa ccttgataaa tggaacgaaa ttaaacacgc tgagaaagct atggttgagt   3660
gaaaaaggtg ggaaatgttg actgttgtag ctgattaagg ggtgtattct atatttcggt   3720
taaatttaag aggcttttaa aatttaacgt ttagcagtct tctttttaga ataacattga   3780
cattctataa agacgttaga gaggttcact aaaaaaatatt aggaatccac tacaaggttt   3840
tcaatagggc attctaacat gtcaaaatta aatcaatatg gcggctgacg ggcaaacaaa   3900
tgttatttgt cagttcttaa tatggtttta gattcgtttt tagttgcctt tctttgtaat   3960
tttgttttgt acaatgatta atttaacatt ttcagtggaa gaattaattt aaaaagataa   4020
tattcctcat ttctgttgtg ttttgaggtg tggaatgcga agtaattgtg atacaagttc   4080
agttttatca gttaccatga gtgcaaattt tgagtgaaat gagagaagaa cagtggttaa   4140
atgctataaa aggtcctata aaaatgctaa ataactacct gtgccatgct agtagtctac   4200
caacaacttt caaaaatatt cactcatgtt catttattca ccggttaaaa ctaaataaag   4260
tcgttcaagt aattctacaa ctaaaaactt cacaaaactg acaacaaaat gttcggaaaa   4320
tacaactaga aaactattaa aggtaaaaaa caaaatgtgg tacaaatata aacagagaca   4380
agttttgtat ttccgaccat attggtgtca ttaacgtcaa gtctcgaaat gccctgttag   4440
atacagcaaa ttgatcgtgt ttaaactact tgtaatgtag aagttgtcca aaaactgtca   4500
gaggccaaaa cacttaaaaa taagaaattg acatgaagtg aagacttctt ttttagctaa   4560
atctattgta agaaatcctt tcgcaaaaaa cgatcgcaga aacttttcca tccacatcgg   4620
ggcggatatc agagaataat aacttaaata gtagtagatt ttgcgttgtg gtgaaaaaaa   4680
aatagagatt ggaacacatt aaaaatattc ataaatctat tagagctaga aattttaagt   4740
gtaacacatg tggtaatttt ttaaaggaaa tcactctgga gcatcctagc gtgtgttcta   4800
cgatagttca tcatagtact ctcttttttt tgtaactcat tttcccatta accattttta   4860
tttatcaaac tatttaatca taaagttacg attttaaggg atatagaata caaaaatatt   4920
ttaacagacg gtaaaatttt agaggcctct taaatttaac gaaagtgtta cagaatacac   4980
ccctaaggca agattaaaaa acggcaacga aggaagagga aattgctgga aattttagta   5040
attctcacat tgtttccgaa aactcaggaa attatctgaa aaactgcaac cgatatttca   5100
taatgttgcc agatttctgc aaatgattgt attttacctt ccagtattcg cgtagatttt   5160
caggagaagc atagttgcat cgagagaccg atattaattg aacgttagtt tttgaaaaaa   5220
```

aaaagcccca acaacttggg cttttaggat gaataatacg tacatattct tcaagaaaca 5280
gaaattttaa tcagataaac taaatgtggt attactgtta atgcagagaa ggttcctatc 5340
ttcaatgaga tgatggcgac cacattgacc catcttattc tattcacatc agtcttgcct 5400
attcacaatc ttgccttgta gaatcaactg tatgaaaatt aaaaatctaa tttttatatt 5460
gaaatggtgt agaagacaat gcttaaaaat tgagaaaatt gtcattacaa acaacggtat 5520
ttgaagatgg atcgtatgaa gacgaggata ccgaatacac agtaaatatg tgtaaataag 5580
atcacgagaa ctagacgaaa aacacagaaa ggaacttagt gaaaacaata gttgatcaga 5640
accactaaat gttagtatgg aaaacaggga agaagatgaa agtgaaatga ctgaagatca 5700
accagtagga aatggcatta ataatacatg tatatcttga gcgcagaaac gacgaaataa 5760
aaaggaactc gaagcaaagg aaaggaaaaa tctaatttta gagcaagcta agaagaataa 5820
agagggaccc agaattgtta aaatccttaa aatcagctgt agacgcagta ctaccataca 5880
acgtgacagt gtgacaaaca aaatttcgac caatcaagtg ccaaatttca tacaattttc 5940
gatacaagaa cttgcatatt gttatacagg gcacaaatgt acgtacaaga aacgatacaa 6000
gaaaatgtat atcagaaatg atattagaaa tgatacaaga aaatgcatag tgtcatacag 6060
ccataagttg gtaaatgatt taagaaaagt tacagcagat tttgtaagac aaaacaaaga 6120
tgacttcaaa ccatttatgt gcaatgaatt aggtgaatcc gaagtagtta gcgaggaaca 6180
gtttgagaat tattgtaaag atgttgcaac aacaaattaa tggggaggtc agttagaact 6240
gcgagcttta tcgaatattc ttacttactc cattgaagtt attgaggccg cgattccttc 6300
cacactgtag gaaaaaattg cagtttgctc actttcatca atatcaaaaa ttgaactttg 6360
acccggtctg ccagaccgtg cgcgactact ggaaggttta aaataccttt ttatcgcata 6420
ttccccataa aagtgaaatc tggcagtaca gtgttgcgaa attgagggct ttttctggaa 6480
aataagatta tgctcttttt gatttttgtg aacggtgatt gtggaagagc aaacacctcg 6540
actggttctt tgggtataag cgacggtgtt tcctcgtcgg caatcgctgg gttctaatta 6600
acatatatgt caatagaaag tttttaggca caaaccgtca atacatatag gcatgctatt 6660
gtcgaagatg tctaaagatc cctagaactg tagaattgt 6699

<210> SEQ ID NO 168
<211> LENGTH: 1463
<212> TYPE: DNA
<213> ORGANISM: Diabrotica virgifera

<400> SEQUENCE: 168
cctccgaaca gcattatcaa aaaatgaatc caccgaaaat ttagacatac aattagcggg 60
atcttcgaaa aaagccttgc tgtccaatat cgagttcgaa tcggctggga gctatcataa 120
tactgtctta gataggctaa aatcgaaata tatagtgctc agaagtcctg aatcaccacc 180
cccaagtaaa cctgaagatg acatgaactc cagtgaatcc ttaaaattag caaaatatga 240
actatttcca ctgagcgatg tacaactcgg ttggaataac tgtgattggt ctgttggtgc 300
tggaatggtt aatatgggaa atacatgtta tttaaactct actctgcaag ctctctttca 360
tgtaccagct tttgttaatt ggttgatgtc agacaaagat catactgcca tctgtcaaga 420
ttcaggaggt ctctgtataa tctgcgcgat gcgcaaaact ctccaagact cacaacaacg 480
taacgccaac tcgatccgtc cattgttgat ctacaacaaa ttgagattgg tgtgtcgaaa 540
cctcataccc ggtcgacagg aagacgccca cgagttcttg agatatctag tcgaagcgat 600

-continued

```
ggagaaagca ttcttgagcc ggttcaacaa ttataccgaa ttcgactcga aagtcaaaga    660

aaccacccct ctgaatcaaa ttctcggggg gtacctgagg tcggcggtta ggtgcttgaa    720

gtgtggccat gtcagtacga cgtttcagca ttttcaggat ttgttgttag atataagaaa    780

ggcccaaact ttggacgaag ctttagaatt gtacttttct agagaaaagc ttgacgacga    840

atcttatcag tgcgaatctt gtcagaaaaa ggtaccggcc acaaagcagt tttcgataga    900

acggacgccc atggtgcttt gcatccaact taaaagattt tcagttagta acaataaaat    960

aacgaaacac atcaacttta gacaaagact ggatctaacg aagtacgcta gacatcgccc   1020

taacgtacct ctgatctaca ggctcgtagc gttggtcacg cacatgggcc ctaccgtcag   1080

ctgcgggcac tacacggccg tcgcgcaagc accttcaggg aatttctttc aatttgatga   1140

cagtatggtt agaccaatat cccaccaagc agtgttcaac accaacgcat acattatgct   1200

atatgagttg gaatcctcgc cctactcacc taaatctgcc cccgccacgg taactagcaa   1260

actgaagact tcaaccccaa ctgccgaaac cagttcagtg gcttgttcct cgaattccag   1320

caccgtaaat tcggtgaccg cctccacaaa gtcgtacgcc aacggcattg ggtttactag   1380

cgggaaggtt tatggtccag aactgcctcc ggataggata gagaatagtc ggaatggata   1440

tgtgacaagc agtaatggta aag                                           1463
```

```
<210> SEQ ID NO 169
<211> LENGTH: 2813
<212> TYPE: DNA
<213> ORGANISM: Diabrotica virgifera

<400> SEQUENCE: 169

aacagcaacc tggagcgaga caacagcagc atcaaactgt tcccccacaa cagactggtc     60

ccccacaaca gactggtccc acacaacaga ctggtcccac acaacagact ggtcccacac    120

aagggcagca aaaaggtgcc caacaacagc aaacgggtcg aaatgaacgt caacaacaaa    180

gttccccacc aaagcaaatg ggtccacatg gagatgtacc acaacaacct aaatcggcaa    240

acgggcaaca aaggggtgga ccacaacaac agcgtaggcc tcaggatagg cagcagacag    300

cttctgttaa agaattgaca tctcgtatga gtgaactgca agctggtcca cttgtaccta    360

tgaggttaag aaaccctgaa cctggaaaag caggtcgcaa aatacccgta gaaacgaatc    420

atctcagcct cgcgctaggt aaattaaaca cggcttatca ctatgatgtt gatttggtac    480

cagatacccc gaaaaagttt ttaagaaccg tgatggaact ctttaggcag caacattacc    540

caaaaagata tccagccttt gatggaagaa aaaatttata cagcactact atgttacctt    600

ttggagaaca aaaagaaggc gaggttacta ttcacgacag tcaaaataga gagaaaatat    660

ataaagtgaa agtcaaattt gcaaattcgg ttgatttatc cccctttgaaa gattacgatt    720

tatctagagc aactccgacg gaagctatac aagtggtcga tattgtttta cgttgtgctc    780

cttcacaaaa tctacttcaa gtgggcagaa gtttttttcca taagccagtc ggagaaatta    840

tcgacttagg agaaggcatg gaaatgtatc acggatttta tcaatcggcc attcgaggct    900

ggaagccact tttaaatgtt gatgttgctc ataaaccgtt tcctaaagct ataccagtta    960

tagaagcttt gcttgaagta ataaatgcag acagatataa taataaactt acgagaaatg   1020

accttagcag acctcttgat aggcgagatt tggaagtttt cggcaagtac atgaagcagt   1080

taagagttgt ttatgaaatt ccaaatttgc ccagttctag aagaagttat aaggttaacg   1140

gtataaatga cccaccggcc gtgaaaacct ttaaagatgc gaataataga gaaattacca   1200

tccaacggta ttttgaaaca gaaaaaaggt gcaaattaag atatcctcag atgccgacac   1260
```

```
tatgggtcgg atcttcagct agatcggata atcctatact tgtacctatt gaattgtgta   1320
caatagaaga taatcagaca attaatagaa aaatgacaga aggacagaca agaaacatga   1380
taagatatgc tgcaacctct actacagtac gcaagaataa gattatggaa ggaataacac   1440
gggctaattt taacaaccat cccactgtac gagaattcgg tttttcagtt tctagcgcat   1500
ttgaaaaatt agatgccaga atcttgcccc ctcccagatt aggctatgcc ggtaaagaag   1560
tgaatgttga taaaggaata tggagaggtg acaaattctt ccaagcggtc acgattaaca   1620
aatggacaat cgtgtgcgct gataggaggc caccaagacc agatgactta cggaacttag   1680
cttcacaatt acttagagaa gcacgcggaa gcggtatgca gattggtgaa gcagaacaac   1740
cattctgtac aattggtgac agaaatatgg acatcaagaa atacttcaca tctgttaaag   1800
gcaaatatga tgtaatcttt gtcgtcgtac caaatagcgg accacaatat agttacgtta   1860
aaacagcagc tgagattaat gtaggctgtt taacacaatg tgttaaagta agaactgtgt   1920
taaaaatgaa ttctcaaacg gcgttaaacc ttttacttaa ggttaatgcc aagttaaatg   1980
gtactaatca ttttctatct acccgtccgc ccattttgaa tagaccaacc atgatcatgg   2040
gcgctgacgt cactcatccc agccctgatt cgcaacatat accgagtgtg gcggcagtca   2100
ctgcatctta tgatccaaaa gcctttaagt acaatatctg ctggagattg caaccaccca   2160
gacaggagat catcgaagat ttggagaata ttgtggtaga ccaattgaag ttcttttatg   2220
agtctaataa aggtcaaaaa ccccaaagaa ttatcttttt tagagatgga gtatcggatg   2280
gacaatttga acaagttaca agtgccgaag tacgagctat tcgagcagca tgcaagagag   2340
tccaaagaga aggttatgaa ccggcaataa ctttccttgt tgtccagaaa cgtcatcata   2400
ctagactttt cccattgaat ccaagagatt ctcatgacag aaatttaaac gttccagcag   2460
gtacttgcgt ggacacgcat attacacatc catttatgca ggacttctat ctagtttccc   2520
acgccagtat acagggagtg gcgaaaccaa caaagtattg taccttgtgg gatgacaacg   2580
atatgtcaaa cgacgacatt gagcaactta cgtattttct atgtcacatg ttcactcggt   2640
gcaacagatc cgtaagctat ccagctccga cgtactatgc ccatttagct gcggccagag   2700
gcaaagtcta catagaaccc gaaaatgtgg atttacaaaa tttaaatagg gaatatgaaa   2760
gatttaaaat ccaggacagt atccagaagg gactgcctat gttctttgtc taa          2813

<210> SEQ ID NO 170
<211> LENGTH: 4075
<212> TYPE: DNA
<213> ORGANISM: Diabrotica virgifera

<400> SEQUENCE: 170

caaaacaatc ggagctgagc tacgcctaga gtcatggttc aaaacgagta ctacgaaaag     60
gccagcgggg caaaggccca cttccacggg gcaggcagca cgtcccaatt cggagataga    120
tacaggagac gctgacgatg aagacctaaa acttatcgac gtcatgagcg agaaggaagt    180
taatgctaag atcgaggagt tattgagtga catgaacctc aacgacgaca aaaagaaacc    240
ccttagagaa atgcccatgg aacagaaacg tgcaatgttg aagatgcaga acaaaaagaa    300
aggacaacac gacacgggca gtcgattcaa cgatcccgaa gattattaca gatatctgga    360
tcaacacata aatccggagt acttgcagtt gaacaaatgc ctgaactgtg tggaaagctt    420
gagggtagcc ttgactaaca acccagtcag ttgggtagag aagtttggga ctataggagg    480
tttacagaaa cttgaacaag tattggatac gggaataagg aataaagatg ttcgacttca    540
```

-continued

```
aacagaatgt ttacgatgtt tagaaaaatt catgaacaat acgacgggac ttaaagcttt    600
tttcaaattt tcaaaagcgc atttgactgt agccagatgc ttggaccacg aaaagcctac    660
tgtgatgtta caagccttaa agattcttgc acctctatgt atcctgaact tggaaaagag    720
cggcgaggaa gaaggtgtaa aaaaggtgct tagagccatt accgaggtgg gagagataca    780
ttcgagagaa cggttcctat ctgtggtact tggaatcact gccagcgata atgccgaatt    840
acagagtatg tgtttccaat tcatcaatgc cttattaagc gaaacggagg acttcgagtt    900
ccgtatgcat ttaagaaacg aaattgtaag aaacggactt tacgaaaaac tacaagaact    960
aaggaacgag agtaatcccc aactaaaaac tcagttcgaa atattcgaaa acagacgaga   1020
agatgacgcg gacgaatggc acgaacgatt tgacaaggtc aggctcgaca tggacgatat   1080
tcaagattgc ttcgaggtct taaaaaatat cactctagat acgccgtcgg agccttattt   1140
tttgagtatc ttgcaacatc tcttgttcat taaggaagat gtcaatatca ggccagctta   1200
ttttaaatta attgaagaag tgataacgca gatagtactc aataaggcgg ggctagatcc   1260
tgattttaag aaaaaacata tagacatcga ccttcagccg cttctagagg aacttaaaga   1320
caaaccaatg caaattgaaa gtgcagaagt cgagagccta aaaaaacaac tcgaggaagc   1380
aatcgcagca aaaacagagg cagaagccaa actagaactc gtccaaggca gagcgggtac   1440
cacacagcct tccggaaaac tagatccagc tttagtaaac aaaatcaatg tgccaccacc   1500
tcccccaatg ccaggcgccg gtgcgcctcc accacctcct atgccaggaa tgggaggcgg   1560
tcctccccca cctccgatgc ccggaatggg tggcggtcct cctccacctc cgatgcctgg   1620
aatgggaggc ggtccacctc ctcctccaat gcctggtatg ggtggtgggc caccaccacc   1680
tcctatgatg cctggaatgg gcgggggacc gccgccgcca cccatgatgg gtggtatgcc   1740
tccacctcca cccggcatgg ttcccttacc gggtttggcc aggccggatt tgttaccaca   1800
cggtttaaaa ccaaagaaga agtgggaagt tacgggacca ttaaagaggg ccaattggaa   1860
aacgattcta ccacaaaaaa tgtccgaaaa ggccttctgg gtaagggcaa aagaggaaga   1920
ccttgccgaa ccagatattc tcgacggttt ggctaagaag ttctcgtcta aacctgccaa   1980
attaccagaa gatgtgacag ataagagcaa taatacggga acgatgaaga aagttaagga   2040
acttaaagtg ttggacggaa aaactgccca aaatattagt atattattag gtggatcgct   2100
caaacacata ccatatgaag atattaaaaa cgctctactc agatgtgacg aagctattct   2160
atctgataat gttactgaac aacttattca atacttaccc cctgccgatc aattaaacaa   2220
attccaaaac ttcaaagagc aatacaaaga cctgaccgag gctgaacaat tctgcgtgaa   2280
gatgtccgaa gtgaagaggc tgttgcctag gttgaaatct ctcagcttta agcatcatta   2340
cgggaaaagg gagcaggata tcaaaccggg aattgttgct gctacagctg cttgcgacga   2400
agtgaagaag agtaaaaagt tcgccagaat tttagaacta attttattga tgggtaacta   2460
tatgaatacg ggaagtaaaa atgcgcaagc gttcggattt gaaatgtctt tccttaccaa   2520
gttaacctcg acaaaagatg tttcgaataa gcaaacgctt cttcattaca ttactgaaac   2580
gatagagaac aaatttccag atctgcttaa tttttacgat gaaatgcctc atatagatca   2640
agccagccga gtatcgttag atacgataca gaaagcgtta caacaaatgg acactagcat   2700
aagaaattta aagacggatt tgacaaataa cagggtacct cagagtgaag aagacaaatt   2760
tttagaagtt atggagaaat tcgccgaaga agccagagaa caatgcgaca tcatgcaaaa   2820
aatgttaaag aaagtagaaa acctctacag cgatctagct gaatattacg tgtttgacaa   2880
acagaaatac gcattagaag aattctttgt ggatttgaaa acgttcaaaa atagtttcct   2940
```

```
gcaagccaaa gccgataatc agaaagaaaa ggaaatcgaa gagaagaaag agaaggcgag   3000

gttagcgaaa ctaaaacaag aaaaagaaaa ggaagagaga aacaaacgaa ggctgattga   3060

tatgaatcct tcagaaacgc aagaaggagt gatggacagt ttgctagagg ctctttctac   3120

gggtagcgca tttggaaggg agcagaaaaa gcgaagaggc catcgaccag caggagctga   3180

aaggagggcc cagttagtta gatctaggtc gagaacggcc ttaatagctg gaagagaatt   3240

aactagtgaa atattggcgt agcattaagt aataataaag aagaacgcac aacgacttga   3300

acgctcaaaa gaaatatatt atataaagaa atattttata cgttgtaata atttattttg   3360

taaattgttt ttccatttgt aaataataat ccgtatatgt atatttagaa attgaacgaa   3420

tgaatctctt atatatagtt ttagttttat cgcagattat tatgtaaata tgataaaaaa   3480

ataaaaaaaa tcagtctttt gttaaacttt atattgccgt aaaagtagat tagtttttta   3540

tatattgttt ttgaaattga acaaattctt gtacgttttg aggtagtgtg cttttataat   3600

atgtaaaatg ttgtaattat tatatacttt actgttcgaa tttttgttag gttttgtatt   3660

ttagttttat ttatttcttt aaaaaaaaaa tgtgtatggt taattaacca aatatatgcg   3720

tactgttttg tttataagtc attttaagtt aagttcaaaa agctctttaa ttggacctct   3780

gttcttgcta ttttttgtag tgggtgacat caaatacaag atggcagata agtttatttc   3840

agaacagaat tttcattcct aaaaaatcct ataaaaccaa ttaaaagatc tgttgcgctg   3900

ctatgatgtt cttcctttca ctgcactaac agaaagagta gtaccctgta ccagtatctt   3960

cctggatcat tcactctccc tggaccactt tttgttacaa aaagaatagt actagggagt   4020

catcattatt tacgtttgtc gctatacagg atgttagtga ataagtgtga gaaac        4075
```

<210> SEQ ID NO 171
<211> LENGTH: 2294
<212> TYPE: DNA
<213> ORGANISM: Diabrotica virgifera

<400> SEQUENCE: 171

```
cttctaccat tgatagtgct atttataaat aaaaatattt tgtgtttatt agaaaaaaac     60

tgttttatat taaaaaagag aaactgtata gtagtgataa agtgtatggt gcaaaatgct    120

gttttctaat gagatctggg cggctacaaa acggcaggca ttgaaaagga cgaattcctg    180

ccaggataga attgaaagga tccctcctag ctcggaagaa cttttcgaaa atatcccttg    240

gatgaatatc atggctgatc tgactgttaa atctgctata gctgaatatg agtttaaacg    300

tatgctgaat aaggagctgt ctcatttctc cgaatctagc aaatctggca atcaaatatc    360

ggaatatatc tgctccactt tcctagacaa acaacaagaa ttggacctac cctcccttcg    420

tgatgaagtc cctgagctcc tcccaaaacc cactcaacgc aaagaacgtg cccgaggacc    480

gcattctacc atgtctcaaa tatcaggtgt taatcgtaaa ccactttgcc acaccaattc    540

ttttaccggt gagaagttac ctttgcacgg cattgaaaca ccttacgaag aagaattagg    600

caaaagtttg attatgatag atcaatgggg tatcgatatt ttccgcatcg gagagttaag    660

caacggaaag cccctaacct gtgtagctta cacgaccttt aacaatagag acctcttgaa    720

gacaatgaac atcccgccga agacgtttat aacttttatg atgaccctag aagaccatta    780

tgtgaaagaa aatcctttcc acaattccct gcatgcagcg gatgtggctc aaagtacaca    840

tgtactgctg aatactcctg cattagaatc tgtatttaca ccgctagaag tgacagcagc    900

tctattcgca gcgtgcattc acgacgtaga ccatcctgga cttaccaatc aatttctaat    960
```

```
taattctagt tctgagttag cccttatgta taatgacgaa agcgtactag agaatcatca   1020
cttagctgtt gcctttaaat tactttctaa cgacggttgc gatattttct gtaatatgac   1080
caaaaagcag agacaaactc ttaggaagat ggtcatagac atggttctta gtactgatat   1140
gtccaaacat atgactcttt tagctgatct aaagactatg gtagaaacga aaaaagtagc   1200
tggttcaggg gtacttcttt tagataatta cacagataga atacaagttt tggaaaattt   1260
agtgcactgt gcagatttaa gtaatcctac caaacctttg gatctctata gacgttgggt   1320
agatctcctc atggaagaaa cttgggcaga tctagtgcat cctgacgctg cagcaaggag   1380
acaaagaaag agaatccaaa atggatatca gtcccatgtg cgataggcat tcagctacaa   1440
tagaaaagac ccaagttggt ttcatagatt atatagtaca tcccttatgg gaaacttggg   1500
cagatctagt gcatcctgac gctcaggata ttttggacac cttagaagaa aaccgcgatt   1560
ggtatcaaaa cgctatacca ccgagccccc ctccagaaga gactcccgag tcccagcgac   1620
caggcatcag attccaagtc actttagaag aaggcgaagg ggaatctgaa gaaggtccga   1680
tgtgacggaa actagggggc ctctgtagaa agctcactga aaaggtgcag caatggtggc   1740
gtatcaggca gtaagcgcaa gtgcaggcgc atgcgcactg actgacgaac gttacaccgc   1800
gcaggcgcgg gtttgttgtg ttttgcaata tatgcttgac tgaaattttg aatttttcgg   1860
gctgagatgc cagcctgttc ttatatatcg cagagttcct gggagtgtac tctttttttca  1920
atttttgtt cggtttttta gcaaatctgg tagatacatc gcttcatggc caaatcgtaa   1980
gcttaaataa tctaggaaat acttttcaac agattcataa ccatccctaa acataaacta   2040
aacagttttt aagaaaaaat agtaatttgt aaatctttta tgtttatgaa ttttgaaacc   2100
gtattgttaa atgtaaacca tgtaaaagta ttgttaattt caaagtgact gtaaacagac   2160
ttaaaatagt aagtcgattt acagtgtgac aatacaaata taggcatgtc aatgtagctt   2220
tttatttata tgaaatagcg gtataaatct tcaaaacatt aagataacta cagtaggaaa   2280
aatgaaagaa tacc                                                     2294
```

<210> SEQ ID NO 172
<211> LENGTH: 3145
<212> TYPE: DNA
<213> ORGANISM: Diabrotica virgifera

<400> SEQUENCE: 172

```
ttttgataca caatatctct tgcgaattat atcagaaatt ttacaaagct actttttttcg    60
attttacttt aaattaggag gtaaaaagta attgtctttc attatatcaa aaagacatct   120
gagcattatg cattacaata tgacagcatt tttggggaaa aaatatgaac gtttttgttt   180
tctgaaaaac cgtcatattt ttttccaaaa aatatttgat tggtgtaata gcctaaatat   240
atttgaaaac gctaaatact ggcgaaaaat actaaataca aactaaatga taatttataa   300
tttatcacaa aaattccaaa atggtcttat ttaagtgtcc agtaaactag tgctgctaat   360
ttggagatag gactagctca caccaatcat agcttaaata aaaaaggaaa gcagacttta   420
acacctcatt attttaggtt ataaaacaaa ataagtattt gaaatttatg tcatagttat   480
aaaaaaacat ggtatagttt tttactacaa aagtcaggtt aagtcatagt ctatacaaac   540
tgacgtcact tgtagttctt caatgacagt ttatacaaac tgatgtcaat tatagttctt   600
caatgacagt ggggcgattg gaaaaaacgt ttacagcatt gccaacaatt tatagtaaga   660
attgtgtttg ttttgatggc atctacacca acgaccaacc aatgcaccgc cagactgaga   720
gttttgttta cgctgacgac ctcggtatcg ccgtaaaaga gaaaacacat acacaagtaa   780
```

agtcgacaat ggaagaggct ttaaacgtga tgtcaactta ctacaaacaa aactcattaa 840
agctaaaccc tactaaaacc caagtatgtg cattccatct caacaaccat ttggcgcatg 900
gcaaactgaa tgtatcttgg gagggacaac gcttggaaca tactgatagg cccaaatatc 960
ttggagtgat actagactgg tcactaacat ataaattcca ctgtccgagc acaagacaaa 1020
aggtttctga gagaaaaaga cttctccgga aacttgtagg gagcaagtgg gtgcaaaccc 1080
ccaggtgtta aagtcaatag ctgaggcctt atgtttctca acaggggaat atgcttgtcc 1140
cgcctggggt aaatctatgc acgcccaaca agtcaccacg gcgttaaata aaacatgtag 1200
aataactacc agttgtatga agcctaccct tctacccta ttgtatcggg cagctggatt 1260
cgcatcacca gatgaccgta gatgcgcctc acaatgtggg gaagttgaat gaaaggcatt 1320
aattatacga gtttgacgac ccgtcaggaa ccagccgact taaatcaggg aaatagttta 1380
tgagaaatgt cagcgtcaaa ctacccgacc tgttccctct acagccagaa cgacctaatg 1440
gaatgaacct ggactggaga aactggcgga cacttaaccg catacgcacc ggttttgtcc 1500
ctctaaaaca gaacctcatt aaatgtggca tcaagacaga taacgacgct ctttgtgaat 1560
gtggggaaat acaaaatttt gtggttctga cgtcagaaaa cttgaatgat gtaagttaat 1620
ttttgtagta aaaacaccat agttggacaa ttactataag agaaaaaata tcacaatgtt 1680
agtaggtttt tccatttgac tttctacaga aaaagcttag taaaatgcaa tcaactaaaa 1740
gttcacttac actgtctcat ttttaacaaa aaaaatgttt tataacctaa agcaaaaggt 1800
tttttttgaa aacttaaaaa gccaataaac aaatttcact ttacactgtt aaaccgtata 1860
aatattttgt gcttactcta accctttttc tgataaattc cgtttttaga tcccacatcg 1920
gcactattac aaaaagcaca ggagcccagg agaaaggaga agggtcgaaa ataaaataga 1980
gacagcagga ctagagattt ttttattaaa aaatcctaaa ctgtaagttc ttcagtatca 2040
aatgttttta gagatagcaa tggtatgaga aaagcttaac aagaaaaatg cgctttatta 2100
taattaaaaa aatcacatca tgttccggaa acttatctca gttaagtttg cgaaacactc 2160
tcaaaaaaaa acttaaaata tcctaaatac tcttaaaaaa caatgataat tgagaccaca 2220
gtcataaatt atgattggca aattggcgca gtcgtgttag gaggtcacgt attgtataaa 2280
aggttttaaa agacaaattt ttttgttata aatttaatat tatgaccctc gtaacataac 2340
tggaaccaca cgatggacaa cgatgaaaaa attaatgatt ttgaccgata tataatatat 2400
attttatgtt gtttgtttgg taaaaaaagg aaaatacaat attgtccgat tctatgactt 2460
ttttccatgt atttttaat gatgatgcac tcggtatacg cattgccggt tcgctgttat 2520
tttgaaaaaa atacaaattt aataataatt aatttttcgc cgcacggcat ggctgcttac 2580
agcggcacac actatctcta gtaaccgcag gtaattaagt aatcacctag cttttctacc 2640
actgacgctg cttgctgagg ttggattgga tcttcataaa gggatactac aacagcttgt 2700
gtcgttttca tgcaatgtac accaactttg cccaatttcg ccctaattac acggtctgtg 2760
ccagagaggt atatgtatct gttaccggct aatgttacgc ctgaggatgt gagaatgtct 2820
tgtttttcga agccctgaac taattttgct agttcttctt ttgatacatc gaaattttct 2880
gatttagccc aaacgtttcc gtcgtggcca gcgattgccg ctttcgtaac gcattttgaa 2940
gccaagagct gtttgtctac gtaatcctgc cagctcatat tgttgtaaat ttaaaaaatc 3000
actgcacaca cggttctact cactaataaa attggtgcaa ttagagcagt tgccgcacga 3060
cgaactgaag ccgaatactt ttgtctacca aggaagattt tgtagtggca gcggaagctc 3120

-continued

```
taaagagaca agtgcgactg ccccc                                        3145

<210> SEQ ID NO 173
<211> LENGTH: 1208
<212> TYPE: DNA
<213> ORGANISM: Diabrotica virgifera

<400> SEQUENCE: 173

aaaaggatgt ttagcacaca attaggaaat tttccatttg ctaatactag gaacagccaa     60

gagacaactt ccaacagttt gaataatcat ataatggatg ccaacaatgg agctggagat    120

agtaatgatg gttccataga taaaaccaaa ctaattatta attacatacc acaatatgcc    180

actgaaggtg aactaactca aatattttca accgttggaa aactggaaga tgtaaaaatt    240

atgagagact ttaagactgg ttacagtttt ggatttggtt ttgttaaata ttccactgaa    300

gaagaagcag ccaaagcaat tgcagttcta aatggatata atttgatgaa taaaagatta    360

aaagtctcct actcacgccc accagggaca ggcatgaaag attcaaatct ctacattaca    420

aatcttccaa aaaacattac tgaacaagaa atagataaca tatttaggaa atttggcgaa    480

attgtacaaa gaacgctgtt aaaagataaa attactggaa tgccaagggg agttgctttt    540

gtaagatttg ctaagggcga agaagcacaa gcggcgatca atggcttgca tggaacaacg    600

ttggcaggtt cgatgctacc tcttagtgta agagtagctg aagatcatgg aagacagaag    660

gcacagtatg tggacgtgtg ggatccgatg ggttttaata gagaatctga agaatcattt    720

tcatttggag acgaaggtcc tgacttagaa gaaattctta ttactgaagt gtcatataga    780

agacccctct gggacttatc aattcactcg acgaaaatgc aaattgacaa tctttgggag    840

cagatctatc gtgtatttaa gaataaatat tcgataggtt ttctaactaa catgtggtct    900

aatcttaaag aaggctatat aagagataag agatcatttc cgtattacta tcaaatgaga    960

tttttggatg agtttgaaaa tgttgctcta tgtggatcta gtcgaaggca tacaggaagt   1020

cctttaggaa aaaaattaaa aatggattac cagccacctt cacctgacgg cgttgatgat   1080

tttttgcaac tgttgggaga aggcttacgt agattgcccg ctggaaacag aactaagtta   1140

cagtttaaat ttgtggaatt acttaaagat gaagaatcgc gtatatcaga ttaacttttt   1200

aatatgtc                                                           1208

<210> SEQ ID NO 174
<211> LENGTH: 2297
<212> TYPE: DNA
<213> ORGANISM: Diabrotica virgifera

<400> SEQUENCE: 174

gggacctcta aagcagtacc atgtggataa gacattcgcc gacagaagat acaaagtaca     60

gtcagcgagg acatacttct acctcaatga agcccagtgc gagaagaaca cggaaacatt    120

catcaaatgc ttggaaacca tagcagagtt tcagcaaaca tctcaaggct ctacttatgg    180

caccgggatc gcagctgtta aattcactgc tttgggcaga ccacaactgt tgcttcaact    240

ttctgaagta attatgagag caagacagta catgaccgaa attgttggag gtgaaggtaa    300

cgttttgtgt catcacatga agtatgaaga tttggaggcg aaattcgaaa aaattcaaga    360

taaagaatcc ttacgaaaat tcttgaagca agttacatac gataaacaag gtgttctcca    420

cttattcccc tggtcgggta ttattgacga gaaccaagag ttgagtgctt ccttcagagt    480

tccagactta aaatcaggaa ggatgatcag gctattaaca cagctatcac caaaggagga    540

ggagatgttc agaaatatgg ttaggagatt taataccatt gtgaaagcag cacaggaaat    600
```

```
ggatgttagg ataatggttg atgcagaaca aacttacttc caaccagcaa ttacccgaat    660

tactctggaa tatatgagaa agtacaacaa acaaaaagcg atagtattta atacttacca    720

atgttatttg aaaaatgctt ttgatgaagt ttcgactgat ttggaacaag caaaacgtca    780

agacttctat tttggagcta aactcgttcg gggagcatat ctcgaacagg aacgagccag    840

ggcagccgcg atgggctatc ctgacccaac caatccagat tacgaagcta cgtctgagat    900

gtatcataaa actctttcag aatgtttgag gaggataaag gccttcaaac aaaaaggaga    960

agacaagaaa attgctataa tggtagcttc tcacaatgaa gataccgtgc gatttgctat   1020

taaaaaaatg gaggaatttg ggatagaacc caaagataaa gtgatatgtt ttggacaatt   1080

gtttgctatg tgtgattata ttactttccc attaggtcaa tctggatatt catcttataa   1140

atacatcccc tatggacctg taaaagaagt attaccgtat ttatctcgaa gagctcacga   1200

aaataaagga gtattaaaga aaattaagaa agaaaagaaa ttacttgcaa gcgaaatttt   1260

caggcgctta tctagaggtc aattatggta tacacctaaa ggaaattatg ttcccgtata   1320

aacactagat ctcaaacaca gcaaccataa aaccactgtg caggttttac ctagttttgc   1380

gacttaccta cccgttttgt agataactag ttggcagaca aataaaacta acgtcgttac   1440

agaaaaatct gcgtgacaaa ttccaaaaat ttaacatcaa ttggcctaaa tatacataaa   1500

ataagcagtc cctatatttt tacaaacatg taaatataaa gcaaataaag gtcattttta   1560

atactgtctg ataacggaaa gaaaagactg tgtttgataa tattttgaaa tgtcattgcc   1620

ttaaaatata taacgaagga atgttttaag tcatgaattc aaatcaaaac attttactaa   1680

aacagatcat tgataaatga tctgttttta gggtatctta tgattgcata ttgaagcgaa   1740

cctcgtttgt tgatttgctg atttttattt ctaaatcgaa tttatagtta tagaaataaa   1800

aataatttta gtttatatct tattgttaac atatttttta ggattgtgat ttttgtgttt   1860

actgatgatt attacagaga aaggacttaa acgtcgcaca tgtttttaac tgcgttaatt   1920

atttgtttac atgtatattt accgttgtga agtaggtatt tttttatttt gactaatgca   1980

aaaaacacat ttcagtatag atgcgtgttg gtaacattac tgttaattac ttcttaaagt   2040

taaaatttga tttggtttcc agtaacagga cttaaagagg taccaacaag gtatgaaaaa   2100

aagcaaaagt aaattattaa accttttaca tgccactata cgtgtagtcc agtcgggtta   2160

gacgaataac tgacctaacc ttgcatgccg agctgtccca gatttggttt ttctgatctt   2220

tgggggaggc cagtagtggt gtgaatttgg aatctcgact gaatgccgcc gttgcgttgg   2280

ctcttatttt gatttcg                                                  2297
```

<210> SEQ ID NO 175
<211> LENGTH: 3120
<212> TYPE: DNA
<213> ORGANISM: Diabrotica virgifera

<400> SEQUENCE: 175

```
atgaatgatc cctcaaagaa agtaaaaaat ccgttgttta acatatcggt aactggagga     60

acctttgaag attttactca acatgctata ttattacccg caaaagaaaa acaaccacct    120

catacactaa atatatccca tgaacaaatt ttaaatgata taatctccgg atcttcaaaa    180

tcaagtgaag ttgtttctaa tcaagagata gaaacagttg tggaaaatca acagcatctt    240

cccgaaggaa ttaatcagtc agaatttact tattcacaac aactgccaga tctgtcaact    300

ttgcaacctc acttaagtgc tgccccgcaa cacagttcgc acttgtcttc ggtattttca    360
```

-continued

```
tctttttcta gtatcttgaa tattggaggt tctaataata atcctaaaga agaagtgata    420
gtatctccac ctgcaggaat agaaagtctg attagccaaa gtaacaacaa ccctgagcca    480
gtgccgcttt tttcggccag tttacctgaa tatagtatcc aacagcctcc tccgcctaca    540
ggtccaacaa atttattcag aagagctggt ctaaaaaaac cggcttatgc acaagtacca    600
ggtttatctt cagcccccat agcaccccaa aatttgaatg tccaaaatat tcctccacca    660
aaccttcccc cattacctcc agcagcgcca gtaccatcag cagcatcaca aaacatatta    720
gtaccaacag ccccttctcc atccacttcc atttcatcaa cttctagtgt agaccatata    780
aaccaaggat taccaaatca gtttaaacca atatctccgc ctccttctaa tttgcaatcc    840
ttccatccta tcacccaacc tgtagctcct gtgccggtac aaccttttgc ccaatctgta    900
gcgataacgc atccatacag aaatatagta ggcccagtta tggatgccat accagctagc    960
gaactatcac aaaatgctaa tttcagtagt tccctcgtga attctccaga gtctctgcca   1020
aaaaataata acacaggtga tgctagtccc cctgttaacc aagtgtatag acctgtctac   1080
catcactggt ttcatcagag agaaatagag ggaaggaaat tatgggaacc gttttctatg   1140
ttggattcat tagctttaga acaagctttc acttcaaatg atttagatcc agataaagtt   1200
attgctactg acggcggtcg ttatgatgtg aatattttaa gaagacaaag gaatcctgtg   1260
tattggaaaa cgaatcccaa tgaagtacga agatgttctt ggttccacaa agccagttca   1320
gacggaaggt tggtcccata tgaagaaaat atcgctacaa agttagaaga agaatacaaa   1380
tctgcgtttg aatctaataa gtggcacaaa acaatcgaat tacctcaagg agaaagtatt   1440
gtctttcatg gacctgatgt tttagtactt ttctctccca cgcaggttcc tgacgcatgg   1500
ggcaacacaa caaaccagtc ccgaccgaga gttgtaaaaa ggggtatgga tgaatttgat   1560
atagatgaag gagaacctgc tcaagtcgat cacatcttgt tcatggtaca tgggattggt   1620
tcagtctgtg atttaaaatt tagaacagta gaggaggtag ttgatgaatt ccgcagtatt   1680
gcctttcagt tagttcagtc tcactacaga tcgtcctgtg accaaggaac agtcaaccgt   1740
gtggaaattt tacctataag ttggcacgat aggctacatt ctgaagaaac tggaatcgat   1800
gatcaattaa aaagtattac tctggagagt atacctagac tgagaggctt tacaaatgac   1860
actttgctcg atattttgtt ttatactagt cccatttact agtcaaaaaa ttactacaac   1920
tgtgggaaca gagcttaata gaatatatga cctttttaaa caaagaaatc ctgattttaa   1980
agggggtgtt tcacttggtg gtcacagttt aggcagcctt atactcttcg acctcttgtg   2040
ccaccagcac tctaaacctg aatctgacgg agaagaaagt gatgaaattc tttctagtag   2100
tccaggctcg gtcaaaccag ctccacctca gcgaaagatg agtaaaagaa taagctatat   2160
gatgggtgct atcggtacgg gacagccgga aatacactac actcgactta atttcgaacc   2220
aaagaatttc tttgctttgg gatctccaat aggtatgttc gtgatcgtta gaggtctgga   2280
cacattaggt gaacactttt cgttacccac ttgtccagcg ttcttcaaca tttttcatcc   2340
atacgatcca atagcataca ggatagaatc tttaatcaaa ccagaatttg caaagttaaa   2400
accagtattg attccccacc ataaaggaag gaaacgaatg catttagagt taaaagaaac   2460
gatgacacgt gttggagctg atttaaagca gaaagtaatc gattctatga gaagtacttg   2520
gaattccgtt taccaattgg caatgtttca caaacagtcg ccccctagtt tggaagaaga   2580
ggtgtctaag gcatttaaag atcaaatggg gcaactggaa aacgagtcca tcccagaatc   2640
tacgggaact cctgtaggga atttgaatag tggaagaaga gttgattatg tcctgcagga   2700
agcacctttt gagttcttca atgagtacgt gtttgcctta acgagtcatg tttgttattg   2760
```

```
gcaatcggag gacaccatat tgatgatgtt aaaggaaatt tatacttcta tgggagtaac   2820

ttctgacagt caaattcctc agcaaaccat gacaatagag agaccaccat catctcctac   2880

agcaacaagg tccccaaatg ttcaaattcg tgcattccaa caacctattg gagttgatcc   2940

aacaaagccc atgcaattga actcgtctct tgaaccacca ccagtaagtg gctttgttcg   3000

aaaaacatag tatatgctct acgagtggtt gtacaagcca cttgccgaac gttatgctcc   3060

atatttgttg cacagtaaca ccaactctaa aattacaaaa aaaaaaaaaa aaaatgcgag   3120


<210> SEQ ID NO 176
<211> LENGTH: 275
<212> TYPE: DNA
<213> ORGANISM: Diabrotica virgifera

<400> SEQUENCE: 176

tgctcaaatt tctcacccac aaattaagaa ctcattctat aaatgaggat aactatgcag     60

ggaaggccga tgaagaccat gattctggta cggaatcaga tgaagagatt gatgctccag    120

tatcaggatc agcatcctgt tcagaacgcg tttgtaacgt atcaccggca gacacaggat    180

gttcgatgga aagtccagct cctgatcaac acgatgctca cagctccgaa gaagagttgg    240

aagttatcaa tagcaatagt aaaatgaggc gatca                               275


<210> SEQ ID NO 177
<211> LENGTH: 274
<212> TYPE: DNA
<213> ORGANISM: Diabrotica virgifera

<400> SEQUENCE: 177

tgattccttt atcttttgta aataaaaatt ctggccaaat tatattagca ggtgatccta     60

tgcagctagg gcctgttata ttatctaaag ttgctaccga atgtggacta gcagagtctt    120

atttggaacg aattatgagc agatttccat attgtcgtga tccagaagga tttccagaaa    180

cgtctggatt tgatccaaga tttgtaacga aattattata taattacaga gcccttccgg    240

acattcttac tttgtacagt acactctttt atca                                274


<210> SEQ ID NO 178
<211> LENGTH: 275
<212> TYPE: DNA
<213> ORGANISM: Diabrotica virgifera

<400> SEQUENCE: 178

tggcctccat gccgagcaag actcccgtca gcgtcctcca ggagttgctg agccgtcgcg     60

gcatcactcc caaatacgaa ctggtccaaa tcgagggcgc catccacgag ccaatcttcc    120

gctaccgcgt gttccttaac aacgatctgg tggccaccgg aaccggaaga tcgaagaaag    180

acgccaaaca ttcggcagcc aagaacttgc tggatctctt ggtcggaaaa gtgactcccg    240

aacaagccaa tcagaccaac ggaacgcccg gagcg                               275


<210> SEQ ID NO 179
<211> LENGTH: 273
<212> TYPE: DNA
<213> ORGANISM: Diabrotica virgifera

<400> SEQUENCE: 179

tgaactccag tgaatcctta aaattagcaa aatatgaact atttccactg agcgatgtac     60

aactcggttg gaataactgt gattggtctg ttggtgctgg aatggttaat atgggaaata    120
```

catgttattt aaactctact ctgcaagctc tctttcatgt accagctttt gttaattggt 180
tgatgtcaga caaagatcat actgccatct gtcaagattc aggaggtctc tgtataatct 240
gcgcgatgcg caaaactctc caagactcac aac 273

<210> SEQ ID NO 180
<211> LENGTH: 273
<212> TYPE: DNA
<213> ORGANISM: Diabrotica virgifera

<400> SEQUENCE: 180
tgggtccaca tggagatgta ccacaacaac ctaaatcggc aaacgggcaa caaaggggtg 60
gaccacaaca acagcgtagg cctcaggata ggcagcagac agcttctgtt aaagaattga 120
catctcgtat gagtgaactg caagctggtc cacttgtacc tatgaggtta agaaaccctg 180
aacctggaaa agcaggtcgc aaaatacccg tagaaacgaa tcatctcagc ctcgcgctag 240
gtaaattaaa cacggcttat cactatgatg ttg 273

<210> SEQ ID NO 181
<211> LENGTH: 272
<212> TYPE: DNA
<213> ORGANISM: Diabrotica virgifera

<400> SEQUENCE: 181
tgagcgagaa ggaagttaat gctaagatcg aggagttatt gagtgacatg aacctcaacg 60
acgacaaaaa gaaacccctt agagaaatgc ccatggaaca gaaacgtgca atgttgaaga 120
tgcagaacaa aaagaaagga caacacgaca cgggcagtcg attcaacgat cccgaagatt 180
attacagata tctggatcaa cacataaatc cggagtactt gcagttgaac aaatgcctga 240
actgtgtgga aagcttgagg gtagccttga ct 272

<210> SEQ ID NO 182
<211> LENGTH: 275
<212> TYPE: DNA
<213> ORGANISM: Diabrotica virgifera

<400> SEQUENCE: 182
tgctgttttc taatgagatc tgggcggcta caaaacggca ggcattgaaa aggacgaatt 60
cctgccagga tagaattgaa aggatccctc ctagctcgga agaacttttc gaaaatatcc 120
cttggatgaa tatcatggct gatctgactg ttaaatctgc tatagctgaa tatgagttta 180
aacgtatgct gaataaggag ctgtctcatt tctccgaatc tagcaaatct ggcaatcaaa 240
tatcggaata tatctgctcc actttcctag acaaa 275

<210> SEQ ID NO 183
<211> LENGTH: 275
<212> TYPE: DNA
<213> ORGANISM: Diabrotica virgifera

<400> SEQUENCE: 183
tgacagtggg gcgattggaa aaaacgttta cagcattgcc aacaatttat agtaagaatt 60
gtgtttgttt tgatggcatc tacaccaacg accaaccaat gcaccgccag actgagagtt 120
ttgtttacgc tgacgacctc ggtatcgccg taaaagagaa aacacataca caagtaaagt 180
cgacaatgga agaggcttta aacgtgatgt caacttacta caaacaaaac tcattaaagc 240
taaaccctac taaaacccaa gtatgtgcat tccat 275

<210> SEQ ID NO 184
<211> LENGTH: 275
<212> TYPE: DNA
<213> ORGANISM: Diabrotica virgifera

<400> SEQUENCE: 184
tgtttagcac acaattagga aattttccat ttgctaatac taggaacagc caagagacaa 60
cttccaacag tttgaataat catataatgg atgccaacaa tggagctgga gatagtaatg 120
atggttccat agataaaacc aaactaatta ttaattacat accacaatat gccactgaag 180
gtgaactaac tcaaatattt tcaaccgttg gaaaactgga agatgtaaaa attatgagag 240
actttaagac tggttacagt tttggatttg gtttt 275

<210> SEQ ID NO 185
<211> LENGTH: 275
<212> TYPE: DNA
<213> ORGANISM: Diabrotica virgifera

<400> SEQUENCE: 185
tgagagcaag acagtacatg accgaaattg ttggaggtga aggtaacgtt ttgtgtcatc 60
acatgaagta tgaagatttg gaggcgaaat tcgaaaaaat tcaagataaa gaatccttac 120
gaaaattctt gaagcaagtt acatacgata aacaaggtgt tctccactta ttcccctggt 180
cgggtattat tgacgagaac caagagttga gtgcttcctt cagagttcca gacttaaaat 240
caggaaggat gatcaggcta ttaacacagc tatca 275

<210> SEQ ID NO 186
<211> LENGTH: 275
<212> TYPE: DNA
<213> ORGANISM: Diabrotica virgifera

<400> SEQUENCE: 186
tggatgccat accagctagc gaactatcac aaaatgctaa tttcagtagt tccctcgtga 60
attctccaga gtctctgcca aaaaataata acacaggtga tgctagtccc cctgttaacc 120
aagtgtatag acctgtctac catcactggt ttcatcagag agaaatagag ggaaggaaat 180
tatgggaacc gttttctatg ttggattcat tagctttaga acaagctttc acttcaaatg 240
atttagatcc agataaagtt attgctactg acggc 275

<210> SEQ ID NO 187
<211> LENGTH: 2593
<212> TYPE: DNA
<213> ORGANISM: Diabrotica undecimpunctata

<400> SEQUENCE: 187
acgattcgtt tggtagtaca tagagaaatc gtttttagtt ttataacctt ttctgtgttg 60
gaatattgaa caaattctaa tgattcgtaa agtaacactt ctgctaaaaa ccaaaactga 120
tagttttttt caaaaaaagt acaatttttc tgggcttgct actgaaataa tgtgccatac 180
tctaattgtg gaaaaaattg taggtatatg ttgaaagtta acaaataact aatgcttaca 240
ataatgtcga catcaagtca aaataatggt aaaaagagtt cagccagctc tattgttaac 300
accccttcca gcactcccat tactaatctt gcaaatggta gtagtaccca aggaacagca 360
catagttcac ctccacctaa tagcaatgct ccaaagtatg gtaccctagt gcctaacaga 420
atattcgtgg gaggaatatc agctaacaca acggaaggag aattaatgca actttttagc 480
aactatggta ctgttaaagc tgctaaaatt attcaggaca gggctggtgt atcgaaagga 540
tatggtttca ttacctttga gagtgaggat gatgctaaaa gacctcttag agaagctgaa 600
aacatagtgc taagagaaag aaaacttaat atagcacctg ctattaaaaa acagcctttt 660
agtcgagcat ttgatgcatc cagtccacct gctgttgctg caaataatgc cagtcaattc 720
ttttttcctc cgggtgctgc cgtgccatat tttcagagtg gagttacata ttatactcag 780
ccagcccctg ctgcacctgg agatcccact cctcaacaac ctgtttatca acctcctcca 840
atgtatccca cacaaactgg tcctccacag ccagctacat acccttctat gatgtttccc 900
gctcaaacta tatatatgcc acaacagtat cccatgccta ttccgtacga gtacaacttc 960
taccagggta acggcccatc gctgccaact cagtatctgg ccggaggcca aagtggttcg 1020
ggaagctctc attgcacctc attaccatca tcaaacagtc cacccagacc caatggttat 1080
ggtcaacagg tacctaccta taattcagga gatcccgtct actacaactt accaatctac 1140
ggagctactt tggaaggtcc gccattatac gctgatgcct tcgatctaag cgctagtgga 1200
acttatgcgg aggaaaccta cagcagcatg attacaactc ttactcaaga aaatgtagaa 1260
gcttctcttg gatcatcgat aaattcaact catgcagctt ccgacaattt cacacaacat 1320
ctggatcaat ctctcgttga gtctgattca agtattgtga atgttggagg taaaccacca 1380
ctacataaat cctcagagac aattgtttct gctctttccc aacctcagga ggatagaaac 1440
tcacatacgc ctattgtttc actactttcc atagatcatc aacaagaaaa agactattca 1500
tcaatgcaga gcggtcgtag acgtaaaatt ctggttcaaa gcaatcaaaa taacgtgccc 1560
atgtatccta caaatggata cgtcaaccag ttcgtcggat ataatcctca acaaccaccc 1620
ccacattcat tcggtcaacc tctctttaac aacggttacg gtttttcgga atatcgtcga 1680
tttaacggat acccagatat caggtcaatt aataatagta ataaaccgag gagacgaata 1740
tacgaaaata ggcggtcgaa cgatcattct agccgttcta gtcttcgcac agactcaaac 1800
tcatcggcaa gttgtgtcga cgaaaataaa aatgaagaaa aaacttttcg aactactgtt 1860
aacactcctc cacctgcccc atactcacct atgactaatc aacaattcaa atttattaat 1920
tacagtaaca cgaaaaacat ttataatcat aagtacgcta ataacaataa ttattataat 1980
agaactgcta cacaccatga ccgatttaaa cataccgaac ctctagcgaa taaaaacaat 2040
tacagttcca tttatccctt aacaaataat ttcctaacta atagccatac ccaaagtaat 2100
tctgattccc ttccctccca aaattcccag gtacatgtga cgactacggg tcagagcttc 2160
gtcccggtga ctatccaagc tcagacgaaa cgcaacaagc gttctttgag acggagcggt 2220
gccagtgctg gaggcatcaa cgaaatcggc gccggtgacg ccccttacc aggcgaagaa 2280 tgcgaagacg tctacaagaa gctggagacg cttaagttgt aacgaaaaag tggtatattt 2340
tcttgtatat ttttttctat ttatttaaga ctgtacaata atgtaaaata ctagaaattt 2400
aatgtaaact aaagaggaaa aatatataat acatatttat taaagatgat ggagatgtaa 2460
caagttttta tttattaaaa acttattttt attcgttgtt aacaaatggg agctgatttc 2520
ttcaattata acgtgttggt atcttgtaat tgaaaaacgt caattatagt acatattatc 2580
gtacaattat tag 2593

<210> SEQ ID NO 188
<211> LENGTH: 2585
<212> TYPE: DNA
<213> ORGANISM: Leptinotarsa decemlineata

<400> SEQUENCE: 188
gccgttgaac agtagtgaaa atgtttagtt tttggatgat ttgtgtattg agttaacaag 60

-continued

```
aatattctaa taatacaaga atttatgaga acgtctttcg atacatctaa cggggcttta    120
cttaatcact agtgaaacca gacagttcaa tttttcccgg aaaacaatag aaatgtgttc    180
taacctaatt gttgtatgga aaaaattgta ggtatctcct gaaagtgaac gaataaggaa    240
aagctgaaaa atgtcgacgt caagtcaaaa taacggaaga aagagttcaa acagctctat    300
tgtcaacaca ccctccagta cgcccctcac aaatgctgct aatggaaatt cgcaagttag    360
cacacaaagt tctccaccac ctaataacaa tgctcctaaa tatgggactc tagttccaaa    420
ccgaatattt gttggtggaa ttacggccaa taccaccgaa ggtgatttaa tgcagctctt    480
cagtagctat ggaactgtaa aggcagcaaa aataatacag gatagagctg gcgtttcaaa    540
gggatatggt tttataacgt ttgaaagtga agatgacgcc aagagaccat taaaggaagc    600
tgataacatt gttttcaaag aaaggaagtt gaacatagca ccagctatca aaaaacagcc    660
attcagtcgg gcatttgatg catccagtcc accaaatgta gcagctggaa accctgcaca    720
tttttttttc ccacccggag ctgcgatgcc atattttcaa gggggtgttg cctattatcc    780
acaacctcca cctgctgctc ctggagaccc aaatgcccag caacaagttt accaacctcc    840
cactgtgtac cccactcagg caggccctcc tcaaacggcc acctatcctt ctatgatgtt    900
ccccgcacag ccaatttaca tgccgcaaca gtatcctatg cccataccgt atgactacaa    960
cttctaccag acaaatggag ctccgccctc cgcacagtat attgttggag gccagggtgg   1020
ccccggagga ccacaatgtg gcccaatcgc gccttccaat agtcccccaa ggccaccttg   1080
ttatagccaa cagatgccag cctataatcc agcagatccc atgttctaca acatacccgt   1140
ctatggtccc acaatggagg gaccacctgt ttacaccgag gccttcgact tgggaaatgg   1200
tggaccatac gcagaggaca cctacaacat gggtgataac aacattacac aacaaggcat   1260
agagacttca atcccgcctc ctgtctcagt acctgctgta caaacactca cttttcctac   1320
tcataacatc aatgttcctc ctcctcctat tcctacaagc attgagttga atgtccccaa   1380
tgcctcttct cggcaccaga tggatcctgt tgttgcagaa gatgtgtcta cacctaggaa   1440
ttcagacaca cctgtagttt ctatcctttc tatcaacgaa cagcaagaaa aagactattc   1500
atcaatgcag ggtggtcgaa gggttaaaat tcccccgcca aacctgcata acaactttca   1560
aattcagcac gctcaacatc caaatggtta cattaaccat ttttctggtt acaacggtcc   1620
accaccgact cagtttggaa tgtacaatgg ttattctcag aatggtccca ttttcccgga   1680
ctatcgtcga gtgaatgggt ttgacaaccg tatcaacaaa aatagaaggc gttcatatga   1740
caatcgaaaa tccaacgatc actcaagccg ttccagtata cgcactgatt ccaactcctc   1800
ggcgagttgc gttgatgaaa acaaaaatga agacaaatct cacacgcgca cttctgtcaa   1860
cacgccacct cctgcccctt attcaccgat gacccatcaa tttaaaacta ttgcaaacag   1920
caacacaagg aaccaccaaa attccttcag atattataat aataataatt attacaaacc   1980
agcatattta gaccgatcaa aaacaaatga cttgaccact cataataaac ccagcaacaa   2040
ctcctctagt aataacagca ccttttcttg cccaaactcc ccacaatcct ccatttccca   2100
ggtgcatatg tcggcaactc agaccttcgt accgcaagct aggcgcaata agagatctgt   2160
tagacgtagc ggcaccggcg gattgaacga aattggcgct ggcgacgccc cccttcccac   2220
tgaagtcggc ggtgaggtgt gcaagaaatt ggagacgctc aagttgtagt aggtgggaga   2280
aagtcattat tatgtatatt tttttctatt tatttaagac tgtacaataa ctgtaacata   2340
ttataaattt aatgtagaaa catattataa atttaatgta gacctatgag agggatatta   2400
```

-continued

```
atataatata tatttattga aaaatgtgta gatgtgacga tttgattttg agaaaggatt   2460

tttttggtg gtacagatga cttggaaacg tcttgtcaga tatcttaatg tgtcatttct   2520

atccatgata aataattgat gacttttcat attgtgaact ttgttcaaga cgcgtttcac   2580

tgtgc                                                               2585


<210> SEQ ID NO 189
<211> LENGTH: 2154
<212> TYPE: DNA
<213> ORGANISM: Phyllotreta cruciferae

<400> SEQUENCE: 189

gtacgatccg ttttcgtagg aactagtgaa attggttttt agtttttcgt ccttaatagt     60

gttgaatttt tgaatgcatt ctaatgattc gtaaactaac gctgcattta aacgacgtat    120

attttgaaag cgaacgaata acgaatgccc tcaaaaatgt cgacctcaag tcaaaataat    180

ggtaaaaaga gttcgaacag ctctattgtc aacacaccat ccagcactcc tgtcacgaat    240

atcgccaacg gtaccaccca agtgagcacg cagagctcgc cgccgcccaa caacaatgct    300

cccaaatatg gtactttggt gccgaacagg atcttcgtgg gcggcatatc ggccaacacg    360

accgaaggcg agctgatgca attgttcagc gcctacggca cggtgaaggc ggccaagata    420

atccaggaca gggcgggcgt atcgaagggc tacggtttca tcacgttcga gagcgaggac    480

gacgcgaagc gacccctacg ggaggccgag aacatcgtgt tgcgcgagcg gaagctcaac    540

atcgccccgg ccatcaagaa acagccgttc agcagagcct ttgacgcgtc cagtccgccg    600

acggtggcgg cgggcaatcc cacgcagttc ttcttcccgc cgggagcggc ggtgccgtac    660

ttccagggag gcgtagctta ctatccccag ccggctccgg ccgcccccgg ggacccgtcg    720

acgcaacagc cggtgtatca acctcctcca atgtacccga ctcaaacagg cccaccgcaa    780

acggccgcct actcgcccat gatgttccca caaactattt atatgccgca acagtatccg    840

atgcccatgc cgtacgatta caacttctac cagggcaacg gagcctcgcc ctctgcccaa    900

tacatggcgg gagcggcgca aagcggatcg gcggcgggac cgccgcaatg ctcgacgatg    960

ccgccttcga atagtccgcc cagaccgcct tgttacggcc aacagatgcc tgcctacaat   1020

ccgggggatc ctatgtttgc ttataatttg cctatatacg gttcaacgtt ggaaagcttg   1080

ccaatctaca ctgaagcttt tgatctcggc gcgagcggtt catacgctga ggaaacaatc   1140

tacaacaatt tggatcgaac ggtaaccccg tcgcacgacg acgacccgac caacatacag   1200

acggtttcct actgcaacac gacaaacaac acgaacggcg gcaccgccgc ccccgaccca   1260

gcacaacaac aacaccccgc gttcgtcaaa gacgagagaa acaacgcgcg cacgcccgtc   1320

gtttctctcc tctcgatcga ccaccaacag gagaaggact actcgtcgat gcagagcggc   1380

cgccgccgca aaccgccacc cccgccgcag ccacagccgc cgccgccgca gctacacaac   1440

caccacaaca acccgaccta tcaccaccac catcacggcg cgttcgtctc gcattcgcat   1500

ccgttcgtcg gcttcaatcc gcaacagccg cctccgttgc cgccgccgcc cgccaacggc   1560

tacgcgccgc caccgcaggc tatttacaac gactatcaca ggcgcgttaa cggttgtttt   1620

gttagtaata gcgtgaagaa tgtaaataat aacggtaaaa atcgcaacga ggacggtaag   1680

agtaccgtac gaacggcggt gaatacgccg cctcccgccc cttactcgcc gatggcgaat   1740

caccaattca aagtttacac gaacagtagc gttaagaatt ttatgaacaa taataacagc   1800

aacaagaaca ataattacgc tagaagcaac aaaaagtacg ctgtaatggg cgtgccgcct   1860

ccaccgccgc caccgcccgc ctctaacgca tccactacga ccccaacaac atccaccaac   1920
```

```
gacaaaatct actgtaacaa caacaataat aacataacta gtagtagtag tagtaatagc   1980

gccgccttgc ctacgcctgc ttcctataat tcgaatacta ataataataa tagtagccgc   2040

ctccttcact ataataataa ccattcccct tcgattaacc acgtggattt gggggtgacg   2100

caggtgcacc tgtcgacgac gacgtcgcag agcttcgggc cgcagacggc gcgg         2154


<210> SEQ ID NO 190
<211> LENGTH: 2036
<212> TYPE: DNA
<213> ORGANISM: Phyllotreta striolata

<400> SEQUENCE: 190

ttgaaattgt ttttgaactt ttgctgtttt gtattcgttc tattttcatt ttaaacggtt     60

taaaatgctt ctctgagtat tttaaaataa gcaactaaaa acaaattcga atttttaaca    120

attttggaat cgactaaacg taaggtatat tttgaaagcg aacgaataac gaatgccctc    180

aaaaatgtcg acctccagtc aaaataatgg taaaaagagt tcgaacagct ccattgtcaa    240

cacaccatcc agcactcctg tcacgattgt cgccaatggt actacccaag tgaatacgca    300

gagctctccg ccgcccaaca acaacgctcc caaatatggt actttggtgc cgaacaggat    360

ctttgtgggc ggcatttcgg ccaatacgac cgaaggtgag ctgatgcaat tgttcagcgc    420

ctacggtacg gtgaaggcgg ccaagataat ccaagacagg gcgggcgtat cgaagggcta    480

cggtttcata acgttcgaga gcgaggacga cgcgaagcgg ccgctgcgcg aggccgagaa    540

catcgtgttg cgcgaacgca agctcaacat cgcaccggcc atcaaaaaac agccgtttag    600

caggaccttc gacgcgtcca gcccgccgac ggtggcggcc ggtaatccga cgcagttcta    660

cttcccgccg gggcggcgg tgccgtactt ccagggaggc gtcgcttact atccgcaacc    720

ggcccaggcc gcgcccgggg acccgtccac gcaacaaccg gtctatcaac cgcctccgat    780

gtacccgacg cagacggggc cgcctcaaac ggccgcctac acgcccatga tgttcccgca    840

gatttatatg ccgcaacagt atccgatgcc catgccgtac gattacaact tctatcaggg    900

caacggagcc tcgccctctg cccaatacat ggcgggagcg gcgcaaagcg gatcggcggc    960

gggaccgccg caatgctcga cgatgccccc atcgaatagt ccgccgagac cgccttgtta   1020

cggccaacag atgcctgcct acaatccggg ggatcctatg ttctataatt tgcctatata   1080

cggatctacg ttggaaagtt tgcctatcta cactgaagct ttcgatctcg gcgctggtgg   1140

ttcgtacgcg gaggaaacaa tctacaacag tttggatcga acggtaacgc cgtcgcacga   1200

cgacgaatcg accaatttgc agacggtttc ctactgcaat acgacaaaca acaacaacaa   1260

caacacaaac ggcggcgccg ccaccgccga acaacacgcg tcgtacgtca aggaggagag   1320

gaacaacgcg cgcacgcccg tcgtttctct tctctcgatc gaccaccaac aggagaagga   1380

ctattcgtcg atgcagagcg gccgccggcg caaaccgccg ccgccgcaac cgccgccgcc   1440

tccgccgccg caattacaca acaacacgac cgcctatcat catcaccatc acggcttcct   1500

gccgcattcg catccgttcg tcggtttcaa tccgcaacaa ccgccgccgt tgccgccgtc   1560

gaacggctac gcgccgccgc aaccgccgcc gccgcctatc tttaacgatt accatcggcg   1620

cgtcaacgtc aacggttgct tcgtcagcaa caacaacaat cacattagcg gcggcaagat   1680

tgttaacaac gcgaaaaatc atcgcaacga cgatggtaaa agtaccgtac gaacggcggt   1740

gaatacgccg ccgcccgccc cctactcacc catgacgaat caccaattta aagtttacac   1800

gaacagtaac gttaaaaact ttatgaacaa taacaacaat agcaaacaga acaataacta   1860
```

-continued

```
cgctagaagc aacaaaaaat acggatcggt gggtgttcct acgccgccac ctcccgtttc   1920

taacaccgcc tcgtccacca ccaccaccac caccgccgcc acctccacat ccacatccac   1980

atttgtaacc aacgacaaaa cctattgcaa taacaacaac aatagtacta gtagta       2036
```

```
<210> SEQ ID NO 191
<211> LENGTH: 4893
<212> TYPE: DNA
<213> ORGANISM: Vibidia duodecimguttata

<400> SEQUENCE: 191

gtcgtcgcca ttttcgatgg ttccgttttg tagtgcaaac ttcgttagtt tttgatagtt     60

ttgtgtgtta ttttatcaaa attcactaat gaatcttatt aaactatcgc taaaatcctt    120

tgaagtgttc ctttgcaggt agtactcgag agtggaagag aaatttaaag cttctaaaga    180

tgtcgatacc taatcagcct aacggtagaa agagttccaa tagttctgtc gcaaacactc    240

ctgccagcac ccccgtagcg aattcgaatg ggtctgtcca aacggtcgtg cacaactcgc    300

ctccacccgc caacaacgct ccgaaatatg gtaccctggt gccgaacaga atattcgtag    360

gcggcatatc ggccaacacg accgagggcg agctgctgca gctcttcagc tcctacggca    420

cggtaaaggc ggccaagata atacaggaca gggccggcgt gtcgaaaggc tacggtttca    480

tcaccttcga gagcgaagac gacgcccagc gcccgctcag ggaggccgat aacatcgtgt    540

tgagggagcg caaattgaac atagcgccgg ccgttaagaa gcaaatacct tccccgcagc    600

ccttcagttt caacagagcc ttcgacggtt cgggatcgac gacagtggcg gtcggtagtc    660

cccagtactt cctgccccg acgatgcctt atttccaggg cggcgtgagt tactacccac    720

cgcccccgaa cggtccggtg cccggcgatc cgaacgccca gcagccggtc taccagcctc    780

cagccgttta ttcggcacag gccggcccgc cgcagcccgc cagttatccc tcgatgatgt    840

tccccgcgca gccgatctac gtgccgcagc agtatccgat ggccttgccg tatgaattca    900

gctattatcc gaacgccgga gcccccccgg cacagtacgt ggtcggtacc caaggcggtc    960

ctccgccgcc gcagccacca ccaccaccat cagcacaagg tcccccgctg cctccgtccg   1020

gtagtccccc tcgtccgcca ccctgctaca accaacagtt gcccttcggc gccgagccca   1080

ttttctacaa cgtgcccatg tacggcggac ccatggatca tccgcccgtc tacgccgaac   1140

ccctcgaagg cgcaccatct aattacgccg aggaacaatt cacaatcgtg cctcgagccg   1200

gcgcatacga ggtagacgcc atgtacaacg gccgtcccgg ctccggcttt aacgaatcga   1260

cacccgatcc atctttatcg cacaacgtgc cgccgtgtcg gtacagcaac aatacgacgc   1320

cttacgctga tcaacagcaa cagcagcagc tgcaacaaca acaacagagg gattcggagg   1380

cggacaacct aagacagtcg aacacaccgg tcgtttcgtt gttgtccatc gagagcacca   1440

tggagaagga cgtgaatgcc atgcagtgcg gaaggaggag gagaacgtat gcctcctgca   1500

gtcccggtcc gtttttcggg ccgctaatgg gcggcatgcc gcccatcatg ttcccgcctc   1560

cgaattatcc cccgcccccc atcaactatc atccgcacgt tcccttcccg caatttccca   1620

accatcggcc gttcaacggt tacgatagcg ctcggccgaa gctctacaac gccaacggct   1680

actcgaagaa gcagcagaag aaattcaaca ataattatag accggtggac aactcgaaca   1740

ggtcgagcct gaggacggag tccagttcat cggccgccag ctacgcggaa gacgcacgcc   1800

acgcccacca gcatcgcacc aatgtgacat cgcccccgcc cgccccctat tcgccgctaa   1860

cgaaccacgg tttcacgtcg ccgatcaacg gcatctcgaa tccgcccaac gttccgtaca   1920

acaacgttcc tcatccgcga cctagaaact attacaacaa caataataat aataacaacc   1980
```

-continued

```
acgcgcatca cgataagaaa agaaataata acaataaatc tcgaacgtcg aatggtaacg   2040
gttaccacaa taataagaac aataatcaaa ggggcgagac cagcccagtg aatcagactc   2100
atgacacgaa tacatcgcag gtccataacg gcgggagcgc aaccggcttc gcggcccccc   2160
tgcccagtcg caggaacagg aagaacgtgc gcagaagcaa cgtcgcggcc acagtggcag   2220
cagcagcagc cggcgccgcc ttgagcgaga tcggcgccgg agacgcgccc cagcagtcgc   2280
aagaaccggt gtcggaagcc tgcaagaaat tggacagcct caagttgtag aaaggtaaaa   2340
aggggatgcg tgtgttaatt ttttttcttt ctttttaatc gatgccatcg ccattgacat   2400
gaaaaaacca caacaaacga ttatcttcga ataagactgt aaattttata tataacaaga   2460
aattacttga tattacgtaa gaaagggaaa tattaaatat ttattgtaaa ttcaaagtat   2520
tatttttttt gttttgtata ttttaaatta ttatttagaa aaaaaatgaa gcaagttgtt   2580
caccgtagga catcactttg tatataacga taataatgat gcaaaaacga aaaaaatctc   2640
tagctatggt atatgcaata tttatttaga gtataaacga caatattaat tgtatatgta   2700
atacaaaaat taaacgagat gccatattgg actagatatt aaaatgaaat cggtaacgtg   2760
ctgaaaaaaa aagtagactc gcgtttctcg gtttagatcg aaatcgtgcc gcgccgcatc   2820
agacaaaaat tgttatttaa tatctaagga tcgtgcgtcg ctctgttttc gttttctttt   2880
tgtttctttt tttttttact tcaaacgcgt cgggtcctct tgcgctcatt tcgtatacaa   2940
ttatgttttg acgtttctcg acgttagcaa tttctcaatg aaaaaaaaaa gatctctgaa   3000
gcgaccagtt gtcaattcta ctcggtgatt aaaaaaaaaa ttaaatttaa aacgaaaaaa   3060
attcggttcg tctagacgaa aggagaagtt gtgtgcgaaa caccgttctg ccttattttc   3120
ctcttctctc ggtggttaga ttaggttttg atagaaaata ttcgttttgt ttattttttt   3180
tttgtaattg aattttttca cggtagtttg acttgtatat gcataacaaa aaggtgccgt   3240
gatctgctcc atcgcgtttt taacctcaaa cgtcatatct tctgtcaaaa cctccgtcta   3300
cgccgtcttg cgaattatcg aaatttttct tgtcaagtct tattcgaatc tccccccctcg  3360
gacggaacaa tggagcatcg tccgcttttt gttgtgcgta cttaacgaga ttttgctcaa   3420
aacggctgcc atcgtctttc gtacgttgtt ttattgaggg tgcgcgatcg agggactcgc   3480
gacatccacc cgatacgagg agggtagttt tttttcttttg ttccctcgat tttccgagcc  3540
gtctgcaagt ttccatcatc gaacgtcgat gagttctctc tttctctctc tctcccccct   3600
ccagttaccg gtacgttcga agttttgtgt cattttgaat tttaggctgt gacataaagt   3660
tatttattgt tgaatttggt agatttttta aggaagagaa tctgtgtttt ttgtagctat   3720
ttattcgata agtttcgacg aaatcggttg atctcttgga acccgactcg gctttgcaaa   3780
ttttttccgt tttgacaatc gtcgttgcgc ggcctcacct tgacgactcg acgtcgcggg   3840
ttccaagact gcgcgcaggc tcgaaacgtt tttaggatca tccggggctc gtttggatta   3900
tttttcgtag attttttttt cgcgctcgaa cgccgagata tttcgtagat ggacgaattc   3960
gccccccccca aaccccccttc gaacccccccc aaaaattcga tgcgccagtc ggatcggatg 4020
tttcaaatgg ccctaagcga tcgagaaata caaaaaattg atgtgaaatt ttggtttccc   4080
caaagaaata tgtaaacttt aggctcatca attgatattt atccaaatta gatgtgtaag   4140
ttagtattag taacttagtt gtagttttag gataaatgaa ctatctctta ttcaaataga   4200
tgataagacg gcaattgtct ccgttcatca ttaaaacata caggattttg ctcaaagaac   4260
ttttttcgtt ttcttcttaa aaatgtgata aaaaaaaacg tgaggcaacg agaggttctt   4320
```

gtttttttct ctctatctct ctcgttcgta gggaaatgct tcctcatgtt gcaaagattt 4380
cactgagctg tgtaaatacg ttcattttgt tatattgttc cattttttttc tctccaaaat 4440 caaagggcag ggtcggttgt tgttgctgtt gaaattcctt aatttttttct tcaactccct 4500 cgaaatcttc aatctgacga aaatttattg aaaaatatga tatttccacg tttccattga 4560
atttatcgat gtggtattaa tttacttctt tcttttttcg agattattgt gtgaaaatta 4620
aattttcttt ctatgatgtg tggagttgaa gaaaaacggt cttttgtcat ctaaccgatt 4680
tgtgtgaatt tcgtgtccgg ccctacgtcc attttttttcc aagaatatct caagattttt 4740
cgcagcagta cggtcttcaa accttgaacc cttcattttc ctctctcccc aaaccctcgc 4800
ctcgattctc tttctctcac acacacacac acattgaacc gatttgaaat agtacctgca 4860
aaatattttg taaatattct gtttgtaaat tac 4893

<210> SEQ ID NO 192
<211> LENGTH: 2051
<212> TYPE: DNA
<213> ORGANISM: Orius insidiosus

<400> SEQUENCE: 192 ttttttatg ttactttgtc ctttaatatc atactcttaa aaatcaaata atcctttaaa 60
tgtcttaatt cgtctattat tttttctttc ccaccatttt ctttatcata aattttttttt 120 tggaatccat ccgaaaggtg aacccaacgc ccgccattgt tcgcactacc cccatttttc 180
gggccgactt ataaaattcc gtcagaaaat attaattttg tcaaaaaacg agaatctatt 240
tagaacatga gaaactcttt tcctttcgga actcgcgtta tactttaaaa aatttaaata 300
tcaaataagg atggcggttc aaaccaacag agggatgacg agcgaaaatg aaatgaaaga 360
tcaagacgtg gcgccggtct ttaacatcaa cgcacccaaa tatggaacag tcgtgccaaa 420
cagagttttt gtcggtggca taacatctgc gacgactgaa gacgatctca atcagctttt 480
ctccaactac gggaaagtgg tcaacgcgaa aataatcgtc gaccgtgccg gcgtctctcg 540
aggttacggc ttcgtcacgt ttgaatccga cgaagaagca aggcgccttc agaaagatgc 600
tgataacatt gtacttaaag aacgaaaact aaatatcgct cctgccatta agaaagtcca 660
gcctgtctac acaagaggtt atgacccttc aagcggacct ggaagccctt ctcaatattc 720
aagctacatt caaagacaaa acggagtcgt cagctcatac tacatgaaca gtctaacgta 780
ctttcctcaa caggcagccc aacaatctgc accttcgatg accccgttac cttccaacca 840
tgtagaacct tccgtttatc ccggaaatta cccagcgatg cctcagtgta attcgcctcc 900
aagttatcaa tatggatatc ctcagcaagc gccgatcttc attcctcatt atccgtttgc 960
tatccctcag tatgatgggt gttatcaagg agaggtacaa aactgttatg ctcaacctgg 1020
aatggaatct aataatcagg tcgcgtatcc gcaatatttt gtatcgcagc aacacccaga 1080
aataacgtat tatcaacagc cggtacctca ggagttggtt tatacacaaa gaacttatga 1140
ttcgtcgact gtatatttta ctgagcctaa gtttgacgat tcgtgtgaac catcaccgac 1200
atcgccaaat caacaatcac ctgggccacc aatgttacca cctgcaccct cgttgccgcc 1260
gatttccgaa atcgataagc caaaagcgag aaacgacgaa acgccagtcg tttcgctttc 1320
gaaagtatac cacgaccaaa acgacgacta ccagcccaat ccgagatata aaccccatca 1380
aggtttcaaa cggaaacctc ccccgaggca cgaaaacaac aacaacaatc cggatcttac 1440
ggataaaaat aggatgaatc gatatgataa aagtaggaac gttggtcaaa aacctgtccg 1500
tcctatggct tcgcagaatc gtagacccat ccacaatcca cgtcccacca acctctttca 1560
atatcgtaat caatctatgc aggtaccgca gtttccttca tactacgcct caaggccata 1620
tgtgaaccaa tcgcagactt actacaacca gcgaaaacca tttcaacgcg gcaaattcag 1680
tgcaaaggcg aaaaaataca gagacgagac agaacctgaa ggtgcagaag atgaagacgt 1740
ctgcgaaatc gatcagttaa ctcctcccat aacacccatt tcgccgaaac aacatgacat 1800
atcagaatcc gatcgtaaag acgaattaat ccgatctttt gaaaacttga aaatgtaaaa 1860
agcttatttt gaacttcaaa attttctaaa aatataaaaa gtgtcgaatt cgggtcacat 1920
taaaaatttt tgatatattt gtaaattttt ttctttttca gaaaaaatgt gccaaaacta 1980
aggtttgtga taaataagcc ataatgtaac tttgaggcct taaaattgtt tatacctcac 2040
ttcttttttt t 2051

<210> SEQ ID NO 193
<211> LENGTH: 2837
<212> TYPE: DNA
<213> ORGANISM: Lygus hesperus

<400> SEQUENCE: 193
ccgctgttag ttgggtggta gttatatttt ttgggggtgt tacctatttc ttccctttttg 60 ttttactcta agttggtggt aatttggatc cgaatttgtt ttatttggtc gttgaagaga 120
gtagtaaact tgtagattag tttttcaacc ccagccccca gttttaactc cctagtgcag 180
ctcgtcgtgc tgccgccatt ctgcttggac tgggtttttc gctgatttgc ttatctcgta 240
atatggacgt aatccggtgc cacctgatcg gaaatagttt ctaagaagaa cgtgttttgt 300
atcgagctcc tgcgttgtta attcaatcaa ctagtatcat ggagaaccct tctgaaaagg 360
atggaaagga ttcgaatgag tctcaagtgt cttctccggt gagcactgtc atcaatgctc 420
ctaaattcgg gtacgtcatc ccaatcgcg tattcgttgg agggatttcg tcgcagacaa 480
cggaaaacga tctggcccag ctttttttcca gctacggaaa cgtagttaac actaaaatca 540
tagctgacag ggccggtgtc tcaaagggat atggttttgt gactttcgaa actgaagaag 600
aagccaaaag actgcaagca gatgctgagt ctatagttct ccgagagaga agacttaaca 660
tcgcccctgc tattagaaaa cagaactacc aaccgagaac ttatgacggc gtccctggaa 720
gcccagtttc tatctcacct ggtcagcttt acagacagac tggtgtaccg ttcttccaaa 780
atggaatggc tttttatact gcagctcccg ctccccagcc tcctcagcca atgacacccg 840
tgcagagtcc agtggaagct cctcaagtgt atccacctgg tgcttacggt ggtgtccccc 900
aaaattcaac tgcacaaaac ttcacttttt cctaccctgc tcaaagtcac gtctattacc 960
cagcccatta cccttatcag cttgctttgg aaggataccc tgtcactgat gtcaacaatg 1020
tgctcatacc cgccggagga ggtgctgaaa atggaggggt tgtctttgct gcttcaccct 1080
acatattcac tcaacagcct ggaacccaac aaaacgcctt ttttgatcct caaaacattg 1140
cacaaattgc tccgactcaa gaacaaatct tctatcctgc atctagaggc tacgagacgc 1200
ctacttttct atacactgaa caaagcgggc gtggaaagaa ccccaaagga accgggtggt 1260
acaaggacag taacgagtca gtgactgaag aagggaatgt gctggccaac gccctcaccc 1320
ctccgatcac ccccagatct ccccacgacg cctcggagga cctctccgcg tcccttcaag 1380
gtctcaacat ttagtcatcc agatttcgtg tcatttttaa ggcatatctt ccctctaaag 1440
acttgaatat tctaatacta atttcgttct agcacagtat ctttttgata gcaaataaaa 1500
atgattaaat ctctaagtgg ttgttggtaa tacggaagct acgaaatgga aggaacacat 1560
tgattagctt tcccacttca ctaaaaaaaa tttaaaaaaa cctcgggtgc cttattcatc 1620
ttaaaatgac tgacccaagt gccatacaaa ctctttctca tctaaatttc ctaacttttg 1680
ctaaaatttc aattttgatc taggaacgct aggaagctca acaccaaaag taaacttgac 1740
tgccctaatt attaactaaa accaccaata taaagtacaa tgacttcctc tggatacgac 1800
ggttaagact cgtcttgcct tgtccattta ccatgtaaat ttattttcga ataacttgag 1860
tatttttcta gaacgcttta acagtaataa atcttttata aatatagatt tatttctact 1920
ctaaggatag aattaccttt ttgtacctgt agacttgtta cagttataag taataataaa 1980
ttttataaaa gacaaagtca ttgttgaata gttcgtaaaa ctctttagta agttttctag 2040
ttgattgcgt tgaagcactt taaaactcgt ttttcttaag ttattgactc tatgtgattt 2100
tgctcttaag aaatacttac cgaccccttt gtgtttttcc tctcaaaatt ctataggcgg 2160
tctctgtagt ttttttcgtt aacaatgaac aacctaaaat ttgcatgtct ctgtcgaggc 2220
attccttcga aaaatctttg aaactcgaag attttttgtt tctcttttc tcttgattta 2280 gttcctactg attcgtgttg tataccctcc cttgtgatat ttacttataa ataagtcggt 2340
tgtgtacagt attttttgtc attgttacaa actgaaacta gtcaatttga ctataaaatg 2400
ttaagtgata aattctcgaa tgtgactttg aattaaggta gcactcacta tgtctaccta 2460
aaagatgatc ctctgtagtt atctatgaag aactagtagt taagtgattg acgttactgc 2520
attttttcta tcgtcagacg ctatttgtat ttttcttttc acacgaaaag aaagaccatt 2580
tagatgtatt tcctacttgt tttgattgca tctcgagaga ttcctctctt tgtatcagtt 2640
ctttagaacg tatcaaaacc taaaggctga catcttctgc caatattggt aatttctcgc 2700
tatgcttgat agctaaacaa acacttcatg tattcatcct atataacgat tttgacaata 2760
cgaatttatt ttggaacagc cctcaactta ttggttcatt gactattttc aataaaagac 2820
gtcagattca aaaaaaa 2837

<210> SEQ ID NO 194
<211> LENGTH: 3780
<212> TYPE: DNA
<213> ORGANISM: Megacopta cribraria

<400> SEQUENCE: 194
ttttgcctga cgttagagtg tgtgttgtgt tttttttatt ttctttagtc gctgttatat 60
tttctatttt tgcatttatt ttaatttttt ttgttctggc acctcttatt taaacaataa 120
cctgtatatt ttattagttg tcagttaatt ttttttgatc tctgtaacgt ttagtttacc 180
gtaatactag atattcattt gtctgccgcc atattattta ggtcattttt tcttaacaag 240
aaataagtga aaatgaatct tgacaactat ttaaacttga aggtatttta gaatttttttg 300 atctgaggtg acaaggacaa gaaccccctt cttctacttg aaagtttttt tacaagttag 360
aatttttgag tacaaaaatg gtgttggaga acatcaccga agaaaacaat agtaaagaaa 420
gcctggaaac accgtccacc atccttaatc ttaatgcccc aaagcatggg actattatac 480
caaatagagt gttcgttggt gggattgctc ctgctacaac tgaaatggat ttaatccatc 540
ttttctctag ttacgggaat gtaacaggaa caaaaataat ttcagatagg gcaggagttt 600
ctaaaggtta cgggtttgta acatttgaaa cagaggatga agctaaacgg cttcaaaaag 660
atgctgaaaa catagtttta ggacaaagac gacttaatat tgccccagct ataaagaaac 720
agggtttcag tcgagggaat tttgactgct cgactaatag tcctctccca ccaacacagc 780
tatatcgcca caatggtttt acctatgcat ttcacaacgg gatggcattt tttcagcagc 840

-continued

```
catcgcctac agtccccaca tcacctcatg tggagccttc tccagttttt cagactggtt    900
cttcatatgg tgcagtagca ccgagcagtc cagcagggcc agcttaccct tttccattcg    960
ctcctcaagg acaaattttc tatcaaacac ctcaatacca gtaccaccta cctcagtttg   1020
atggatgtta tgatgctgga cagatgatgg taacagatgg gagtttagtg atcccccagt   1080
actatctagc acctcaacca ccaccagaac ttgcatttta tcctcctacc cttcacaatc   1140
ctgaaacaac agcaccaata caacaggtga tttatacatc acctcgagcc tatgattcat   1200
ctttaatgta ttctacagag ccaaagtgcg gaatggagag cagcgtagga gctcacagtg   1260
gcgttagtat ggctgtggtc agtaaggagg agggagaacc accaacatcc aaccatcaga   1320
gacgaccacg tgaatcttcc accccagtgg tttccctcct caagctgtac aaagggaagg   1380
atgaccattc aaaaaagaaa cagcataaca cccatgatga gggaagaaga caatattacc   1440
tcaataacaa taatcctgat accaccaatc ggaacctaaa acaccaggaa tcctccagac   1500
atggaaacct tccctcccta ccttcttatc ctcctgtaca tactagtcct aaccttaagc   1560
accctactgt acaggttccc cagtttccct tctactccag acaggtgctc gccccgccag   1620
cgaccctagc atccttctat ccacccccaa ttccgcatag caggcctagg tccaactaca   1680
ggccaagata tggtggtggg agaggtggag gccgtggaag tggcaataag tggctaccca   1740
aagaagagga aatggggcag cctttgacac cgcccataac ccctcgttcg gagccctctg   1800
gtgtcactgg agccactact ggacctgaag atgtcgtcca gtctattcaa gctctagcaa   1860
tctagtccta gacactattt gtcttaaacc ataccaaata aggaagagaa ccttcgcctg   1920
ttataataat aacaattgaa gaaaaaaaaa taacaaaaaa aaactgaata gtcatttgtt   1980
taagagaata tatatacatt tgtttatgta tataaaatgt atatttataa ataaatttaa   2040
agcataattt gatattttc tctatgatgt ttaaaacatt ggaattttag ttcttaaaac   2100
acaacacacg ataatttgtt agattctagt ccaggaagga ctcatcgaga tttgagactg   2160
tttgatataa tttgtaatta ttataatgtg acatttcact tgttaactta aatgcacatt   2220
atttgataaa tagtgccatt tatttttact gtatggatgt ttgtttaatt cttttcactt   2280
gcttagactt tatcagactt ttctacttct gctaaagatg agatcattct aaagatatta   2340
aattgaaatg catcatttta tctgaaatat agatcagttt taatcttcat ttgtttgtgg   2400
taagctttta cataaatgtt taaagttctg ttattacaac ctcgaaacaa aattctctag   2460
atggccaaat caaaactttt gtacctgtta aacttcttta ataagttagt ttaattttta   2520
taaaagacat ggtcttcaga taggtaggtg tacttaaaac ataagacaga gtatccagat   2580
ttttgaatgc atttctggtc tttgtgataa tttagtccaa agctgagaat gtagtaattg   2640
tataaaatat tagtatatat ttaaatatat ataaaattta atatattttg gttaatatgt   2700
atgttatata tttattgtac tttaatgtaa gtgttaatgt taagtagttt ctagatctgg   2760
ttatagttaa ttttttttga aatcgctaag atatgtttaa ggttgagatt agatacaata   2820
caataaactt gcatttattt taccctttaa aaatttattc tatattaata tcaaaattgt   2880
gctctgttca tcaggatagt ttgtaattgt tagactgtaa gacgactttt gattgattaa   2940
tcaattgtaa aattttagtt gttgctcata ttccattatt catattataa cttgataata   3000
atatttttta taggttaaat gttagatatt aaggttcatt caattagtta catgtctggt   3060
aattgtcttc cttaagtttt caattttcag atttgttttt taagttccta catttttaag   3120
aaacccttta gtattcgttg cttaaaagca caagtatcct taactatggt ttcataccta   3180
```

cttctgaaaa gataaaattt tttttctttt ctgtggctta ggtgtaagac aactagtcaa 3240
acacaaaatt tattcataaa aaaaagaaaa aaaggatttg ttaatgtaag attggacaag 3300
attttgttat accaataaga taaaactgtt gagatgagat ggactatttg ttcatgtatt 3360
ttcgatgtat attataaaag attttgttac atcaaaatga taagtacgat ttgagcagtt 3420
agaagaatag ttatttttta aaaatataaa tacaacaaaa atcatcagca tagcatatat 3480
ttataattaa aaccactact tcaggctgtg atttttattg taatacattg tgttagtaat 3540
gatgagttta atcttaaaaa atgtaagttt atttatgatt ataacttaat tactttccac 3600
cagttaagtg tataagttac aagaaaatat ttgtaccata ttccaaggct gatgataatc 3660
gccatactgc catgaaagtg tgttgtactt atagattttt tttttataga accacttgta 3720
ttcaatttac tatttgaaaa taattgcctt atattctact aaattctttc agataaaaaa 3780

<210> SEQ ID NO 195
<211> LENGTH: 2816
<212> TYPE: DNA
<213> ORGANISM: Euschistus servus

<400> SEQUENCE: 195
tggatggtgg agatggcctg gcgttagagt gtgtgttgtg ttttttttat tttctttagt 60
cgttgttata ttttctactt atgcatttat ttttattttt gtgtgtccgc gcctcttatt 120
taaactagtt tccgtagatt tgttaagttg tcacttaatt tttttaatga tctctgtaac 180
gcttagttat ctgtaataat agatgttcat ttgtctgccg ccatattatt taggtcattt 240
tttcttaacc gaaataagtg aaaatgaatt gtaagaactg tttaaacttg aaggtatttt 300
agaattttga tctgaggtgt gacacttgtg gtgaacattt cttaataatt taaaaggcag 360
aattgagtga atctcttact gctttataat ggctgtacaa ctaaaaaatc aaaaaaattt 420
agcagctttg agtgaagaaa aggatataaa taaagatcac atagagtccg caacttcaaa 480
tataagtaat aatttaaatg caccaaaaca tggaactgtt attcctaaca gagtgtttgt 540
gggtgggatt gcacctgcca caactgaatt agatttaatc caactattct ccagttatgg 600
caatgtcact gggacgaaaa taatatctga ccgcgcagga gtttctaaag gatatggttt 660
tgttactttt gaaacagaag atgaagccaa gcgtctacaa aaggatgctg agaacattgt 720
tttaggacaa cggaggttaa atatagcgcc tgccataaag aaacagagct ttggtcgagg 780
cggttatgat tgtactgcag gtagcccaat acctcctact caagtctacc gccacaatgg 840
tataacattt actttttcaca acggaatggc attttttcca cagccttctc ctccagtccc 900
tccatcatca catgtcgagc cttcacctgt atttcaatca ggtgcatcct atggagctgt 960
aactcctagc agtcctggac ctgcatatcc ttttccatat gcacctcaag ggcagatatt 1020
ttatcaagct ccacaatatc aataccatct tcctcaatat gatggatgct atgaaggagg 1080
gcaggtaatg gttactgatg ggagcctcgt tatccctcag tactatctgg cagcagctcc 1140
tcaaccaaca cctgaattgt tctatcaaac tgctgcaatt catccacagg aggcatctcc 1200
tcagtctgtg cccccgttat tatatgcctc ccctcgggcc tatgattccg gacttgttta 1260
ctccacagag cctaaatgtg gattggagaa tggtatgagc aatcataatg gcggtggtat 1320
ggctgtgata aataaggagg agggagaacc accagtcact aacaaccaca ggcgaacacg 1380
tgagtcggcc cctgtggtct ccctcctcaa gctgtacaaa ggaaaggagg accagcctcg 1440
gaggaaacaa caccatcagc aggaggaggg gaggagacag catcatttga acaataataa 1500
tccagatgct gccaacagaa acctaaaaca ccaacacgat actaggcgtg gcactccccc 1560

```
ctctgttcct ccatatcctc agaaccatgc tagtcctaac cctagacacc ctcctgtgca   1620
ggttccccag ttcccgtact atccccgcca ggtcctcgcc cctccaacag ccctcacgtc   1680
tttctaccca cccccgccac cgcctcctag gcctagatca tactacaggc cgagatatgg   1740
aggaggaaga ggtggtagcc gaggaggggg gaacgccaag tggttgccga aagaagaaga   1800
gatggggcag ccattgacac cacctataac accacgttct gaggcagctg ctgttactgg   1860
cactacgact ggacctgaag atgttgtcca gtcaattcaa gcacttgcaa tctagttcag   1920
cagttgcctg gccggacagt ataagacaac atatgtctat atacctcacc gtaacagata   1980
accttcatcc tacatcgtct tataacaaca ttgaagaaaa aaaaaaccaa aaaaaactaa   2040
aatagtcctt tgttttctct taaatgcaag agaatataca taaacttgtt tataaatata   2100
tacacataat atatgtaaaa taaatttgaa aacaatattt gtttgttttc tgttatgact   2160
taaatttttt aagttaaagg atagcacaca aataatttgt taattctagt ccaggaataa   2220
atgggactta ttgtgagaaa agagactgtt tgatataatt gtaaatatta tatatgtgac   2280
gttcacttgt taacttaagc acattgttat ataaatagtg ccattttttt ttttactgta   2340
tggatcttga attatttcac caattagact ttatcagact ttttctaact tgaacgaaaa   2400
cattattgct caaaattcgt gataaaattt tatgaaagta gaattttgga attatgaagc   2460
atctcattag aacgttgtag tctcatctag ataaatcagt tttaatctcc atttgaaaaa   2520
tttttgtcaa gatttcttg ataaattgag atcttaaagt ccaaaagtgt aacagttata   2580
aaatggcaac gattagcact tgtacctgtt aacgcgttgg ggtttagtta gtttaatttt   2640
tataaaagac actatcttga aaagatgtac ttattatgtt tggaatttgt atggaagtcc   2700
gagttagcag tttttaaag tgcatttctg gtctttgtga taatacaata tcagaagtaa   2760
gttaaataaa tgtgtatttg tgtaaaataa tataaatata tatttagtta tatata      2816
```

<210> SEQ ID NO 196
<211> LENGTH: 2823
<212> TYPE: DNA
<213> ORGANISM: Nezara viridula

<400> SEQUENCE: 196

```
ggtgcttaag cctgacgtta gagtgtgtgt tgtgtttttt ttattttctt tagtcgttat     60
attttctact tatgcattta tttttatttt tgtgtgtccg cgcctcttgt ttaaactagt    120
ttccgtattt ttgttatgtt gtcacttaat ttttttaaag atttttgtaa cgcttagtta    180
tctgtaataa tagatgttca tttgtctgcc gccatattat ttaggtcatt ttttcttaac    240
cgaaataagt gaaaatgaat tgtaagaact gtttaaactt gaaggtattt tagaattttg    300
atctgaggtg aaattgttgg taaagatact tggaaattta taaggcagaa gtgagtgaat    360
ctcttactgc ttaatatggc tgctccaata aaaaatcaaa aaaatttggc agcattaaat    420
gatgataaag aactcatcaa caaagaacac actgatacag catcaaatat cagtagtaac    480
catttaaatg ccccaaaaca tgggactgtg attcctaaca gagtgtttgt tggtggaatt    540
tcaccttcaa caaccgaatt agatttagtt catttatttt ccagctatgg aaatgttact    600
ggcactaaaa taatttctga tcgtgcagga gtttctaaag gatacgggtt tgttacgttc    660
gagaccgaag aggaagccaa acgtttacaa aaggatgcag aaaatatcgt attaggacag    720
cgacggctga atatagcacc tgccattaag aaacagagct tcggtcgcag tacctatgat    780
tgttcagcgg gtggtccagt atctccttct caactgtacc gtcaaaatgg cgttacatat    840
```

gcttttcaca acggtatggc ttttttcaa caaccaactc catcattacc tccatcagcc 900
catattgaac atatgccagt cttccaatca ggtccgccat atggagcgat gacgcctagc 960
agtcctggac cagcataccc atttccgtat gcgccgcaag gacaactgtt ttatcaagct 1020
ccacagtatc aatatcatgt tcctcaatat gaaggctatt acgaagcaag ccaggtgatg 1080
gttactggat tatataattg tgattttcag caatatgaag gctgttacga agcaagccag 1140
gtgatggtta ctgacggaag cctggttatt cctcagtatt acctgacaca tcaaccaaca 1200
cctgaattgg ctttttacca gccagctaca gtgcacccgc aagaggcatc accacaatct 1260
gtgccacctt tgttatatgc ttcacctagg acttatgagt ctgctattat ctattccacg 1320
gagccaaaat gtggattgga gaatggtatg atcaatcata atggaggtgg tatggctgtg 1380
ataaataagg aggagggaga accaccagcc caaaacccga ggcgaacccg tgaggcagcc 1440
cctgtggttt cctacgttaa aatgagtaaa ggaaaggagg accagcctcg aaggaaacat 1500
caccaccaac acgacgaggg gaggaggcag catcatcatt tgaacaataa taatccagat 1560
gctgctaaca ggaacttgaa acatgatgca aggcgtggca ctccccccctc tgttccccca 1620 tttccagcca accatacttg tcctaaccca agacaccctc ctgtacaggt tcctcagttc 1680
ccgtactatc cccgccaggt cctcgcccct cctacagccc tcacgtcttt ctacccaccc 1740
ccaccaccac ctgcccggcc aaggtcatac tacaggccga gatatggagg aggaagaggt 1800
gggagcagag gaggaggaaa tgccaagtgg ttgcctgttc ctaaagaaga agagctgggg 1860
ttgtcccagg cactgacacc acccgtaaca ccccgtaatc ctgatacagc tgctgttact 1920
ggcactacga atggacctga cgacgtcgtc cagtcgatcc aaggactttc actctagtct 1980
agagctgttg cctggccgga cagtataaga cacgatatgt ctatatacct cacatcagat 2040
aaccttcatt ctgcaactat caacttgatc tcattgaaga aaaaaacccc aaaaaaaact 2100
aaaatagtcc tttgttttct cttaaatgca agagaatctg cataaacttg tttataaata 2160
tatacacata atatatgtaa aataaatttg aaaacaataa ctgcttgttt tctgttatga 2220
ctttaaattt ttaagctcaa acacaacaca ccaaatattt gtgaaatcta gtccaataca 2280
ggactcattg agaatagaga ctgtttgata taattgtaaa tattatatat atgacgttta 2340
cctattaact taagcacatt gttgtaaaat agtgccattt tttttttact gtatggatct 2400
tgaattattt cactatttag actttatcag actttttcta ccttaaacga aaacattatt 2460
gctcaaaatt ggtgataaaa ttttatgaaa gtagaatttt gggtttataa aggtttatag 2520
tttctcaata gaacactgta gtctcatata gataattcag ttttaatctc catttgaatt 2580
ttttgcaatc caaaagtgta acagttataa aatggcaagg attaacactt gtacctgtta 2640
acgctattgg aattggctag ttaaattgtt ttaaaagaca ttatcttgaa aagaaagatg 2700
tacttatact gaaatttgta tgaatgagtt ggcagttgtt taagtgcatt tctggtcttt 2760
gtgataatac cagtctatta aagtatctaa taaatgtact tatactgaaa tttgtatgaa 2820
tga 2823

<210> SEQ ID NO 197
<211> LENGTH: 2006
<212> TYPE: DNA
<213> ORGANISM: Helicoverpa zea

<400> SEQUENCE: 197
caactgttga cctagttccc tcgcctagta aaaatagcgg tcgacaatag ctcaaacact 60
atttatagtg cgtatctaaa aaaatctcaa atcacacact gttatctcgg ttgttttttt 120
tcgaaacatc actcgaatac cgtccgtgtg tcagtcacgt cgtggtccgt acggcgcaag 180
tctggagccc acctatacaa cacaagtgct accgtaatcg ataaaacctc gcgtgaaaga 240
cagtcagttg ttttttcgtg aataccagtg cccttttagt tgccgctaga gattttagtt 300
tagtaaacaa gggaacatgt tatattagtg ttttaaagtg ttagaaacaa tggaaagtgt 360
taagaggtac ataaggagtg agtctgcgag ttgcgctcat atggttgaag aaagcacggc 420
gaataacagg aagacggcag acccccacga gaagctgaag gctttgttga actcccctga 480
tgacgatacg gacgacacct tgcctccatc agatgctcct aaattcggga cagttataca 540
caatagaatt ttcgtgggag gcttctcttt gaccacgact gatgaggacc tgtggaagtt 600
cttctcaggg ttcgcgacgg tcacagcagc cagggtgatc tacgacagag ctggcgtctc 660
caagtgttac ggcttcgtca cattcgccag ccccagggtc gcgaggctga tcgttaaaca 720 gagcgggggga gtgatgttct cgccactggg gcgactgcgg gtggcacagg ctgtcaggaa 780
acagatgagc caactcccag tgctaggctc agaggcagcc ccgctccagg ctccactttg 840
ctaccagctg ctgtgtgctc cacccctcgc gcctctgcag ccctgcgcgc catgcgagtt 900
gcctccacca ccgtatgctg tgtacccgct gccgtttgac acaaccccag cgatctacgg 960
tcccccagct cagtacgcgc tggtgccagc tccatacagc actccatgct gtgagccctc 1020
atgctgtgca cccctcgaca agcagccccg ggtgccgccg ccaccgttac accccgcgtt 1080
catttactag actcaccccc caagaaatat attaaaggca ttctcgttta gatttggaag 1140
tacttaaaaa ttactactga tggtggattt aaggtatatt tgtgagagaa tgaactattt 1200
attggaagta aaacacgttc taataacagt atggaacata ataacaactg tatggtataa 1260
agcgcattgt acatggaatc gtgagtacag atgctgtgaa ttttttaatg gaatgtacag 1320
ctgtaacaaa gtatacaaaa agccagcaaa agataccgca agatacgaaa ctttaacaag 1380
ataaggccac aacagcaatg catcttgtag ataacgtagt atttgtcaaa atattaacat 1440
tctctatatg aaataagatt ttttccactg tcacgataat atctcctaaa aatactatca 1500
ataattctta tagccaatgt ctttgatata tttctgctca taacatcatt cgcgaagaag 1560
gtttatttac aaattgttca gcttcttcga tgtattccat cttgattgct caagtcttcc 1620
aatccagttc atgctcatct tcaaacataa ctcctctatg aataaactgt ctgtgagttt 1680
gtttgtgact aatctacgga catccagctg cgatggtgta agtgttcaag ttgtcacgtt 1740
tgtttacatt tctctgattg tctggtcgct tttatttata gacgtaagta cctatattta 1800
gcttcaacct ggtatattta agaaaccgtg gattcacgtg ctatcattat tattatagtg 1860
aattttattg gtgtatcaaa ttgctattta aatcagataa ccttgatcat tccgtgtcgt 1920
gactttcaag tttagataac aataattatg tcatccacat acctacaacg atctaaatgt 1980
gacatgcttg tatctgtgtt aaattt 2006

<210> SEQ ID NO 198
<211> LENGTH: 6665
<212> TYPE: DNA
<213> ORGANISM: Ostrinia nubilalis

<400> SEQUENCE: 198
agtgcgtatc tttaaatctg aaagcataca gtcttatctg gttgttgttt cggcgacaga 60
tgtggagtgc gtaaggccgc tccgcgcacc catgtacacc tcgcaaaatc gatagctcag 120
cgtccgtctc agtgtcgact tgttttccat cgaatttagt gctcgcttag tccgctagcg 180

-continued

```
tttttgttag aagtatcatg ttaaattaat aatggaatcg tcagtaaaga ggtacattag    240
gagtgattca gcgaactgcg cgcatatggt tgaggagagt gcagcgagtt gtagaaaagt    300
ggtggatccc cacgagaagt tgaaagcgct gctgaactcg cctgaggagg acacggacga    360
ctcgttgccg ccgacggatg ccccgaagtt cgggactgtg atacataata gaatttttgt    420
gggggtttc tcgttgacga cgactgatga agacctgtgg aagttcttct ctgggttctc    480
gacggtgacg gcggcgaggg tgatctacga cagagctgga gtctccaagt gctacgggtt    540
cgtgacgttc gcgagtcccc gggtcgccag gctgatcgtg aaacagagcg gcggagtcat    600
gttctccccg ttgggacgtc tccgagtagc acaggcggtc agaaagcaga tgacccagtt    660
accagtgctg gactcgggag cggcgccgct acaagcgccg ctgtgctacc agctgctatg    720
tgcaccgccg cttgcgcctc tgccaacctg tgcgccctgc gagctgccgc ccccgccata    780
tgctgtgtac cctctgccat ttgacaccac tccagcaata tacggccccc cagcgcagta    840
cacactagtc ccggctccct actcggctcc ctgctgcgag ccagcttgct gcgcacccct    900
cgacaagcag ccccgtatcc cgccgccacc actgcacccc gcgttcatct actaggccag    960
ggccattagt ttccagaagt gtgtcttctg aaagcctggc tctgggagct ggtaaggttt   1020
ttgctttgga atttccaggt tttgatgaaa tcggcaataa agtaaacttt tcaggaggct   1080
ttgattcctt tgaagatgaa gaaatgcgac tgcaaaggat aaggttgatg atgaaagtta   1140
tgatttcgtc gatagcaaag tgaagttttc aagaggcttt gattcgttgg acgtaaagga   1200
aaagtaaccg aatgcaaagg ataggattgt tgatgaatga attgttaagg aagtagacta   1260
attaaaagca ataaattctc aggttaagta gattggaaga agtaatgcta aggaagtaaa   1320
ggacaaaatg cctctcgaaa gttcttggaa attcaggaaa ttagcactca agccttgtaa   1380
catcaatgct cccagaaccc agaacctttt ggttagttct caagtagacc agtttcctgt   1440
tcattatgcg ttttatatct atcgcataat gttccagtca ctggctttga tatttgagaa   1500
cgatgacgta cacttttgga aactaatcta agtagatatt taagtgtgta tttaggggat   1560
catcgtcaga aactagaact ggttggtgca gtgagagcat cctcgttaat tttatcagaa   1620
gacgaataaa aatgacgtga attttaacgt aatcgatggg aaattttcga tcgtctgcaa   1680
gcttcctaaa taccccaatt ccatattgtc tatcaccact cccccattgg taattaaaca   1740
tggttcctct ccttaaggtt tggtttctta ggttagtttc atttgaaggt tgttcccaaa   1800
ttgttccttt tgctcaagtc ttccaacttt atcatgctca agttgtttca cttccattat   1860
ttcaagccat tgtaatcagg cgattttgtt gtggtattag agtaaaacta gctgtactat   1920
taaattttgc tgaatttgaa ataatgatag aggaaactta ttcgaaagaa atatcaggtg   1980
atctgtattc ttcttataat gatgagccta aatcctggtg ttttatcatc ttgctaatga   2040
agtgtgaaat atttcaatga agtttatatc atcatcatca ccaacagccc tttatagtcc   2100
actgctggac tcctttagtg gaggaaagtt acttgatgtt attcaataca aaggtgtccc   2160
taatgccaca agaaaatcgc ctgaacaaat tcctccatta ccctatttat agaatttcga   2220
attgattggg aaacgtgaaa gatctggtgt tgaaagtgtt catggtaggt ataactttct   2280
ggtgtgtttt gaccgttttg tctcctgtac gtagtctggt tgcttttatt tttagactta   2340
agtgttagct tggacaatcg gtgtaaaaac tgtgggttcg tgtgctatca gtaccatagt   2400
gtgtaatata atagatatat aaaatcattt taacttcttt acttgacgga aattttctat   2460
ttgcaagaga attttgtctg tcaccatgtg cagagttgtt cttagcaagt ccatgtacca   2520
caagataatt aatttctaaa cttgatttga aattcaaaaa tcattgaaga aattggtcat   2580
```

-continued

```
tttgaagtag aattttgtgg caaaagaaaa catgaagtga ttttatgtat ctatgaaaga   2640
tgggtgttag ataataaagt gcaaaatgag cacaacgatt catagcacaa aacggctaag   2700
ttgctagatg tagaagacgt tacctccgtg gaaaaagaca tatttgttgt attagcttgt   2760
tatccttgaa aaggagtttc gtttacctta gtgtaaggtt gttttcgaaa gcaattgaca   2820
tagacagaga tataaaccta ttttttaata aatttagttt ttacatgttg ttgattgtca   2880
ctttattaaa tctggggtcc aaatgtgaag gcatgtaaac attgaaactt atttctttta   2940
gcagatgtct gtggtgtatt tgatgtttat atttctacac atgaatgttt gttgaaaaga   3000
cgacgataag aactttgttt cagatataca atagttgttg cagtgttaaa taatcctttt   3060
gacgttgtta tttgcttgtt tggtaaataa atagatgacc aggatgttat agttctcata   3120
agactaattg caaagtcagg aacgtttatt aatatgatta gttatatcga attctattaa   3180
aaatgttaca ctgtcatgtc ttccttgttt ttctgagctt catcgttatt taccaaacaa   3240
catggtttat tttatagaca gtttgatggc taccttacgt taggtgtaat gttagttgtt   3300
attacgttgt ccacaagttt tgatggatcg aagtacacaa atcgtcaacg atgtgatatg   3360
ggatattcaa taacgtagca ttagttttat ttgttagaag acttaatagt tttagattca   3420
acacattttt aaataacgtc gtttgtctat cactcggaaa aataggacca aagacattcg   3480
cagaagcgtg caaatggtca cctgtagtag tgagtcacaa agtctcttaa tacgtaaatt   3540
cgttgtaagt gggtgttgat aatttttata ttcgtcactt ttagagctct ttaatagagt   3600
ttcctgtaga cctagagagc cgatgctctt caacatttcc aaattgtgtt gtattattaa   3660
aattttatca cgagaactag cttgctcgtc caagcaataa attcttgctc tgcccttagt   3720
aataaggctt atctcaatta ttatattaca tcatatacga ttagtattac tggaaatgcg   3780
gtcaatttgt cgttttggat ttttatgact attattgtta gtactaagtc tagtatattg   3840
tgtaatcttg cgatgctttt gtgctcaagg tgttatcttt ttttttgtt ttatttattt   3900
ggtacacttt tcgcaacttg ggctatgttt tcacagcgct tacaattaaa gctttctttt   3960
cagcttttaa tgtatgctag tacttggcta gtaagctttg ctttaggaac gacactggag   4020
catttggtaa gtgtgattga atgtacacac tcaaaaatag tcgcatctga tcttgcattg   4080
atttttctct ggccagcatg agatggtatt gccgtatcct ctaaaataaa ttttatctta   4140
attatcacag tggaaatcta agtgcttggc caggttgcac agacgggtgc atagcgtcaa   4200
acatataacg cgtacgggcg ccattatcga cactcgatta agatttcata atatgtttga   4260
gtacaacaaa gcgatgcgcc tttgtgtgca gcctggtcaa gcaccataag tagtactatt   4320
ttatcgtata gttaaatcgt cgttttatta tttcaaagca aagtgaaagc atagccatta   4380
attattgtgg tcgtataact atcatgatgt tatggatgtt tcggcatgtt ctgttgatgc   4440
aaagtgttgt gaactcgtag tctcttctgt gctatgtgaa gtacaagata ttttatatgc   4500
gagctattgt aggttattat taagcatgaa actctatcta tcacttatcg ctgcttggtc   4560
tctatcatga atatgtatgt ctatttcttt atgtggtatc aatagcaaaa tttgtaggac   4620
aaacaaaact ttttcatttt attctgtcta aactgccaag tttatattat tatcttttct   4680
cttcaacttt tttctactat ttctttaaat attattcaac ttaaagtacc tagtaatact   4740
cattattgtt acaagcatta tagtagtaaa gtttccgtat taaatggaaa aaaatatcaa   4800
tttcgtgtat tgatggcatg ataagagttt gttataggta atttatgatt ctagctacaa   4860
taataataat tatgcaagat atagaatttt taagtaatta ttttgatgtt ttttttata   4920
```

```
gtattttata tcagtaaaaa catatgtatt catggtattg gccttttcta ccaatattgc   4980
gtggcctagt gacaactgcc tgacatatcg gataattaat cactatgcta tagtatatta   5040
tttttgtat aacttgtctt gtatataatc tctcgctaga tatattagat tcgtgaaatt   5100
aaaatgatgt aatttagaca atattactct aaactatatt aggaaaaata ctaaggtaag   5160
taatatagtg taatctatgt ctatattctg tgtaagtgga tcactcctat atcttttagc   5220
aaaggcttag aaaacgttgt gattcagaag ttttgaatat ctaaatgttg ctaaattgtg   5280
taagaaatat aaaagtatat tagggaagct accctcctca gatatcgcta gattagcagt   5340
aaaatttgc agacacgtct ttaataaaat atagcttaaa ctgtcattta tattatatta   5400
tcattaataa tatatttgtt cgtactttat attattttct agctgaaact gttaataata   5460
ttcaaatttt catataggta atatagccgt tcaggacttg aaacaaaaac atttttttaa   5520
tccgtttacc aaagtacttg aacaaaaaaa gcagcagtca caccagcaaa tgtcaccttt   5580
gattatattt ttgttatttc atagaatata tctaaatccg tctgaatttc cgctgattta   5640
tttatactta tatgtatata cagggacgat gacaatatac aaaagttgtt aagaaaaaat   5700
aaacttttg agtagttggt aatcctgaga agaatgaacg tccaatttgt ttttgtttac   5760
atttcgcaaa ggcagaatgt atgctgttta attgtaatgt tgttaccatg ttgatatcaa   5820
atatcaacag ctgtgtgtta tgtcatccgt taaaaatagc atcattatta gcaagaataa   5880
taaatcataa tttaacaata ttatttagtt gattaataaa ttatattatg gttgtcacct   5940
aaaaggctta aaatgactac tttttcagta gttaattaat ttacaaattg taaaacaaaa   6000
aagcaatcga aaaaaactta acattcatgt tgttgttcaa attctatttc taaatctcga   6060
tggtataatt attaaggtgg atacatactt tgtgaaacga acctacatta ttatttcagc   6120
aaatgcttca caatcaaaat gcctcagtgt gagctgtgca taactatgca gtagtagagt   6180
agctgttcag catgctcttt ggaacatatt tacgtgaatg acatacaggt agatagattg   6240
tatttgcttg cttttcacgc aaaggataat gctggtatgc ttacaaaagc acctttaaca   6300
gaggcattcg ttttacaccg tgtacggtgt atgcctcaaa aagtctgtat ctacctttat   6360
atgcactttg cttcggcggg tagtctacat gggagcttcc ttatttctat acaacgactt   6420
gtaatataac aaaagctttt gaaatattct aaactacgcc taccagaaat tatctattta   6480
actagtcaaa ctctatttaa ttttattcaa accaagaagc tgtcacgcat ttgtctaaag   6540
cgttaccgct atttagttat gaagagttca taattattgt tgtacttaat aatgagttgc   6600
taactaatta actgcgtact taaataaaaa tatatcaaaa taatatttat atttttgtc    6660
caggt                                                               6665
```

<210> SEQ ID NO 199
<211> LENGTH: 6032
<212> TYPE: DNA
<213> ORGANISM: Spodoptera frugiperda

<400> SEQUENCE: 199

```
gtcaaccgct gacctagttc cctcgcctag taaaaatagc ggtcgacaat agctcaaaca     60
ctatttatag tgcgtatcta aaaaaatctt aaatcacaca ctgttatctc gcttgttttt    120
tttttaaaca tcactcgaat accgtccgtg tgtcagtcac gtcgtggccc gtaacgcgca    180
actcccaaaa cctacctata caacataagt gccaccgtaa tcgataaaac ctcgcgttac    240
agacaatcag ttgtttttc gtgaatacca gtgccctttt agttgccgct agagatttta    300
gtttagtaaa caagggaaca tgttatatta gtgttttaaa gtgttagata caatggaaag    360
```

-continued

```
tgttaagagg tacataagga gtgagtctgc gagttgcgct catatggttg aagaaagcac    420
tgcgaataac aggaagacgg cagacccgca cgagaagctg aaggcgctgc tgaactcccc    480
cgaggatgac acggacgaca ccctgcctcc gtcagacgcc cccaagttcg ggacagtcat    540
acacaataga atcttcgtgg gaggcttctc tctgaccacg actgacgagg acctgtggaa    600
gttcttctca ggtttcgcga ccgtcacagc cgccagggtg atctacgacc gagctggtgt    660
ctccaagtgt tatggtttcg tcacattcgc cagccccaga gtcgcgaggc tgattgtcaa    720
acagagtggt ggagtgatgt tctcgccgct gggacgactt cgggtggcgc aggctgtcag    780
gaaacagatg agccagctcc cggtgctggg tacagaagca gctcccctgc aggctccgct    840
ctgctaccag ctgctgtgcg cccctcccct ggcaccactc cagccctgcg ccccctgcga    900
gctgccccccg cccccatacg ccgtctatcc cctgccgttt gacaccacac cagcgatcta    960
cggcccccca gcccagtacg ccctggtacc agctccgtac agcaccccgt gctgcgagcc   1020
ctcatgctgt gcccccctgg acaagcagcc cagggtacca ccgccgccgc tgcaccctgc   1080
attcatctac taaactcact cactcacgaa atatctcgaa gacattcaaa ttcaaggtaa   1140
ccatttcata ctagatgtcg agtaagcgac aaaaatgtat tgtgaagcta atatagcaaa   1200
aatcgaacag aacatagttg aaattagtaa aacagataga gttaatatgt gtaccaatga   1260
tgtaactagt caggtgtaag tcaaaacaat aatggcaata attgtggaca acgaatgtaa   1320
tgcactaacg taagtactga gttttgtttg tagcactgat cgtgtacata gatgtaatgg   1380
gatgacgcgc tgataacgac ggagtaccga gcgatctaaa gataaagcga gatatcaact   1440
cgaagcaaga taagacgaga gcgatgcagc tccttacaaa tacatttcac cacgtctgtt   1500
tgttctatct cgttcctctc ataaataatt catatttcaa tgtcttcgat atatttccac   1560
acgacaccat tcgcgaagaa gattacttta ctaattatat tcagcttctt cgtatgtatt   1620
ccatcttgat tgctcaagtc ttccaatcca gttcatagtc atctgtcttc aatacattac   1680
ttccctataa tgaaactatt tgtgagagat tgtctgtgac tattcaatgg acatcaaagc   1740
tgagagaagg cgatgtatgt gttcaagtta gctctcgggt ttgtttagat ttttctgaat   1800
gtctgtcttg tcgcttttat ttatagattt aagatattta gcttgaaact ggtatattta   1860
agagaccgtg gattcgtgtg ctatggttat tattatagtg aattatatcg atgtatcaaa   1920
ttgatgtttg aataaaagtc gtgcgatgtc ccgtggaaat actttaacca caaatattta   1980
atgtcatctg catgtataaa tccaattatc ataatgtgta tattcatata tctatttaca   2040
cagtcttgta tttgaatgcg aaaagtaatt caacattttt atcaaagtta tcgctctata   2100
gtaatattgt aacgcgccca agggaaatca atttgataca tctttagttt ttctcatgat   2160
aagtgtgaaa ataccgaata taaaataact ctagtgcgga tatttctaca aaatatttaa   2220
ctgaatcata tttacagaat gtatgttaga gcagtccaca gcctcggtct aagtcattgt   2280
aataatgttc acgtaatgta tgctaatgaa attattcaaa tatgtaccgt acctagtttc   2340
catatatccg cactcgagtc aagtatttac aaacacagtt caaaaatgtg cgttataagc   2400
acaacgaatt aagcacaaaa tcgaatagca gctagtttta gatgacgtta cctctgataa   2460
aagacagatt tgttattgct tgttatcctt gaaaaggatt tttgtttatc cttagtgtaa   2520
gattgttttg tgaaacccca ctgttggttg gcggacgtct tgggggtggt gggagacacg   2580
attttgatag aagacaattt gtagaataat cataacttgt aattgagtaa gaagatattg   2640
gtaagagaga tatatcgctt gtacgagctg tagatgtgga ggtaggtaga caattagaga   2700
```

-continued tcttatcggt tggctgcttg cctacttaac gagggaccta gtttgaagat aataatagta 2760
cttttagagc cagattttag aaccaacctc aagacgtcag acaacgcgtg actagaacag 2820
agagaaacaa aaatattttt taatattatt tagtttttac atgttgctgt tgaaatacac 2880
tggggtccaa tatgtgataa ggaaatgtga aattcaaagt tgaacgaaca ttttggaaat 2940
cacatttcta tacccgttat tgttgcgttg gaaataagaa tcgaatcagt tttatgatg 3000
cacacattaa cttgctaaga cgtgacgtgt ttcagtaaga tctacttaaa gttaccggag 3060
aatgttgtca aagtatttat gaggaacgaa atgaagtata gatgttactg agacatgtta 3120
acgatgcaat cacgaatagt atttgttttg taattgttaa cattgattga acagccgctg 3180
ttcgcttcga agtgatcaac aatagacttg acaaacggat ccataaagca ataatgtcgt 3240
caagatgtga tatgggataa tttgttgact agcaatagtt ttatttagat acattagaga 3300
gtagattgtt ttaaaatcct tcattttacg gcccgttgca tcgtatttaa cataaatatt 3360
gaagaattta aataattatt gtataaggtc tctagcacat gtgataactt ccatgtcctc 3420
gttcttcgtc ctatggcgta tatgtggctt gtctaagcta gaatttcccc ctgatgcaat 3480
tgggttctca cttagtacca gattatttat aggaccaaac aaagattccc ttacatcacg 3540
actaacgcag agatcttcgc atctattctg tctagactag tatacctatc acaaatctct 3600
atacgtaaaa ttgttgtatt aatattaatc attttgatat tatattctat cactttttat 3660
ggccgctagt tgtgtgatgc tacggtgaat gaatttgcgt ttatatcaag gtcttccttg 3720
ttgtttttta tatcactggt taagacaact tcactgttat tgttattatt tattttcatg 3780
tttactgtcc cattgtttgt aggtgatggt tctttaagat caatttctag tactgtcgtg 3840
ttattacctc ataggtttga ggtaatgtct acatgattct tccactagtc agatcgacag 3900
attgtcagca gagttagcag tacctgttag ataagtaaag gttccattaa tttcttcgtc 3960
caaatgttaa gttgtttcta ctctatcagc aagttcattc acccaagcac gttcgatgtg 4020
gtcttctgcc tttagatgta aggctttcgt ctcaattact attgtacatc ataattatac 4080
gattagtgtt attgaaaatg ctgtcaattt atcgtcttgg atttttataa tgtatgtatt 4140
tattgttagt tgtaagtata gtacttatgc gatgcttcgc tcgagtatca tttatgtctg 4200
tatcttcgtg tgcttataac ttaagttcct tggatttgtg ttacctcaga ctaaagttta 4260
tatctaaaat attgttgtta tatcatattc tatctatgtt ggttcatgcg atgggagttt 4320
tattttgaat ttggggaaaa tgggccatgt ttgtggaatg tcgttattgt ccgaaacgtc 4380
aaaagatact aactttaatt caaggtcact gaaagtatga ttcgatctaa ttgaagattt 4440
taatcatgat caaggtttag agcagctgat gtgttcacac aaaatccgta acgaaatatg 4500
aaaatgtctt agagatggct gttgctaggg ttgcttcaat gttggtcagc tatgaccatt 4560
ttctccaaca tcaaatcatc gcgtgaacca gattagcact catcgtatac atttcgatgt 4620
tgcactatcg atgtttcgag tacaaggaat ctatatccaa gctaaactta agtctaataa 4680
ctatcacttt cattgcttct aaggtttctc acgtaaatac atattaagca ttcaaaaacg 4740
catttattaa gattgaaaca cccataaaaa attgtgaaaa atgtcttaaa ctgtgagttt 4800
ttgttccaaa ttatgaatta tacgactatg aagtgctcat atagcaattt tttgatgaaa 4860
gaaatgagtt gttttctgct gtagatatgt atttacgtga gaaacatact acgaacataa 4920
taagtggcct agagacatac tgcctaacat atcggataac gaatcactac gctatagtta 4980
gttatttttt ttataactgt atataatctc tcgctaggtg gtcatagttg tgtggacgaa 5040
tataatgtta gacaatatta atgtaattat aggttaggaa gattaacgtg tatttattga 5100

```
aattgtcact tatcttagga ttggcttagt attgtgaatt gtttttata ggactgactt   5160
tagtatggga agcaatgatg gtaatgagta atttaaagga gaggatgtgt taagaaaagg   5220
taaacatcga gtgggagaaa gggatgttta aagatttcta tttaaagtag aggttcaatt   5280
tatccttgga ataaagatca gaatgcaaaa gataactaaa aatgagatta taagaaagga   5340
ccacacacat aaatggtcat ttgacttcct aaaatcttgg agattttgaa ataggttctc   5400
tggaaagcgt tagtgttctc ttaaaggata attagagtca gttctataaa aacactatct   5460
gtcgccatgt gaactgtagt tataattaat tttagtgtga aagctatcaa tagcagtagt   5520
gacactcact gtatcactgt cggtcacttt ctcatcatcc tgattggtta ctggttcgat   5580
attatctttt attactttat cattattatc tgtaccctta gtacgaattt gctttacgtt   5640
taacgagatc gaaattttag cgcatttggt actctgattg gttggtttat tgtagccggc   5700
caatcacggc gctgaacgcg gtaaagcaaa cttatactaa ggtctcagta acccccaaaa   5760
tcacttcgat gtcgtatttg tttgtgactc gatatcggat cggaaaatct gaagacgctc   5820
ctattgaatg cggtttttat tcctacatgg aacaattaat ttggaatgtt ttcttaaatt   5880
acggtacggt acctatgttt tctcgtacaa aattcaacgc gttcggtgct ctgattggcc   5940
tggttaattc gcaacggcca atcagagcgc cgaacgcggt ctcatttcgt taatgagcac   6000
aatttttata gctgttagca ctcagatttt ag                                 6032
```

<210> SEQ ID NO 200
<211> LENGTH: 3624
<212> TYPE: DNA
<213> ORGANISM: Diabrotica undecimpunctata

<400> SEQUENCE: 200

```
aagaataatc atacaacaac tattaccggc aaagtttttt cgaataagtt gttcatggtt     60
taatttgttc caggagacca ctttaattta gagcccactt aaaatgccac ctaaaaacaa    120
atctagaaat gcattttact actttatgga agatttcaaa caaagacaag gatttacttc    180
taaatccatg aaggatgtag cagaagctgc aggtccccat tgggctagga tgtctaaagc    240
agaaagaaga ccttatgaag acagagcaaa caaagagaag ggaggtttga gatatacttg    300
ggatggacaa tgcgttgaag aaatagagaa gagacaaaaa gctgaagaaa ataatattgc    360
taaaatgaaa gatgacatcg actgcacctt gaaatttgcg aaagaaaatt gtcgcctccg    420
agatgaaatg ttcttcttaa tccatatcaa tactttctgt tatcatgcca gtggtaatcg    480
gtattatccc gctgaaattg ctatttcctg ctttagtttg gaagatggcg ttttacctca    540
aaatgttttt cataaaacta ttaagccagg tagactaccg ctggggtatg ctagtgatgc    600
aaaaaagcaa tctgaagatt cacatcaact tcctatccct ttaactggtg aatatgacga    660
caatgtggaa gaagtttata cagaaatgaa agagttttta tcctctaaaa caggaaattc    720
aaaaaatttt cctcccttat atgctaagaa agatatcgtt aaaatggttc aacacgtgtt    780
agatagttgg tgcgctgatt ttgatgagcc gccattattt aaagtttatt atttacagta    840
tatgtttcaa gtactaaaaa actcggtagc taatgacaat gtatggccct tgtattcaat    900
ggcagagacg gaagttgata aggatcttta ttcccatact gctggaatat gttgtgactt    960
tcattctgtt agtgaagctt gtcaattctg tagccgttct gtggttgtca gacttgctta   1020
tacaatttgt gataattgct gttcatttct taatattcct atagagtctg gaagacatgt   1080
acctgatcaa gcttttacag catccagttt gagttcaaga gcttcatcaa aagctagttt   1140
```

-continued

```
gtattcagct tctagtaaat cttctaagaa gcaatcagtt cgtgaagatg acaaagacac   1200
cgttatatcg ttttctagtg cctctcaatg ggagaacgaa tctgtaatgt cagactcctc   1260
tacatctact ttcaataatg gctttccagg tttgaaatct aaatggacat taagcaattc   1320
tcaacctgta gcatccgact caatgagcca aatgtcaggc ccgagctatg caagtgctat   1380
gggaaataga agacctaata gagattttc tagtgctgtg ggaaacagag gacctcaaaa   1440
agagtttcct aaaaattccg ataatgatca ctccagtgat tcgactaccg attatttaaa   1500
cagtcaatca tttccggctc tgggaagagg aagaggtttg ggcagaaatc gacgaaattg   1560
atcattttg actgcaatgg gtcttgttcc acttcataag attgttaaaa gaatatgtaa   1620
ctgtttacat taggcggcta gccaatactc acattgtctc taaaaccact aactgaacaa   1680
ataatcacta actattgctt ttattatatt acagcgaaat taaacaactt tatgagactg   1740
ttttacctta attcacaatt tttctttata tgtatttgaa taaaatagaa acaaatctaa   1800
tacttcctct gtcacttttc tttaaaaggc actagatggc gcctgatatg ttgatataat   1860
gatctaaaat cgcccgccat gtaaaaaaaa caatttgcaa ctttctgctt taactctaga   1920
atactaacct tatttttact atcatttaca ctaaccatcg taaaatttac tacgctggga   1980
aaaaaatgtg gttgctgaaa aagtatttta tataacgcaa ttttacaaat tattttgaac   2040
aaagagatgt ttctaaaacc tgaaaatcac aaaaaaatat aaattctaaa ttttagaact   2100
acactgctga caacaaaggg cgcgatgttc accacaaaat ggacgtcggc agtgttcgca   2160
atgatgagtt gtcattcgac gtttttaga cggacaaaat tgacacatgg cacgttttga   2220
cacagtaggg catattcgtt cttgctgcgg ctccagattt aaaatatttt caataagtaa   2280
ctttaccgag cggttcaaag ttggccaatt tacacgatgc tgtagccaag gtttagtcag   2340
ttgttcagac aaaatggcca taaatttttt tctggtgatg gtttttttct gctgtcgttg   2400
ttggttatga ttataaatta tccaagagtg tatgcaagct atatttaaca tgccatagaa   2460
caggcaaaga ggccatcttg ttttttaga gatgttcatg tttccgcaca tttggtcaaa   2520
ttttggtcaa tccgtacttg gttgcattat aaaatataat gatatctggc tttcctgttc   2580
gatcacattc tactggacca ttgtggattg tcgacagaag aagcacagac ttatttactt   2640
ttgtcttata ggataccatt gtttttcac catcaaagca aaataaggaa tgaccaattt   2700
cacgattttt gagatttatc atctcgggag gtatttctct tttattttgc cgtagggtac   2760
caacaatagt taaatcgtaa ggaggtttta agagctccgt tgctagtggt actgacgtaa   2820
accaattatc catggttacg ttacggttac ttccatactc accctgagtt aattgtttta   2880
cataatattc ttctagaggc tgtccgttga tgttagttcc atcgaacata tatttggtat   2940
ttacgtcaca cagcatctat tttgagtcca tatttggctg gcttgtttgg gatatataga   3000
aaggacatct ttccctaaaa gccaataact actcatcgat tgttaggtat gatccgggct   3060
tataggacgt tttgcagttc tgtataagat catcccatat ttcacgaatg gctgctgata   3120
ggtatgtttc gtttctgcct ggtctagaca ttttatcatc aaaacgtaga cattccataa   3180
gaaattcaaa tctttcccgg tccataattg ctttttatat cgccccagaa attttgtgat   3240
aaagcatttg tcttgtcgct aaatgattgt ccttttgggc agcagcaaaa ataagtagtc   3300
ctagaagtgc atacaattcg tcaatattta gtttcgagtt tgtaagtttt tcgactttat   3360
atttttgtgc cctaacagaa atttcggcat ttgtatattc tagaattttt tccagtgaat   3420
ttggactcat aaaacaatga aaagcatcta agggagtttg tgcttccttg gttttattag   3480
tgaggccttg aacaaaatgt acgaaattac gttttggagt tttagttgcg gcctttggtt   3540
```

gagaggacca tctgtgtcca tttttacctt ttagactcga cagcaaccga gtttgcttcc 3600
ctttagctgc aatttctgga gatt 3624

<210> SEQ ID NO 201
<211> LENGTH: 1520
<212> TYPE: DNA
<213> ORGANISM: Leptinotarsa decemlineata

<400> SEQUENCE: 201
atcactttca ataaattcat tcaattaaag gatttttctt atttgtgaaa ctcttcaact 60
acaattacaa tgcctcctaa gaaaaaacag acttctggaa atgctttctt ccacttcatg 120
caagacttca aaaatagaca aggaagacat ttcaaaaata tgcaagaggt agccgaggct 180
gccagtccgc attggaacag gatgtcaaag gaacaacgaa aaccatacga agagatggct 240
ttaatggcta agaataattt gcgtggaggt aaatttacct ccgatggttt ggatattgaa 300
gtattagaaa atattgagaa ggaagagcag gcaaaaattc aacagatgaa aaatgatatt 360
aattatatat ggaaagtggc gagttcaaat ggaaggattg cagatgaact tatttttatt 420
atacatatca atatatttgt ccattgtacc tctgaagacc gacattatcc agcagaaata 480
gctattgcct gtttcaactt agaggatggt gttttgccgc aaaatgtttt tcatagaata 540
ataaaacctg gaatgctgcc tttaggctat gccagtgacg caaatgcaca ttctaagaaa 600
acccatcagt tacgaccacc gatggctggt gaggacgata ataatattaa agaagttttt 660
gaagaaatga agcactttct ttctaataaa ttatctggat caagaagaat gccaattctt 720
tacaccactg aaaggaatat gaaaatgatt caacatgttt tagatacgtg gtgttacgat 780
tatgacgagg atactcccct ttttaaagtt tatagtttgg aatatatgtt cagaattttg 840
aggaacactg ttgctgggga tgacgtttgg acaaccgata cattcagtac gagagaaata 900
gaaaaagatg tgtacagttt tgctagaggt atttgctgtg agtatcacga agttaccaat 960
gtacccctat attgcagtcg ttcaatttgt gttaggcaag ctttcaatat ttgcgataat 1020
tgctgctccg atctgcgtat caccttatta cctggagtac acttacctga tgctgctctg 1080
acgacggtcc gaagaggatc tagtagaact gcttcatccg cgccttccat ttcttcccaa 1140
tcttcaaaat atactaattt gaagcaatcc acacgtgacg acgattccga aagtgttata 1200
tctttttcga gcaaatcaga atgggataat caatccctaa tctcagaaac gtcaacttcc 1260
gcaactttgg atagcgaagc caattttcct tcacttggag caagaaagaa agtgacctca 1320
tcaccattca acaacttctc ttctaatgac ttgaacagca gtcagagtaa cacctctagc 1380
gtcaaaagtt acgcaggtgc catgggtaca tcagggttga gcaagcgtgc aatggatatg 1440
ccatcatctt ttaccaacac ggaaagaaat tttgaatctt caaaatcttc agattatgct 1500
ccgggccgag gaagaggcgg 1520

<210> SEQ ID NO 202
<211> LENGTH: 1554
<212> TYPE: DNA
<213> ORGANISM: Phyllotreta striolata

<400> SEQUENCE: 202
aatatgtgca ttcagcatta acattcaatg tttaaaagtt tcgttattaa attttgaatt 60
taaggaaatc gcaaaccgct tgatttgtta aaatggcgcc caaaagaaaa gaagccccga 120
aaaatgcatt tttctacttc atgctcgatt tccagaaaac acagggccgc aaatttaaaa 180

```
atttaaaaga ggtttctgaa gcagcaggcc ctcattggtc taaaatgtcg ccggagcaaa    240

gacaacctta cgaagatcgt gcaagaaaag aaagatccgg cgtcagatac accacgactg    300

gcgaaaatat agatgacata gagagaagag aacgtgaaga acaaatgaga atccaagaga    360

tgcaggaaaa aatcaattgc gatttaaaaa tggccaacga ttcgggccag ctccaagaca    420

agctcttctt tatcatacat gttaatattt tctgcgaggc tcaaggtcgg tactatcccg    480

ccgaaatagc tatagcctgc tttagtcttg aggatggagt ccatccacaa aacgttttcc    540

atcatatcat caaacccgga cctcttccct tgggatatac aggaactgct aagctgatat    600

ccgatgaaac acatcatata ccatatcctc tagtcgacga ctgtgacgac accacagctg    660

aggtgtttca tgacatgaaa caatttttat tctcgaaatt accgggtaaa acagttcccg    720

ttttatacgc tgacgagaag ctagcgaaaa tggctcaaaa aatattagac acctggtgcg    780

aagatttcga agacgactgc cgtttcaaag tctttaatct ccaataccta ttcatggagc    840

tgaaaaactt cgctgccaat gacacggttt ggcctaacgg aacgatgagc gccagagaac    900

tcgagaaaga tccatacgta tacgccagag gcatcgtctg cgatttcac gaaaggaata     960

acgtttatac ttattgtagc cgttccatag tgatcagaag cgcgttcgtg atttgtaaca   1020

actgctgtaa gcacttaaac atcgttttaa atcaaggaac tcacgtaccc gatggagcca   1080

tgacgcctgc ttcatctaga gcctccagta gggccagtac ggtttcttcg agatcctcca   1140

aattccagcc ttcgattcat gatgatgatt cggaaactct ggtttcgttc tccgtcaaat   1200

ccgaatggga cagtcgatcg gagatgtcag aaacgtccga attcagcctg actaatgaca   1260

atttccctgg gttggggttc aatccgaaga gcgcgtcttc taattcccaa ccttattatt   1320

caatgtcgca ggaatccaat atgagccagt cttcttctag aagttacgca ggggcaactg   1380

gttcatcgaa atggggcagg gaacctgcaa atagttctgt tccacagaaa ttttccaatt   1440

taaacataca ccaatcttct agtaatttta acgaaggtga caatccagtc ggagctctca   1500

gggatccgag acgttatcct gctttgggaa gaggaagaag atcataagtt tttt         1554
```

<210> SEQ ID NO 203
<211> LENGTH: 1574
<212> TYPE: DNA
<213> ORGANISM: Phyllotreta cruciferae

<400> SEQUENCE: 203

```
gacaacccta cgaagacctt gcaaaaagag accgagccgg tatcagatac accacaacgg     60

gcgaaaatat cgaagacgta gaaagaaggg aacggcaaga acaattggac attcaaaaca    120

tgcaagaaca aatcaattgt gatctaaaag cggccaacga ttcgggccag cttcaagaca    180

agattttctt tattatacac gttaacatat tctgctatca taagactcaa gatcggtatt    240

atcctgccga aatagctata acttgcttta gccttgagga tggagtccat ccgcaaaacg    300

ttttccatca tctcatccgg ccaggacctc ttcccttggg ctacgctgga gaagctagga    360

tgatatccaa cgagacacat cgcatacaga tgcctttggt agacgattgc gatgacaaca    420

cggcagaagt gtttcatgac atgaaacaat ttttaatatc aaaatcacca ggtcccaaat    480

gtattcctgt tttatacgct gacgagaagc taatgaaaat ggcgcaacgt atcttagata    540

cctggtgcga ggatttccag gatgattgtc gtttcaaagt gtacaatctt caatatttat    600

tcatggagct gaaaaatttc gctgctaacg acacagtttg gcccaacgga acaatgagcg    660

ctagagaact cgagaaagat ccatttgtat acgccagagg cattgtatgt gaatttcacg    720

atataaatag cgtttatgtt ttttgtagcc gatccatagt catcagaagc gcgtacgtca    780
```

```
tatgcaacaa ctgctgcaag cacttaaaca tcgttttgaa tcctgggact catgtgcccg    840
atggagccct gacgcctgct tcgtccagag cgtctagcag ggccagtacg atttcgtcga    900
gatctactaa attcgagccc tcgactcgcg atgacgattc cgatactctg gtttcgttct    960
ccaccaaatc cgaatgggac agtcgatcgg aaatatcaga aacgtccgaa ttcagcctga   1020
ccaatgacaa tttccctgga ttgggtttca atcccaagag cgcgtcttct aattctcagc   1080
cgtattattc gcaagattct aacacgagcc agtcttcttc cagaagttac gcaggcgcta   1140
ccggcgtacc gaaatggggc aacagatctg taaataatgc tccgtctgct tcacacaata   1200
tgtaccaatc ctctagtaac ttcgatgaag gccacaatag aatcggagct ctgaatgatc   1260
cgagacgtta tcctgcattg ggaagaggaa gacgaacata aaagttttta cccttttttt   1320
aacgcagtaa attttgttaa atttacaatg tatctttaat catttgttca caatgttttt   1380
tttttgcaag agttgatttt atttttgtca cattgttatt aaaatgtgtt tagaagttaa   1440
gtttgagtac tgttacattg ttgttgtcag aacaaatgta aatacagttg taataataat   1500
ttaacttggt acacgaacaa gtgtatgaaa attaatatga ttggtaaagt tgtgtaaaaa   1560
aatgttatta tttt                                                     1574
```

<210> SEQ ID NO 204
<211> LENGTH: 1695
<212> TYPE: DNA
<213> ORGANISM: Epilachna varivestis

<400> SEQUENCE: 204

```
gtcagttgct tctacgggta attctacgat tgtgtgtatc agtctgtcta ctttttgtat     60
taaaggaaat aagttttcgg gcatttggtt attgattaag tttccaccag aatgtcgaaa    120
cctaatgcat tctacttctt catgttagat ttcaaatcaa aacatggcag aacttatact    180
aatatgaaag atgttgctgc agcagctgga ccacactgga aaaacttatc aaaagataaa    240
aaaaaagtat atgaagaaag agcaaaagca gccagaggaa ctgaaaaact caattcagat    300
agaagacctg tggaagagat tgagcacatg gaacgtgaag aaatgcggta taaacaatct    360
atgaaagatg acattacgac aacattagca actttgaaga gggaaaatgc actaaagacc    420
catctattct tcatagtaca tatcaatagc ttctgccagc atgatcacac taaaatatac    480
agcccttgtg aaattgctat tgcggcgttt tcattgcaag atggagtgca gcattctaat    540
gtctttcatt cgatgatcaa accaggtctc gtgccccttg gatatgctgc tgttgcacaa    600
cagcattcaa atgaaactca tcaaatcgat ttgccgactg acgatgaaga caaccaggat    660
aatatattcc ttcaagttat tgaattttta tcacgtagaa aaggacattc tgaaaaactt    720
cctattctat atgctgctga aaaaaatatt cctatggtaa gtggtgtatt tgaggattgg    780
tgcactaaag ttgatataga tccaagtcgg tttcgaattt ataatctgca gtatatgttc    840
aaaatattgc gcaacacagt ggcaggaagg gactgttgga catcagatac catgagttat    900
catgaaattg agaaggatgt ctacaactat gcttcaaata tagcttgcga atttcacgaa    960
acctgtgata tactcacttt ctgctctcgt tccattgcta ttcgttatgg ctatacaata   1020
tgtgataatt gttgcgaaga tgcgaatatt gaacttattc cggggcgtca cgtgccagaa   1080
ggctccatga caactccgga tttgagttac gagattgtga aatcatcccg aaaaaagaaa   1140
tctaccaagt atacatctga tagcagtagt attagggacg atagcagtga tgttgacact   1200
ctaatatcaa atgctagtgc aaggtgtcga aacattgata gaagaggtga tccaggtcaa   1260
```

acaagtagtt actcaactga aagttctgca ggccttgcaa ctgctcaagg ggccagtagt 1320
agtgttcatg ctactggaag ttacgccaga gcaacaacct caaacattgg aagttctgga 1380
ttcagcaaaa ggcctgcagc tatgcccttc aatgtaacag aagatttgaa tgctctgaac 1440
cttaatccag aatcaatgga tgctcatttt cccactattg gcagtagcat gggaagaggt 1500
cgtaatacta accgaaatac tattctaaag ggaagaggaa gaggaaaccc gttccagagg 1560
actacatcga gatcataaac tcgtaataaa ttgcccattt gtaatttttt ctttatgttt 1620
attttaaatt cttatgacaa gttcttattg atgaattaaa gaagtttact attgtttata 1680
ctacttaagg acaat 1695

<210> SEQ ID NO 205
<211> LENGTH: 1314
<212> TYPE: DNA
<213> ORGANISM: Tribolium castaneum

<400> SEQUENCE: 205
atgcctccta agaagaataa gaaatccggc aaaaacggct attgggagtt tgttttggat 60
tgtcggaata aacatccaaa taagcaaaat atgcacgaag tacaagaata cgctgcaagg 120
aaatgggcgt ccatgtcaaa ggaagaacgc cgcccgtatg aagaacgtgc cctactagcc 180
cgagaaatgt actctcctgc caggtacaca actgatggta ttgacattga agtggttgag 240
agaaaagagc gagatgaagc aaggaagaaa caagaaatga aagatgacat tacgcgaaca 300
ctgaaagcgg cttatttcgc cactgatctt gacgaaaaaa tattcttagt tattcatatc 360
aatcatctgg cgtattaccc tactgaggat aaatatttta tttgtgaaat agccatagct 420
gctgtaagtc ttaaaaacgg agtggaggat gtgtttcata gaattgtcaa acccggaaaa 480
cttccgttgg ggtattatgg aggagcatta actcattcga aggaaactca ccaaatgctt 540
gagttggttc aggatgaacc ttatgagaac aatactcgtg aagtttttaa tgaaatgact 600
tctttcctga aactttggag aggcaaggga agtgattcta tcgtttatgc ggatgagaaa 660
actcatgaaa tgataacaaa agtcattgat aatttttgcc aagaattcaa ttatcctgac 720
gaaattaaag tctacaactt ccaatatctg ttttttgctt tgagaaactc agtagctgcg 780
cgaaccgtct ggcctacaga aacctacagt tctaccgaac ttgaaaaaga cctctacagc 840
tacacacctg atatttcttg cgaatttcat gaaatgtcgg acatttccgt ctactgtagc 900
aagtcaatcg tgaccagata ctgctacaca ctttgtgacc attgctgtac tgacttaaac 960
attcaactag tggctgggtt tcacgtcccg aaaaattcca gaattgcggt agattcgagc 1020
aggactaatt ccaaagcccc ctcagtctgc agcactgatg attatcgtca agccgcgaga 1080
agccgagttg gttcattcag ttcaacatac gatgagaatt atccagcttt ggggagcagc 1140
agatcaagcg cttcttcggt tgtaagtttc tcctcaatga ggactccccg aaatgtggga 1200
caaccgacca aagctgccac cagaattgaa caatccttca aagccatgtc tgtgagagat 1260
caccgcaatc tgaatttccc cccgaaaggc tacgaaaaac aaaatgaaaa ataa 1314

<210> SEQ ID NO 206
<211> LENGTH: 1644
<212> TYPE: DNA
<213> ORGANISM: Vibidia duodecimguttata

<400> SEQUENCE: 206
aattgtcatt tccataatct ctgacccaaa aacttaataa aatgccaaag aagaaaataa 60
atcctttttg ggcattcctt atggactata aacgggacaa taaaattgag tcaatcgatg 120
aagcaaaggc taaggctgat gttatatggc gaagcatgac tgaagctgaa aagaagatgt 180
atgctggaag atcaaaacag tctcaagcat ccaatgaggc tccattgact ccgattgaaa 240
ttagagacaa agaagaaata ttattcaagc aaaaaatgct ggaagacata actgccgaat 300
tgaatattgc tcggaaatac aacaaattgt ctagctctaa atttttcatc atacacataa 360
atagtttttg ttctgaccat caaaggaatc gaacatatcc ctgtgaaata ggtatcagca 420
gtttttcact tcagagcggt gtttctaaag atgatgtgta ccattcattt atctatccag 480
gttctttgcc gcctggatat tctggtcaag ctaaaattat ttccgaacaa actcatcaac 540
tgccatggga aaacagtaat ttagataatc agcaagaagt atttgaggaa gttatagact 600
ttctgtcaca aagatcacaa ggttcacaaa aactccctaa actgtatgcc ataagagaaa 660
aagaattgga aattgttaaa aacgttcttg acacatggtg tgatgacttt gatccaaaga 720
ttagtttcac agtgtataat gctcaaacat tgttcacttt gttacataaa aatattattg 780
aaaactcacc atgttcttcg gaagctctgt gttatcgtga atttgaaaaa gatgttcacc 840
agtacgcacc aaaaattgct tgcgagtacc atgaagaatc ggaatgtcct gtttattgtt 900
cgagatcaat agcaataaga tatggttaca ttatttgcca aacttgttct cctagtttgg 960
gtattcaact tgtatctgga tttcacattc caagtaatat gaaacaagct gtaatagaat 1020
caaaaaaaac cttcaagtac cgtgaggttg acagctgtag tacagaaaga gatactgaag 1080
atacttgtac tgttagagac gatagtagtg atgtggatac tttggtctct atagggagga 1140
acagtacata tattgaggat tcagcatcgt ccatttattt tccagaatat gatgatatgg 1200
cacaaaatgt ttctagtgac attcgaacag gaggaagatc gggttttagc cgaaaacctg 1260
ctgctttacc atctactgtg gatagagtat tttctaatct gacattgagc caagattcac 1320
tcggacgaag gaacaatgaa tggccaagct tacgtggaag agggggagga gcaatcccaa 1380
gaaccaaagg aagaggtcaa ccgtttaaga ataagtgata cattgaagct ttacactctt 1440
ttctgttcct aaatttctat atttgttggg ctaatcatta ttgtgttatt tcagttttat 1500
ttactgacaa tgcaactgat tgttgttcaa gaaatgacat tatttcattt caattctttt 1560
ttaaattcat taattttttc tgaaaaattg tactagttta tattattctg ttattgtttt 1620
gtttatgttc atgtttaatt ttct 1644

<210> SEQ ID NO 207
<211> LENGTH: 2052
<212> TYPE: DNA
<213> ORGANISM: Helicoverpa zea

<400> SEQUENCE: 207
gttgaaagtg tcctgtttca gcagttttct ttaatttcac tttgtcagca atttcaactg 60
catttcaact tttcagtctt gctcttgtat tctgtgcatt agcatcagac agaattcaat 120
tttggtgtgg tagcgtgtta tcttacgtga attgtttctg gcacagtaca aaatgccgaa 180
gaaagctccc aaaaacgctt tcttctattt tatgctgaat tataaagacg aacagcagaa 240
gaaaggcatc aactatggat cattggctga tgtctcagtt gcagcgggcg aagtctggaa 300
gactgtaaac ccacaagaga gagcccgttg ggaagccaaa gccaaacaag agaggacaaa 360
acaaaatatg ccagttgcca agtacacgtc taccggggtc ccgctaacgg tcatcgaaca 420
gcagcagaaa gaaatacaag aggcaatcca gaatgaaatc gatgatatcc ggaatatggt 480
caaaataaag gcttttaatc aaagcattca ggatgaagac ttctacgtaa tagatgtgaa 540

```
ctattactgc aaagcgggaa acacgtatgt gatcggagag agcactgtgt tacgattcaa    600
cctgaggctt ggataccagg atttctatca tgaactcatc aatcctggtc gcatccccgt    660
cggctacgca tcagacgtga aacacggcag cactgagcta ggtctagaca tgccagacga    720
aactgaaaac cagtctaact acatagaaat actagccaac atcattgact acctgaaaca    780
gaaggataag aacttgaaag ttctgccgcc tttgtacact atgcctgaga aagtgctggc    840
tgttcaagat tttattctgc aaatgagcaa taaagcccgt gaggacgagc atatcttccg    900
cgtctacaag ttggacacgc tgttcttcta cctgataaac agcatcaagt ccaacaagaa    960
cgagggtttc cctaaggagt cgctcgctct catacaactc aagaaggacc ccttcaagta   1020
tacaccggga ttgggctgtg agcatcacga agccaacgag aaatcaatgg agtgcacgag   1080
ttcccgcacg cagcgctggg cgtacaccgt gatggacagc tgctgcccag tcgtgggcat   1140
cgacatccag cccggacaac atgtgcctaa ggaatatgat gttgatggca tcctgaagta   1200
cagagacgct aagaaggtgt ggagcggtcc cactgtggct ggatttaatg atgcatcgtc   1260
atcttgtaac tcaacagtga acgattcttt cgaggcccct cccagtctcc ttgaatatgt   1320
gggcaaaacg aagcgactcg aagctcgcgt gcacgcgccg caacgactcc ccgacgtcaa   1380
tttcgccaag cctatgctac ctcccgagct gacggaggaa gccttcccgg cactgtctgt   1440
gagccacgga agaggtcgcg gattggccgg gaggaggaac gtcagaaaat aaagcattca   1500
atgccaatct tatttttgta ctgttatgta acatatctga cattattatt attaatggct   1560
gttcctaata ttctgtctat ccatttattt actcactata gaattttgac atgagcccca   1620
tacaagtaat gtaaacttcc tatctctggt aagatcaaaa caaaagatag ataaaatata   1680
gggaacggcc acagacagac gaactacaca atacgtgatt gaaattatac tttcaaatgt   1740
catcgaatta tgcaccttat tgtttgtgtg ataaagtgca aaattgtttg aaagttaaac   1800
gggttgatta tgttatgatg gaaaactcta ttggtggatt ttaataacca atcatttgtt   1860
gttttacttc ctcgagacag atcattttac actacttgta tggggcctat gtaaacattc   1920
aatctctgta gggactgaat caacagattc gttatagaaa ttgctaataa gagtactcga   1980
ttagtaagga taaatgtagt ttgtttgtct acagttaagt tttgttataa tttcatccag   2040
cggtactcaa at                                                       2052
```

```
<210> SEQ ID NO 208
<211> LENGTH: 1596
<212> TYPE: DNA
<213> ORGANISM: Megacopta cribraria

<400> SEQUENCE: 208

gtttcttaca ttattccctt atccgtcaat tgctagactg atcccggaat tcaaaatcat     60
gccaccaaaa aagaagcaaa agggtggaag gaacggcttt tattatttca tgttggatct    120
acagaagcaa gaagcactaa aggggaaccg ttactccctt caagaaattt caggattagc    180
aaaccccttta tggtcggata tgtctttaga ggaaaggaaa ccttttactg atttggccct    240
taaaaatgcc tctaaaaact ctggagactt aactaagaag ttcacttctt taggaataag    300
ttatgctgag ttagacgctg aggaaagaga aatagaggat gccagaaaca ttatgattgc    360
aacaattaag aatactattg caaatctcga tttaaattct actctgaaga gtcatatatt    420
ctttgtgtgt catgcaaatt atttctataa atctgaaaag caagtctatt tcccagctga    480
agttgctgtt gctgcatttt cccttgagct aggtgttctt gcaactttac attttttttgt    540
tgatcctggg aaaatccctc tcggttttaa gtatgaatct tcagaatggt cttcaaggac    600
```

```
ccatcgcata cctgtcagtg acccatcttg gaaagaggga ataaaagatc cattagaaat    660
gtatcgaaga gttaaagaat tcatcaagaa atttacagtt gggactgaag ttcctccaat    720
ttatactttg tttgaaacct cgaactcaca ctatcgtctt tctgttgtaa aatctgcctt    780
gaatatgatg tgcgaagcgg catatgaaga tacatcctta tttcgagtat attgtctagc    840
acatttattt tttgaaataa gaaataaatg ttctgcagaa atacctagtg tagctattat    900
gaagaatgaa cttgaaaaag acgtgttttc ctatgcaaga gatttaggat gttattatca    960
tgaggaaaag gatctctcaa tacattgctc actctctatt gtaactaggt gggtttttat   1020
tatttgtgac cattgctgta aacatcttgg tattaaactg attctaggaa gacatgtccc   1080
aaaagataca gctttattag atagggcaca ttatgtgaga aagagtgatg gcttatcacc   1140
gaaacaaaat gttgctgaat ccagcagtaa accattgaca ataattgacc atggaagttt   1200
aaaagaacaa agagctgaag agagaagatc tcaagagatg tacttaagag aaagtgaaaa   1260
aatcagacct ccaaagtact gttacagtga taaaattggt gctagattta gtcaaaatag   1320
ttcctcacaa ttgtctcctg aaataggagc aacatccaat gaaaatgaat ggtgtctggc   1380
taaaggaaag tcttctgggc gaggtcgtgg aattttaagt tattcatctc cagaacatcc   1440
tcaatggcca atatctggac gaggacgagc ttttgcaaat tttcataatt aaagatttta   1500
ttttgttcct ataaaaagca aagtggttct aatttttagc gttaatatat ttttgtttta   1560
ttaaggaaag gtgacagttc ctattttaat gcgata                             1596
```

```
<210> SEQ ID NO 209
<211> LENGTH: 1574
<212> TYPE: DNA
<213> ORGANISM: Nezara viridula

<400> SEQUENCE: 209
```

```
acctcgttgt cagacaggca gaagtggccg cgttaccgta aacaagtaat aacaacaatt     60
atagatacca aataatgcca cagaagaaaa aacaaaaagc tgggaaaaac gggtttttatt   120
tttttatgct ggaggttcaa aagcaggaag ctctaaaggg ggttcaatat agtttgcctg    180
aaatttctga aattgcaaat cccatgtgga ctaacatgac cccagaagaa cgtaaaccat    240
ataatgacaa ggcatcaacg agtgtttcca aaaatagcga agacaattca aaaaaatata    300
cttctttagg cattagctat gccgatgtag atgctggaaa gagagagttg gacgaagctc    360
gtgatcttat gatagcaact attaaaaaca ctgtcgcaaa tcttgacatc agaacatctc    420
tgaagactca taagttcttt gtgtgccatg ctaactattt ctataagtct gatcatcata    480
tttattatcc tgctgaaatt gctcttgcag ccttttcttt ggagttgggt gttcttggca    540
ccattcattt ctttgtagat cctggaaaaa tacctcttgg tttcaaatat gaagcggcag    600
attggtcaac tagaactcat ggaattccag taaatgatgc tagttggaat gaagggatta    660
aagatcctct ggaaatgttt ggaatggttc agtcgtttat caagaaattt actgagcccc    720
ctgaagtacc tccaatctac acaatgttcg atactttaaa tgctgacagt cgtctttctg    780
ttgtgaaatc tgcattgaat atgttgtgtg atgctgcaaa tgaagattcc tctctatttc    840
gtgtctattg tttatcacat ttattctatg aaattagaaa taaatgttct gcagaaatac    900
caagtgtagc cataatgaaa agtgaattag acaaagatgt tttctcatat gccagggacc    960
taggttgtta ttatcatgaa gaaaaagatc tttcgatgta ttgttcgctt tctatagtaa   1020
caagatgggt gtttacaatt tgtgatcatt gttgcaaaca tctgggtgta aagctcatcc   1080
```

-continued ttggaagaca tgtgccaaaa gatacagatc tttcagaaag tgctcgattt atagatgata 1140
aacaatcttc taataagtta gatcatggtg cttcttgtag taaacccttg accatcattg 1200
accatggccg tttaaaagaa caaagagctg aacaaaaacg ggcgcaggat atgcatttgc 1260
gtgcaagtga aaaaataagg cttcctaaat ccagttatag caacaaaatt ggtgccagat 1320
tcagtcaaga aggtgccagt agttctcaaa gctctctgga aacaaaagaa gaatccaatg 1380
aaaatgaatg gtgcatcgta aaaggaaaag gatttggacg cggacgtggt ttcactgtag 1440
aaaaatcttc agctgaagag cctatctggc cagtttctgg aaggggtcga gcatttcaac 1500
aataaatttt aaaagacatt ttaatataga caaaaaattt taataatttt gatacaagtt 1560
ttttatactg tttt 1574

<210> SEQ ID NO 210
<211> LENGTH: 1640
<212> TYPE: DNA
<213> ORGANISM: Euschistus servus

<400> SEQUENCE: 210
tagattcacg tttggttgaa acctctaaga ctgacagacc aaaaaggccg cttttgttta 60
acttgtttat atcgttcacc caggactgtc agtatgccac agaaaaaaaa acaaaaagct 120
gggaaaaatg ggttttatta ttttatgtta gaagtacaaa agcaagaagc tcataaaggc 180
aataagtatt ctttgcctga aatttctgaa attgcaaatc cattgtggtc tgctatgtca 240
ccagaagaac gtaagccata taatgacaaa gcactaatga acgtttccaa aagtaatgaa 300
gacttaacaa agaaatatac ttctttggga attagttatg ctgaactaga tgccgaacaa 360
agagagttgg atgaagcccg aaatatgatg attgctacaa ttaaaaatac aatagcaaat 420
cttgacccca gaaattctct gaagactcac acattctttg tatgccattc taattatttt 480
tataagactg atcatcatgt ttattatcct gctgaaatag cttttgctgc cttcaatctg 540
gagcttggtg ttctagccac cctacatttc tttgtagacc ctggaaagat tcctcttggt 600
tataaatatg aagctgcaga ttggtcagct aggactcatg gaattccagt aaatgatcct 660
agttggaatg aaggggtcaa agatcctcta gaaatgttca gaagggttaa ggatttcctt 720
aagaattttg ctggagactc tgaagtacct cctatctaca caatgtttga taatttaaat 780
gctaacagcc gtcattctgt agtaaaatct gctttgaatt tgatgtgtga tgctgcaaat 840
gaagattcct ctctatttcg tgtttattgt ttaccccatt tattctttga gattagaaat 900
aaatgttctg caggaatacc aagtgtggcc ataatgaaaa gtgagttaga taaggatgtt 960
ttttcatatg gcagggatat aggatgttac tatcatgaag aaaaagatct ttctatgaat 1020
tgttcacttt ccatagtaac tagatgggta tttaccattt gtgatcattg ttgcaaacat 1080
cttggtataa agctcatcct agggagacat gttccaaaag atacagacat ttcagaaagt 1140
gctcgattta tagaagataa atattctcca aataagcttg atcatagtga ttcctatagt 1200
aaacctttaa ccatcattga ccatggacgg ttaaaagaac aaagagcaga acaaaaaaga 1260
attcaggata aacacttgcg tgaaagtgaa aaaattaggc ttccaaaatc tgtttacagc 1320
aacaagattg gtgccagatt cagtcaagat tcaggcgcta atagttctca aagctctttg 1380
gaaatgaaag gaacaaaatc agaagctaat gaaactgatt ggtgcattgt taaagggaga 1440
agcttagggc gtggacgtgg ctttatccca gaagaacctt caactgaaga gcctaactgg 1500
ccagtttctg gaagaggaag agccttccaa taataattta tttgagaaat tttaatatag 1560
acaaaaaact ttgtaatttt aatatggacg aaaaagattg ttatttttaa tattttttta 1620
tgtaacagtt tactatactg 1640

<210> SEQ ID NO 211
<211> LENGTH: 1500
<212> TYPE: DNA
<213> ORGANISM: Orius insidiosus

<400> SEQUENCE: 211
ttctggcttg caacttgaaa aaaagactcg tgattttact tgtagtctca actctcaaga 60
gtcacgctgg aaaagtaaag ttgagctgct tatttgttgt caacgtacca tttttcgtaa 120
tatgcctaat aaaaagaaga ataaagccgt gagaaacggt tatttttatt ttatgcaaga 180
tgtccgtgaa cgcgaggcac tgaaaggcca ttattttcca agtcaaaagc aagtcgccga 240
tttttgtgct ccactttggg cgaatctctc tccacaagaa aaggaagatt acaacgatca 300
tgccaagcag aaaaggcttg aagagaaaaa ttctgtcgat gaagctgcca ctaagttcaa 360
ttcaatggga atatctattg cccatcaaga cgctgaatta cgtgaacaag aagaaaacga 420
aatgattatg aaaagtcaca ttaaaaactt aatgaccgat tgtggaaaag ctggaattat 480
gacgtacaag ttttatttgt gccatgtcaa ctacgcattt aaagtcggcg ataagaagtt 540
cgctcctgct gaattagctt tggtcgaatt ctcactttat gagggaatca caaatagatt 600
tcacactttt attcatcctg gaaaaattcc tttggggctc agatacgagg cgatcgaatg 660
gtccaatatg tcacaccaaa tacctgttga gggtggattg ggtgaaaaat tggataaaaa 720
tatcttcaac tccatcatct cattcttaaa tagcaaaggt agaaataaag cgttgccggt 780
tatttacacg atgccagatt cgttaaattc aaacgattct atgaaggccg tcgtgagtgc 840
ttttcagcag ttatgcgagg tggctgaagc agaccctgat attttccgca tttatgaatt 900
acctcatttg ttctacgaac tccgcaataa atccgtagaa gacggccaag tggattatag 960
atttccgagc gttgccttag ccagagagct tttacaacgt catgtttata gctcttgtag 1020
caatatggga tgtgaatttc atgttcaaaa tgactatgaa ttgaaatgct cattgagtgc 1080
tgtgacccga tgggcatacg ccatttgcga tcactgctgt caatatttgg gaattaaagt 1140
tatccctggt gtacacatcc ctatccccac cctactgggt aacgaaggat attctgctgc 1200
tgtgccttgt gtatcgccaa aaggcaattt gccaactcat gcttctcttc ctgaacctgc 1260
ggaagttcat gaacaattgt cttctgattg ccctgatgaa tcttttggat ataaatatga 1320
tgaagacgat ttccccggtt taggtggcaa ttcaaagaat gtaagaagtg aaaacgcccg 1380
ttcttggggt aatccatgga gaaaatgatt ctttttatat taaaactttt aataaataat 1440
ttacctttct ttatagacaa agaaatacat ttattttaac ttctgaattg tttaaaaaaa 1500

<210> SEQ ID NO 212
<211> LENGTH: 1810
<212> TYPE: DNA
<213> ORGANISM: Manduca sexta

<400> SEQUENCE: 212
tgctattaat tttagctcct tacgatttac gaattggcat tttcaactaa aagttttaca 60
gctatatatt tgaaatatat atttataatt gaataagatt aataaaggtt gactttagac 120
aattattcta aatttaaact ggtaccaata ggaagatgcc gaagaaaccg ccaagaaatg 180
cattctacta ctacatgctg gacttcaggg aaaaccagaa gaagttggac atcacttacc 240
aaagtctaaa ggaggtggca gaagctgcag gaccatcctg gaagaccatc tcaccaaccg 300

```
caaaagccaa atacgaagct atggctagaa aagagagggg tacaaaccag aagttcacat    360
ctactggtgt gcctctcgcg tatttggagc agcaacaaaa agaaatgcag cttgtggagg    420
aggctgaact caaagatatc aagaacatta tcaatcttaa gtgttttaat caaagtattc    480
tggatgaaga cttcttcctg ttggatgtga ttgagttgtg caaagctgga ccggactatc    540
tcattggaga gttcactgtc ttacagttta acctgcgtga aggcattaag aacagttatc    600
acgagtttgt tagaccagtt agcgtgacta tactgaccta cggccttgac acgctggacg    660
acagcctacc caaggagaac tacgtgcaga tcctggccaa catcatagac tatctgaaac    720
agaatgatcg tggcacgaac acactaccgc ccatattcac aatgccagag aaagttgagc    780
cgatacagaa ttttatatgg cagctgtgta acagagctgc cgaggacgac gcgttattcc    840
gcgtatacaa gctggacacg atgttcttca cgctggccaa cgcgattcgc agcggcgaca    900
acgaggggtt cccgaaggag tcgctcgcca ccgcgcagct gaacaaggac ttgttcaagt    960
acacgcccgg gttggcttgc gagcaccatg agaccgtgga caaaagcaac gagtgcacat   1020
cctctcgcgt gaagcgctgg gcatacacaa tcctggacgt gtgctgccca ctgctgggca   1080
tcgccgcgca gcccgggaaa cacgtgccgc acgacttcga tatagacagc atcctctcgt   1140
acaaggaaga gaagcgtgaa cgagcgctac cgagtgtagc tcgtcggcag gtgccgcacg   1200
acagtatgtc gtcttgcagt tcgtcgatca tcaacgacac agtcgacgat tccaccgtgt   1260
atagctttaa cgcctcccac accagtgctc caaagggcaa gaggacctac acgccgctgc   1320
gtatgccgag gactgattat tcgcaacgtc tccaacaagc cccgagctg accgagacga   1380
acttcccaac gctcggcagt acaggacacg gcagaggtcg cggcctcgcg agcagtttcg   1440
atcggatgaa cttgaagaag taaataaaaa ttaagaataa cttgcaatgt gccaacgtat   1500
caacaagatt tcattgtgaa tttgtaataa gctaaaataa atgactattt ttctgtgttt   1560
tatgaatctc ggtgtttaag tatacatggt gctgtaaaag cgtaaatatt gaacttttca   1620
gggcacgctg tataacgtag tagttgtgac attgtttata cgcacaaaaa gaactatcaa   1680
aaaacttagt aaatatgtct taagtcatat ctaaatttgt tccatcatca ttgaacatat   1740
tttgtaccag agtgaataga ggcacagtca taaactcgcc atgttgataa cttcatacaa   1800
ttggaaacgt                                                           1810
```

<210> SEQ ID NO 213
<211> LENGTH: 4514
<212> TYPE: DNA
<213> ORGANISM: Spodoptera frugiperda

<400> SEQUENCE: 213

```
cgggaattgc acgaattgaa ccggctacaa aaaaagacgt tttgcgaaat agaaattatt     60
ttgcgttgtg ccttgactgc ttagactgca ctaagtgtct gcatctgcga acgaaaccta    120
cccattgtac tttgtaatta atcacctgct atattatttt tttaattcaa ttcgactaat    180
atgcctaaga aaaagaccgc ctactggttc ttcttacaag atttcaaaga agaacaaagg    240
ctaaaaggca ttacgtatac ggaaaaacag gaattggata aagatgccga taaagcatgg    300
aggagtctac ctccttcagt tcgtgctaag tacgaacaaa cggcgaagaa tgagaaggaa    360
aaaaacaatg taactgttat aaagtatacg tctaatggca tcccgttgac tgtgattgaa    420
aaacaaaaac aagaacacga gatggcgcaa atcaatgagg ttcaagatat tacaaatata    480
attaaaacga agtccttcaa ccaagaaatt ttagatgaat acttctacat catcgacgta    540
aattcttatt gtaagtggga tgacaaatat ttgattggcg agtgtaccgt tttgaggttc    600
```

-continued

```
aatctgcgga atggtattcg agattattac ccagtattga tcaaccctgg agaaataccg     660
atggggtacg cgtcggatgt aagagtggcg tgtatagagt tagggctgga catgccggat     720
gcagaatcac cgagtaacac gatggacatc ctcgccaata tcatcgactt ccttagacag     780
aaggacctga aggccggatc tctaccgcct ctgttcacta tgtcggagaa agtactgcct     840
actaagagct tcctggaaca gatgtgctac acagctcatg aggatgaaat gatcttccgt     900
gtgtatcgcc tggagaagtt gttgttccat ctggtgaata gcctgaagtc cgacaagtac     960
gacgggttac ctcatgagtc tctcgcgctc gagatactga agaaagactg tttcagatac    1020
agcgaaggac tggcttgcag acaccacgca gccagagaca aggccacgga gtgcacggac    1080
tcgcgcgtgt tccgctgggc gtacagcatc atggacgagt gctgcgcccc cgcaggcatc    1140
actccccgct ccgggaccca cgtgccaaag gacatgaaca tcgaaaaata caagcttcta    1200
aggaacccta ctcctagagc tacagtcgct ggatatgagg cggcaccatc gtcctccaac    1260
accacggcca acgattctat gtgggaaggg agctttgaag cctctctcgt cagtgagccg    1320
tcgggagctt ggggtgaacc ttctggagct tggggtgaac cttctggaag tcaggcggcg    1380
agtgcctggc ctcaacccac tggcattccg tcgtcggaaa cctggccaca actccctggc    1440
agtgggccgt cgagtgcctg gcctctacct tctggtagcc agtcgtcgaa tgaatggccc    1500
gggctccctc ggagtcagtc gtcgagagcc cgcggtcaac actccggcag cggtcgtggt    1560
ggccgggaat ctgagtctgg gaggcgaggg cgccgcacac acgagcctat gcgcatgccg    1620
caagccgact attcccagaa cctccaggcg acgagcgaat taatggagaa acacagtccg    1680
ctcctaccag gccttggacg tggtcgcaat ctagctggca gcttgagcaa gatgaacatc    1740
aataagaaaa agtaaagcat tgaatgccat ttaaatttct accctattat tattatgtaa    1800
tgaatctgat ttactttgta agtatagtgt tgtcagatgg gctgtgttta caccgactta    1860
ggtggacaac acaaatatca tacaggaata tcgggaaaaa atacttggaa ccagtggcgg    1920
aataaattga caacccggca aagttctcag taactcaatt cttcttttta tattaggaga    1980
ttgggctcat ccgatgaatt tgccacgggt ctcgaatcat acagttactg cttaaaattc    2040
tatttacatt ctacgactat agagctatgg acaaaaagtc tattgattta tctctttttt    2100
aatctataat ccataaacaa tattgacaac tatcctacct cacaactatt tgaccaaatt    2160
gctttaatat cttaaatcta ttgacaaata actagtaatg tataaaaata ttttcctcta    2220
tcatattttc aaaagagtgt agtttaaatg aaactatatt tttagacatc tatcccctaa    2280
tcttataaat taagccatgt aagtctagga ccattacatt acattgacca actttttcca    2340
tagctccaat tattaaccat acgtatctat agcacaatat agcttaacga tagctaagcc    2400
catctggcta cacgaaaaca tgattatttt gtattacaat ccgacgatac tcaatctttt    2460
cagtctaact gctcaatgta tatgtaaata atgtggcaaa caataagtca tttatatatg    2520
taattgactg attaggctac ataggattgc ctaaatatat ttaagatata tagattgtat    2580
tggtatgtag gtacttaata aggaaaactg aggaacctta agactagtga agtgtgatat    2640
taggatggtc taggagtgta ctaagtacgt tttgaaaagt caaaattttg agggaaggct    2700
ggtttattaa cgtattgaca ttcgatgtca ataaattcat tttatttgga tttaatcctt    2760
taaacttacc tacaatttga tacgggagta tcaaggtagg attaaaattt aaaataaaat    2820
ttgaataata ttcaaaatta aatggtttac ttcattaatt acccattaaa gttaactctt    2880
cgagtcgttt gcattacggg tatttcgttg ttccttttcc gtaaaacatt gagtatcgtt    2940
```

```
ggatttactt attaattaaa aactttttga tatttttata atgtgggatt tatgctaatc   3000
tccgtacatt ccgtattcat attgactgtt ggaaagccaa tttgtaaacc cggaattatc   3060
gtagatccca catgtttaga atagttctga caatcggaac ttaaaaattc tgaaagaaac   3120
cttttacacg tgttatattt tacactatcg tctatcgttt tagtaaaact tcgtgcaggg   3180
ttgacaaaga gttagttata agtataattt tgttgctttt cattgaaaac atattttatt   3240
taccctaagt tttatataag ttttcaactg ggctaagaat gtgactacat ttacataaaa   3300
ataagaagaa attccaccaa agttctctcg tttgtctggt atagattcag tatcgaatgg   3360
ttaaatgaca ttacacattt attaaagatg tcttgagaaa taatcagcat cttattaaaa   3420
agtataatta aataatgttc aatgttcata tatgtctatt gtagtggttc cagaattccc   3480
cccaccgacc tgtagtacgt agatgcagaa tagacacaaa atatctcaga tgttgtacga   3540
tttagctgac cggtcaatat agctcaccac gccaaatttt tagtgccacc tgtgctcaaa   3600
aacttaacct aatcagttgg ttatatcacg tattccttca gtacgagcat tactttgtga   3660
tcgtcttaaa tagtggtatc tttgtctatc tagtcggaat gaggcagttt tctcattata   3720
ttcagtagta tatagtttgg acaaaatctc aatgttggta gtgtttagta tacgtaagaa   3780
agtctatata aatcgcggtg atttaaaaaa aaaaaaataac caaatgatgc tttggtccag   3840
aacttgcctg agttccaagg cttcgaacat ataacaacat gttcagtaaa atttaaattc   3900
tttctgtgtt ggattgccgc gagtccagtg ttacattcat agggatatac ccttttaata   3960
ctataagtac tatcatagtg taggtatcaa taaatatgta ttttgatatc gtatttatta   4020
atctccttta ctcgttttga aagcggatat tatagaaaag gggtttata aacccaattt   4080
ggacaagaga tataattgac aatgtatgtt tcccgtcgaa attattttga atagtatttg   4140
tagttatata aggtacataa tacctatata caattttata tagttcttcg catgtggcgt   4200
tggtttattt aagggtaata actatataac ataactacag tcatagatat catatttacc   4260
tatattcaaa tataataaaa tctttcaata aactatgtaa tgttttctgg ctcaataata   4320
tttgaaaatg gcaacctcta agtcaactag cgccacctat atattaaagc ttaatatgtg   4380
tgatatgtat acgtagtagt gtgtttatgg atataaaacc tgtctgactg tagattacaa   4440
atatctatta cgaattctat gtgtgatagc cataggtacc tatgtagtac tttcaatgtg   4500
tgtttaatga ataa                                                      4514
```

```
<210> SEQ ID NO 214
<211> LENGTH: 2917
<212> TYPE: DNA
<213> ORGANISM: Ostrinia nubilalis

<400> SEQUENCE: 214
```

```
aaaaatttgg ttggtttgca aaaattcgct tgtgccggca aatttatttt gaccaccgtc     60
tcatattcgt tatattgtaa tattttacat actctctgtg ttattctact ctccgtgacg    120
atacgatagc catttgagta gggcatttat ttcaatatgc cgaaaagaca agtaaggaac    180
gcattttatt tctatatgat tgacttcaga gaacaacaaa agaaaattgg aattcagtat    240
gggaacataa gagaagtctc tgaagctgca ggtccttcgt ggagggaggc accaccaact    300
gtacgcgcca agtttgaaga aatggctcgc caagaaaaat tgaaaagaaa tgtacctgac    360
cagaagttta cttcaacagg gataccattt tctgagatag aacgacaaga gagagagttg    420
cgtgaagcag aggaagccga gagagaatac attaataatg ttgttaaact aaagtctttt    480
aattcagaaa ttatacatga gtacttttat gtgatggatg tgaactacta ctgtaagttc    540
```

```
aactcggatt acctaatagg ggaatgtacc gctctacgct tcaatgttaa aaatggcatc    600
aaagatcaat ttcatactat gatcaaccca ggtccaatac cagttggata tgcttatgat    660
gtcaaactcg gagctcaaga acttgggctg gatatgccgg atgcaattac ttataagaca    720
ttgccataca tagacacttt agccatcatc gtcgactacc tgaagcatgg ccttccgact    780
tctagcaaga cagtaccacc gatttacaca atgccagaga gggtgcaacc agtcctgaat    840
tttatattgc aaatgtgtgc aaagacaggt gaagacgacg gcatgttccg cgtgtacaag    900
ctggacacgc tgttctacac gctgctgaat ggcgtcaaga accgcggcga cgagggattc    960
ccccgcgagt cgttggcgct cgcgcagctg aagaaggacc cattccggta cacgcccggc   1020
ttggggtgcc ggcaccacga ggacatagac aaggctgcgg agtgcactac ctctcgcgtg   1080
aagcgctggg cctacaccat catggacagc tgctgccccg tggtcggcgt ggacatgctg   1140
ccgtcgaagc atgtccccgg cgacttcgac ctggacacca tcataaattt tagagagcaa   1200
aagaaagaaa gagctgggcc gtcagtggct gtccctcggt ggggggaacc ttctaacgcc   1260
tcagccagcg atatcaatca gtcttcgttc aacgagtctg ctaatacttc agcctcaact   1320
tcagctcctt cgacttcatc aaagaaggaa aaaaaagccc agcctcctct acgtatgcca   1380
aagacagatt attcgcaaac ccttcgccca gcgcccgagc tcaccgaagc caacttccca   1440
agtttctctg ctggacgcgg ccgtggctta gcgagcagct taaacaaaat gcatattgga   1500
aaaccaaaga agtaaacgta gacagtctac ctttaatctt gtcttgacct gtactcaatc   1560
ttgactgcta actttatttt aagacttcct cttgtgctgt gggacttaga tacaaatatt   1620
ctattaatgt ttacacttcg tgtatctaat acacttaagt caggacttgt taccctttta   1680
ggattgtgtc tacaaaatta ttgggcgagc ttatatggcc gacagggtat ggtcatttaa   1740
tgggtgaaag ttcgatatgg atatttctat aatgcagcta ttcatcacta tcgaatatgt   1800
atttagaagc taaattttag ccatgtatgc tcgctatcgt gcattatggg tgcataaaaa   1860
ataaaattag tctcttgata tgacaccttt acatttcggt cttggttcga cttttacgtg   1920
catttatctg ctatgtatgt ctgatatgga gcaaagcaag tattaataaa atatttcata   1980
gtaaataata gaatattcag tagtaaataa ccgtatataa tatacctaat aatactatat   2040
tcctgtgtat aaagcttgga tacattgtgg tgaaatgacc ctcagtgacg cacaacgctc   2100
gaactacttg acgccacgtt gtcgcactgt gtcaagcatg acatagattt acttaacatt   2160
ttcctttatc cgagatacca cttcatttgt ttcctagtgt gtccaatgtt ttaaattgac   2220
tcaacaaaaa gatttcaaaa attgtcgtag cgaatgattg ttaatgtctc tagtgtatcg   2280
gcgttcaatg acttaagtat attgctatct ctagatgatt gtctatttca ttgatcaaat   2340
atgagaatac atgattatgt tttatgtcga tgtgaggtta taagtaaatg aatagcattt   2400
agtattaaat ttaactaaac atataaaata tgatattatc tctacatgtt atttgatgtt   2460
gtaacaatcg atgtgataaa taatattaag tcaaatactt ttgtgattgc tttagttatt   2520
taagcattag tgccatttcc gcttcctctt ctctgagata taattttcga aagaaacaaa   2580
actattttta tatttcgttt attaaatctt taaaagaagt gtatcatatt tttaaggttg   2640
gccaagtaga ataagtttta atgtaatcac caaagtgata cttgatctta atgttgatat   2700
tatttcggtt ttttttacga taaagactct agcaaacagc cggctagagt gtaatgtgaa   2760
gtatacgtac ttattgatag ttagaaccta ccgctttgtc gcactcgtgt gggctgtgct   2820
agaggcttta gtaactaagt ttcttatgtt aaaatgttga agtatttgtt tgtacttgaa   2880
```

-continued

```
tttatagttt cgtatgacaa cttaatgacg attaaaa                          2917


<210> SEQ ID NO 215
<211> LENGTH: 1713
<212> TYPE: DNA
<213> ORGANISM: Lygus hesperus

<400> SEQUENCE: 215

accaaagttc aaagcattga atactaacgt cgttctgagc aattcaaagt caaagagtgc     60

atgaaactgc tgcagatgtg tgtcctctgg ggacaccttg ccctgacgtc caaactcccc    120

actacaccaa ggataaggat caaggatcgc taaggataac ggaactccat ttgaacagtt    180

gacttacctc tctgcaatca tgggcagtaa aaacaaagga aggaacggat tttactactt    240

catggtagat ttgcagaaag aaaaggctga cgatgggcac ttctatagaa tggatgagat    300

gtcaggaatt gctggcccac tctggaagaa tttatcgctg gatgaaaggg aatattacaa    360

cagaagggct aaggaagaaa aattaaaagg cgcctcggat atggatcgca agtacaattc    420

tctgggagtt agtttttcgg tcgtcgaagg cattgagaga gagttggacg aacaggagag    480

agtcatgaaa gctaccatca ggaatattgc acagtcctcc agtccggagg cactcatccg    540

aaaacctttt tatttctgcc acgtaaacta ctacttccaa cccgataaag atagctacca    600

acctgcagaa attgctctcg cggaattcac cctggaagac ggccttcgag agacgaggca    660

tttcattctc cacccaggta aaatccctct ggggatgaaa gccgaggcac aaacctgggc    720

tgataaaact cacgggatcc gactagtaga caagcctggc gaggaaatcg aacgtgaagg    780

agacttcgtc aaagtatttt cgaacattgt gaacttcttg aagaacgacg ctggagtggg    840

gcagggagga gggggaatgg tgctcccagt gatgtattcc atgccggatt cgctgaacaa    900

caataccagt ctgtctgctg tgaagtcctg catgaacttc ctaagtggat gtgcccatga    960

gaatcgcgat ctcttcaggg tctacccgct accagagttg ttctatcatt tgtggaagaa   1020

gttcgagaag aagggcgacg aaacacccac ggttgctgtc ttggagaacg aagttgaaaa   1080

agacattttc agtggcgctg ctgatttagg gtgtgagttc cacgaagcga aggacctgag   1140

cctccactgc agtctgtcaa tggtgaagcg ttgggtgttc acagtatgcg atttcgtcaa   1200

caaaatgacg ggtatagaga cgattcctgg atgtcacgcg cctgacaatg cggacctcca   1260

atgggctgcc atacaatcca gcaagcgcat gaacccagac gtgaaagttg gatacgtcga   1320

tccaccaccg ccaaaatctc ctcccaagtt tgttgatttg acgaaaatgc aggaactgag   1380

gatacgagaa aaagaagctg tggaagaaga actctcccaa gccgaacgtc ttccacctcc   1440

tgtctctgct gtcttcagag gagggccgct ccctcctaat ctcaatgata gagatttccc   1500

tcctattgga acgagtggtc gcggaatgta cctccccaga tccaagtggc cagcagtctc   1560

ttcgcaaaga gggaggcgtc agtaatgaaa gtggaagaac ctatttcgaa acctacgcga   1620

ctttggttga ttataaacca atctaccctc gatttattgt tcatttttca attgttttat   1680

tgtttattcg tgccagaatc gtttaggata ttc                                1713


<210> SEQ ID NO 216
<211> LENGTH: 601
<212> TYPE: DNA
<213> ORGANISM: Pectinophora gossypiella

<400> SEQUENCE: 216

tcaactttca gttcagttcg ttcgttcagt cagttgattg gaaaaaaaag ttagttctaa     60

aatctaaatt atttttgaag gaaaaagttg atcaaaatgc cgaaaaagcc accaagaaat    120
```

-continued

```
gcattttact attttatgtt agattttaaa gaacaacaaa gaaagaaggg tataaactat    180
gggaatatga acgaagtagc gcaggcggcg ggccccgaat ggacgtcagc aaaaccacaa    240
gtgcgcgcga aattcgaagc gatagcgaag gctgagaagg cgaaatcaaa tgtgccggag    300
cagaagttca catcaacggg gcagtcgctg gccgagctgg aggcgttgga gaacgagcgg    360
cgcgcggccg agaaagccga ggagcgagac atcctcaact ttgtcaagca gaagagtgtc    420
gacggcagta tactggacga ggacatgtat ctcatggatg tgaactacta ctgcaagact    480
ggatcctcat acctgatcgg ggaattggca ctgctgcgct tctctatcag agacggcatc    540
aagaacactt accatgagat cattaaccca ggtggcatcc ccatggggta cgcgctggac    600
g                                                                    601
```

<210> SEQ ID NO 217
<211> LENGTH: 1396
<212> TYPE: DNA
<213> ORGANISM: Diabrotica barberi

<400> SEQUENCE: 217

```
aaaacattca ccacatcaac acgtgaatta atattcgaaa atggagtacg aaaatacaca     60
acaaaatata aacttcgtac cgtgtgtaag atgggttaaa cgaggagtgg ccaattcaag    120
cccagtaaaa ttgcaactgt cgaaaaacga gctggctcaa attattaatg acaccaagat    180
taaattacaa gaatccaatg aaaatgaaga cgagcccatg gaagaaggtg aaacgtctca    240
aacagatgag tttgccttag aggattacga taaagaagac gaaaatgagg acactgcaaa    300
tgctttagga attggatcat tggcagaact cgataatgat gctgcagaca atttttctga    360
gtcagacgat tctgaaaaag aagatgataa aatcaaacca tctgacaatc tcatactagt    420
aggacatgta gaaggggatg caagtctatt ggaagtctac atatacaatg aacaagaaga    480
gtcattgtat gttcatcatg atattatgtt atcatccttt cctctgtgtt tagaaccgct    540
aaactatgaa ccgaagatgc ccaaaggaaa ttattgtgca gtgggatcaa tgtcacctgt    600
tatagaggtc tgggatgtag atattatgaa tgttattgaa ccttcattta ctttagggag    660
acctgctagt aaaaagaaga acaaggaaca tataggccat acggatgcag tgctttcatt    720
agcttggaac aaaacctttg aacatgtgtt ggctagtgga tctgtagatc aaacaataca    780
cttgtgggat atggaaatca aaaaaccaag tacaaccatt aaatccttcc aagaaaaagt    840
tcaatgtctc gaatggcatc ctttagaggc acaaacactt ttaggtggag gttgtgacaa    900
atctgcaaga gtatttgatg gcaggacccc tgaaacccac caaacttggc tacttgatgg    960
agaagctgaa aggctatgct ggaacccttt agaacctttc acatttttgg caggtaccag   1020
cagtgggtct gtacagtgtt tcgactgtag aaaaggacag ctatggtcag ttaaagcaca   1080
cagcaaggaa gtaacagggt tagtccttag caaacaatgc caaggattgt tgattacttc   1140
ttctacagat gaaacagtta aaatttggga cttggctaca ctggaagctg aacctaagct   1200
tgttaatgaa aaggagttta atatggggaa tattcactgt ttggatttat gtccagactt   1260
gccgtttgtt atatctgtag gtggagataa gaagtcaaat aattttactg tttttgatgt   1320
acagaatatt gatgttgtta aacacacatt tgggccaaga ggattggtac agctagttcc   1380
agatacagaa gaaaat                                                   1396
```

<210> SEQ ID NO 218
<211> LENGTH: 1402
<212> TYPE: DNA

<213> ORGANISM: Diabrotica undecimpunctata

<400> SEQUENCE: 218
caaacatgta tataaaaaca tatttcaaca cgtgaaatat tcgagaatgg agtacgaaaa 60
tacacaacaa aatataaact tcgtaccatg tgtacgatgg gttaaacgag gagtggccaa 120
ttcaaatccg gtaaaactgc aattgtcgaa aaacgagctg gctcaaataa ttaatgacac 180
taagattaaa ttacaagaat ccaatgaaaa tgaagatgag ccaatggaag aaggtgaagc 240
gtctcaagca gatgagtttg ccttagagaa ttacgataaa gaggacgaaa atcaggatac 300
tgcaaatgct ttaggaattg gatcattggc agaacttgat aatgatgctg cagacaactt 360
ttctgagtca gacgattctg aaaaagaaga tgataaaatc aaaccatctg acaatctcat 420
actagtggga catgtagaag gagatgcaag tctattggaa gtctacatat acaacgaaca 480
agaagagtca ttgtatgttc atcatgatat tctgttatca tcgtttcctc tgtgcttaga 540
accattaaac tatgaaccaa agatgcccaa aggaaattac tgtgcagtgg gatcaatgtc 600
acctgttata gaggtctggg atgtagatat tatgaatgtt attgaacctt cctttacctt 660
gggaaggcct gctagtaaaa agaagaacaa ggaacatata ggtcatacgg atgcagtact 720
ttcattagct tggaacaaaa cctttgaaca tgtgttagct agtggatctg tagatcaaac 780
aatacacttg tgggatatgg aaatcaaaaa accaagtaca accattaaat ccttccaaga 840
aaaagttcaa tgtctcgaat ggcatcctct agaggcacaa acacttttag gtggaggttg 900
tgacaaatct gcaagagtat ttgatggcag gactcccgaa acccaccaaa cttggctact 960
tgatggagaa gctgaaaggc tttgctggaa tccattagaa cctttcacat ttttagcagg 1020
taccagcagt gggtctgtac aatgttttga ctgtagaaaa ggacagctat ggtctgttaa 1080
agcacacagc aaggaagtta ctgggttagt acttagcaaa caatgtcaag gattgctgat 1140
tacttcttct acagatgaaa cagttaaaat ttgggacttg gctacattag aagctgaacc 1200
taagcttgtt catgaaaagg agtttaatat ggggaatatt cactgtttgg atttatgtcc 1260
agacttgccg tttgctatat ctgtaggtgg agataagaag tcaaataact ttagtgtttt 1320
tgatgtacag aatgttgatg ttgttaaaca cacatttgga ccgcgaggat tggtacagct 1380
agttccagat acagaagaaa at 1402

<210> SEQ ID NO 219
<211> LENGTH: 1436
<212> TYPE: DNA
<213> ORGANISM: Phyllotreta striolata

<400> SEQUENCE: 219
aatttcaatc gaaaaaacat tgcacgtgaa gtaaaacaaa tttttcaatt tcacaatgga 60
aatagatgca cagacagaat caaatataaa cttcatacca tgcgtaaaat gggtaagaaa 120
aggtatagct aacacgaatc ccgtgaaact ccaactgtcg aaaaacgagt tagtcgatat 180
aataaatgaa acgaaagtga agctccaaga agctgaagaa aatgacgagg aacttatgga 240
aagcgatgta ccgagacaag atgaattcaa tctggaacaa tacgatgaag atgaagccga 300
agaaaacact gcaaacgcat tagggatagg ctcgttagct gaactagata atgcagccga 360
ggataatttc tccgagtccg acgattctga taaagaagac gaagtcatta aacctacaga 420
taatctgata ttggtggcgc acgtagaagg agacgccagt ttcttggagg tgtacgttta 480
caatgaagaa gatgaatctt tgtatgtaca tcacgacatt cttttaccat catttccgct 540
ttgtctcgaa cacttgaact acgaacccaa aatgcctaag ggaactact gcgcaatagg 600

```
atccatgtcg cctattatag aaatttggga tttagatatt atcaatgtaa tcgaacctag    660
ttttacgtta ggtcaagtaa agacgaagaa aagcaacaaa gttataggac acacagatgc    720
agttttagca ttggcttgga acaaaacatt cgaccatgta atagcaagtg gatcagtaga    780
ccaaacaatt catctatggg atatggaaat taaaaaaccc agtacaacca ttaaatcgtt    840
tacggataaa gtacaatgtt tggaatggca cgctttagaa gctcaaacgc ttttagcagg    900
aggttgcgat agttctataa gagtatttga ctgtagaact ccagaagctc atcaaacttg    960
gctcttagat ggcgaagctg aacggatatg ttggaatcca ttggaacctt ttagtttttt   1020
ggctggtacc agtaaaggtt cagtccaatg tttcgactgc agaaaagggg aactgtggtc   1080
tatttcagct cacagtaaag aagttagtgg cctatgtgcc agtacacaat gcccaggtct   1140
actaataacg tcttctactg atgaaacagt gaaaatatgg gattataaag acctagcaaa   1200
tgctccttgc ctaataaatg aaaaggaatt taacttgggt aatgtgcact gcttagatct   1260
ttgccctgat ttacccttcg ttatatcagc tggtggagat aaaaagtcgc ataattttac   1320
agtgtttgat atacagaata ttgatgttgt tagaaacaca tttcaaccga gaggcttaat   1380
taaatcagaa tctgttaaag aagaaggtgc ttctacctca acttagagat atgcac       1436
```

<210> SEQ ID NO 220
<211> LENGTH: 1420
<212> TYPE: DNA
<213> ORGANISM: Phyllotreta cruciferae

<400> SEQUENCE: 220

```
aattaacctc aatttcaaac caaaaacact acacgtgaaa gaaaacaagt atttcaattt     60
cacgatggaa atagacgcac agacagaatc aaacataaat ttcataccat gtataaaatg    120
ggtaagaaaa ggcatagcta atacgaatcc cgtgaaactc caactgtcga aaaacgagct    180
agtcgatata ataaatgaaa cgaaagtgaa gctccaagaa gctgaagaaa acgatgatga    240
aattatggaa ggcgatgagc cgaggcaaga tgaattcaat ctagaacagt acgatgaaga    300
tgaaggcgac gagaacactg cgaatgcttt aggcataggc tcgatagctg aattggacaa    360
tgcagccgag gataatttct cagagtctga cgattctgat aaagaagatg aagtcattaa    420
aaccaccgat aatctactat tggtggcgca tgtagaagga gatgcgagca ttttggaggt    480
gtacgtttac aatgaagaag aagaatcttt gtatgtacat cacgacatta tcttaccatc    540
gtttccactt tgtctagaac acttgaatta tgaacccaaa atgcctaagg gtaactactg    600
tgcaatagga tccatgtcac ctattataga aatttgggat ttagatatta tcaatgtaat    660
tgagcctagt tttaccttag gtcaagtaag gactaagaaa agcaacaaat ctatagggca    720
cacagatgca gttttagcat tagcttggaa caaaacattc gaccatataa tggcaagtgg    780
atcagtagac caaacaattc atctatggga catggaaatt aaaaaaccca gcacgaccat    840
caagtcgttt acagataaag tacaatgttt agaatggcac tcgttcgaag ctcagacgct    900
tttagcagga ggttgcgata attctataag agtatttgac tgtagaactc cagaagccca    960
tcaaacgtgg ctcttagacg gtgaagctga gagaatatgt tggaatccgt tagaaccttt   1020
cagtttttg gctggtacca gcaaaggttc agttcaatgt ttcgattgca ggaaaggaga   1080
actgtggtct ctttcagctc acagtaaaga agttactggc ctatgtgcta gcaaacaatg   1140
cccaggtttg ctaataacat cgtctactga tgaaacagtg aaaatatggg attataagga   1200
cttaacaaat gctccttgct taataaatga aaaggaattt aacttgggta atgttcactg   1260
```

```
tttggatctt tgccctgatt taccctttgt tatatcagct ggtggtgaca ataagtcgca   1320

taattttaca gtatatgata tacagaatat tgatgttgtt agaaacacat ttcaaccgag   1380

gggcttaatt aaatcagaat ctgttaaaga agaaggtgcc                         1420


<210> SEQ ID NO 221
<211> LENGTH: 1282
<212> TYPE: DNA
<213> ORGANISM: Leptinotarsa decemlineata

<400> SEQUENCE: 221

tttttttaa gtttcgtcaa aacatggaag aaaattcgca aagtaacata aattttgtac     60

cctgtgttcg ttgggtgaaa cgaggagtag caaatgcaaa tccagcaaag gttcagctat    120

caaaaaatga gttgatacag ataataaatg atacaaaaaa caaactgaat gtggctgata    180

atgaagacga agtcatggaa ggagaaccgt caggaacaga cgagttcaat tttgaaaatt    240

atgatgaaaa tgacgaggct agcactgcaa atgcacttgg gatcgcatcc ttagccgatt    300

tacctaccgg agcagaagat aatttctccg agtcagatga ttccgagaaa gaagatgatt    360

taatcaagcc tacagataat ctaattctag tgggacatgt tgaaggagat tccagtattc    420

tggaagtgta cgtatacaat gaagatgaat gttctctgta tgtccatcac gatatcgtct    480

tgccgtcctt tcccttatgc cttgagtggc tgaactatga gccaaacatg ccggcaggca    540

attattgtgc agtaggtacg atgtctccaa tcatagaagt gtgggacatg gatatgatga    600

acgtaattga accatcgttt actcttggaa aagcaggcag caagaagaaa aaccgcaaga    660

ggataggtca cactgatgct gtcctttctt tggcctggaa tcatacctac gatcatgtca    720

tggcaagtgg atcagtagac aaaagcataa tcctgtggga catggaacag aaagtgccca    780

gcacaactat taacgttttt ggggacaagg tgcagtgcct cgaatggcac aggatggaag    840

cccaaactct tttggcaggt ggttgcgata gcactgcaag agtctttgac tgccgaactc    900

cagaacctca tcaaatttgg caattagatg gagaagcaga aaggcttatg tggaatcctt    960

tggagcctta cgtgtttcta gctggtacca gcaacggctc tatccaaagc ttcgattgta   1020

gaaaaggtca actttggtca attaatgctc attctaaaga agtaactggt ctggcgatca   1080

gtcgtcagtg tccgggtctt ttggtgaccg cttctcccga tgaaatggtc aagacttggg   1140

attttgcatc aggaagcgtg ccgaagcttg tacacgaaag ggagttcaaa ctgggtaaca   1200

tccactgttt ggaactttgc cccgattccc cattcgttat aactctagga ggggataata   1260

agtcgaacaa tttcgccgtt tt                                            1282


<210> SEQ ID NO 222
<211> LENGTH: 1353
<212> TYPE: DNA
<213> ORGANISM: Tribolium castaneum

<400> SEQUENCE: 222

atggaagaaa acgacaccga aaatcgagtt aatttcatca cttgcgtcaa gtgggtgaag     60

aaaggagtgg caaaaagcca acccgaaaag gtccaattgt ccaaagccga gctcgtacaa    120

gtcataaaag ccacaaaaaa gaaacttcga gtcacaaatg aggaaaatgc tcaaggtgaa    180

tcatcggctc aagatgagtt caatttggaa aattatgacg aacaagacga aggcaccgct    240

gaggctttgg ggataagttc actggctgat ttacaaaata atgaggaaga aaacttctct    300

gaatcagacg attcggacaa agaagacgaa gttatcaaac ctaacgataa tttaattcta    360

gttggacatg tggaaggtga cgcaagttcg ctagaagtgt acatttacaa cgaggaggaa    420
```

```
gaatcacttt acgtccacca cgatatctta cttcccgcct ttccactttg tttcgaatgg    480

ttggactacg aacccaacgc cccaaaaggc agttactgtg ctataggttc catgaccccc    540

attatccaag tctgggactt ggacataatt aactgcatag aacccgcgtt taatttaggc    600

cgagccgcaa gtattaaaaa aaaccgacct cacgtcggcc acaaagacgc agttttaact    660

ttggcttgga acaaaaccta cgaacacgtc ttagctagcg gttcagttga caaaactata    720

cttttgtggg acttggagaa caaaactcca agtacgacca tttccgcgtt caaagacaag    780

gtccagtgca tgcagtggca caaactggaa gcgcaaactt tactagctgg gtctagcgac    840

aagaaagcaa aaattttcga ttgtcgcaac cctgagacac atcagacgtg gaaaataaat    900

ggggaggttg aaactctggt ctggaacccg ctacaaccgt tttcattttt cgccggtagt    960

gataccggaa atttgcaata ttttgattgt agaaaaggta gtcaagtgtg ggctgttgaa   1020

gcccatgaaa aggaagtcac tgggttggtt gtgagtccgc aatgtcccgg tttattagtc   1080

acatcgtcgc cagatgggac gataaaaatt tgggactaca ccgaaaatga agccactttc   1140

gtgttcgaaa aagattttag tttagggaca gtccagtgcc tggatttgtc gcccgatttg   1200

ccgtttgtca tagcggcagg aggggataat aaatctaata attttctagt tcacgatttg   1260

agaaacatcg atgttgtaaa acacaagttt ggagaccggc aattagaaga attagtcgca   1320

gaaagtacag aagaaagcat gaacactgat tag                                1353
```

<210> SEQ ID NO 223
<211> LENGTH: 1435
<212> TYPE: DNA
<213> ORGANISM: Epilachna varivestis

<400> SEQUENCE: 223

```
tataactaaa agtagcaata ttgactttga gaattataag gcattgcata aataaataag     60

aggtgatatc aatggaacac gagttggaag aagaattgga atcgcagagt agaattaatt    120

ttataccttg tttaaaatgg gttaaaaaag gtgttgccaa cacaaatcct atgaaggttc    180

aactctcaaa gaatgaattg gtaaaaatta tcaaagatac acaaaaaaag ctagtccttg    240

ccaaaaatga atcaaataga gatggcgacg aagaagcagt tgatgacctc aatctaagtg    300

attatgacaa tgaagatgaa aacactgcta atatacttgg catcggttct ttggcggagt    360

taacaaatga tgcacaagat aatttctcag aatctgatgg ttctgatata gaagatgatt    420

taatacttgt gggacatctt gagggtgata caagcatttt agaagtttat gtctacaatg    480

aggaagaaga gtccttatat gttcatcatg atatattatt accaagtttt ccattatgct    540

tagaatggct agactatgaa acaaattccc ctaaaggcag ctattgtgct ataggttcca    600

tggatcctat aatagaagta tgggatttag atataatcaa ctcagtggaa tcagctttta    660

aattaggaca aatgggtagt cgaaagaagg gtcgacccca tataggacac agggatgcag    720

tattatcttt agcatggaat aggtcattcg agcatatatt agctagtggt tcggcagata    780

aaagtgtaat attgtgggat ttggatagaa aagaacctag tactacaatc aaagcatttg    840

aagataaagt acagtgtcta gattggcata aattagaggc acaatcttta ttagcaggtg    900

cttgtgatgg tcgtgtaaaa gtctttgatt gccgaactcc tgatagtcat ttgacttgga    960

atttagatgg tgaatgtgaa cagctctcct ggaatcccct acagccattt actttcattg   1020

caggcacaag tgtaggttct ttgcaatgct ttgactgtag aaaaggtcag ttatggtcga   1080

ttccagctca tgaaaaggaa gtcaccggac tctttgtgag tggtcaatgc ccaggattaa   1140
```

-continued

```
ttgtcacatc ttctccagat gaaacagtga aaatctggga ctatagtggg gaaaattctc   1200
ctgaattgat tcacactaat gactttaatt gtggaatgtt acattgcttg gggggttctc   1260
cagattctcc atttgtaata gcttcaggtg gagataagaa gtccaataat ttcttagttt   1320
acgatatacg aaatatagat gctgtaaaac acaggtttga gggcagggaa ttagtacagc   1380
tggttcctac cactccatca gaaactccag aggtcatgca acaagatgat taatg        1435
```

<210> SEQ ID NO 224
<211> LENGTH: 1432
<212> TYPE: DNA
<213> ORGANISM: Vibidia duodecimguttata

<400> SEQUENCE: 224

```
gtatcctgtg taaaatggat agaaaaagga aaagctcgtg cagaaccttt gaaggttaaa     60
atttcgaagg aagaactggt agaaatgatt aaaaatacta aggaacaact cagtctcagt    120
aacttagaaa atcaagaaaa tgaaccatca gatgacgttg atatggagaa tggagatggt    180
aataatgtgg ggttagatct catcgatgac ttatccacga atcctgaaga ttatttgagt    240
gaatctgaag aagaatccga taaagaggat gacatgataa aaaccagtga taatttggta    300
cttatcggta aatttgatgg tgacgcttgt tcgttagagg tccacgttta taacgacgaa    360
gaggtttcgt tttattgtca ccacgatttc ttattgacaa gttttccggt ttgtttcgaa    420
tggttgaatt acgaggcgaa cagtccgttg ggtaactacg ttgcagtcgg tatgatggaa    480
ccggttatcg aggtttataa tttggacgtt ataaacgtta tgacgccttc gtacgaactt    540
ggacgaaaag ctaacaggag gaaaaattta cctcaaatcg gtcataaaag ttcagttctt    600
tccctggctt ggagtagagc gtacgaacac gttctagcta gcggttcttc cgataaaagt    660
attattctgt gggatttgga aaagagggag ccgagtacta cgattaaatc gttcgaagga    720
gacgttcagt gtctcgagtg gcataaagtg gagacgcaat ctttattagc gggtgcatgt    780
gatagtcaag tgaaactttt cgattgtaac agtccgagta gtcatttaac ttggaaatta    840
gacggagaat gcgaaacttt gaattggcat ccgcatgagc cgttcacgtt cttagcaggc    900
accaatgttg ggtctttaca atgtttcgac tgcagaaaag gtctgatctg gtcgttggct    960
gctcacgaga aagaaatcag tggggttttt atcagtagcg aatgcccggg attaatgatt   1020
acgggatctc atgacggcat ggttaaaacg tgggattaca aaggggagga tgtacctgaa   1080
ttggtctatt ccaaagactt caatttagga acaattttat cccttgaagg ttcaccaaac   1140
tcacccttcg taatagcagc aggtggcgac aacaaagata ataattttgt aatatacgac   1200
gttcgtaaca ttgacgttgt gaaacacaag ttcgagaata gggaattgaa aaaattggaa   1260
acttccacac ctgccgagca gacatgaaga gtaattaaaa tgtaattaaa ggagaatgga   1320
atggatataa gagggagtga atgtcattat gatgggcttt catgaaagta gattgagaag   1380
tgaaaattta tatttgttat attttgaata aatatagtta atttaaaaaa aa           1432
```

<210> SEQ ID NO 225
<211> LENGTH: 1470
<212> TYPE: DNA
<213> ORGANISM: Pectinophora gossypiella

<400> SEQUENCE: 225

```
aaaactcaaa agagtgaagt gagcacgtga aatcaagaaa attcgtgaat ttgcgcgttg     60
tttcctccat aataatggaa gaaaattcgc ccacggtcag cttgatttca tgcatgcatt    120
ttgtacgccg tggcgtagcg aaatcggtgc cagaaaagat tgagcttaca gaaaaagagt    180
```

-continued

```
tagagagcat aattaagcaa actgctgaag atttacggct tactgagaat cctgaggaca    240
gcgaggatga ggaaggagaa gcgggtgcta gtgctgtcag agatccacca gcaaatccta    300
atgatgagtt tgattttgaa aaatatgacg aggaagatgc aagtgttaac ccaatcggga    360
ttggctcagt ggctacccta cctaatttag gtgatttgag tgaaaatgtc caaatcagga    420
ctgaagggcc agatagtgac gaagaagatg acataatcaa gccagatgac aacttgcttc    480
tggtcggcca tgttgagagt gatgctagca tactagaggt atacatattc aacaaagaag    540
agggttcatt ctatgtgcac catgacgtta ttctgccttg gttcccgtta tgcattgaat    600
ggctgagtca tgatccatct gatcctaatc caggtaatct ttgcgctctt ggtggtatgg    660
acccagtcat ccaagtatgg gacttggata ttgaaaactg tctagaacca gcgttcaaac    720
tcgggaaaaa gccgaataaa aagaaaaaga taaaacgggt tggacacaaa gacgctgtat    780
tagatctatc ttggaatagg aacttcacac atgtactagc aagtggttca gcagacaata    840
cagttttgct atgggacctg gatcaagggg cacctcacac gacactcagc tactttgaag    900
ataaagtaca atcgctaacc ttccatccat tagaagctca aacattacta tctgggagtt    960
gcgacgggcg cgcacgagtg accgactgcc ggacaccaga cgcacatcgc gcctggcaac   1020
ttgcagggga gatagagagg gtcacgtggg acaaacagaa tcccttctgt tttgcaatga   1080
gcaacaacga aggcaaggtg tcgtacgtag actgcagaca agacgaacct ctatggacca   1140
taactgcaca tgaaaaagaa gtcacaggtc ttattctcag tgaacaagtg ccagggctaa   1200
tggtcacaat aagcacagat ggcaaacaga agacttggga tatatccaac gctccaccag   1260
tccaggtgag cgagcgaagc ggccgcgtcg gccaagcgtt gtgcgcggcc agctgcccag   1320
acgcaccctt ctccatagcc gtcggcggcg acaacaagga atgctgcatc gagatggtgg   1380
acctcaccat caacgaacaa tttgtccacc ggttcgggtc gcgacccctc gtgcaagtca   1440
ctacagaatc aaatgacgac gcaatggaat                                    1470
```

<210> SEQ ID NO 226
<211> LENGTH: 1361
<212> TYPE: DNA
<213> ORGANISM: Spodoptera frugiperda

<400> SEQUENCE: 226

```
acagtcagct taatatcatg tatgcacttt gtgcgtcgcg gagtggcgaa agcagtgccg     60
gaaaaaatag aattaacgga gaaagaattg gagaaaatta tcaaacaaac agctgatgat    120
ttgaggatag ctgaagctgg tgatgatgag agtgatgaag aaggagaagc aagtgctgcc    180
ccgagagacc caccagcaga tcctaatgac gagttcaact ttgaaaagta tgacgaagaa    240
gataatatta accctgtcgg tattggtact gtagctacat taccaaattt gggtgactta    300
agtgaagggg tacagataag gacagaaggg ccagacagtg atgaagagga tgacatcatc    360
aaaccaaatg ataatctgct tttagtcggc catgttgaga gcgacgccag cgtcttagaa    420
gtatacattt acaacaagga agaggattcg ttctacgtac accatgatat cattctcccg    480
tggttcccgc tgtgtattga gtggctcagc catgacccct cggatcccaa tcctggcaac    540
ctctgtgccc tcggtggtat ggacccggtt atccaagtgt gggacttgga catcgagaac    600
tgtctggagc cagccttcaa gttgggtaaa aaacctaata aaaagaagaa aactaaacgg    660
gtcggacaca aggatgctgt tctagatcta tcgtggaaca ggaactttac acatgtgcta    720
gcgagtggat cagctgacaa cacagtgtta ttatgggacc tggatcaagg cacgccacac    780
```

accaaaatcg actgcttcca ggataaggta caatccctag cattccaccc gctggaagcg 840
cagacgttgg tgagtggttc gtgcgacggg tacgcgcgcg tgtcggactg ccgcgcgccc 900
gacgcgcacc gcgcatggaa cctcgggccc gagatagagc gggtcgtctg gaactcacag 960
aatccgttct gttttgctat gagtaacaac cagggtaagg tagcgtacgt ggactgccgg 1020
aacgacgcgc cgctgtggac ggtcgacgcg cacgagaagg aggtcaccgg cctcatactc 1080
agcgaccgag tgcccggcct catggtcacc gtcagcaccg acgagaaact caagacttgg 1140
gacatttctg gtgcatcacc gcaacaagta agcgagcgca catgtcgcgt gggccaggct 1200
ctgtgcgccg cgctgtgtcc ggacgcggcg tacagcgtcg ccgtcggcgg ggacaacaaa 1260
cagaactaca tcgaactcgt cgacctcacc attagtgaac aatttgaaag tcggttcgca 1320
tcgcgacccc tgctcatacc acccactgcg cctagtgaag c 1361

<210> SEQ ID NO 227
<211> LENGTH: 1482
<212> TYPE: DNA
<213> ORGANISM: Ostrinia nubilalis

<400> SEQUENCE: 227
ctcgtgtttc tcagcagaat cgcatgtttt tttgctagta ttttagattt tatttataag 60
tgaattacat aaaaatggaa gaaaacacac ctacagttag cttagtatca tgtatgcatt 120
ttgttaggcg aggtgtggct aaagcggttc ccgaaaagat tgaactaacg gaaaaagaat 180
tagagaaaat aatcaaacag accgcaaatg atttaagatt aacggaagcc ggagacgatg 240
tcagcgacga agaaggcgaa agttctcgcg gcccaccaga cccgcccgct aatcccaatg 300
atgaatttga ctttgaacac tatgaccaag acgacacaag taatccagtt ggtattggct 360
cagtggcaac attacccaat ttaggtgact taagtgaaaa tgttcaaatt aggacggaag 420
gaccagacag tgatgaggag gatgacatca tcaaagcaga cgataacctg cttctagttg 480
gtcacgttga aagcgatgcc agcgtactgg aagtatacat tttcaacaaa gaggaagact 540
cgttttatgt ccaccacgac atcattcttc catggttccc actgtgcatt gaatggctga 600
gccatgaccc ttcagaccct aacccaggca acctctgtgc cctcgggggc atggacccag 660
tgatccaggt gtgggacctc gacatcgaga actgtttgga gccggccttc aagctcggca 720
agaagcccaa caagaagaaa aagacgaagc gcgtgggaca caaggacgct gtgcttgatc 780
tgtcttggaa taggaatttt tcacatgtgc tggcaagtgg gtctgcagac aacacagtgc 840
tcctctggga cctggaccaa gggtcgccgc acacaaaact aaactacttc gaagataagg 900
tgcaatcggt gtcattccac cctctagaag cgcagacgtt gttgacgggc gcgtgcgacg 960
ggcgcgcgcg cgtcaccgac tgccggacgc cggacgcgcg ccgcgcctgg cagctgccgc 1020
cggagatcga gcgcgccgtg tgggacacgc agaacccctt ctgcttcgcc atgagcaaca 1080
accaaggaaa agtagcgtac gtggattgta gacaggatga gccgctatgg accatagatg 1140
cacacgaaaa agaaatcaca ggtctaatac taagcgacaa agttcccggc ttgatggtca 1200
ctgtcagtac agatggaaaa atgaaatcgt gggacataac tagcggcgca tgcgtgcaag 1260
tgagcgagcg ttcgggccgc gtgggacagg cgttatgcgc tgcggcgtgt cccgacgcgc 1320
ccttctctct ggctgtgggc ggggacaata aggagtgctt catagaggtc gtcgacctgc 1380
tggccagcga cacagtttca aatcgcttcg ggtcgcggcc gctggtgtct ataacggtgg 1440
aatcaaacga taacgctatg gaagcataga atataatttt gt 1482

<210> SEQ ID NO 228
<211> LENGTH: 1604
<212> TYPE: DNA
<213> ORGANISM: Manduca sexta

<400> SEQUENCE: 228
atagaaaaaa gtcataaatc tgtaacttcc aaacttagtc acctatgatt atactgtctg 60
tgcatcattc attcaatcat tgttctagtt ttaaatttgt ttatggtctt tatcagagtc 120
tttatcattt gtcaatgtta tgttaacgtg ttttgtctgg gttatgtgca tgtgtttata 180
aaataaatat atacaaatta aactagaaaa tggaagaaaa taccccaaca gtaagcttag 240
tatcatgcat gcgttttgtt cgccgtggta tagctaaagc tgtaccagaa aagattgaat 300
tgaccgagaa agaattggaa aagattatta aacagactgc tagtgaatta agaatttcag 360
aacaggggga tgacaatagc gacgaagaag gtgaagaagc tgcaagtgcg cctccagatc 420
ctcccgcaga ccctaatgat gaattcaatt ttgaacagta tgatgaagaa gatacaaata 480
caaatcccat tggaattggg actgtggcca caatgcccaa tttaggagac ctcagtgaac 540
atgtgcagat cagaactgaa ggcccagaca gtgatgaaga agatgacatt atcaagccta 600
cagacaacct gttgctagtg ggacatgttg agagtgatgc cagcatactc gaagtataca 660
ttttcaacaa ggaagaagga tcattttatg tccatcatga tatcattctg ccctggttcc 720
ctctatgtat cgagtggttg agccatgacc cttcagaccc aaatcctggc aacctttgtg 780
ctctcggcgg aatggaccca gtgatacaag tgtgggattt agatatagaa aattgtctgg 840
agccagcttt caaactcggg aaaaaaccga acaaaaagaa aaaaacgaaa agagtaggcc 900
ataaagacgc agtgcttgac ttatcatgga atagaaactt cacacatgtg ttagcaagtg 960
gatcggcaga caacaccgtg ttattatggg atctggacca aggcactcca cacaccaaac 1020
ttgactactt ccaagacaag gtgcaatcgg tgtcgttcca cccgctggag gcgcagacgc 1080
tgctgtcggg cgcgtgcgac ggctcggcgc gcgtgacgga ctgccgcgcc gccgccgcgc 1140
accgcgcctg gccgctcggg cccgagatcg agcgcgccgt gtgggacacg cacaacccat 1200
tctgcttcgt gatgagcaac aacgagggta aggtggcata tgtcgactgc aggcaaaacg 1260
aaccgctatg gacaatgaca gcacacgaaa aagaagtaac aggtctctta ttaagtgaac 1320
atatacctgg tctaatggtt accgtcagca cagacggcaa aatgaaaact tgggatataa 1380
cagggtctgg cgctactcag gtgagcgagc gcgcgggccg cgtgggccag gcgctgtgcg 1440
cggcgctgtg tcccgacgcg ccgcactcgc tggccgtcgg cggcgacaac aaggagaact 1500
tcatcgaagt cgtcgacctc accattagcg aacagtattt gaatcgtttc ggaagtcggc 1560
agccagtatc catcactaca gaagacaact ctatggaaac atag 1604

<210> SEQ ID NO 229
<211> LENGTH: 1291
<212> TYPE: DNA
<213> ORGANISM: Helicoverpa zea

<400> SEQUENCE: 229
ttttgatctc atgtgcacat tgtttttgta catgtgatcg aagataaata catatattta 60
agttataaat tttgctatta caatggacga aacaacgcca acagttagtt taatatcatg 120
catgcacttc gttagacggg gtgtggctaa agcagttcca gaaaagatag agttaacgga 180
gaaagagttg gagaagatca ttaaacagac tgctgatgat ttgaggataa cagaggccgg 240
tgaagatcag tcggatgatg aagacgaggc tgctgcagcc cctagagatc caccggccga 300

-continued

```
ccccaacgat gagttcaatt ttgaaaaata cgacgaagag gatgatgtaa accctgttgg    360
catcggtaca gtggctactg taccaaactt aggtgatcta agtgaaaatg tacagataaa    420
cacagaaggg cccgacagtg atgaagaaga tgacattatc aagcctaccg acaacctgct    480
tctggtcgga catgtagaga gtgatgccag tatcttggaa gtatatattt ataacaagga    540
agaggattca ttctatgtac accatgacat catcctgcca tggttcccgc tgtgtgtcga    600
atggctcagc catgacccaa cagatcctaa tcctggcaac ctatgtgccc tcggcggcat    660
ggacccagtc atccaagtat gggacttgga catagagaac tgcttggagc cagcgttcaa    720
gctcggcaag aaacctaata aaaagaagaa gaccaaacgg gttggacaca aggatgctgt    780
gcttgatatg tcttggaata ggaattttac acatgtgcta gcaagtggat cagctgacaa    840
cacagtcctc ttatgggacc tggatcaagg cacaccacac actaaaataa aatgttttga    900
agataaggta caatcagtat cgttccaccc gttcgaggcg cagacgttgc tctcgggcgc    960
ctgcgacggg tcggcccgcg tgtcggactg ccgcagcccc gacgcacacc gagcgtggtc   1020
gctggcgccc gagatagagc gggtcacttg gaacgtgcag aatcctttct gttttgctat   1080
gagcaacaac acaggcaagg tagcatacgt ggattgcaga caggactcac ctctgtggac   1140
actggatgct cacgagaagg aagtcacggg actgatactg agcgagtcag tccccggact   1200
catggtcaca ctcagcactg atcagaagat gaagacgtgg gatatttctg gagcggcccc   1260
ggtggcggtg agcgagcgcg tggtgcgcgc g                                  1291
```

<210> SEQ ID NO 230
<211> LENGTH: 2976
<212> TYPE: DNA
<213> ORGANISM: Megacopta cribraria

<400> SEQUENCE: 230

```
ggttactttt gaaaaggtta tttatgtttg ttataaatat taggtccatt tattcattac     60
taaaaatatt ttttttatga aataccttgg aacttgaagt ttcttatcaa attctttttt    120
tggagggtgt ctccgaattt aatgtttctt atatggacat aaagattatt ataaaatgga    180
agtagaaact gaaagacgtg tccttgctaa atttaagtct gataggggggg aggaaattgg    240
tgcgttatat gacctaggaa tttctgtcaa tgttgagcaa ttgacttaca tttgtaatag    300
tctattggag caggaggact ctgctcagta cacctttttat gtgcatgatc aagaaatagt    360
aaacacttta gagggtgtct tggacgtaca gaaactcaac actgaaaatg ttgtcgaaat    420
tatttatcag cagcaagctg tttttaaagt tagagccatt accagatgta caagttctat    480
gccaggacat gcagaagctg taatttcagt caaattcagt cctaatagta gacatttagc    540
aagtggatca ggtgatacca ccgtaagatt ttgggattta actactcaaa cacctctgta    600
cagttgtaaa ggccattcta gctgggttct ttgcatctcc tggtcacctg attctaaaaa    660
gctcatatca gggtgtaaga atggaattat tatattatgg gacccaatat ctggaaaaca    720
aaagggtcca ttaatgaaag gacataagca atggattaca tcattagtct gggagccttt    780
tcacttaaat gcagaatgca gatattttgc cagtagctcg aaagatggtg atatcagaat    840
atgggatgca cctgtgggaa aatgtttacg agttctgact agtcattcaa aaagtgtaac    900
atctttaatt tggggagggt cttctcttct ctattctggc tcacaagatc gaacaattaa    960
agtttggaga cctaacgatg gtgtcctctg tcgaacactg gaaggacatg gacattgggt   1020
taacagtctt tgtgtgaaca ctggctatgt tttaagtttg ggatcatctt tcaggccatc   1080
tgaaaatatt aacaaaaatg atgtcaaagc attgcaaaat gctgctcttg aacggtacaa   1140
```

```
agaagttatc ggttcagaag gagagattct tgtgtctgga agtgatgatt ttactatgtt   1200
tatgtggaag cctgaaacaa ataaaaagtc ttttgaaaga ttgactggtc atcaacaact   1260
gattaatgat gtaaaatttt ctcctgatac aaggattcta gcttcagctt catttgataa   1320
gtctataaag ctttgggatg gaaaaactgg gaaattcatt accaccctac gtggacacgt   1380
gcagtcagtt tatatgttgg catggtcttc tgactcaagg ttgttagttt ctgcaagtgc   1440
tgattcaact ttaaaagtat ggaatatgaa aactaaaaaa cttctgaatg atctgccagg   1500
acatgtagat caagtttttg ctgtggattg gtctgctgat ggtgaaaagg tcgcatcagg   1560
cggcaaagat aaactgttga aactatggca gtattaagaa tgtcttccag gataacatag   1620
gttcatagac ttcaagttct ctcaatgtat atatttttta tatactttaa cttttagcta   1680
cttttaaaat gttaatatat actattattg agttttgttt attttttttt taaaaacgac   1740
acaaatgttt tttagtcacc caaggggttg gaaaaaactt ccaatcaaat atttatttta   1800
tatacaatat ctatacaaag ttgtctaata taaattatca gaaataaatt tgttatattt   1860
tgacaatgta tcaaataaat gctggggctt tggtgccgat aggggatcga caaactggac   1920
agttttcttt catttcttct gagcagtctt cacacaaaca aacatgacca catggtaaaa   1980
taattatttc ttttgggttt tctctgcaag caacacatag ttcgttttct gataactctc   2040
ttctatctct agcatttcgt ctcctttctc ttcttgtttc ttctagtctc ctcctttttt   2100
cttcctcttt cactttaagt tctttcataa cccaccattt tctggccaca atgactccta   2160
gacctaatcc aatgctccca aaaagaagtg acaaccactt ataagtccct tgttgctctt   2220
ctaatttacg tattaaggaa gatatcggca tagtggtaag ataatatgga tatcctgtcg   2280
atggagggga tatttggaga ttaccactag cattgataga aacttctcca acagcgatga   2340
gaggagttcc ctctttcaac aattcttctg ttgtttcaat accccgttgt cttactccat   2400
taaaaaatcc tattatgtgg tccataacac ttagtgtact attctcaaat tgattataga   2460
ctgtgtccaa atccaataac tctgcagaaa caggatcaag gatttcaatt gaaaatttac   2520
ccctctttaa aacaaaaggt accacattat gcgatacatg gataacattt ttctgatctg   2580
cccaaaagcc agaagcattt cgagcaatag catgttccat tatagtcttc ctcaaaagta   2640
cgcctgagta atcatgagag ccagaacttt taactgtttt accaactgct ctgacatctc   2700
cttgatagat tgtatatttc ttttcttcat cagtcaattt tttaatatca ggattcacac   2760
caaggcgctg agcgcgttct aatagattaa tggaccaact gcaatttaaa tacaaccttg   2820
tgcatacccc cacaatgaca gcatcaatgc ctaatgctat aagttcacct aggaaatcca   2880
ttttataaat gcttgtaata cctttttta ttcattaaaa cctaagtatt atgatccata   2940
aattttgtca ttcgttaatt caaaacaaaa agtagg                            2976
```

<210> SEQ ID NO 231
<211> LENGTH: 3053
<212> TYPE: DNA
<213> ORGANISM: Nezara viridula

<400> SEQUENCE: 231

```
gggggttagc aaagcacgtg tttggagagt ataaatgctc atgtatttac ttagtttgaa     60
gttgatgttt atgaggtttt aaatcgaatt tgtaaaaaca cttctatttt aagtatttta    120
aattaatgca atatcataat ttatgataga ttggttataa tgttatagat tgattatcac    180
ttttatcaaa cttagtaaat aagtttatat caataattta taagttccat taaaatggaa    240
```

```
gtagaaactg aggaaaagcg tgtacttgcc aaatttaagt cagaccgcgg tgaagaagtt    300
ggtgccttat atgaattaga tatcaatgtt aatgttgatc agttgacata catttgtaat    360
agcttactag agcaggataa atctgcccaa tacacgtttt atgtcaatga acaagaaatt    420
gttaagacct tagaaggtgt tctagatgtt cagaaattga atactgaaaa tgtcgttgag    480
attatttacc aacaacaagc aatttttaaa gttagagctg ttacaagatg tacaagctct    540
atgcctggtc atgcagaggc tgtcatttct gtcaaattta gtcctaacag taagcatcta    600
gcgagcggct caggtgatac cacagttaga ttctgggatc tcacaacaca aacaccactg    660
ttctgttgta aaggccacaa caactgggtc ctttgcattg catggtcgcc tgactccaca    720
aaattagttt ctggttgtaa ggatggccac atagttttat gggatcccgc cactggcaag    780
caaaaaggtc ctactatgaa aggtcacaag cagtggataa cctcgctggc atgggaacca    840
tatcacctta atgcagaatg cagatatttt gccagcagtt caaaagatgg tgatatcagg    900
atatgggatg caccgattgg aaaatgcttg agaattctta ctagccattc gaaaagtgtc    960
acttcactga tttggggtgg atcttctctc ctttactctg gttctcaaga ccgtacaatc   1020
aaagtttgga ggccgaaaga tggtatactt tgtcgtacct tggaaggtca tgcacattgg   1080
gtgaatagcc tgtcagtcaa cactgactat gttatgcgat tgggttcatc tttcaggcca   1140
tcagaaaatg tcaatcagaa tgataaggaa gctttaaaga aagcagctgt tgagcgatac   1200
cgtgaagtaa gtggttctga aggagaaatt cttgtatctg gaagtgatga ttttactatg   1260
tttatgtgga aaccagaaac aggaaagaaa tcttttgctc ggttaacggg acatcaacaa   1320
ctcataaatg atgtaaagtt ctcacctgat acaaggctac tcgcatctgc atcatttgac   1380
aagtctataa agctgtggga tggtaaaact ggaaaattta taacaactct tcgaggtcat   1440
gtgcagtcag tctatatgat agcgtggtct gctgattctc ggttacttgt tagtgccagt   1500
gctgattcaa cacttaaagt atggactatg aaaacaaaaa aactattaaa tgatctccca   1560
ggccatgttg atcaaatatt tgctgtcgat tggtcggcag atggtgaaaa agtagcttct   1620
ggtggcaaag ataaactttt gaaactatgg cagtattagt tggccaagaa gactacactt   1680
aaatgtaaat atgttttaag atgtatatac atgtatcgat ggaagaaata ttttttaact   1740
attaacaata aacaatactt cactccaatt gtttttaaat accttacact ttgttccttt   1800
caaagttctt ggtattaata aaagaaatac aactatttaa tcgtctactg aacaaaatac   1860
aatgccccta aaatcgatgc cgaaataaaa tttataatat atatatattt tttttaattc   1920
attcatcata taaaagctgc tgctttgctg acaataggcg atcgacagac tggacaggta   1980
tccttcactc cttcagaaca atcttcgcat aagcagacat ggccacaatg taaaattatt   2040
atttctttgg gattgaccct gcatgcaaca cacaattcat tatctgatag ttcccttcca   2100
tctcgcgcat ttcttctcct ttccctcctt gtttcttcaa gcctcctttt tttttcttct   2160
tcttttaacc tcagttcttt cagagtccac catttttttaa cgacaattac tccaagaacg   2220
actccaatgc ttccaaaaag gagtgtcaac cacctatatg tgctttgttg ttcctctaat   2280
tttcttatca gagatgacac tggcatggtg gttaagtaat aagggtaacc agcagatgga   2340
ggagacatct gaagataacc actgtgatta accattactt ccccgatagc tgtcagtgga   2400
gttccttctt tcaaaagttc ttcagttgtt tcaatacctc tctgtcttac tccattgaaa   2460
aaaccaataa tatgatccat aacacttagc gtactgtttt caaactggtt atacactgta   2520
tccaaatcta gtagctctgc agaaactgga tcaaggatct caatagtgaa tttgcctttc   2580
ttaagtacaa aaggtacaac attatgtgac acgtggataa catttttttg atcagcccaa   2640
```

-continued

```
aatccagatg cattacgtgc gattgcatgt tccataatac tccttctcag gatcacacca   2700

gaataatctt gtgagccaga acttttaact gattttccca cagctttgac atctccttga   2760

caaatagtgt atttcttttc ctcatcgctt aaattttta tttcaggatt gattccaagg   2820

cgttgagctc tttctattaa attgatagac caactgcaat tcagatataa cctagtacaa   2880

acacccacaa ttatggtatc aatccctaaa gcgataagtt cccccaagaa atccatcact   2940

tttaattaca ttatttgagt ctcattttaa ttatgaacaa accgataagt taaattttgt   3000

cattgttttc aagttgatgc agtaaggttc agcaaaaaca aagacatgaa aaa          3053


<210> SEQ ID NO 232
<211> LENGTH: 275
<212> TYPE: DNA
<213> ORGANISM: Diabrotica virgifera

<400> SEQUENCE: 232

gctccaaagt atggtaccct agtgcctaac agaatattcg tgggaggaat atcagctaac     60

acaacagaag gagaattgat gcaacttttt agcaactatg gtactgttaa agctgctaaa    120

attatacagg acagggctgg tgtgtcaaaa ggatatggtt tcatcacctt tgagagtgaa    180

gatgatgcta aaaggcctct tagagaagct gaaaacatag tgctaagaga aagaaaactt    240

aatatagcac ccgctattaa aaaacagcct tttag                               275


<210> SEQ ID NO 233
<211> LENGTH: 275
<212> TYPE: DNA
<213> ORGANISM: Diabrotica virgifera

<400> SEQUENCE: 233

tgccagtcaa ttcttttttc ctccgggtgc tgccgtgcca tattttcaga gtggagttac     60

atattatact cagccagctc ctgctgcacc tggagatccc actgctcaac aacctgttta    120

tcaacccccct ccaatgtatc ccacgcaaac tggtcctcca caggcagcta catacccttc    180

tatgatgttt cctgctcaaa ctatatatat gccgcaacag tatcccatgc ctattccgta    240

cgagtacaac ttctaccagg gtaacggacc gtcgc                               275


<210> SEQ ID NO 234
<211> LENGTH: 275
<212> TYPE: DNA
<213> ORGANISM: Diabrotica virgifera

<400> SEQUENCE: 234

ctcagtatct ggccggaggc caaagcggtc cgggaaactc tcattgcacc tcattaccat     60

catcaaacag tccacccaga cccaattgtt atggtcaaca ggtgcctgcc tataattcag    120

gagatcccgt gtactacaac ttgccaatat acggagccac tttggaaggt ccgccattat    180

acgctgatgc cttcgatcta agcgctagtg gagcttatgc ggaggaaacc tacagcggca    240

tgattactca agaaaatgta gaagcttctc ttgga                               275


<210> SEQ ID NO 235
<211> LENGTH: 275
<212> TYPE: DNA
<213> ORGANISM: Diabrotica virgifera

<400> SEQUENCE: 235

cggtaaattc aactcgtgca acttccgata attttacgca acatatggat caatctctcg     60
```

-continued

```
ttgagtctga ttcaaatatt gttaatgttg gaggtaaacc accagcacat aaatcttcag    120

agacaattgt ttctactcct tcccagcctc aggaggagag aaactcacac acgcctattg    180

tttcactact ttccatagat catcaacagg aaaaagacta ttcatcaatg caaagcggtc    240

gtagacggaa acttctgatt caaagcaatc aaaat                               275


<210> SEQ ID NO 236
<211> LENGTH: 275
<212> TYPE: DNA
<213> ORGANISM: Diabrotica virgifera

<400> SEQUENCE: 236

gtacccatgt atcctacaaa cggatacgtc aaccagtttg tcggatataa tcctcaacaa     60

ccatccccac cttcattcgg tccacctctc tataacaacg gctacggtta ttctgaatat    120

cgtcgattta acggataccc agatctcagg tcaaataata atagtaataa accgaggaga    180

cgaatatacg aaaataggcg gtcgaacgat cattctagcc gttccagtct tcgcacagac    240

tcaaactcat cggctagttg tgttgacgaa aataa                               275


<210> SEQ ID NO 237
<211> LENGTH: 275
<212> TYPE: DNA
<213> ORGANISM: Diabrotica virgifera

<400> SEQUENCE: 237

cgaagaaaaa acttttcgaa ctactgttaa cactcctcca cctgccccat actcacctat     60

gaccaatcat caattcaaat ttattaatta cactaacacg aaaaacgttt ataatcataa    120

gtacgctcac acgtttataa tcataagtac gctaacaaca ataattatta taatagaaca    180

gctacacaca atgaccgatt taaacatacc gaacctttag cgaataaaaa caataacagt    240

tccatttacc cattaacaaa taatttccta aataa                               275


<210> SEQ ID NO 238
<211> LENGTH: 373
<212> TYPE: DNA
<213> ORGANISM: Diabrotica virgifera

<400> SEQUENCE: 238

tagccatacc caaagtaatt ctgattccct tccctcccaa aattcccagg tacatgtgac     60

gactacgggt cagagcttcg tcccggcggc tatccaagct cagacgaaac gcaacaagcg    120

ttctttgaga agaagcggtg ccagtgccgg aggcatcaac gaaatcggcg ccggtgacgc    180

ccctttacca ggcgaagaat gcgaagatgt ctacaagaag ctggaaacgc ttaagttgta    240

acgaaaaagt ggtatctttt cttgtatatt tttttctatt tatttaagac tgtacaataa    300

tgtaaaatac tagaaattta atgtaaacta aagaggaaaa atatataata catatttatt    360

gaagatgaaa aaa                                                       373


<210> SEQ ID NO 239
<211> LENGTH: 381
<212> TYPE: DNA
<213> ORGANISM: Diabrotica virgifera

<400> SEQUENCE: 239

cgtttagtag tacatagaga aatcgctttt agttttaatc ttttctgtgt tggaatattg     60

aacaaattct aatgattcgt aaaataacac ttctgttaaa aaccaaaact gatagtttgt    120

tcaaaaaaag tacaattttt ctgggcttgc tactgaaata atgtgccata ctctaattgt    180
```

ggaacaaatt gtaggtatat gttgaaagtg aacaaataac taatgcttac aataatgtcg 240
acatcaagtc aaaataatgg taaaaagagt tcaagcagct ctattgttaa caccccttcc 300
agtactccca ttaccaatct tgcaaatggt agtagtagta cccaaggaac agcacatagt 360
tcacctccac ctaataacaa t 381

<210> SEQ ID NO 240
<211> LENGTH: 271
<212> TYPE: DNA
<213> ORGANISM: Diabrotica virgifera

<400> SEQUENCE: 240
tgcccaaatc aaataaatct agaaatgcgt tttactactt tatggaggat tttaaacaaa 60
gacaaggatt tgcttgtaaa tcgatgaagg atgtagcaga tgctgcaggt ccccattggg 120
ctaggatgtc taaagcagaa agaagacctt atgaagagag ggcaaacaaa gagaagggag 180
gtttgagata tacttgggat ggtcaatgcg ttgaagatat agaaaggagg aacaaagctg 240
aggacaataa aattgctaag atgaaagatg a 271

<210> SEQ ID NO 241
<211> LENGTH: 275
<212> TYPE: DNA
<213> ORGANISM: Diabrotica virgifera

<400> SEQUENCE: 241
cagtgggaga gcgaatctgt agtgtcagac tcctctacag ctactttcaa taatagcttt 60
ccaggtctga aatcgaaatg gacattaagc aattctcaac ctgtagaaac tgactcaatg 120
agccaaatgt caggtcagag ctatgcaagt gctatgggaa ctagaagaca gttttctagt 180
gcaatgggaa atagaggatc tcaaagagag tcctctaaca attccaacaa tggtgacact 240
agtgattcga ataccgatta ttttaacagt caatc 275

<210> SEQ ID NO 242
<211> LENGTH: 500
<212> TYPE: DNA
<213> ORGANISM: Diabrotica virgifera

<400> SEQUENCE: 242
tatcgactgc accttgaaat ttgccaaaga aaattgtcga ctccgagatg aaatgttctt 60
cataatccat atcaatactt tctgttacca tgccagtggt gatcggtatt atcccgctga 120
aattgccatt tcatgcttca gcttggagga tggcgttttg cctcaaaatg tgtttcataa 180
aattattaag ccaggtagac taccactggg gtatgctagt gacgcaaaaa agcaatctga 240
agattcacat caactgccta tccccttaac tggtgacgac gacgacaatg tggaagaagt 300
ttatacagag atgaaagaat ttatattatc taaaaccgga gatactaaga aattccctcc 360
cttgtatgct aagaaagata ttgttaaaat gttgcaacat gtgttagaca cttggtgcgc 420
tgattttgat gagccgccat tatttaaagt ttattattta caatatatgt ttcaagtatt 480
aaaaaactcg gtagctaacg 500

<210> SEQ ID NO 243
<211> LENGTH: 350
<212> TYPE: DNA
<213> ORGANISM: Diabrotica virgifera

<400> SEQUENCE: 243

-continued

```
ataacgtatg gcccttatat tcaatggcag aaacggaact ggataaggat ctttattccc     60

atactgttgg aatatgttgt gaattccatt ctgttagtga agcttgtcaa ttttgcagca    120

agtcagtggc agtacgactt gcatacacaa tttgtgataa ttgctgttcg ttcctagata    180

ttcctataga gcctggaaga cacgtacctg atcaagcttt tacagcatcc agtttgagct    240

caagagcttc atcaaaagct agtttgtata caggttccag taaatcttct aagaagcagt    300

cagttcgtga agatgacaaa gacactgttt tatcgttttc tagtgcctct               350
```

<210> SEQ ID NO 244
<211> LENGTH: 500
<212> TYPE: DNA
<213> ORGANISM: Diabrotica virgifera

<400> SEQUENCE: 244

```
atttccggct cttggaaggg gaagaggtat ggccagaaat cgaagaaatt gatcattttt     60

gactgcaatg ggtcttgttc cacttcatga gattgttaaa tgagtatgta actgattaca    120

ttaggcgaca atattttttt tagtgtcaga ttatttgatg taattgtcct tttgacaatt    180

ctttaatcat tgatgttttc ttctattgtg gtgtttttag atgtcatatt tttatgtatg    240

taaattggtt ttttatctaa gtatagaata ttacatttta gtttaataag ataccagtaa    300

agtatattgg tttaccagtc gcctaatgta aactagtata tacataccta tattattttt    360

ctttaatagt tttaagtcaa ttttgataca gatcacgaga cagatatttt ttccgtctag    420

tccgaattgc gttccgtttc ttgggccttg tcgaattgcg tcccaaatat tttgcttacc    480

tggccaccga taacgtctag                                                 500
```

<210> SEQ ID NO 245
<211> LENGTH: 500
<212> TYPE: DNA
<213> ORGANISM: Diabrotica virgifera

<400> SEQUENCE: 245

```
tccgaattgc gtttcatttc ttaattagcc aacccaattg cggtcagaag atagcttaat     60

aaatattagt taagcaggga aatacaatca acgtaatatc aactaacagt ttatttttat    120

tttagcaccg aatttataac taacacattt aacgaaattg tatcttgaaa tttcacccct    180

gttatactgg ttaattttct gttcgagaaa aatatatttg ctggaggtag ctttatctac    240

atttctagaa atattttgtt taacagaatt tatttttata taagaatcgg tttgaatgcg    300

ctttaatgtt tcaacaaaca aaaaaatatt aggatgtgga gacaaacaat aatttttaaa    360

ttttgaatga aatcactcac aagaattagt tgttctatat atagatgcgc tattctttgc    420

ccaaatttgt ggaggaaatg tgtagtcctc ttcgatatac ctttcaacta gatagtttgc    480

aaatgcgtca actcgatgat                                                 500
```

<210> SEQ ID NO 246
<211> LENGTH: 500
<212> TYPE: DNA
<213> ORGANISM: Diabrotica virgifera

<400> SEQUENCE: 246

```
catctggttt ttcaggcata aaatcttcca caaaacaatc tccaacttgg ctcggaggaa     60

gatacattag gccaaaaata tgcttcagcc atttacctat ttctgagttc tcgttcttat    120

actcagaact caaccccata ttttgtactt tacgccacct gtaacaagat tatagaataa    180

attctttatt tcagaaagta cttgcattca agaaaaagtt tgaaacaggt cagattttat    240
```

aaaaaaaata catctttaaa aaataatgag aatatttagg agccaatttt ttgacagagg 300
ttatgacgac atcttttttt tatgtcaaaa atttgaagat attttaccta caattcttgt 360
tttaacttat atcaaatgct gtttttgta aaaaaaaatt gaaaaaagaa attacagtga 420
agtttgaaat aaacatattg aaatgtttag ttttacagca aaaaaaatag gatgacgtca 480
taactcaagt ttttcttaac 500

<210> SEQ ID NO 247
<211> LENGTH: 500
<212> TYPE: DNA
<213> ORGANISM: Diabrotica virgifera

<400> SEQUENCE: 247
aatctactat ttgccagtta cattgccata cgtattactt accaagcttg agcaagatga 60
agtcgataac caacaacatt tgcttccgga aaaacttctc gtacgctgga gtggatacct 120
aattcgtaat caatcactat tttcgttgga tttaaattgc atcccaaatc ttgacatttt 180
ttctttaata attcgaataa tgatttgtaa gtgaattttt gcttattagg taacaaacaa 240
aatgcaaccg gaacataagt gtcattaatc aatgtatgta atgtaaacat ttaaaaaaaa 300
attgtgcaat aatcgaatgt tccatccata aataaagtgg aattgttaca cataaatgaa 360
agattagaca ttcatgaaaa aacaaaaata ttaaactgtt catcattaat caacaaaaac 420
tgttcatttt tgatagtaaa tatttcaatt tgttccaaaa attcttgaac atccttggct 480
gattttggca attttggaac 500

<210> SEQ ID NO 248
<211> LENGTH: 322
<212> TYPE: DNA
<213> ORGANISM: Diabrotica virgifera

<400> SEQUENCE: 248
cgttttcaat cgcgtgcgat taatgttctt tttttatgta ttggacatct tttgttgaca 60
gagaggtaag tacttcgctt tgcttttcga tttccttgtg taacaacttc gcaggtcgtt 120
ccgcaatatc ttctgttgct tttcttttaa gagaattgtt aactttctgg cgaattaata 180
cttcttcagc aagctcatga ttgtgttcac cactaacttt tgaaaacaca ttatttaatg 240
tatatagttt tgctttacac tttttgaagt tatacttctt taggcgcgat tgagtaatta 300
tttattatta atctgcgcgc at 322

<210> SEQ ID NO 249
<211> LENGTH: 272
<212> TYPE: DNA
<213> ORGANISM: Diabrotica virgifera

<400> SEQUENCE: 249
tggagtacga aaatacacaa caaaatataa acttcgtacc gtgtgtaaga tgggttaaac 60
gaggagtggc caattcaagc ccagtaaaat tgcaactgtc gaaaaacgag ctggctcaaa 120
ttattaatga caccaagatt aaattacaag aatccaatga aaatgaagat gagcctatgg 180
aagaaggtga aacgtctcaa acagatgagt ttgccttaga ggattacgat aaagaagacg 240
aaaatgagga cactgcaaat gctttaggaa tt 272

<210> SEQ ID NO 250
<211> LENGTH: 275
<212> TYPE: DNA

<213> ORGANISM: Diabrotica virgifera

<400> SEQUENCE: 250
tggaaatcaa aaaaccaagt acaaccatta aatccttcca agaaaaagtt caatgtctcg 60
aatggcatcc tttagaggca caaacacttt taggtggagg ttgtgacaaa tctgcaagag 120
tatttgatgg caggacccct gaaacccacc aaacttggct acttgatgga gaagctgaaa 180
ggctatgctg gaacccatta gaacctttca catttttagc aggtaccagc agtgggtctg 240
tacagtgttt cgactgtaga aaaggacagc tatgg 275

<210> SEQ ID NO 251
<211> LENGTH: 248
<212> TYPE: DNA
<213> ORGANISM: Diabrotica virgifera

<400> SEQUENCE: 251
caccggctta cgtaataatt aatttattcc tttcatttgc accatactat atattattta 60
ttgagtggac aaatgttaaa aagtaagtct ggcagcgaac gtgttaatga aacctagtaa 120
aaggctccaa catttgacac ttcttcatgc aacatgttct gttctgtgtc aatctaacct 180
aacctaacat tttcaaatac gaatatggaa acatttcacc acatcaacac gtgaattaat 240
attcgaaa 248

<210> SEQ ID NO 252
<211> LENGTH: 272
<212> TYPE: DNA
<213> ORGANISM: Diabrotica virgifera

<400> SEQUENCE: 252
tcctctgtgt ttagaaccgc taaactatga accgaagatg cccaaaggaa attattgtgc 60
agtgggatca atgtcacctg ttatagaggt ctgggatgta gatattatga atgttattga 120
accttcattt actttaggga gacctgctag taaaaagaag aacaaggaac atataggcca 180
tacggatgca gtgctttcat tagcttggaa caaaaccttt gaacatgtgt tggctagtgg 240
atctgtagat caaacaatac acttgtggga ta 272

<210> SEQ ID NO 253
<211> LENGTH: 486
<212> TYPE: DNA
<213> ORGANISM: Diabrotica virgifera

<400> SEQUENCE: 253
tcagttaaag cacacagcaa ggaagtaaca gggttagtcc ttagcaaaca atgccaagga 60
ttgttgatta cttcttctac agatgaaaca gttaaaattt gggacttggc tacactggaa 120
gctgaaccta agcttgttaa tgaaaaggag tttaatatgg ggaatattca ctgtttggat 180
ttatgtccag acttgccgtt tgttatatct gtaggtggag ataagaagtc aaataatttt 240
actgtttttg atgtacagaa tattgatgtt gttaaacaca catttgggcc aagaggattg 300
gtacagctag ttccagatac agaagaaaat actaatacgt tttattgttt aataaagttt 360
ttattttatt tatttgtaat aatttcatgc ttcttcttta agtaccgtgc ccaaatatta 420
gtcattggta gattccttga caatttgccg atactgtttt cgattactga acaattcatc 480
ttctga 486

<210> SEQ ID NO 254
<211> LENGTH: 600

-continued

```
<212> TYPE: DNA
<213> ORGANISM: Diabrotica virgifera

<400> SEQUENCE: 254

ggggctttct gatttttgac agcttctata gaagtttatc aagatgttga tgccaaaaaa     60

gaatagagta tgtatttacg aatacctctt caaagaggga gtcatggtag ctaaaaaaga    120

ttaccatgcc ccaaaacacc tcgaactaga aactatccct aaccttcaag taattaaggc    180

tttacaatca cttaaatcaa aaggttacgt aaaggaacaa ttcgcctgga ggcattatta    240

ttggtatttg actaactctg gcatcgaata cctccgcaca ttcttacact tacctggaga    300

aattgtccca tctaccttga aacgcccagc aaggacagaa accaccccgtc ctagaccagc    360

tgctctcaga tctgagacat ctaaaccttc agaagaccgt gcaggataca gaaggactcc    420

tggaggccct ggagctgaca agaaagctga tgttggtcca ggaactggag atgttgagtt    480

caggcaagga ttcggacgtg gacgggcacc acaataaatt tattgataag ttaattttta    540

taaattgatc agccaataaa aagtttggtt aaaaaaaaaa aaaaaaaaaa aaaaaaaaaa    600
```